United States Patent
Deninno et al.

(10) Patent No.: US 10,233,191 B2
(45) Date of Patent: Mar. 19, 2019

(54) FUSED PIPERIDINE AMIDES AS MODULATORS OF ION CHANNELS

(71) Applicant: Vertex Pharmaceuticals Incorporated, Boston, MA (US)

(72) Inventors: Michael Paul Deninno, San Diego, CA (US); Corey Anderson, San Diego, CA (US); Erica Lynn Conroy, San Diego, CA (US); Bryan A. Frieman, La Jolla, CA (US); Peter Diederik Jan Grootenhuis, San Diego, CA (US); Sara Sabina Hadida-Ruah, La Jolla, CA (US); Dennis James Hurley, San Marcos, CA (US); Fabrice Jean Denis Pierre, La Jolla, CA (US); Alina Silina, San Diego, CA (US); Johnny Uy, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/903,475

(22) PCT Filed: Jul. 8, 2014

(86) PCT No.: PCT/US2014/045675
§ 371 (c)(1),
(2) Date: Jan. 7, 2016

(87) PCT Pub. No.: WO2015/006280
PCT Pub. Date: Jan. 15, 2015

(65) Prior Publication Data
US 2016/0159815 A1    Jun. 9, 2016

Related U.S. Application Data

(60) Provisional application No. 61/844,499, filed on Jul. 10, 2013.

(51) Int. Cl.
| | |
|---|---|
| *C07D 491/056* | (2006.01) |
| *C07D 221/04* | (2006.01) |
| *C07D 401/06* | (2006.01) |
| *C07D 405/06* | (2006.01) |
| *C07D 405/12* | (2006.01) |
| *C07D 487/04* | (2006.01) |
| *C07D 491/044* | (2006.01) |
| *C07D 491/048* | (2006.01) |
| *C07D 401/04* | (2006.01) |
| *C07D 403/06* | (2006.01) |

(52) U.S. Cl.
CPC ....... *C07D 491/056* (2013.01); *C07D 221/04* (2013.01); *C07D 401/04* (2013.01); *C07D 401/06* (2013.01); *C07D 403/06* (2013.01); *C07D 405/06* (2013.01); *C07D 405/12* (2013.01); *C07D 487/04* (2013.01); *C07D 491/044* (2013.01); *C07D 491/048* (2013.01)

(58) Field of Classification Search
CPC .. C07D 221/04; C07D 405/06; C07D 405/12; C07D 401/04; C07D 401/06
USPC ........... 544/281, 335; 546/112, 115, 116, 15, 546/168
See application file for complete search history.

(56) References Cited

U.S. PATENT DOCUMENTS

| | | | |
|---|---|---|---|
| 4,150,135 A | 4/1979 | Ripka | |
| 4,301,290 A | 11/1981 | Pfaffli et al. | |
| 5,616,705 A | 4/1997 | Steiner et al. | |
| 6,028,073 A | 2/2000 | Steiner et al. | |

FOREIGN PATENT DOCUMENTS

| | | |
|---|---|---|
| GB | 2 016 012 | 9/1979 |
| GB | 1 568 976 | 6/1980 |
| RU | 2 136 678 | 9/1999 |
| RU | 2 163 604 | 2/2001 |
| WO | WO 2008/130319 | 10/2008 |
| WO | WO 2009/005459 | 1/2009 |
| WO | WO 2010/151595 | 12/2010 |

OTHER PUBLICATIONS

Sandoz (AN 1983:539795, HCAPLUS, DN 99:139795, abstract of AT 371445).*
International Preliminary Report on Patentability dated Jan. 12, 2016, prepared in International Application No. PCT/US2014/045675.
International Search Report dated Oct. 17, 2014, prepared in International Application No. PCT/US2014/045675.

* cited by examiner

*Primary Examiner* — Sabiha N Qazi
(74) *Attorney, Agent, or Firm* — Brinks Gilson & Lione

(57) ABSTRACT

The invention relates to fused piperidine amides useful as inhibitors of ion channels for the treatment of pain. The invention also provides pharmaceutically acceptable compositions comprising the compounds of the invention and methods of using the compositions in the treatment of various disorders.

32 Claims, No Drawings

FUSED PIPERIDINE AMIDES AS MODULATORS OF ION CHANNELS

CROSS-REFERENCE TO RELATED APPLICATIONS

This application claims the benefit of U.S. Provisional Patent Application No. 61/844,499, filed Jul. 10, 2013, the entire contents of which are hereby incorporated herein by reference.

TECHNICAL FIELD OF THE INVENTION

The invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Pain is a protective mechanism that allows healthy animals to avoid tissue damage and to prevent further damage to injured tissue. Nonetheless there are many conditions where pain persists beyond its usefulness, or where patients would benefit from inhibition of pain. Voltage-gated sodium channels are believed to play a critical role in pain signaling. This belief is based on the known roles of these channels in normal physiology, pathological states arising from mutations in sodium channel genes, preclinical work in animal models of disease, and the clinical usefulness of known sodium channel modulating agents (Cummins, T. R., Sheets, P. L., and Waxman, S. G., The roles of sodium channels in nociception: Implications for mechanisms of pain. *Pain* 131 (3), 243 (2007); England, S., Voltage-gated sodium channels: the search for subtype-selective analgesics. *Expert Opin Investig Drugs* 17 (12), 1849 (2008); Krafte, D. S. and Bannon, A. W., Sodium channels and nociception: recent concepts and therapeutic opportunities. *Curr Opin Pharmacol* 8 (1), 50 (2008)).

Voltage-gated sodium channels (NaV's) are key biological mediators of electrical signaling. NaV's are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role NaV's play in the initiation and propagation of neuronal signals, antagonists that reduce NaV currents can prevent or reduce neural signaling. Thus NaV channels are considered likely targets in pathologic states where reduced excitability is predicted to alleviate the clinical symptoms, such as pain, epilepsy, and some cardiac arrhythmias (Chahine, M., Chatelier, A., Babich, O., and Krupp, J. J., Voltage-gated sodium channels in neurological disorders. *CNS Neurol Disord Drug Targets* 7 (2), 144 (2008)).

The NaV's form a subfamily of the voltage-gated ion channel super-family and comprises 9 isoforms, designated NaV 1.1-NaV 1.9. The tissue localizations of the nine isoforms vary greatly. NaV 1.4 is the primary sodium channel of skeletal muscle, and NaV 1.5 is primary sodium channel of cardiac myocytes. NaV's 1.7, 1.8 and 1.9 are primarily localized to the peripheral nervous system, while NaV's 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), 397 (2005)).

NaV channels have been identified as the primary target for some clinically useful pharmaceutical agents that reduce pain (Cummins, T. R., Sheets, P. L., and Waxman, S. G., The roles of sodium channels in nociception: Implications for mechanisms of pain. *Pain* 131 (3), 243 (2007)). The local anesthetic drugs such as lidocaine block pain by inhibiting NaV channels. These compounds provide excellent local pain reduction but suffer the drawback of abolishing normal acute pain and sensory inputs. Systemic administration of these compounds results in dose limiting side effects that are generally ascribed to block neural channels in the CNS (nausea, sedation, confusion, ataxia). Cardiac side effects can also occur, and indeed these compounds are also used as class 1 anti-arrhythmics, presumably due to block of NaV1.5 channels in the heart. Other compounds that have proven effective at reducing pain have also been suggested to act by sodium channel blockade including carbamazepine, lamotragine, and tricyclic antidepressants (Soderpalm, B., Anticonvulsants: aspects of their mechanisms of action. *Eur J Pain* 6 Suppl A, 3 (2002); Wang, G. K., Mitchell, J., and Wang, S. Y., Block of persistent late Na+ currents by antidepressant sertraline and paroxetine. *J Membr Biol* 222 (2), 79 (2008)). These compounds are likewise dose limited by adverse effects similar to those seen with the local anesthetics. Antagonists that specifically block only the isoform(s) critical for nociception are expected to have increased efficacy since the reduction of adverse effects caused by block of off-target channels should enable higher dosing and thus more complete block of target channels isoforms.

Four NaV isoforms, NaV 1.3, 1.7, 1.8, and 1.9, have been specifically indicated as likely pain targets. NaV 1.3 is normally found in the pain sensing neurons of the dorsal root ganglia (DRG) only early in development and is lost soon after birth both in humans and in rodents. Nonetheless, nerve damaging injuries have been found to result in a return of the NaV 1.3 channels to DRG neurons and this may contribute to the abnormal pain signaling in various chronic pain conditions resulting from nerve damage (neuropathic pain). These data have led to the suggestion that pharmaceutical block of NaV 1.3 could be an effective treatment for neuropathic pain. In opposition to this idea, global genetic knockout of NaV 1.3 in mice does not prevent the development of allodynia in mouse models of neuropathic pain (Nassar, M. A. et al., Nerve injury induces robust allodynia and ectopic discharges in NaV 1.3 null mutant mice. *Mol Pain* 2, 33 (2006)). It remains unknown whether compensatory changes in other channels allow for normal neuropathic pain in NaV 1.3 knockout mice, though it has been reported that knockout of NaV 1.1 results in drastic upregulation of NaV 1.3. The converse effect in NaV 1.3 knockouts might explain these results.

NaV 1.7, 1.8, and 1.9 are highly expressed in DRG neurons, including the neurons whose axons make up the C-fibers and Aδ nerve fibers that are believed to carry most pain signals from the nociceptive terminals to the central nervous system. Like NaV 1.3, NaV 1.7 expression increases after nerve injury and may contribute to neuropathic pain states. The localization of NaV 1.7, 1.8, and 1.9 in nociceptors led to the hypothesis that reducing the sodium currents through these channels might alleviate pain.

Indeed, specific interventions that reduce the levels of these channels have proven effective in animal models of pain.

Specific reduction of NaV 1.7 in rodents by multiple different techniques has resulted in the reduction of observable pain behaviors in model animals. Injection of a viral antisense NaV 1.7 cDNA construct greatly reduces normal pain responses due to inflammation or mechanical injury (Yeomans, D. C. et al., Decrease in inflammatory hyperalgesia by herpes vector-mediated knockdown of NaV 1.7 sodium channels in primary afferents. Hum Gene Ther 16 (2), 271 (2005)). Likewise, a genetic knockout of NaV 1.7 in a subset of nociceptor neurons reduced acute and inflammatory pain in mouse models (Nassar, M. A. et al., Nociceptor-specific gene deletion reveals a major role for NaV 1.7 (PN1) in acute and inflammatory pain. Proc Natl Acad Sci USA 101 (34), 12706 (2004)). Global knockout of NaV 1.7 in mice leads to death in pups presumably due to a disruption in olfactory-guided feeding. Selective NaV1.7 ablation in both sensory and sympathetic neurons in mice prevents mechanical and thermal hypersensitivity induced by inflammation and nerve injury, and attenuates normal withdrawal responses to noxious heat (Minett, M. S. et al., Distinct Nav1.7-dependent pain sensations require different sets of sensory and sympathetic neurons. Nat Comm 3, 791 (2012)) recapitulating the pain-free phenotype of humans with NaV1.7 loss-of function mutations.

Treatments that specifically reduce NaV 1.8 channels in rodent models effectively reduce pain sensitivity. Knockdown of NaV 1.8 in rats by intrathecal injection of antisense oligodeoxynucleotides reduces neuropathic pain behaviors, while leaving acute pain sensation intact (Lai, J. et al., Inhibition of neuropathic pain by decreased expression of the tetrodotoxin-resistant sodium channel, NaV1.8. *Pain* 95 (1-2), 143 (2002); Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)). Global genetic knockout of NaV 1.8 in mice or specific destruction of NaV 1.8 expressing neurons greatly reduces perception of acute mechanical, inflammatory, and visceral pain (Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)). In contrast to the antisense experiments in rats, genetic knockout mice appear to develop neuropathic pain behaviors normally after nerve injury (Lai, J. et al., Inhibition of neuropathic pain by decreased expression of the tetrodotoxin-resistant sodium channel, NaV1.8. *Pain* 95 (1-2), 143 (2002); Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)).

NaV 1.9 global knock out mice have decreased sensitivity to inflammation induced pain, despite normal acute, and neuropathic pain behaviors (Amaya, F. et al., The voltage-gated sodium channel Na(v)1.9 is an effector of peripheral inflammatory pain hypersensitivity. *J Neurosci* 26 (50), 12852 (2006); Priest, B. T. et al., Contribution of the tetrodotoxin-resistant voltage-gated sodium channel NaV1.9 to sensory transmission and nociceptive behavior. *Proc Natl Acad Sci USA* 102 (26), 9382 (2005)). Spinal knockdown of NaV 1.9 had no apparent effect on pain behavior in rats (Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)).

The understanding of the role of NaV channels in human physiology and pathology has been greatly advanced by the discovery and analysis of naturally occurring human mutations. NaV 1.1 and NaV 1.2 mutations result in various forms of epilepsy (Fujiwara, T., Clinical spectrum of mutations in SCN1A gene: severe myoclonic epilepsy in infancy and related epilepsies. *Epilepsy Res* 70 Suppl 1, S223 (2006); George, A. L., Jr., Inherited disorders of voltage-gated sodium channels. *J Clin Invest* 115 (8), 1990 (2005); Misra, S. N., Kahlig, K. M., and George, A. L., Jr., Impaired NaV1.2 function and reduced cell surface expression in benign familial neonatal-infantile seizures. *Epilepsia* 49 (9), 1535 (2008)). Mutations of the NaV 1.4 cause muscular disorders like paramyotonia congenital (Vicart, S., Sternberg, D., Fontaine, B., and Meola, G., Human skeletal muscle sodium channelopathies. *Neurol Sci* 26 (4), 194 (2005)). NaV 1.5 mutations result in cardiac abnormalities like Brugada Syndrome and long QT syndrome (Bennett, P. B., Yazawa, K., Makita, N., and George, A. L., Jr., Molecular mechanism for an inherited cardiac arrhythmia. *Nature* 376 (6542), 683 (1995); Darbar, D. et al., Cardiac sodium channel (SCN5A) variants associated with atrial fibrillation. *Circulation* 117 (15), 1927 (2008); Wang, Q. et al., SCN5A mutations associated with an inherited cardiac arrhythmia, long QT syndrome. *Cell* 80 (5), 805 (1995)).

Recent discoveries have demonstrated that mutations in the gene that encodes the NaV 1.7 channel (SCN9A) can cause both enhanced and reduced pain syndromes. Work by Waxman's group and others have identified at least 15 mutations that result in enhanced current through NaV 1.7 and are linked to dominant congenital pain syndromes. Mutations that lower the threshold for NaV 1.7 activation cause inherited erythromelalgia (IEM). IEM patients exhibit abnormal burning pain in their extremities. Mutations that interfere with the normal inactivation properties of NaV 1.7 lead to prolonged sodium currents and cause paroxysmal extreme pain disorder (PEPD). PEPD patients exhibit periocular, perimandibular, and rectal pain symptoms that progresses throughout life (Drenth, J. P. et al., SCN9A mutations define primary erythermalgia as a neuropathic disorder of voltage gated sodium channels. *J Invest Dermatol* 124 (6), 1333 (2005); Estacion, M. et al., NaV 1.7 gain-of-function mutations as a continuum: A1632E displays physiological changes associated with erythromelalgia and paroxysmal extreme pain disorder mutations and produces symptoms of both disorders. *J Neurosci* 28 (43), 11079 (2008)).

NaV 1.7 null mutations in human patients were recently described by several groups (Ahmad, S. et al., A stop codon mutation in SCN9A causes lack of pain sensation. Hum *Mol Genet* 16 (17), 2114 (2007); Cox, J. J. et al., An SCN9A channelopathy causes congenital inability to experience pain. *Nature* 444 (7121), 894 (2006); Goldberg, Y. P. et al., Loss-of-function mutations in the NaV 1.7 gene underlie congenital indifference to pain in multiple human populations. *Clin Genet* 71 (4), 311 (2007)). In all cases patients exhibit congenital indifference to pain. These patients report no pain under any circumstances. Many of these patients suffer dire injuries early in childhood since they do not have the protective, normal pain that helps to prevent tissue damage and develop appropriate protective behaviors. Aside from the striking loss of pain sensation and reduced or absent sense of smell (Goldberg, Y. P. et al., Loss-of-function mutations in the NaV 1.7 gene underlie congenital indifference to pain in multiple human populations. *Clin Genet* 71 (4), 311 (2007)), these patients appear completely normal. Despite the normally high expression of NaV 1.7 in sympathetic neurons (Toledo-Aral, J. J. et al., Identification of PN1, a predominant voltage-dependent sodium channel expressed principally in peripheral neurons. *Proc Natl Acad Sci USA* 94 (4), 1527 (1997)) and adrenal chromatin cells (Klugbauer, N., Lacinova, L., Flockerzi, V., and Hofmann, F., Structure and functional expression of a new member of the tetrodotoxin-sensitive voltage-activated sodium channel family from human neuroendocrine cells. *EMBO J* 14 (6), 1084 (1995)), these NaV 1.7-null patients show no sign of neuroendocrine or sympathetic nervous dysfunction.

The gain of NaV 1.7 function mutations that cause pain, coupled with the loss of NaV 1.7 function mutations that abolish pain, provide strong evidence that NaV 1.7 plays an important role in human pain signaling. The relative good health of NaV 1.7-null patients indicates that ablation of NaV 1.7 is well tolerated in these patients.

Unfortunately, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

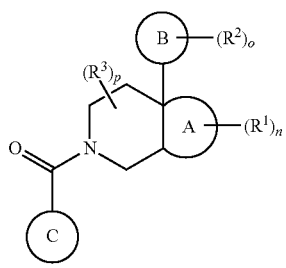

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpatic neuralgia, general neuralgias, epilepsy or epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abnormal gastro-intestinal motility.

DETAILED DESCRIPTION OF THE INVENTION

In one aspect, the invention provides compounds of formula I:

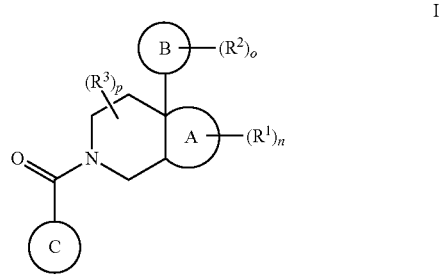

or a pharmaceutically acceptable salt thereof,
wherein, independently for each occurrence:
ring A is a fused cycloalkyl or heterocycloalkyl ring;
ring B is a substituted or unsubstituted aryl or heteroaryl ring;
ring C is a substituted or unsubstituted aryl or heteroaryl ring;
$R^1$ is C1-C6 alkyl, C1-C6 alkoxy, halo, fluoro-C1-C6 alkyl, fluoro-C1-C6 alkoxy, or oxo;
$R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$;
$R^3$ is C1-C6 alkyl, C1-C6 alkoxy, halo, CN, fluoro-C1-C6 alkyl, or fluoro-C1-C6 alkoxy;
n, o, and p are integers from 0 to 4 inclusive;
$R^7$ is H, C1-C6 alkyl, $CHF_2$, $CF_3$, or C3-C8 cycloalkyl; and
$R^8$ is H, $CF_3$, $CO_2R^7$, OH, aryl, heteroaryl, C3-C8 cycloalkyl, heterocycloalkyl, $N(R^7)_2$, $NR^7COR^7$, CON$(R^7)_2$, CN, or $SO_2R^7$.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. The phrase "optionally substituted" is used interchangeably with the phrase "substituted or unsubstituted." As described herein, the variables in formula I encompass specific groups, such as, for example, alkyl or cycloalkyl. Unless otherwise noted, each of the specific groups for the variables can be optionally substituted with one or more substituents of halo, cyano, oxoalkoxy, hydroxy, amino, nitro, aryl, haloalkyl, and alkyl. For instance, an alkyl group can be optionally substituted with one or more of halo, cyano, oxoalkoxy, hydroxy, amino, nitro, aryl, haloalkyl, and alkyl. As an additional example, an aryl group can be optionally substituted with one or more of halo, cyano, alkoxy, hydroxy, nitro, haloalkyl, and alkyl. As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The term "aliphatic", "aliphatic group" or "alkyl" as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" or "cycloalkyl" mean a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

Unless otherwise specified, the term "heterocycle", "heterocyclyl", "heterocycloaliphatic", "heterocycloalkyl" or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", "heterocycloaliphatic", "heterocycloalkyl" or "heterocyclic" group has three to fourteen ring atoms in which one or more ring atoms is a heteroatom independently selected from oxygen, sulfur, nitrogen, or phosphorus, and each ring in the ring system contains 3 to 7 ring atoms.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N,N-disubstituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl," "arylkyl," "aralkoxy," "arylkoxy," or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring atoms, wherein at least one ring in the system is aromatic, at least one ring in the system contains one or more heteroatoms, and wherein each ring in the system contains 3 to 7 ring atoms. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and cis and trans conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Thus, included within the scope of the invention are tautomers of compounds of formula I.

Additionally, unless otherwise stated, structures depicted herein are also meant to include compounds that differ only in the presence of one or more isotopically enriched atoms.

For example, compounds of formula I, wherein one or more hydrogen atoms are replaced with deuterium or tritium, or one or more carbon atoms are replaced by a $^{13}C$- or $^{14}C$-enriched carbon are within the scope of this invention. Such compounds are useful, for example, as analytical tools, probes in biological assays, or sodium channel blockers with an improved therapeutic profile.

In one embodiment, the invention features compounds of formula I wherein ring A is a fused cycloalkyl ring, ring B is an aryl ring and ring C is a substituted or unsubstituted aryl; $R^1$ is C1-C6 alkyl, C1-C6 alkoxy, halo, fluoro-C1-C6 alkyl, fluoro-C1-C6 alkoxy, or oxo; $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; $R^3$ is C1-C6 alkyl, C1-C6 alkoxy, halo, CN, fluoro-C1-C6 alkyl, or fluoro-C1-C6 alkoxy; n, o, and p are integers from 0 to 4 inclusive; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$. In another embodiment, $R^1$ is C1-C6 alkyl, halo, or oxo. In yet another embodiment, $R^1$ is $CH_3$, F, or oxo. In another embodiment, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. More specifically, $R^2$ is $CH_3$, $OCH_3$, $CF_3$, F, Cl, Br, CN, $OCH_2CH_2OtBu$, $OCH_2CH(CH_3)_2$. In a further embodiment, $R^3$ is C1-C6 alkyl. In a further embodiment, $R^3$ is $CH_3$.

In some embodiments, ring A is

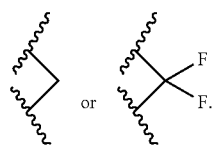

In other embodiments, ring B is

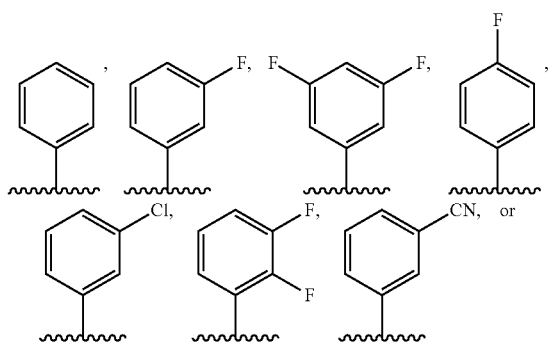

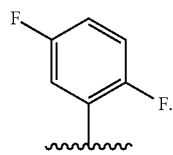

In one embodiment, ring C is

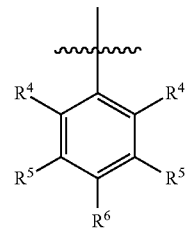

wherein $R^4$ is H, C1-C6 alkyl, C1-C6 alkoxy, halo, CN, or OH; $R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-C6 alkyl, or fluoro-C1-C6 alkoxy; $R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$.

In a further embodiment, two occurrences of $R^4$ and $R^5$, or $R^5$ and $R^6$ together with the carbons to which they are attached form an optionally substituted ring comprising up to 2 heteroatoms.

In a further embodiment, $R^4$ is H, C1-C6 alkoxy, or halo. $R^4$ may also be H, $OCH_3$, or F. In one embodiment, $R^5$ is H, C1-C6 alkyl, C1-C6 alkoxy, halo, CN, OH, or fluoro-C1-C6 alkyl. In another embodiment, $R^5$ is H, $CH_3$, $OCH_3$, F, Cl, CN, OH, or $CF_3$. In certain embodiments, $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$. In some embodiments, $R^6$ is H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CHO_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$,

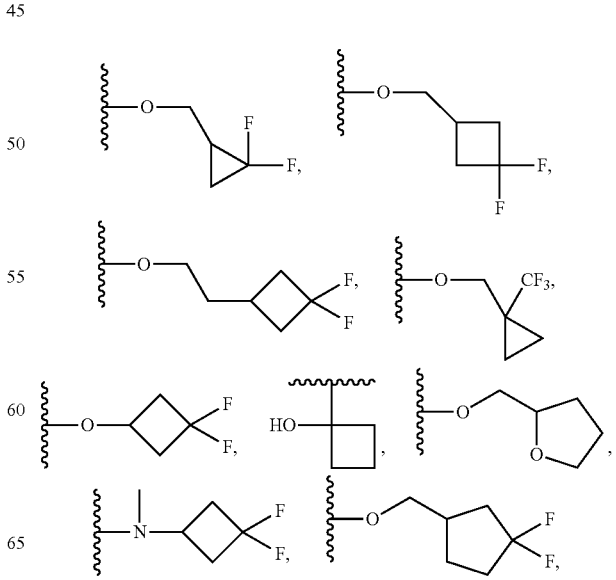

-continued

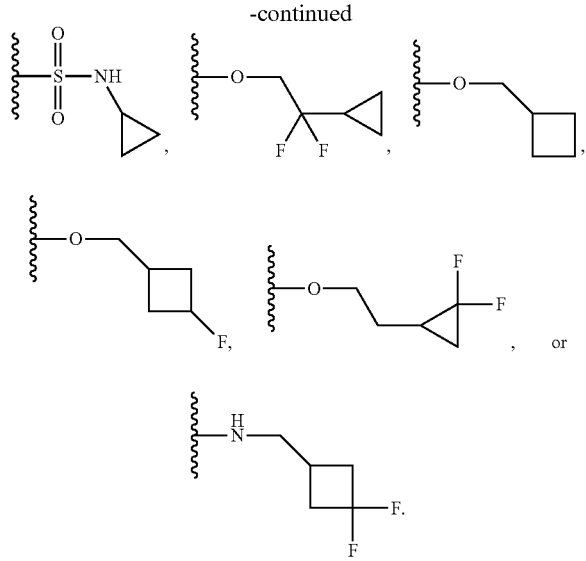

In one embodiment, $R^4$ and $R^5$ together with the carbons to which they are attached may also form an optionally substituted ring comprising up to 2 heteroatoms.

In another embodiment, ring C is

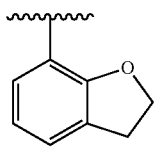

In further embodiments, $R^5$ and $R^6$ together with the carbons to which they are attached form an optionally substituted ring comprising up to 2 heteroatoms.

In one embodiment, ring C is

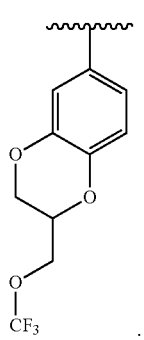 [SMILES: *c1ccc2c(c1)OCC(COC(F)(F)F)O2]

In another embodiment, the invention features compounds of formula I wherein ring A is a fused cycloalkyl ring, ring B is an aryl ring and ring C is a substituted or unsubstituted heteroaryl; $R^1$ is C1-C6 alkyl, C1-C6 alkoxy, halo, fluoro-C1-C6 alkyl, fluoro-C1-C6 alkoxy, or oxo; $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; $R^3$ is C1-C6 alkyl, C1-C6 alkoxy, halo, CN, fluoro-C1-C6 alkyl, or fluoro-C1-C6 alkoxy; n, o, and p are integers from 0 to 4 inclusive; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$. In another embodiment, $R^1$ is C1-C6 alkyl, halo, or oxo. In yet another embodiment, $R^1$ is $CH_3$, F, or oxo. In another embodiment, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. More specifically, $R^2$ is $CH_3$, $OCH_3$, $CF_3$, F, Cl, Br, CN, $OCH_2CH_2OtBu$, $OCH_2CH(CH_3)_2$. In a further embodiment, $R^3$ is C1-C6 alkyl. In a further embodiment, $R^3$ is $CH_3$. In some embodiments, ring A is

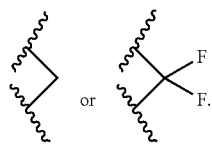

In other embodiments, ring B is

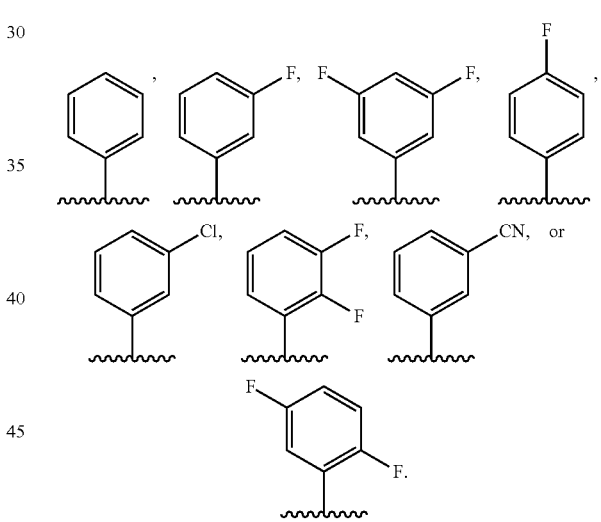

In some embodiments, ring C is a pyridyl or quinoline ring. In a further embodiment, ring C is selected from:

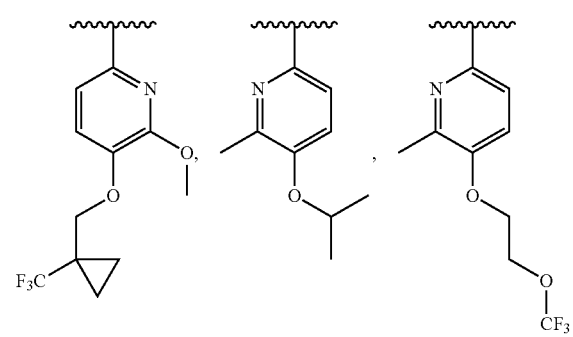

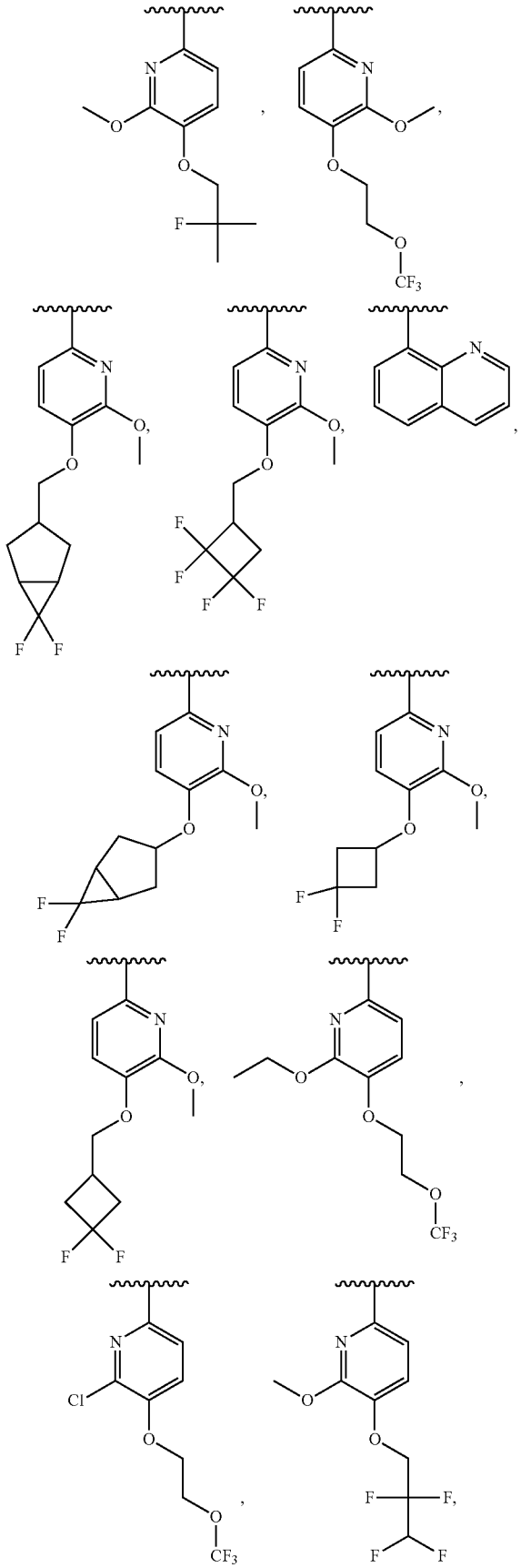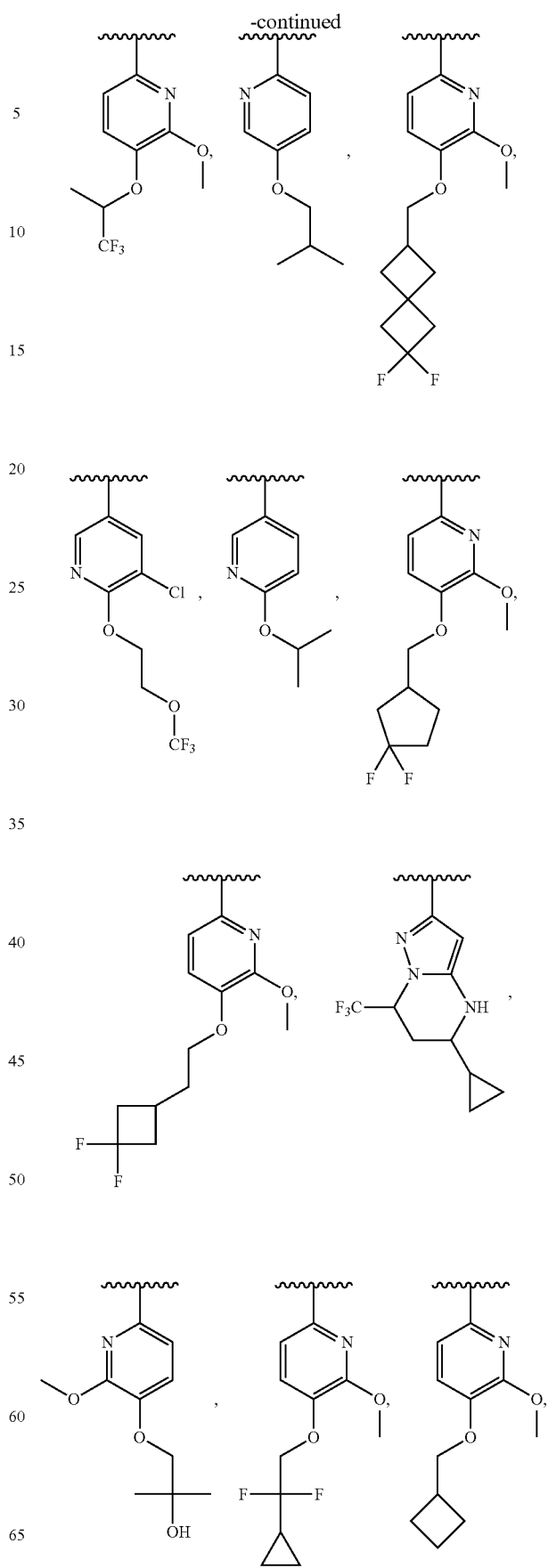

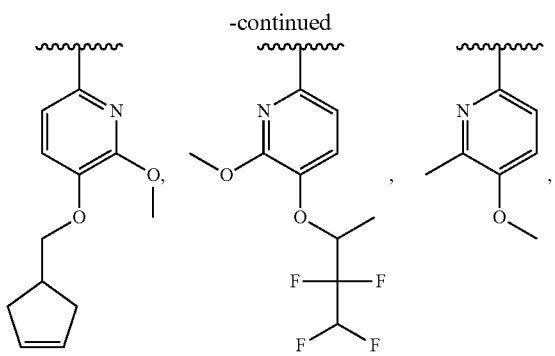

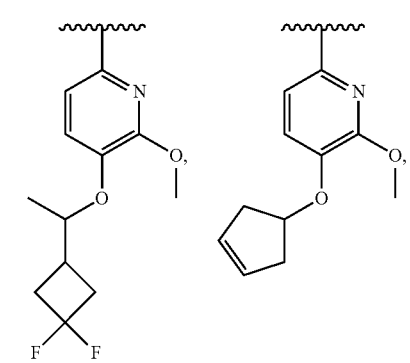

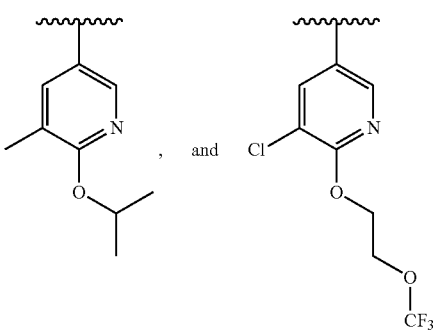

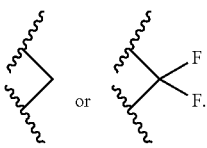

In one embodiment, ring B is a pyridyl, thiazole, pyrimidine, pyrazole, furan, thiophene, pyrrole, oxazole, imidazole, isoxazole, isothiazole, pyridazine, or pyrazine ring. In another embodiment, ring B is

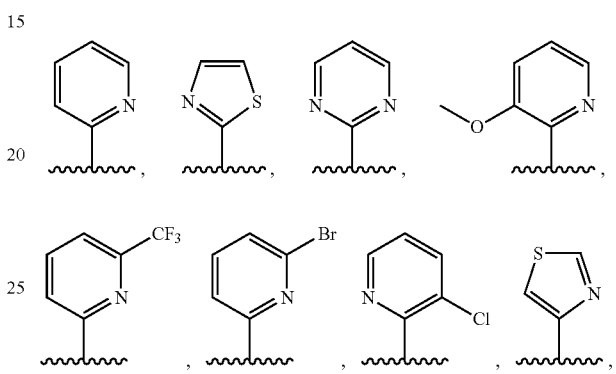

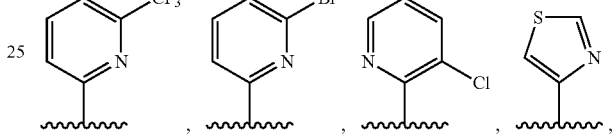

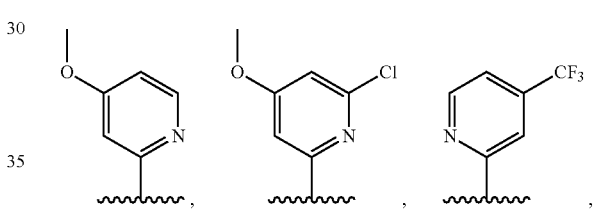

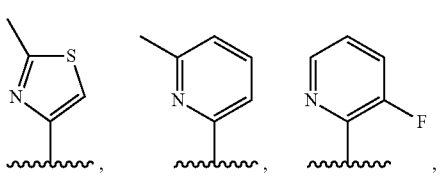

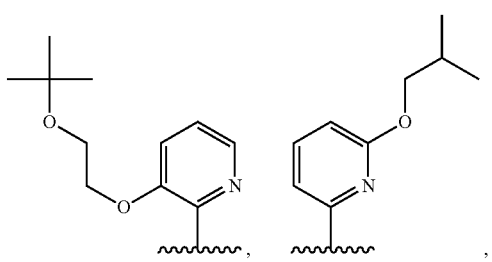

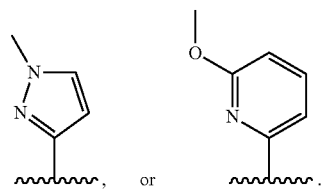

In another embodiment, the invention features compounds of formula I wherein ring A is a fused cycloalkyl ring, ring B is a heteroaryl ring and ring C is a substituted or unsubstituted aryl; $R^1$ is C1-C6 alkyl, C1-C6 alkoxy, halo, fluoro-C1-C6 alkyl, fluoro-C1-C6 alkoxy, or oxo; $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; $R^3$ is C1-C6 alkyl, C1-C6 alkoxy, halo, CN, fluoro-C1-C6 alkyl, or fluoro-C1-C6 alkoxy; n, o, and p are integers from 0 to 4 inclusive; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$. In another embodiment, $R^1$ is C1-C6 alkyl, halo, or oxo. In yet another embodiment, $R^1$ is $CH_3$, F, or oxo. In another embodiment, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. More specifically, $R^2$ is $CH_3$, $OCH_3$, $CF_3$, F, Cl, Br, CN, $OCH_2CH_2OtBu$, $OCH_2CH(CH_3)_2$. In a further embodiment, $R^3$ is C1-C6 alkyl. In further embodiment, $R^3$ is $CH_3$. In some embodiments, ring A is In one embodiment, ring C is

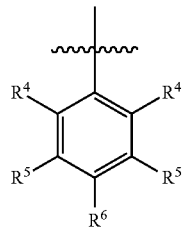

wherein $R^4$ is H, C1-C6 alkyl, C1-C6 alkoxy, halo, CN, or OH; $R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-C6 alkyl, or fluoro-C1-C6 alkoxy; $R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$.

In a further embodiment, two occurrences of $R^4$ and $R^5$, or $R^5$ and $R^6$ together with the carbons to which they are attached form an optionally substituted ring comprising up to 2 heteroatoms.

In a further embodiment, $R^4$ is H, C1-C6 alkoxy, or halo. $R^4$ may also be H, $OCH_3$, or F. In one embodiment, $R^5$ is H, C1-C6 alkyl, C1-C6 alkoxy, halo, CN, OH, or fluoro-C1-C6 alkyl. In another embodiment, $R^5$ is H, $CH_3$, $OCH_3$, F, Cl, CN, OH, or $CF_3$. In certain embodiments, $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$. In some embodiments, $R^6$ is H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$,

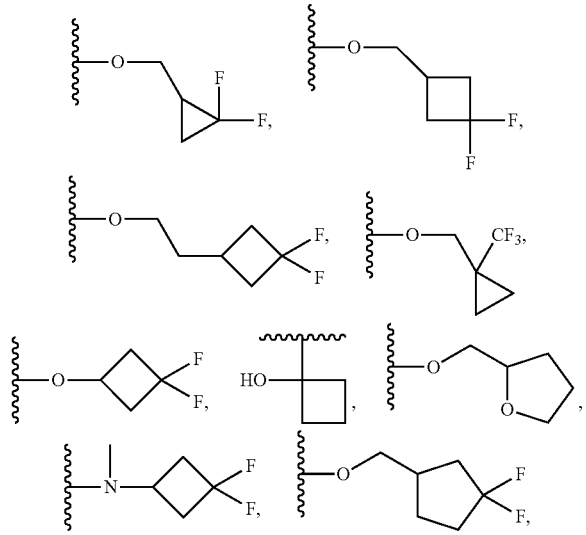

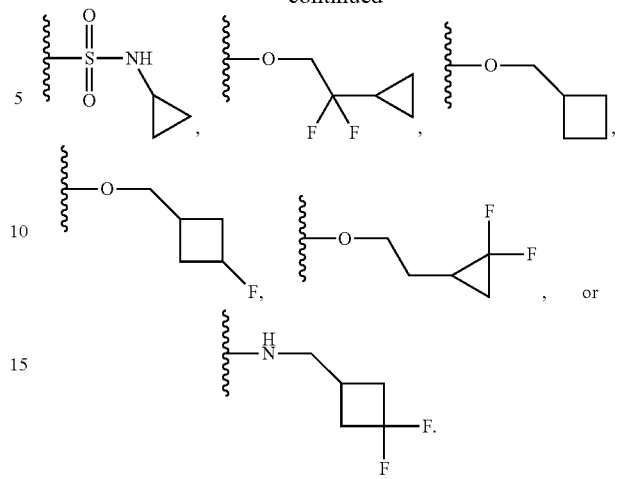

In one embodiment, $R^4$ and $R^5$ together with the carbons to which they are attached may also form an optionally substituted ring comprising up to 2 heteroatoms.

In another embodiment, ring C is

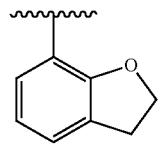

In further embodiments, $R^5$ and $R^6$ together with the carbons to which they are attached form an optionally substituted ring comprising up to 2 heteroatoms. In one embodiment, ring C is

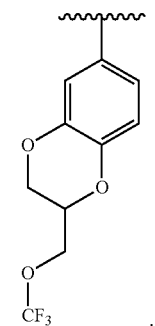

In another embodiment, the invention features compounds of formula I wherein ring A is a fused heterocycloalkyl ring, ring B is an aryl ring and ring C is a substituted or unsubstituted aryl; $R^1$ is C1-C6 alkyl, C1-C6 alkoxy, halo, fluoro-C1-C6 alkyl, fluoro-C1-C6 alkoxy, or oxo; $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; $R^3$ is C1-C6 alkyl, C1-C6 alkoxy, halo, CN, fluoro-C1-C6 alkyl, or fluoro-C1-C6 alkoxy; n, o, and p are integers from 0 to 4 inclusive; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$. In another embodiment, $R^1$ is C1-C6 alkyl, halo, or oxo. In yet another embodiment, $R^1$ is $CH_3$, F, or oxo. In another embodiment, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. More specifically, $R^2$ is $CH_3$, $OCH_3$, $CF_3$, F, Cl, Br, CN, $OCH_2CH_2OtBu$, $OCH_2CH(CH_3)_2$. In a further embodiment, $R^3$ is C1-C6 alkyl. In further embodiment, $R^3$ is $CH_3$.

In some embodiments, ring A is

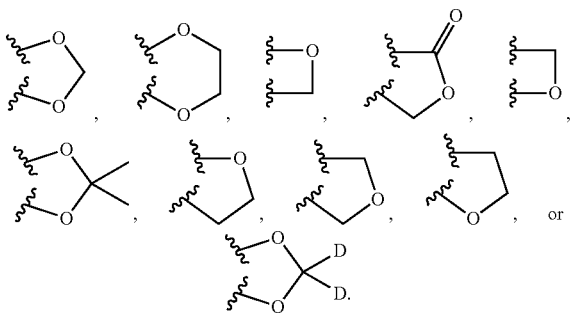

In some embodiments, ring B is

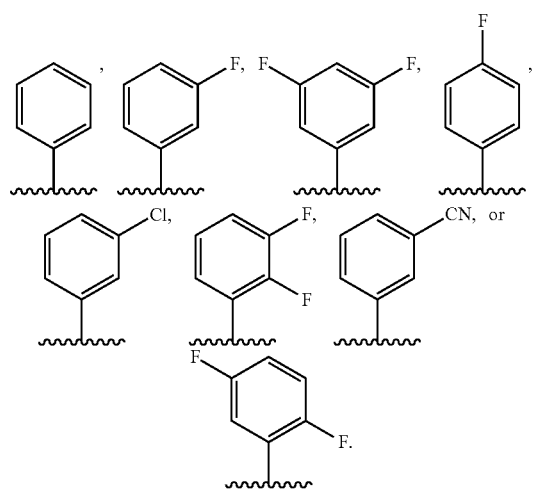

In one embodiment, ring C is

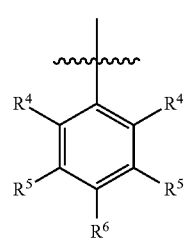

wherein $R^4$ is H, C1-C6 alkyl, C1-C6 alkoxy, halo, CN, or OH; $R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-C6 alkyl, or fluoro-C1-C6 alkoxy; $R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$.

In a further embodiment, two occurrences of $R^4$ and $R^5$, or $R^5$ and $R^6$ together with the carbons to which they are attached form an optionally substituted ring comprising up to 2 heteroatoms.

In a further embodiment, $R^4$ is H, C1-C6 alkoxy, or halo. $R^4$ may also be H, $OCH_3$, or F. In one embodiment, $R^5$ is H, C1-C6 alkyl, C1-C6 alkoxy, halo, CN, OH, or fluoro-C1-C6 alkyl. In another embodiment, $R^5$ is H, $CH_3$, $OCH_3$, F, Cl, CN, OH, or $CF_3$. In certain embodiments, $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$. In some embodiments, $R^6$ is H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$,

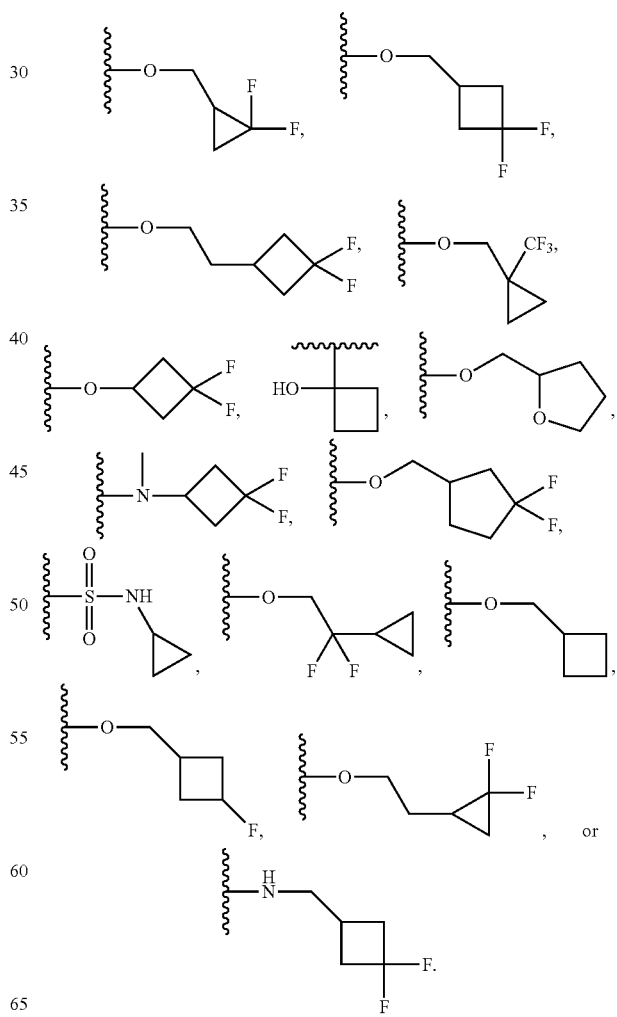

In another embodiment, $R^4$ and $R^5$ together with the carbons to which they are attached may also form an optionally substituted ring comprising up to 2 heteroatoms.

In another embodiment, ring C is

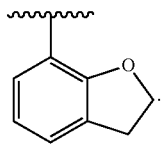 [SMILES: *c1cccc2c1OCC2]

In further embodiments, $R^5$ and $R^6$ together with the carbons to which they are attached form an optionally substituted ring comprising up to 2 heteroatoms.

In one embodiment, ring C is

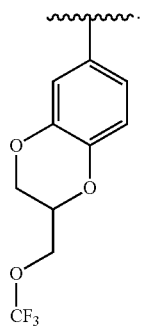 [SMILES: *c1ccc2c(c1)OCC(COC(F)(F)F)O2]

In another embodiment, the invention features compounds of formula I wherein ring A is a fused heterocycloalkyl ring, ring B is an aryl ring and ring C is a substituted or unsubstituted heteroaryl; $R^1$ is C1-C6 alkyl, C1-C6 alkoxy, halo, fluoro-C1-C6 alkyl, fluoro-C1-C6 alkoxy, or oxo; $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; $R^3$ is C1-C6 alkyl, C1-C6 alkoxy, halo, CN, fluoro-C1-C6 alkyl, or fluoro-C1-C6 alkoxy; n, o, and p are integers from 0 to 4 inclusive; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$. In another embodiment, $R^1$ is C1-C6 alkyl, halo, or oxo. In yet another embodiment, $R^1$ is $CH_3$, F, or oxo. In another embodiment, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. More specifically, $R^2$ is $CH_3$, $OCH_3$, $CF_3$, F, Cl, Br, CN, $OCH_2CH_2OtBu$, $OCH_2CH(CH_3)_2$. In a further embodiment, $R^3$ is C1-C6 alkyl. In further embodiment, $R^3$ is $CH_3$. In some embodiments, ring A is

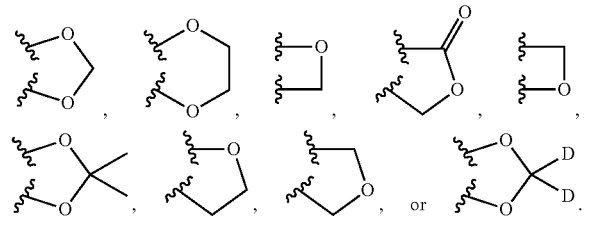

In some embodiments, ring B is

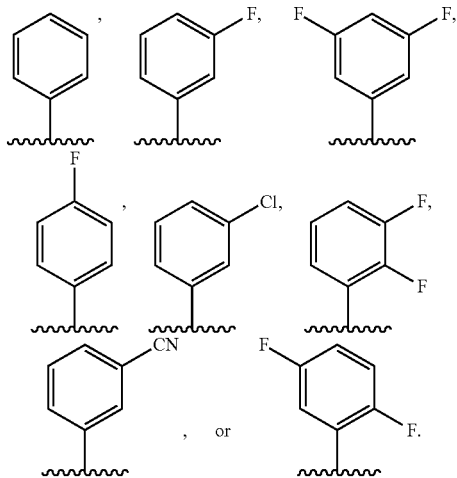

In some embodiments, ring C is a pyridyl, pyrazolopiperidine, or quinolone ring. In a further embodiment, ring C is selected from:

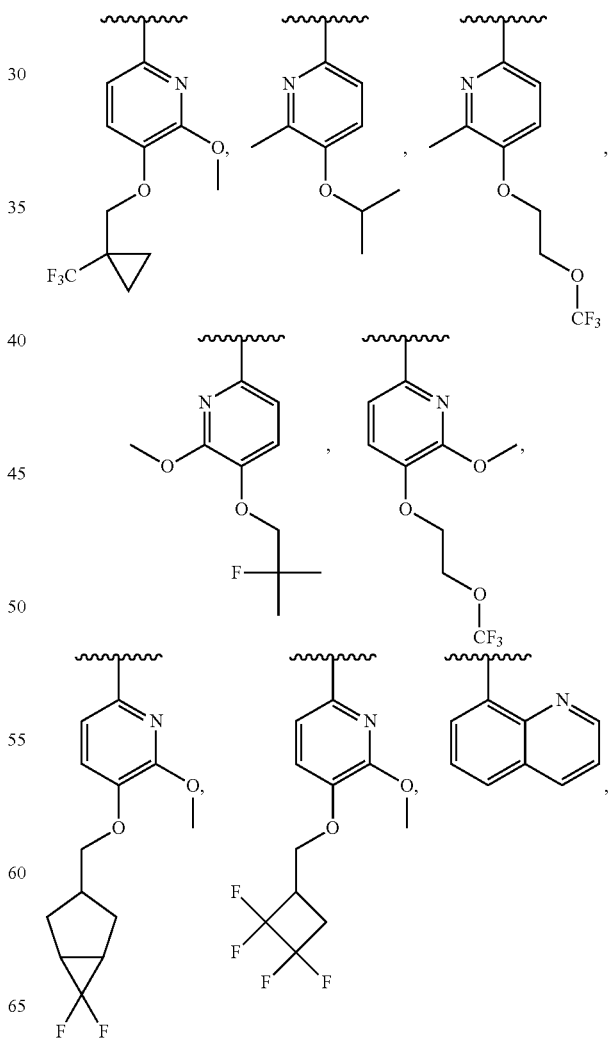

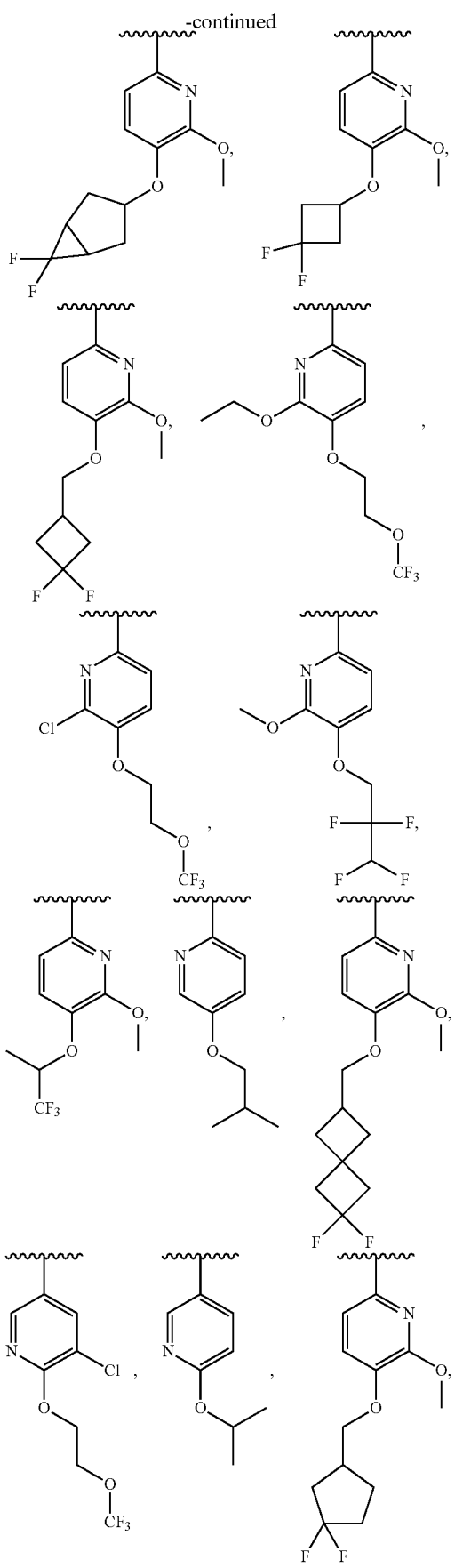
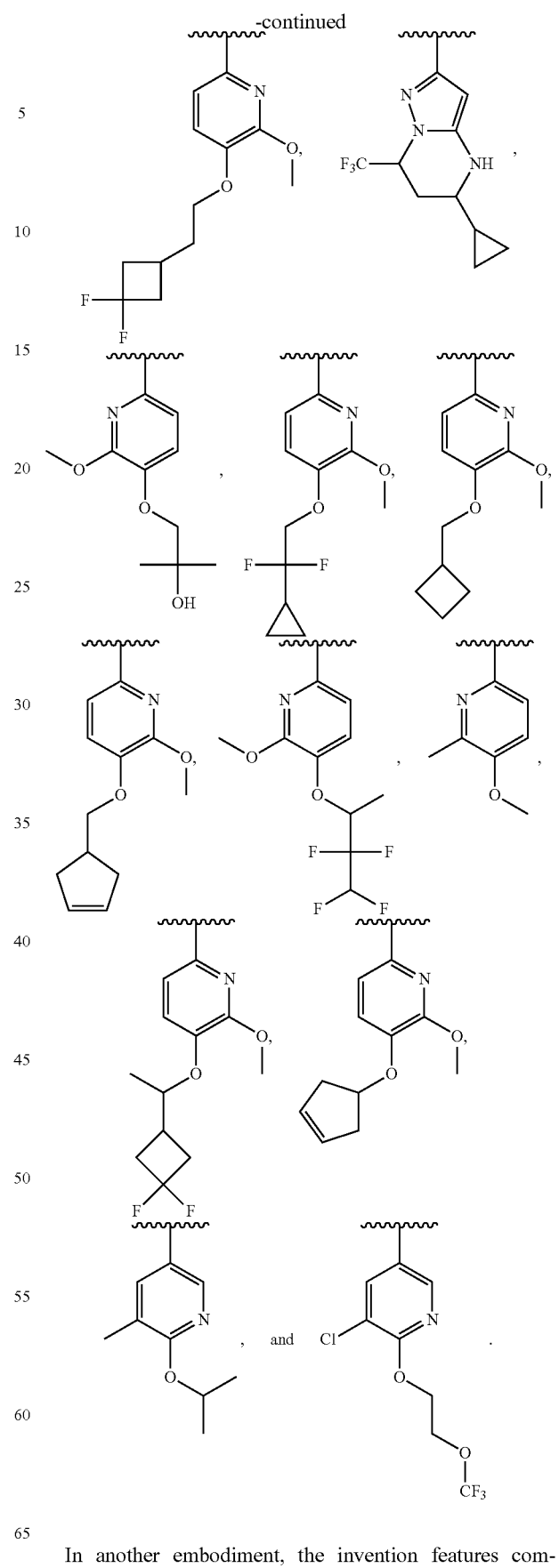
In another embodiment, the invention features compounds of formula I wherein ring A is a fused heterocycloalkyl ring, ring B is a heteroaryl ring and ring C is a substituted or unsubstituted aryl; $R^1$ is C1-C6 alkyl, C1-C6 alkoxy, halo, fluoro-C1-C6 alkyl, fluoro-C1-C6 alkoxy, or oxo; $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; $R^3$ is C1-C6 alkyl, C1-C6 alkoxy, halo, CN, fluoro-C1-C6 alkyl, or fluoro-C1-C6 alkoxy; n, o, and p are integers from 0 to 4 inclusive; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$. In another embodiment, $R^1$ is C1-C6 alkyl, halo, or oxo. In yet another embodiment, $R^1$ is $CH_3$, F, or oxo. In another embodiment, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. More specifically, $R^2$ is $CH_3$, $OCH_3$, $CF_3$, F, Cl, Br, CN, $OCH_2CH_2OtBu$, $OCH_2CH(CH_3)_2$. In a further embodiment, $R^3$ is C1-C6 alkyl. In further embodiment, $R^3$ is $CH_3$. In some embodiments, ring A is

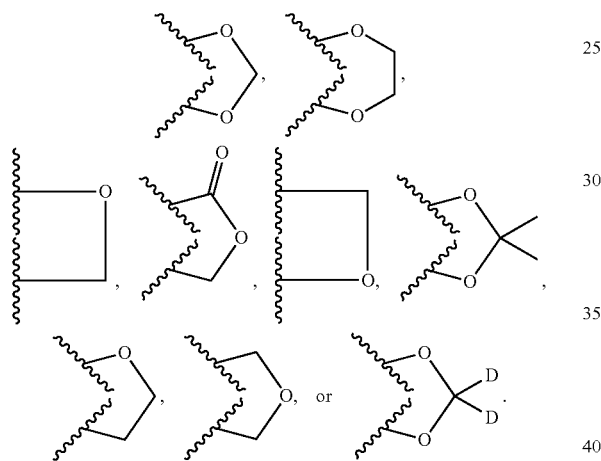

In one embodiment, ring B is a pyridyl, thiazole, pyrimidine, pyrazole, furan, thiophene, pyrrole, oxazole, imidazole, isoxazole, isothiazole, pyridazine, or pyrazine ring. In another embodiment, ring B is

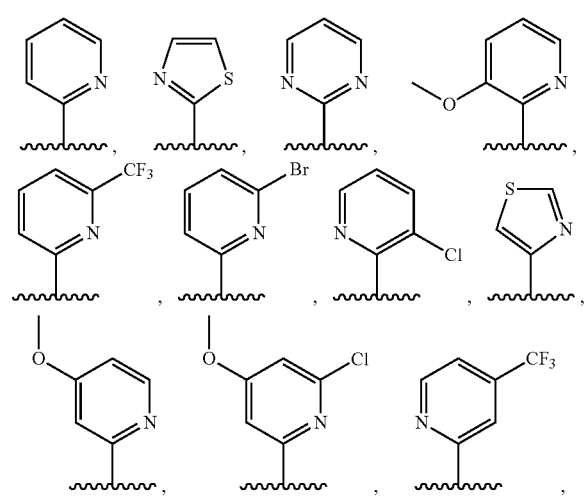

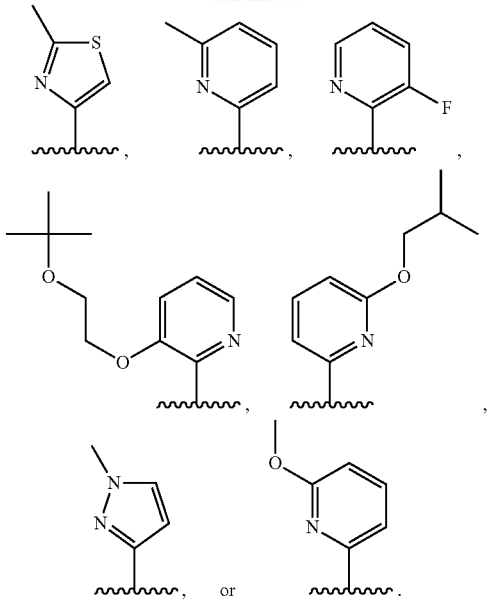

In one embodiment, ring C is

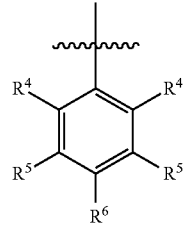

wherein $R^4$ is H, C1-C6 alkyl, C1-C6 alkoxy, halo, CN, or OH; $R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-C6 alkyl, or fluoro-C1-C6 alkoxy; $R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$.

In a further embodiment, two occurrences of $R^4$ and $R^5$, or $R^5$ and $R^6$ together with the carbons to which they are attached form an optionally substituted ring comprising up to 2 heteroatoms.

In a further embodiment, $R^4$ is H, C1-C6 alkoxy, or halo. $R^4$ may also be H, $OCH_3$, or F. In one embodiment, $R^5$ is H, C1-C6 alkyl, C1-C6 alkoxy, halo, CN, OH, or fluoro-C1-C6 alkyl. In another embodiment, $R^5$ is H, $CH_3$, $OCH_3$, F, Cl, CN, OH, or $CF_3$. In certain embodiments, $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$. In some embodiments, $R^6$ is H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, OCH₂CH₂OCF₃, OCH(CH₃)CF₂CHF₂, SO₂CHF₂, OCH₂CF₂CH₃, OCH₂CH₂OCH₂CF₃, OCH₂CF₃, OCH₂C(CH₃)₃, OCH₂CH(CH₃)CH₂CF₃, SO₂CH₂CH₃, OCH(CH₃)CH₂CF₃, OCH₂CF₂CHF₂,

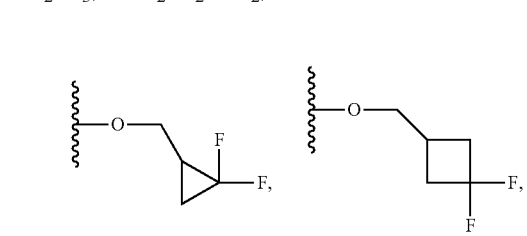

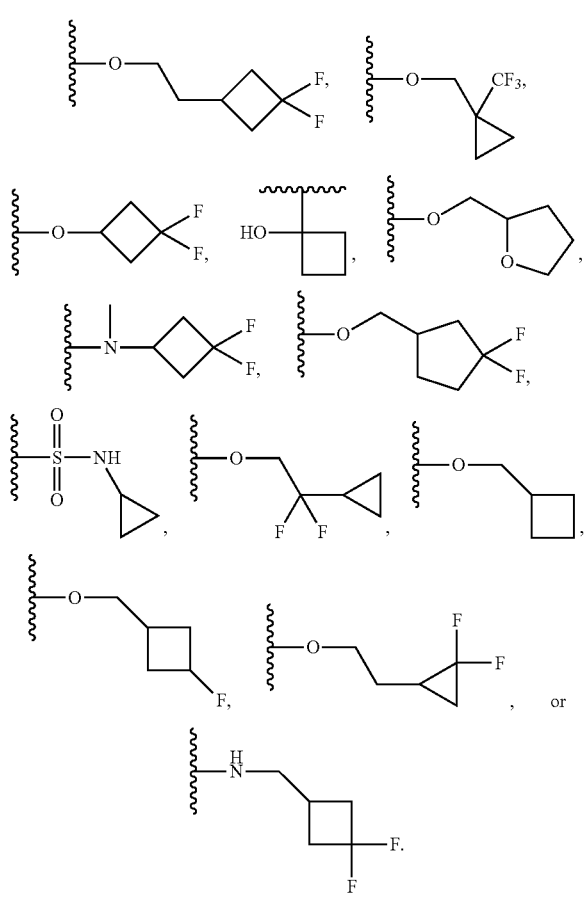

In one embodiment, $R^4$ and $R^5$ together with the carbons to which they are attached may also form an optionally substituted ring comprising up to 2 heteroatoms.

In another embodiment, ring C is

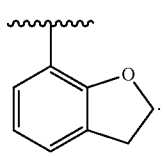 [SMILES: *c1cccc2c1OCC2]

In further embodiments, $R^5$ and $R^6$ together with the carbons to which they are attached form an optionally substituted ring comprising up to 2 heteroatoms. In one embodiment, ring C is

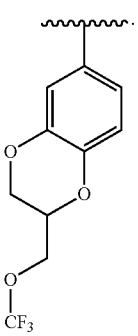

In one embodiment, the compound has formula IA:

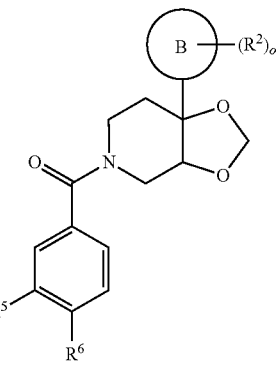

IA or a pharmaceutically acceptable salt thereof, wherein, independently for each occurrence, ring B is an aryl or heteroaryl ring; $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two CH₂ units may be replaced with O, CO, CF₂, or $NR^7$; o is an integer from 0 to 4 inclusive; $R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-C6 alkyl, or fluoro-C1-C6 alkoxy; $R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three CH₂ units may be replaced with O, CO, S, SO, $SO_2$, or $NR^7$; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$.

In some embodiments, ring B is an aryl ring. In one embodiment, $R^2$ is C1-C6 alkyl, C1-C6 alkoxy, fluoro-C1-C6 alkyl, halo, CN, or (C1-C8)-$R^8$ wherein up to two CH₂ units may be replaced with O, CO, CF₂, or $NR^7$. In another embodiment, $R^2$ is $CH_3$, $OCH_3$, $CF_3$, F, Cl, Br, CN, $OCH_2CH_2OtBu$, $OCH_2CH(CH_3)_2$. In a further embodiment, ring B is a phenyl ring.

In certain embodiments, ring B is

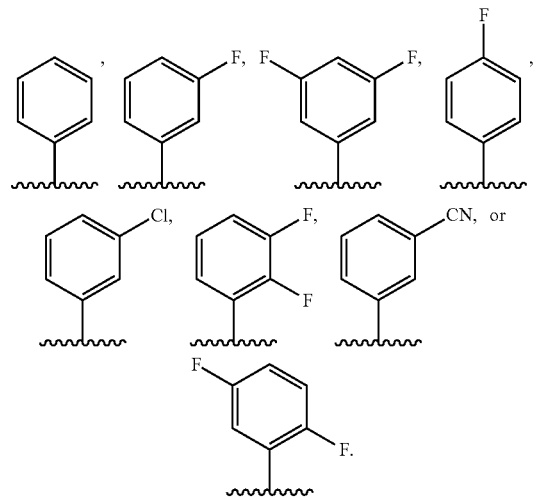

In certain embodiments, $R^5$ is H, C1-C6 alkyl, C1-C6 alkoxy, halo, CN, OH, or fluoro-C1-C6 alkyl. In others, $R^5$ is H, $CH_3$, $OCH_3$, F, Cl, CN, OH, or $CF_3$. Yet in others, $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$. $R^6$ may also be H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$, In one embodiment,

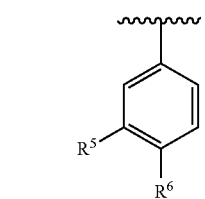

of compound of formula IA is selected from:

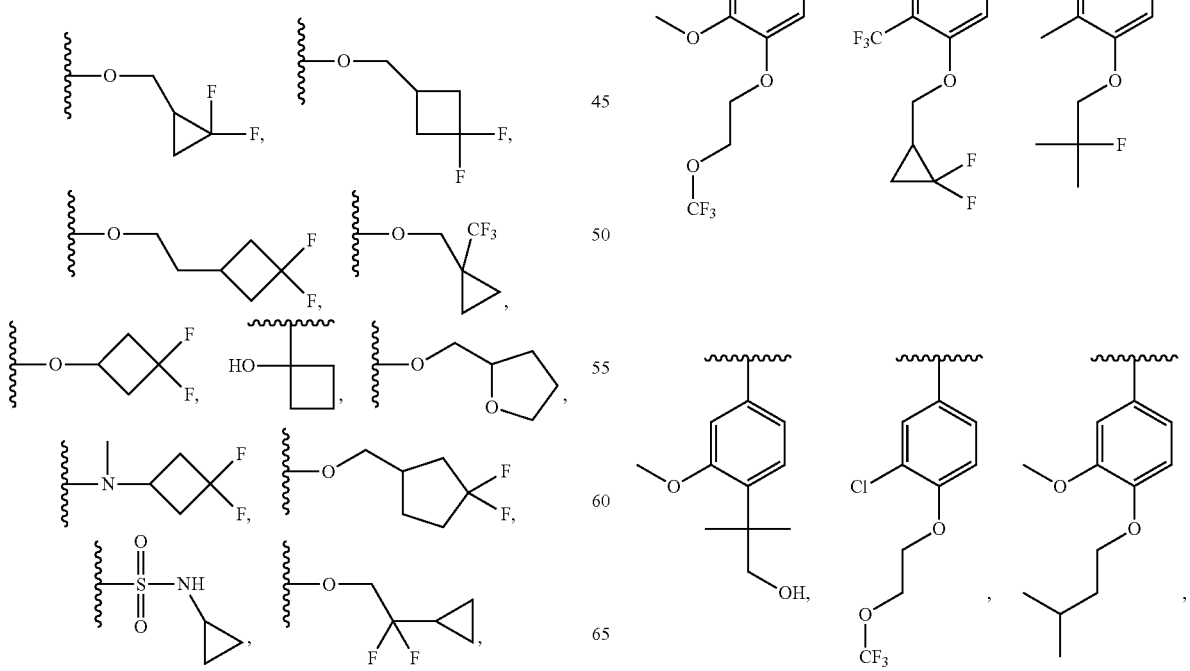

-continued
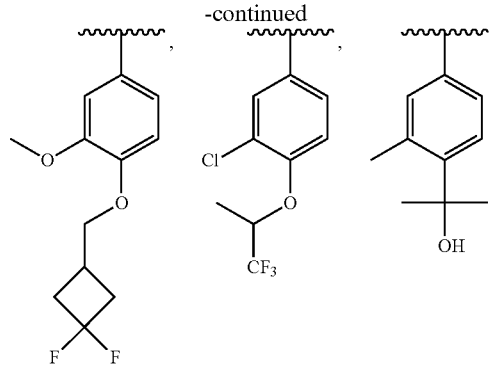
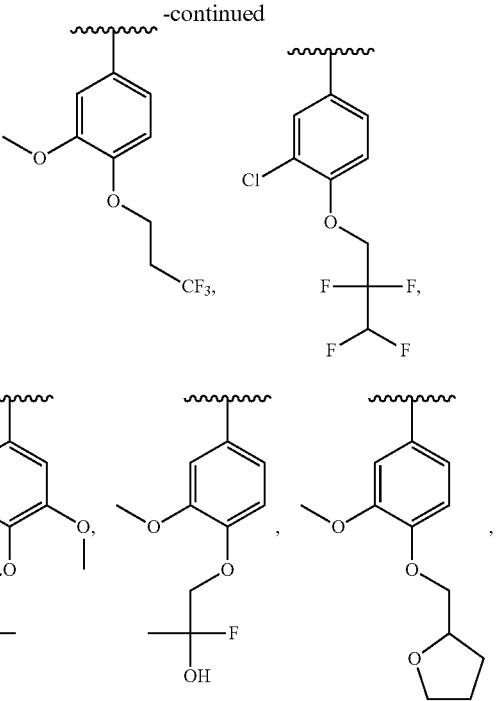
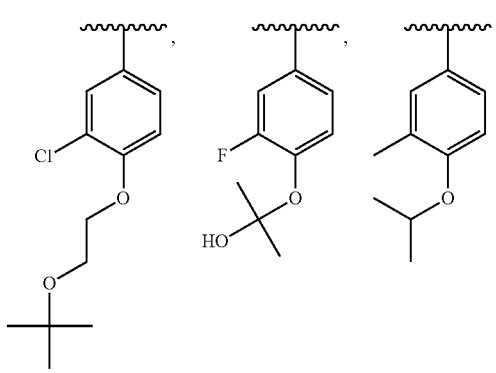
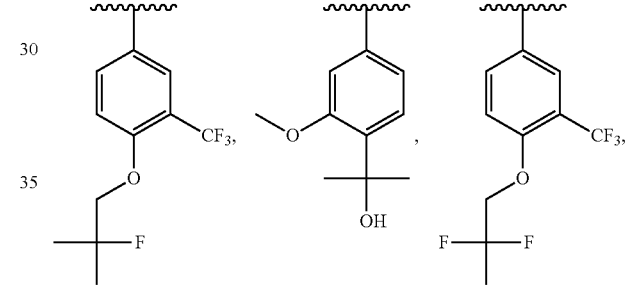
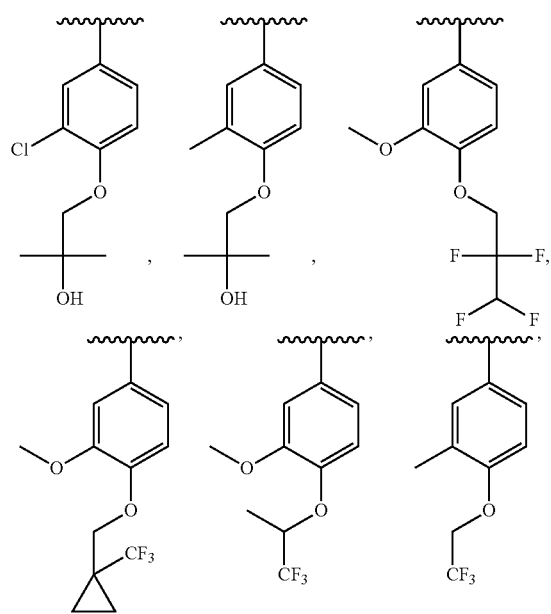
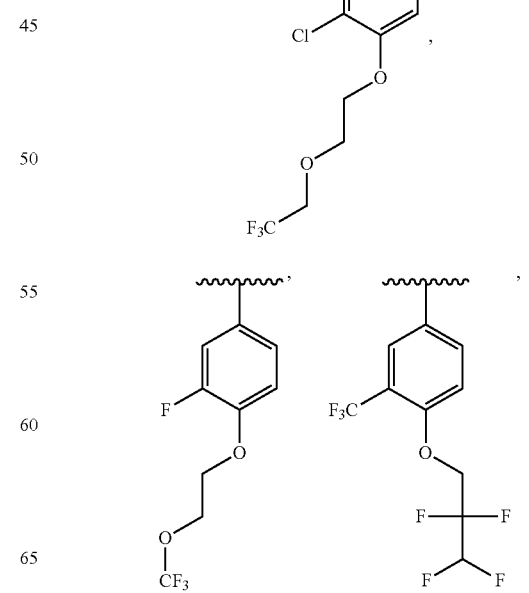

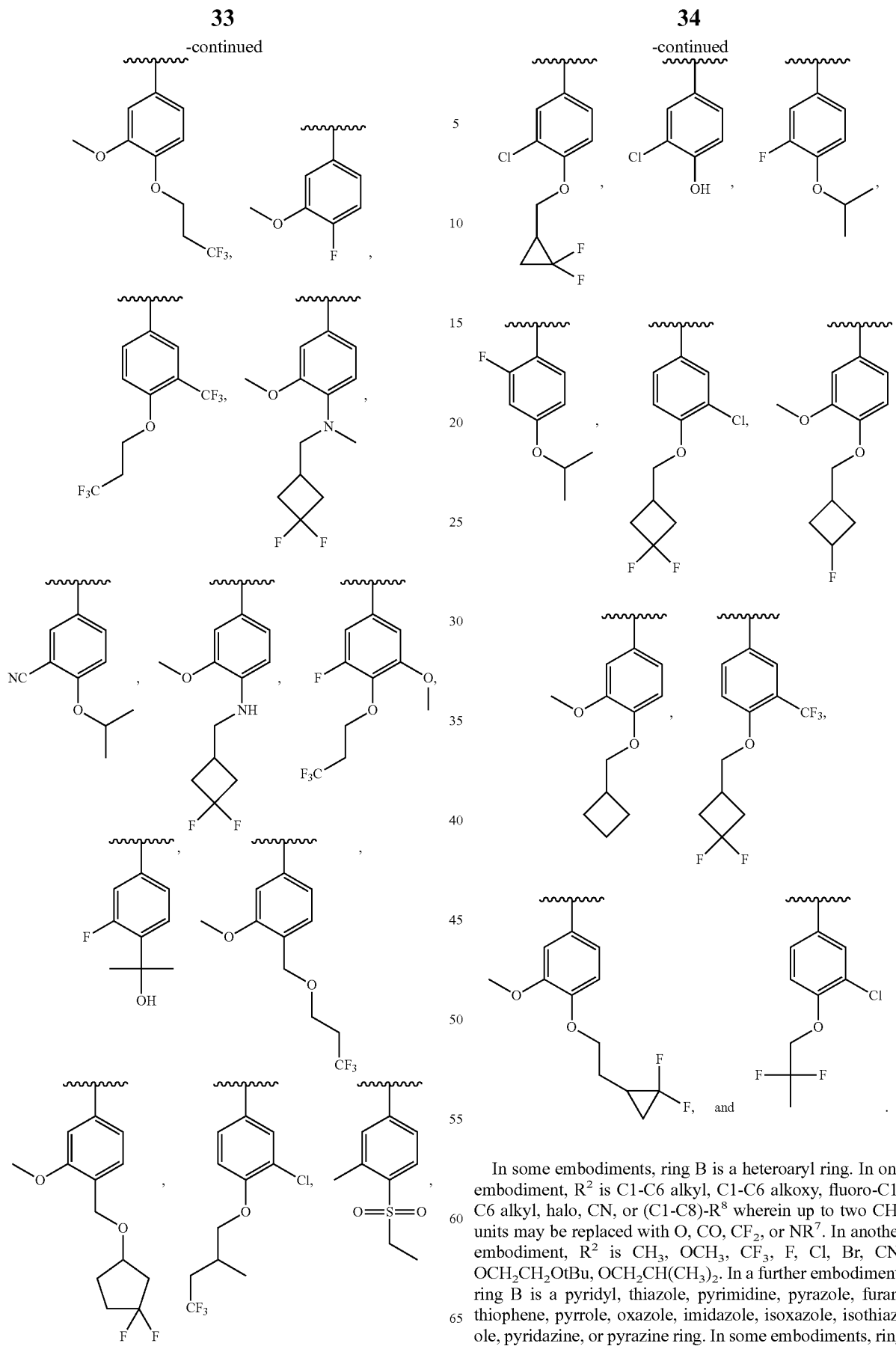

In some embodiments, ring B is a heteroaryl ring. In one embodiment, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. In another embodiment, $R^2$ is $CH_3$, $OCH_3$, $CF_3$, F, Cl, Br, CN, $OCH_2CH_2OtBu$, $OCH_2CH(CH_3)_2$. In a further embodiment, ring B is a pyridyl, thiazole, pyrimidine, pyrazole, furan, thiophene, pyrrole, oxazole, imidazole, isoxazole, isothiazole, pyridazine, or pyrazine ring. In some embodiments, ring B is

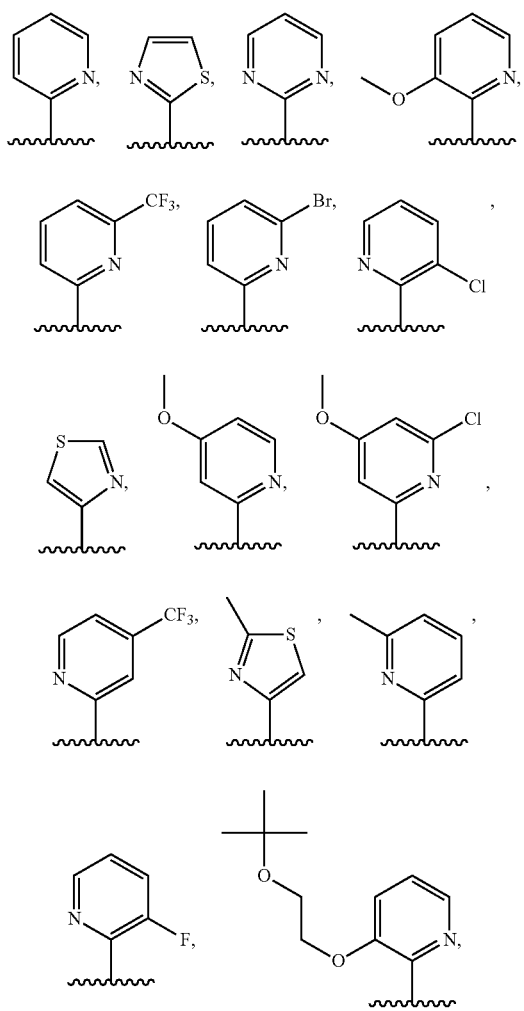

In certain embodiments, $R^5$ is H, C1-C6 alkyl, C1-C6 alkoxy, halo, CN, OH, or fluoro-C1-C6 alkyl. In others, $R^5$ is H, $CH_3$, $OCH_3$, F, Cl, CN, OH, or $CF_3$. Yet in others, $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$. $R^6$ may also be H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$, In certain embodiments, the compound has formula IB:

or a pharmaceutically acceptable salt thereof, wherein, independently for each occurrence, $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; o is an integer from 0 to 4 inclusive; $R^5$ is H, C1-C6 alkyl, C1-C6 alkoxy, halo, CN, OH, $OR^7$, N(R⁷)₂, NR⁷SO₂R⁷, SO₂R⁷, CO₂R⁷, SO₂N(R⁷)₂, fluoro-C1-C6 alkyl, or fluoro-C1-C6 alkoxy; R⁶ is H, C1-C6 alkyl, C3-C8 cycloalkyl, C1-C6 alkoxy, halo, CN, OH, OR⁷, N(R⁷)₂, NR⁷SO₂R⁷, SR⁷, SOR⁷, SO₂R⁷, CO₂R⁷, NR⁷COR⁷, NR⁷CO₂R⁷, CON(R⁷)₂, SO₂N(R⁷)₂, CF₃, OCF₃, OCHF₂, heterocycloalkyl, aryl, heteroaryl, or a straight chain, branched, or cyclic (C1-C8)-R⁸ or fluoro-(C1-C8)-R⁸ wherein up to three CH₂ units may be replaced with O, CO, S, SO, SO₂, or NR⁷; R⁷ is H, C1-C6 alkyl, CHF₂, CF₃, or C3-C8 cycloalkyl and R⁸ is H, CF₃, CO₂R⁷, OH, aryl, heteroaryl, C3-C8 cycloalkyl, heterocycloalkyl, N(R⁷)₂, NR⁷COR⁷, CON(R⁷)₂, CN, or SO₂R⁷. In further embodiments, R² is C1-C6 alkyl, C1-C6 alkoxy, fluoro-C1-C6 alkyl, halo, CN, or (C1-C8)-R⁸ wherein up to two CH₂ units may be replaced with O, CO, CF₂, or NR⁷. Alternatively, R² is CH₃, OCH₃, CF₃, F, Cl, Br, CN, OCH₂CH₂OtBu, OCH₂CH(CH₃)₂. R² may also be F, Cl, or CN. In some embodiments, o is 0, 1 or 2. In others, R⁵ is H, C1-C6 alkyl, C1-C6 alkoxy, halo, CN, OH, or fluoro-C1-C6 alkyl. In some embodiments, R⁵ is H, CH₃, OCH₃, F, Cl, CN, OH, or CF₃. In certain embodiments, R⁶ is H, C1-C6 alkoxy, fluoro-C1-C6 alkoxy, SO₂R⁷, SO₂N(R⁷)₂, or a straight chain, branched, or cyclic (C1-C8)-R⁸ or fluoro-(C1-C8)-R⁸ wherein up to three CH₂ units may be replaced with O, CO, S, SO, SO₂, or NR⁷. In others, R⁶ is H, OCH₂CH₂CF₃, OCH₂CF(CH₃)₂, C(CH₃)₂CH₂OH, OCH₂CH₂CH(CH₃)₂, OCH(CH₃)CF₃, CH₂OCH₂CH₂CF₃, C(CH₃)₂OH, OCH₂CH₂OtBu, CH₂C(CH₃)₂OH, OCH(CH₃)₂, OCH₂C(CH₃)₂OH, OCH₂CF₂CHF₂, OCH₂CF₃, OCH₂CH₂OCF₃, OCH(CH₃)CF₂CHF₂, SO₂CHF₂, OCH₂CF₂CH₃, OCH₂CH₂OCH₂CF₃, OCH₂CF₃, OCH₂C(CH₃)₃, OCH₂CH(CH₃)CH₂CF₃, SO₂CH₂CH₃, OCH(CH₃)CH₂CF₃, OCH₂CF₂CHF₂,

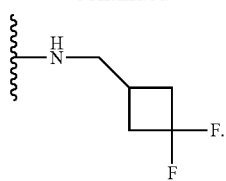

In some embodiments,

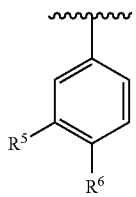

is selected from:

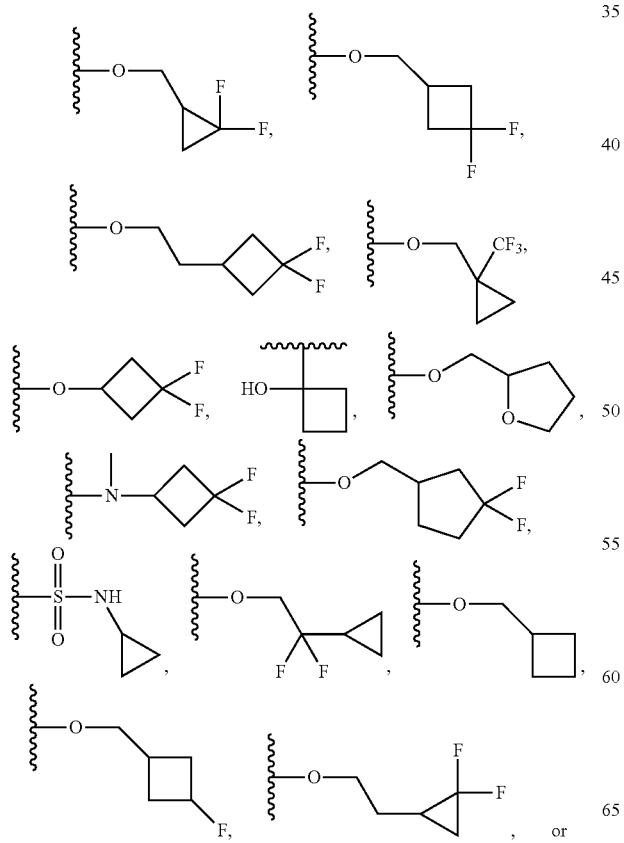

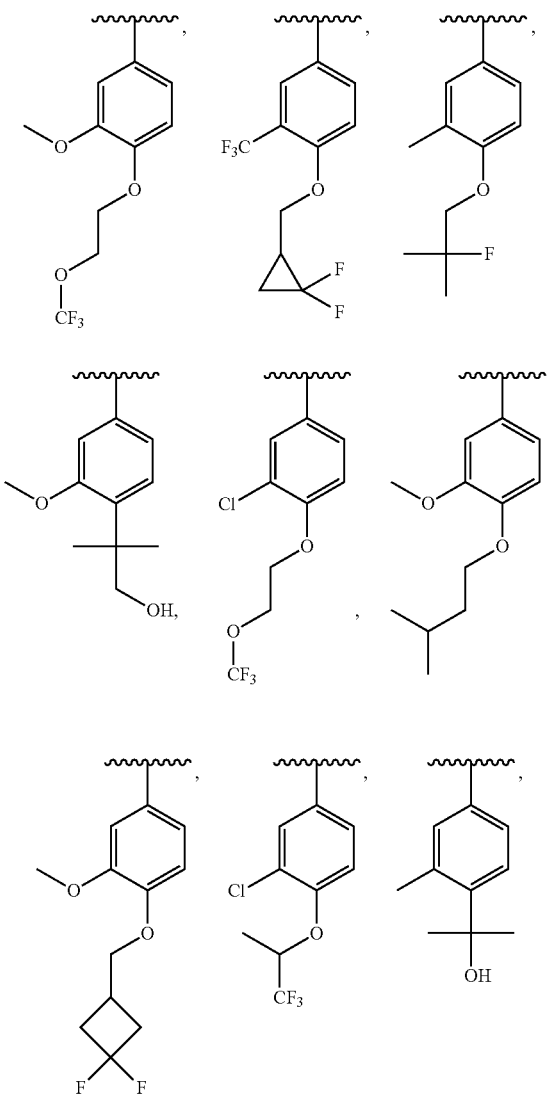

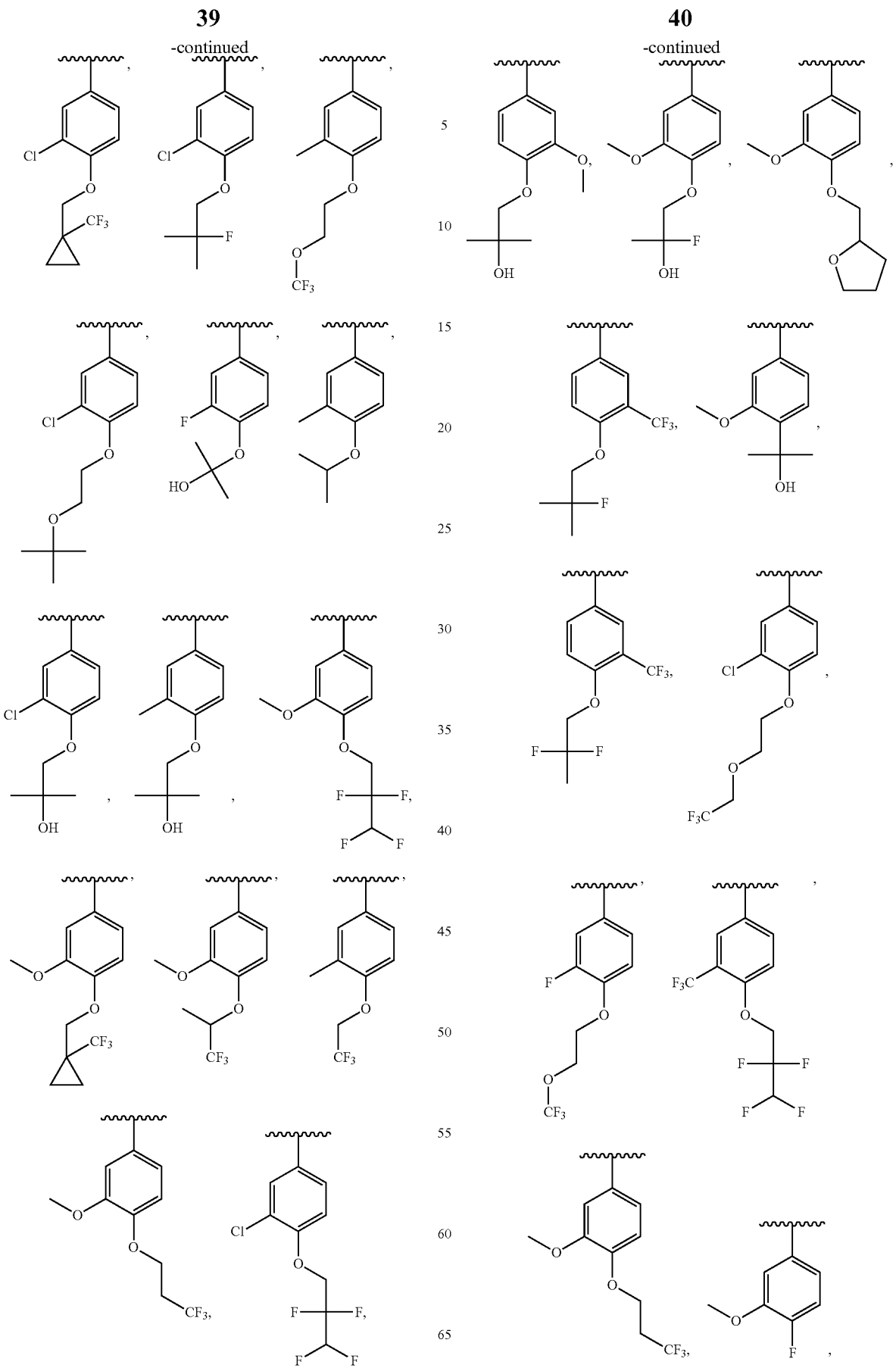

-continued

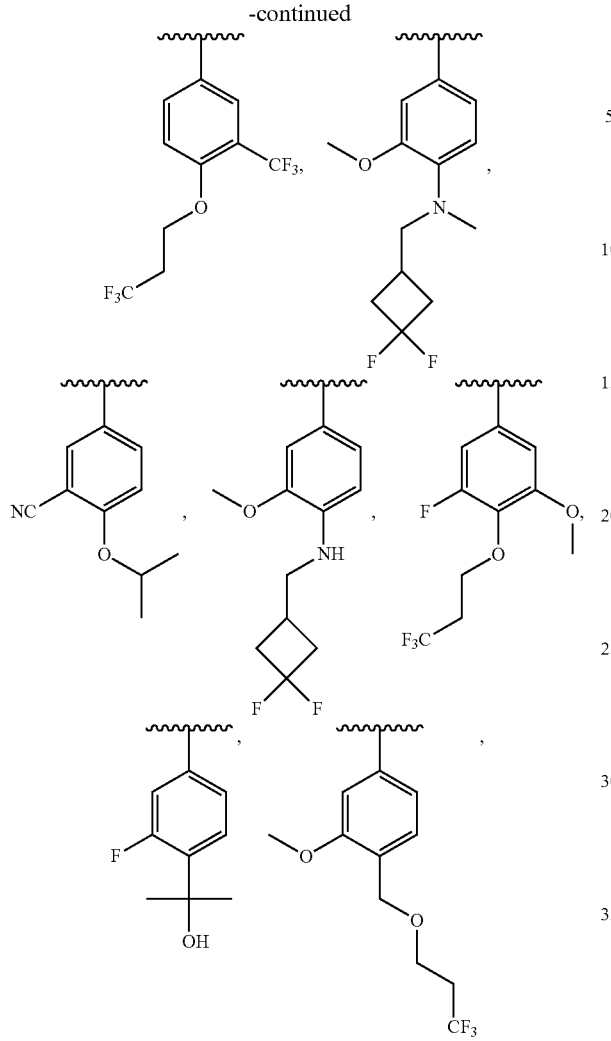

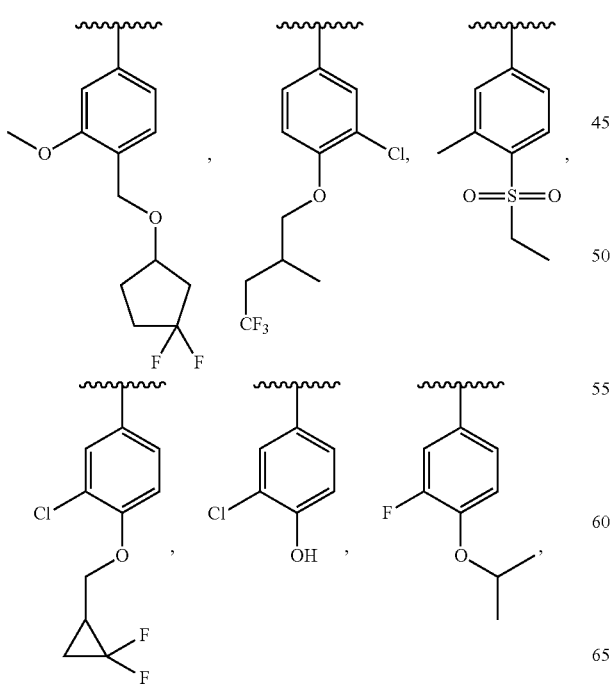

-continued

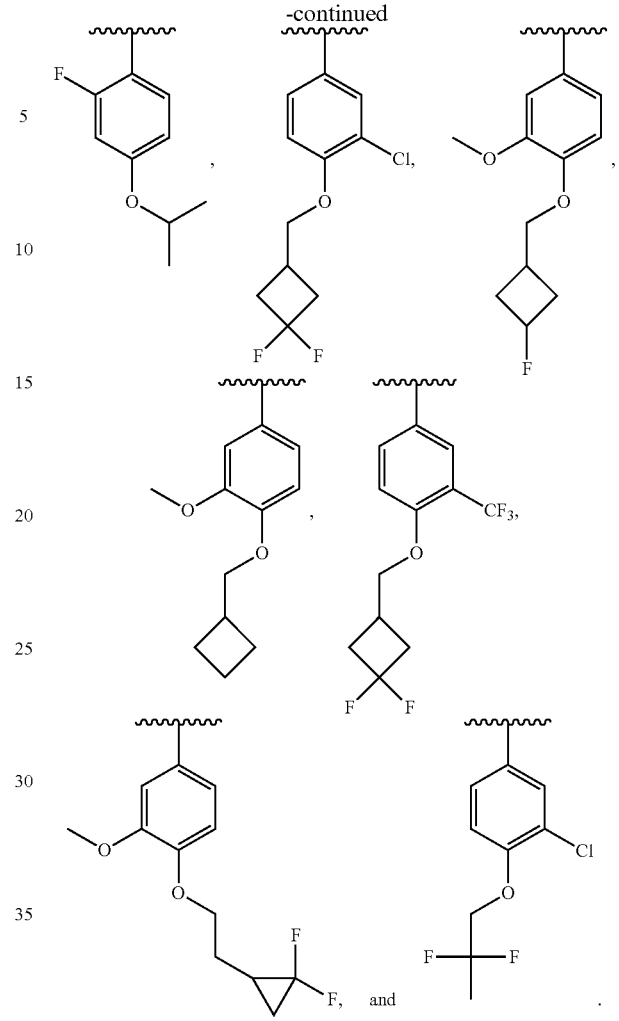

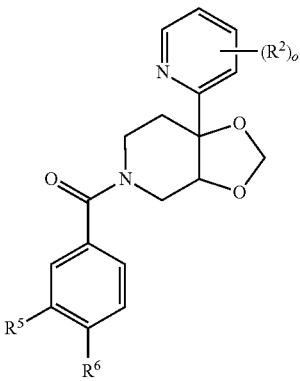

In some embodiments, the compound has formula IC:

IC or a pharmaceutically acceptable salt thereof, wherein, independently for each occurrence, $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$; o is an integer from 0 to 4 inclusive; $R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-

C6 alkyl, or fluoro-C1-C6 alkoxy; $R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$; $R^7$ is H, C1-C6 alkyl, $CHF_2$, $CF_3$, or C3-C8 cycloalkyl; and $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$.

In some embodiments, $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$. In others, $R^2$ is $CH_3$, $OCH_3$, $CF_3$, F, Cl, Br, CN, $OCH_2CH_2OtBu$, $OCH_2CH(CH_3)_2$. In some embodiments, o is 0, 1, or 2. In further embodiments, $R^5$ is H, C1-C6 alkyl, C1-C6 alkoxy, halo, CN, OH, or fluoro-C1-C6 alkyl. Alternatively, $R^5$ is H, $CH_3$, $OCH_3$, F, Cl, CN, OH, or $CF_3$. In some further embodiments, $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$. In others, $R^6$ is H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$,

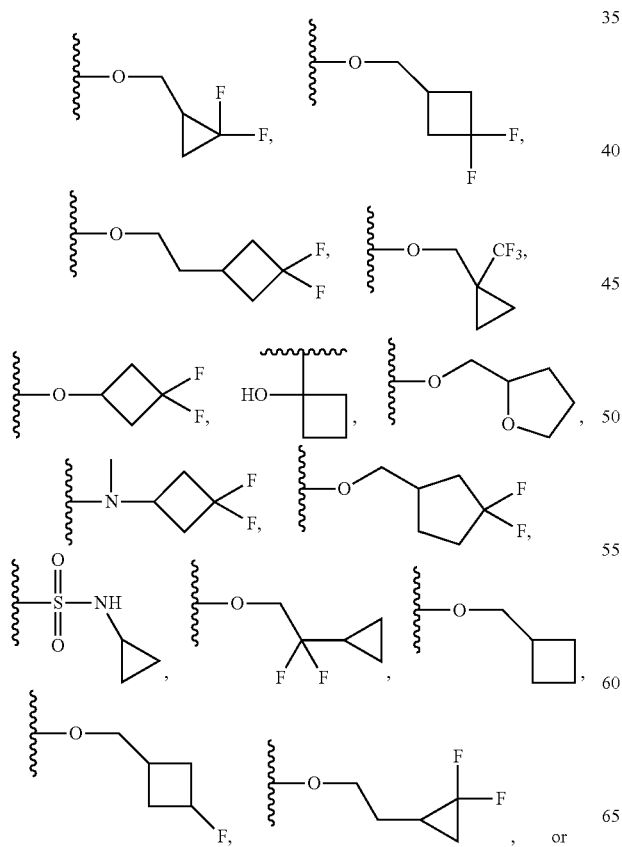

In one embodiment,

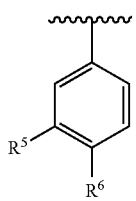

is selected from:

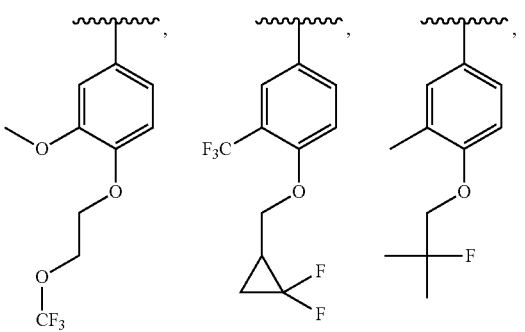

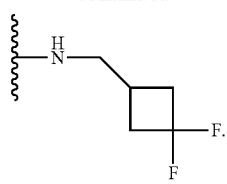

-continued

-continued
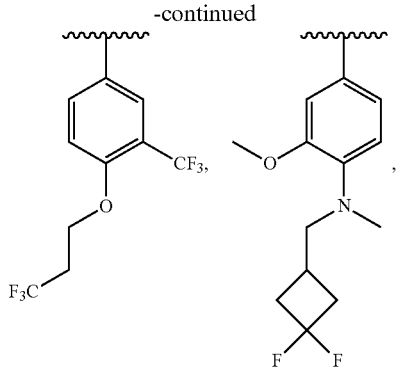
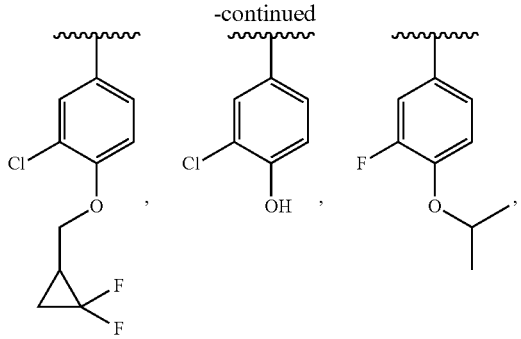
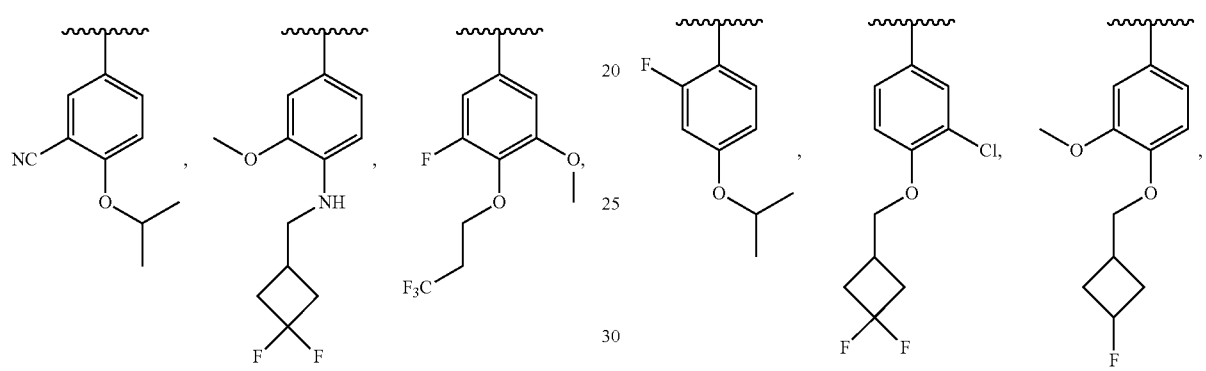
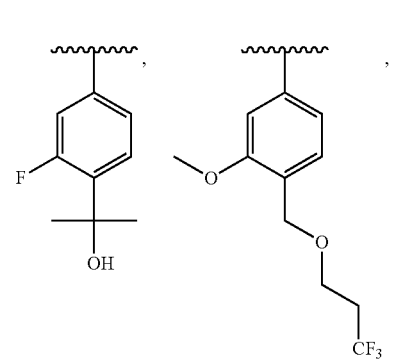
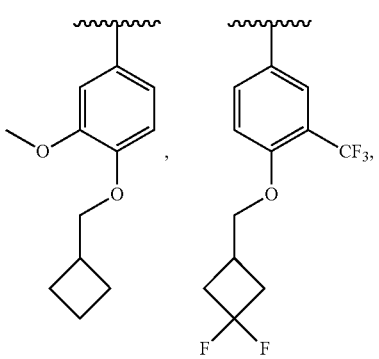
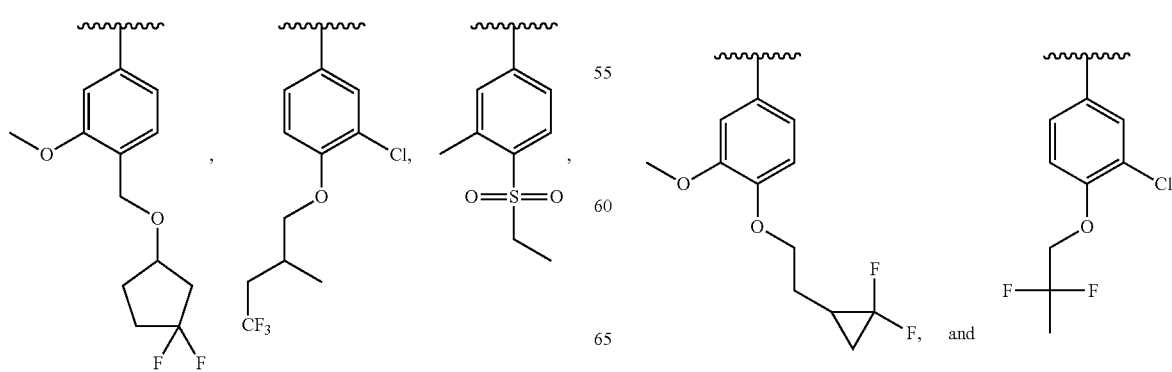

In one embodiment, the compound is selected from Table 1:
TABLE 1
1
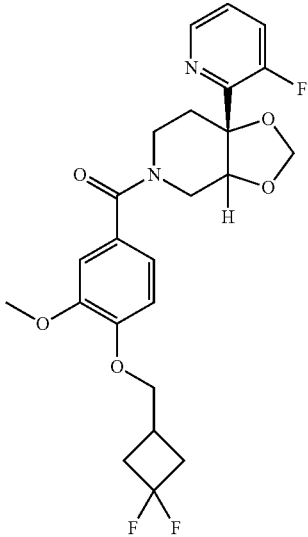 [SMILES: COc1cc(C(=O)N2CC[C@]3(c4ncccc4F)OCOC3C2)ccc1OCC1CC(F)(F)C1]
2
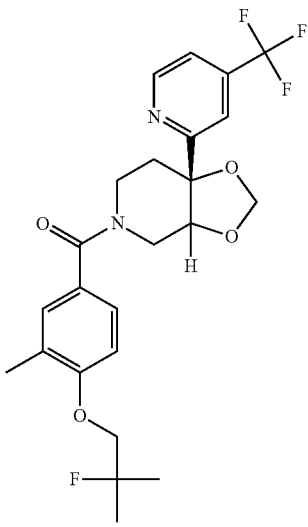 [SMILES: Cc1cc(C(=O)N2CC[C@]3(c4cc(C(F)(F)F)ccn4)OCOC3C2)ccc1OCC(C)(C)F]
TABLE 1-continued
3
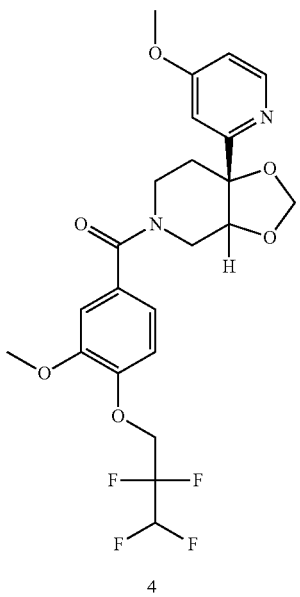
4
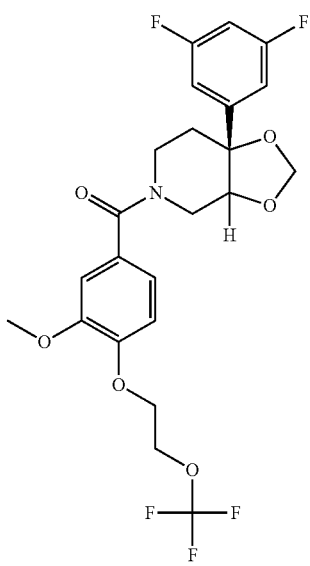 [SMILES: COc1cc(C(=O)N2CC[C@]3(c4cc(F)cc(F)c4)OCOC3C2)ccc1OCCOC(F)(F)F]
5
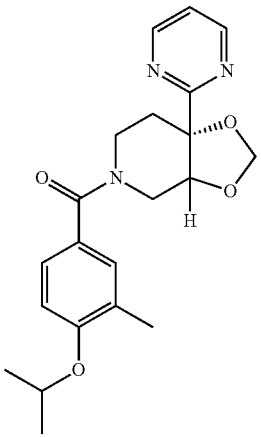

TABLE 1-continued
6
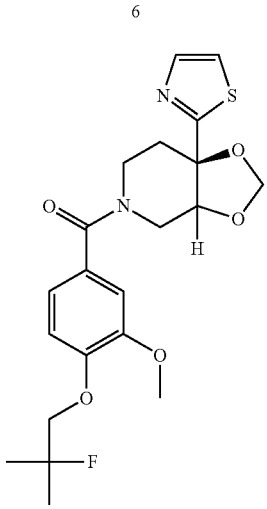
7
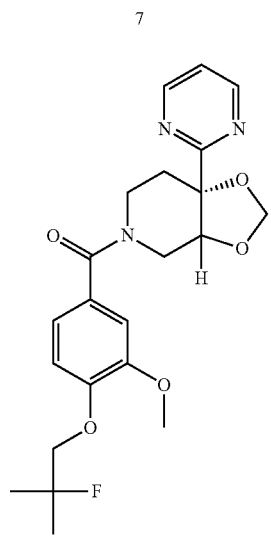
8
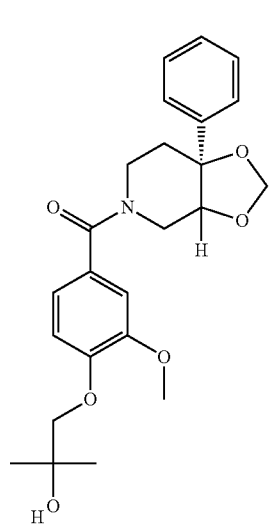
TABLE 1-continued
9
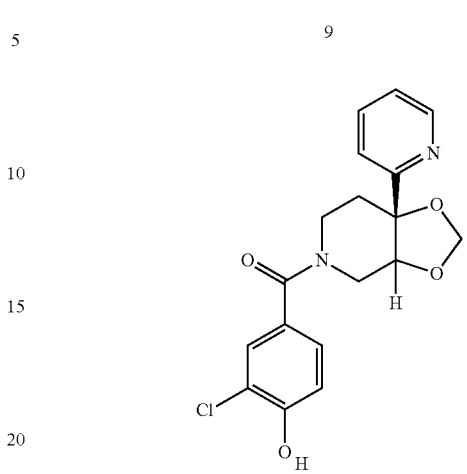
10
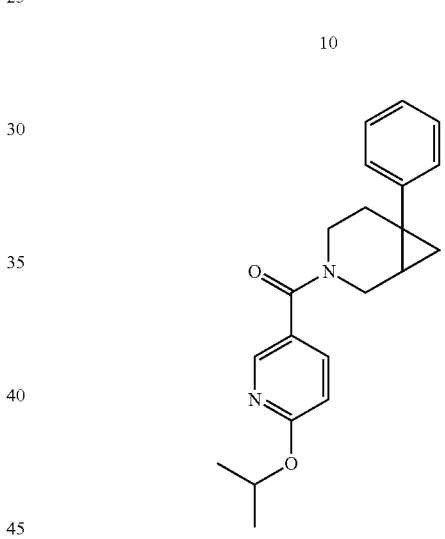
11
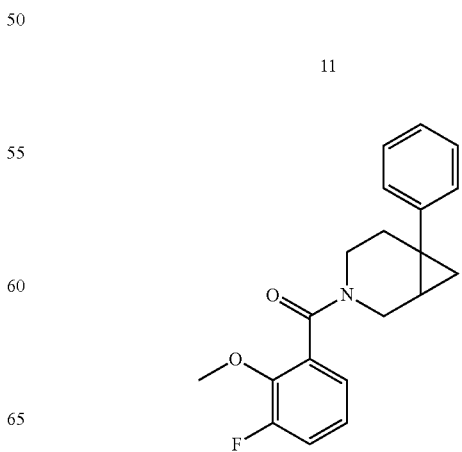

TABLE 1-continued
12
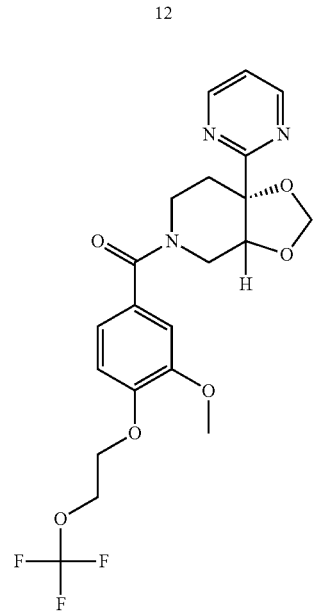
13
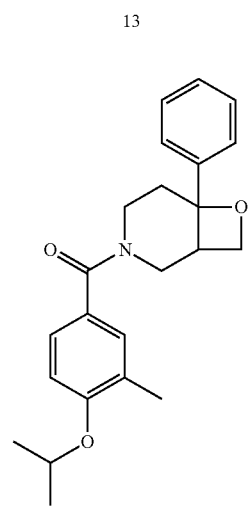
14
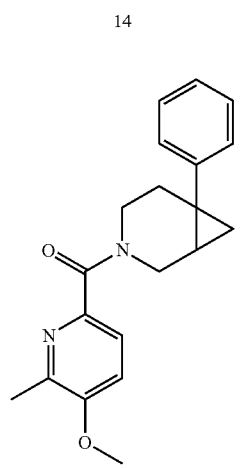
TABLE 1-continued
15
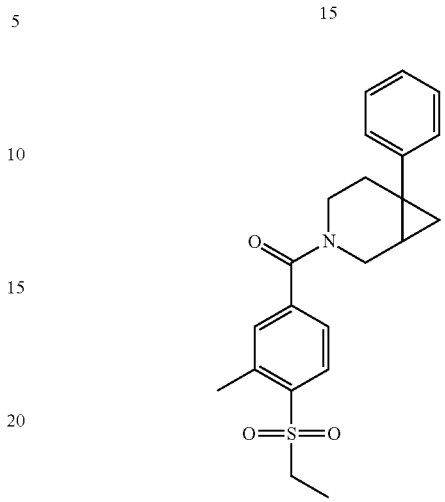
16
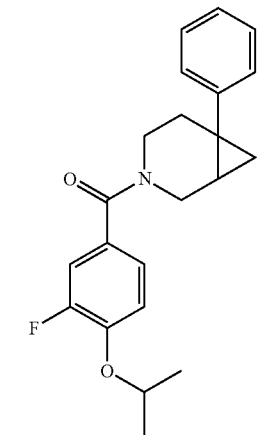
17
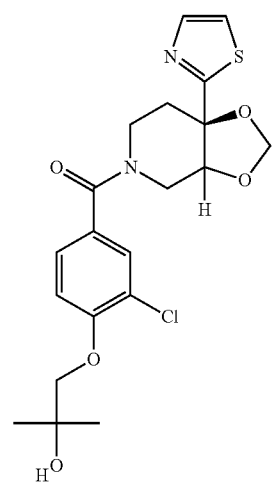

TABLE 1-continued
18
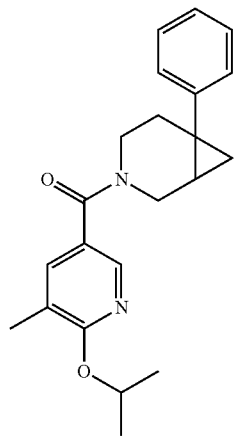 [SMILES: Cc1cc(C(=O)N2CCC3(c4ccccc4)CC3C2)cnc1OC(C)C]
19
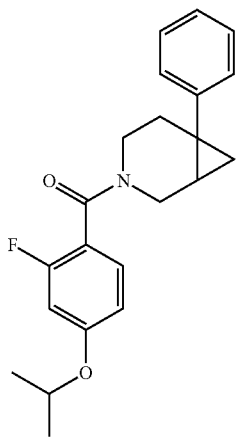 [SMILES: CC(C)Oc1ccc(C(=O)N2CCC3(c4ccccc4)CC3C2)c(F)c1]
20
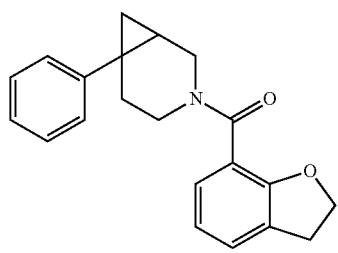 [SMILES: O=C(c1cccc2c1OCC2)N1CCC2(c3ccccc3)CC2C1]
TABLE 1-continued
21
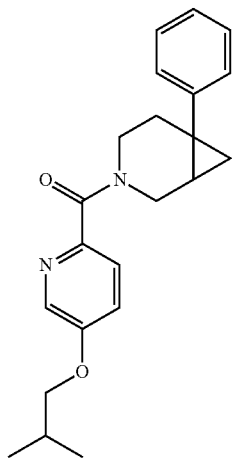 [SMILES: CC(C)COc1ccc(C(=O)N2CCC3(c4ccccc4)CC3C2)nc1]
22
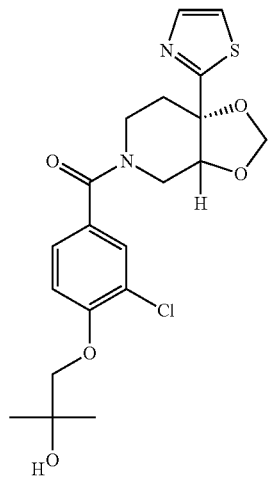
23
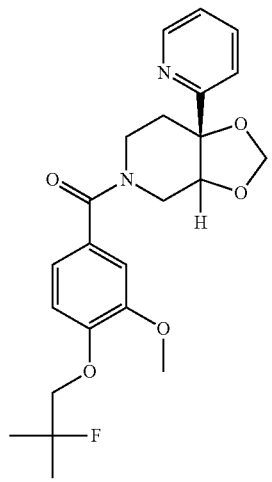 [SMILES: COc1cc(C(=O)N2CC[C@]3(c4ccccn4)OCOC3C2)ccc1OCC(C)(C)F]

TABLE 1-continued
24
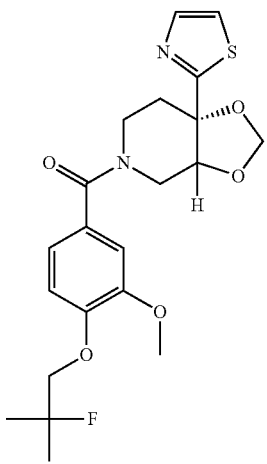
25
26
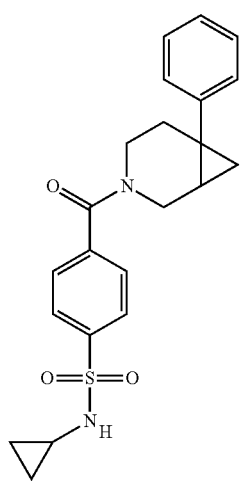
TABLE 1-continued
27
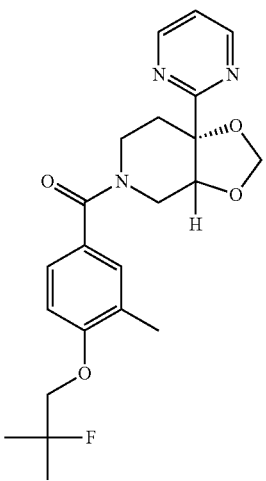
28
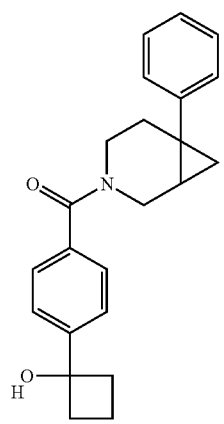
29
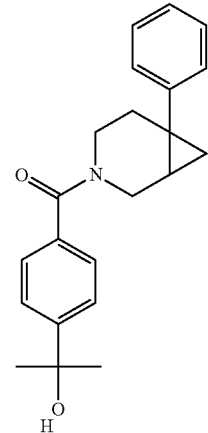

TABLE 1-continued
30
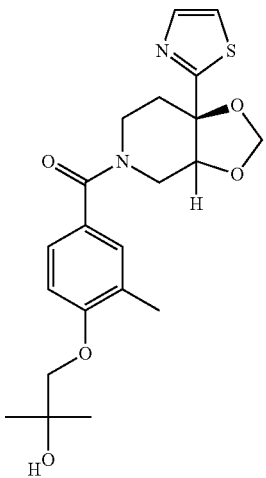
31
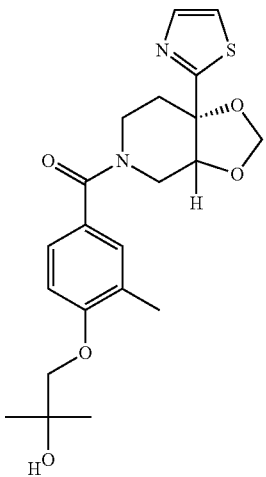
TABLE 1-continued
32
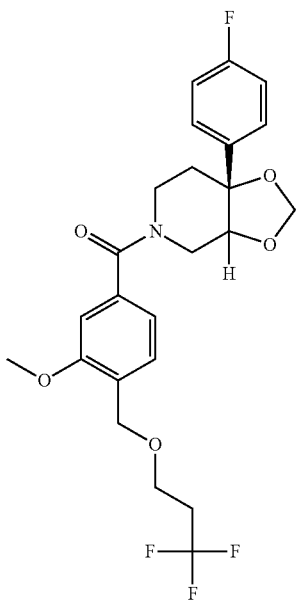 [SMILES: COc1cc(C(=O)N2CC[C@]3(c4ccc(F)cc4)OCOC3C2)ccc1COCCC(F)(F)F]
33
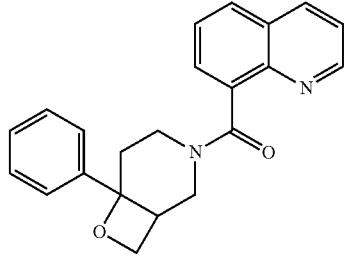 [SMILES: O=C(c1cccc2cccnc12)N1CCC2(c3ccccc3)OCC2C1]
34
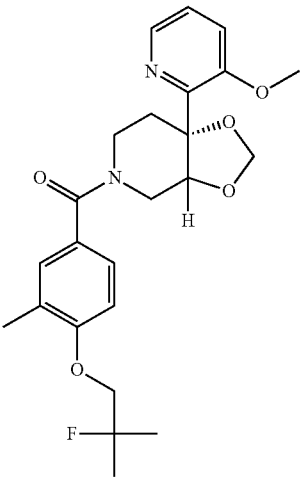

TABLE 1-continued
35
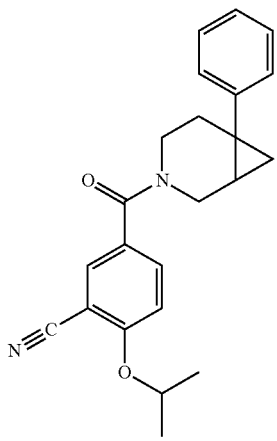 [SMILES: CC(C)Oc1ccc(C(=O)N2CCC3(c4ccccc4)CC3C2)cc1C#N]
36
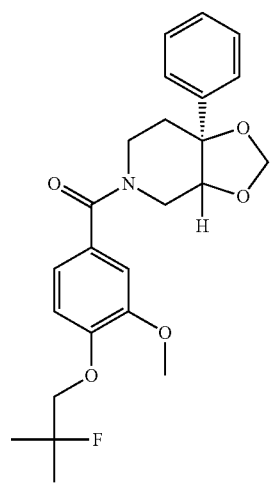 [SMILES: COc1cc(C(=O)N2CC[C@@]3(c4ccccc4)OCOC3C2)ccc1OCC(C)(C)F]
37
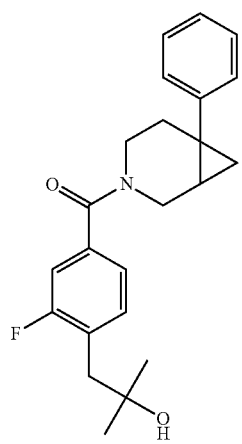 [SMILES: CC(C)(O)Cc1ccc(C(=O)N2CCC3(c4ccccc4)CC3C2)cc1F]
TABLE 1-continued
38
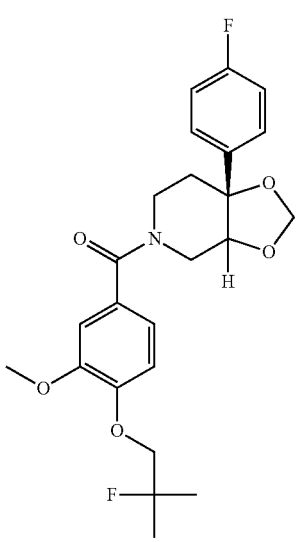 [SMILES: COc1cc(C(=O)N2CC[C@]3(c4ccc(F)cc4)OCOC3C2)ccc1OCC(C)(C)F]
39
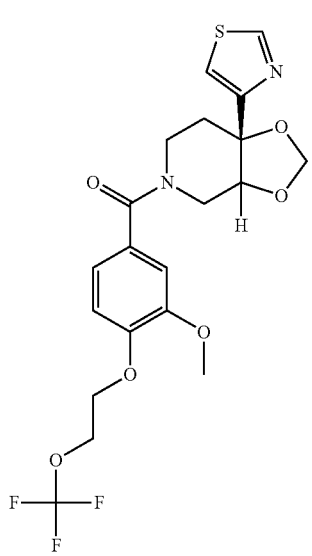

TABLE 1-continued
40
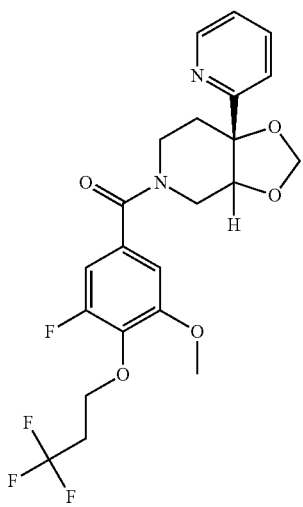 [SMILES: COc1cc(C(=O)N2CC[C@]3(c4ccccn4)OCOC3C2)cc(F)c1OCCC(F)(F)F]
41
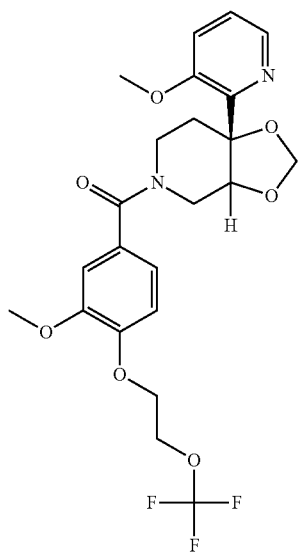 [SMILES: COc1cc(C(=O)N2CC[C@]3(c4ncccc4OC)OCOC3C2)ccc1OCCOC(F)(F)F]
42
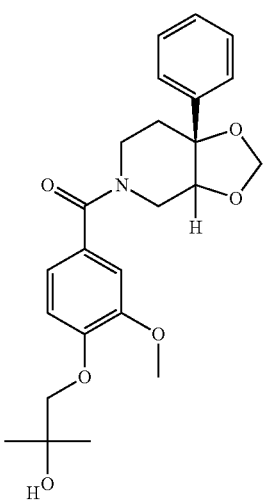
43
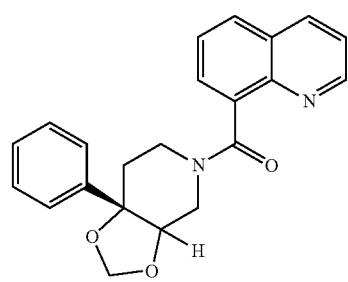 [SMILES: O=C(c1cccc2cccnc12)N1CC[C@@]2(c3ccccc3)OCOC2C1]
44
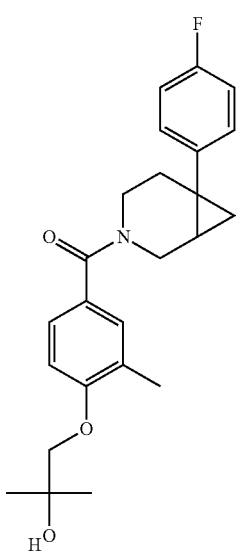

TABLE 1-continued
45
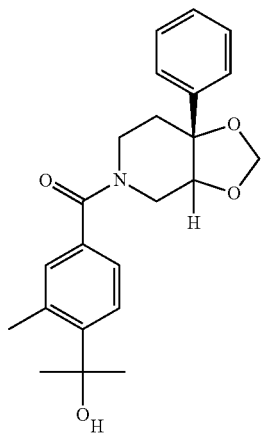
46
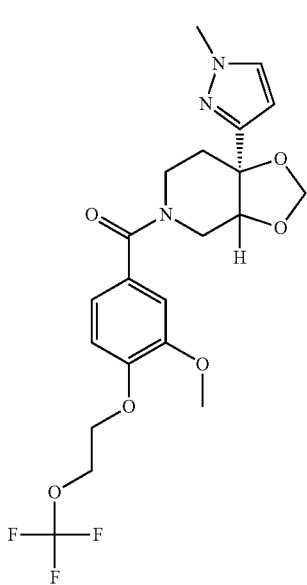 [SMILES: COc1cc(C(=O)N2CC[C@@]3(c4ccn(C)n4)OCOC3C2)ccc1OCCOC(F)(F)F]
47
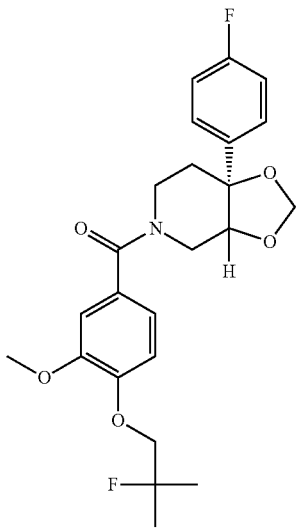 [SMILES: COc1cc(C(=O)N2CC[C@@]3(c4ccc(F)cc4)OCOC3C2)ccc1OCC(C)(C)F]
48
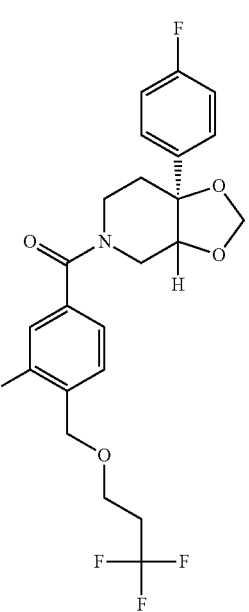

TABLE 1-continued
49
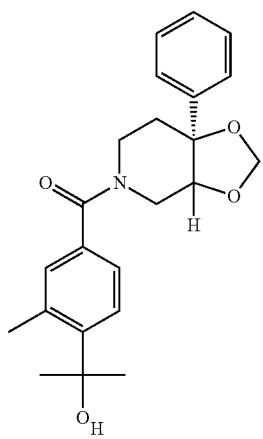
50
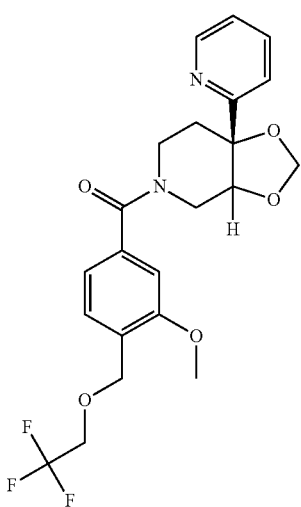 [SMILES: COc1cc(C(=O)N2CC[C@]3(c4ccccn4)OCOC3C2)ccc1COCC(F)(F)F]
51
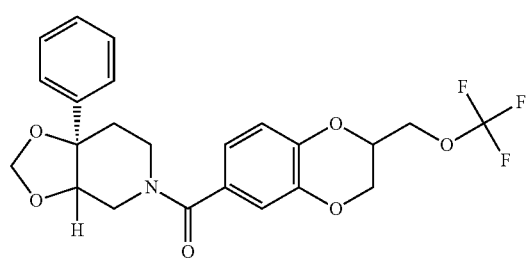 [SMILES: O=C(c1ccc2c(c1)OCC(COC(F)(F)F)O2)N1CC[C@]2(c3ccccc3)OCOC2C1]
TABLE 1-continued
52
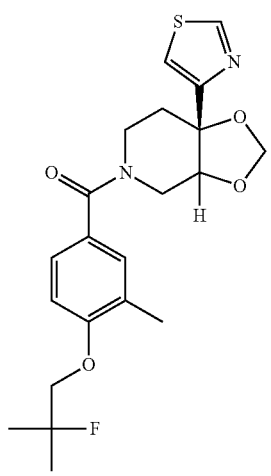 [SMILES: Cc1cc(C(=O)N2CC[C@]3(c4cscn4)OCOC3C2)ccc1OCC(C)(C)F]
53
54
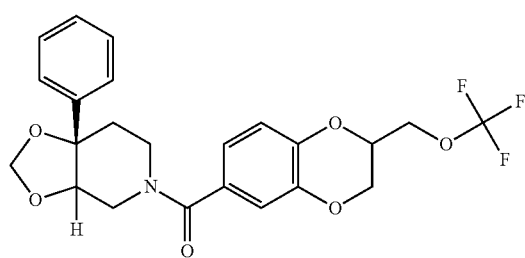 [SMILES: O=C(c1ccc2c(c1)OCC(COC(F)(F)F)O2)N1CC[C@@]2(c3ccccc3)OCOC2C1]

TABLE 1-continued
55
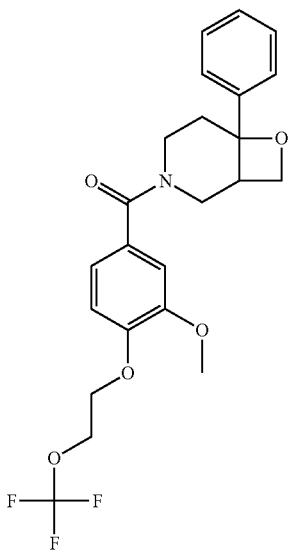 [SMILES: COc1cc(C(=O)N2CCC3(c4ccccc4)OCC3C2)ccc1OCCOC(F)(F)F]
56
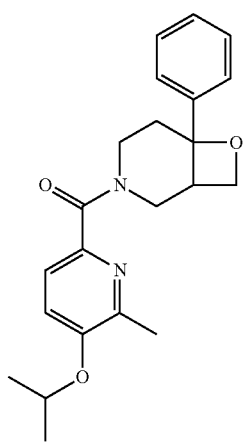 [SMILES: Cc1nc(C(=O)N2CCC3(c4ccccc4)OCC3C2)ccc1OC(C)C]
57
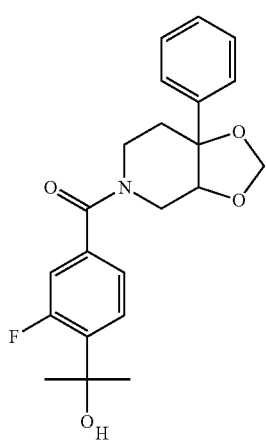
TABLE 1-continued
58
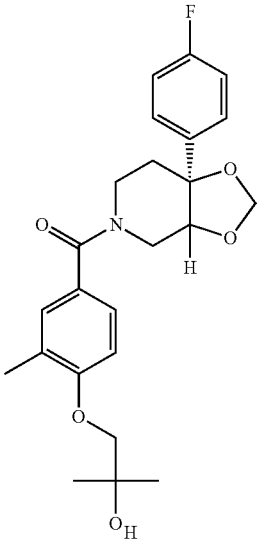
59
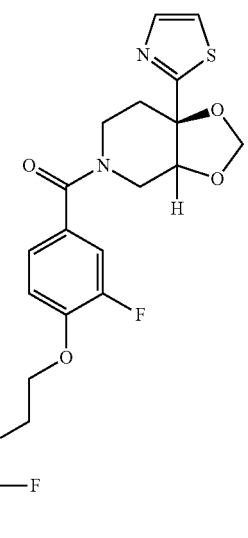

60
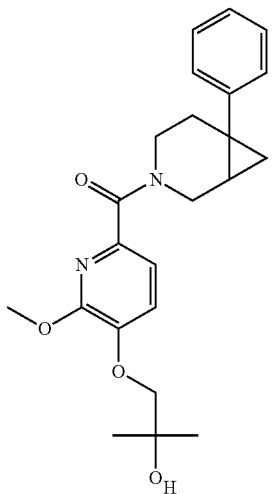
61
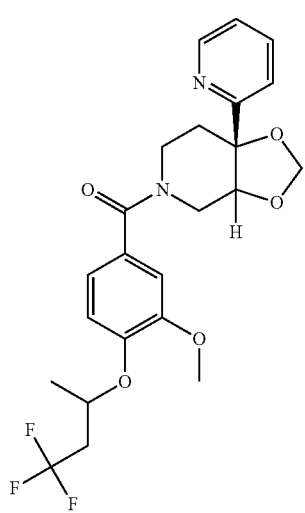 [SMILES: COc1cc(C(=O)N2CC[C@]3(c4ccccn4)OCOC3C2)ccc1OC(C)CC(F)(F)F]
62
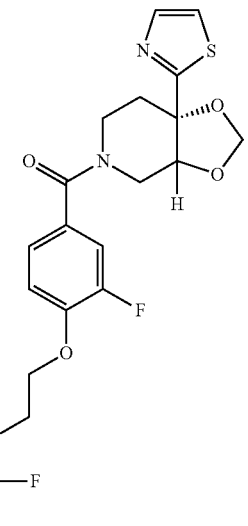
63
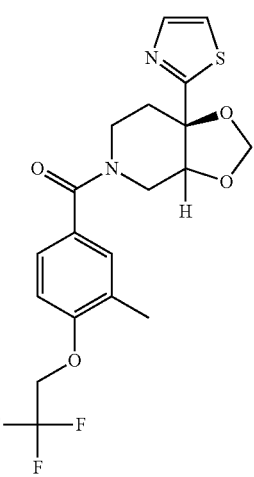

TABLE 1-continued
64
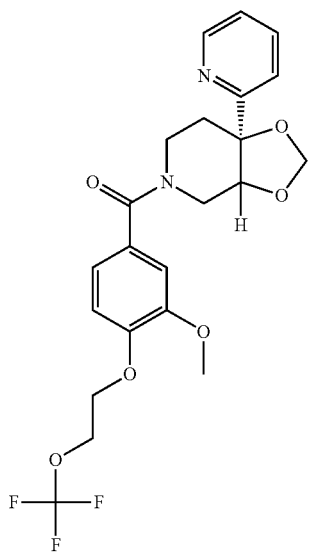 [SMILES: COc1cc(C(=O)N2CC[C@@]3(c4ccccn4)OCOC3C2)ccc1OCCOC(F)(F)F]
65
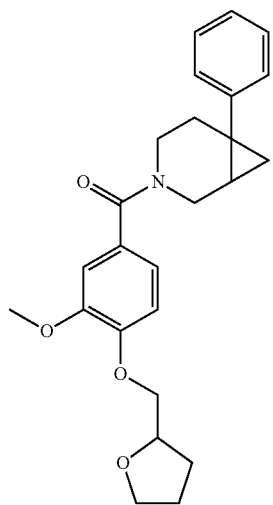 [SMILES: COc1cc(C(=O)N2CCC3(c4ccccc4)CC3C2)ccc1OCC1CCCO1]
66
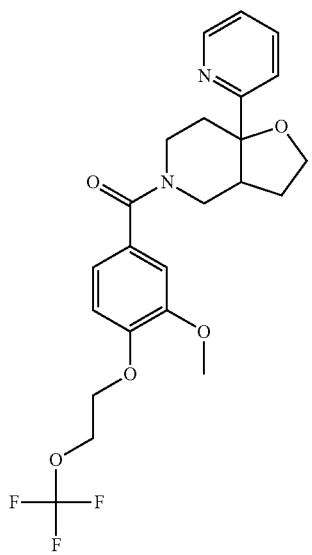
67
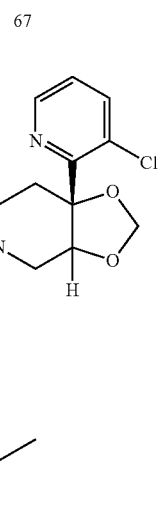

TABLE 1-continued
68
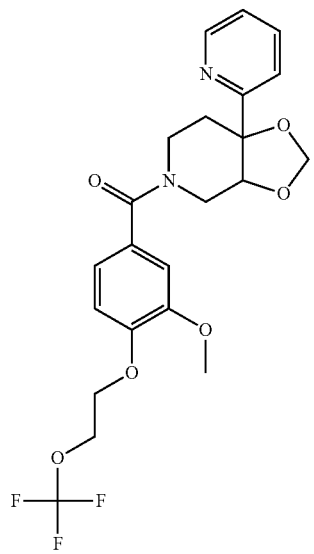
69
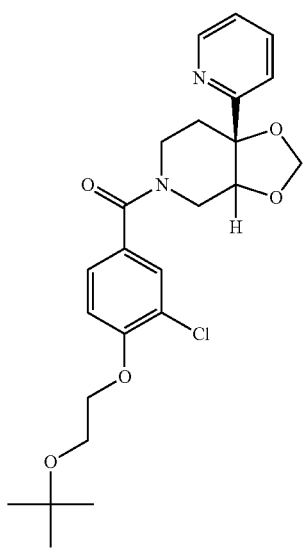 [SMILES: CC(C)(C)OCCOc1ccc(C(=O)N2CC[C@]3(c4ccccn4)OCOC3C2)cc1Cl]
TABLE 1-continued
70
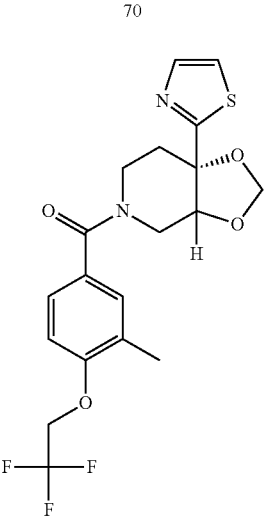
71
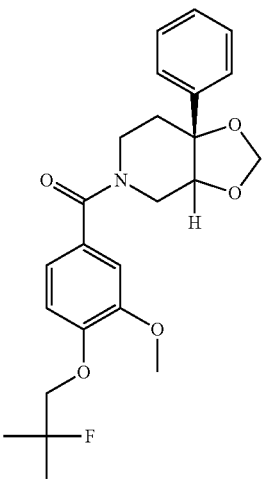 [SMILES: COc1cc(C(=O)N2CC[C@]3(c4ccccc4)OCOC3C2)ccc1OCC(C)(C)F]
72
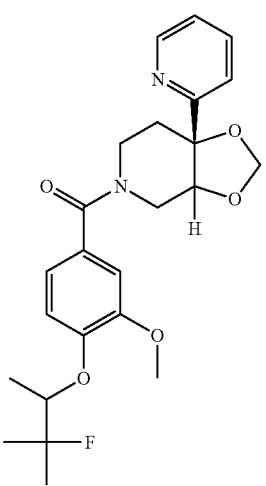 [SMILES: COc1cc(C(=O)N2CC[C@]3(c4ccccn4)OCOC3C2)ccc1OC(C)C(C)(C)F]

TABLE 1-continued
73
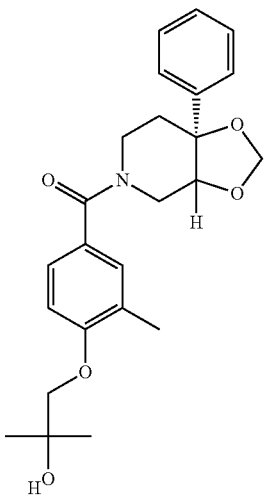
74
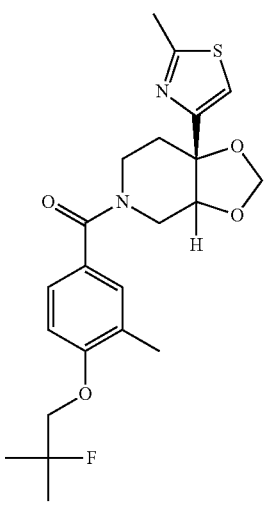 [SMILES: Cc1nc([C@]23CCN(C(=O)c4ccc(OCC(C)(C)F)c(C)c4)CC2OCO3)cs1]
75
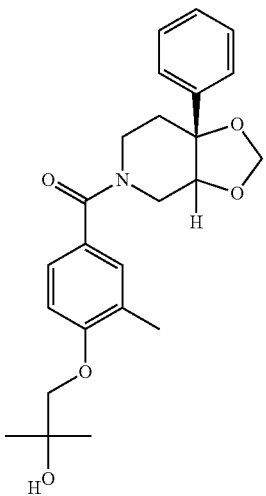
TABLE 1-continued
76
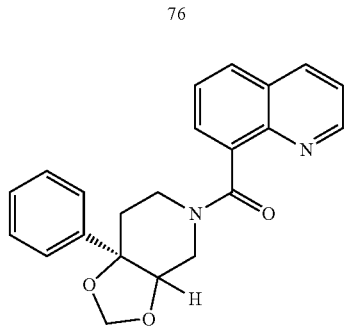
77
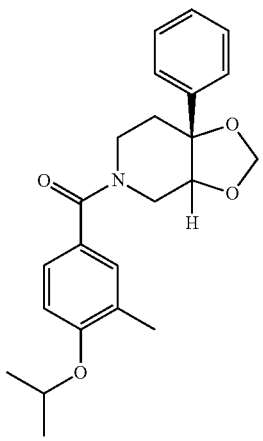 [SMILES: Cc1cc(C(=O)N2CC[C@]3(c4ccccc4)OCOC3C2)ccc1OC(C)C]
78
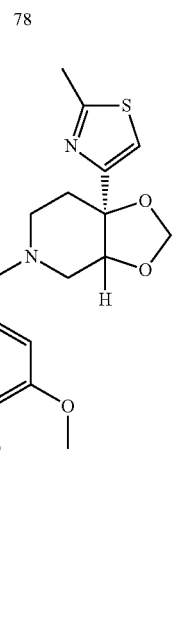

TABLE 1-continued
79
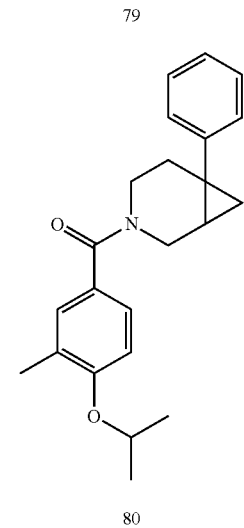
80
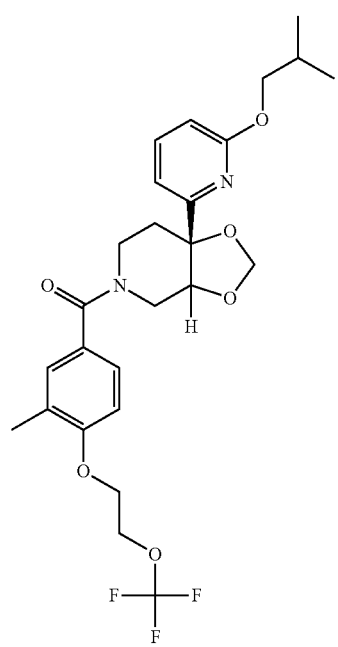 [SMILES: Cc1cc(C(=O)N2CC[C@]3(c4cccc(OCC(C)C)n4)OCOC3C2)ccc1OCCOC(F)(F)F]
81
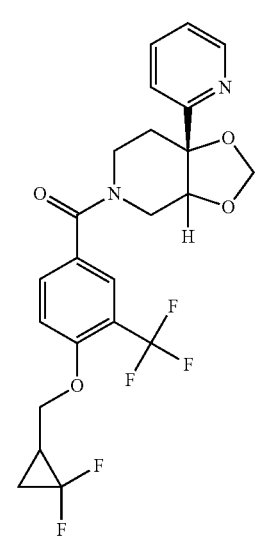 [SMILES: O=C(c1ccc(OCC2CC2(F)F)c(C(F)(F)F)c1)N1CC[C@]2(c3ccccn3)OCOC2C1]
82
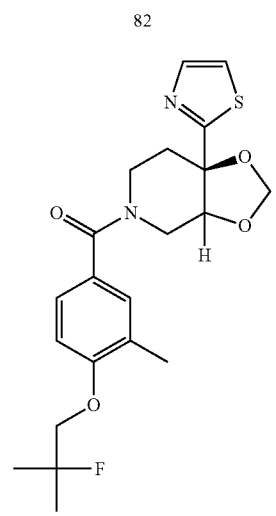
83
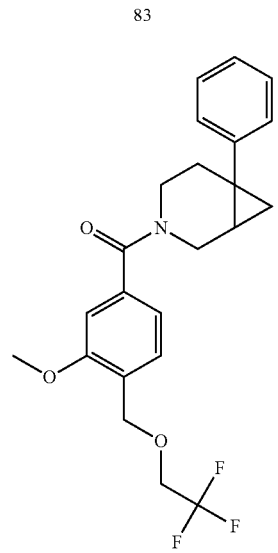
84
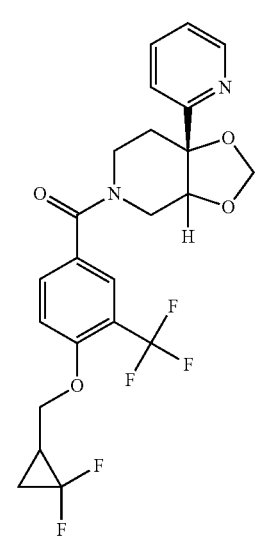 [SMILES: O=C(c1ccc(OCC2CC2(F)F)c(C(F)(F)F)c1)N1CC[C@]2(c3ccccn3)OCOC2C1]

TABLE 1-continued
85
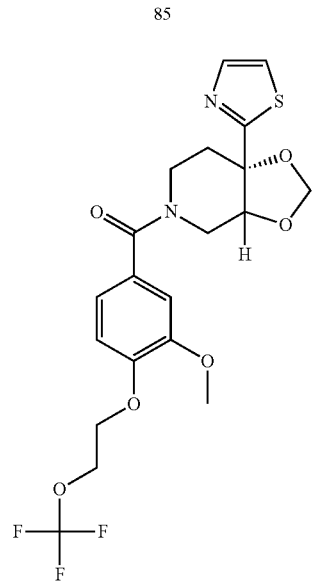
86
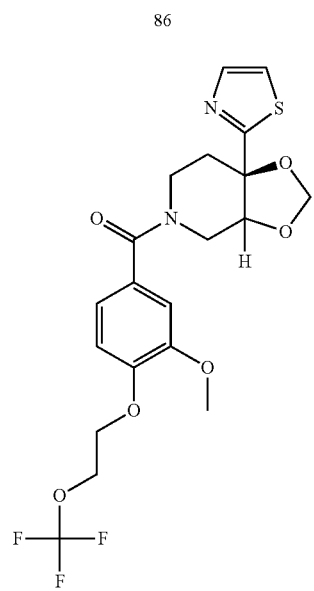
TABLE 1-continued
87
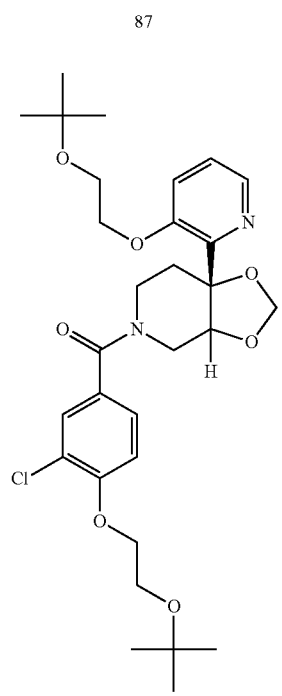
88
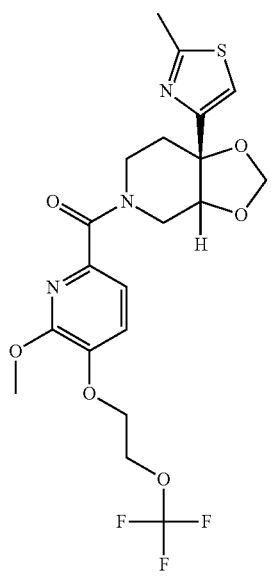 [SMILES: COc1nc(C(=O)N2CC[C@]3(c4csc(C)n4)OCOC3C2)ccc1OCCOC(F)(F)F]

TABLE 1-continued
89
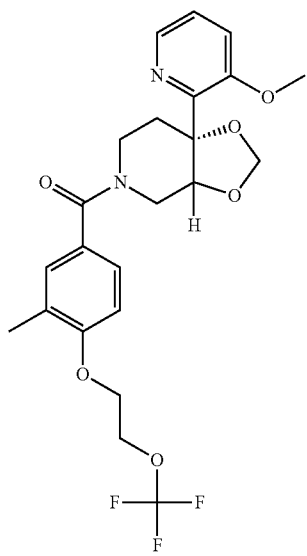
90
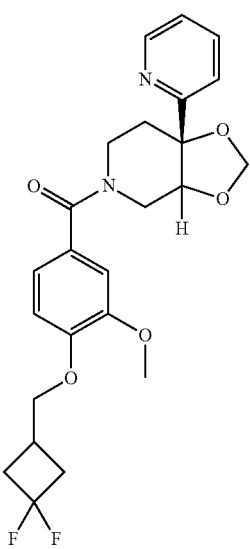 [SMILES: COc1cc(C(=O)N2CC[C@]3(c4ccccn4)OCOC3C2)ccc1OCC1CC(F)(F)C1]
TABLE 1-continued
91
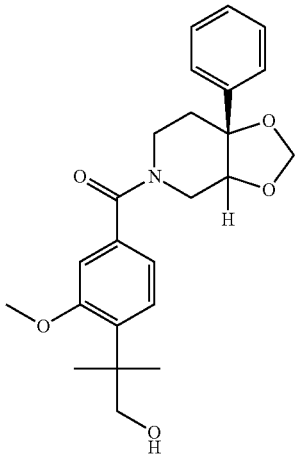 [SMILES: COc1cc(C(=O)N2CC[C@]3(c4ccccc4)OCOC3C2)ccc1C(C)(C)CO]
92
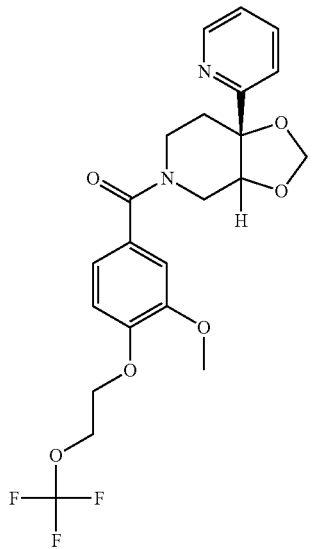

TABLE 1-continued
93
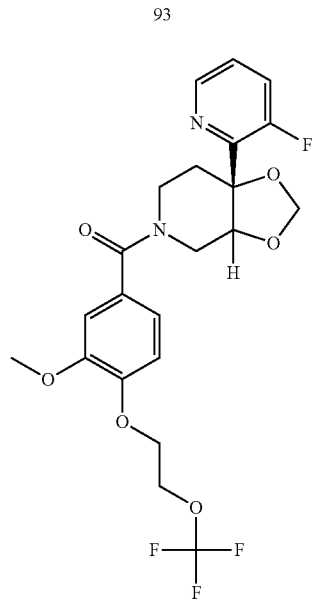
94
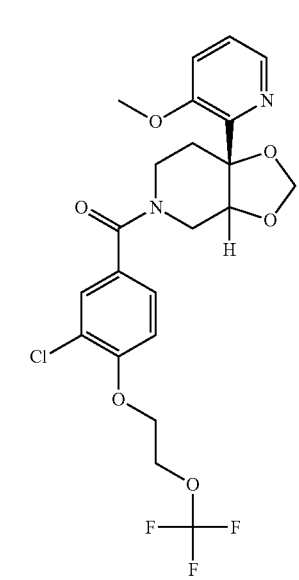 [SMILES: COc1cccnc1[C@]12CCN(C(=O)c3ccc(OCCOC(F)(F)F)c(Cl)c3)CC1OCO2]
TABLE 1-continued
95
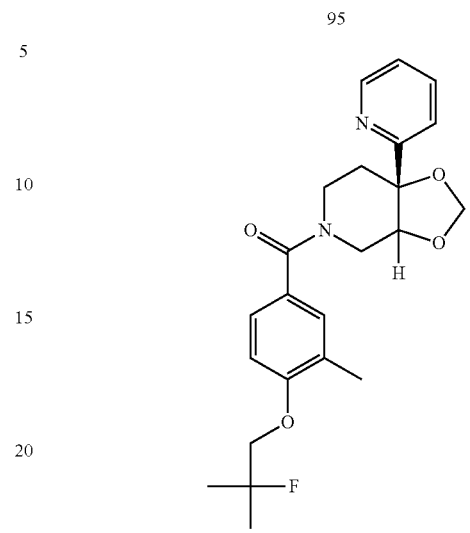
96
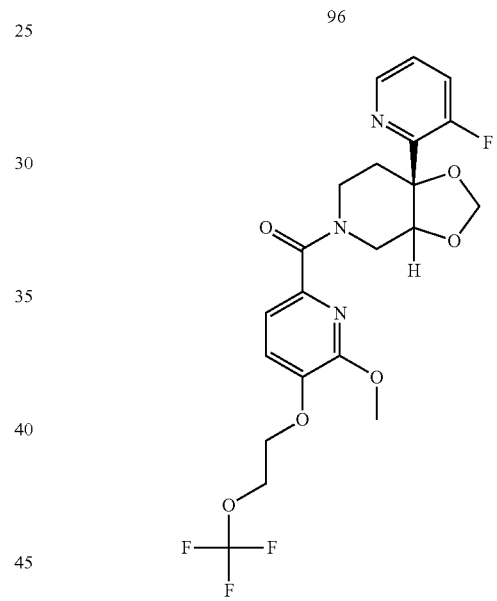
97
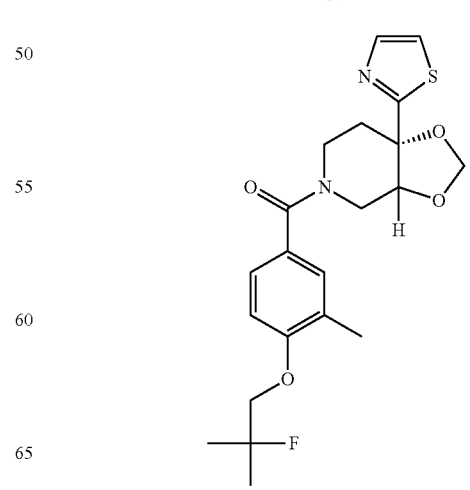

TABLE 1-continued
98
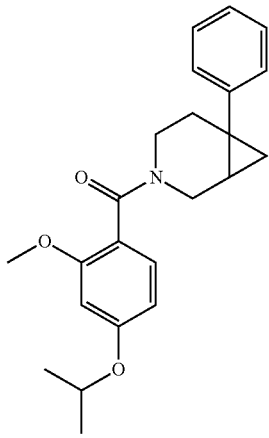 [SMILES: COc1cc(OC(C)C)ccc1C(=O)N1CCC2(c3ccccc3)CC2C1]
99
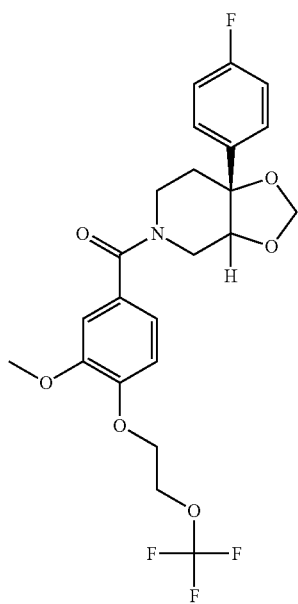 [SMILES: COc1cc(C(=O)N2CC[C@]3(c4ccc(F)cc4)OCOC3C2)ccc1OCCOC(F)(F)F]
100
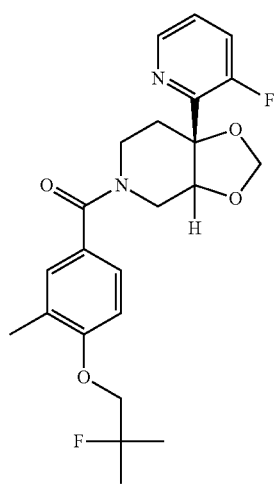 [SMILES: Cc1cc(C(=O)N2CC[C@]3(c4ncccc4F)OCOC3C2)ccc1OCC(C)(C)F]
TABLE 1-continued
101
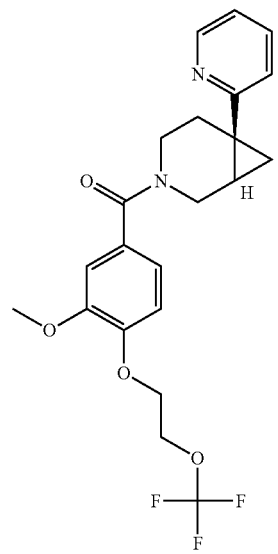
102
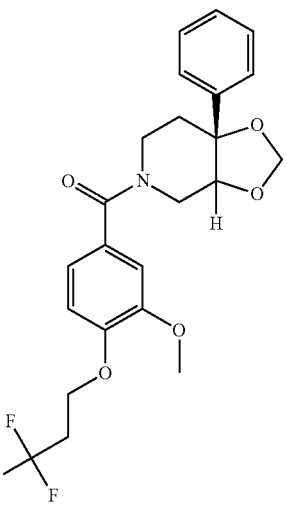

TABLE 1-continued
103
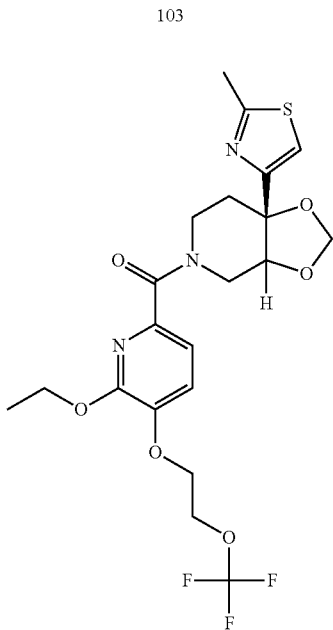
104
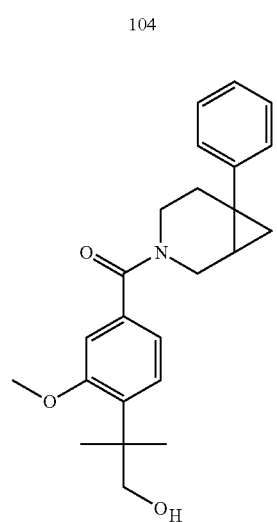
105
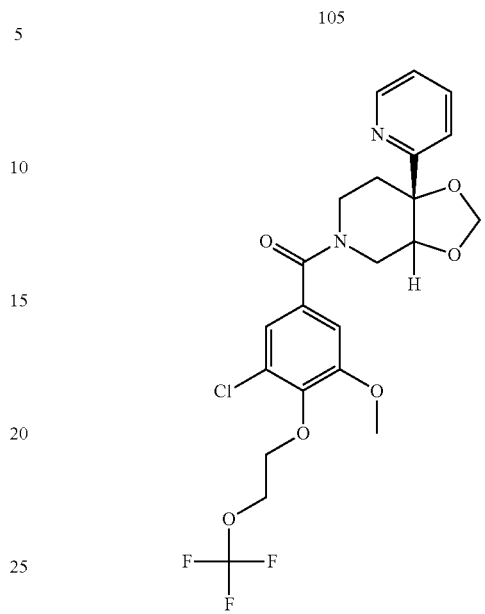
106
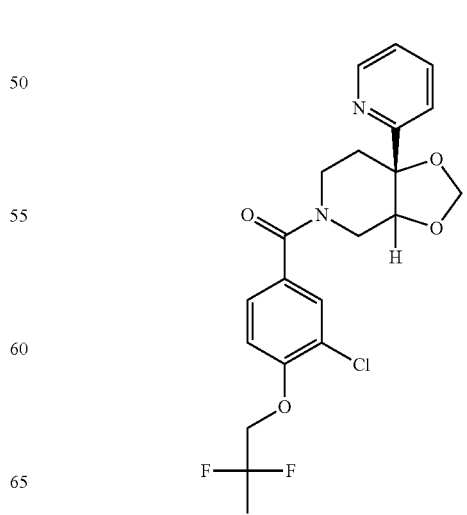

TABLE 1-continued
107
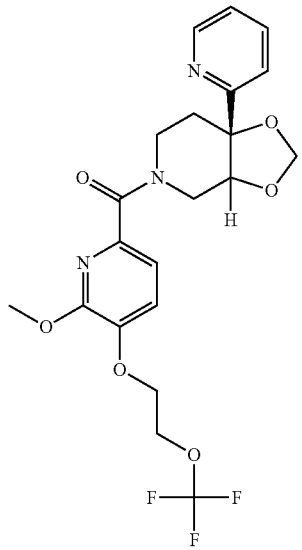 [SMILES: COc1nc(C(=O)N2CC[C@]3(c4ccccn4)OCOC3C2)ccc1OCCOC(F)(F)F]
108
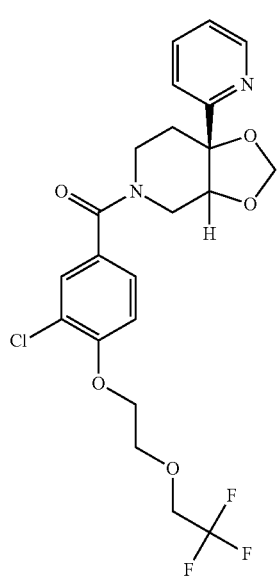 [SMILES: O=C(c1ccc(OCCOCC(F)(F)F)c(Cl)c1)N1CC[C@]2(c3ccccn3)OCOC2C1]
TABLE 1-continued
109
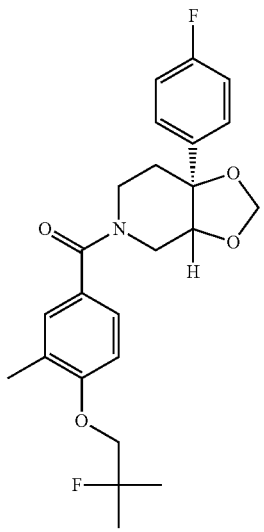 [SMILES: Cc1cc(C(=O)N2CC[C@@]3(c4ccc(F)cc4)OCOC3C2)ccc1OCC(C)(C)F]
110
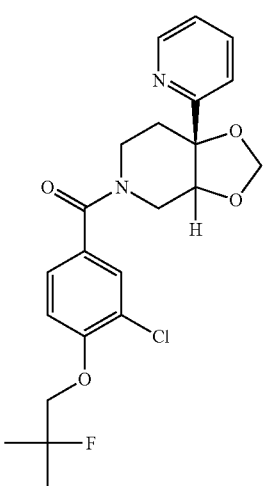 [SMILES: CC(C)(F)COc1ccc(C(=O)N2CC[C@]3(c4ccccn4)OCOC3C2)cc1Cl]

TABLE 1-continued
111
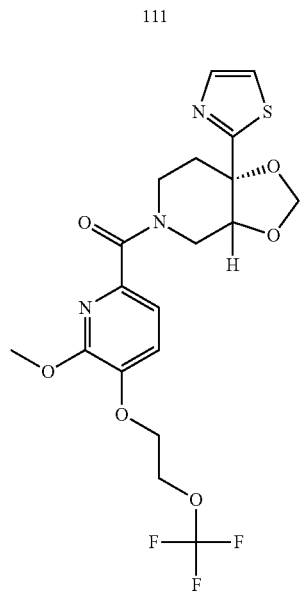
113
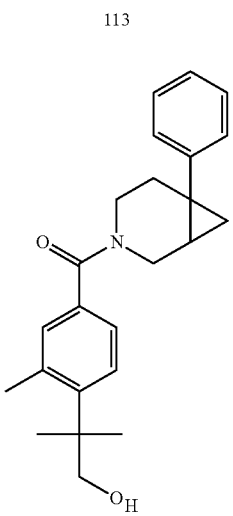
112
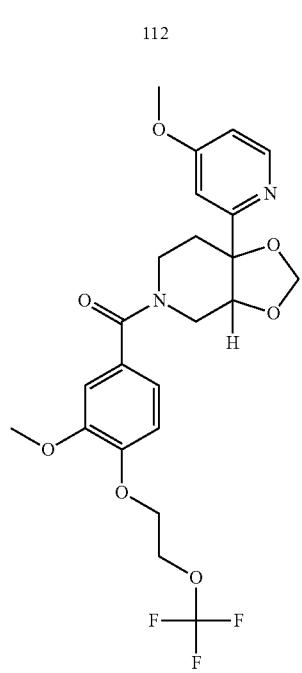
114
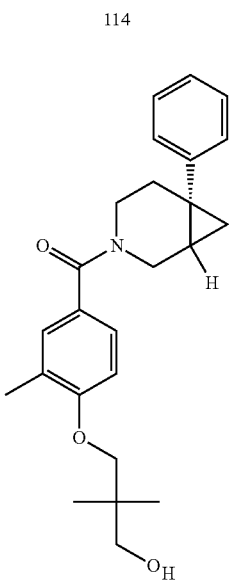

TABLE 1-continued
115
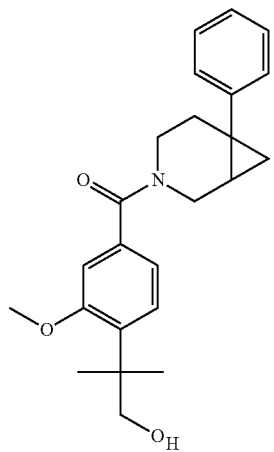
116
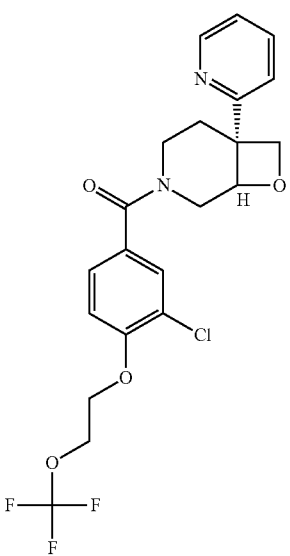
117
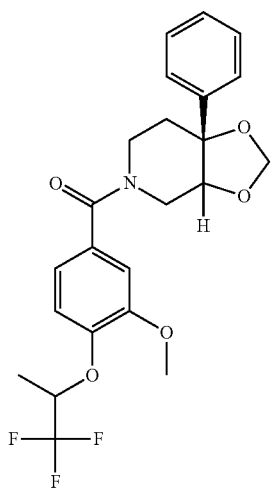 [SMILES: COc1cc(C(=O)N2CC[C@]3(c4ccccc4)OCOC3C2)ccc1OC(C)C(F)(F)F]
TABLE 1-continued
118
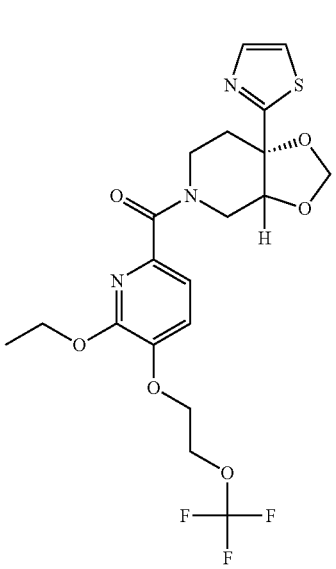
119
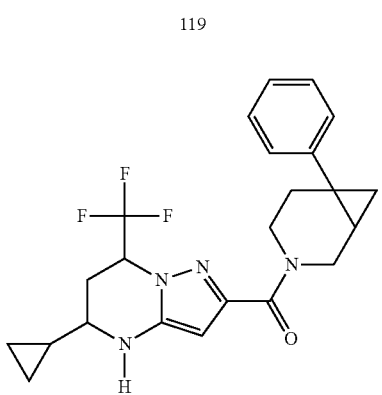
120
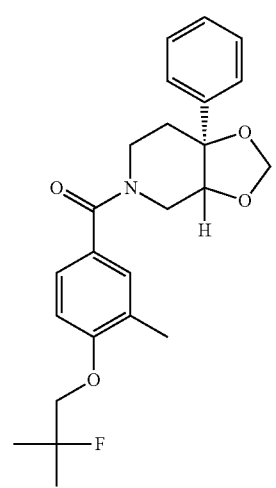 [SMILES: Cc1cc(C(=O)N2CC[C@@]3(c4ccccc4)OCOC3C2)ccc1OCC(C)(C)F]

TABLE 1-continued
121
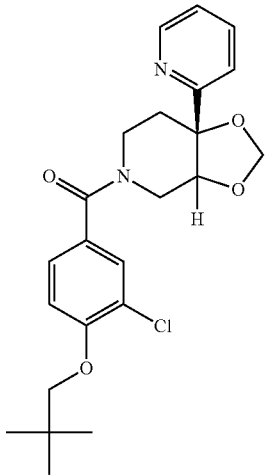 [SMILES: CC(C)(C)COc1ccc(C(=O)N2CC[C@]3(c4ccccn4)OCOC3C2)cc1Cl]
122
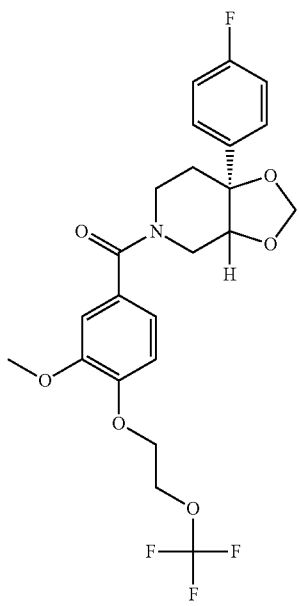
TABLE 1-continued
123
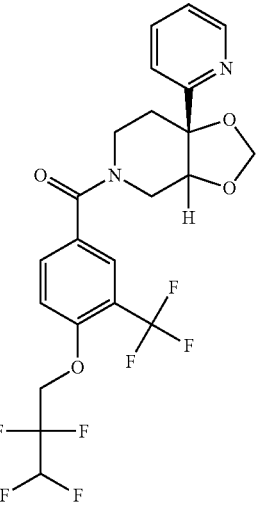
124
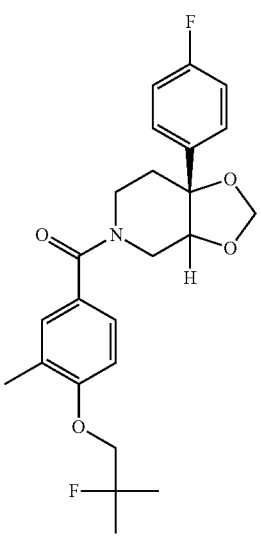 [SMILES: Cc1cc(C(=O)N2CC[C@]3(c4ccc(F)cc4)OCOC3C2)ccc1OCC(C)(C)F]
125
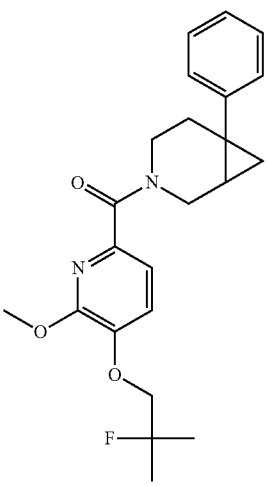

TABLE 1-continued
126
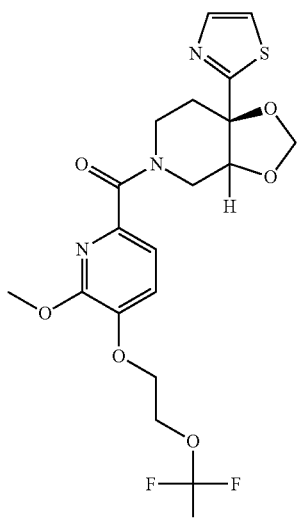
127
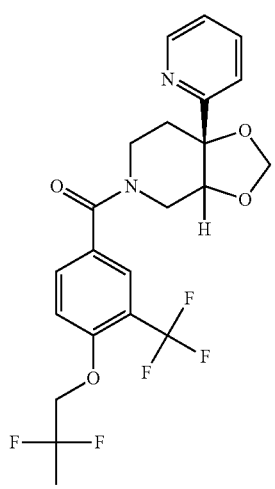 [SMILES: CC(F)(F)COc1ccc(C(=O)N2CC[C@]3(c4ccccn4)OCOC3C2)cc1C(F)(F)F]
128
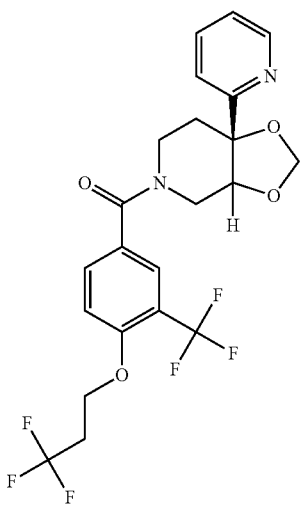 [SMILES: O=C(c1ccc(OCCC(F)(F)F)c(C(F)(F)F)c1)N1CC[C@]2(c3ccccn3)OCOC2C1]
TABLE 1-continued
129
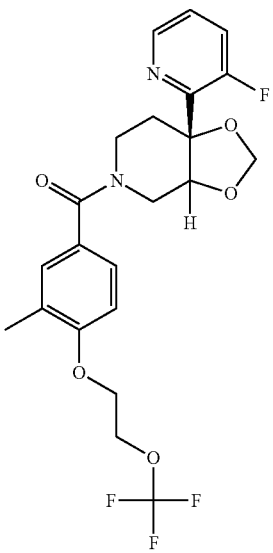 [SMILES: Cc1cc(C(=O)N2CC[C@]3(c4ncccc4F)OCOC3C2)ccc1OCCOC(F)(F)F]
130
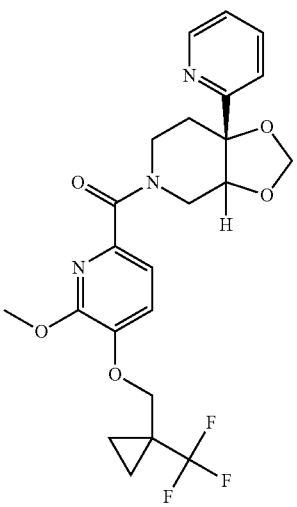 [SMILES: COc1nc(C(=O)N2CC[C@]3(c4ccccn4)OCOC3C2)ccc1OCC1(C(F)(F)F)CC1]

TABLE 1-continued
131
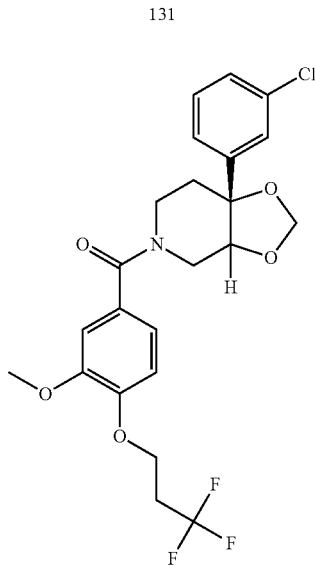
132
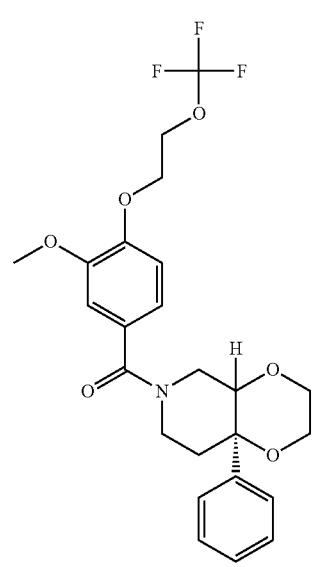 [SMILES: COc1cc(C(=O)N2CC[C@]3(c4ccccc4)OCCOC3C2)ccc1OCCOC(F)(F)F]
TABLE 1-continued
133
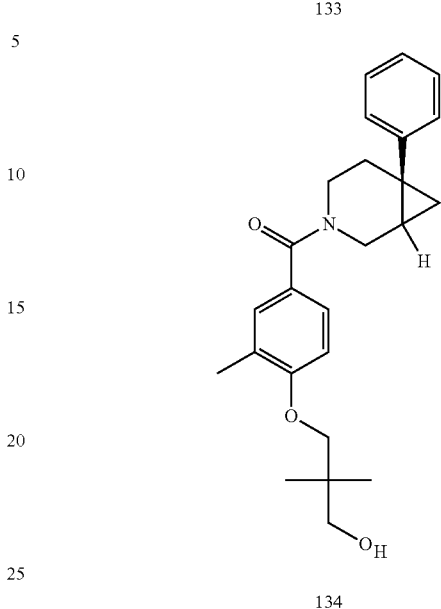
134
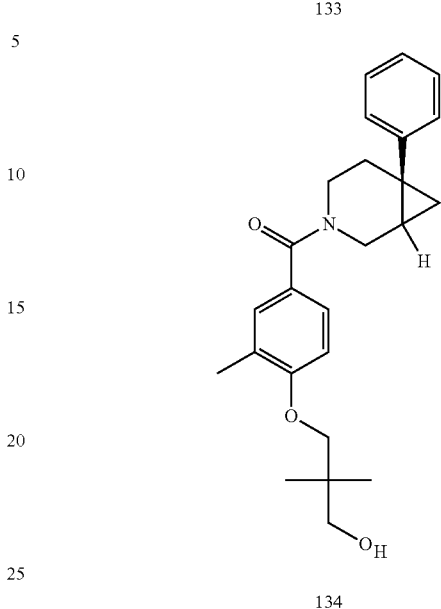
135
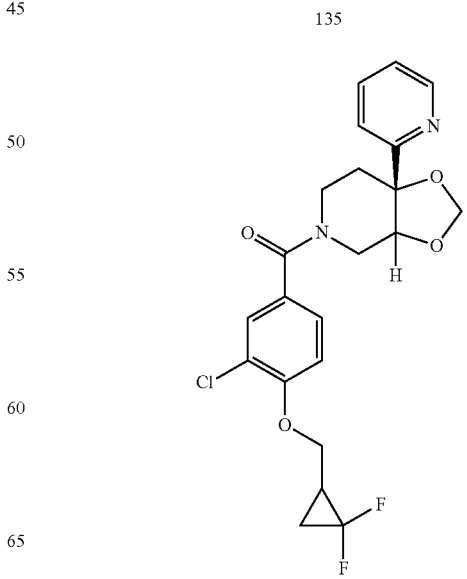

TABLE 1-continued
136
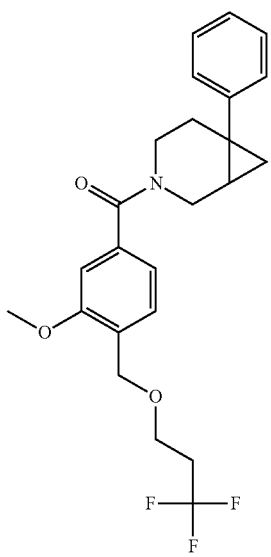 [SMILES: COc1cc(C(=O)N2CCC3(c4ccccc4)CC3C2)ccc1COCCC(F)(F)F]
138
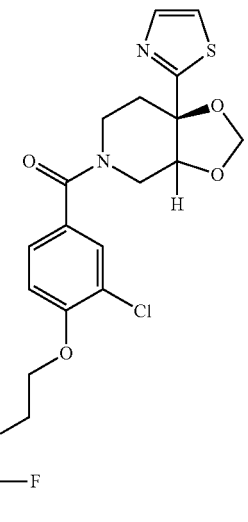
137
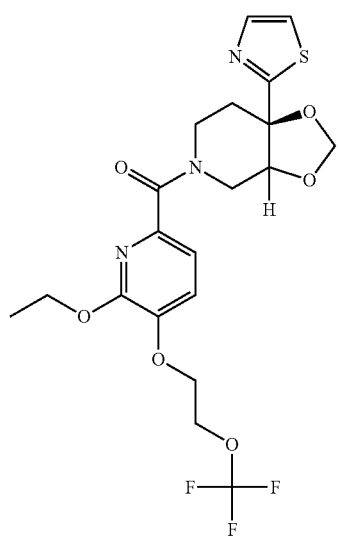
139
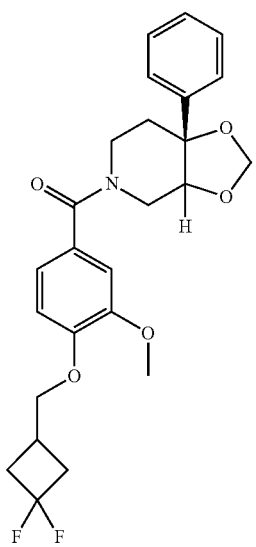 [SMILES: COc1cc(C(=O)N2CC[C@]3(c4ccccc4)OCOC3C2)ccc1OCC1CC(F)(F)C1]

TABLE 1-continued
140
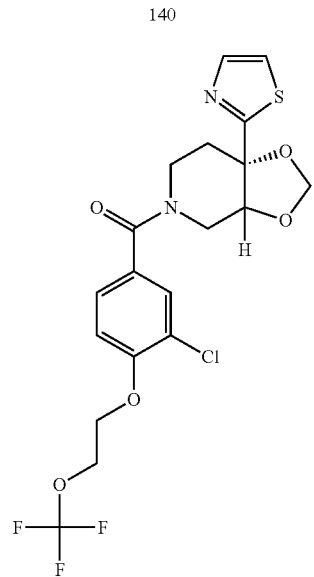
141
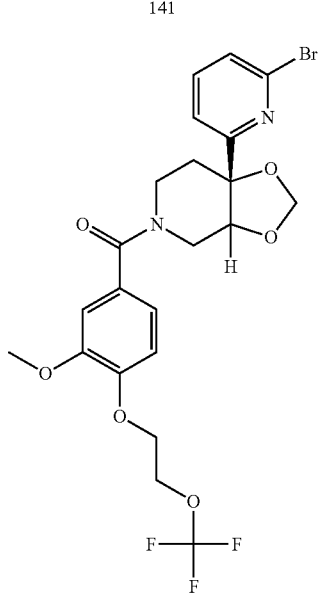
142
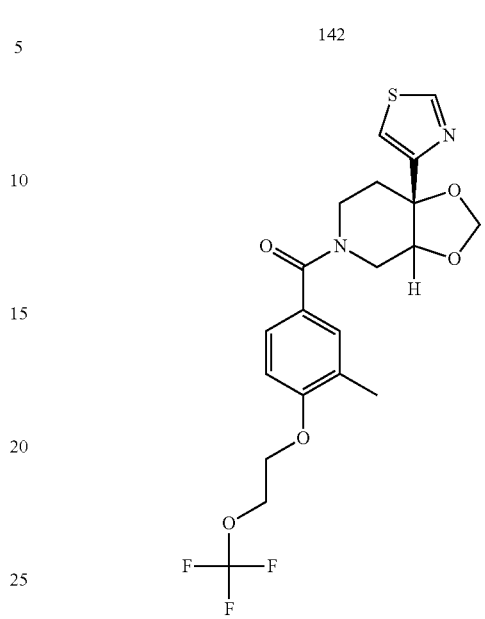
143
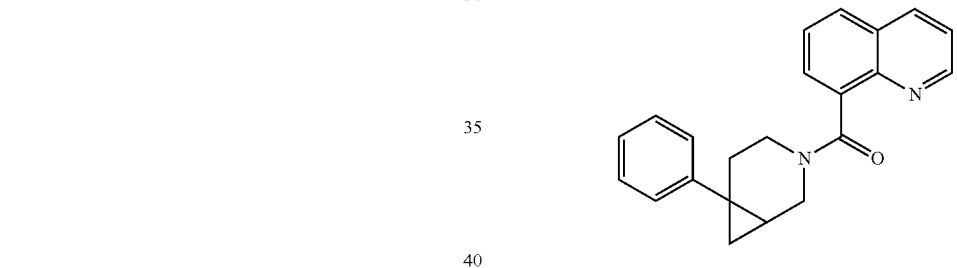
144
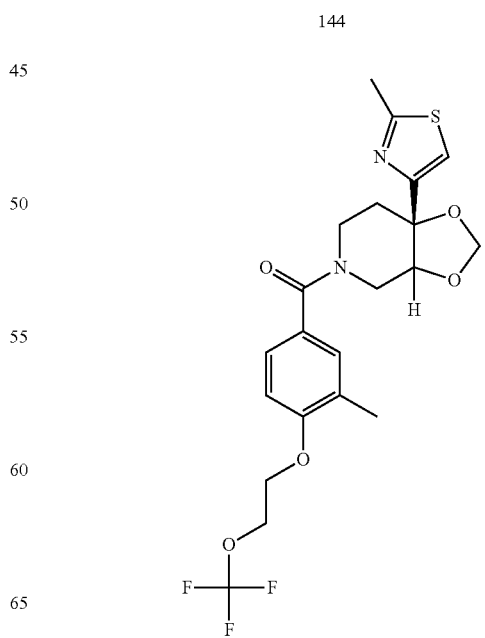

TABLE 1-continued
145
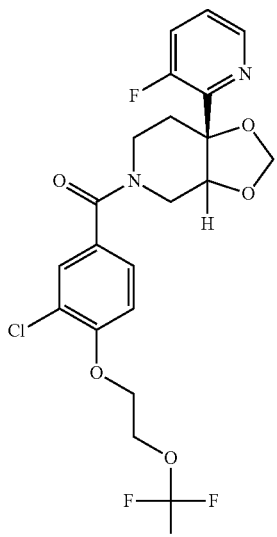
146
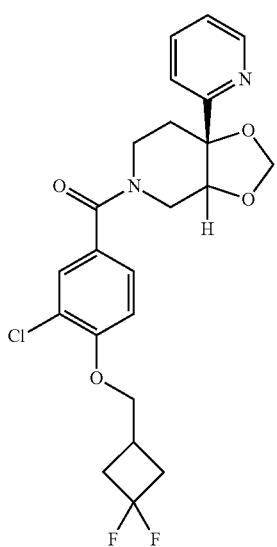 [SMILES: O=C(c1ccc(OCC2CC(F)(F)C2)c(Cl)c1)N1CC[C@]2(c3ccccn3)OCOC2C1]
147
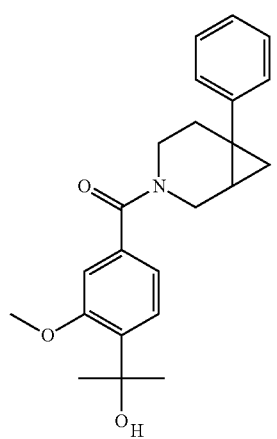
TABLE 1-continued
148
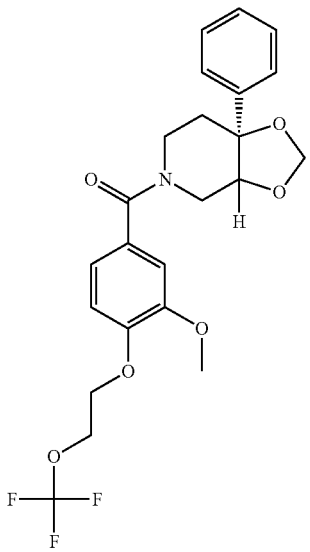
149
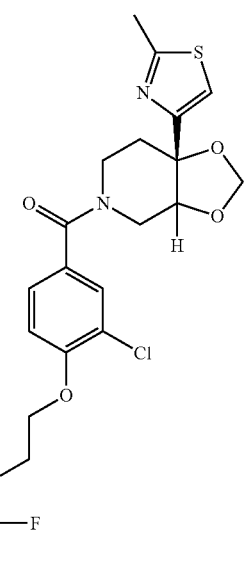

TABLE 1-continued
150
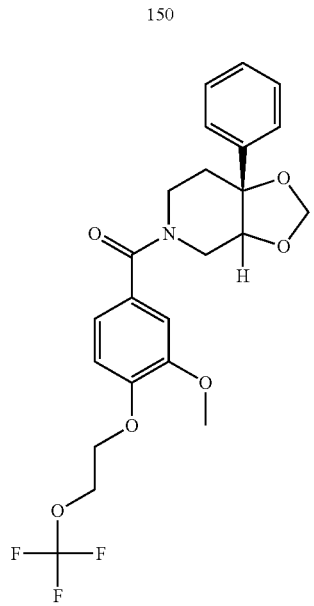
152
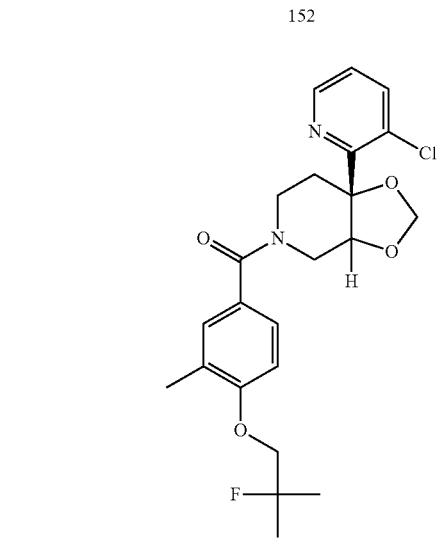
151
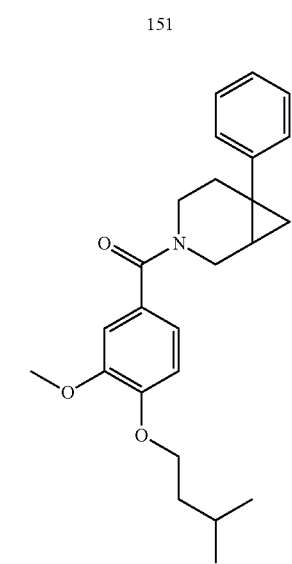
153
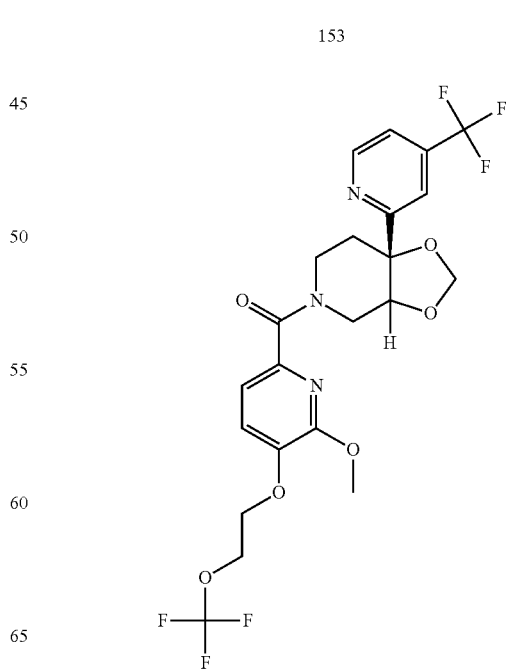

TABLE 1-continued
154
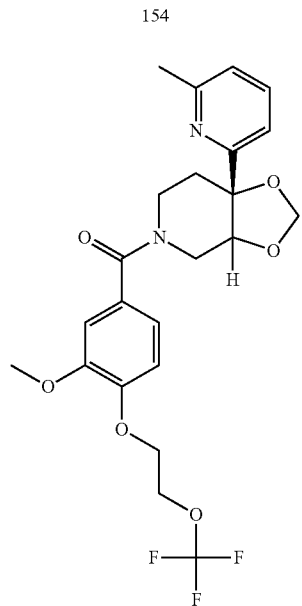
155
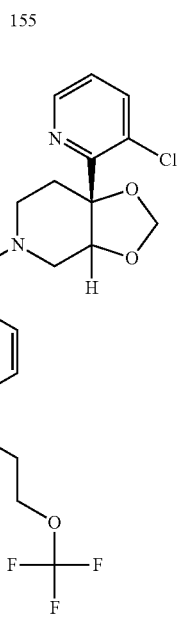
TABLE 1-continued
156
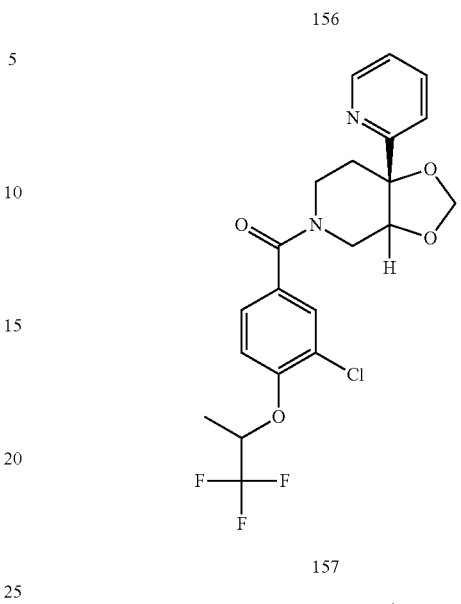
157
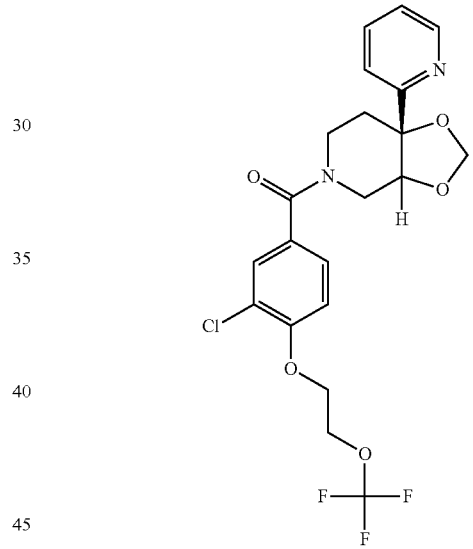
158
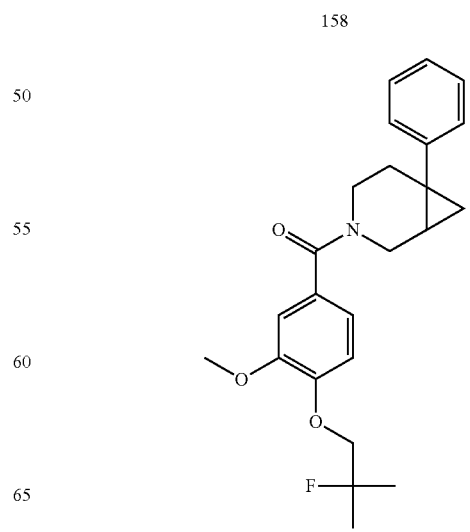

TABLE 1-continued
159
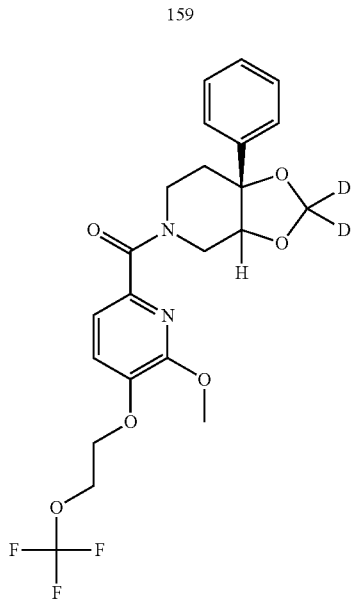
160
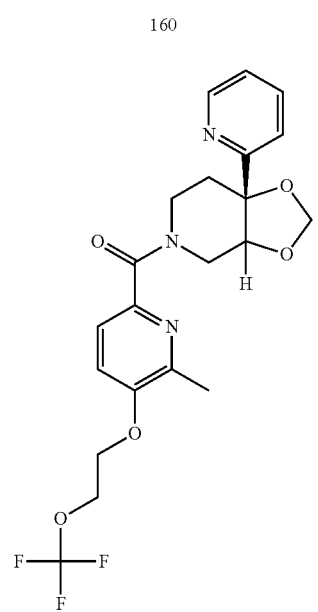
TABLE 1-continued
161
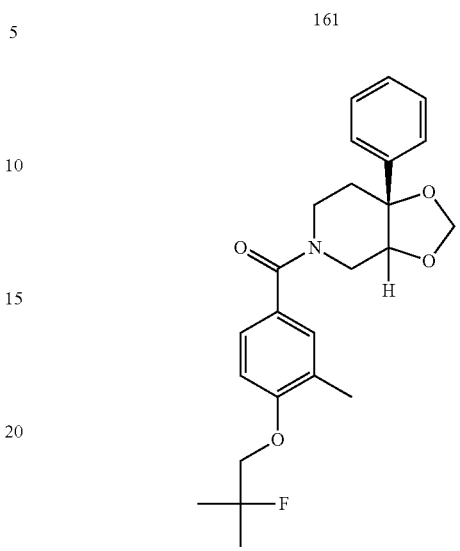
162
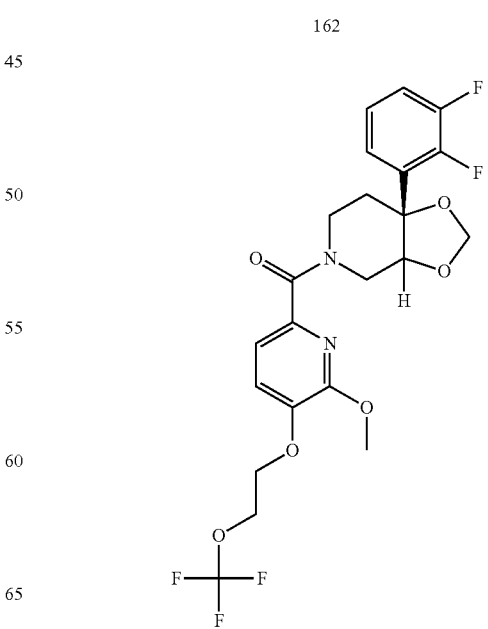

TABLE 1-continued
163
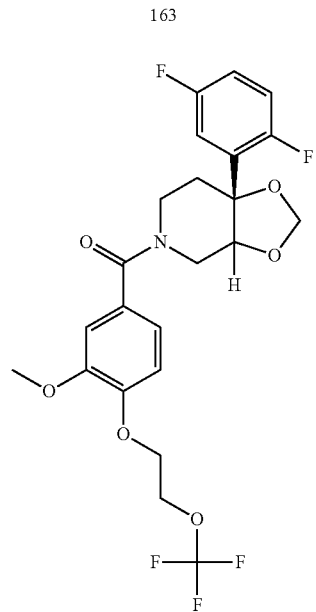
164
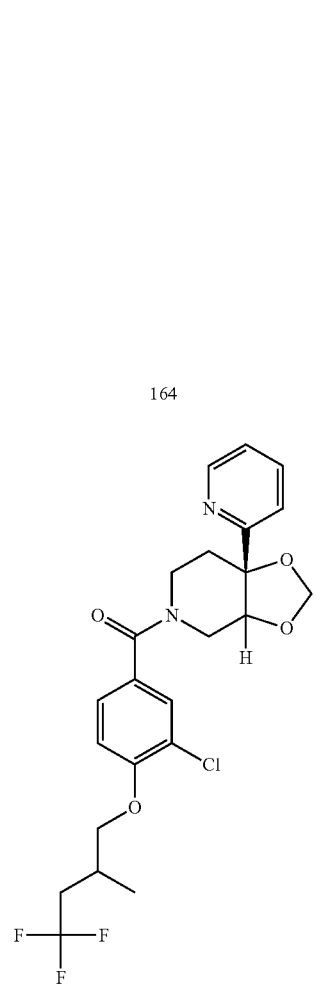
165
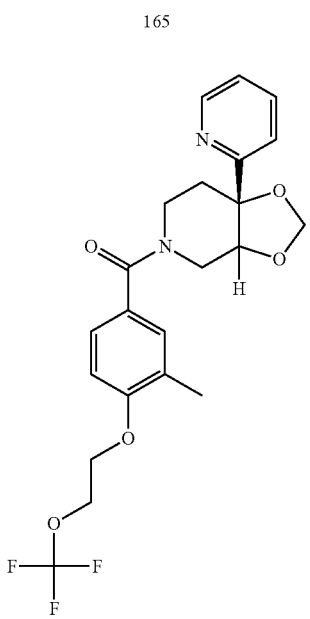
166
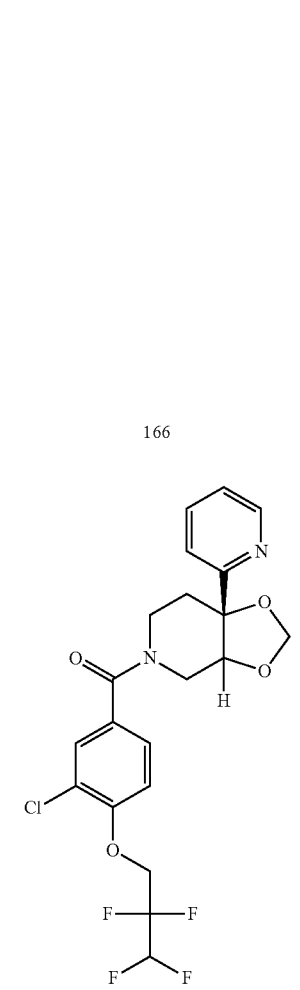

TABLE 1-continued
167
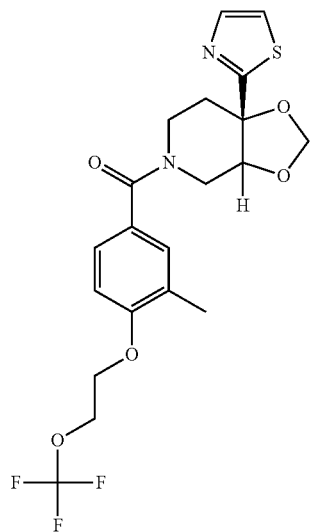 [SMILES: Cc1cc(C(=O)N2CC[C@]3(c4nccs4)OCOC3C2)ccc1OCCOC(F)(F)F]
168
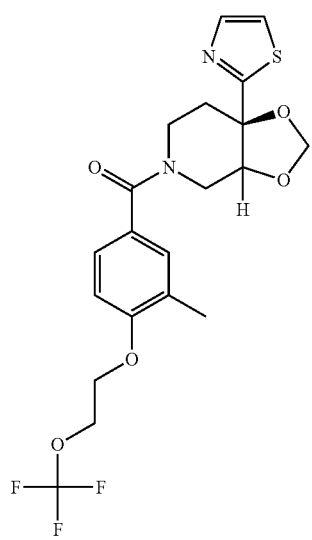
TABLE 1-continued
169
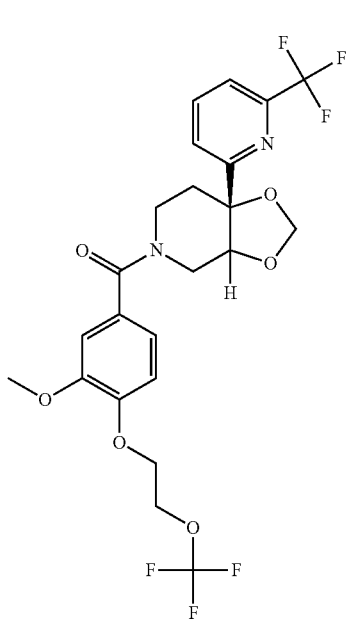 [SMILES: COc1cc(C(=O)N2CC[C@]3(c4cccc(C(F)(F)F)n4)OCOC3C2)ccc1OCCOC(F)(F)F]
170
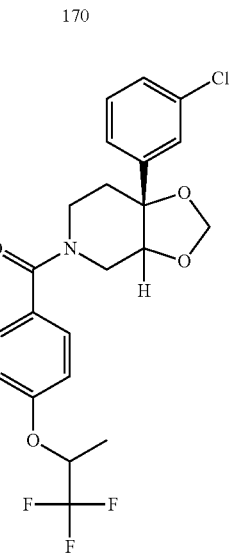

TABLE 1-continued
171
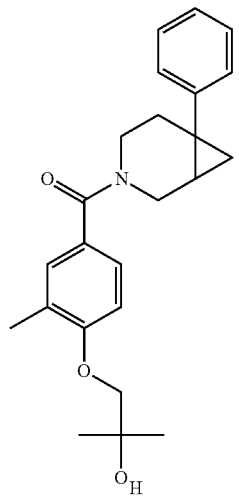
172
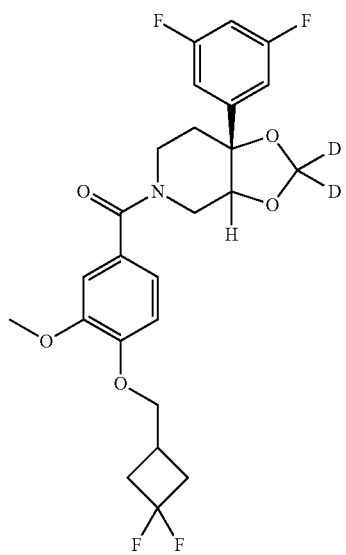 [SMILES: [2H]C1([2H])OC2CN(C(=O)c3ccc(OCC4CC(F)(F)C4)c(OC)c3)CC[C@]2(c2cc(F)cc(F)c2)O1]
173
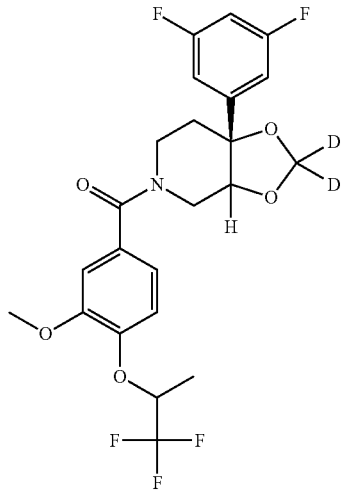 [SMILES: [2H]C1([2H])OC2CN(C(=O)c3ccc(OC(C)C(F)(F)F)c(OC)c3)CC[C@]2(c2cc(F)cc(F)c2)O1]
174
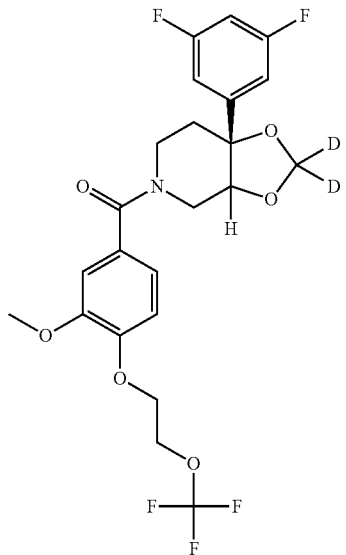 [SMILES: [2H]C1([2H])OC2CN(C(=O)c3ccc(OCCOC(F)(F)F)c(OC)c3)CC[C@]2(c2cc(F)cc(F)c2)O1]

TABLE 1-continued
175
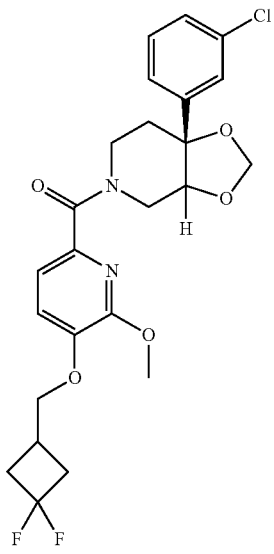 [SMILES: COc1nc(C(=O)N2CC[C@]3(c4cccc(Cl)c4)OCOC3C2)ccc1OCC1CC(F)(F)C1]
176
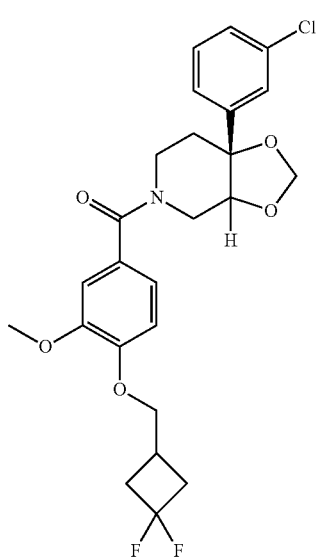 [SMILES: COc1cc(C(=O)N2CC[C@]3(c4cccc(Cl)c4)OCOC3C2)ccc1OCC1CC(F)(F)C1]
TABLE 1-continued
177
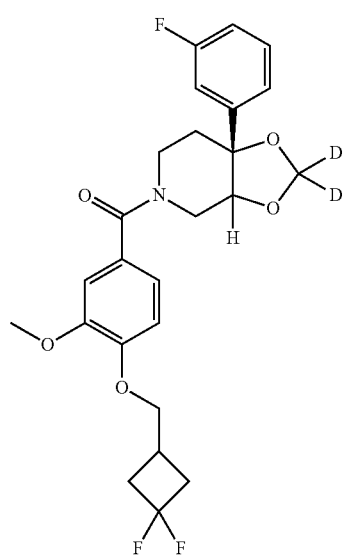 [SMILES: [2H]C1([2H])OC2CN(C(=O)c3ccc(OCC4CC(F)(F)C4)c(OC)c3)CC[C@]2(c2cccc(F)c2)O1]
178
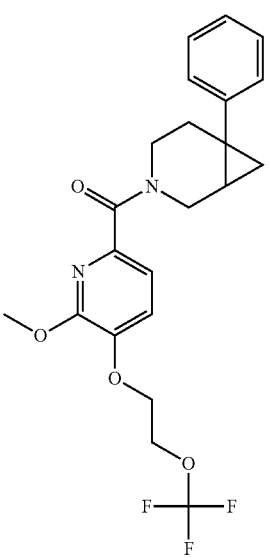 [SMILES: COc1nc(C(=O)N2CCC3(c4ccccc4)CC3C2)ccc1OCCOC(F)(F)F]

TABLE 1-continued
179
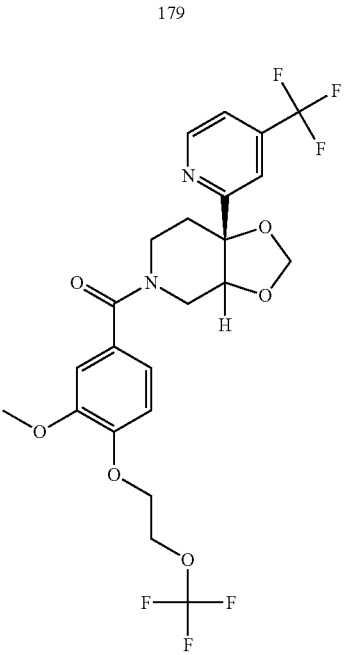
180
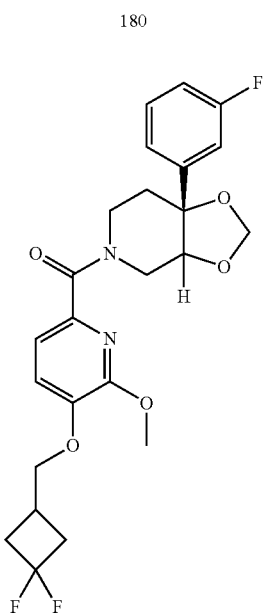
TABLE 1-continued
181
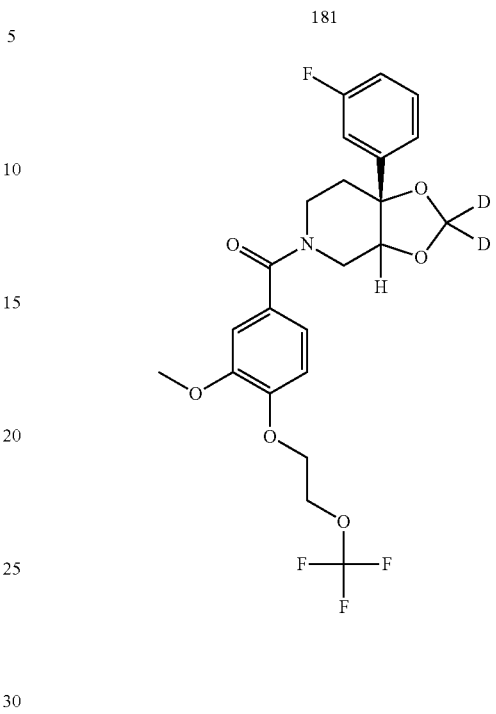
182
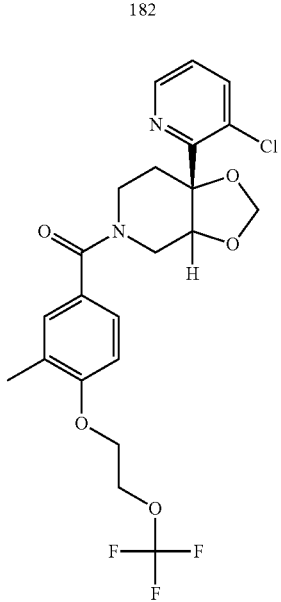

TABLE 1-continued
183
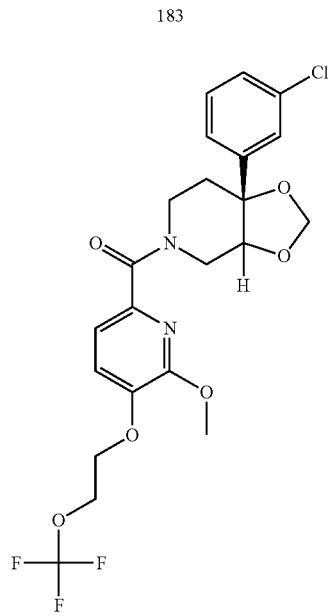
184
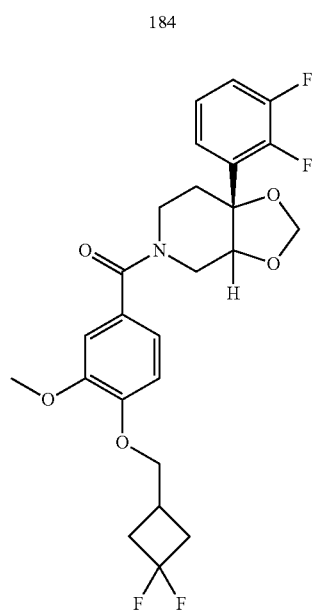
TABLE 1-continued
185
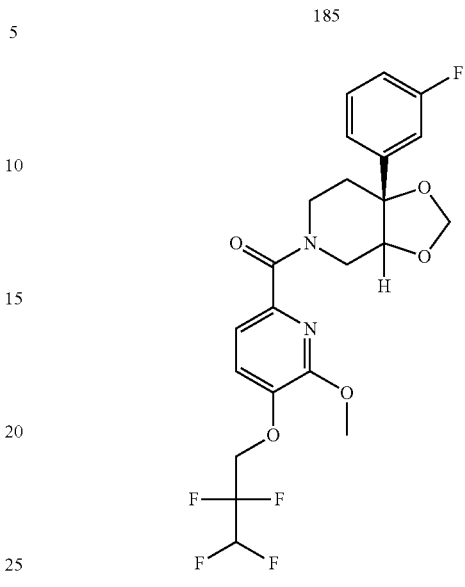
186
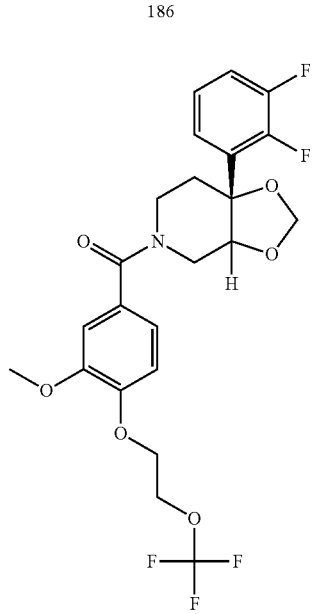

TABLE 1-continued
187
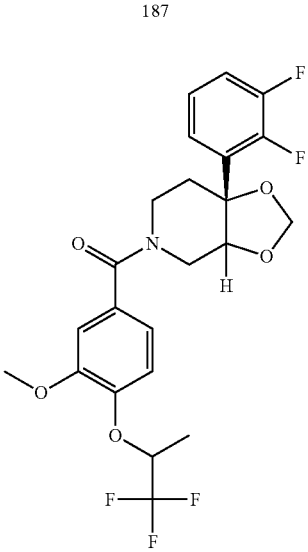
188
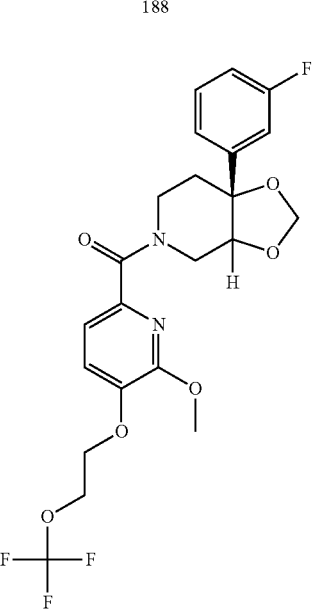
189
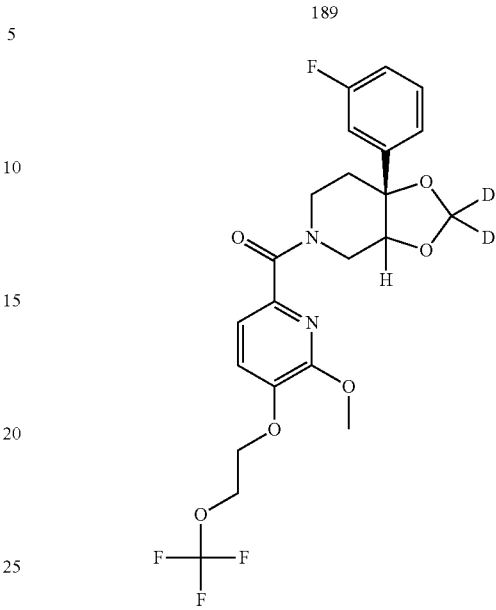
190
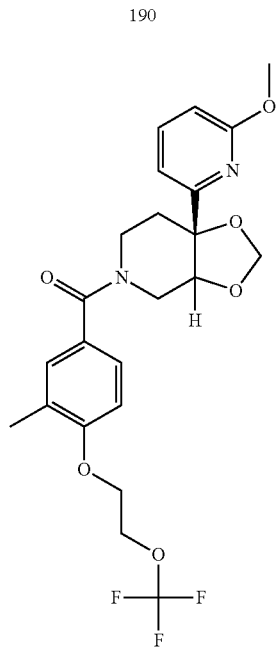

TABLE 1-continued
191
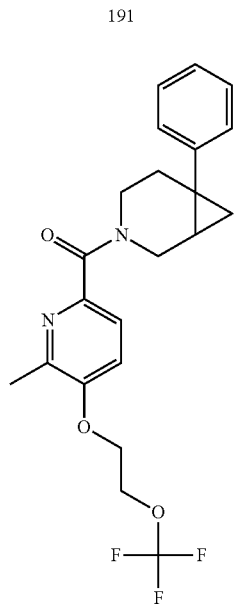
192
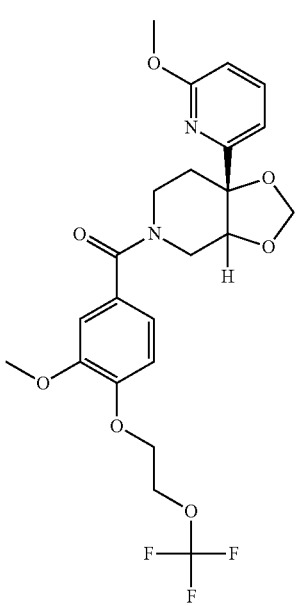 [SMILES: COc1cccc([C@]23CCN(C(=O)c4ccc(OCCOC(F)(F)F)c(OC)c4)CC2OCO3)n1]
TABLE 1-continued
193
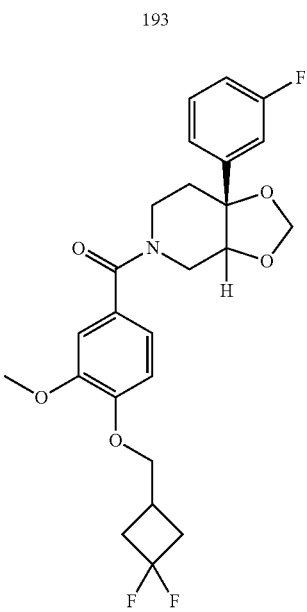
194
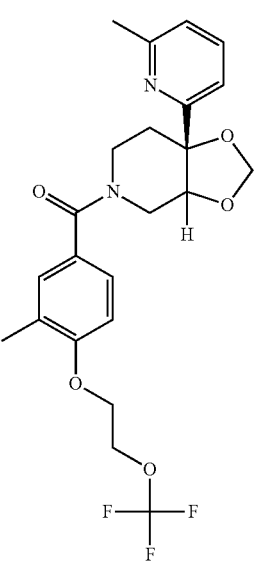 [SMILES: Cc1cccc([C@]23CCN(C(=O)c4ccc(OCCOC(F)(F)F)c(C)c4)CC2OCO3)n1]

TABLE 1-continued
195
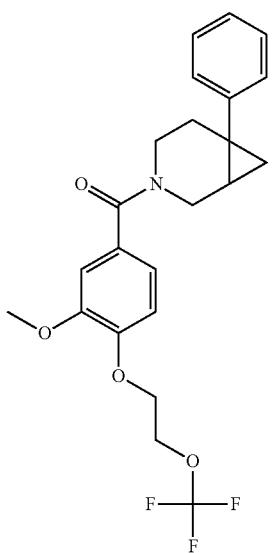
196
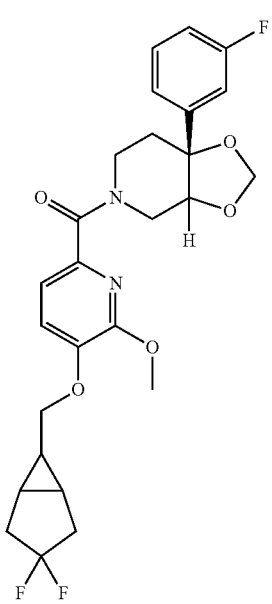 [SMILES: COc1nc(C(=O)N2CC[C@]3(c4cccc(F)c4)OCOC3C2)ccc1OCC1C2CC(F)(F)CC12]
TABLE 1-continued
197
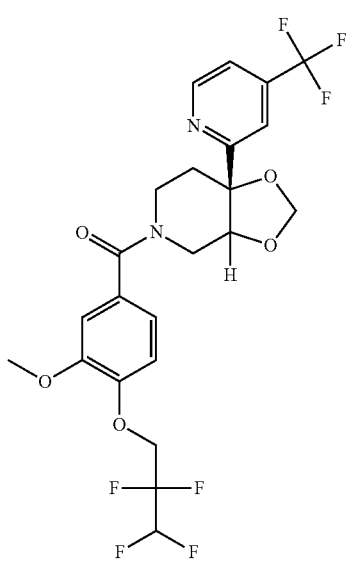 [SMILES: COc1cc(C(=O)N2CC[C@]3(c4cc(C(F)(F)F)ccn4)OCOC3C2)ccc1OCC(F)(F)C(F)F]
198
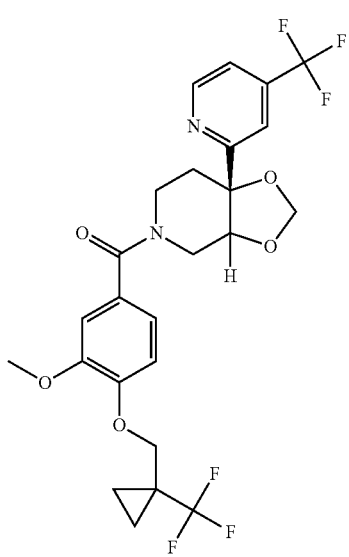 [SMILES: COc1cc(C(=O)N2CC[C@]3(c4cc(C(F)(F)F)ccn4)OCOC3C2)ccc1OCC1(C(F)(F)F)CC1]

TABLE 1-continued
199
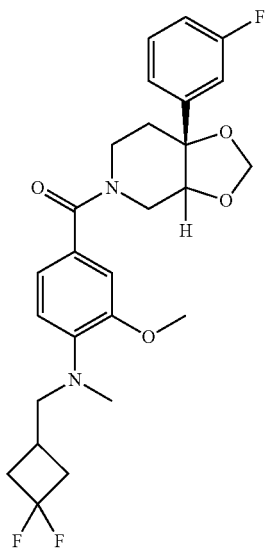
200
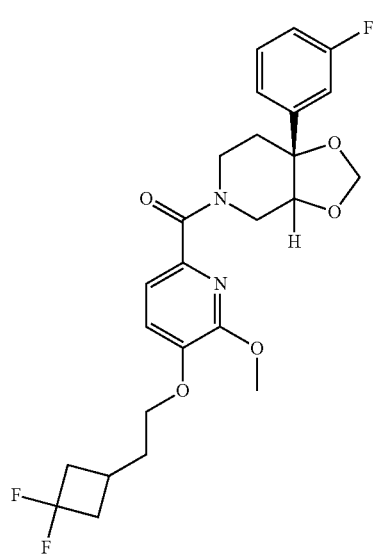 [SMILES: COc1nc(C(=O)N2CC[C@]3(c4cccc(F)c4)OCOC3C2)ccc1OCCC1CC(F)(F)C1]
TABLE 1-continued
201
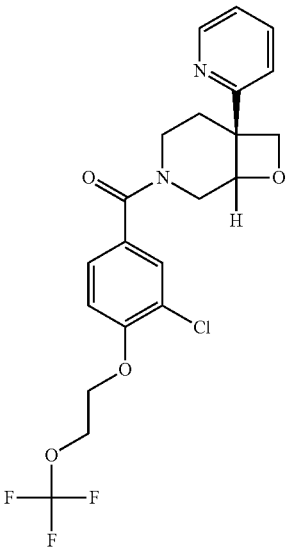 [SMILES: O=C(c1ccc(OCCOC(F)(F)F)c(Cl)c1)N1CC[C@]2(c3ccccn3)COC2C1]
202
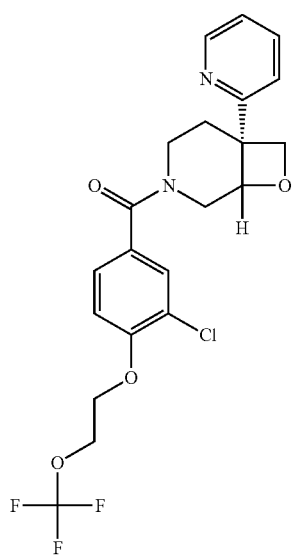 [SMILES: O=C(c1ccc(OCCOC(F)(F)F)c(Cl)c1)N1CC[C@@]2(c3ccccn3)COC2C1]

TABLE 1-continued
203
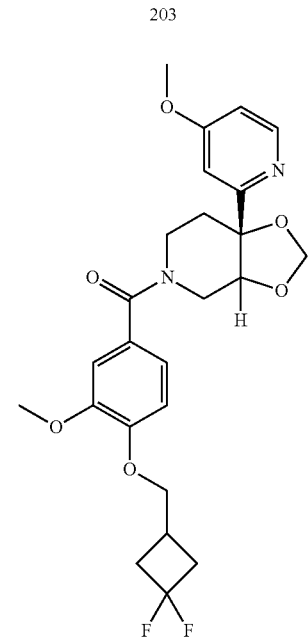
205
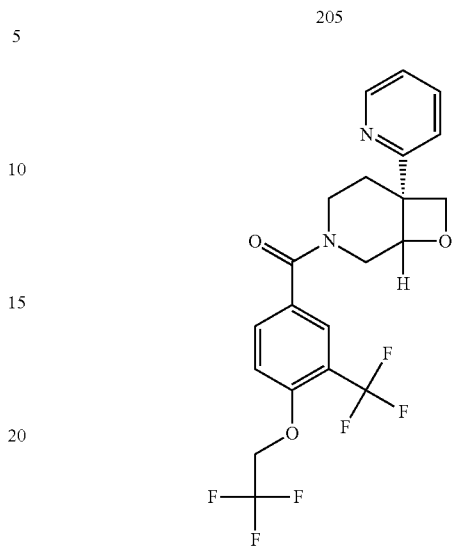
204
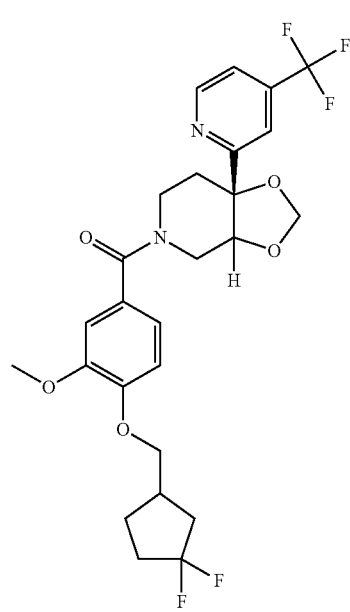 [SMILES: COc1cc(C(=O)N2CC[C@]3(c4cc(C(F)(F)F)ccn4)OCOC3C2)ccc1OCC1CCC(F)(F)C1]
206
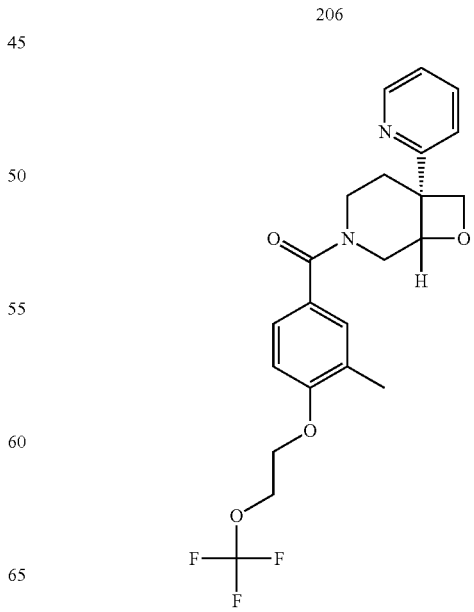

TABLE 1-continued
207
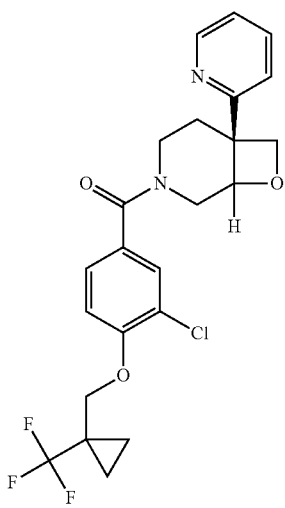 [SMILES: O=C(c1ccc(OCC2(C(F)(F)F)CC2)c(Cl)c1)N1CC[C@]2(c3ccccn3)COC2C1]
208
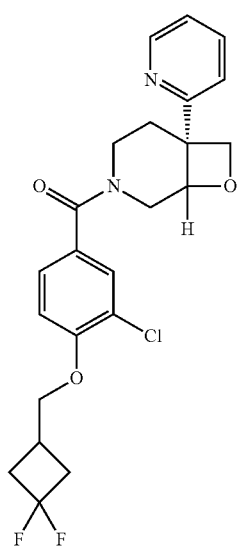
TABLE 1-continued
209
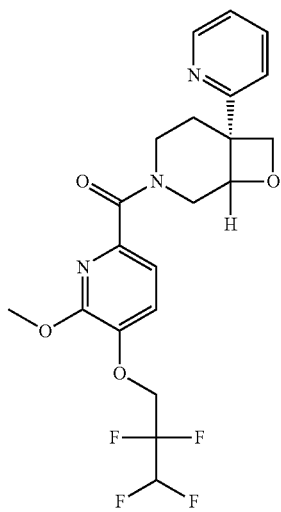 [SMILES: COc1nc(C(=O)N2CC[C@@]3(c4ccccn4)COC3C2)ccc1OCC(F)(F)C(F)F]
210
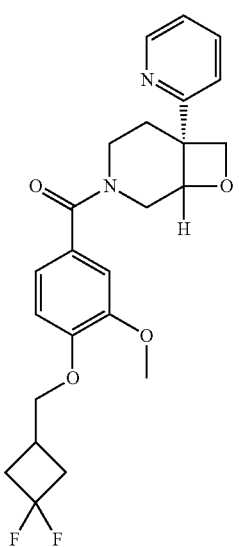

TABLE 1-continued
211
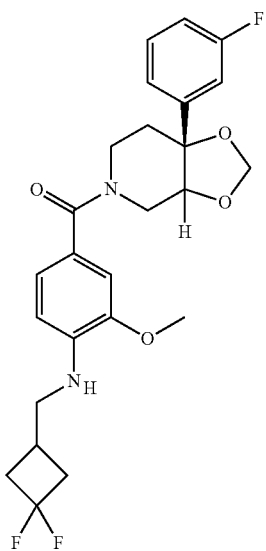
212
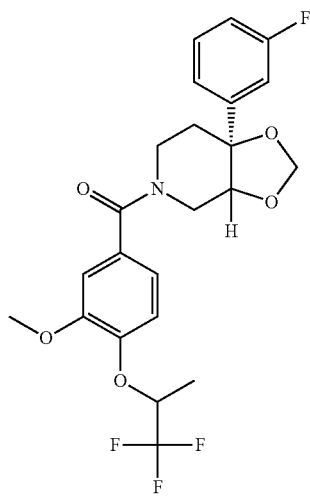 [SMILES: COc1cc(C(=O)N2CC[C@@]3(c4cccc(F)c4)OCOC3C2)ccc1OC(C)C(F)(F)F]
213
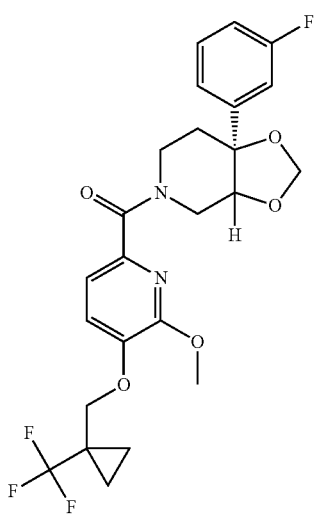 [SMILES: COc1nc(C(=O)N2CC[C@@]3(c4cccc(F)c4)OCOC3C2)ccc1OCC1(C(F)(F)F)CC1]
214
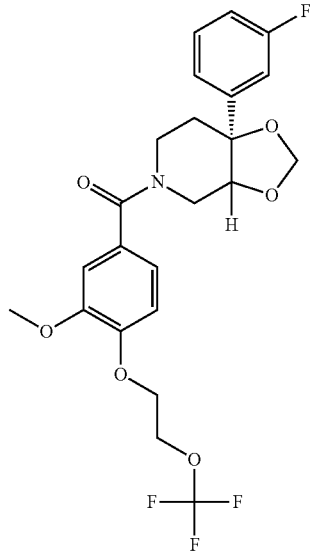 [SMILES: COc1cc(C(=O)N2CC[C@@]3(c4cccc(F)c4)OCOC3C2)ccc1OCCOC(F)(F)F]

TABLE 1-continued
215
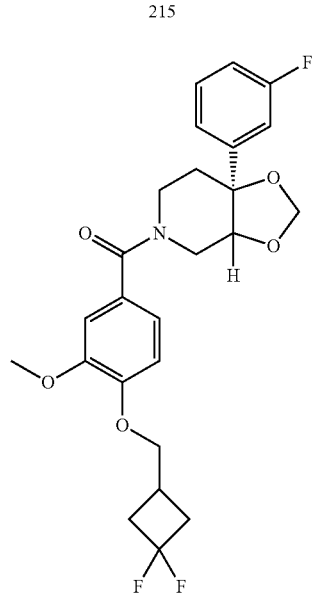
216
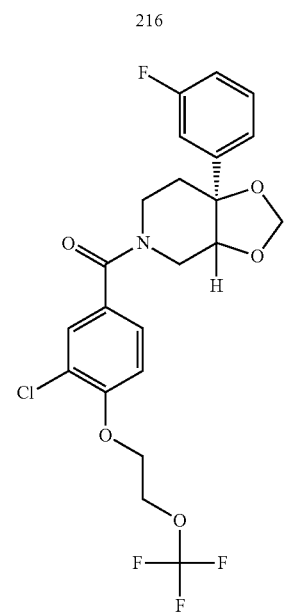
TABLE 1-continued
217
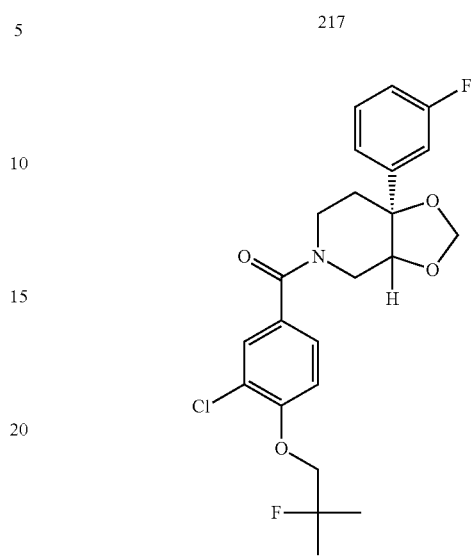
218
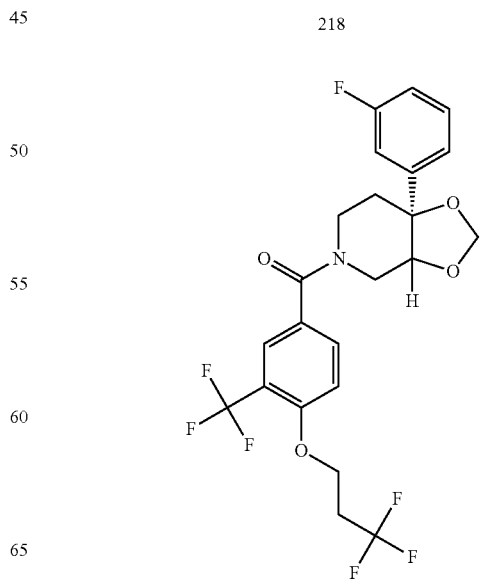

TABLE 1-continued
219
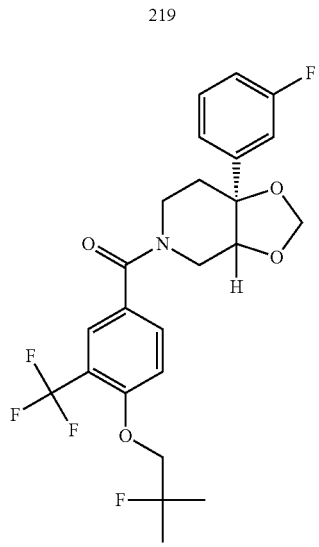
220
221
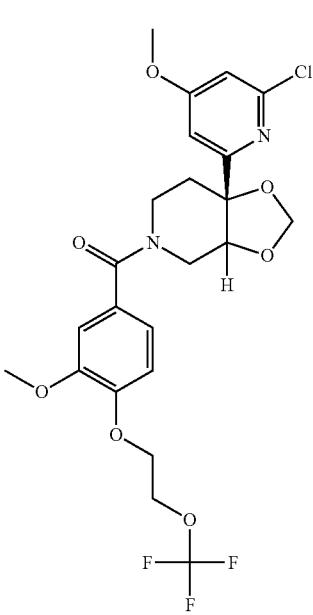 [SMILES: COc1cc(Cl)nc([C@]23CCN(C(=O)c4ccc(OCCOC(F)(F)F)c(OC)c4)CC2OCO3)c1]
222
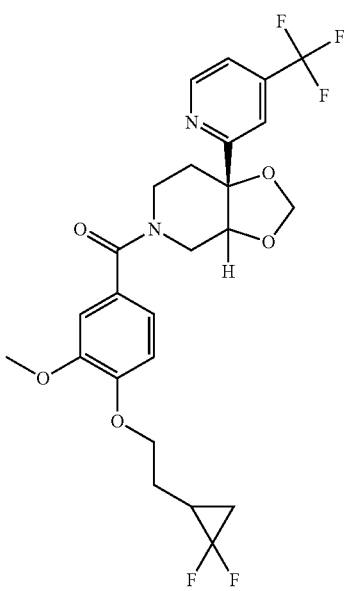 [SMILES: COc1cc(C(=O)N2CC[C@]3(c4cc(C(F)(F)F)ccn4)OCOC3C2)ccc1OCCC1CC1(F)F]

TABLE 1-continued
223
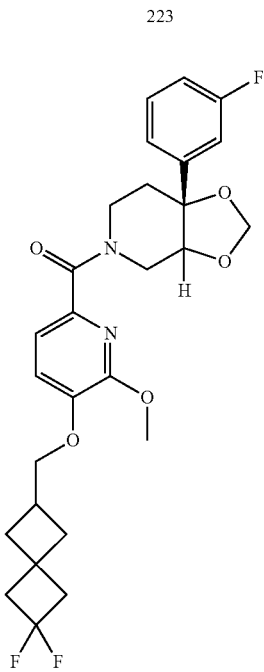
224
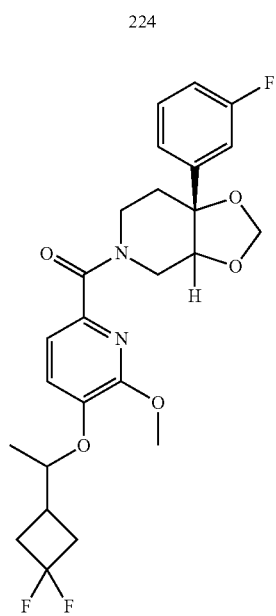
TABLE 1-continued
225
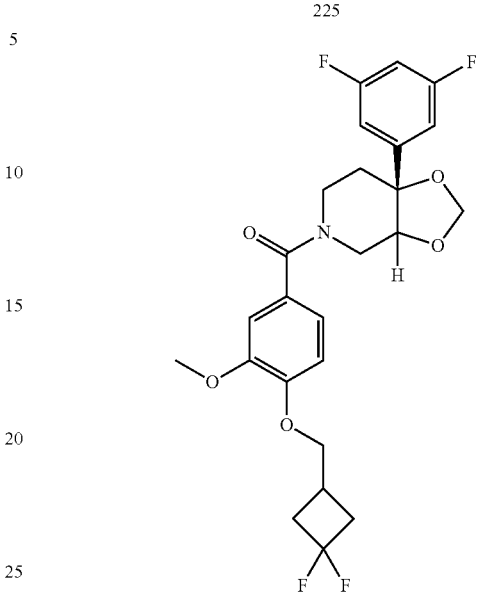
226
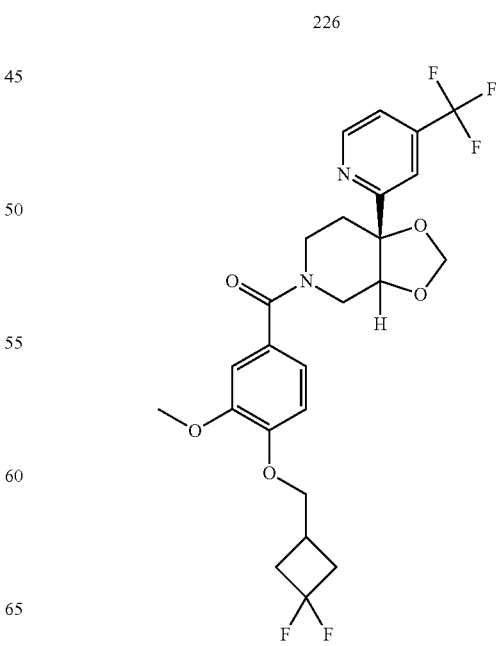

TABLE 1-continued
227
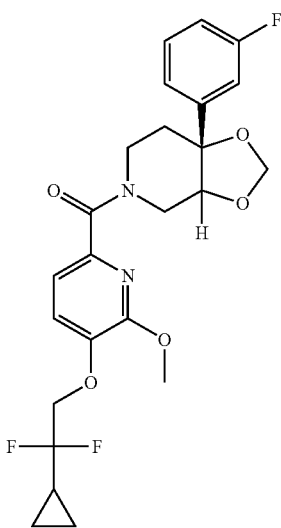 [SMILES: COc1nc(C(=O)N2CC[C@]3(c4cccc(F)c4)OCOC3C2)ccc1OCC(F)(F)C1CC1]
229
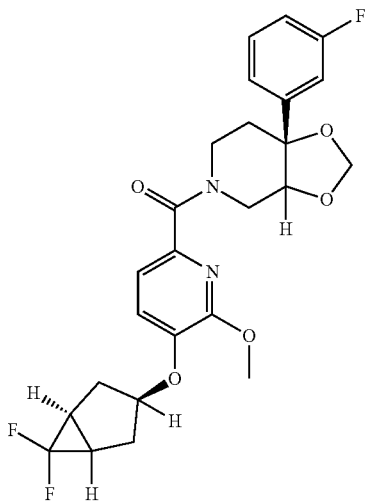 [SMILES: COc1nc(C(=O)N2CC[C@]3(c4cccc(F)c4)OCOC3C2)ccc1O[C@H]1CC2[C@H](C1)C2(F)F]
228
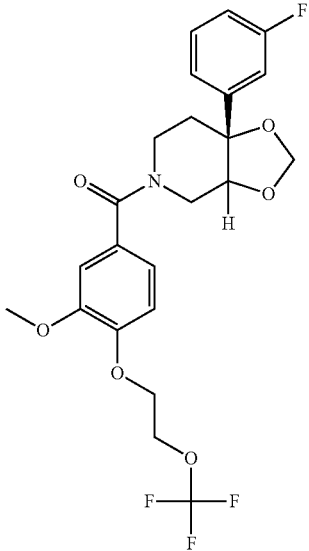
230
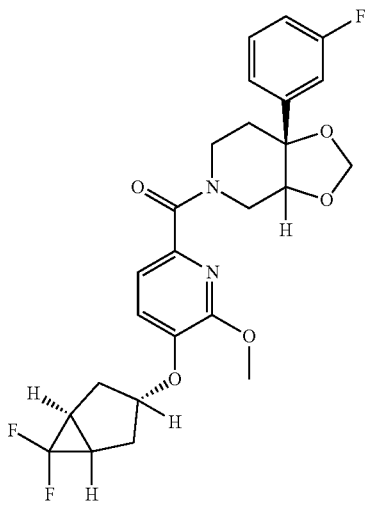 [SMILES: COc1nc(C(=O)N2CC[C@]3(c4cccc(F)c4)OCOC3C2)ccc1O[C@@H]1CC2[C@H](C1)C2(F)F]

TABLE 1-continued
231
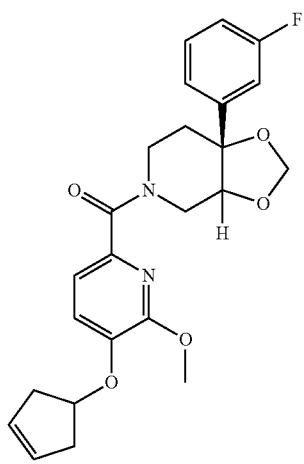 [SMILES: COc1nc(C(=O)N2CC[C@]3(c4cccc(F)c4)OCOC3C2)ccc1OC1CC=CC1]
232
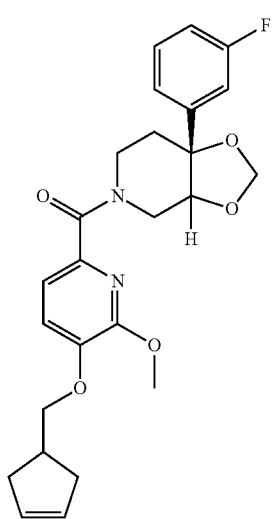 [SMILES: COc1nc(C(=O)N2CC[C@]3(c4cccc(F)c4)OCOC3C2)ccc1OCC1CC=CC1]
233
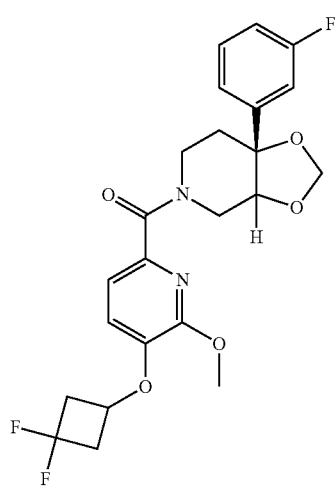 [SMILES: COc1nc(C(=O)N2CC[C@]3(c4cccc(F)c4)OCOC3C2)ccc1OC1CC(F)(F)C1]
TABLE 1-continued
234
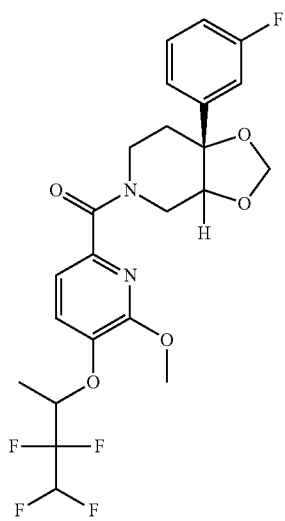 [SMILES: COc1nc(C(=O)N2CC[C@]3(c4cccc(F)c4)OCOC3C2)ccc1OC(C)C(F)(F)C(F)F]
235
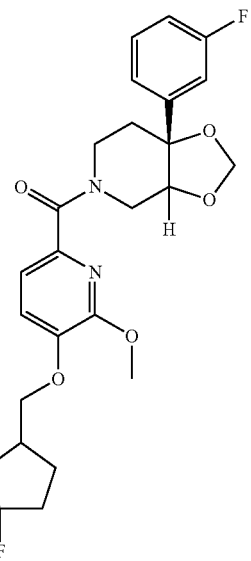

TABLE 1-continued
236
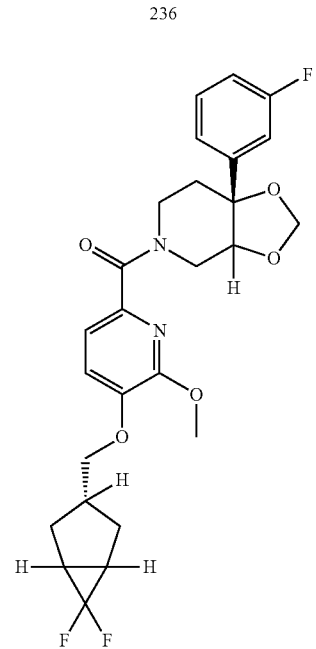
237
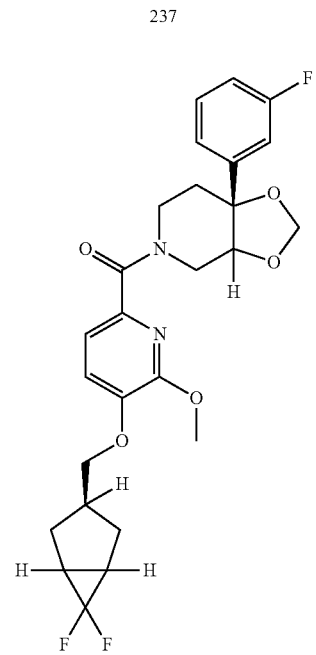
TABLE 1-continued
238
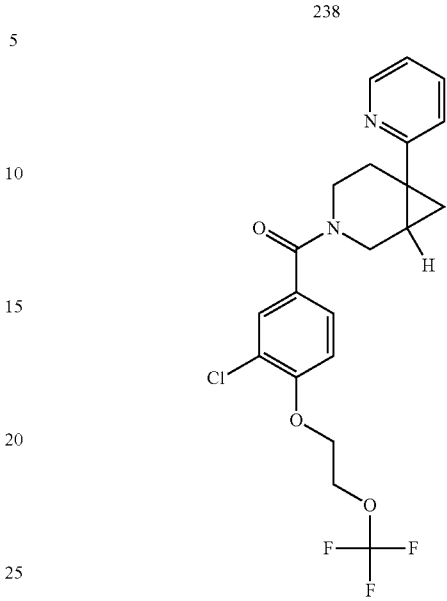
239
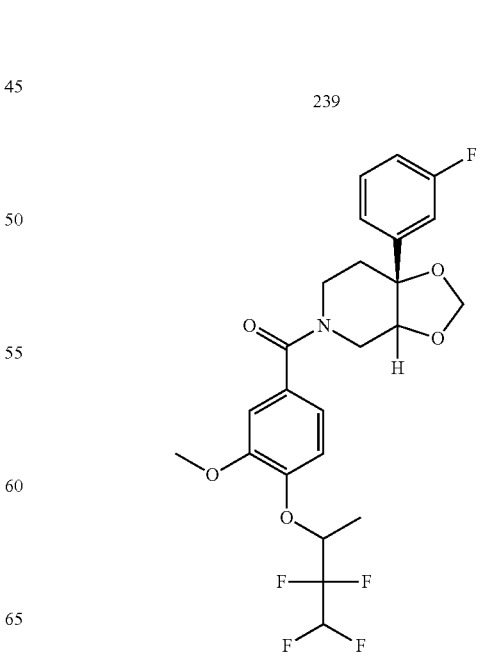

TABLE 1-continued
240
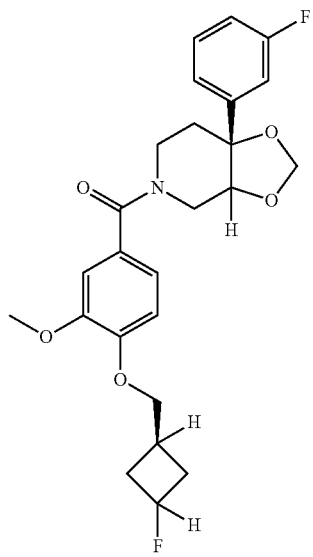
241
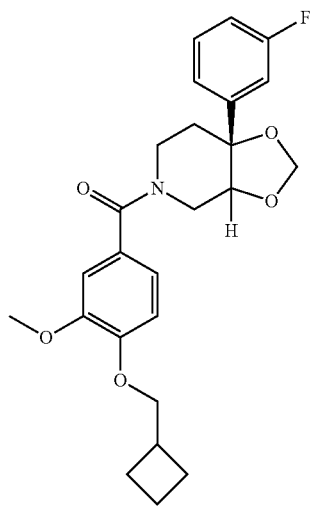 [SMILES: COc1cc(C(=O)N2CC[C@]3(c4cccc(F)c4)OCOC3C2)ccc1OCC1CCC1]
242
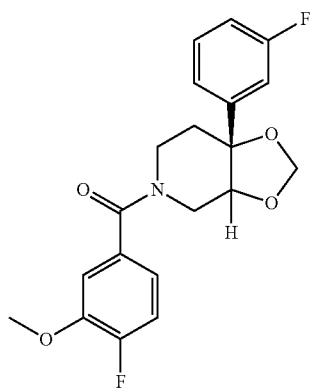 [SMILES: COc1cc(C(=O)N2CC[C@]3(c4cccc(F)c4)OCOC3C2)ccc1F]
TABLE 1-continued
243
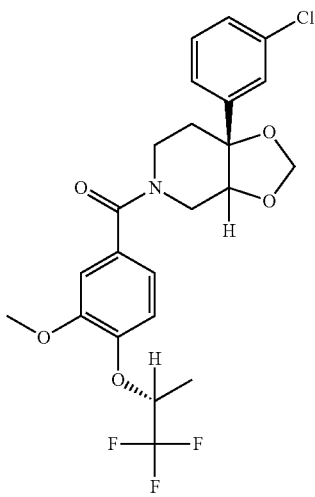 [SMILES: COc1cc(C(=O)N2CC[C@]3(c4cccc(Cl)c4)OCOC3C2)ccc1O[C@H](C)C(F)(F)F]
244
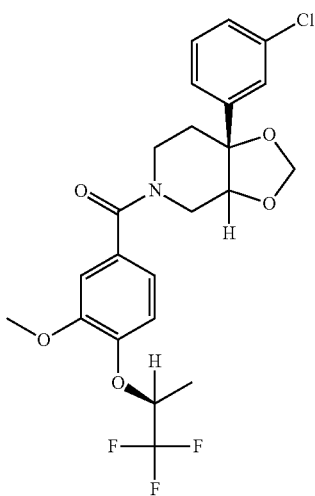 [SMILES: COc1cc(C(=O)N2CC[C@]3(c4cccc(Cl)c4)OCOC3C2)ccc1O[C@@H](C)C(F)(F)F]

TABLE 1-continued
245
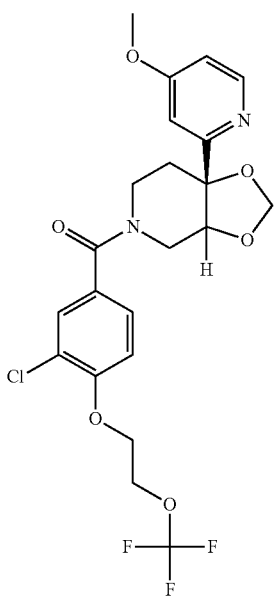 [SMILES: COc1ccnc([C@]23CCN(C(=O)c4ccc(OCCOC(F)(F)F)c(Cl)c4)CC2OCO3)c1]
246
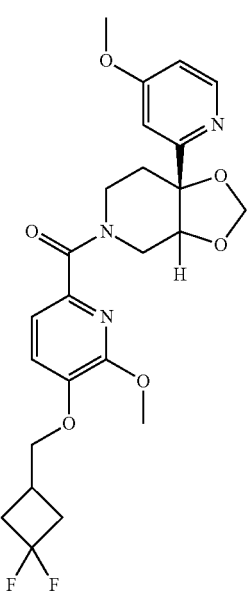 [SMILES: COc1ccnc([C@]23CCN(C(=O)c4ccc(OCC5CC(F)(F)C5)c(OC)n4)CC2OCO3)c1]
TABLE 1-continued
247
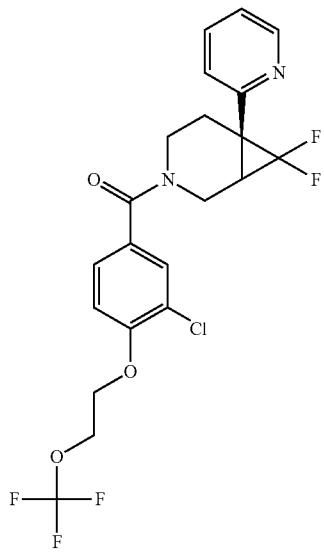 [SMILES: O=C(c1ccc(OCCOC(F)(F)F)c(Cl)c1)N1CC[C@@]2(c3ccccn3)C(C1)C2(F)F]
248
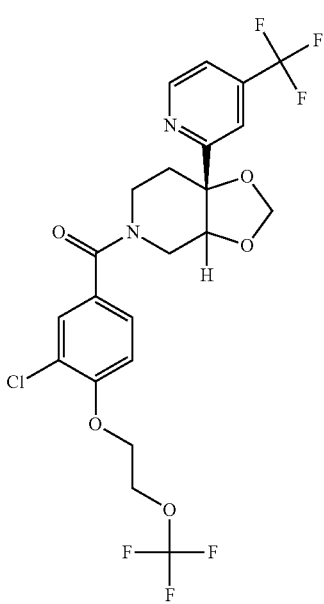 [SMILES: O=C(c1ccc(OCCOC(F)(F)F)c(Cl)c1)N1CC[C@]2(c3cc(C(F)(F)F)ccn3)OCOC2C1]

TABLE 1-continued
249
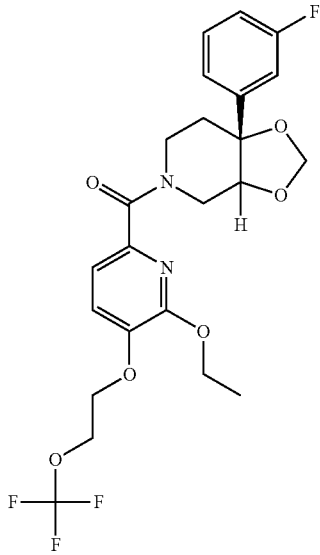 [SMILES: CCOc1nc(C(=O)N2CC[C@]3(c4cccc(F)c4)OCOC3C2)ccc1OCCOC(F)(F)F]
250
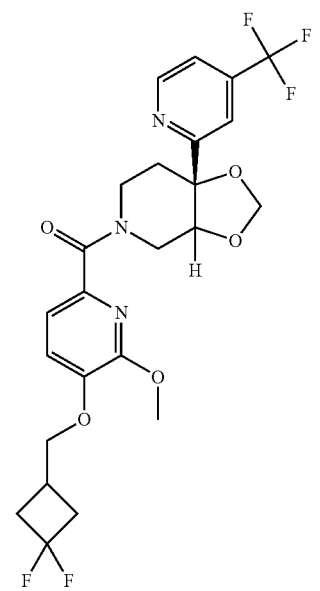 [SMILES: COc1nc(C(=O)N2CC[C@]3(c4cc(C(F)(F)F)ccn4)OCOC3C2)ccc1OCC1CC(F)(F)C1]
TABLE 1-continued
251
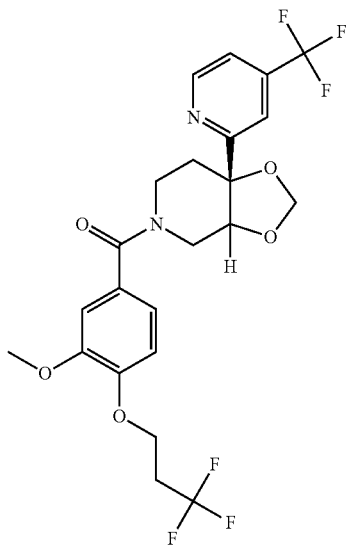 [SMILES: COc1cc(C(=O)N2CC[C@]3(c4cc(C(F)(F)F)ccn4)OCOC3C2)ccc1OCCC(F)(F)F]
252
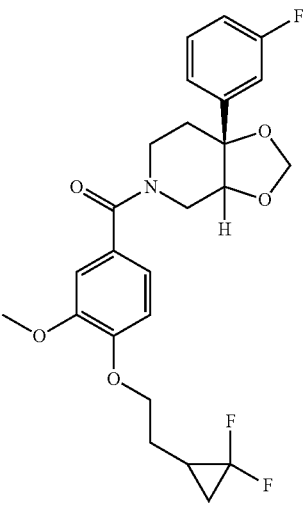 [SMILES: COc1cc(C(=O)N2CC[C@]3(c4cccc(F)c4)OCOC3C2)ccc1OCCC1CC1(F)F]

TABLE 1-continued
253
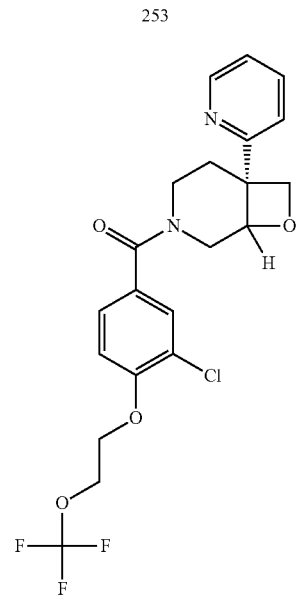
254
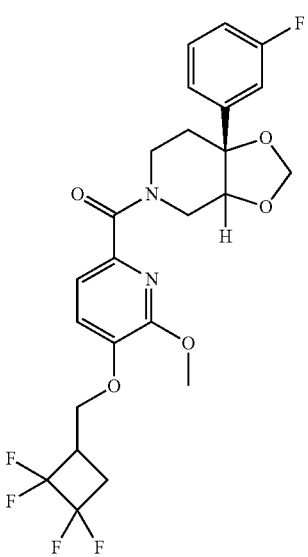 [SMILES: COc1nc(C(=O)N2CC[C@]3(c4cccc(F)c4)OCOC3C2)ccc1OCC1CC(F)(F)C1(F)F]
TABLE 1-continued
255
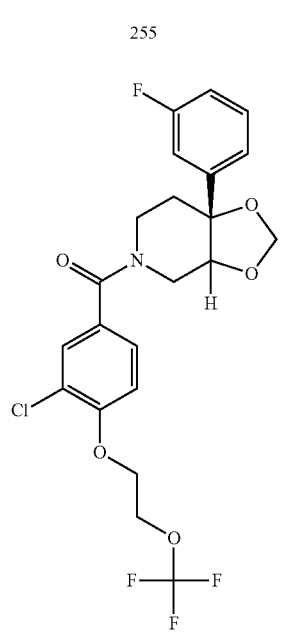
256
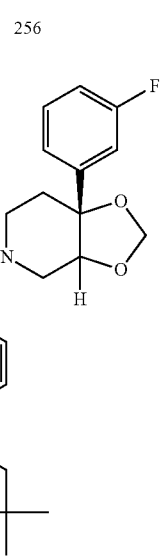

TABLE 1-continued
257
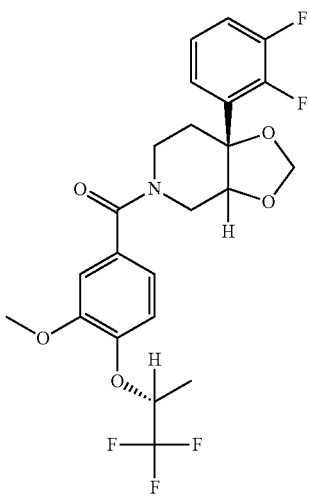 [SMILES: COc1cc(C(=O)N2CC[C@]3(c4cccc(F)c4F)OCOC3C2)ccc1O[C@H](C)C(F)(F)F]
259
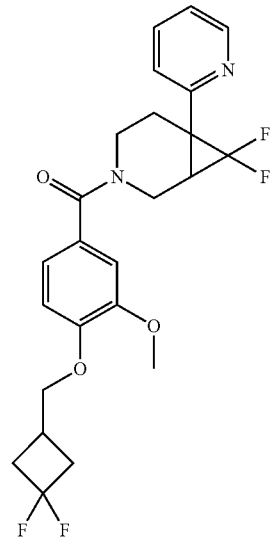
258
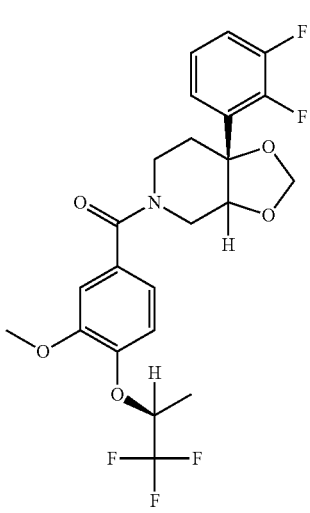 [SMILES: COc1cc(C(=O)N2CC[C@]3(c4cccc(F)c4F)OCOC3C2)ccc1O[C@@H](C)C(F)(F)F]
260
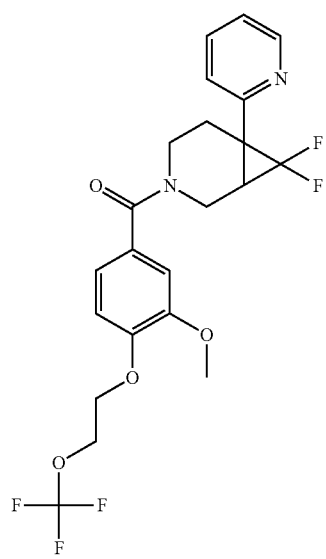 [SMILES: COc1cc(C(=O)N2CCC3(c4ccccn4)C(C2)C3(F)F)ccc1OCCOC(F)(F)F]

TABLE 1-continued
261
262
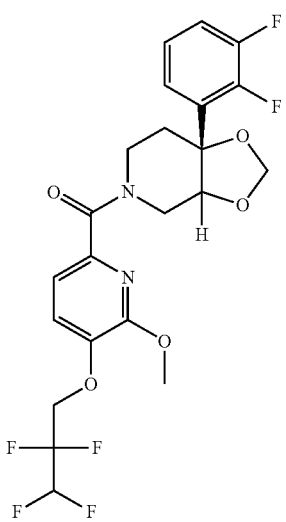 [SMILES: COc1nc(C(=O)N2CC[C@]3(c4cccc(F)c4F)OCOC3C2)ccc1OCC(F)(F)C(F)F]
263
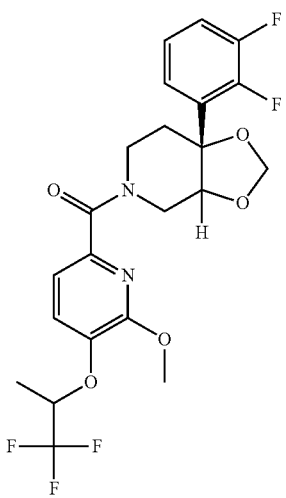 [SMILES: COc1nc(C(=O)N2CC[C@]3(c4cccc(F)c4F)OCOC3C2)ccc1OC(C)C(F)(F)F]
TABLE 1-continued
264
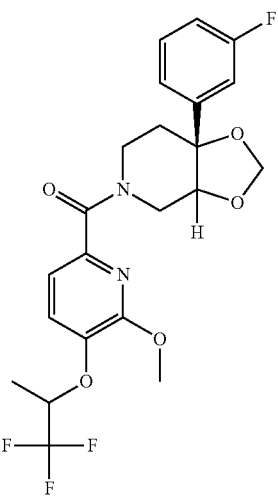 [SMILES: COc1nc(C(=O)N2CC[C@]3(c4cccc(F)c4)OCOC3C2)ccc1OC(C)C(F)(F)F]
265
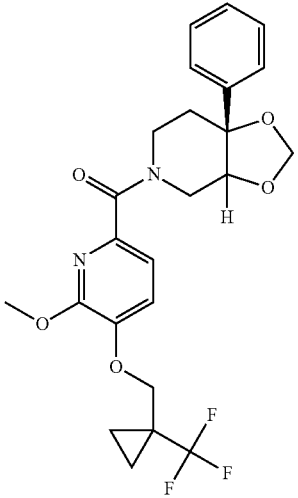 [SMILES: COc1nc(C(=O)N2CC[C@]3(c4ccccc4)OCOC3C2)ccc1OCC1(C(F)(F)F)CC1]

TABLE 1-continued
266
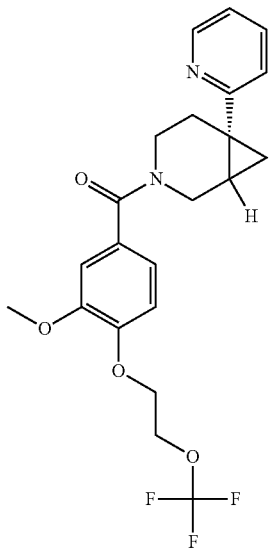 [SMILES: COc1cc(C(=O)N2CC[C@@]3(c4ccccn4)CC3C2)ccc1OCCOC(F)(F)F]
267
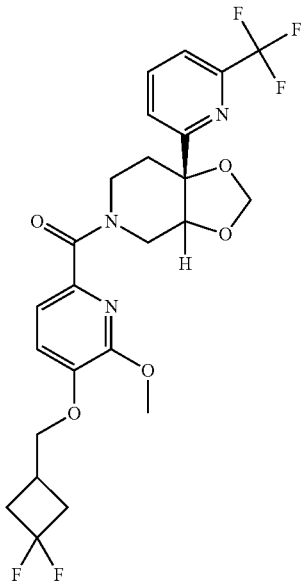 [SMILES: COc1nc(C(=O)N2CC[C@]3(c4cccc(C(F)(F)F)n4)OCOC3C2)ccc1OCC1CC(F)(F)C1]
TABLE 1-continued
268
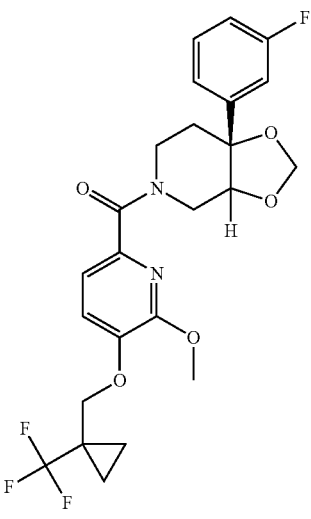 [SMILES: COc1nc(C(=O)N2CC[C@]3(c4cccc(F)c4)OCOC3C2)ccc1OCC1(C(F)(F)F)CC1]
269
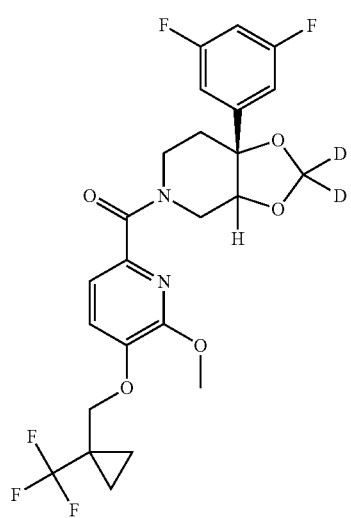 [SMILES: [2H]C1([2H])OC2CN(C(=O)c3ccc(OCC4(C(F)(F)F)CC4)c(OC)n3)CC[C@]2(c2cc(F)cc(F)c2)O1]
270
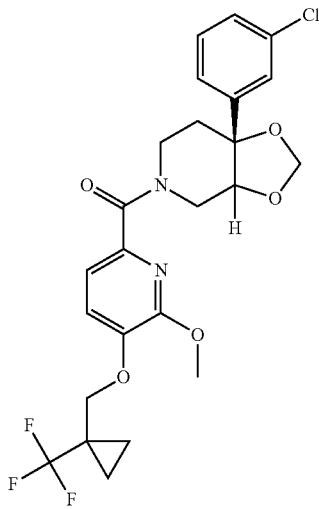 [SMILES: COc1nc(C(=O)N2CC[C@]3(c4cccc(Cl)c4)OCOC3C2)ccc1OCC1(C(F)(F)F)CC1]

TABLE 1-continued
271
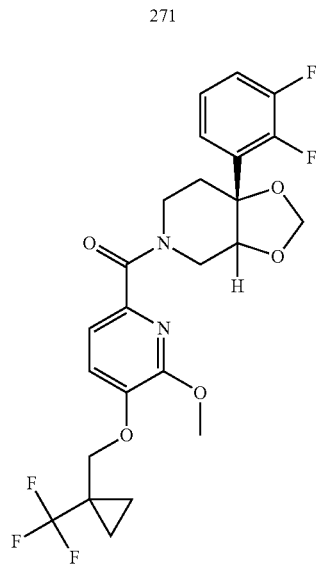
272
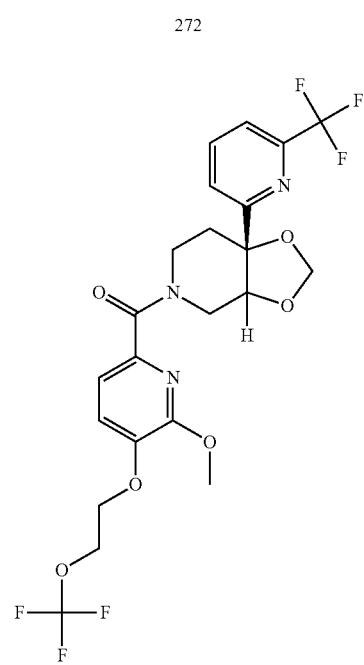
TABLE 1-continued
273
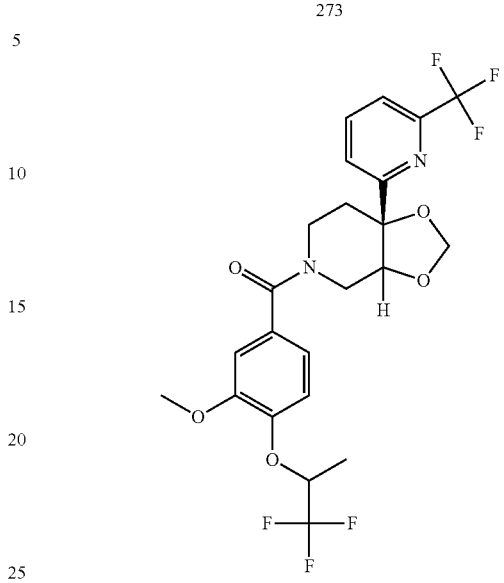
274
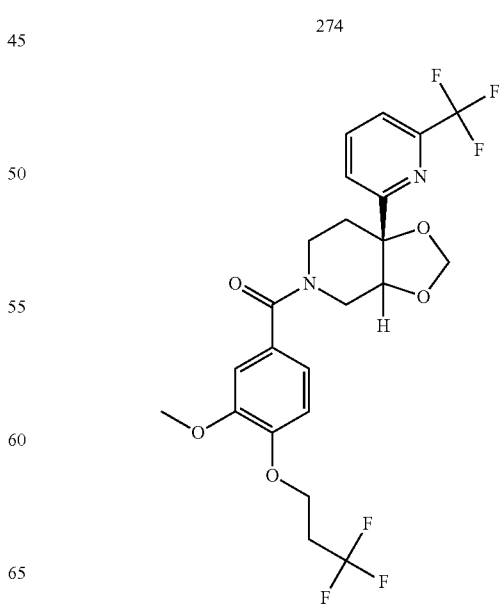

TABLE 1-continued
275
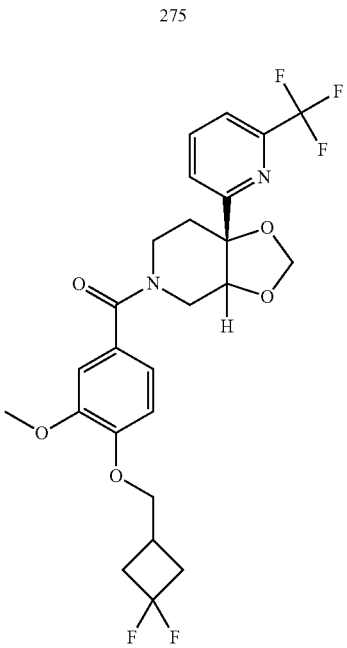
276
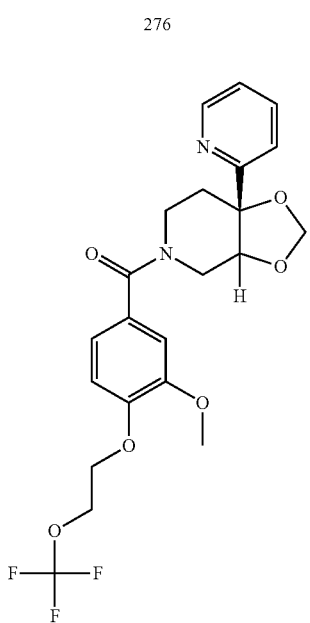
TABLE 1-continued
277
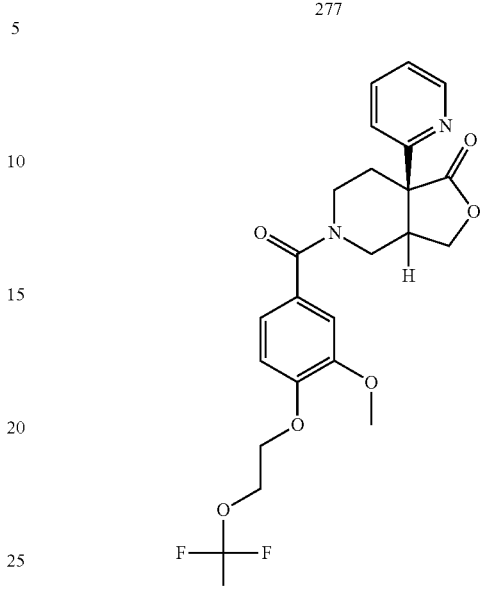
278
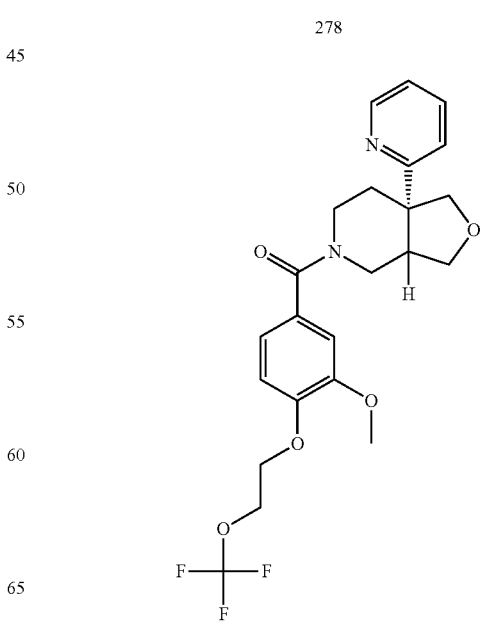

TABLE 1-continued
279
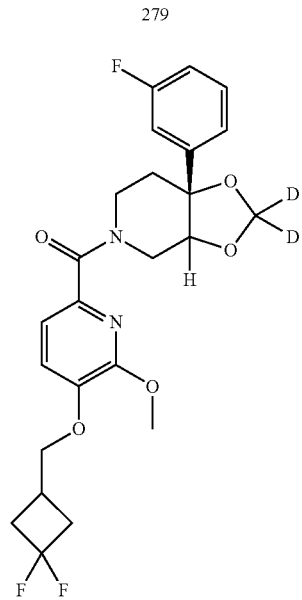
281
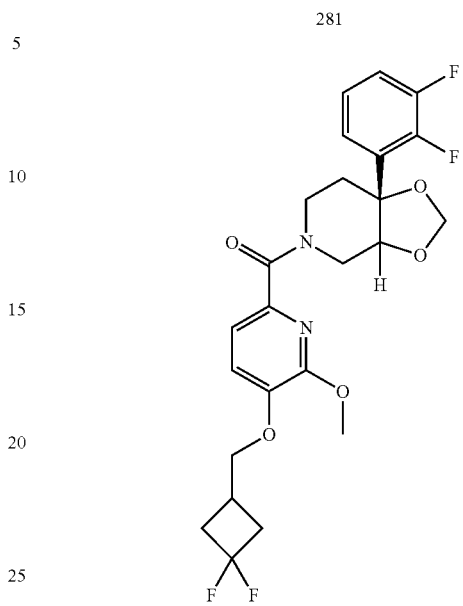
280
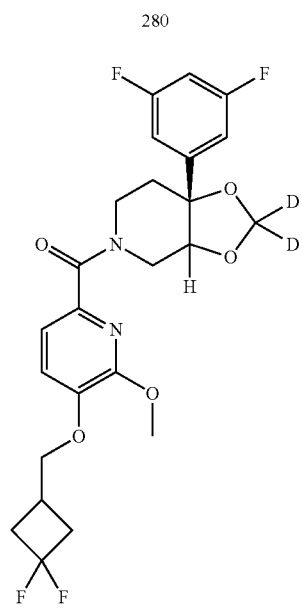
282
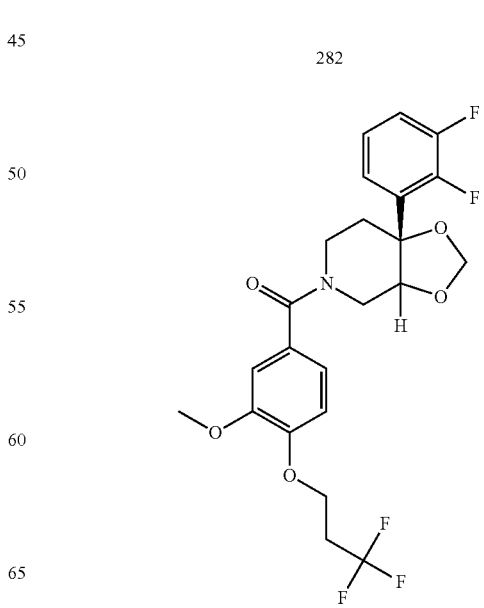

TABLE 1-continued

283

284

285

286

TABLE 1-continued
287
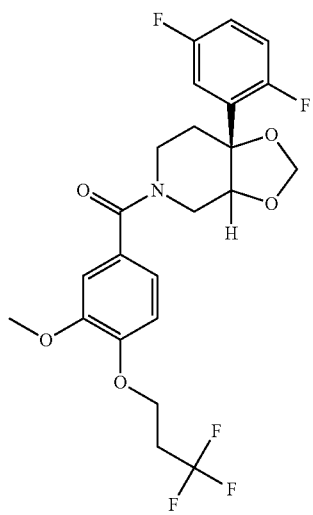 [SMILES: COc1cc(C(=O)N2CC[C@]3(c4cc(F)ccc4F)OCOC3C2)ccc1OCCC(F)(F)F]
288
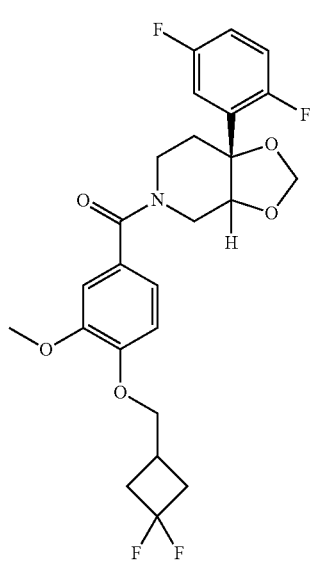 [SMILES: COc1cc(C(=O)N2CC[C@]3(c4cc(F)ccc4F)OCOC3C2)ccc1OCC1CC(F)(F)C1]
TABLE 1-continued
289
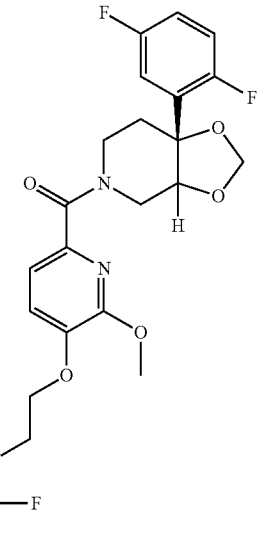
290
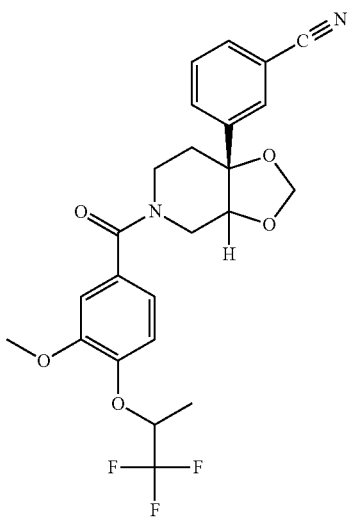 [SMILES: COc1cc(C(=O)N2CC[C@]3(c4cccc(C#N)c4)OCOC3C2)ccc1OC(C)C(F)(F)F]

TABLE 1-continued
291
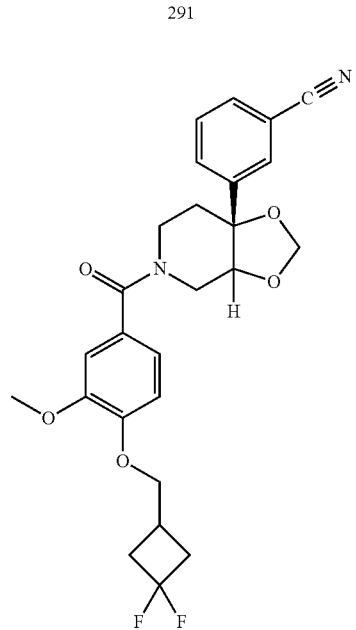
293
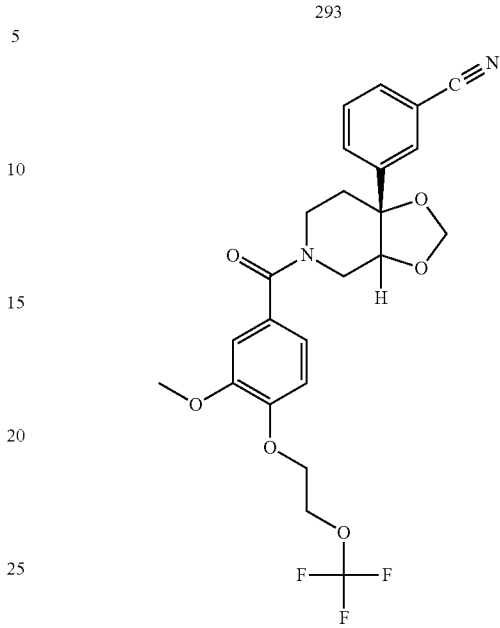
292
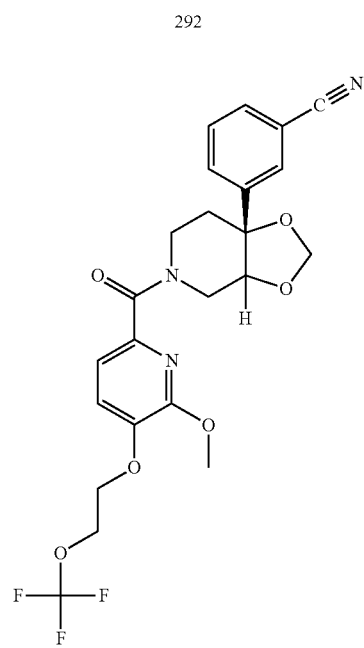
294
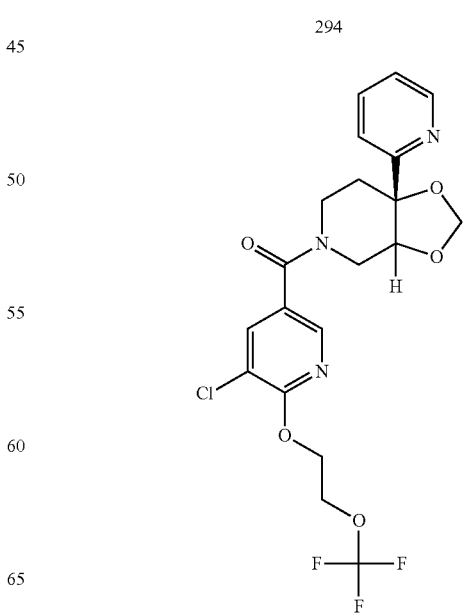

TABLE 1-continued
295
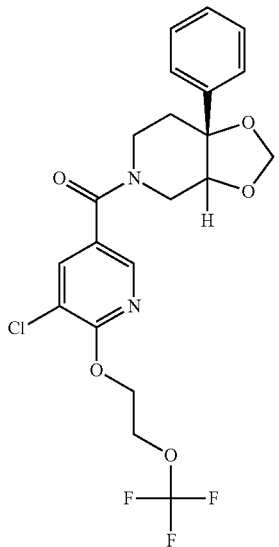 [SMILES: O=C(c1cnc(OCCOC(F)(F)F)c(Cl)c1)N1CC[C@]2(c3ccccc3)OCOC2C1]
296
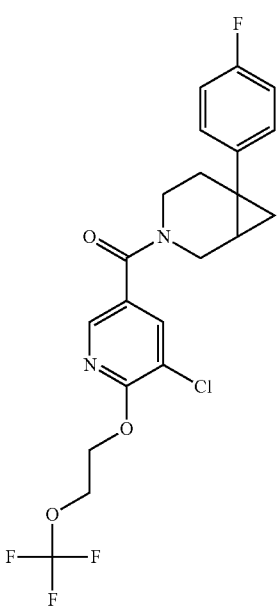
TABLE 1-continued
297
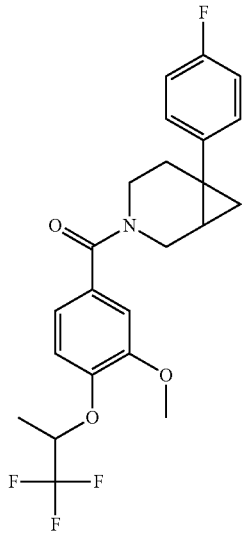
298
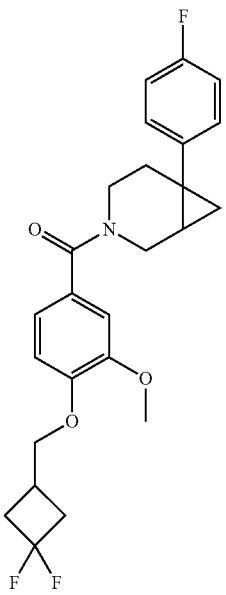 [SMILES: COc1cc(C(=O)N2CCC3(c4ccc(F)cc4)CC3C2)ccc1OCC1CC(F)(F)C1]

TABLE 1-continued
299
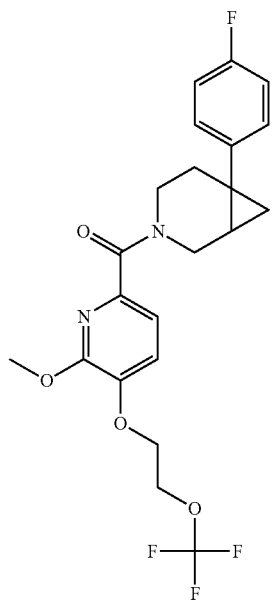 [SMILES: COc1nc(C(=O)N2CCC3(c4ccc(F)cc4)CC3C2)ccc1OCCOC(F)(F)F]
300
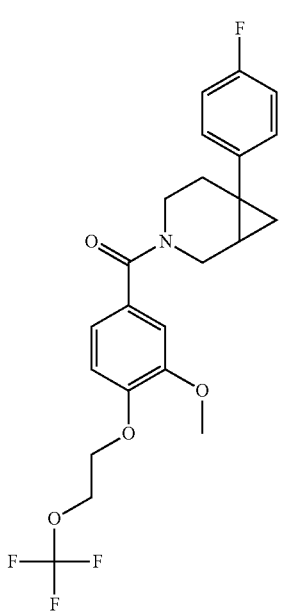
TABLE 1-continued
301
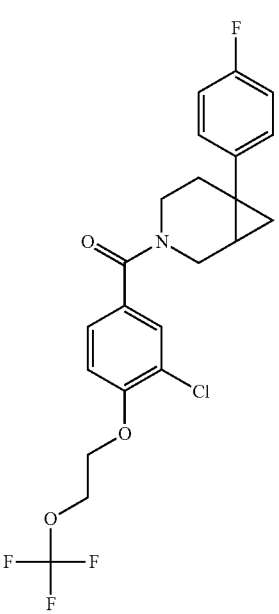 [SMILES: O=C(c1ccc(OCCOC(F)(F)F)c(Cl)c1)N1CCC2(c3ccc(F)cc3)CC2C1]
302
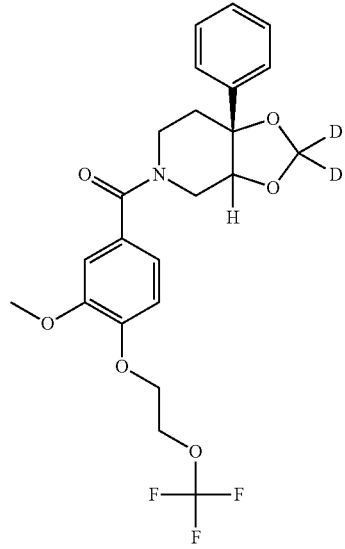 [SMILES: [2H]C1([2H])OC2CN(C(=O)c3ccc(OCCOC(F)(F)F)c(OC)c3)CC[C@]2(c2ccccn2)O1]

TABLE 1-continued
303
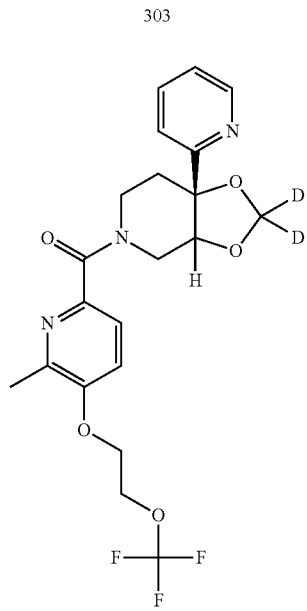
304
305
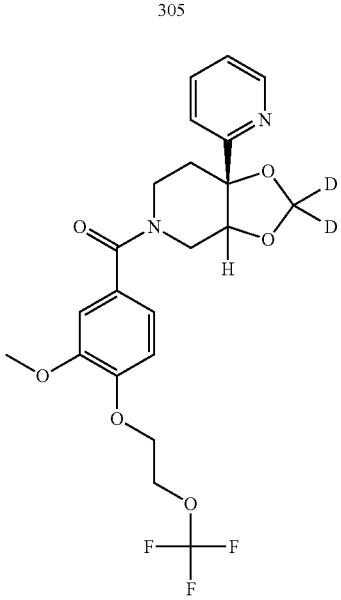
306
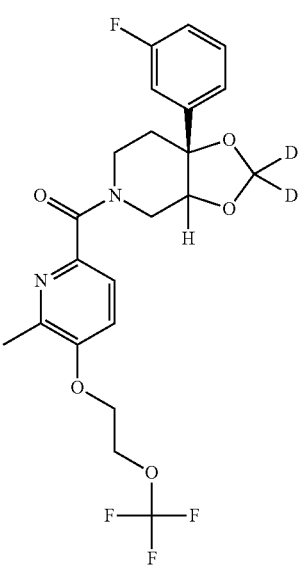 [SMILES: [2H]C1([2H])OC2CN(C(=O)c3ccc(OCCOC(F)(F)F)c(C)n3)CC[C@]2(c2cccc(F)c2)O1]

TABLE 1-continued
307
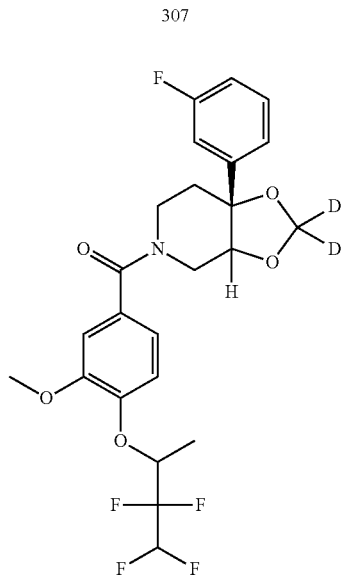
308
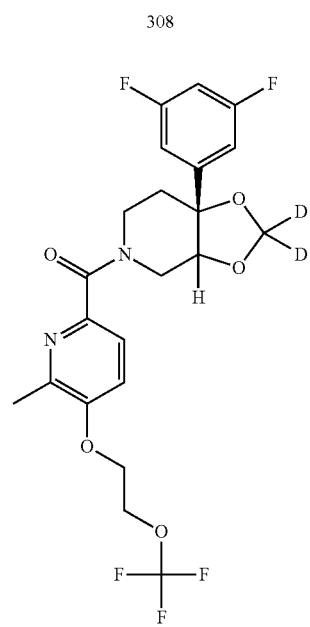
TABLE 1-continued
309
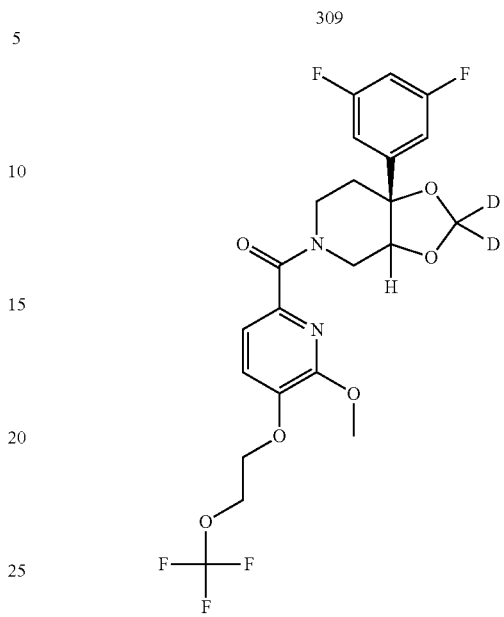
310
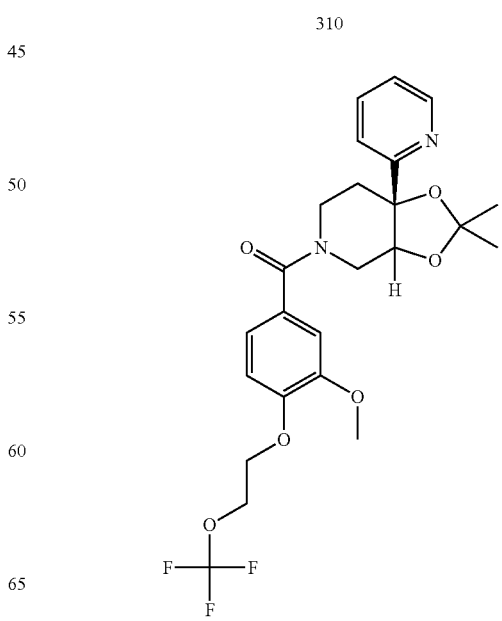

TABLE 1-continued
311
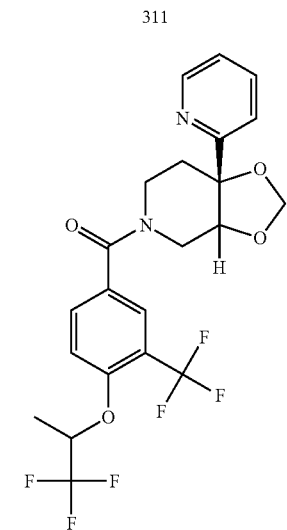
312
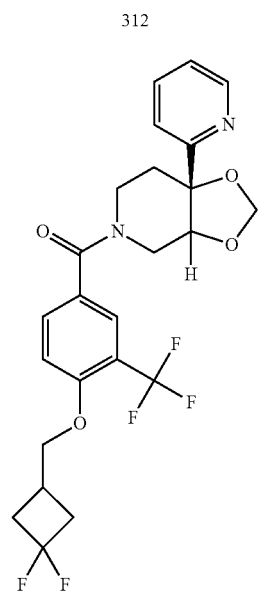
313
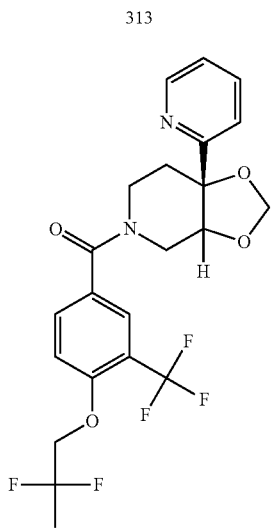
TABLE 1-continued
314
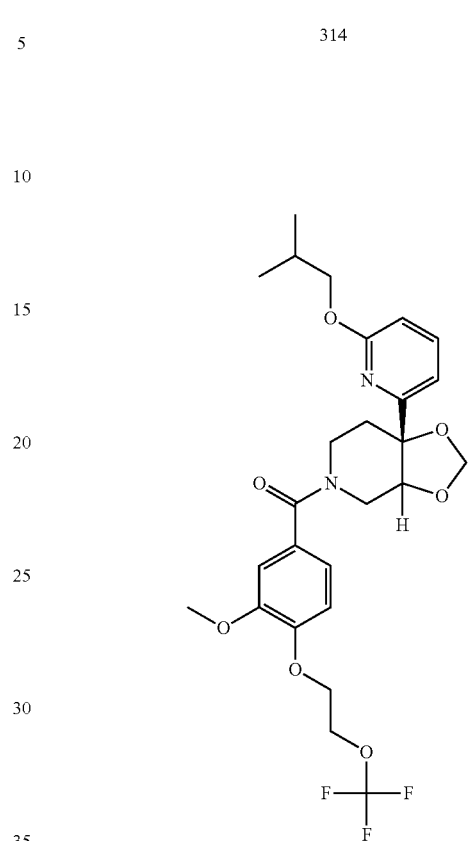
In another embodiment, the compound may exist as a racemic mixture of enantiomers according to Table 2:
TABLE 2
315
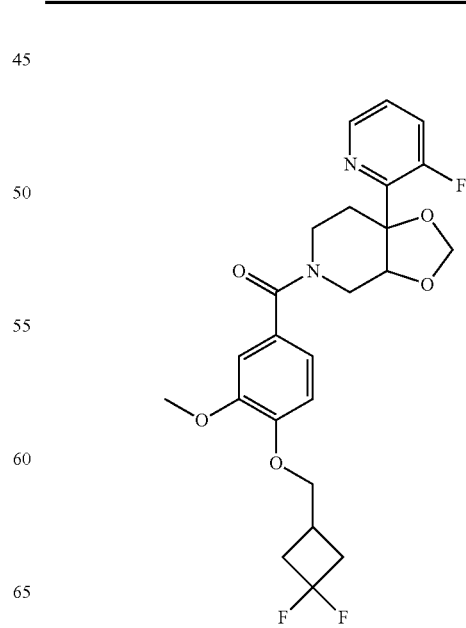

TABLE 2-continued
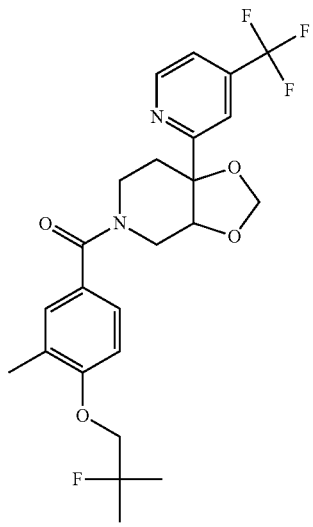
316
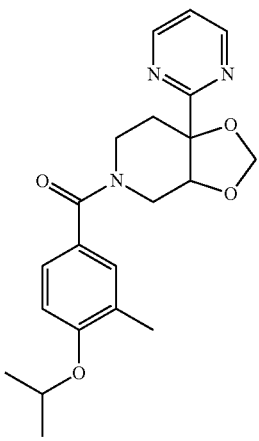
319
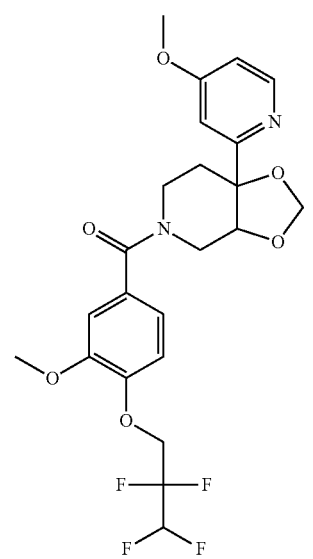 [SMILES: COc1ccnc(C23CCN(C(=O)c4ccc(OCC(F)(F)C(F)F)c(OC)c4)CC2OCO3)c1]
317
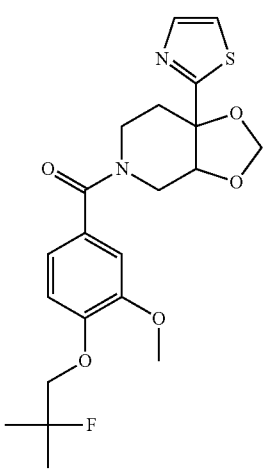
320
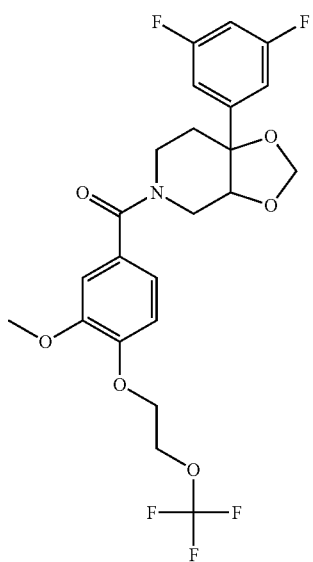 [SMILES: COc1cc(C(=O)N2CCC3(c4cc(F)cc(F)c4)OCOC3C2)ccc1OCCOC(F)(F)F]
318
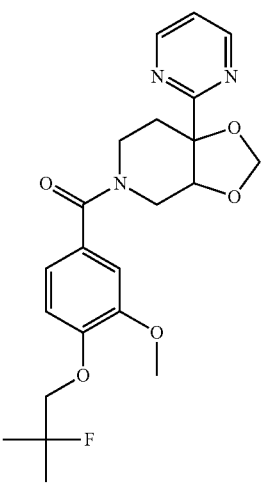 [SMILES: COc1cc(C(=O)N2CCC3(c4ncccn4)OCOC3C2)ccc1OCC(C)(C)F]
321

| 322 | 325 |
|---|---|
| 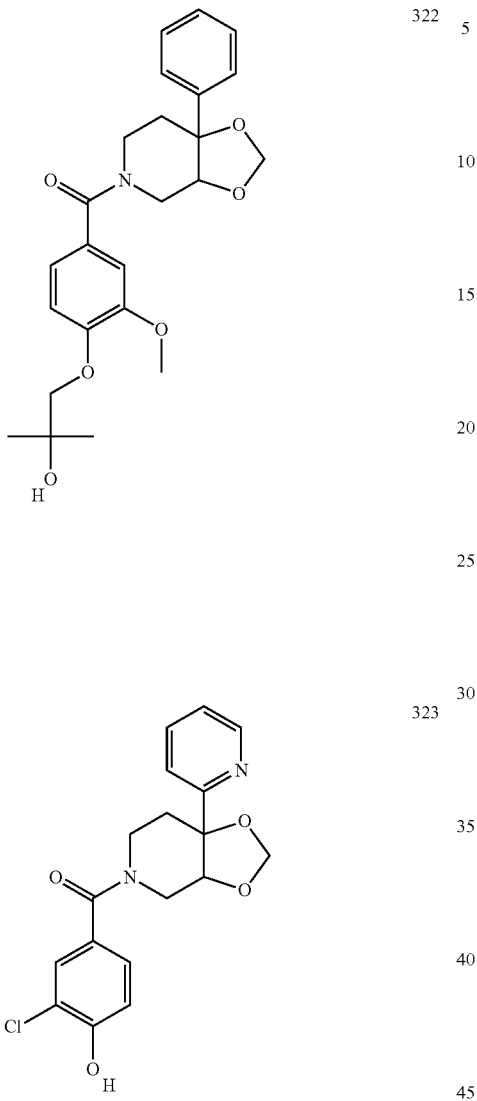 | 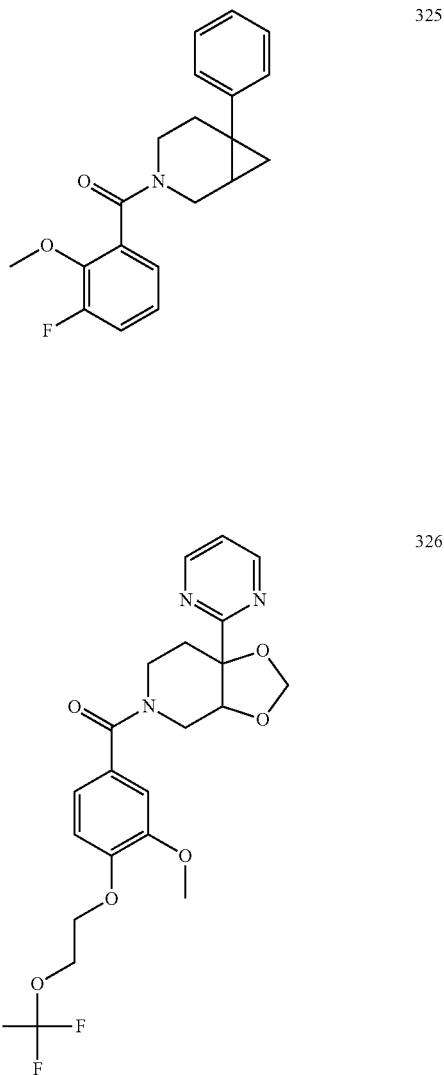 |
| 323 | 326 |
| 324 | 327 |
| 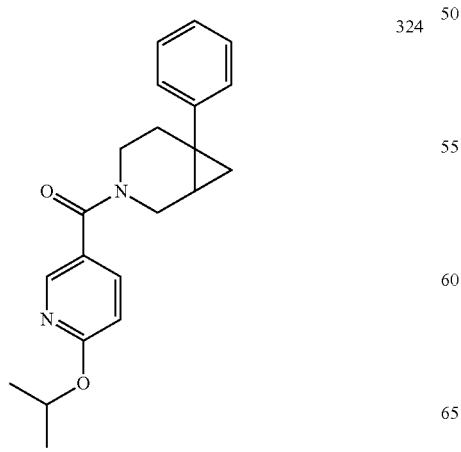 | 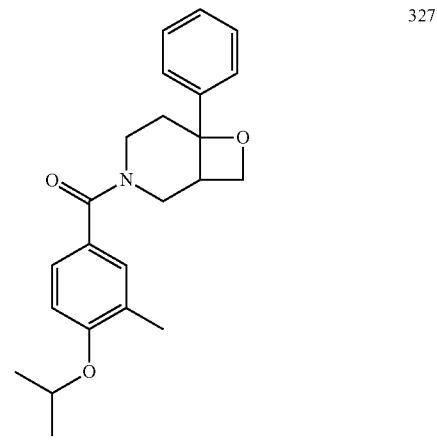 |

TABLE 2-continued
| | |
|---|---|
| 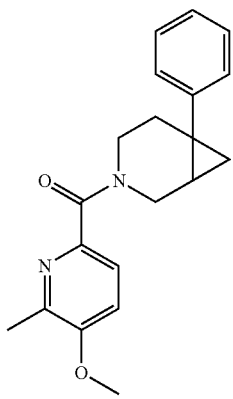 [SMILES: COc1ccc(C(=O)N2CCC3(c4ccccc4)CC3C2)nc1C] | 328 |
| 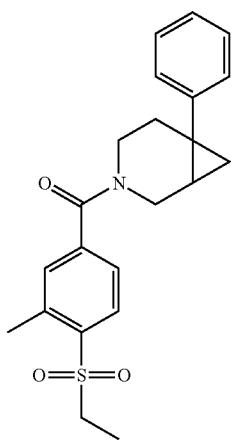 [SMILES: CCS(=O)(=O)c1ccc(C(=O)N2CCC3(c4ccccc4)CC3C2)cc1C] | 329 |
| 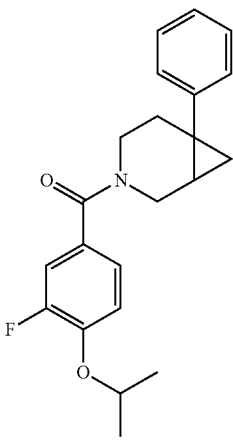 | 330 |
TABLE 2-continued
| | |
|---|---|
| 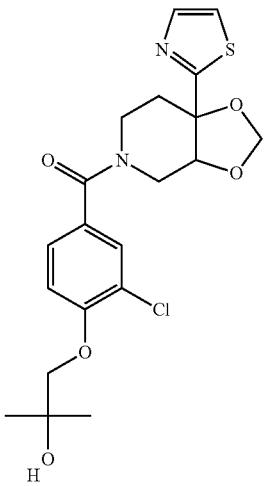 | 331 |
| 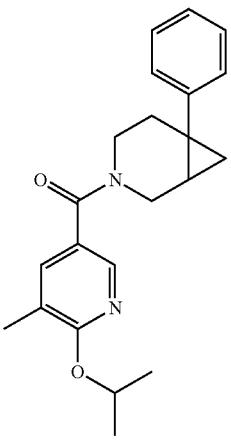 | 332 |
| 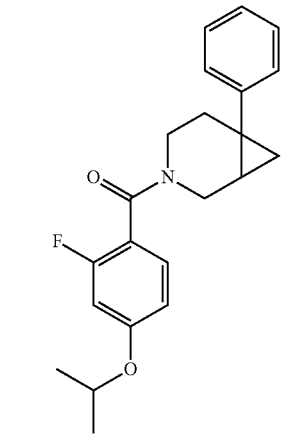 [SMILES: CC(C)Oc1ccc(C(=O)N2CCC3(c4ccccc4)CC3C2)c(F)c1] | 333 |
| 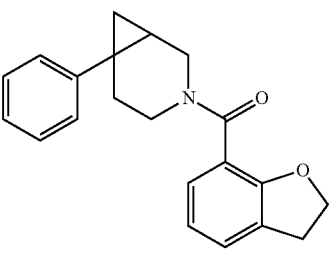 [SMILES: O=C(c1cccc2c1OCC2)N1CCC2(c3ccccc3)CC2C1] | 334 |

TABLE 2-continued
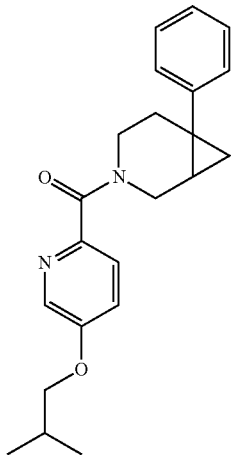 [SMILES: CC(C)COc1ccc(C(=O)N2CCC3(c4ccccc4)CC3C2)nc1] 335
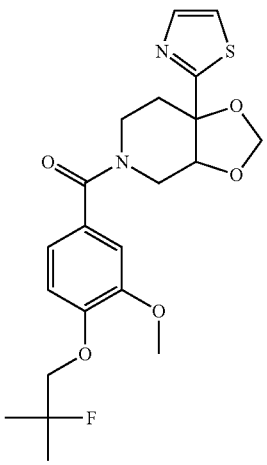 338
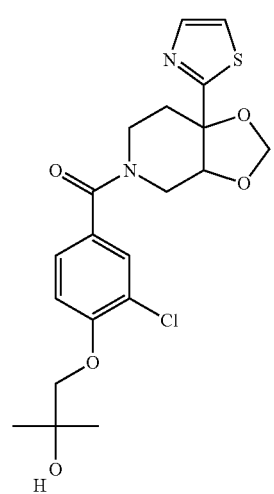 336
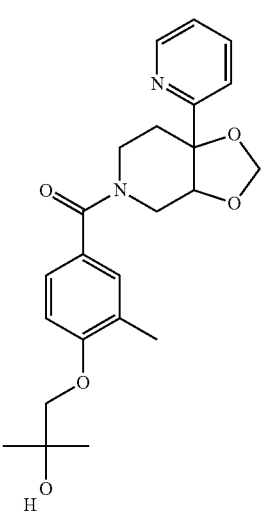 339
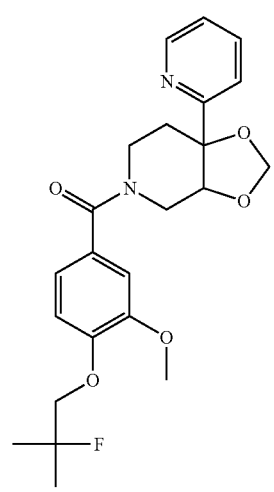 337
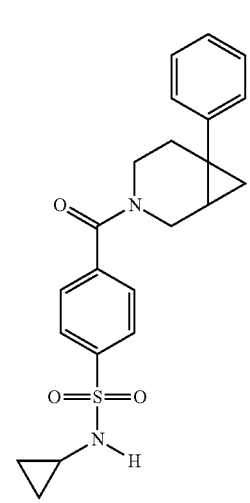 [SMILES: O=C(c1ccc(S(=O)(=O)NC2CC2)cc1)N1CCC2(c3ccccc3)CC2C1] 340

TABLE 2-continued
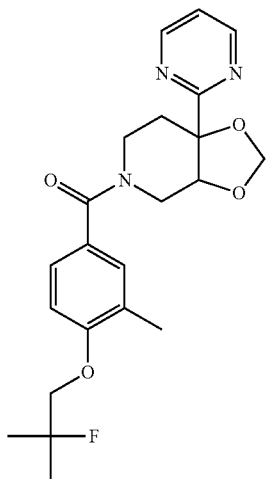
341
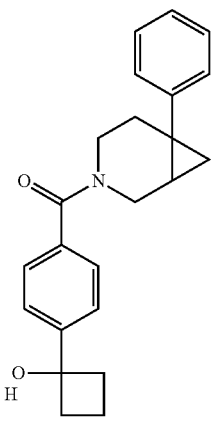
342
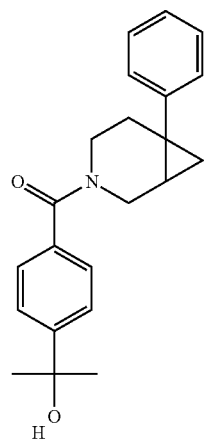
343
TABLE 2-continued
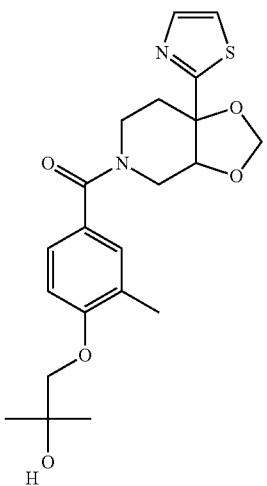
344
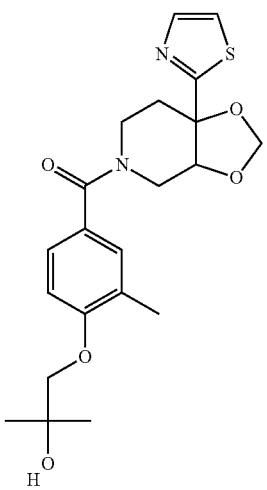
345
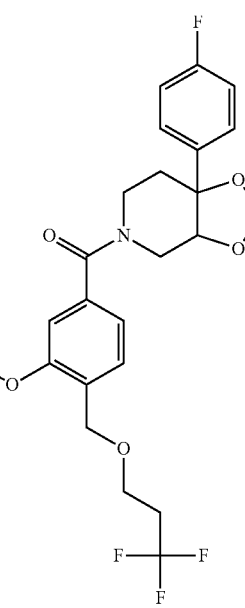
346

TABLE 2-continued
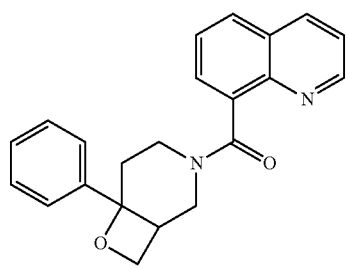 [SMILES: O=C(c1cccc2cccnc12)N1CCC2(c3ccccc3)OCC2C1] 347
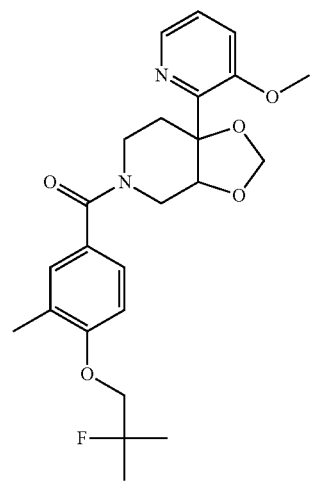 348
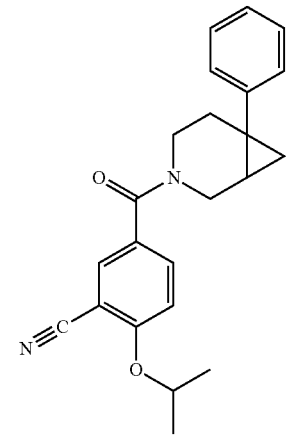 [SMILES: CC(C)Oc1ccc(C(=O)N2CCC3(c4ccccc4)CC3C2)cc1C#N] 349
TABLE 2-continued
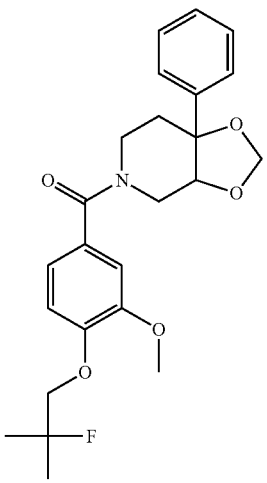 [SMILES: COc1cc(C(=O)N2CCC3(c4ccccc4)OCOC3C2)ccc1OCC(C)(C)F] 350
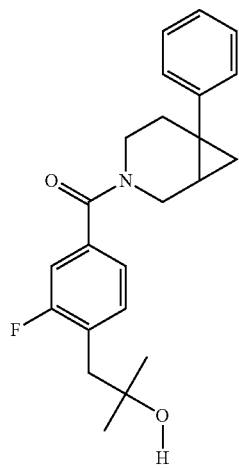 [SMILES: CC(C)(O)Cc1ccc(C(=O)N2CCC3(c4ccccc4)CC3C2)cc1F] 351
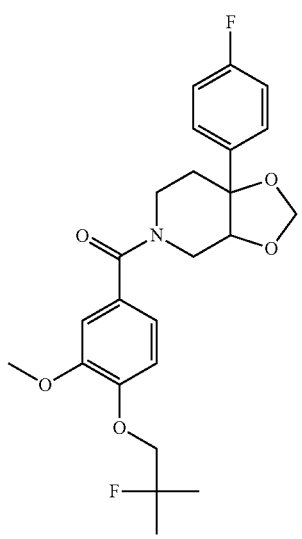 [SMILES: COc1cc(C(=O)N2CCC3(c4ccc(F)cc4)OCOC3C2)ccc1OCC(C)(C)F] 352

TABLE 2-continued
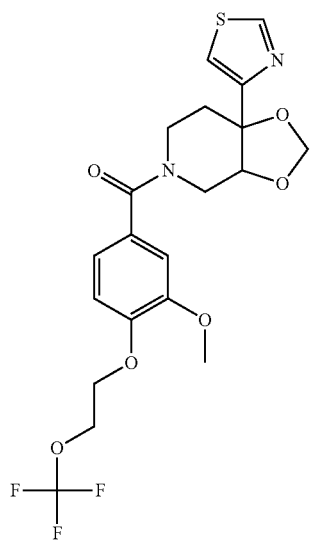 [SMILES: COc1cc(C(=O)N2CCC3(c4cscn4)OCOC3C2)ccc1OCCOC(F)(F)F]
353
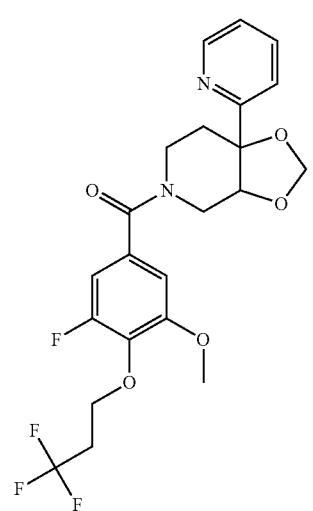 [SMILES: COc1cc(C(=O)N2CCC3(c4ccccn4)OCOC3C2)cc(F)c1OCCC(F)(F)F]
354
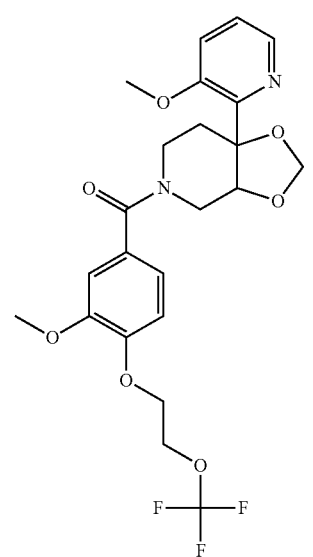 [SMILES: COc1cc(C(=O)N2CCC3(c4ncccc4OC)OCOC3C2)ccc1OCCOC(F)(F)F]
355
TABLE 2-continued
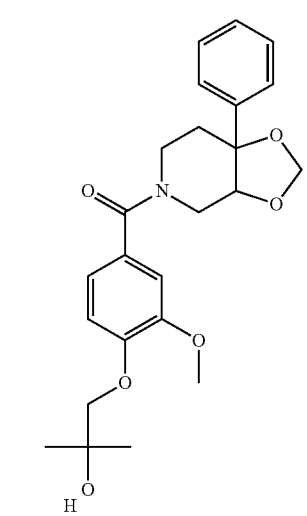
356
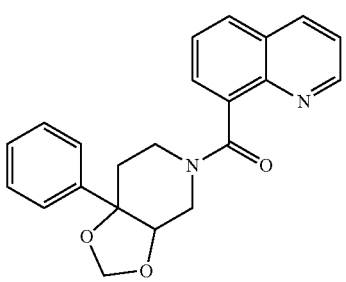 [SMILES: O=C(c1cccc2cccnc12)N1CCC2(c3ccccc3)OCOC2C1]
357
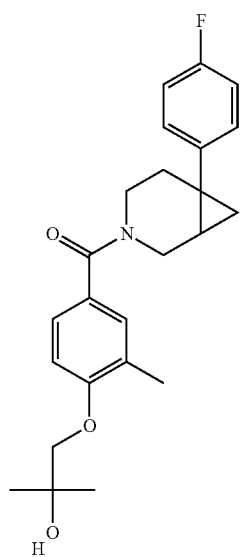
358

TABLE 2-continued
| 359 | 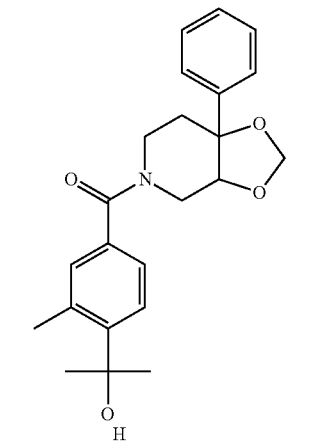 |
| --- | --- |
| 360 | 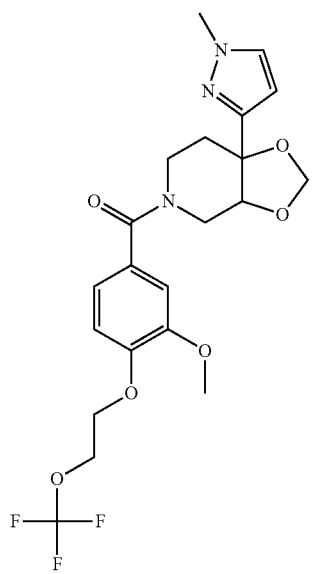 |
| 361 | 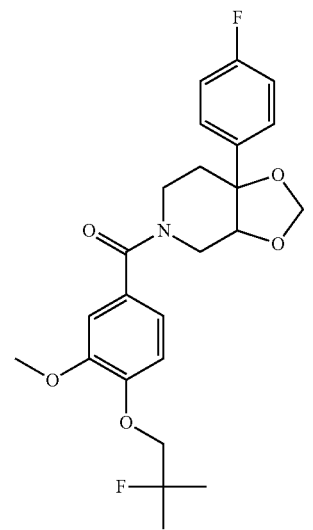 [SMILES: COc1cc(C(=O)N2CCC3(c4ccc(F)cc4)OCOC3C2)ccc1OCC(C)(C)F] |
TABLE 2-continued
| 362 | 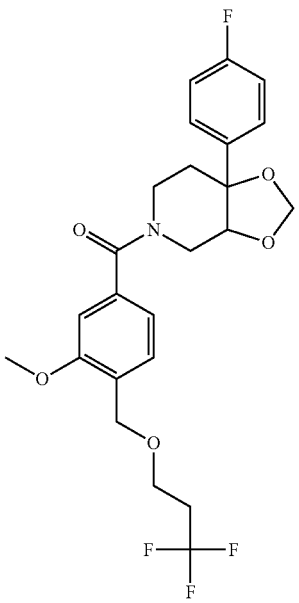 |
| --- | --- |
| 363 | 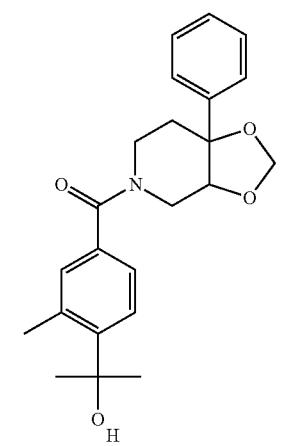 |
| 364 | 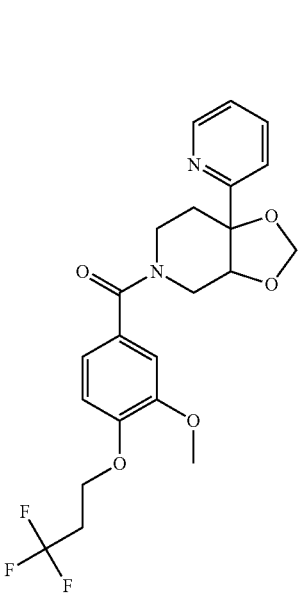 [SMILES: COc1cc(C(=O)N2CCC3(c4ccccn4)OCOC3C2)ccc1OCCC(F)(F)F] |

TABLE 2-continued
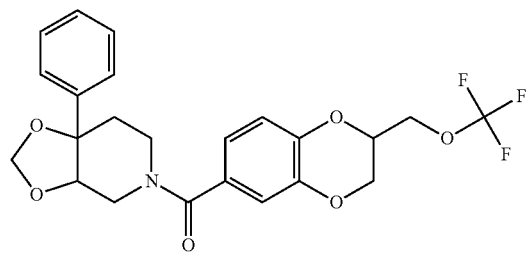 [SMILES: O=C(c1ccc2c(c1)OCC(COC(F)(F)F)O2)N1CCC2(c3ccccc3)OCOC2C1] 365
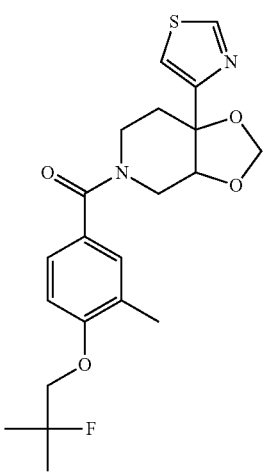 [SMILES: Cc1cc(C(=O)N2CCC3(c4cscn4)OCOC3C2)ccc1OCC(C)(C)F] 366
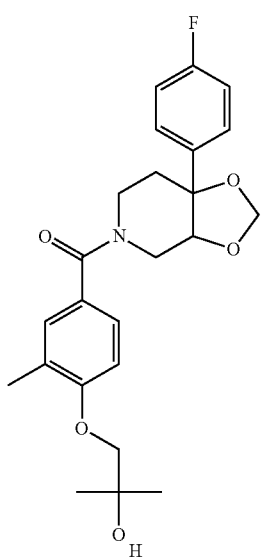 367
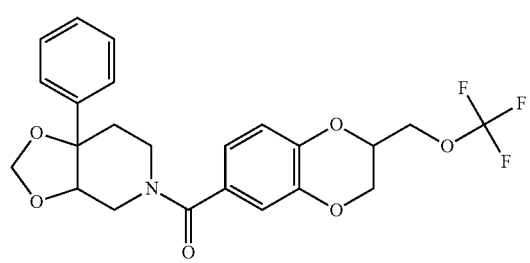 [SMILES: O=C(c1ccc2c(c1)OCC(COC(F)(F)F)O2)N1CCC2(c3ccccc3)OCOC2C1] 368
TABLE 2-continued
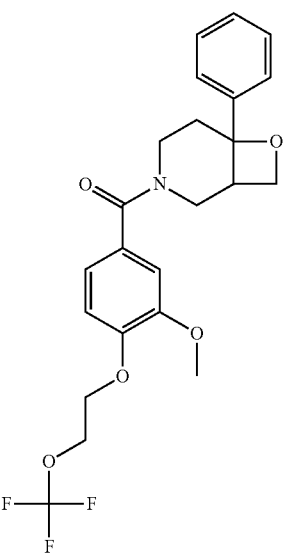 369
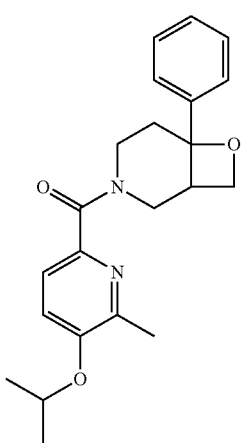 [SMILES: Cc1nc(C(=O)N2CCC3(c4ccccc4)OCC3C2)ccc1OC(C)C] 370
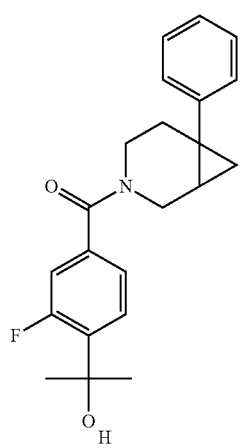 371

TABLE 2-continued
372 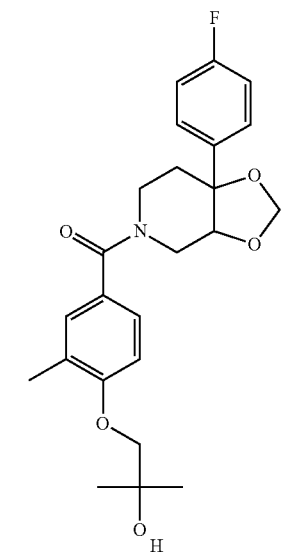
373 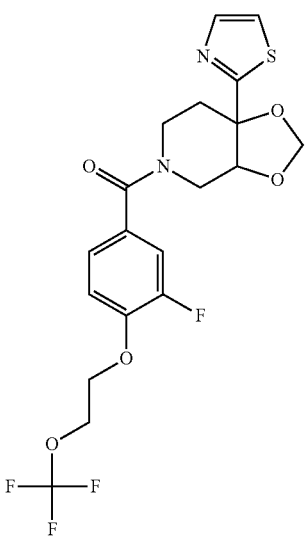
374 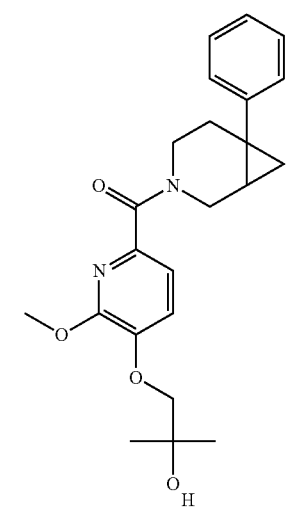
TABLE 2-continued
375 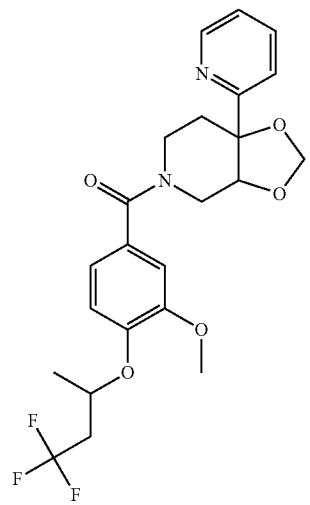 [SMILES: COc1cc(C(=O)N2CCC3(c4ccccn4)OCOC3C2)ccc1OC(C)CC(F)(F)F]
376 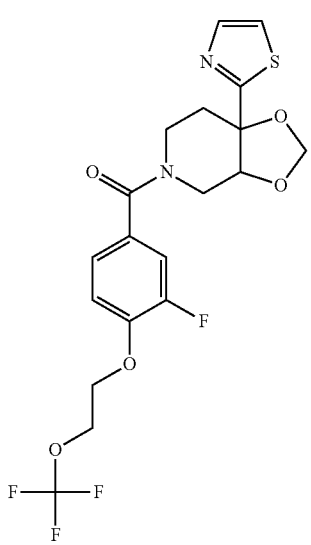
377 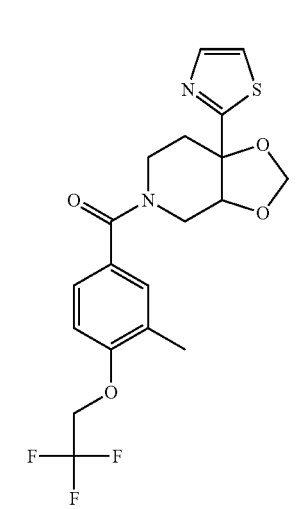

TABLE 2-continued
378 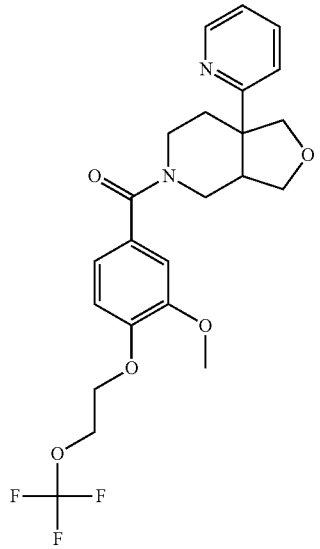 [SMILES: COc1cc(C(=O)N2CCC3(c4ccccn4)COCC3C2)ccc1OCCOC(F)(F)F]
379 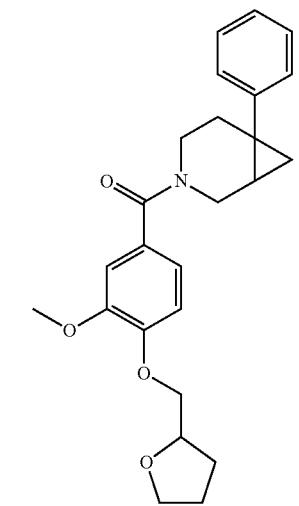 [SMILES: COc1cc(C(=O)N2CCC3(c4ccccc4)CC3C2)ccc1OCC1CCCO1]
380 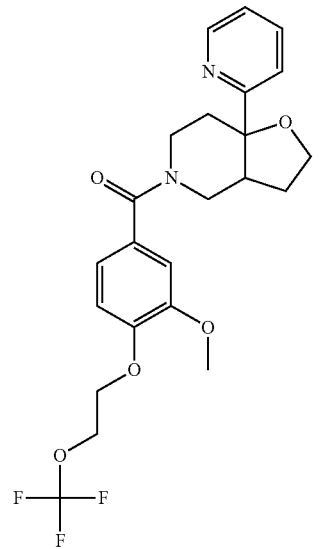
TABLE 2-continued
381 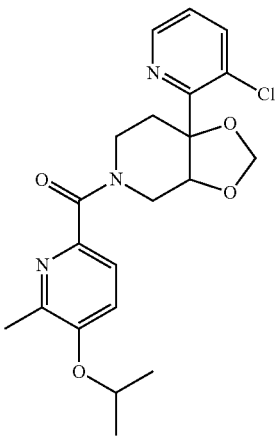 [SMILES: Cc1nc(C(=O)N2CCC3(c4ncccc4Cl)OCOC3C2)ccc1OC(C)C]
382 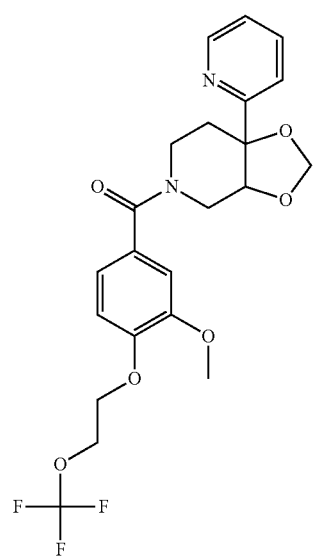
383 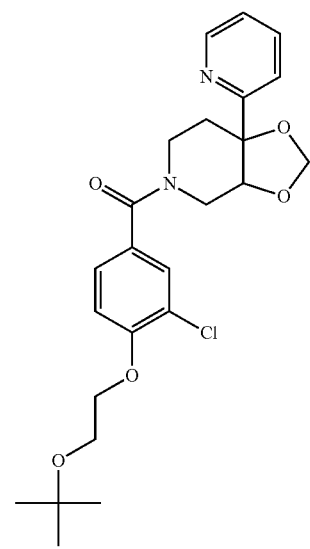 [SMILES: CC(C)(C)OCCOc1ccc(C(=O)N2CCC3(c4ccccn4)OCOC3C2)cc1Cl]

TABLE 2-continued
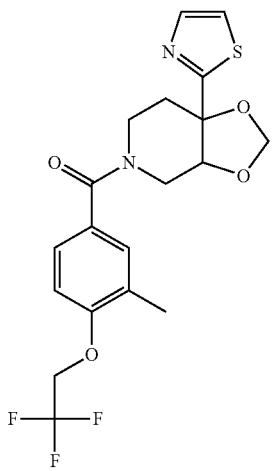 [SMILES: Cc1cc(C(=O)N2CCC3(c4nccs4)OCOC3C2)ccc1OCC(F)(F)F]
384
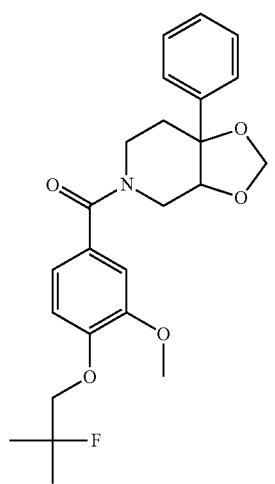 [SMILES: COc1cc(C(=O)N2CCC3(c4ccccc4)OCOC3C2)ccc1OCC(C)(C)F]
385
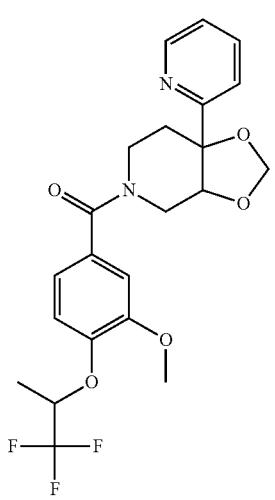 [SMILES: COc1cc(C(=O)N2CCC3(c4ccccn4)OCOC3C2)ccc1OC(C)C(F)(F)F]
386
TABLE 2-continued
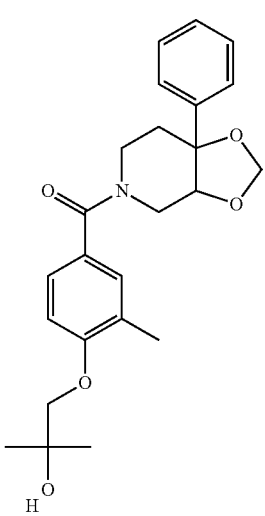
387
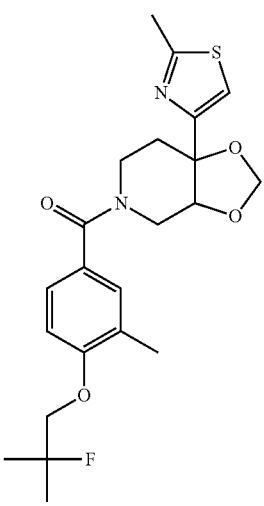
388
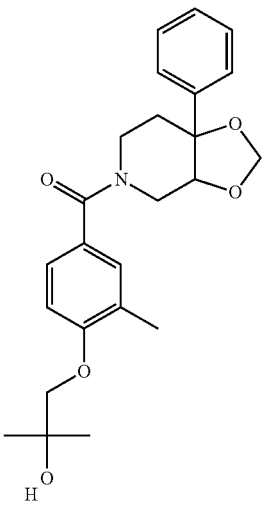
389

TABLE 2-continued
| | |
|---|---|
| 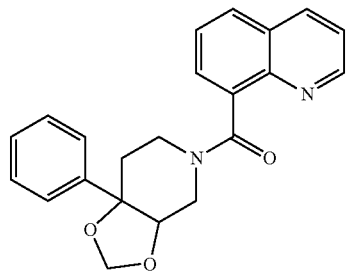 [SMILES: O=C(c1cccc2cccnc12)N1CCC2(c3ccccc3)OCOC2C1] | 390 |
| 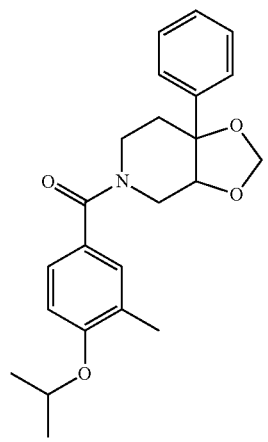 [SMILES: Cc1cc(C(=O)N2CCC3(c4ccccc4)OCOC3C2)ccc1OC(C)C] | 391 |
| 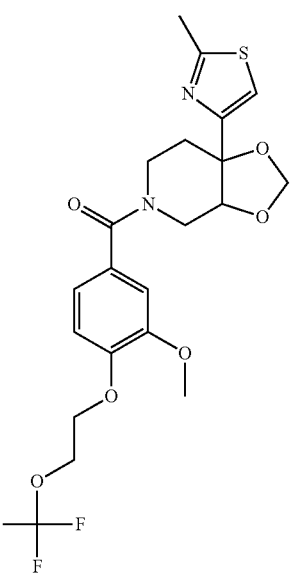 | 392 |
TABLE 2-continued
| | |
|---|---|
| 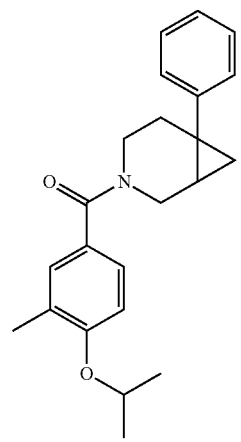 | 393 |
| 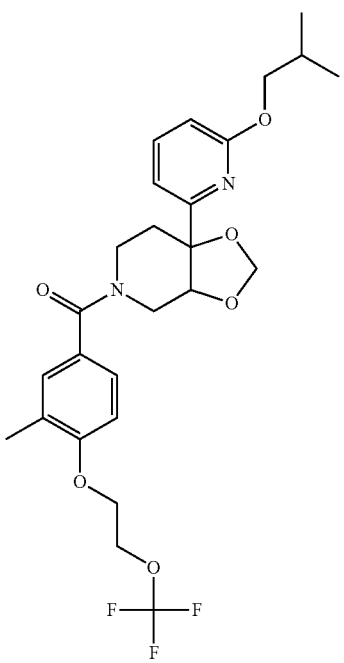 [SMILES: Cc1cc(C(=O)N2CCC3(c4cccc(OCC(C)C)n4)OCOC3C2)ccc1OCCOC(F)(F)F] | 394 |
| 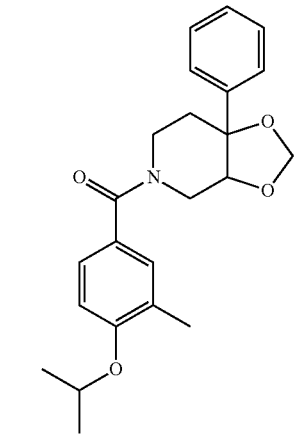 | 395 |

TABLE 2-continued
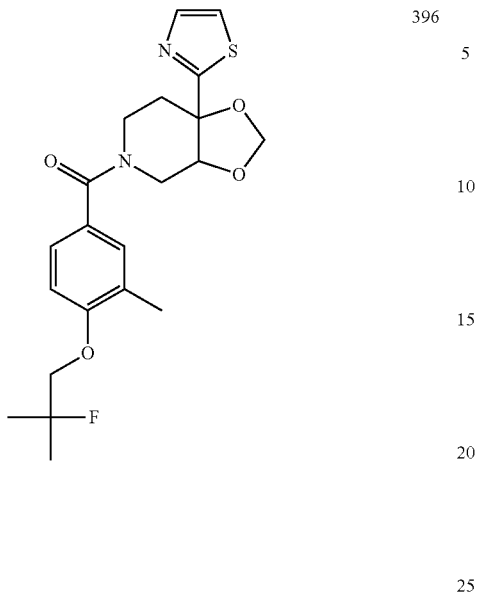
396
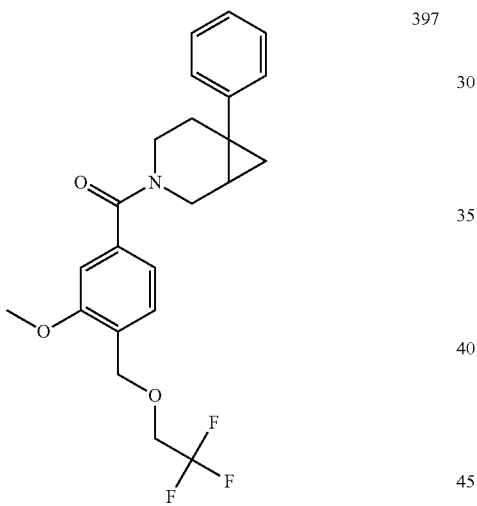
397
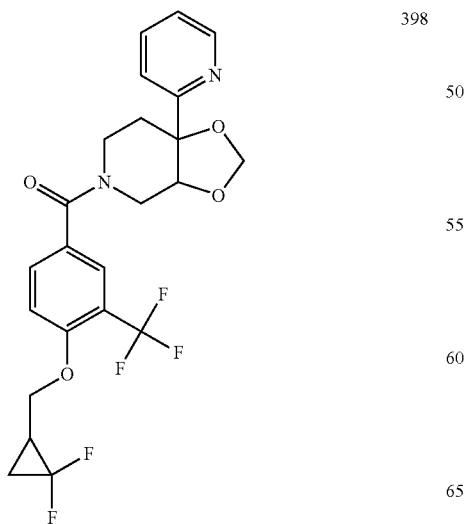
398
TABLE 2-continued
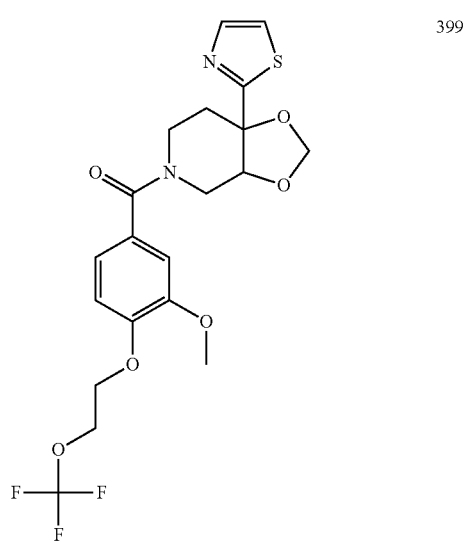
399
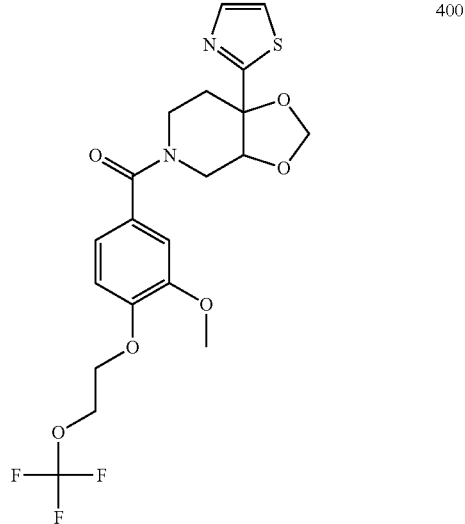
400

TABLE 2-continued
401
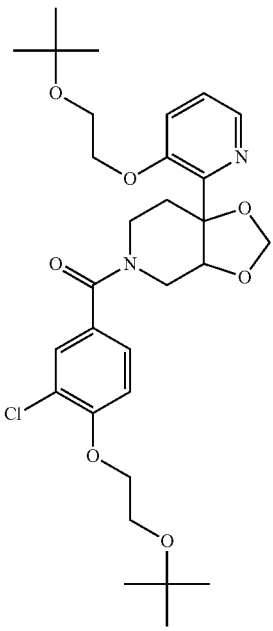 [SMILES: CC(C)(C)OCCOc1ccc(C(=O)N2CCC3(c4ncccc4OCCOC(C)(C)C)OCOC3C2)cc1Cl]
402
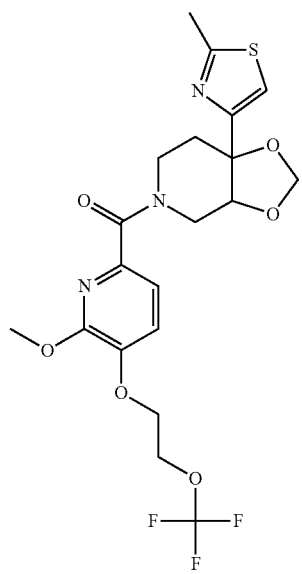 [SMILES: COc1nc(C(=O)N2CCC3(c4csc(C)n4)OCOC3C2)ccc1OCCOC(F)(F)F]
TABLE 2-continued
403
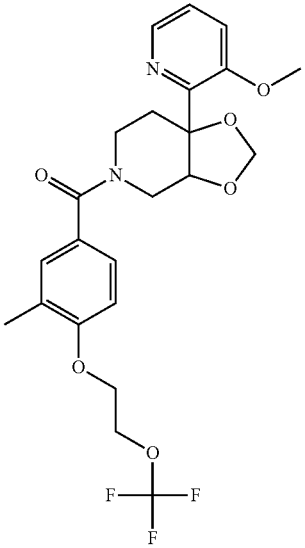
404
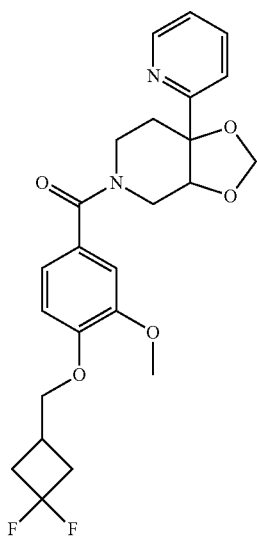 [SMILES: COc1cc(C(=O)N2CCC3(c4ccccn4)OCOC3C2)ccc1OCC1CC(F)(F)C1]

TABLE 2-continued
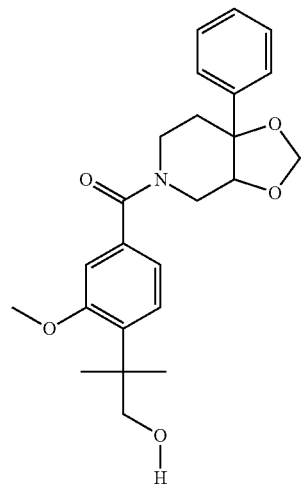 [SMILES: COc1cc(C(=O)N2CCC3(c4ccccc4)OCOC3C2)ccc1C(C)(C)CO]
405
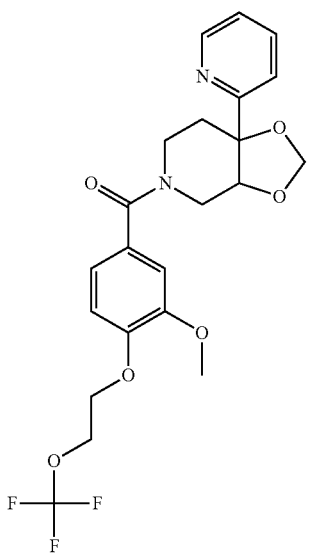
406
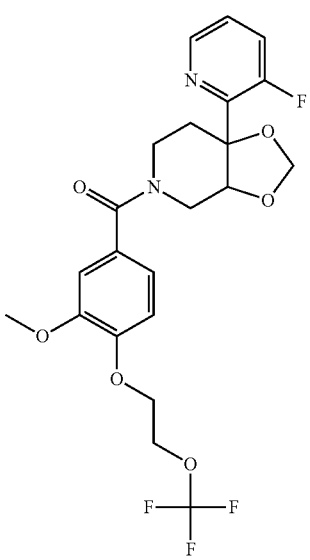 [SMILES: COc1cc(C(=O)N2CCC3(c4ncccc4F)OCOC3C2)ccc1OCCOC(F)(F)F]
407
TABLE 2-continued
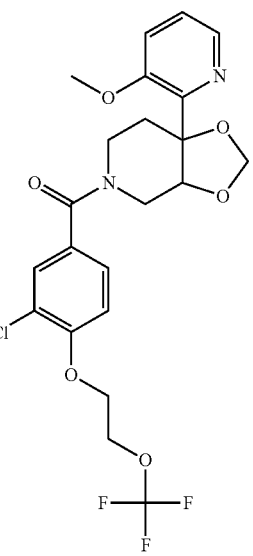
408
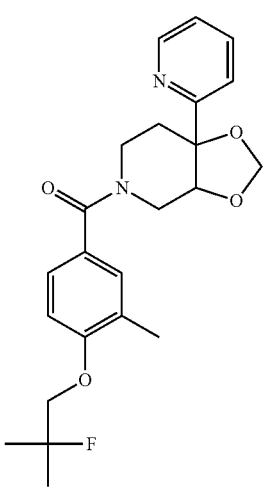
409
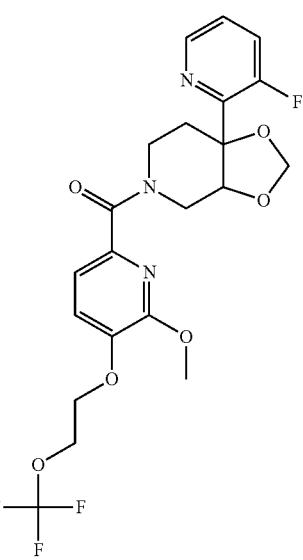
410

TABLE 2-continued
411
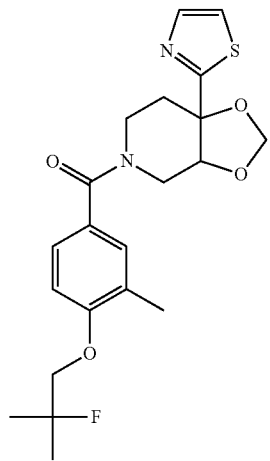 [SMILES: Cc1cc(C(=O)N2CCC3(c4nccs4)OCOC3C2)ccc1OCC(C)(C)F]
412
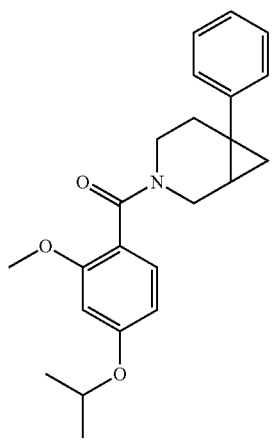 [SMILES: COc1cc(OC(C)C)ccc1C(=O)N1CCC2(c3ccccc3)CC2C1]
413
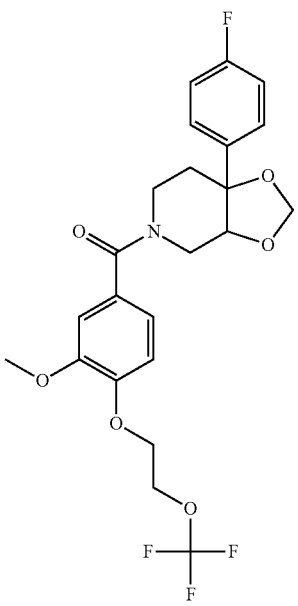
TABLE 2-continued
414
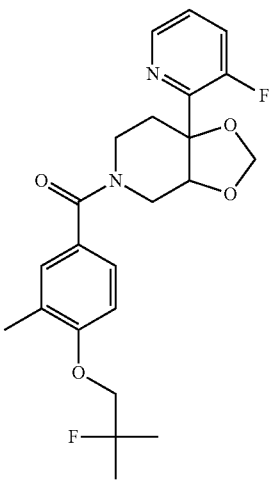 [SMILES: Cc1cc(C(=O)N2CCC3(c4ncccc4F)OCOC3C2)ccc1OCC(C)(C)F]
415
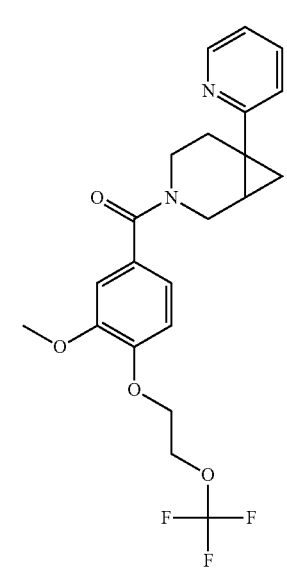
416
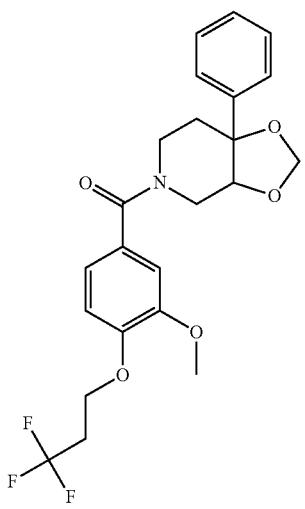 [SMILES: COc1cc(C(=O)N2CCC3(c4ccccc4)OCOC3C2)ccc1OCCC(F)(F)F]

TABLE 2-continued
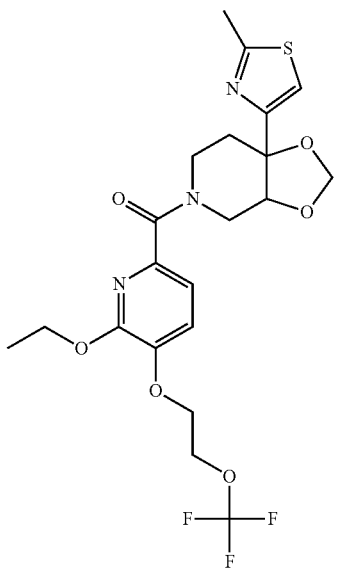 [SMILES: CCOc1nc(C(=O)N2CCC3(c4csc(C)n4)OCOC3C2)ccc1OCCOC(F)(F)F]
417
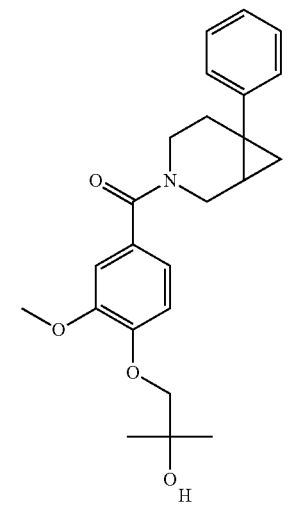
418

419
TABLE 2-continued
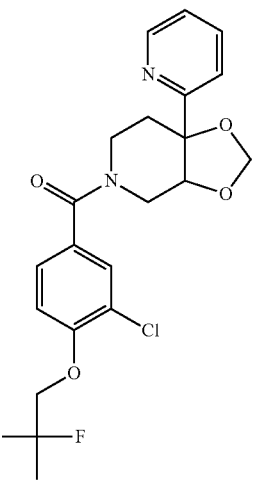
420
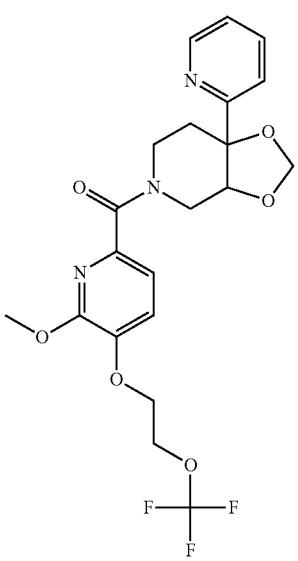 [SMILES: COc1nc(C(=O)N2CCC3(c4ccccn4)OCOC3C2)ccc1OCCOC(F)(F)F]
421
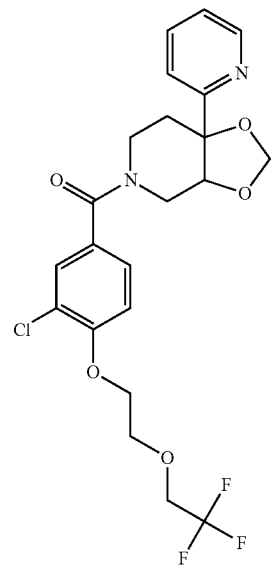 [SMILES: O=C(c1ccc(OCCOCC(F)(F)F)c(Cl)c1)N1CCC2(c3ccccn3)OCOC2C1]
422

TABLE 2-continued
| 423 | 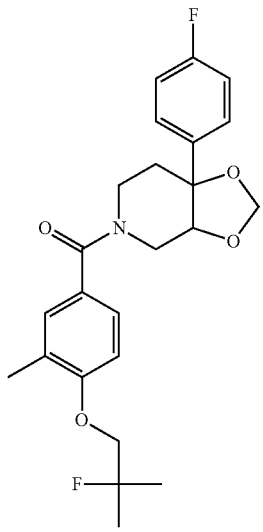 [SMILES: Cc1cc(C(=O)N2CCC3(c4ccc(F)cc4)OCOC3C2)ccc1OCC(C)(C)F] |
| 424 | 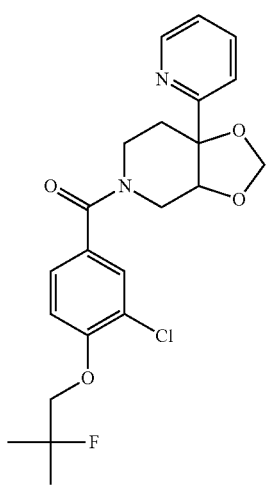 [SMILES: CC(C)(F)COc1ccc(C(=O)N2CCC3(c4ccccn4)OCOC3C2)cc1Cl] |
| 425 | 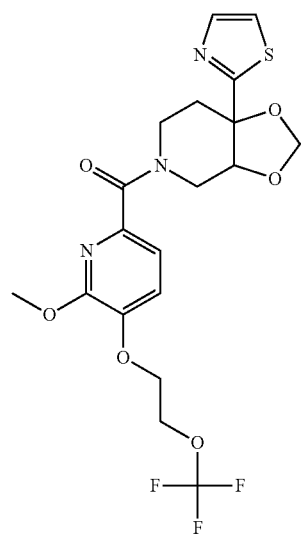 [SMILES: COc1nc(C(=O)N2CCC3(c4nccs4)OCOC3C2)ccc1OCCOC(F)(F)F] |
TABLE 2-continued
| 426 | 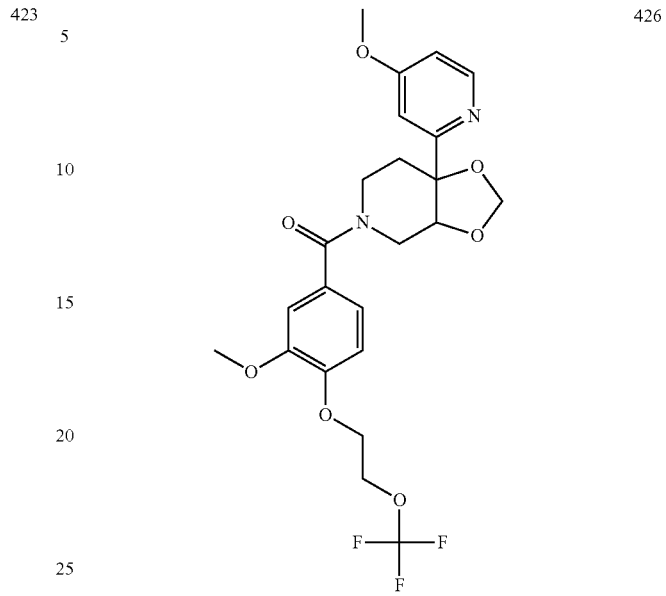 |

TABLE 2-continued
| 429 | 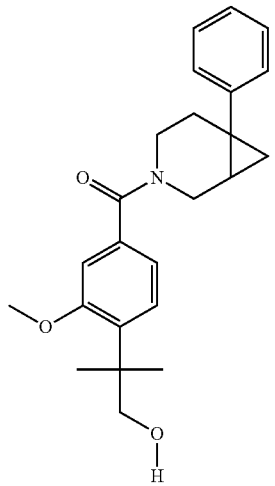 [SMILES: COc1cc(C(=O)N2CCC3(c4ccccc4)CC3C2)ccc1C(C)(C)CO] |
| --- | --- |
| 430 | 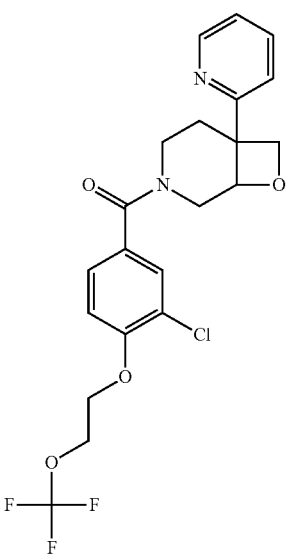 [SMILES: O=C(c1ccc(OCCOC(F)(F)F)c(Cl)c1)N1CCC2(c3ccccn3)COC2C1] |
| 431 | 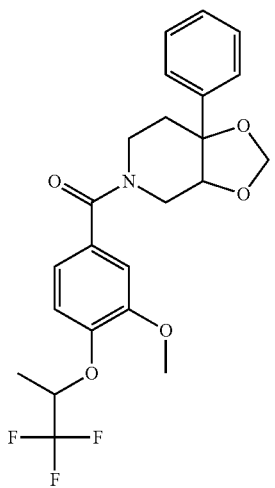 [SMILES: COc1cc(C(=O)N2CCC3(c4ccccc4)OCOC3C2)ccc1OC(C)C(F)(F)F] |
TABLE 2-continued
| 432 | 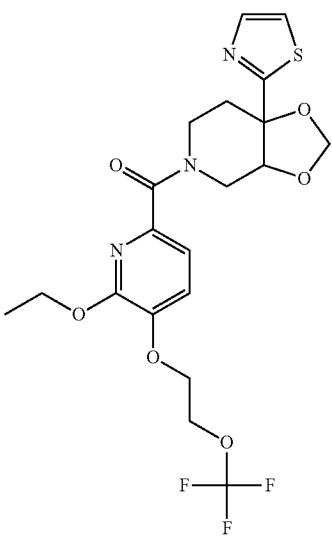 [SMILES: CCOc1nc(C(=O)N2CCC3(c4nccs4)OCOC3C2)ccc1OCCOC(F)(F)F] |
| --- | --- |
| 433 |  |
| 434 | 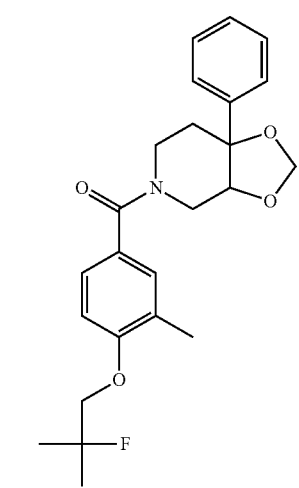 [SMILES: Cc1cc(C(=O)N2CCC3(c4ccccc4)OCOC3C2)ccc1OCC(C)(C)F] |

TABLE 2-continued
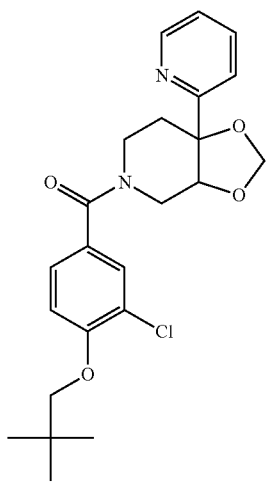 [SMILES: CC(C)(C)COc1ccc(C(=O)N2CCC3(c4ccccn4)OCOC3C2)cc1Cl]
435
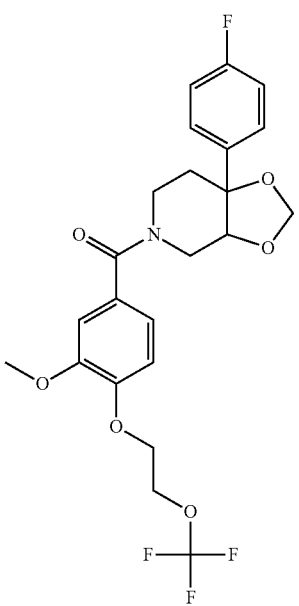 [SMILES: COc1cc(C(=O)N2CCC3(c4ccc(F)cc4)OCOC3C2)ccc1OCCOC(F)(F)F]
436
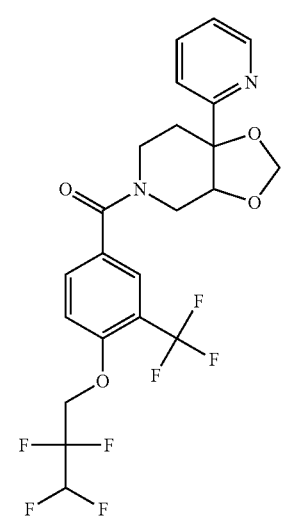 [SMILES: O=C(c1ccc(OCC(F)(F)C(F)F)c(C(F)(F)F)c1)N1CCC2(c3ccccn3)OCOC2C1]
437
TABLE 2-continued
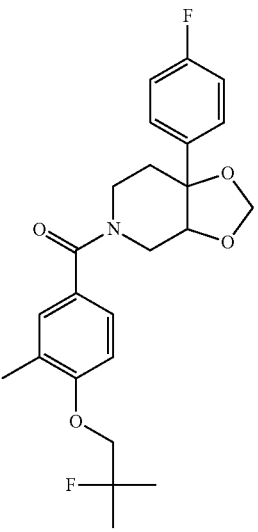 [SMILES: Cc1cc(C(=O)N2CCC3(c4ccc(F)cc4)OCOC3C2)ccc1OCC(C)(C)F]
438
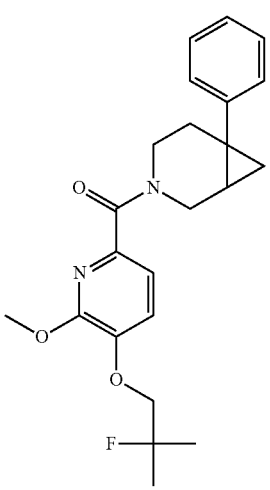 [SMILES: COc1nc(C(=O)N2CCC3(c4ccccc4)CC3C2)ccc1OCC(C)(C)F]
439
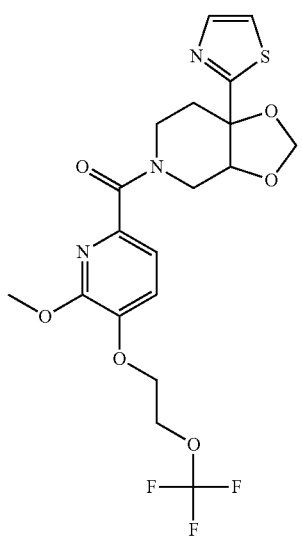 [SMILES: COc1nc(C(=O)N2CCC3(c4nccs4)OCOC3C2)ccc1OCCOC(F)(F)F]
440

TABLE 2-continued
441 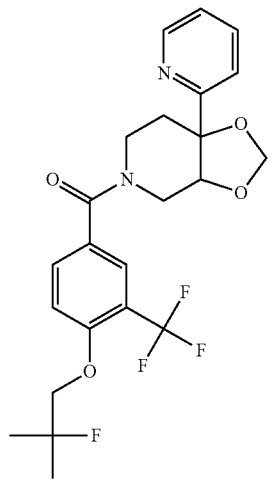 [SMILES: CC(C)(F)COc1ccc(C(=O)N2CCC3(c4ccccn4)OCOC3C2)cc1C(F)(F)F]
442 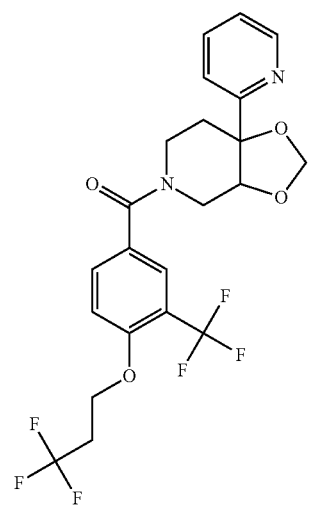 [SMILES: O=C(c1ccc(OCCC(F)(F)F)c(C(F)(F)F)c1)N1CCC2(c3ccccn3)OCOC2C1]
443 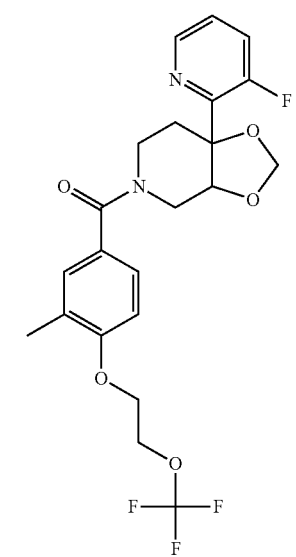 [SMILES: Cc1cc(C(=O)N2CCC3(c4ncccc4F)OCOC3C2)ccc1OCCOC(F)(F)F]
TABLE 2-continued
444 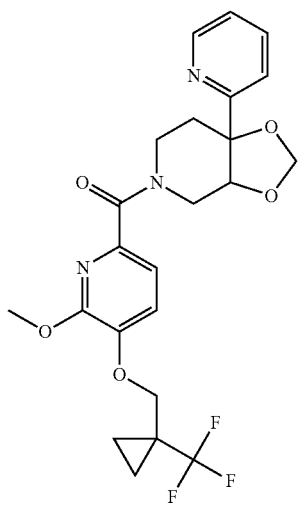 [SMILES: COc1nc(C(=O)N2CCC3(c4ccccn4)OCOC3C2)ccc1OCC1(C(F)(F)F)CC1]
445 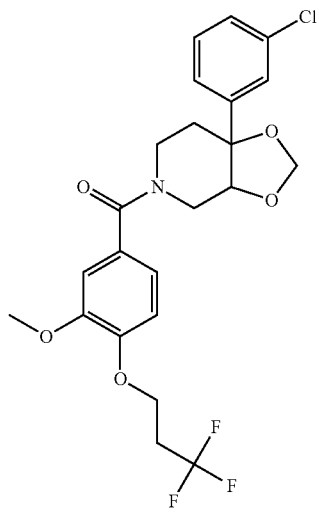 [SMILES: COc1cc(C(=O)N2CCC3(c4cccc(Cl)c4)OCOC3C2)ccc1OCCC(F)(F)F]
446 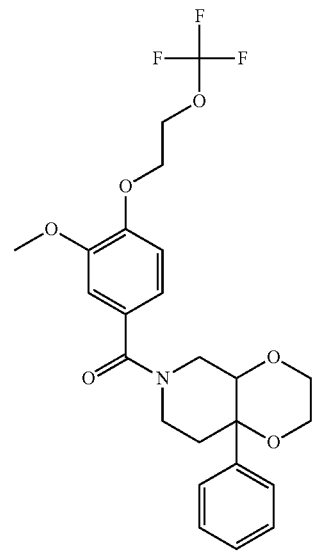 [SMILES: COc1cc(C(=O)N2CCC3(c4ccccc4)OCCOC3C2)ccc1OCCOC(F)(F)F]

TABLE 2-continued
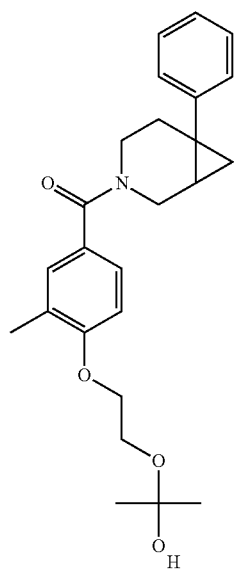
447
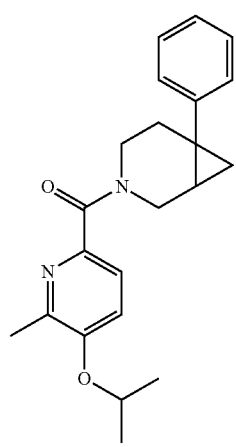 [SMILES: Cc1nc(C(=O)N2CCC3(c4ccccc4)CC3C2)ccc1OC(C)C]
448
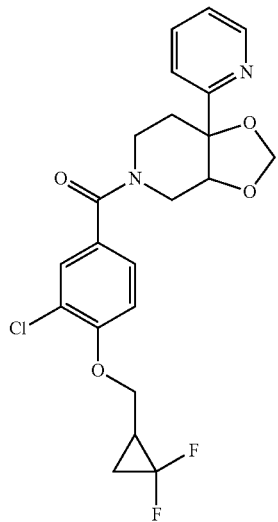 [SMILES: O=C(c1ccc(OCC2CC2(F)F)c(Cl)c1)N1CCC2(c3ccccn3)OCOC2C1]
449
TABLE 2-continued
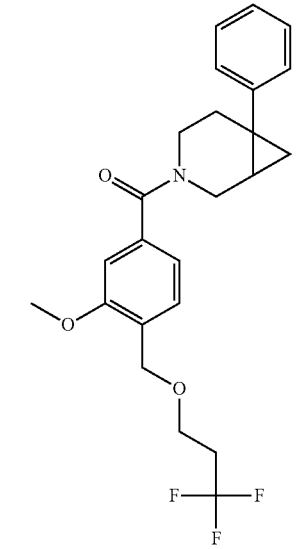 [SMILES: COc1cc(C(=O)N2CCC3(c4ccccc4)CC3C2)ccc1COCCC(F)(F)F]
450
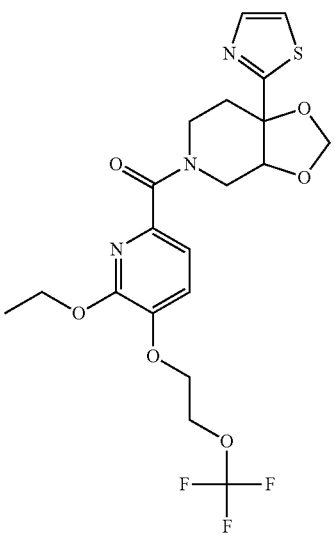 [SMILES: CCOc1nc(C(=O)N2CCC3(c4nccs4)OCOC3C2)ccc1OCCOC(F)(F)F]
451
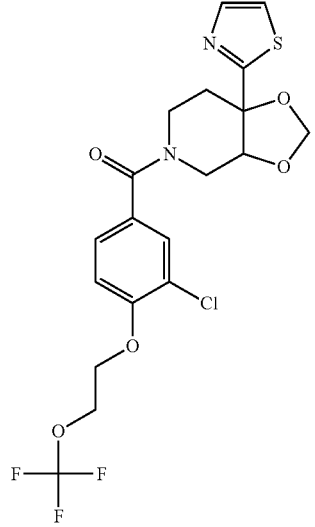
452

TABLE 2-continued
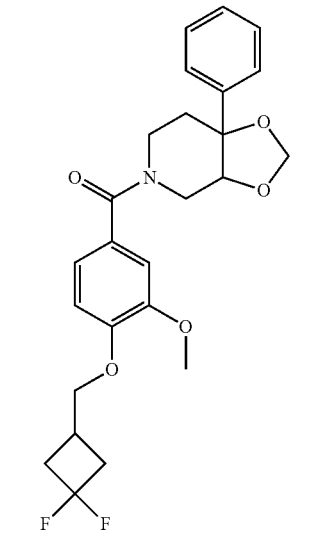 [SMILES: COc1cc(C(=O)N2CCC3(c4ccccc4)OCOC3C2)ccc1OCC1CC(F)(F)C1]
453
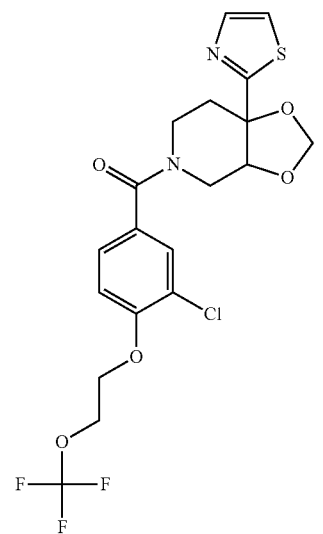
454
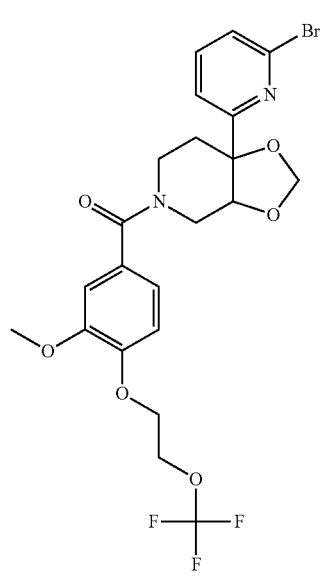 [SMILES: COc1cc(C(=O)N2CCC3(c4cccc(Br)n4)OCOC3C2)ccc1OCCOC(F)(F)F]
455
TABLE 2-continued
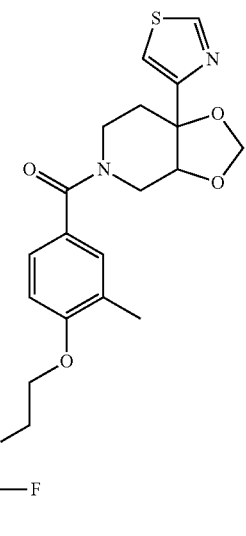
456
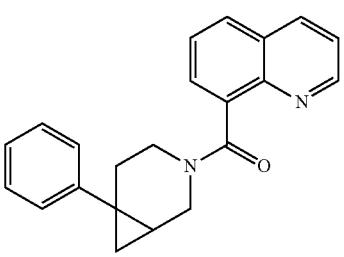 [SMILES: O=C(c1cccc2cccnc12)N1CCC2(c3ccccc3)CC2C1]
457
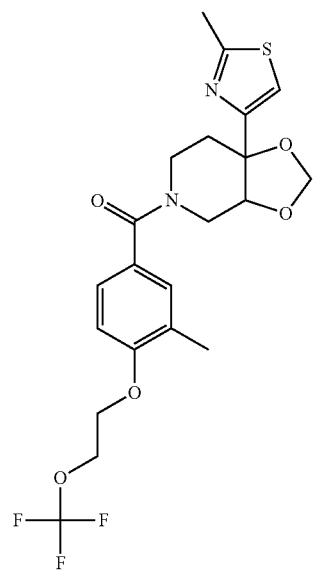 [SMILES: Cc1nc(C23CCN(C(=O)c4ccc(OCCOC(F)(F)F)c(C)c4)CC2OCO3)cs1]
458

TABLE 2-continued
459 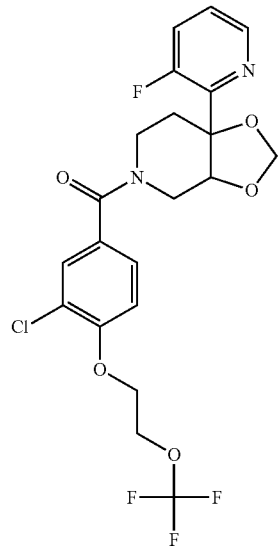 [SMILES: O=C(c1ccc(OCCOC(F)(F)F)c(Cl)c1)N1CCC2(c3ncccc3F)OCOC2C1]
460 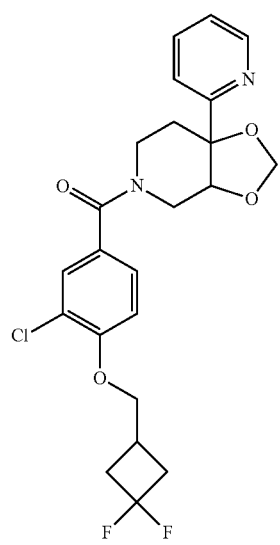 [SMILES: O=C(c1ccc(OCC2CC(F)(F)C2)c(Cl)c1)N1CCC2(c3ccccn3)OCOC2C1]
461 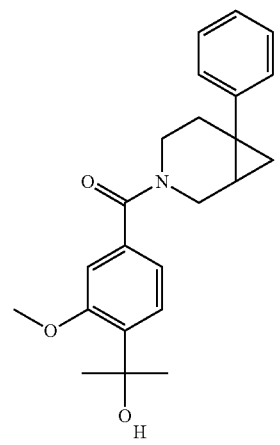
TABLE 2-continued
462 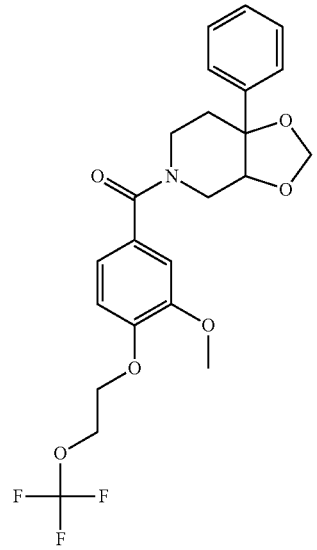
463 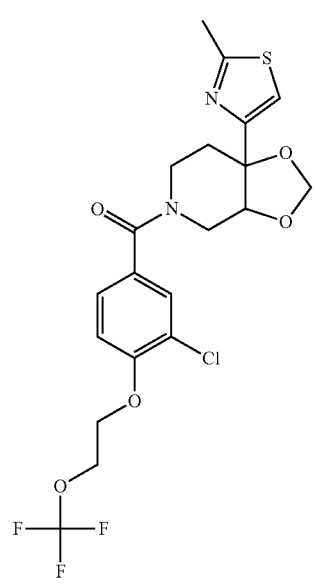

TABLE 2-continued
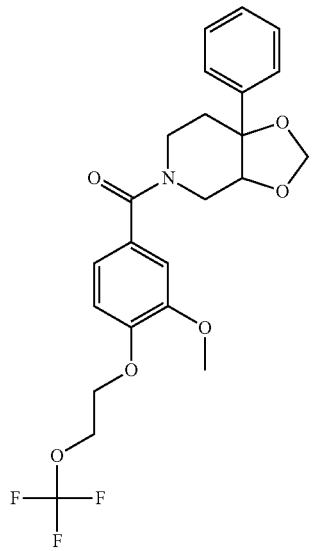
464
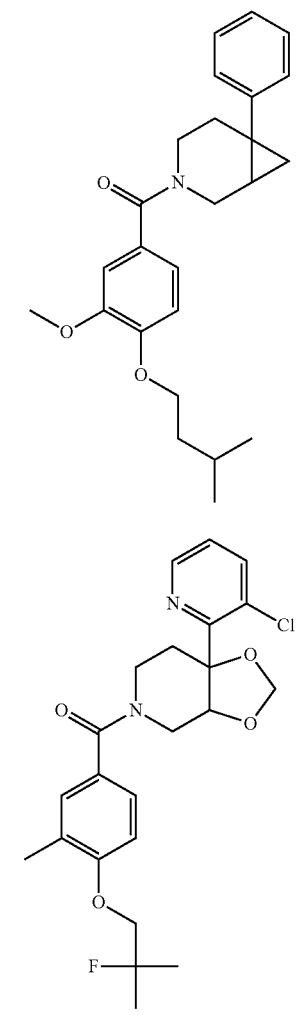
465
466
TABLE 2-continued
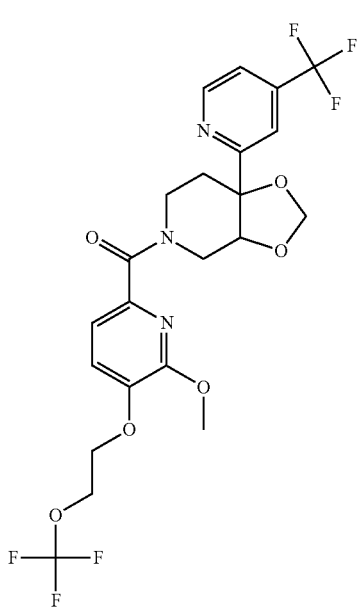 [SMILES: COc1nc(C(=O)N2CCC3(c4cc(C(F)(F)F)ccn4)OCOC3C2)ccc1OCCOC(F)(F)F]
467
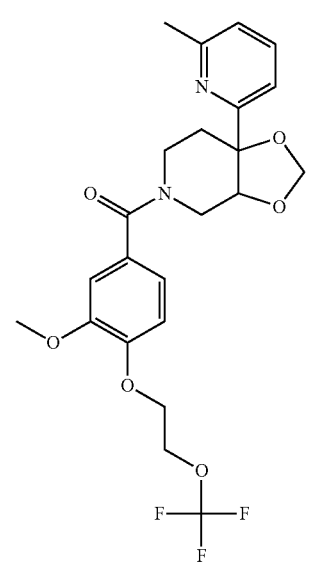 [SMILES: COc1cc(C(=O)N2CCC3(c4cccc(C)n4)OCOC3C2)ccc1OCCOC(F)(F)F]
468

TABLE 2-continued
469
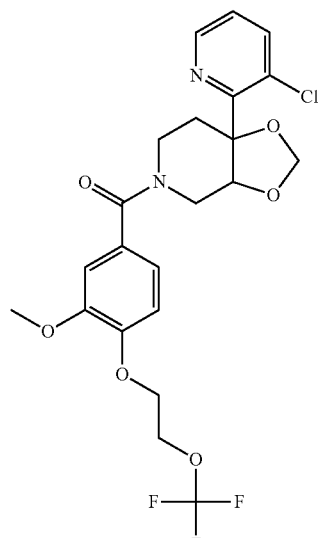
470
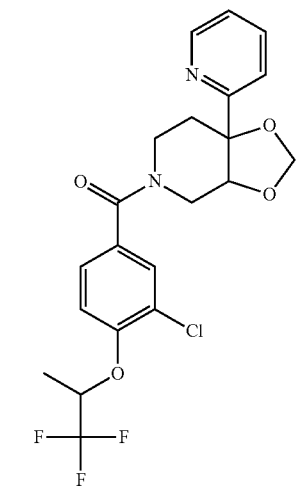 [SMILES: CC(Oc1ccc(C(=O)N2CCC3(c4ccccn4)OCOC3C2)cc1Cl)C(F)(F)F]
471
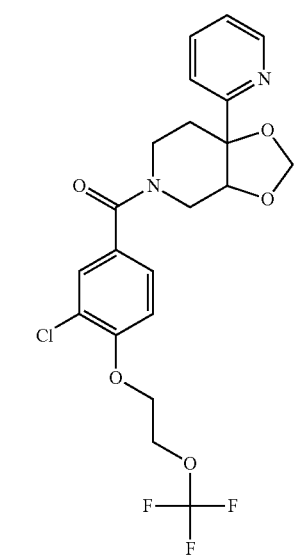 [SMILES: O=C(c1ccc(OCCOC(F)(F)F)c(Cl)c1)N1CCC2(c3ccccn3)OCOC2C1]
TABLE 2-continued
472
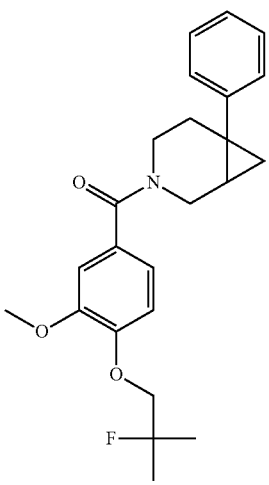
473
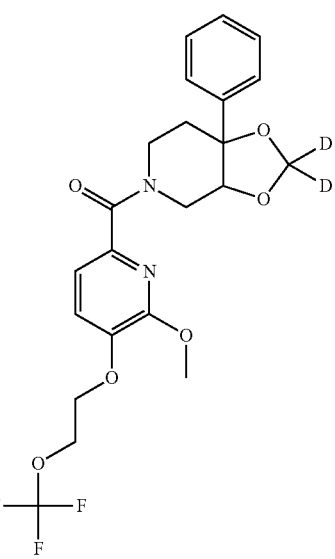
474
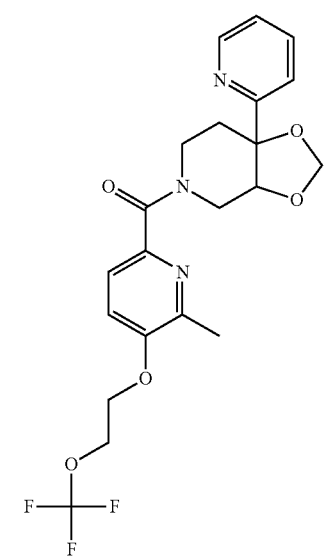 [SMILES: Cc1nc(C(=O)N2CCC3(c4ccccn4)OCOC3C2)ccc1OCCOC(F)(F)F]

TABLE 2-continued
| | |
|---|---|
| 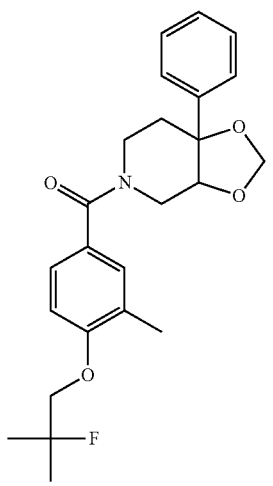 [SMILES: Cc1cc(C(=O)N2CCC3(c4ccccc4)OCOC3C2)ccc1OCC(C)(C)F] | 475 |
| 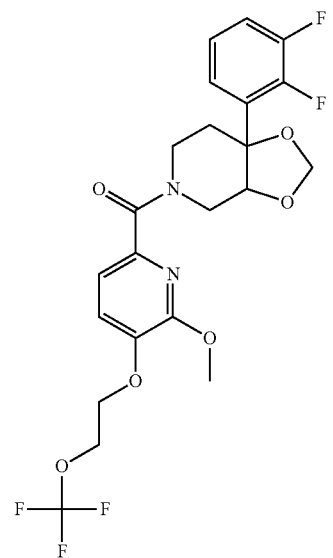 [SMILES: COc1nc(C(=O)N2CCC3(c4cccc(F)c4F)OCOC3C2)ccc1OCCOC(F)(F)F] | 476 |
| 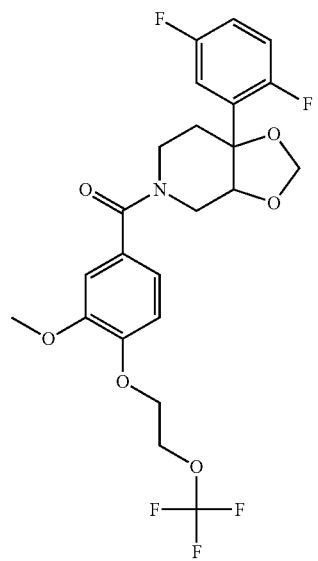 [SMILES: COc1cc(C(=O)N2CCC3(c4cc(F)ccc4F)OCOC3C2)ccc1OCCOC(F)(F)F] | 477 |
| 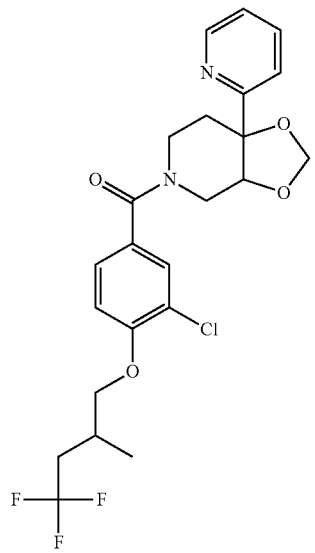 [SMILES: CC(COc1ccc(C(=O)N2CCC3(c4ccccn4)OCOC3C2)cc1Cl)CC(F)(F)F] | 478 |
| 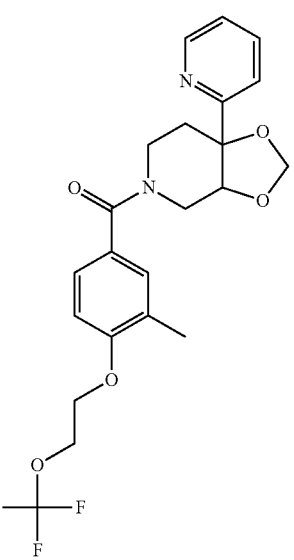 | 479 |
| 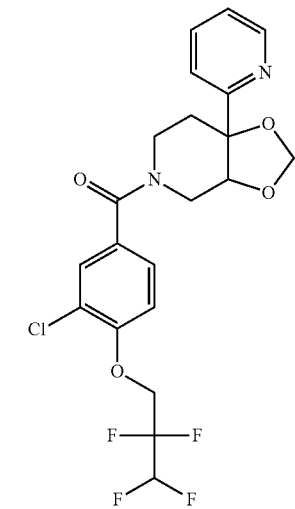 [SMILES: O=C(c1ccc(OCC(F)(F)C(F)F)c(Cl)c1)N1CCC2(c3ccccn3)OCOC2C1] | 480 |

TABLE 2-continued
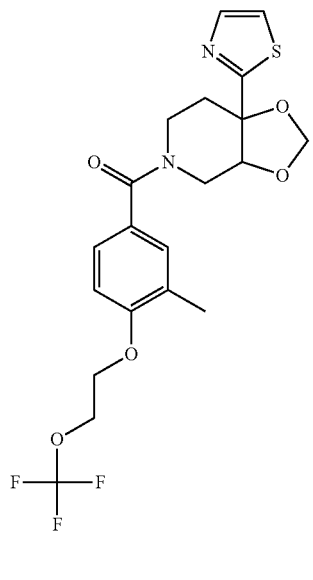 [SMILES: Cc1cc(C(=O)N2CCC3(c4nccs4)OCOC3C2)ccc1OCCOC(F)(F)F]
481
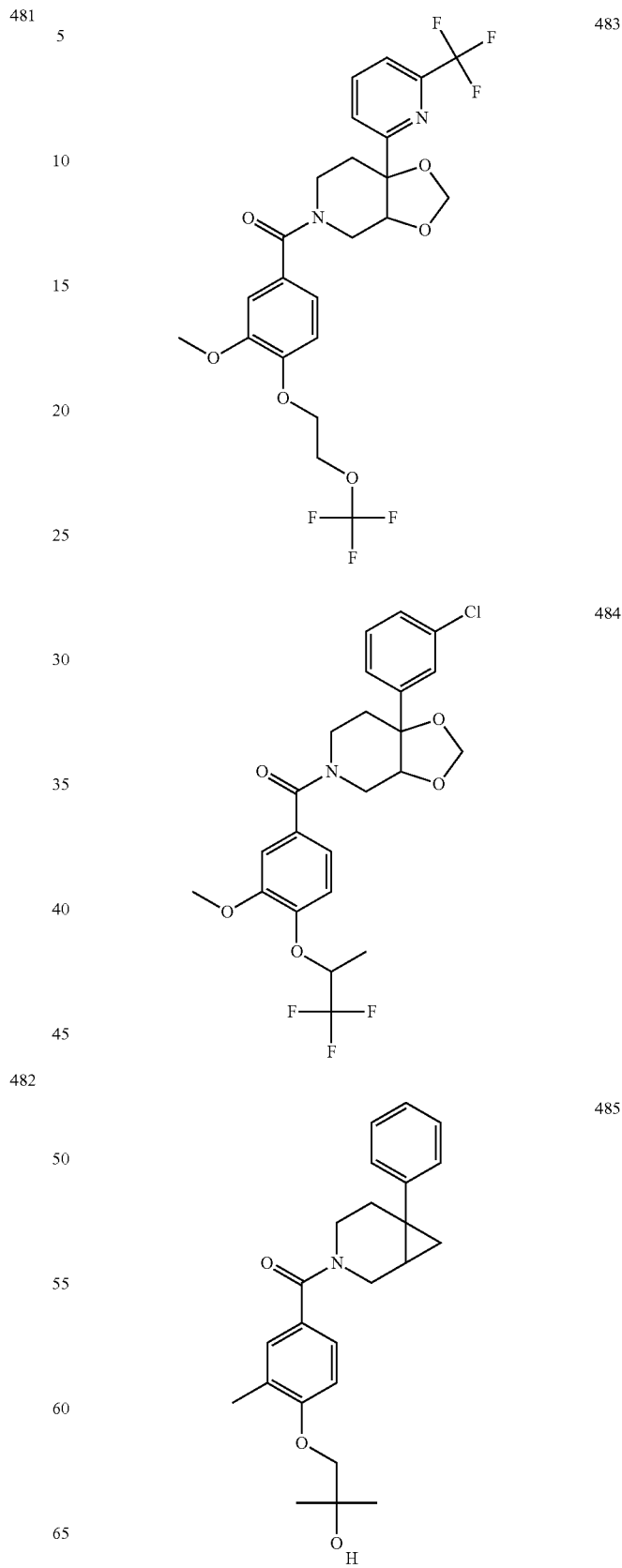
483
484
485
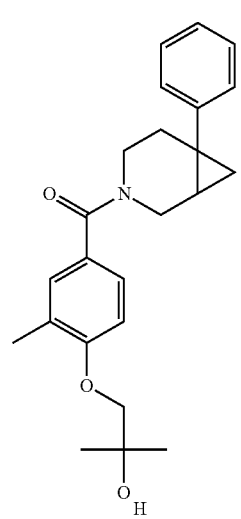
482

TABLE 2-continued
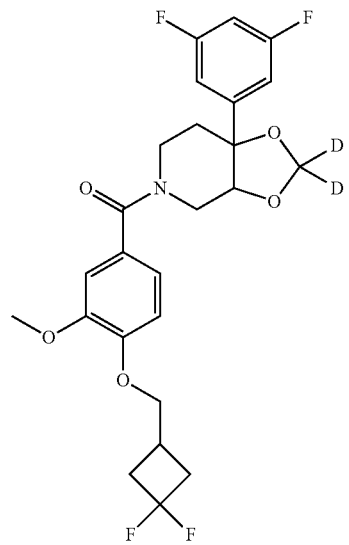 [SMILES: [2H]C1([2H])OC2CN(C(=O)c3ccc(OCC4CC(F)(F)C4)c(OC)c3)CCC2(c2cc(F)cc(F)c2)O1]
486
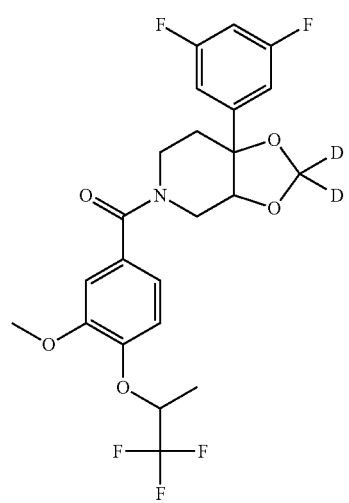 [SMILES: [2H]C1([2H])OC2CN(C(=O)c3ccc(OC(C)C(F)(F)F)c(OC)c3)CCC2(c2cc(F)cc(F)c2)O1]
487
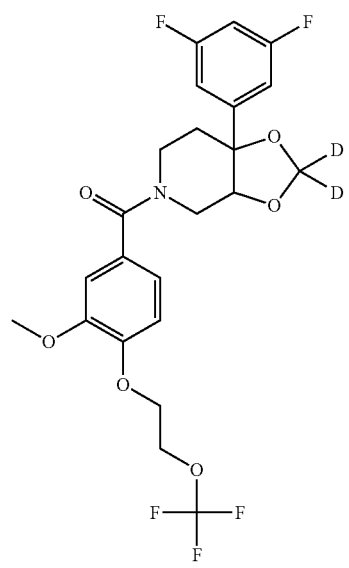 [SMILES: [2H]C1([2H])OC2CN(C(=O)c3ccc(OCCOC(F)(F)F)c(OC)c3)CCC2(c2cc(F)cc(F)c2)O1]
488
TABLE 2-continued
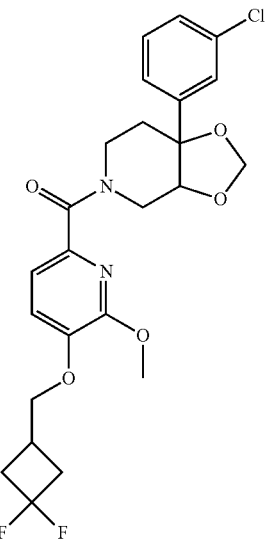
489
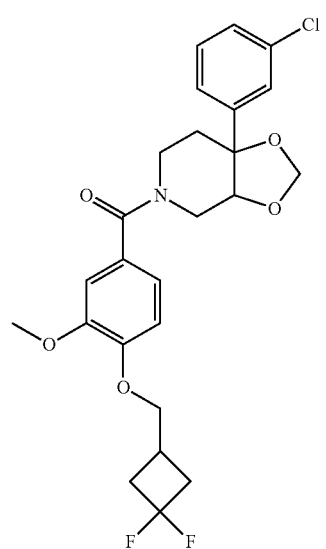 [SMILES: COc1cc(C(=O)N2CCC3(c4cccc(Cl)c4)OCOC3C2)ccc1OCC1CC(F)(F)C1]
490
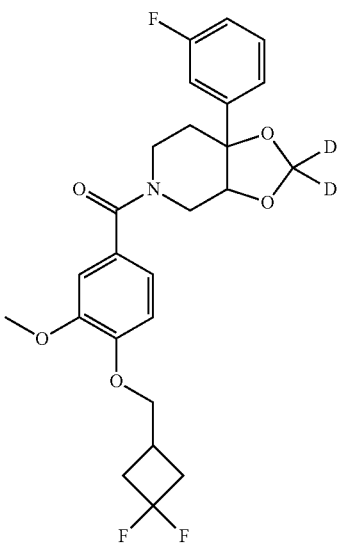 [SMILES: [2H]C1([2H])OC2CN(C(=O)c3ccc(OCC4CC(F)(F)C4)c(OC)c3)CCC2(c2cccc(F)c2)O1]
491

TABLE 2-continued
492
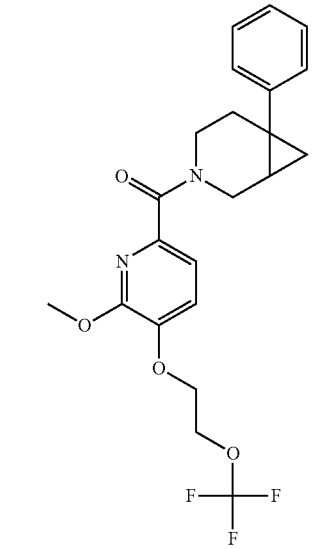 [SMILES: COc1nc(C(=O)N2CCC3(c4ccccc4)CC3C2)ccc1OCCOC(F)(F)F]
493
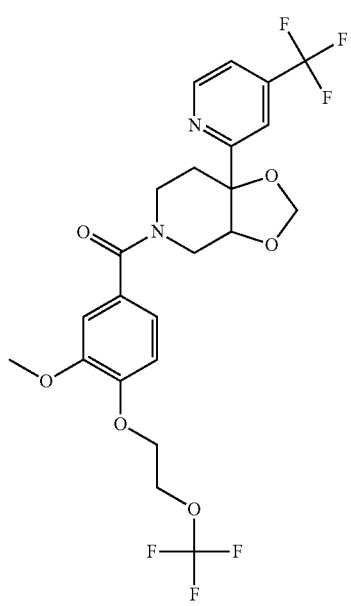 [SMILES: COc1cc(C(=O)N2CCC3(c4cc(C(F)(F)F)ccn4)OCOC3C2)ccc1OCCOC(F)(F)F]
TABLE 2-continued
494
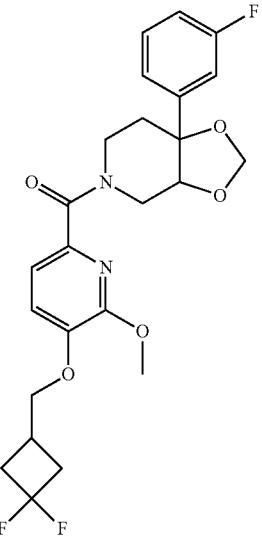
495
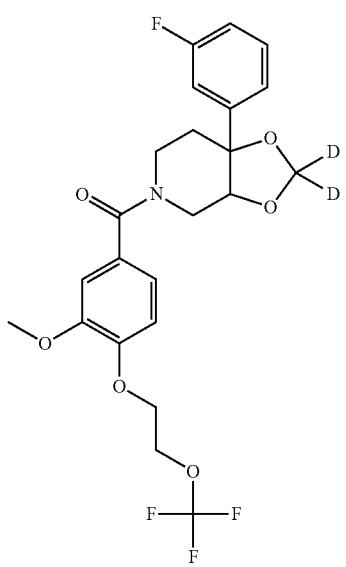 [SMILES: [2H]C1([2H])OC2CN(C(=O)c3ccc(OCCOC(F)(F)F)c(OC)c3)CCC2(c2cccc(F)c2)O1]
496
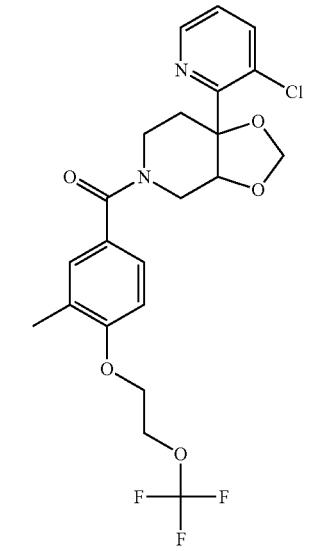 [SMILES: Cc1cc(C(=O)N2CCC3(c4ncccc4Cl)OCOC3C2)ccc1OCCOC(F)(F)F]

TABLE 2-continued
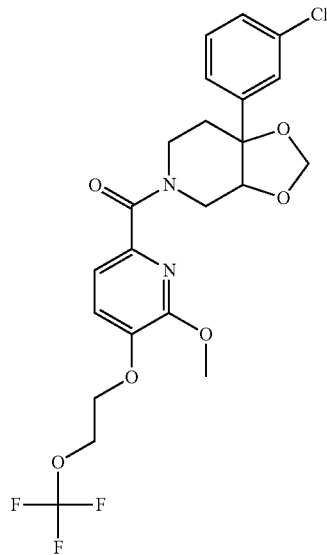 [SMILES: COc1nc(C(=O)N2CCC3(c4cccc(Cl)c4)OCOC3C2)ccc1OCCOC(F)(F)F] 497
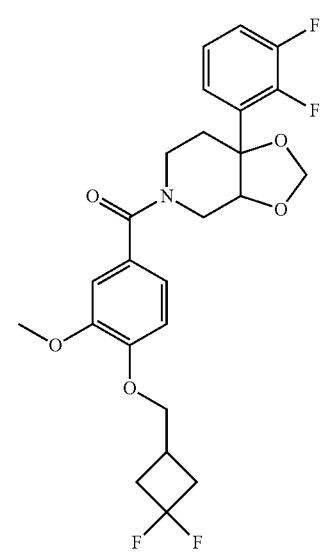 498
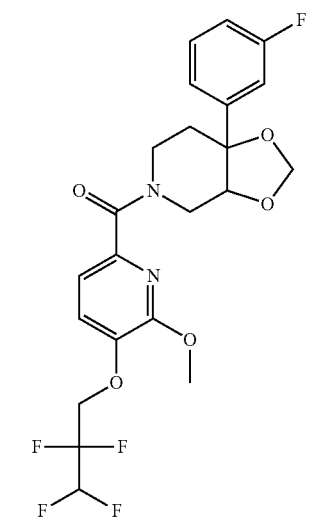 [SMILES: COc1nc(C(=O)N2CCC3(c4cccc(F)c4)OCOC3C2)ccc1OCC(F)(F)C(F)F] 499
TABLE 2-continued
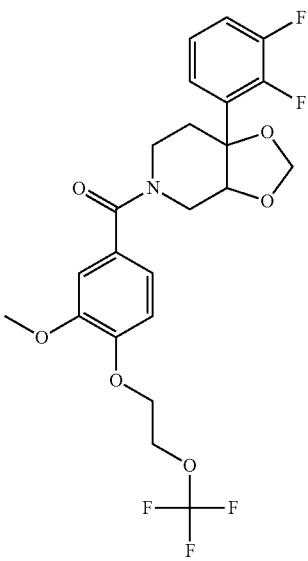 [SMILES: COc1cc(C(=O)N2CCC3(c4cccc(F)c4F)OCOC3C2)ccc1OCCOC(F)(F)F] 500
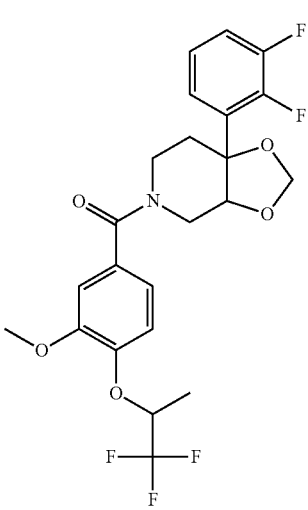 [SMILES: COc1cc(C(=O)N2CCC3(c4cccc(F)c4F)OCOC3C2)ccc1OC(C)C(F)(F)F] 501
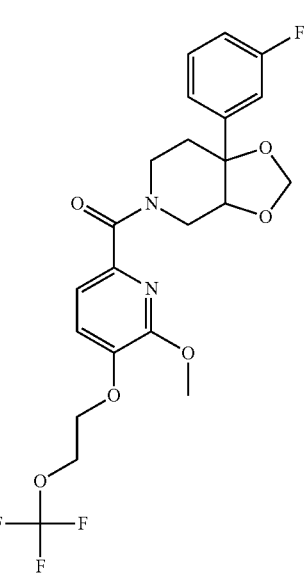 502

TABLE 2-continued
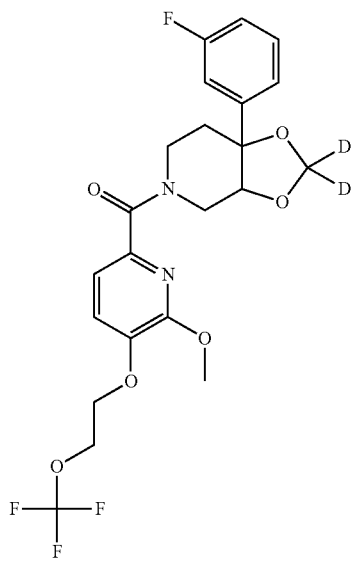 [SMILES: [2H]C1([2H])OC2CN(C(=O)c3ccc(OCCOC(F)(F)F)c(OC)n3)CCC2(c2cccc(F)c2)O1]
503
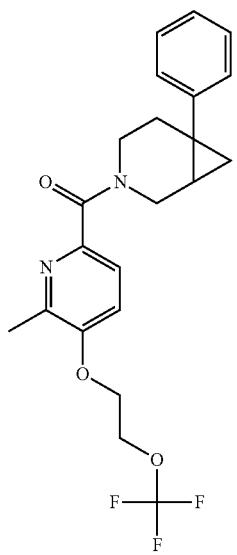
505
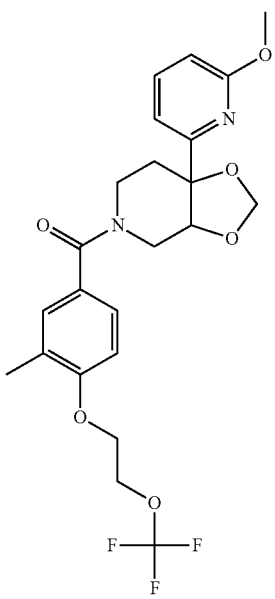
504
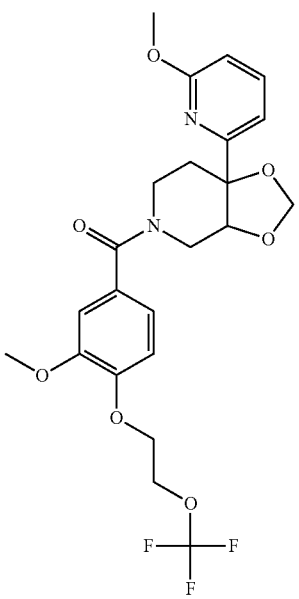 [SMILES: COc1cccc(C23CCN(C(=O)c4ccc(OCCOC(F)(F)F)c(OC)c4)CC2OCO3)n1]
506

TABLE 2-continued
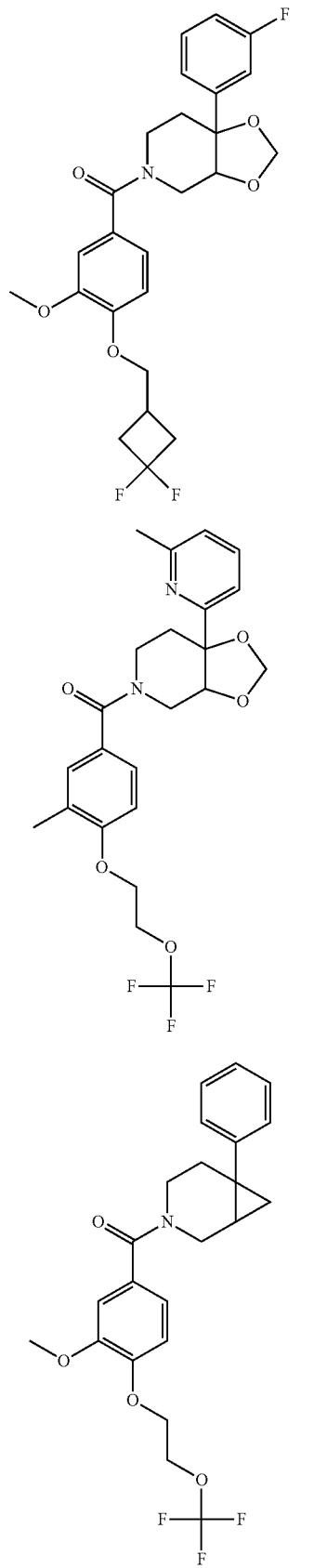
507
508
509
TABLE 2-continued
510
511

TABLE 2-continued
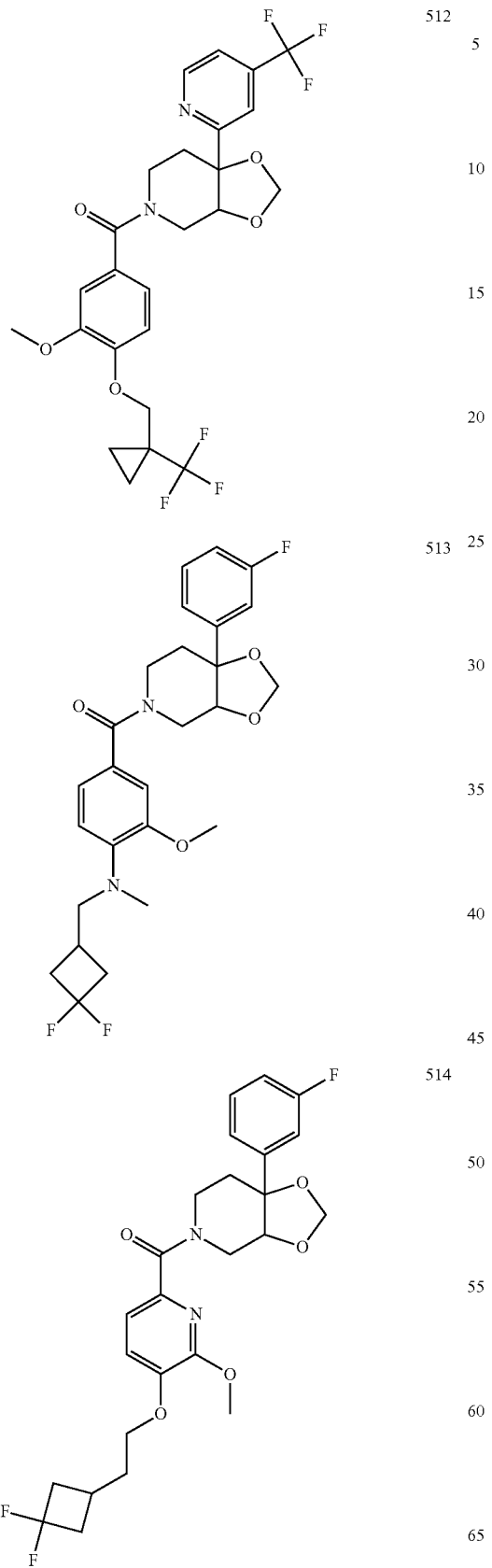

TABLE 2-continued
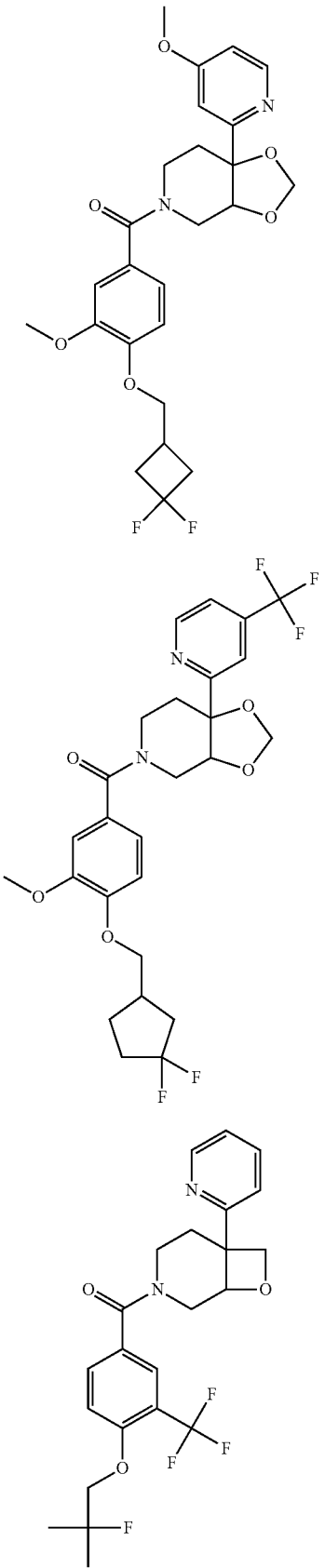
517
518
519
TABLE 2-continued
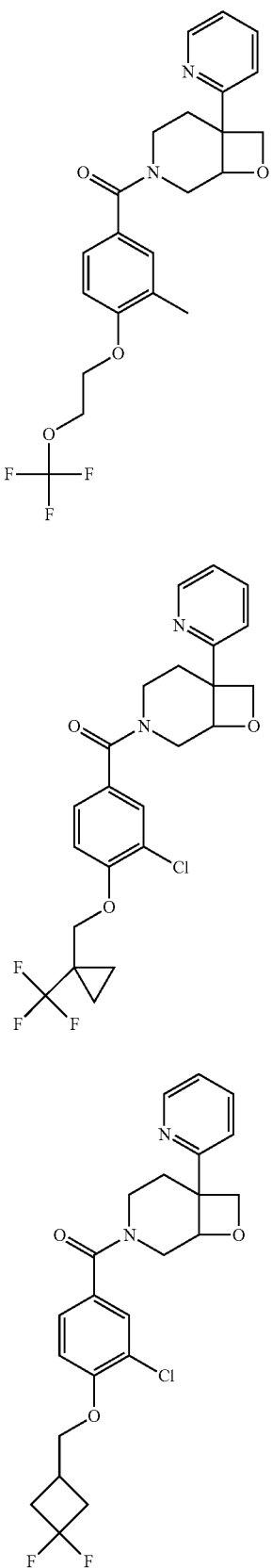
520
521
522

TABLE 2-continued
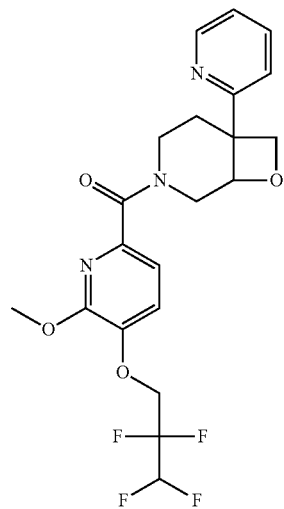 [SMILES: COc1nc(C(=O)N2CCC3(c4ccccn4)COC3C2)ccc1OCC(F)(F)C(F)F]
523
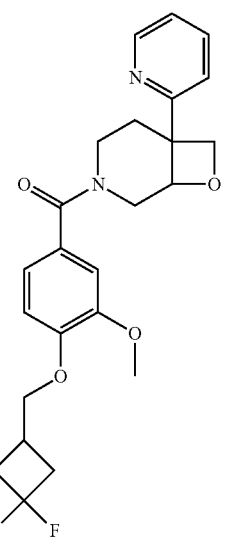
524
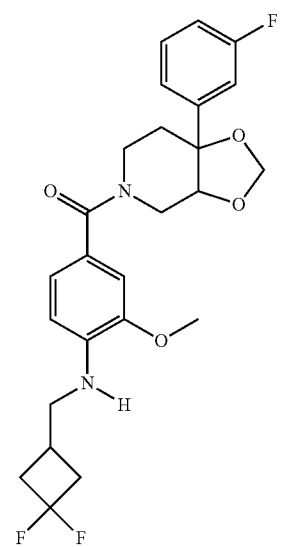 [SMILES: COc1cc(C(=O)N2CCC3(c4cccc(F)c4)OCOC3C2)ccc1NCC1CC(F)(F)C1]
525
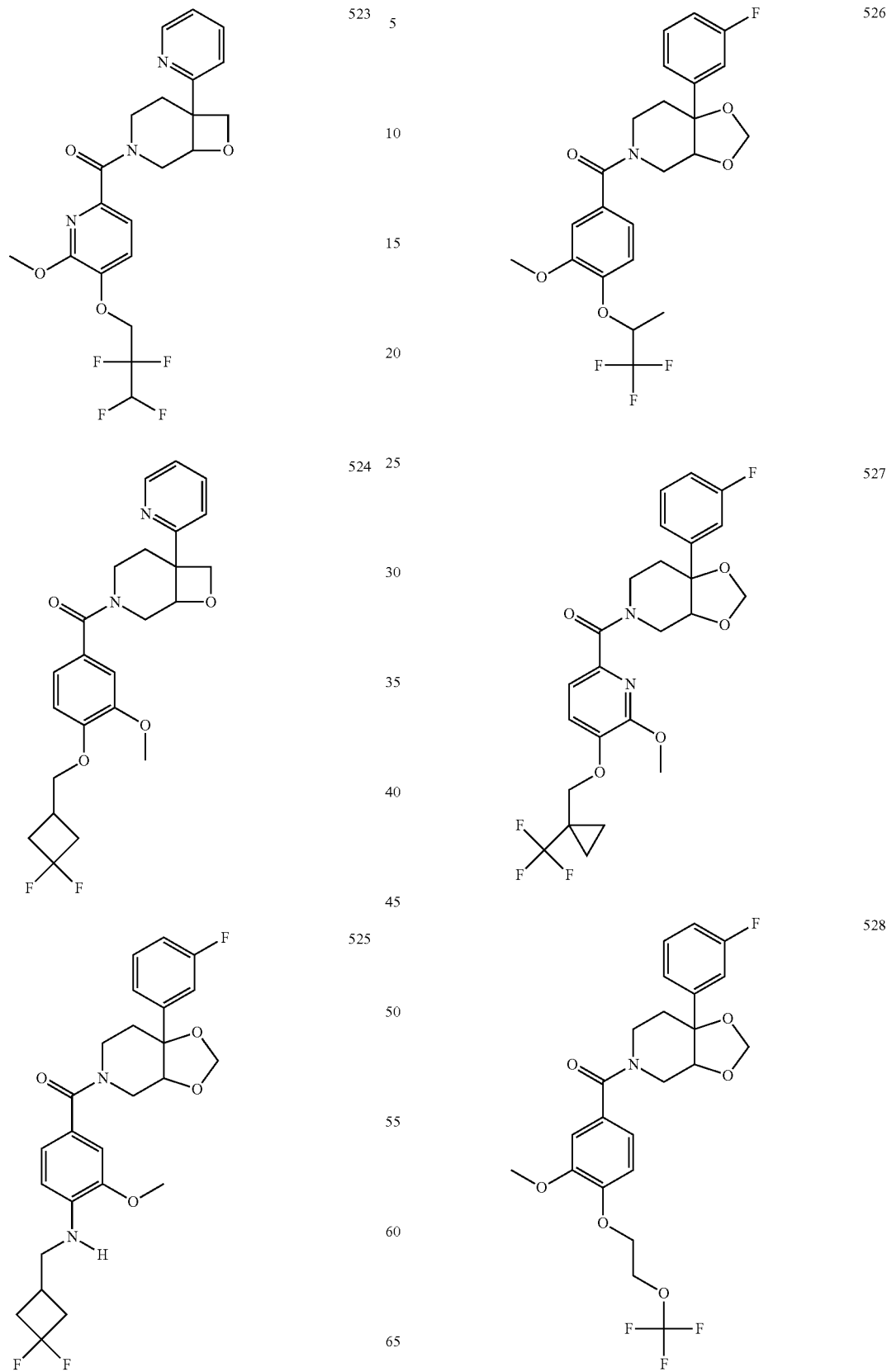
526
527
528

TABLE 2-continued
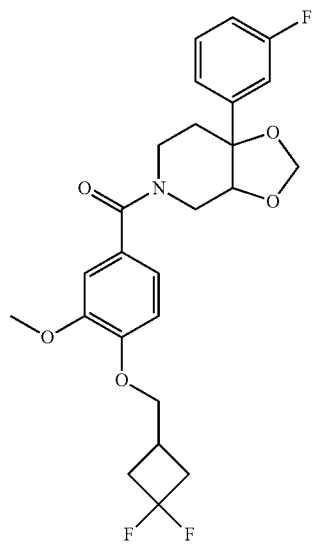 [SMILES: COc1cc(C(=O)N2CCC3(c4cccc(F)c4)OCOC3C2)ccc1OCC1CC(F)(F)C1]
529
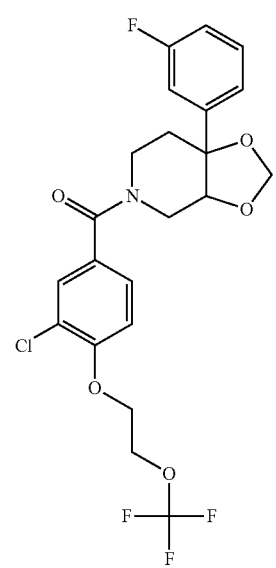
530
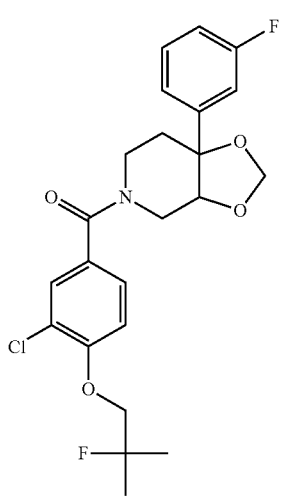 [SMILES: CC(C)(F)COc1ccc(C(=O)N2CCC3(c4cccc(F)c4)OCOC3C2)cc1Cl]
531
TABLE 2-continued
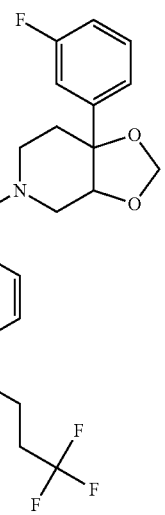
532
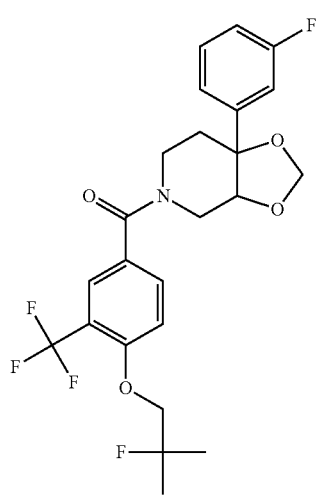 [SMILES: CC(C)(F)COc1ccc(C(=O)N2CCC3(c4cccc(F)c4)OCOC3C2)cc1C(F)(F)F]
533
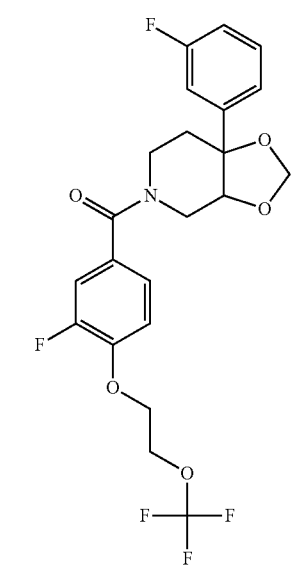 [SMILES: O=C(c1ccc(OCCOC(F)(F)F)c(F)c1)N1CCC2(c3cccc(F)c3)OCOC2C1]
534

TABLE 2-continued
535
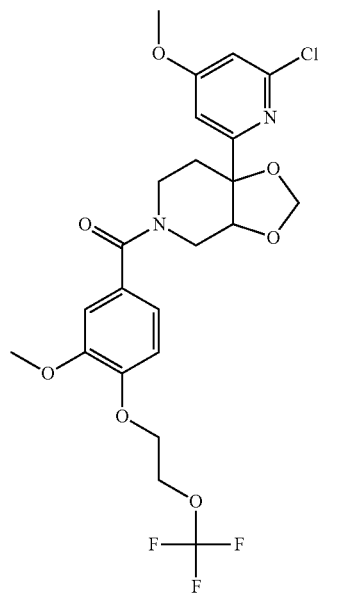 [SMILES: COc1cc(Cl)nc(C23CCN(C(=O)c4ccc(OCCOC(F)(F)F)c(OC)c4)CC2OCO3)c1]
536
537
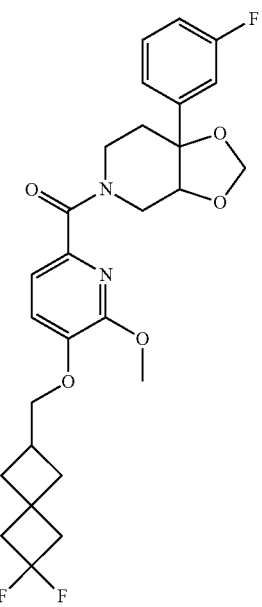
538

TABLE 2-continued
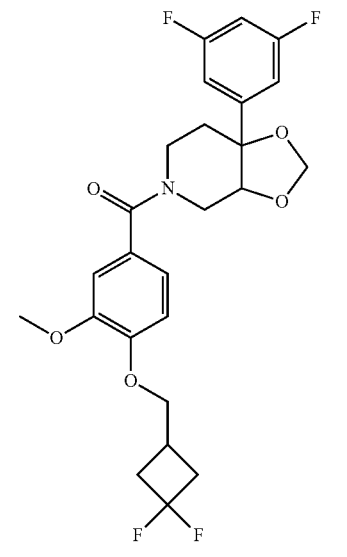 [SMILES: COc1cc(C(=O)N2CCC3(c4cc(F)cc(F)c4)OCOC3C2)ccc1OCC1CC(F)(F)C1]
539
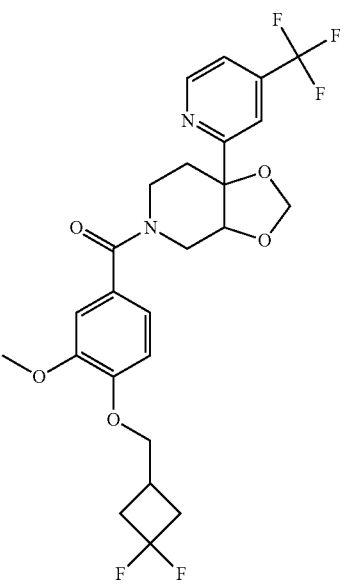 [SMILES: COc1cc(C(=O)N2CCC3(c4cc(C(F)(F)F)ccn4)OCOC3C2)ccc1OCC1CC(F)(F)C1]
540
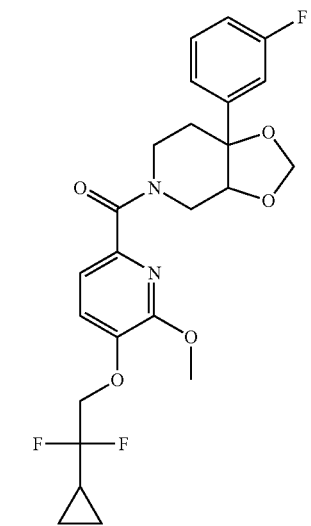 [SMILES: COc1nc(C(=O)N2CCC3(c4cccc(F)c4)OCOC3C2)ccc1OCC(F)(F)C1CC1]
541
TABLE 2-continued
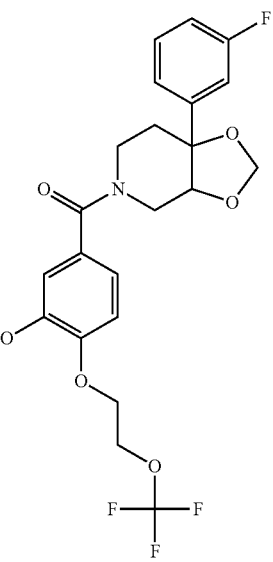
542
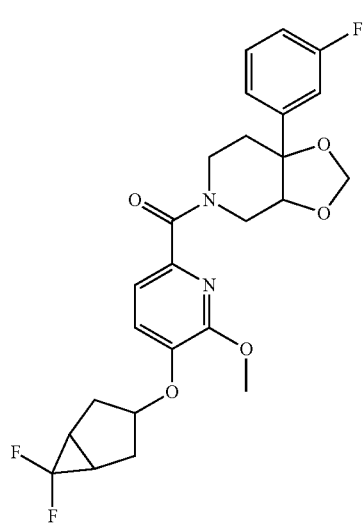 [SMILES: COc1nc(C(=O)N2CCC3(c4cccc(F)c4)OCOC3C2)ccc1OC1CC2C(C1)C2(F)F]
543
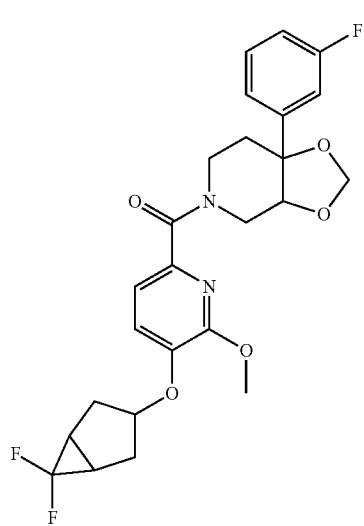 [SMILES: COc1nc(C(=O)N2CCC3(c4cccc(F)c4)OCOC3C2)ccc1OC1CC2C(C1)C2(F)F]
544

| 269 | 270 |
|---|---|
| TABLE 2-continued | TABLE 2-continued |
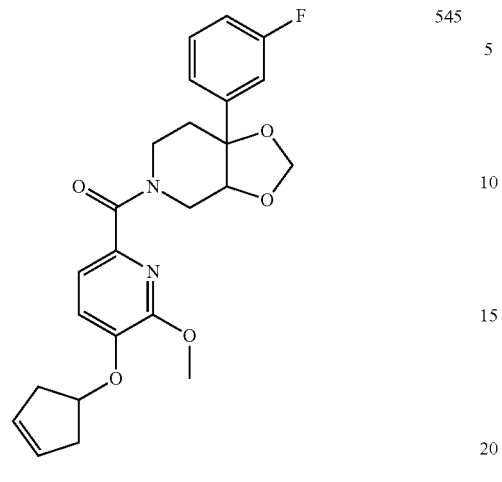
545
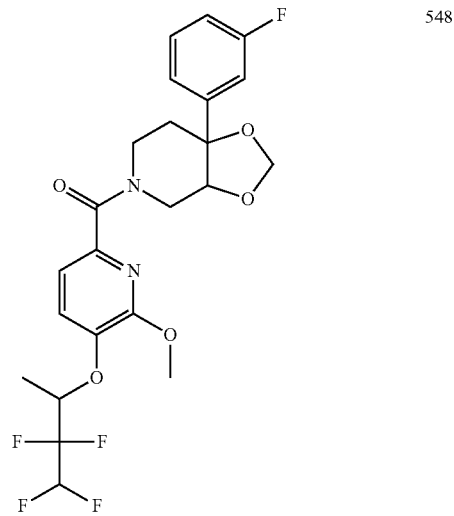
548
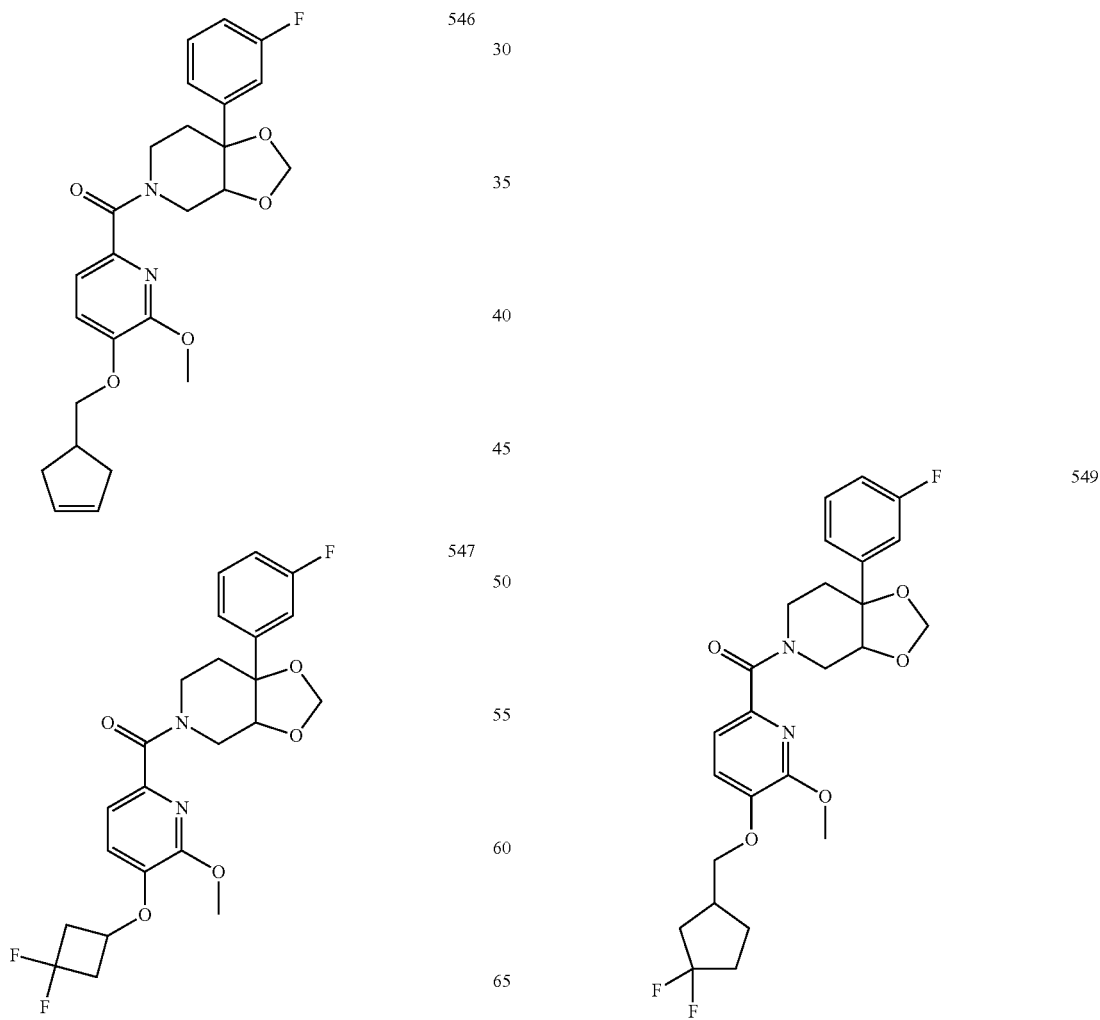
546
547
549

TABLE 2-continued
550
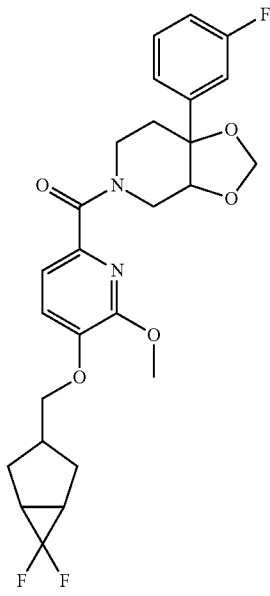 [SMILES: COc1nc(C(=O)N2CCC3(c4cccc(F)c4)OCOC3C2)ccc1OCC1CC2C(C1)C2(F)F]
551
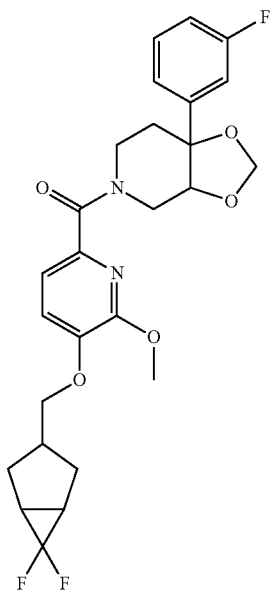 [SMILES: COc1nc(C(=O)N2CCC3(c4cccc(F)c4)OCOC3C2)ccc1OCC1CC2C(C1)C2(F)F]
TABLE 2-continued
552
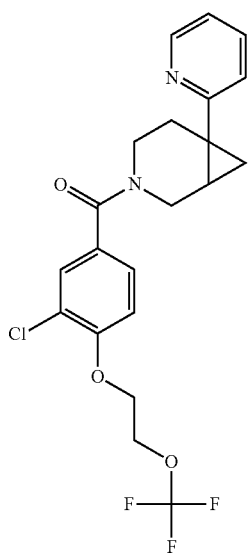 [SMILES: O=C(c1ccc(OCCOC(F)(F)F)c(Cl)c1)N1CCC2(c3ccccn3)CC2C1]
553
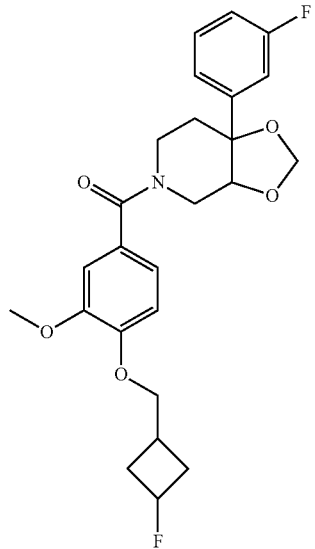 [SMILES: COc1cc(C(=O)N2CCC3(c4cccc(F)c4)OCOC3C2)ccc1OCC1CC(F)C1]
554

TABLE 2-continued
| | |
|---|---|
| 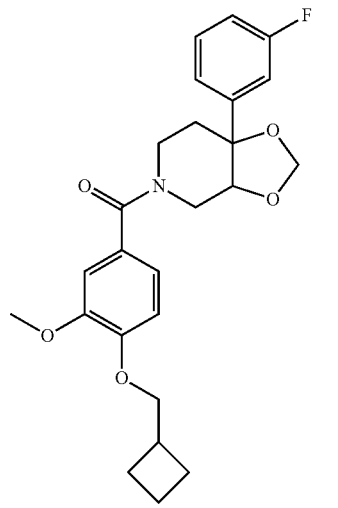 [SMILES: COc1cc(C(=O)N2CCC3(c4cccc(F)c4)OCOC3C2)ccc1OCC1CCC1] | 555 |
| 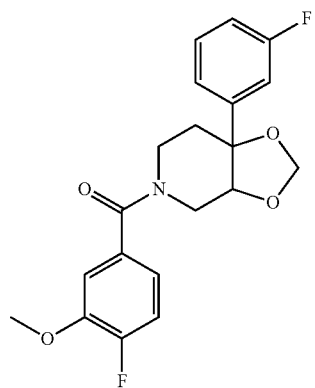 [SMILES: COc1cc(C(=O)N2CCC3(c4cccc(F)c4)OCOC3C2)ccc1F] | 556 |
| 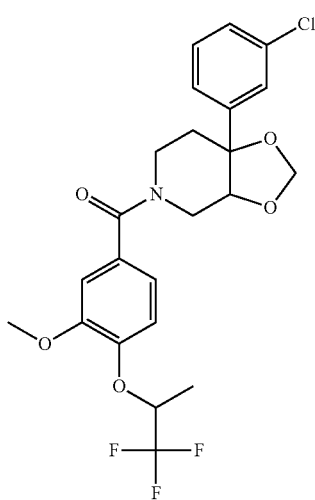 [SMILES: COc1cc(C(=O)N2CCC3(c4cccc(Cl)c4)OCOC3C2)ccc1OC(C)C(F)(F)F] | 557 |
TABLE 2-continued
| | |
|---|---|
| 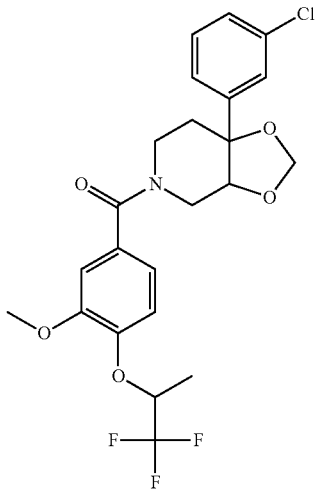 [SMILES: COc1cc(C(=O)N2CCC3(c4cccc(Cl)c4)OCOC3C2)ccc1OC(C)C(F)(F)F] | 558 |
| 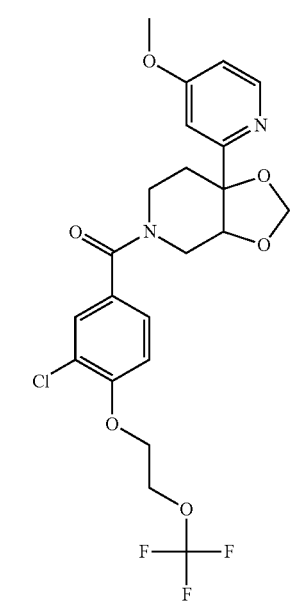 [SMILES: COc1ccnc(C23CCN(C(=O)c4ccc(OCCOC(F)(F)F)c(Cl)c4)CC2OCO3)c1] | 559 |

TABLE 2-continued
275 560
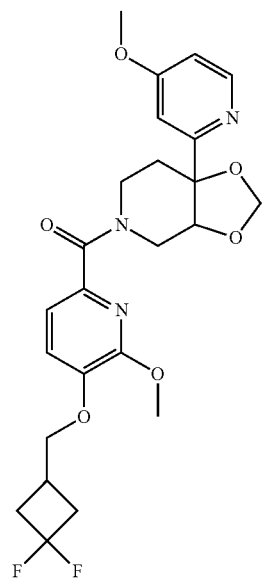 [SMILES: COc1ccnc(C23CCN(C(=O)c4ccc(OCC5CC(F)(F)C5)c(OC)n4)CC2OCO3)c1]
276 562
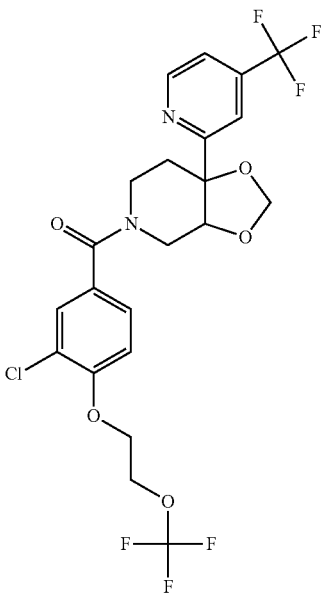
561
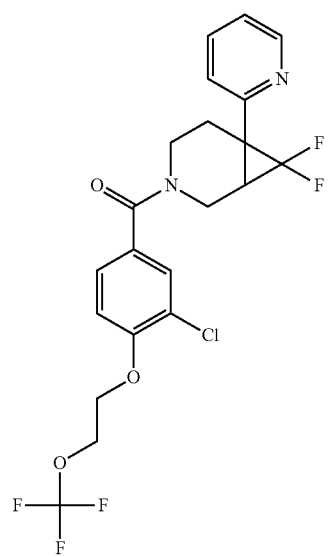 [SMILES: O=C(c1ccc(OCCOC(F)(F)F)c(Cl)c1)N1CCC2(c3ccccn3)C(C1)C2(F)F]
563
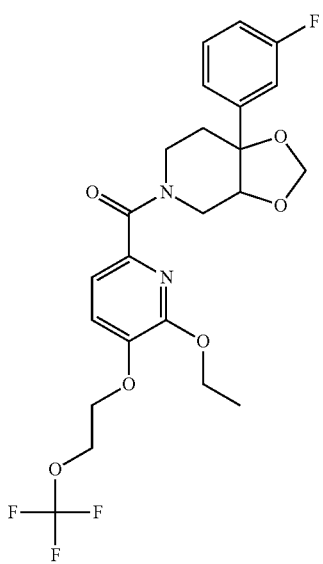 [SMILES: CCOc1nc(C(=O)N2CCC3(c4cccc(F)c4)OCOC3C2)ccc1OCCOC(F)(F)F]

TABLE 2-continued
564 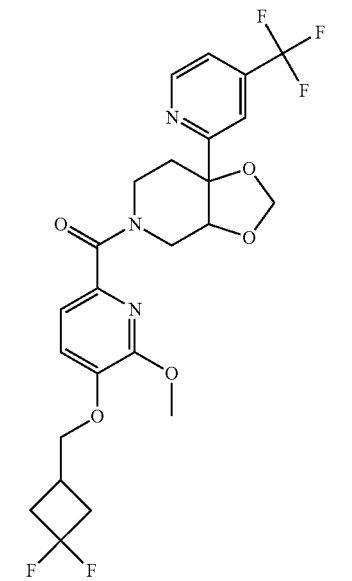 [SMILES: COc1nc(C(=O)N2CCC3(c4cc(C(F)(F)F)ccn4)OCOC3C2)ccc1OCC1CC(F)(F)C1]
565 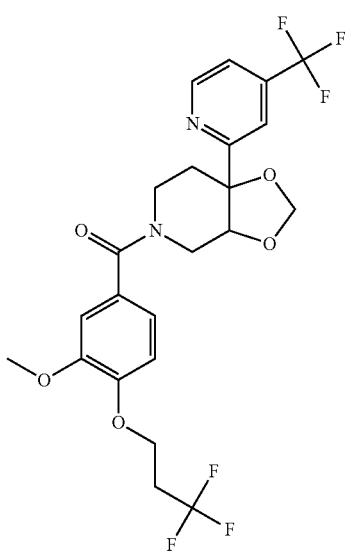 [SMILES: COc1cc(C(=O)N2CCC3(c4cc(C(F)(F)F)ccn4)OCOC3C2)ccc1OCCC(F)(F)F]
566 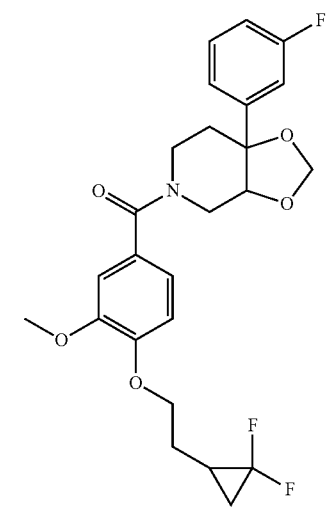 [SMILES: COc1cc(C(=O)N2CCC3(c4cccc(F)c4)OCOC3C2)ccc1OCCC1CC1(F)F]
TABLE 2-continued
567 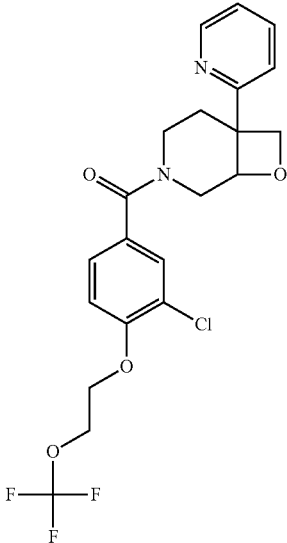
568 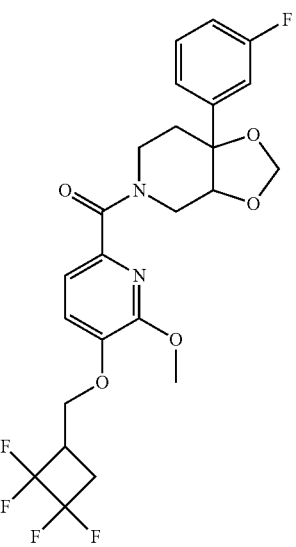 [SMILES: COc1nc(C(=O)N2CCC3(c4cccc(F)c4)OCOC3C2)ccc1OCC1CC(F)(F)C1(F)F]
569 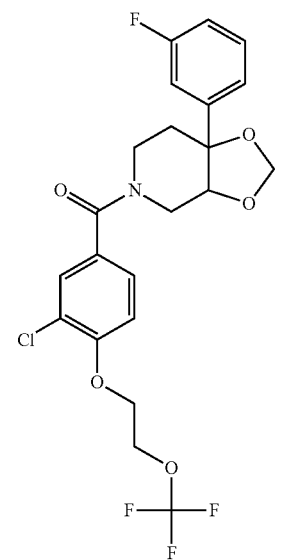 [SMILES: O=C(c1ccc(OCCOC(F)(F)F)c(Cl)c1)N1CCC2(c3cccc(F)c3)OCOC2C1]

TABLE 2-continued
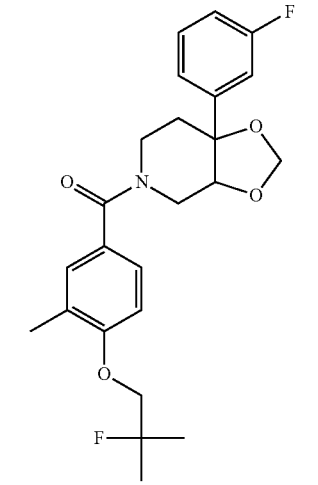 [SMILES: Cc1cc(C(=O)N2CCC3(c4cccc(F)c4)OCOC3C2)ccc1OCC(C)(C)F]
570
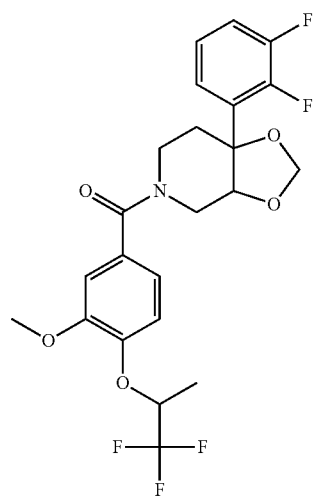 [SMILES: COc1cc(C(=O)N2CCC3(c4cccc(F)c4F)OCOC3C2)ccc1OC(C)C(F)(F)F]
571
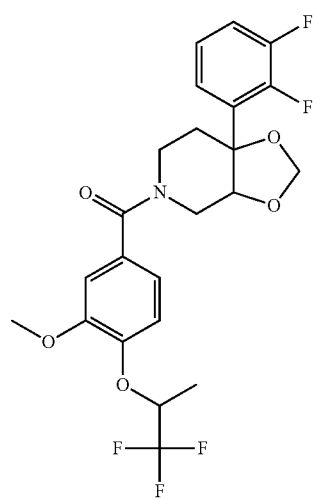 [SMILES: COc1cc(C(=O)N2CCC3(c4cccc(F)c4F)OCOC3C2)ccc1OC(C)C(F)(F)F]
572
TABLE 2-continued
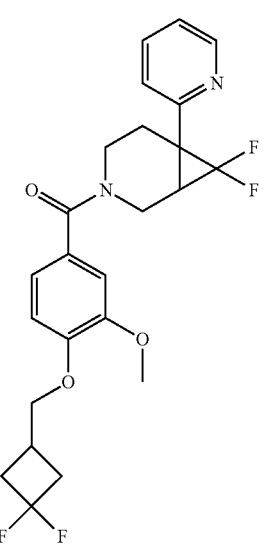
573
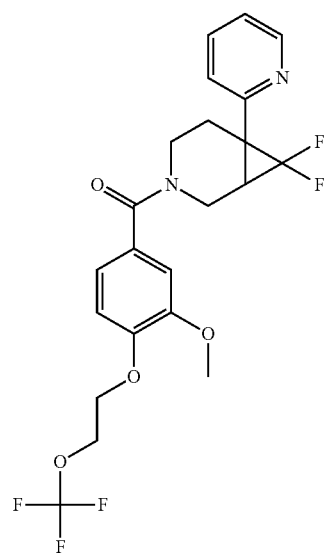 [SMILES: COc1cc(C(=O)N2CCC3(c4ccccn4)C(C2)C3(F)F)ccc1OCCOC(F)(F)F]
574
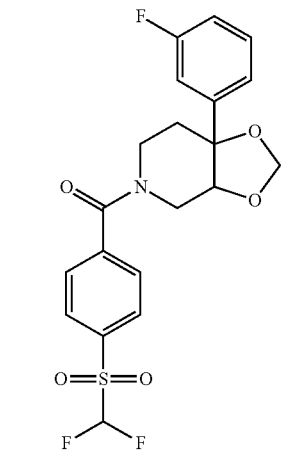 [SMILES: O=C(c1ccc(S(=O)(=O)C(F)F)cc1)N1CCC2(c3cccc(F)c3)OCOC2C1]
575

TABLE 2-continued
576 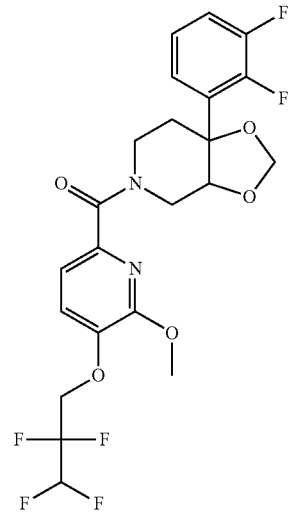 [SMILES: COc1nc(C(=O)N2CCC3(c4cccc(F)c4F)OCOC3C2)ccc1OCC(F)(F)C(F)F]
577 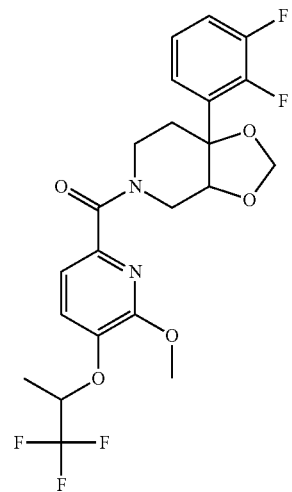 [SMILES: COc1nc(C(=O)N2CCC3(c4cccc(F)c4F)OCOC3C2)ccc1OC(C)C(F)(F)F]
578 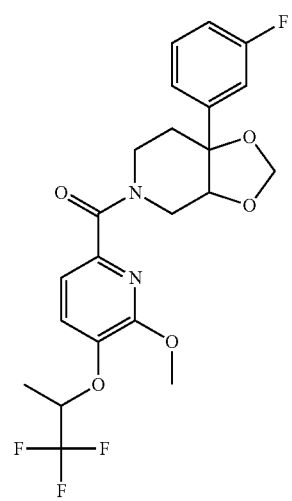 [SMILES: COc1nc(C(=O)N2CCC3(c4cccc(F)c4)OCOC3C2)ccc1OC(C)C(F)(F)F]
TABLE 2-continued
579 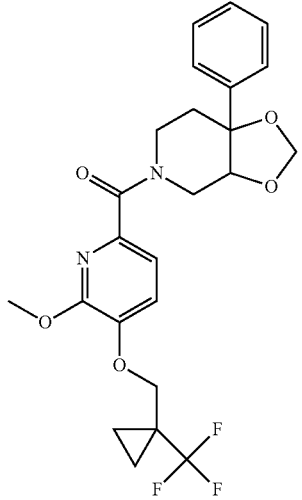 [SMILES: COc1nc(C(=O)N2CCC3(c4ccccc4)OCOC3C2)ccc1OCC1(C(F)(F)F)CC1]
580 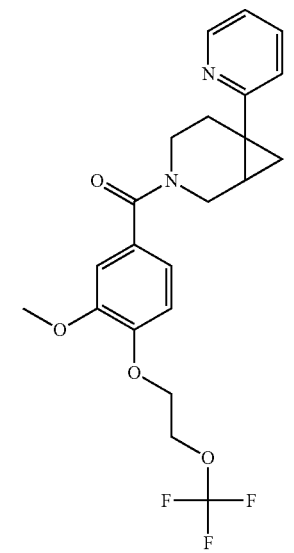 [SMILES: COc1cc(C(=O)N2CCC3(c4ccccn4)CC3C2)ccc1OCCOC(F)(F)F]
581 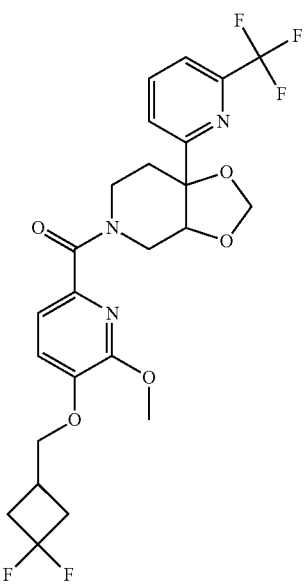 [SMILES: COc1nc(C(=O)N2CCC3(c4cccc(C(F)(F)F)n4)OCOC3C2)ccc1OCC1CC(F)(F)C1]

TABLE 2-continued
582 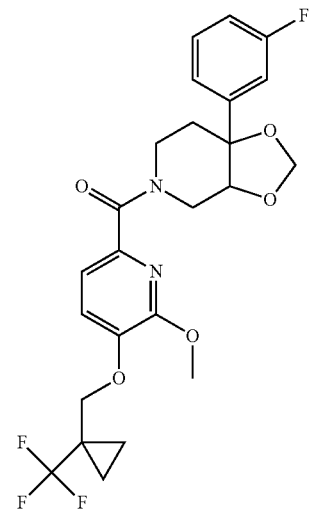 [SMILES: COc1nc(C(=O)N2CCC3(c4cccc(F)c4)OCOC3C2)ccc1OCC1(C(F)(F)F)CC1]
583 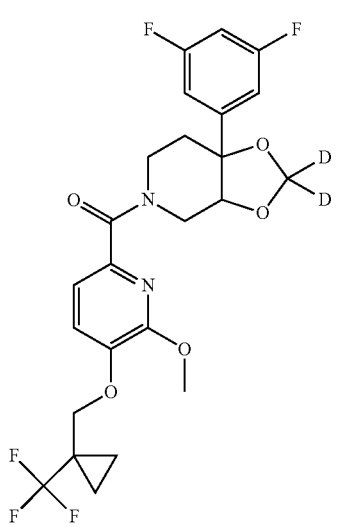 [SMILES: [2H]C1([2H])OC2CN(C(=O)c3ccc(OCC4(C(F)(F)F)CC4)c(OC)n3)CCC2(c2cc(F)cc(F)c2)O1]
584 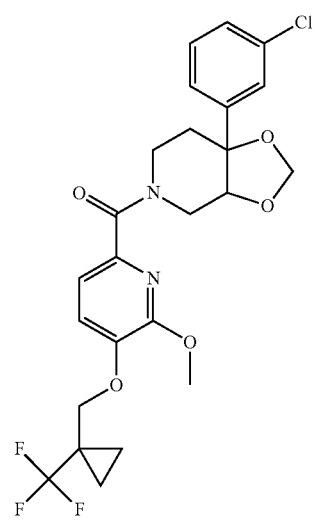 [SMILES: COc1nc(C(=O)N2CCC3(c4cccc(Cl)c4)OCOC3C2)ccc1OCC1(C(F)(F)F)CC1]
TABLE 2-continued
585 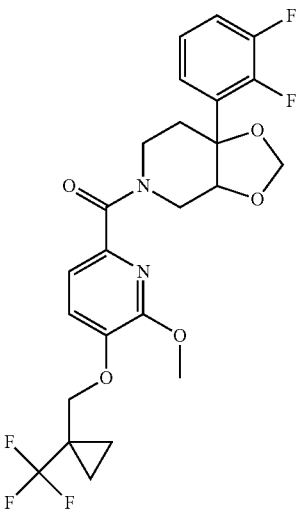 [SMILES: COc1nc(C(=O)N2CCC3(c4cccc(F)c4F)OCOC3C2)ccc1OCC1(C(F)(F)F)CC1]
586 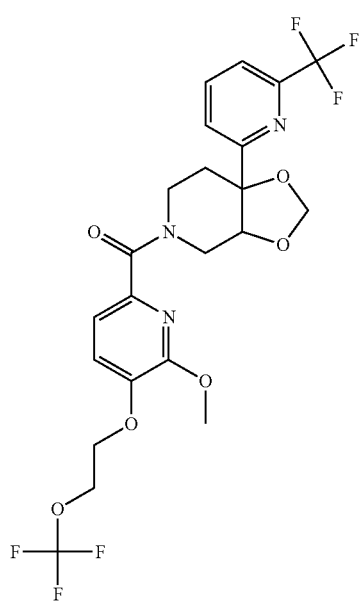 [SMILES: COc1nc(C(=O)N2CCC3(c4cccc(C(F)(F)F)n4)OCOC3C2)ccc1OCCOC(F)(F)F]
587 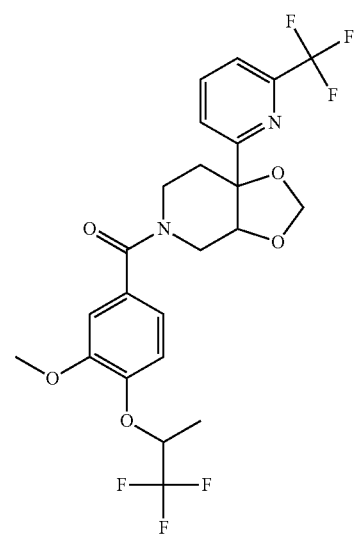 [SMILES: COc1cc(C(=O)N2CCC3(c4cccc(C(F)(F)F)n4)OCOC3C2)ccc1OC(C)C(F)(F)F]

TABLE 2-continued
588
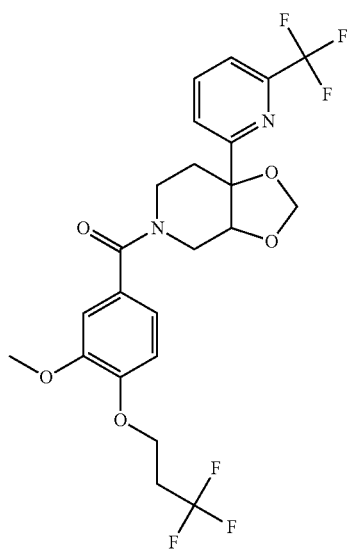 [SMILES: COc1cc(C(=O)N2CCC3(c4cccc(C(F)(F)F)n4)OCOC3C2)ccc1OCCC(F)(F)F]
589
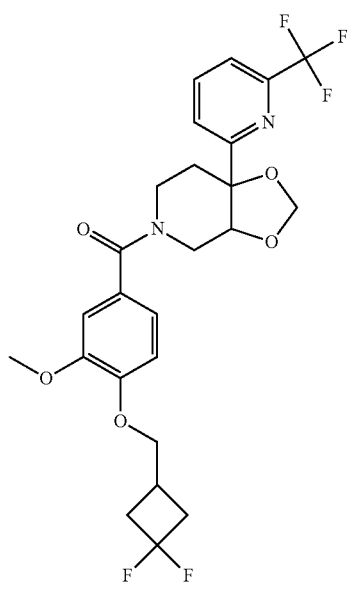 [SMILES: COc1cc(C(=O)N2CCC3(c4cccc(C(F)(F)F)n4)OCOC3C2)ccc1OCC1CC(F)(F)C1]
TABLE 2-continued
590
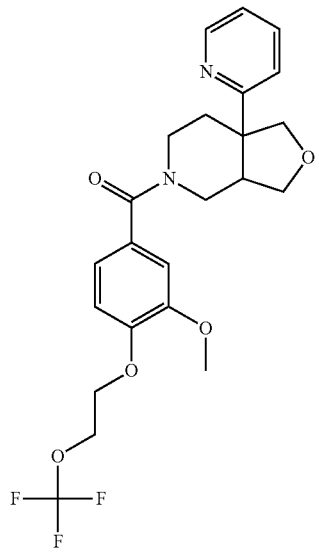 [SMILES: COc1cc(C(=O)N2CCC3(c4ccccn4)COCC3C2)ccc1OCCOC(F)(F)F]
591
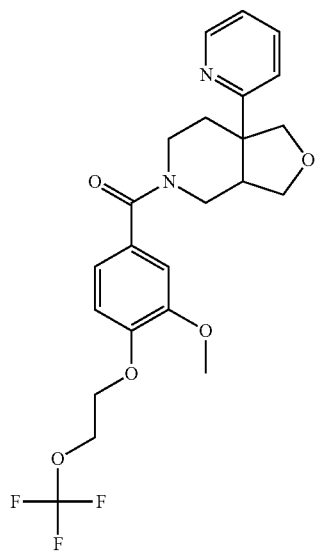 [SMILES: COc1cc(C(=O)N2CCC3(c4ccccn4)COCC3C2)ccc1OCCOC(F)(F)F]
592

TABLE 2-continued
593
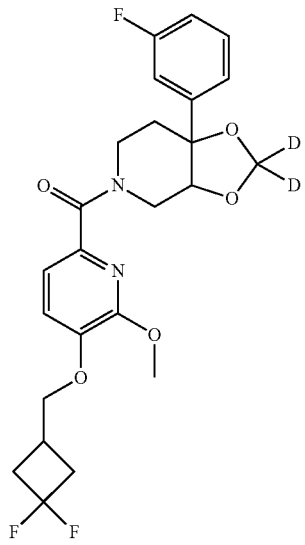 [SMILES: [2H]C1([2H])OC2CN(C(=O)c3ccc(OCC4CC(F)(F)C4)c(OC)n3)CCC2(c2cccc(F)c2)O1]
594
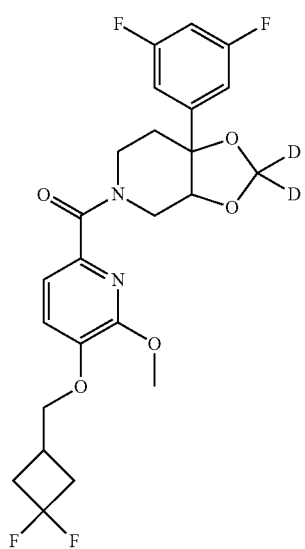 [SMILES: [2H]C1([2H])OC2CN(C(=O)c3ccc(OCC4CC(F)(F)C4)c(OC)n3)CCC2(c2cc(F)cc(F)c2)O1]
595
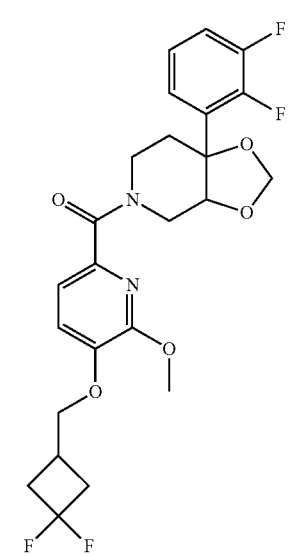 [SMILES: COc1nc(C(=O)N2CCC3(c4cccc(F)c4F)OCOC3C2)ccc1OCC1CC(F)(F)C1]
TABLE 2-continued
596
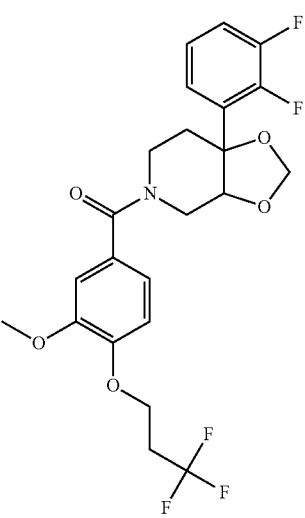 [SMILES: COc1cc(C(=O)N2CCC3(c4cccc(F)c4F)OCOC3C2)ccc1OCCC(F)(F)F]
597
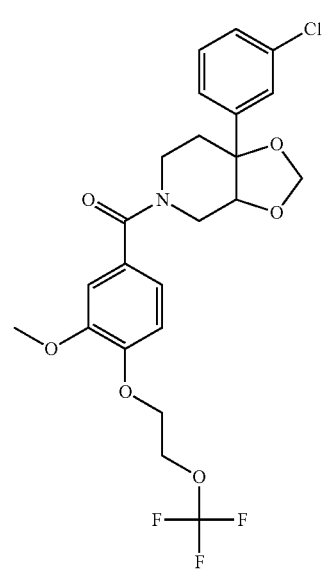 [SMILES: COc1cc(C(=O)N2CCC3(c4cccc(Cl)c4)OCOC3C2)ccc1OCCOC(F)(F)F]
598
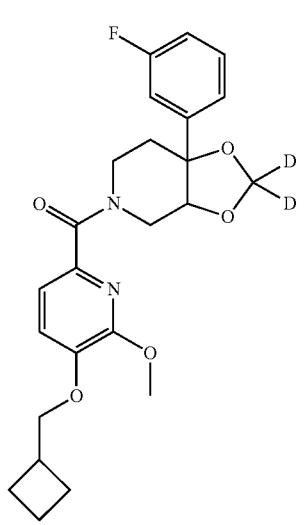 [SMILES: [2H]C1([2H])OC2CN(C(=O)c3ccc(OCC4CCC4)c(OC)n3)CCC2(c2cccc(F)c2)O1]

TABLE 2-continued
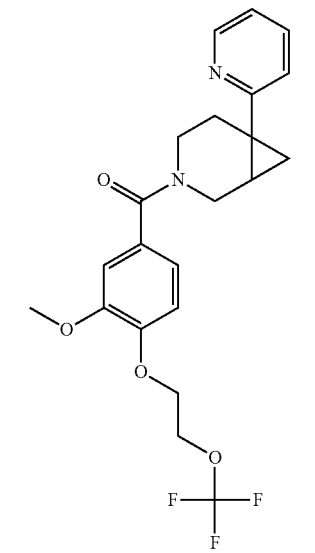 599
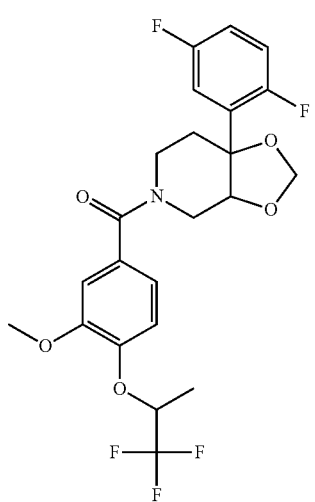 [SMILES: COc1cc(C(=O)N2CCC3(c4cc(F)ccc4F)OCOC3C2)ccc1OC(C)C(F)(F)F] 600
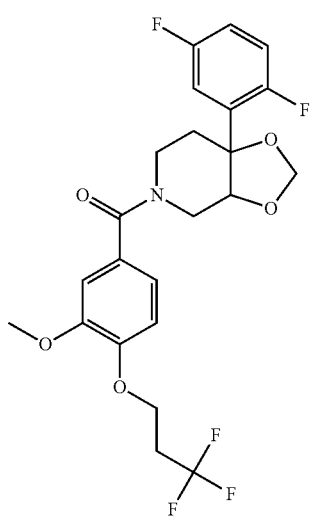 [SMILES: COc1cc(C(=O)N2CCC3(c4cc(F)ccc4F)OCOC3C2)ccc1OCCC(F)(F)F] 601
TABLE 2-continued
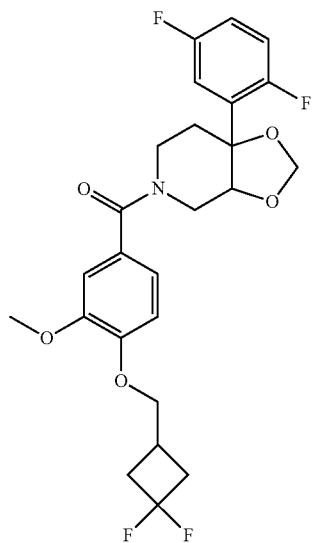 [SMILES: COc1cc(C(=O)N2CCC3(c4cc(F)ccc4F)OCOC3C2)ccc1OCC1CC(F)(F)C1] 602
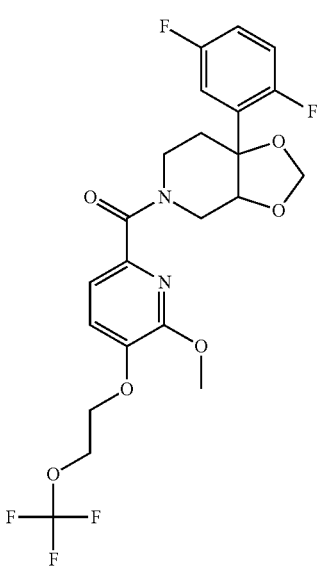 [SMILES: COc1nc(C(=O)N2CCC3(c4cc(F)ccc4F)OCOC3C2)ccc1OCCOC(F)(F)F] 603
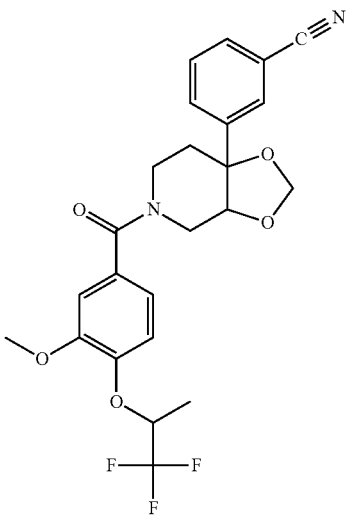 [SMILES: COc1cc(C(=O)N2CCC3(c4cccc(C#N)c4)OCOC3C2)ccc1OC(C)C(F)(F)F] 604

TABLE 2-continued
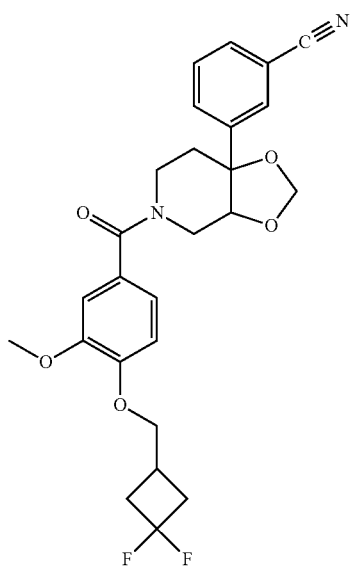 [SMILES: COc1cc(C(=O)N2CCC3(c4cccc(C#N)c4)OCOC3C2)ccc1OCC1CC(F)(F)C1]
605
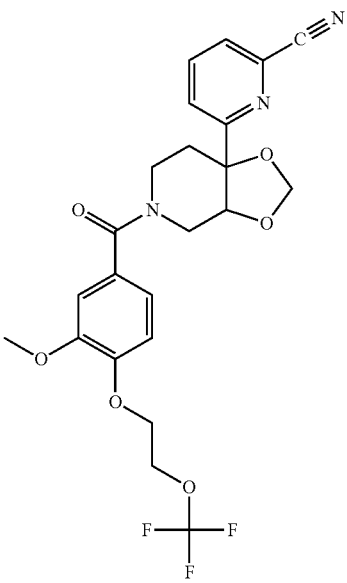
607
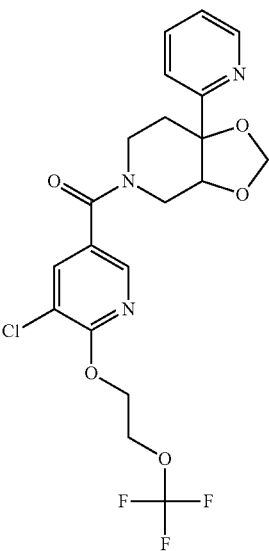 [SMILES: O=C(c1cnc(OCCOC(F)(F)F)c(Cl)c1)N1CCC2(c3ccccn3)OCOC2C1]
606
608

TABLE 2-continued
609
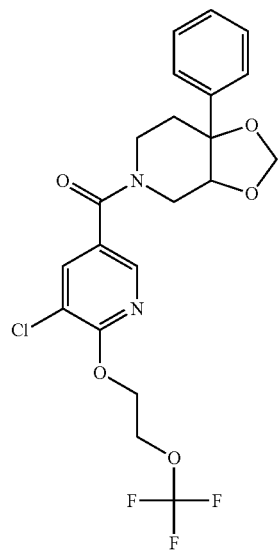 [SMILES: O=C(c1cnc(OCCOC(F)(F)F)c(Cl)c1)N1CCC2(c3ccccc3)OCOC2C1]
611
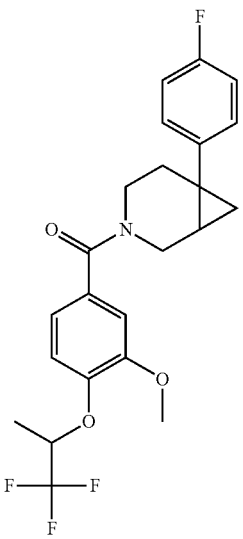
610
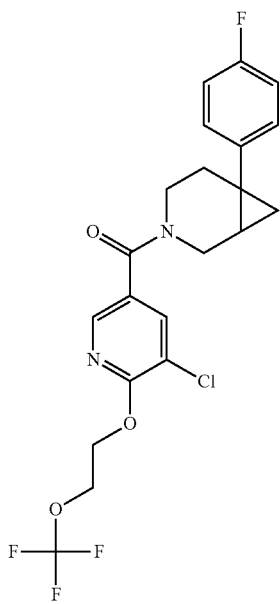 [SMILES: O=C(c1cnc(OCCOC(F)(F)F)c(Cl)c1)N1CCC2(c3ccc(F)cc3)CC2C1]
612
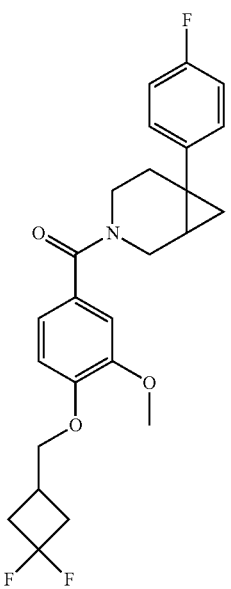

TABLE 2-continued
613
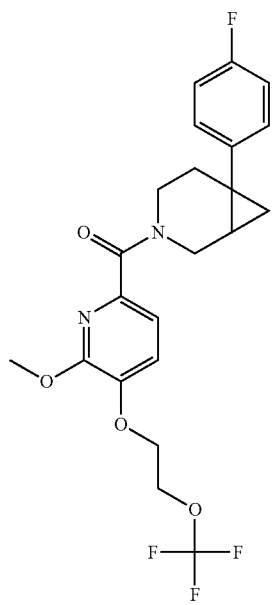 [SMILES: COc1nc(C(=O)N2CCC3(c4ccc(F)cc4)CC3C2)ccc1OCCOC(F)(F)F]
614
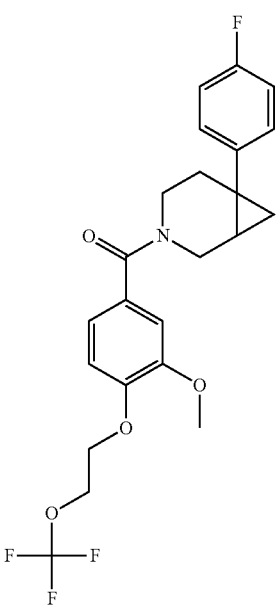 [SMILES: COc1cc(C(=O)N2CCC3(c4ccc(F)cc4)CC3C2)ccc1OCCOC(F)(F)F]
TABLE 2-continued
615
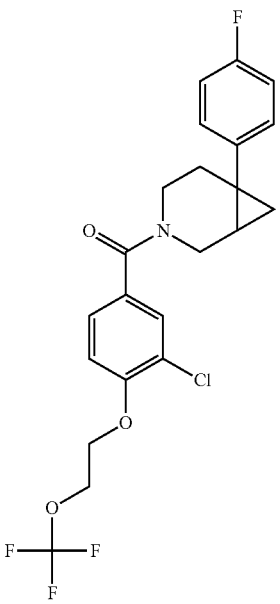 [SMILES: O=C(c1ccc(OCCOC(F)(F)F)c(Cl)c1)N1CCC2(c3ccc(F)cc3)CC2C1]
616
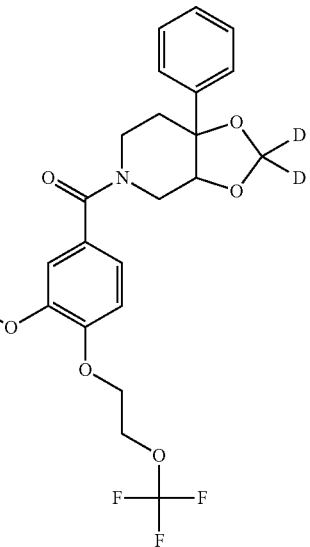

TABLE 2-continued
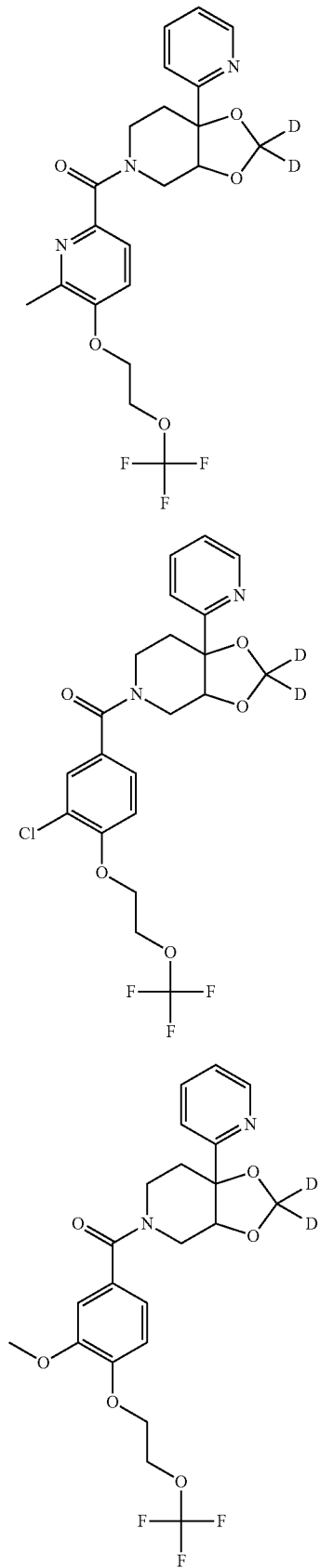
617
618
619
TABLE 2-continued
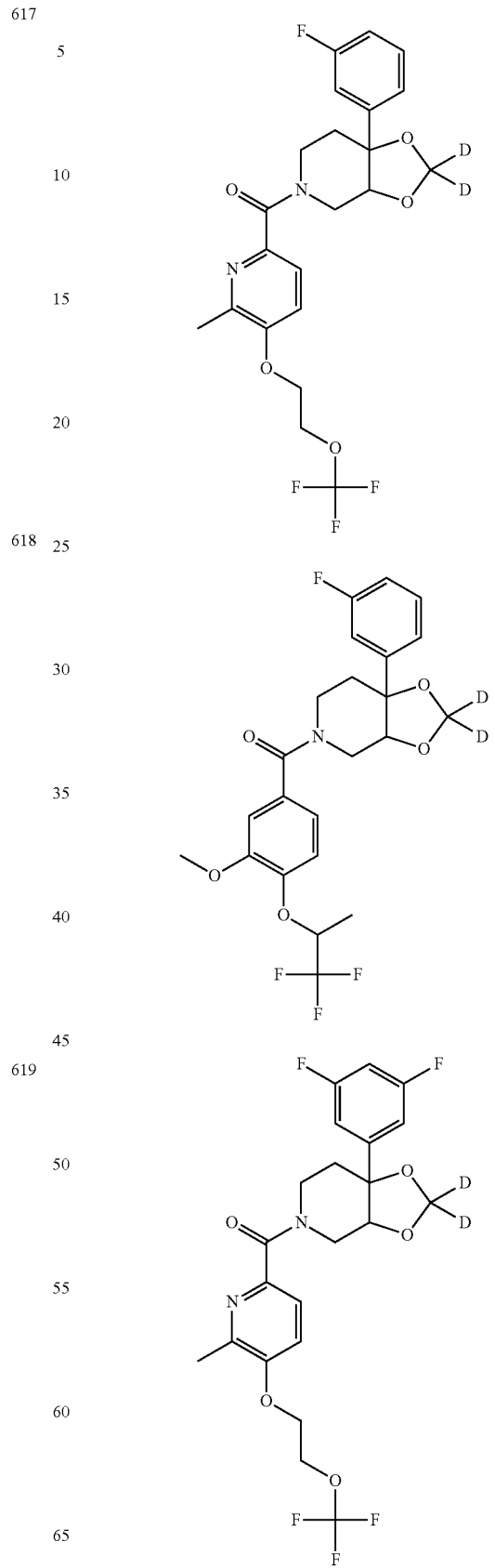
620
621
622

TABLE 2-continued
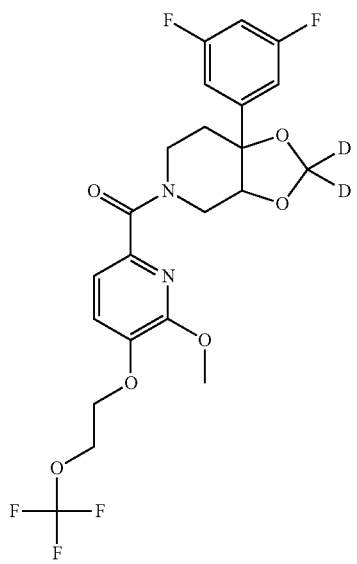 [SMILES: [2H]C1([2H])OC2CN(C(=O)c3ccc(OCCOC(F)(F)F)c(OC)n3)CCC2(c2cc(F)cc(F)c2)O1] 623
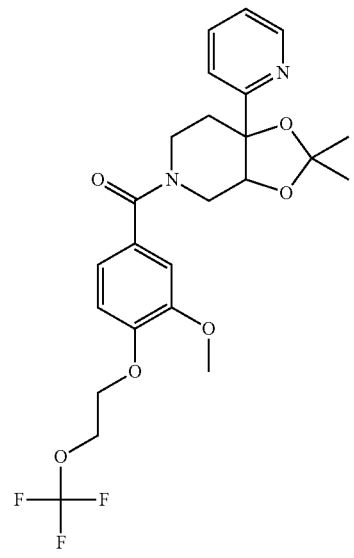 [SMILES: COc1cc(C(=O)N2CCC3(c4ccccn4)OC(C)(C)OC3C2)ccc1OCCOC(F)(F)F] 624
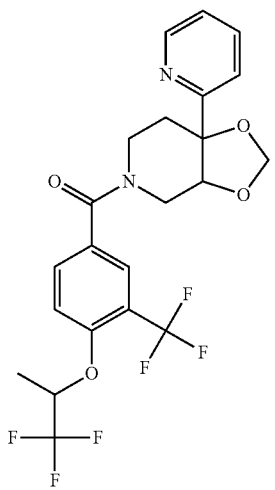 [SMILES: CC(Oc1ccc(C(=O)N2CCC3(c4ccccn4)OCOC3C2)cc1C(F)(F)F)C(F)(F)F] 625
TABLE 2-continued
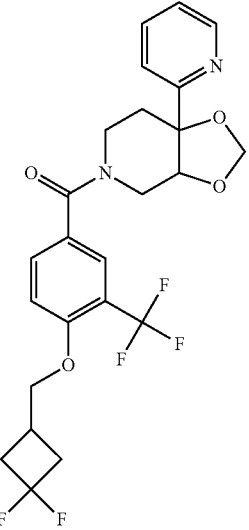 626
 627
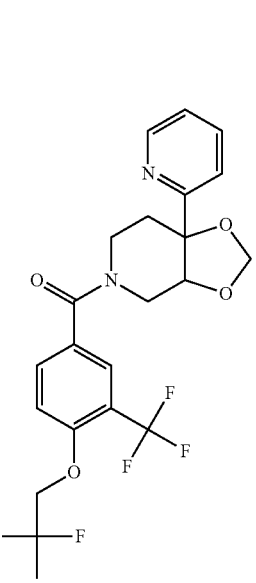

TABLE 2-continued

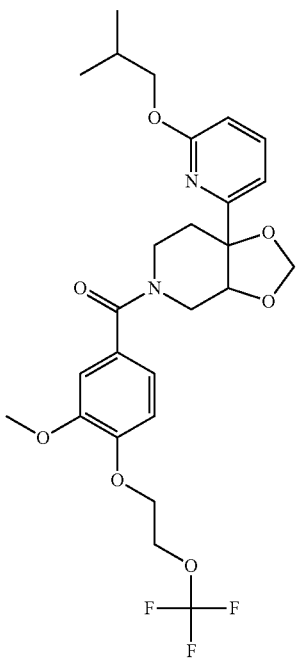

628

In another aspect, the invention features a pharmaceutical composition comprising a compound of the invention and a pharmaceutically acceptable carrier.

In another aspect, the invention features a method of inhibiting a voltage-gated sodium ion channel in:
a patient; or
a biological sample;
comprising administering to the patient, or contacting the biological sample, with a compound or composition of the invention. In another embodiment, the voltage-gated sodium ion channel is NaV 1.7.

In another aspect, the invention features a method of treating or lessening the severity of the pain in a subject afflicted with acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abnormal gastro-intestinal motility, comprising administering an effective amount of a compound or composition of the invention.

In another embodiment, the method is used for treating or lessening the severity of the pain in a subject afflicted with femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, including, cluster headaches; chronic and acute neuropathic pain, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritis, tinnitis, or angina-induced pain.

The compounds of the invention may be prepared readily using the following methods. Illustrated below in Scheme 1 through Scheme 15 are methods for preparing the compounds of the invention.

Scheme 1

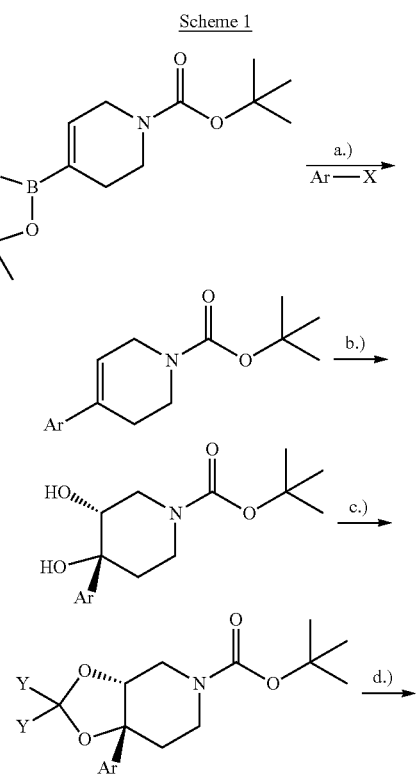

-continued

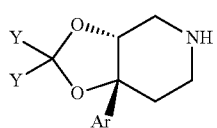

X = Halide, Y = H, D
a.) Na₂CO₃ (2M), Pd(dppf)Cl₂, DMF; b.) AD-mix-β, methanesulfonamide, t-BuOH, H₂O; c.) Br₂CH₂ or Br₂(CD₂), NaH, DMF; d.) TFA, DCM.

Scheme 2

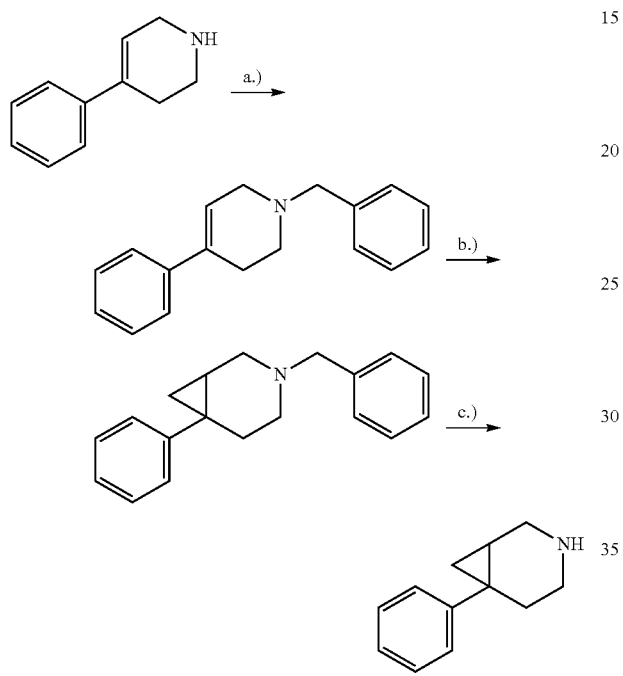

a.) BnBr, DIPEA, DCM; b.) diethylzinc, TFA, CH₂I₂, DCM; c.) 1-chloroethyl chloroformate, DCM, 2.) MeOH (40° C.).

Scheme 3

-continued

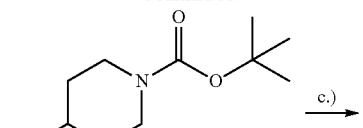
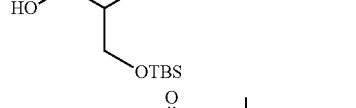
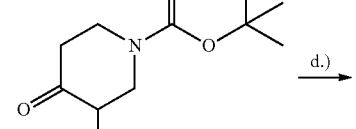

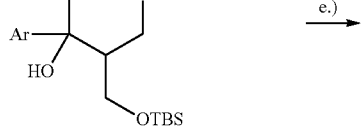
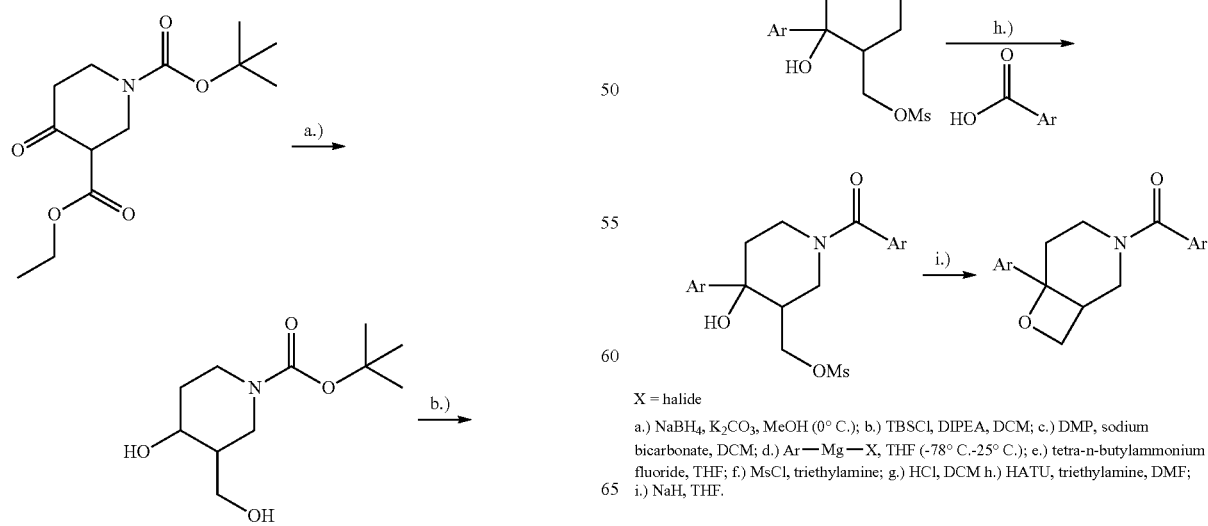

X = halide
a.) NaBH₄, K₂CO₃, MeOH (0° C.); b.) TBSCl, DIPEA, DCM; c.) DMP, sodium bicarbonate, DCM; d.) Ar—Mg—X, THF (-78° C.-25° C.); e.) tetra-n-butylammonium fluoride, THF; f.) MsCl, triethylamine; g.) HCl, DCM h.) HATU, triethylamine, DMF; i.) NaH, THF.

Scheme 4

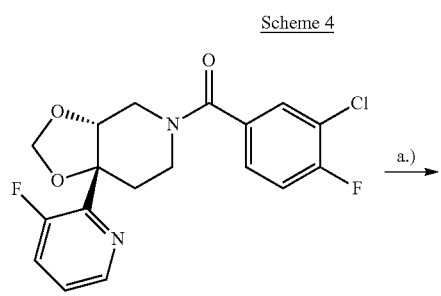

a.) 2-tert-butoxyethanol, NaH, DMF (80° C.).

Scheme 5

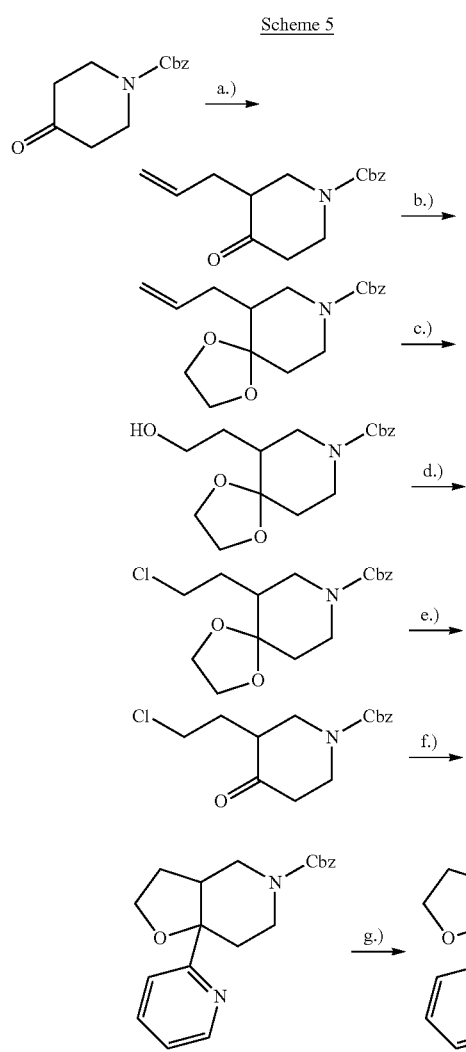

-continued

Cbz = carboxybenzyl
a.) prop-2-en-1-ol, Xantphos, [C₃H₅PdCl]₂, pyrrolidine-2-carboxylic acid, DMSO;
b.) 4-methylbenzenesulfonic acid, ethylene glycol, PhCH₃; c.) 1. O₃, DCM 2.) NaBH₄, MeOH; d.) thionyl chloride, DMF, pyridine, CHCl₃; e.) 1M HCl (aq), EtOH;
f.) butyllithium, 2-bromopyridine, THF (-78° C.-25° C.) g.) H₂ (1 atm), Pd/C, MeOH.

Scheme 6

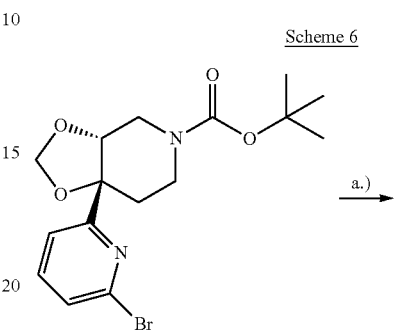

a.) Pd(PPh₃)₄, trimethylalumane, THF; b.) TFA, DCM.

Scheme 7

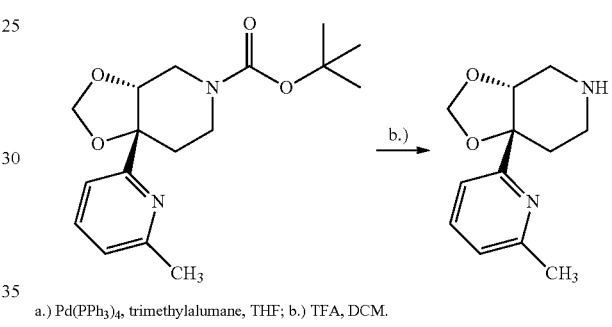

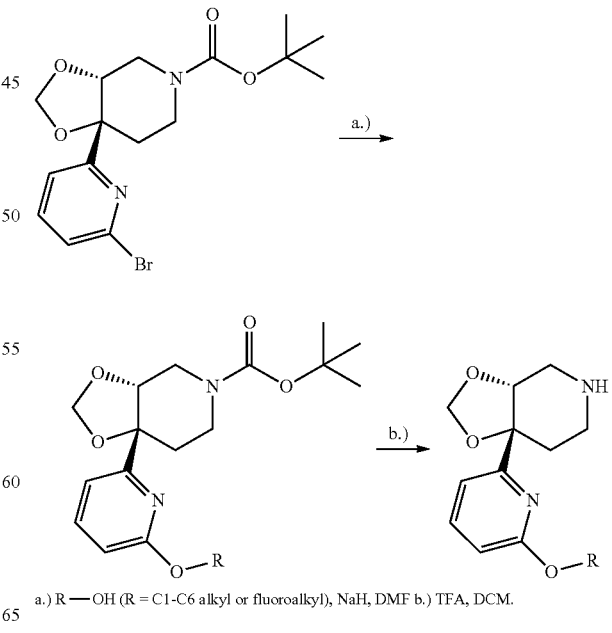

a.) R—OH (R = C1-C6 alkyl or fluoroalkyl), NaH, DMF b.) TFA, DCM.

Scheme 8
Scheme 9
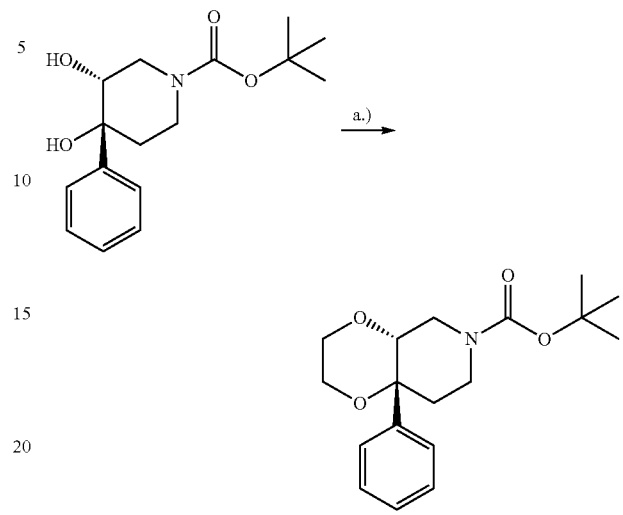
a.) tetra-butyl-ammonium-HSO$_4$, NaOH, Cl$_2$(CH$_2$)$_2$.
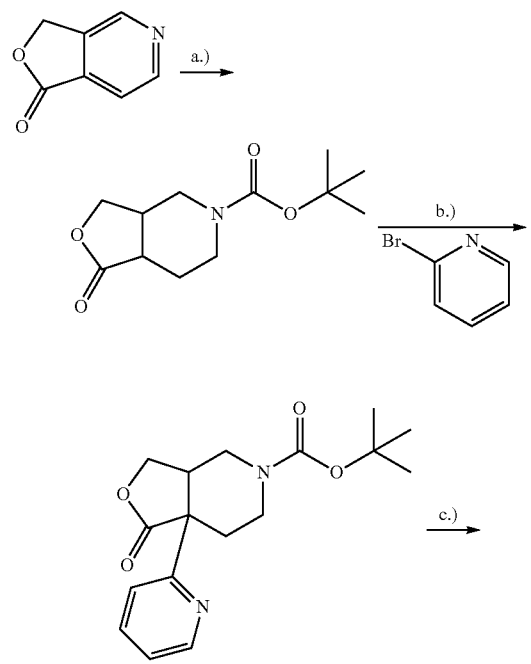
Scheme 10
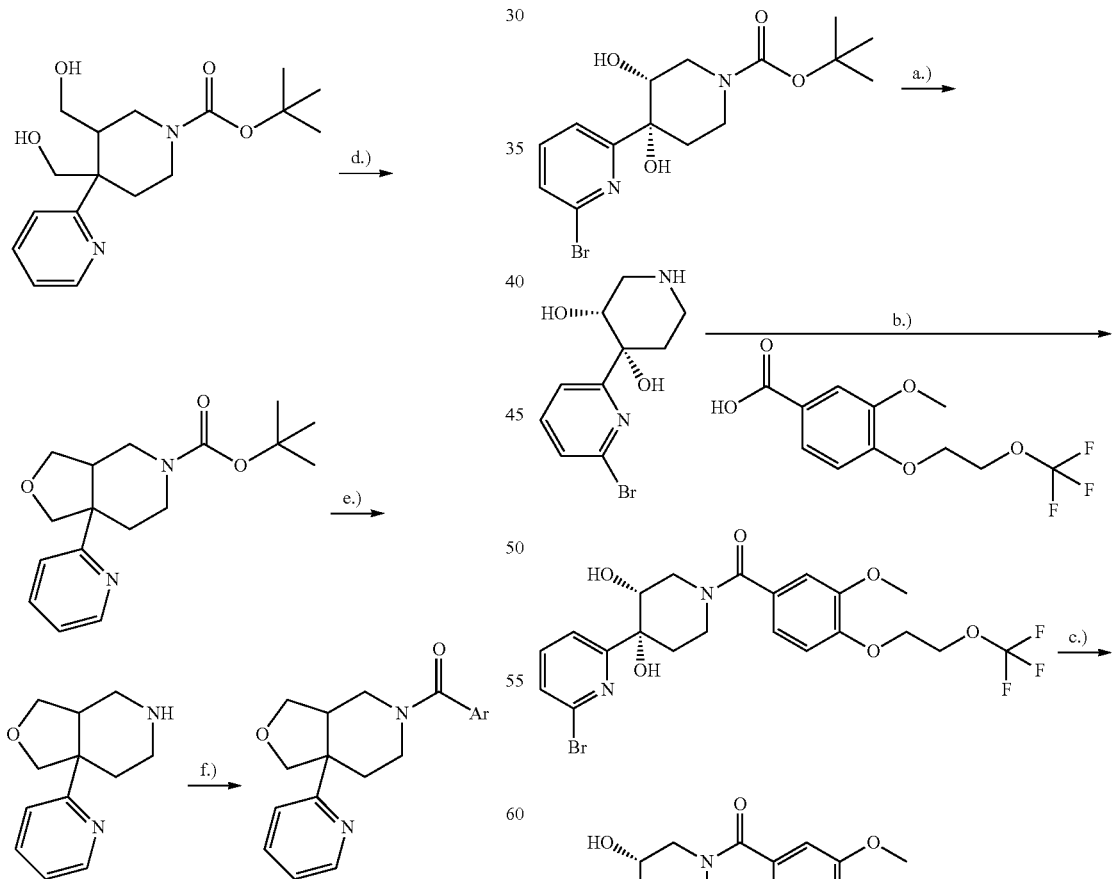
a.) 1) H$_2$ (55 psi), PtO$_2$, HCl, H$_2$O 2.) Boc$_2$O, triethylamine, DCM/MeOH b.) Pd[P(tBu)$_3$]$_2$, LHMDS, toluene; c.) NaBH$_4$, toluene/THF; d.) PPh$_3$, DEAD, THF; e.) HCl, DCM; f.) ArCOOH, HATU, triethylamine, DMF.

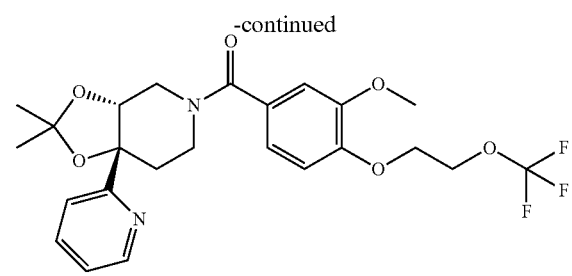
a.) TFA, DCM;
b.) HATU, triethylamine;
c.) H₂ (1 atm), Pd/C, iPrOH;
d.) dimethoxypropane, [(1R,4S)-7,7-dimethyl-2-oxo-norbornan-1-yl]methanesulfonic acid.
Scheme 11
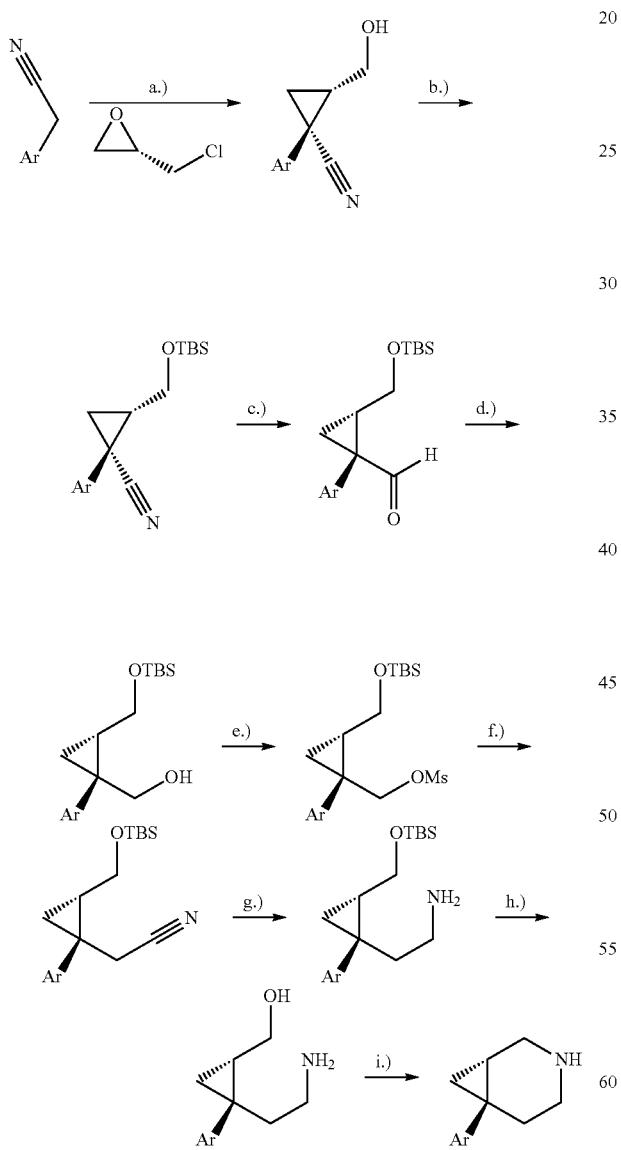
a.) NaNH₂, THF (-78 - 25° C.); b.)TBS—Cl, imidazole, DCM; c.)DiBAl—H, DCM (-78-25° C.); d.) NaBH₄, MeOH (-10-25° C.); e.) MsCl, DIEA, DCM; f) NaCN, DMSO; g.) BH₃—THF, THF; h.) tetra-n-butylammonium fluoride, THF; i.) SOCl₂, DCE.
Scheme 12
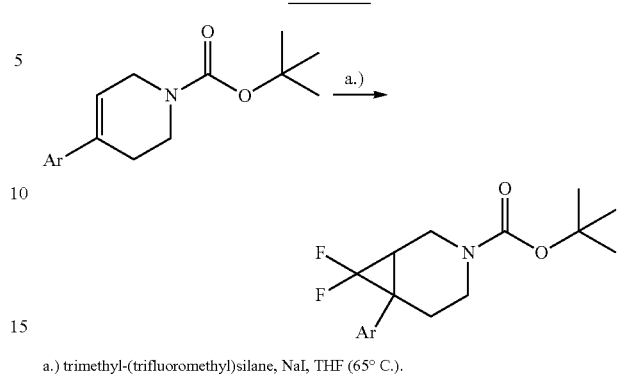
a.) trimethyl-(trifluoromethyl)silane, NaI, THF (65° C.).
Scheme 13
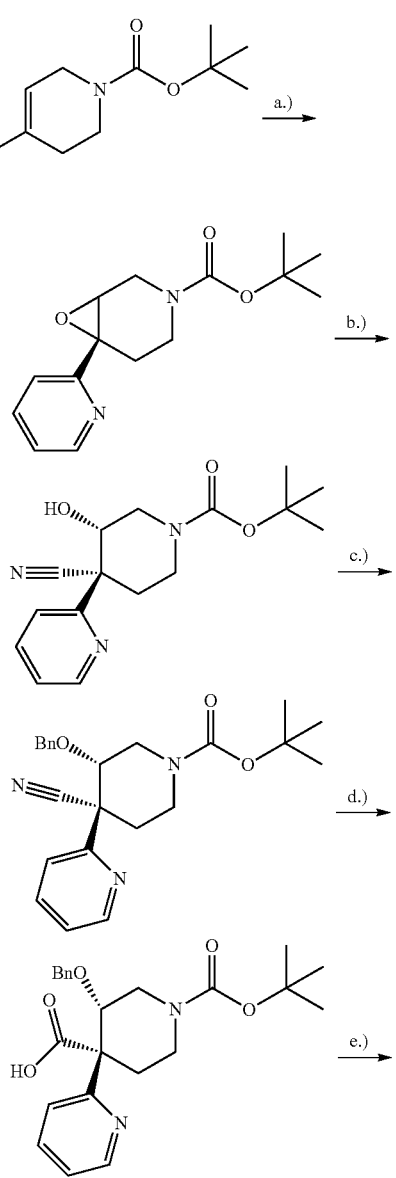

311
-continued

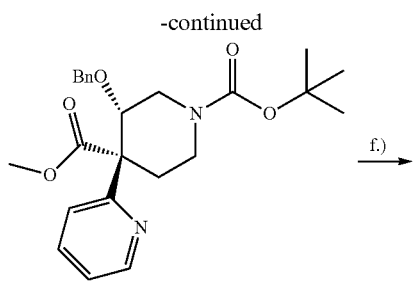

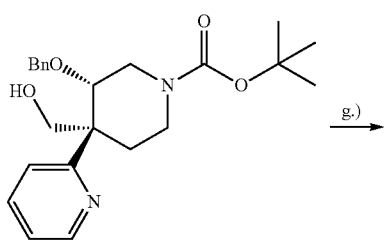

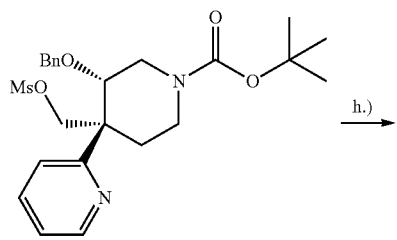

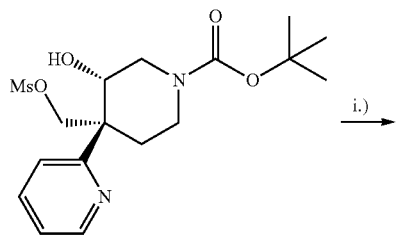

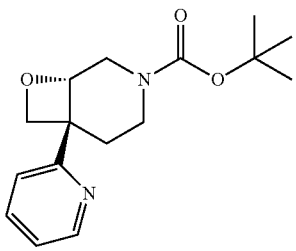

a.) 1.) NBS, dioxane, 2.) NaOH; b.) NaCN, DMSO (90° C.); c.) BnBr, NaH, DMF; d.) KOH, EtOH; e.) MeI, NaH, DMF; f.) LAH, THF (reflux, 1 min); g.) MsCl, triethylamine, DCM; h.) ammonia, formic acid, Pd/C, MeOH (78° C.); i.) DBU, toluene.

Scheme 14

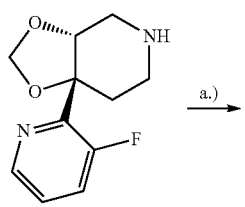

312
-continued

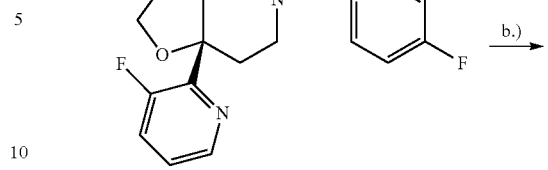

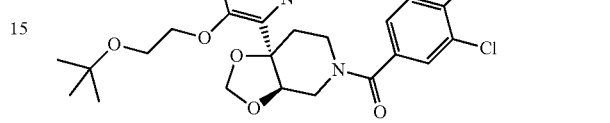

a.) 3-chloro-4-fluoro-benzoic acid, HATU, triethylamine, DMF; b.) 2-tert-butoxyethanol, NaH, DMF.

Scheme 15

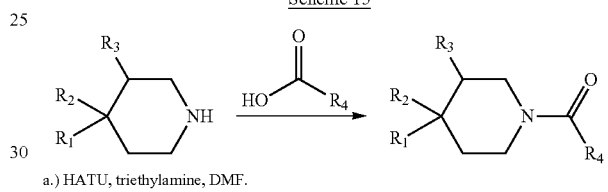

a.) HATU, triethylamine, DMF.

Uses, Formulation and Administration

Pharmaceutically Acceptable Compositions

As discussed above, the invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abnormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject" or "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV 1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.7 and/or NaV1.8.

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) a histamine antagonist of the $H_1$ receptor having a sedative action, e.g. diphenhydramine, pyrilamine, promethazine, chlorpheniramine or chlorocyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1, 2,3,4-tetrahydroisoquinol-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

(12) a tachykinin (NK) antagonist, particularly an NK-3, NK-2 or NK-I antagonist, e.g. ([alpha]R,9R)-7-[3,5-bis (trifluoromethyl)benzyl]-8,9,10,11-tetrahydro-9-methyl-5-(4-methylphenyl)-7H-[1,4]diazocino[2,1-g] [1,7]-naphthyridine-6-13-dione (TAK-637), 5-[[(2R, 3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g. oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
(17) a vanilloid receptor agonist (e.g. resiniferatoxin) or antagonist (e.g. capsazepine);
(18) a beta-adrenergic such as propranolol;
(19) a local anaesthetic such as mexiletine;
(20) a corticosteroid such as dexamethasone;
(21) a 5-HT receptor agonist or antagonist, particularly a 5-HTi B/I D agonist such as eletriptan, sumatriptan, naratriptan, zolmitriptan or rizatriptan;
(22) a 5-HT2A receptor antagonist such as R(+)-alpha-(2,3-dimethoxy-phenyl)-1-[2-(4-fluorophenylethyl)]-4-piperidinemethanol (MDL-100907);
(23) a cholinergic (nicotinic) analgesic, such as ispronicline (TC-1734), (E)-N-methyl-4-(3-pyridinyl)-3-buten-1-amine (RJR-2403), (R)-5-(2-azetidinyl-methoxy)-2-chloropyridine (ABT-594) or nicotine;
(24) Tramadol®;
(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide; an alpha-2-delta ligand such as gabapentin, pregabalin, 3-methyl gabapentin, (1[α],3[α],5[α])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl] acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;
(26) a cannabinoid;
(27) metabotropic glutamate subtype 1 receptor (mGluR1) antagonist;
(28) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
(29) a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;
(30) a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;
(31) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;
(32) an acetylcholinesterase inhibitor such as donepezil;
(33) a prostaglandin E2 subtype 4 (EP4) antagonist such as 7V-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy)pyridin-3-yl]carbonyl}amino)ethyl] benzoic acid;
(34) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;
(35) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);
(36) a sodium channel blocker, such as lidocaine;
(36) a 5-HT3 antagonist, such as ondansetron; and the pharmaceutically acceptable salts and solvates thereof.

In another embodiment, the additional therapeutic agent is an NaV 1.8 inhibitor. NaV 1.7 and NaV 1.8 ion channels are both highly expressed in the sensory neurons of the dorsal root ganglion, where pain signals originate, but the distinct functional behavior of the two channels leads them to fulfill distinct and complementary roles in neuronal excitability. $Na_V1.7$ controls the general sensitivity of nociceptive neurons, and initiating the painful signal in a nociceptor. $Na_V1.8$ amplifies and sustains the pain signal once it has been initiated. Because of these distinct roles, inhibiting both channels should increase the effectiveness of pain relief. Preclinical genetic knockout mice support this idea, as double knockouts of $Na_V1.7$ and $Na_V1.8$ channels in the sensory DRG neurons surprisingly diminish nociceptive behaviors to a greater degree than knockout of either channel alone.

In another embodiment, the additional appropriate therapeutic agent is an NaV 1.8 inhibitor selected from the following: 2-(4-fluorophenoxy)-N-(2-oxo-1,2-dihydropyridin-4-yl)benzamide; 2-(4-fluorophenoxy)-N-(2-oxo-1,2-dihydropyridin-4-yl)-5-(trifluoromethyl)benzamide; 2-(4-fluorophenoxy)-N-(6-oxo-1,6-dihydropyridin-3-yl)ben zamide; 2-(4-fluorophenoxy)-N-(2-oxo-1,2-dihydropyridin-4-yl)-4-(trifluoromethyl)benzamide; 2-(4-fluorophenoxy)-N-(6-oxo-1,6-dihydropyridin-3-yl)-4-(trifluoromethyl)benzamide; 2-(2,4-difluorophenoxy)-N-(2-oxo-1,2-dihydropyridin-4-yl)-4-(trifluoromethyl)benzamide; 2-(4-(2-methoxyethoxy)phenoxy)-N-(2-oxo-1,2-dihydropyridin-4-yl)-4-(trifluoromethyl)benzamide; N-(2-oxo-1,2-dihydropyridin-4-yl)-2-phenoxy-4-(trifluoromethyl)benzamide; 2-(4-fluoro-2-methylphenoxy)-N-(2-oxo-1,2-dihydropyridin-4-yl)-4-(trifluoromethyl)benzamide; N-(2-oxo-1,2-dihydropyridin-4-yl)-2-(o-tolyloxy)-4-(trifluoromethyl)benzamide; N-(2-oxo-1,2-dihydropyridin-4-yl)-2-(p-tolyloxy)-4-(trifluoromethyl)benzamide; 4-chloro-2-(2,4-difluorophenoxy)-N-(2-oxo-1,2-dihydropyridin-4-yl)benzamide; 4-chloro-2-(2-chloro-4-fluorophenoxy)-N-(2-oxo-1,2-dihydropyridin-4-yl)benzamide; 4-chloro-2-(4-fluorophenoxy)-N-(2-oxo-1,2-dihydropyridin-4-yl)benzamide; 4-chloro-2-(4-fluoro-2-methoxyphenoxy)-N-(2-oxo-1,2-dihydropyridin-4-yl)benzamide; 4-chloro-2-(2-fluoro-6-methylphenoxy)-N-(2-oxo-1,2-dihydropyridin-4-yl)benzamide; 4-chloro-2-(2-chloro-6-fluorophenoxy)-N-(2-oxo-1,2-dihydropyridin-4-yl)benzamide; 4-chloro-2-(2,6-difluorophenoxy)-N-(2-oxo-1,2-dihydropyridin-4-yl)benzamide; 4-chloro-2-(4-fluoro-2-methylphenoxy)-N-(2-oxo-1,2-dihydropyridin-4-yl)benzamide; 4-cyano-2-(4-fluorophenoxy)-N-(2-oxo-1,2-dihydropyridin-4-yl)benzamide; 4-cyano-2-(4-fluoro-2-methoxyphenoxy)-N-(2-oxo-1,2-dihydropyridin-4-yl)benzamide; 4-cyano-2-(4-fluoro-2-methylphenoxy)-N-(2-oxo-1,2-dihydropyridin-4-yl)benzamide; 2-(2,4-difluorophenoxy)-N-(2-oxo-1,2-dihydropyridin-4-yl)-5-(trifluoromethyl)benzamide; 2-(4-cyanophenoxy)-N-(2-oxo-1,2-dihydropyridin-4-yl)-5-(trifluoromethyl)benzamide; 2-(2,6-difluorophenoxy)-N-(2-oxo-1,2-dihydropyridin-4-yl)-5-(trifluoromethyl)benzamide; N-(2-oxo-1,2-dihydropyridin-4-yl)-2-(p-tolyloxy)-5-(trifluoromethyl)benzamide; N-(2-oxo-1,2-dihydropyridin-4-yl)-2-(o-tolyloxy)-5-(trifluoromethyl)benzamide; 2-(2-chloro-4-fluorophenoxy)-N-(2-oxo-1,2-dihydropyridin-4-yl)-5-(trifluoromethyl)benzamide; 2-(4-fluoro-2-methoxyphenoxy)-N-(2-oxo-1,2-dihydropyridin-4-yl)-5-(trifluoromethyl)benzamide; 2-(4-fluoro-2-methylphenoxy)-N-(2-oxo-1,2-dihydropyridin-4-yl)-5-(trifluoromethyl)benzamide; N-(2-oxo-1,2-dihydropyridin-4-yl)-2-phenoxy-5-(trifluoromethyl)benzamide; 2-(2,4-difluorophenoxy)-N-(2-oxo-1,2-dihydropyridin-4-yl)-5-(trifluoromethoxy)benzamide; 2-(2,6-difluorophenoxy)-N-(2-oxo-1,2-dihydropyridin-4-yl)-5-(trifluoromethoxy)benzamide; N-(2-oxo-1,2-dihydropyridin-4-yl)-2-(p-tolyloxy)-5-(trifluoromethoxy)benzamide; N-(2-oxo-1,2-dihydropyridin-4-yl)-2-(o-tolyloxy)-5-(trifluoromethoxy)benzamide; 2-(2-chloro-4-fluorophenoxy)-N-(2-oxo-1,2-dihydropyridin-4-yl)-5-(trifluoromethoxy)benzamide; 2-(4-fluorophenoxy)-N-(2-oxo-1,2-dihydropyridin-4-yl)-5-(trifluoromethoxy)benzamide; 2-(2-fluoro-6-methylphenoxy)-N-(2-oxo-1,2-dihydropyridin-4-yl)-5-(trifluoromethoxy)benzamide; 2-(4-fluoro-2-methylphenoxy)-N-(2-oxo-1,2-dihydropyridin-4-yl)-5-(trifluoromethoxy)benzamide; N-(2-oxo-1,2-dihydropyridin-4-yl)-2-phenoxy-5-(trifluoromethoxy)benzamide; 2-(4-fluoro-2-methoxyphenoxy)-N-(2-oxo-1,2-dihydropyridin-4-yl)-5-(trifluoromethoxy)benzamide; 2-(4-fluorophenoxy)-N-(2-oxo-1,2-dihydropyridin-4-yl)-6-(trifluoromethyl)ben zamide; 2-(4-ethoxyphenoxy)-N-(2-oxo-1,2-dihydropyridin-4-yl)-5-(trifluoromethyl)benzamide; 2-(4-methoxyphenoxy)-N-(2-oxo-1,2-dihydropyridin-4-yl)-5-(trifluoromethyl)benzamide; 2-(2-ethoxyphenoxy)-N-(2-oxo-1,2-dihydropyridin-4-yl)-5-(trifluoromethyl)benzamide; 2-(2-methoxy-4-methylphenoxy)-N-(2-oxo-1,2-dihydropyridin-4-yl)-5-(trifluoromethyl)benzamide; 2-(2-fluoro-6-methoxy phen oxy)-N-(2-oxo-1,2-dihydropyridin-4-yl)-5-(trifluoromethyl)benzamide; 2-(2-chloro-4-methoxyphenoxy)-N-(2-oxo-1,2-dihydropyridin-4-yl)-5-(trifluoromethyl)benzamide; 2-(4-chloro-2-methylphenoxy)-N-(2-oxo-1,2-dihydropyridin-4-yl)-5-(trifluoromethyl)benzamide; 2-(4-chloro-2-fluorophenoxy)-N-(2-oxo-1,2-dihydropyridin-4-yl)-5-(trifluoromethyl)benzamide; 2-(5-fluoro-2-methoxyphenoxy)-N-(2-oxo-1,2-dihydropyridin-4-yl)-5-(trifluoromethyl)benzamide; N-(2-oxo-1,2-dihydropyridin-4-yl)-2-(4-propoxyphenoxy)-5-(trifluoromethyl)benzamide; 2-(3-fluoro-2-methoxyphenoxy)-N-(2-oxo-1,2-dihydropyridin-4-yl)-5-(trifluoromethyl)benzamide; 2-(2-fluoro-4-methoxyphenoxy)-N-(2-oxo-1,2-dihydropyridin-4-yl)-5-(trifluoromethyl)benzamide; 2-(5-fluoro-2-methylphenoxy)-N-(2-oxo-1,2-dihydropyridin-4-yl)-5-(trifluoromethyl)benzamide; 2-(3-fluoro-5-methoxyphenoxy)-N-(2-oxo-1,2-dihydropyridin-4-yl)-5-(trifluoromethyl)benzamide; 2-(4-chlorophenoxy)-N-(2-oxo-1,2-dihydropyridin-4-yl)-5-(trifluoromethyl)benzamide; 2-(3-fluoro-4-methoxyphenoxy)-N-(2-oxo-1,2-dihydropyridin-4-yl)-5-(trifluoromethyl)benzamide; N-(6-chloro-2-oxo-1,2-dihydropyridin-4-yl)-2-(4-fluoro-2-methylphenoxy)-5-(trifluoromethyl)benzamide; 2-(4-fluoro-2-methylphenoxy)-N-(6-methyl-2-oxo-1,2-dihydropyridin-4-yl)-5-(trifluoromethyl)benzamide; N-(2-oxo-1,2-dihydropyridin-4-yl)-2-(2-propoxyphenoxy)-5-(trifluoromethyl)benzamide; 2-(4-methoxy-2-methylphenoxy)-N-(2-oxo-1,2-dihydropyridin-4-yl)-5-(trifluoromethyl)benzamide; 2-(2-isopropoxyphenoxy)-N-(2-oxo-1,2-dihydropyridin-4-yl)-5-(trifluoromethyl)benzamide; 2-(2-chlorophenoxy)-N-(2-oxo-1,2-dihydropyridin-4-yl)-5-(trifluoromethyl)benzamide; 5-chloro-2-(2-chloro-4-fluorophenoxy)-N-(2-oxo-1,2-dihydropyridin-4-yl)benzamide; 5-chloro-2-(4-fluorophenoxy)-N-(2-oxo-1,2-dihydropyridin-4-yl)benzamide; 5-chloro-2-(4-fluoro-2-methylphenoxy)-N-(2-oxo-1,2-dihydropyridin-4-yl)benzamide; 5-chloro-2-(2,4-difluorophenoxy)-N-(2-oxo-1,2-dihydropyridin-4-yl)benzamide; 5-chloro-2-(4-fluoro-2-methoxyphenoxy)-N-(2-oxo-1,2-dihydropyridin-4-yl)benzamide; 5-chloro-2-(3-fluoro-4-methoxyphenoxy)-N-(2-oxo-1,2-dihydropyridin-4-yl)benzamide; N-(2-oxo-1,2-dihydropyridin-4-yl)-2-(4-(trifluoromethoxy)phenoxy)-5-(trifluoromethyl)benzamide; N-(2-oxo-1,2-dihydropyridin-4-yl)-5-(trifluoromethyl)-2-(4-(trifluoromethyl)phen oxy)benzamide; N-(2-oxo-1,2-dihydropyridin-4-yl)-2-(2-(trifluoromethoxy)phenoxy)-5-(trifluoromethyl)benzamide; 2-(2-(difluoromethoxy)phenoxy)-N-(2-oxo-1,2-dihydropyridin-4-yl)-5-(trifluoromethyl)benzamide; 2-(2-chloro-4-fluorophenoxy)-N-(2-oxo-1,2-dihydropyridin-4-yl)-4-(trifluoromethyl)benzamide; 2-(4-chlorophenoxy)-N-(2-oxo-1,2-dihydropyridin-4-yl)-4-(trifluoromethyl)benzamide; N-(2-oxo-1,2-dihydropyridin-4-yl)-2-(4-(trifluoromethoxy)phenoxy)-4-(trifluoromethyl)benzamide; N-(2-oxo-1,2-dihydropyridin-4-yl)-2-(2-(trifluoromethoxy)phenoxy)-4-(trifluoromethyl)benzamide; 2-(3-fluoro-4-methoxyphenoxy)-N-(2-oxo-1,2-dihydropyridin-4-yl)-4-(trifluoromethyl)benzamide; 2-(4-(difluoromethoxy)phenoxy)-N-(2-oxo-1,2-dihydropyridin-4-yl)-4-(trifluoromethyl)benzamide; 2-(2-(difluoromethoxy)phenoxy)-N-(2-oxo-1,2-dihydropyridin-4-yl)-4-(trifluoromethyl)benzamide; 2-(2-fluoro-4- methoxyphenoxy)-N-(2-oxo-1,2-dihydropyridin-4-yl)-4-(trifluoromethyl)benzamide; 2-(4-fluorophenoxy)-N-(1-(2-hydroxyethyl)-2-oxo-1,2-dihydropyridin-4-yl)-4-(trifluoromethyl)benzamide; 2-(4-fluoro-2-methylphenoxy)-N-(5-methyl-2-oxo-1,2-dihydropyridin-4-yl)-4-(trifluoromethyl)benzamide; 2-(3-fluoro-2-methoxyphenoxy)-N-(2-oxo-1,2-dihydropyridin-4-yl)-4-(trifluoromethyl)benzamide; 2-(4-fluorophenoxy)-N-(2-oxo-1,2-dihydropyridin-4-yl)-4-(perfluoroethyl)benzamide; 2-(3-fluoro-4-methoxyphenoxy)-N-(2-oxo-1,2-dihydropyridin-4-yl)-4-(perfluoroethyl)benzamide; N-(2-oxo-1,2-dihydropyridin-4-yl)-5-(trifluoromethyl)-2-(2,3,4-trifluorophenoxy)benzamide; N-(2-oxo-1,2-dihydropyridin-4-yl)-5-(trifluoromethyl)-2-(2,3,5-trimethylphenoxy)benzamide; 2-(2,3-difluoro-4-methylphenoxy)-N-(2-oxo-1,2-dihydropyridin-4-yl)-5-(trifluoromethyl)benzamide; N-(2-oxo-1,2-dihydropyridin-4-yl)-5-(trifluoromethyl)-2-(2,4,5-trimethylphenoxy)benzamide; 5-fluoro-N-(2-oxo-1,2-dihydropyridin-4-yl)-2-(2,3,5-trimethylphenoxy)benzamide; 5-fluoro-N-(2-oxo-1,2-dihydropyridin-4-yl)-2-phenoxybenzamide; 2-(4-cyclopropylphenoxy)-5-fluoro-N-(2-oxo-1,2-dihydropyridin-4-yl)benzamide; 2-(4-(tert-butoxy)phenoxy)-5-fluoro-N-(2-oxo-1,2-dihydropyridin-4-yl)benzamide; 2-(4-ethoxyphenoxy)-5-fluoro-N-(2-oxo-1,2-dihydropyridin-4-yl)benzamide; 5-fluoro-2-(4-isopropylphenoxy)-N-(2-oxo-1,2-dihydropyridin-4-yl)benzamide; 5-fluoro-N-(2-oxo-1,2-dihydropyridin-4-yl)-2-(4-propoxyphenoxy)benzamide; 5-fluoro-N-(2-oxo-1,2-dihydropyridin-4-yl)-2-(4-(trifluoromethoxy)phenoxy)benzamide; 5-fluoro-2-(4-(2-methoxyethyl)phenoxy)-N-(2-oxo-1,2-dihydropyridin-4-yl)benzamide; 2-(2-chloro-4-methoxyphenoxy)-5-fluoro-N-(2-oxo-1,2-dihydropyridin-4-yl)benzamide; 5-fluoro-2-(4-methoxyphenoxy)-N-(2-oxo-1,2-dihydropyridin-4-yl)benzamide; 5-fluoro-N-(2-oxo-1,2-dihydropyridin-4-yl)-2-(2,4,5-trimethylphenoxy)benzamide; 2-(4-fluoro-2-methylphenoxy)-N-(2-oxo-1,2-dihydropyridin-4-yl)-5-(trifluoromethyl)benzamide; 5-fluoro-N-(2-oxo-1,2-dihydropyridin-4-yl)-2-(4-(2,2,2-trifluoroethoxy)phenoxy)benzamide; 2-(4-(cyclopropylmethoxy)phenoxy)-5-fluoro-N-(2-oxo-1,2-dihydropyridin-4-yl)benzamide; 4-chloro-2-(2-chloro-4-fluorophenoxy)-5-fluoro-N-(2-oxo-1,2-dihydropyridin-4-yl)benzamide; 2-(2-chloro-3-fluoro-4-methoxyphenoxy)-N-(2-oxo-1,2-dihydropyridin-4-yl)-4-(trifluoromethyl)benzamide; 2-(4-fluoro-2-methoxyphenoxy)-N-(2-oxo-1,2-dihydropyridin-4-yl)-4-(perfluoroethyl)benzamide; 2-(4-fluoro-2-methylphenoxy)-N-(2-oxo-1,2-dihydropyridin-4-yl)-4-(perfluoroethyl)benzamide; 4,5-dichloro-2-(4-fluorophenoxy)-N-(2-oxo-1,2-dihydropyridin-4-yl)benzamide; 4,5-dichloro-2-(4-fluoro-2-methoxyphenoxy)-N-(2-oxo-1,2-dihydropyridin-4-yl)benzamide; 4,5-dichloro-2-(3-fluoro-4-methoxyphenoxy)-N-(2-oxo-1,2-dihydropyridin-4-yl)benzamide; 2-(isopentyloxy)-N-(2-oxo-1,2-dihydropyridin-4-yl)-4-(trifluoromethyl)benzamide; 2-isobutoxy-N-(2-oxo-1,2-dihydropyridin-4-yl)-4-(trifluoromethyl)benzamide; 2-((2R)-bicyclo[2.2.1]heptan-2-yloxy)-N-(2-oxo-1,2-dihydropyridin-4-yl)-4-(trifluoromethyl)benzamide; 2-((1-methylcyclopropyl)methoxy)-N-(2-oxo-1,2-dihydropyridin-4-yl)-4-(trifluoromethyl)benzamide; 2-(cyclopentylmethoxy)-N-(2-oxo-1,2-dihydropyridin-4-yl)-4-(trifluoromethyl)benzamide; N-(2-oxo-1,2-dihydropyridin-4-yl)-2-((tetrahydrofuran-3-yl)methoxy)-4-(trifluoromethyl)benzamide; 2-cyclobutoxy-N-(2-oxo-1,2-dihydropyridin-4-yl)-4-(trifluoromethyl)benzamide; N-(2-oxo-1,2-dihydropyridin-4-yl)-2-(4,4,4-trifluorobutoxy)-4-(trifluoromethyl)benzamide; 2-((2,2-dimethylcyclopropyl)methoxy)-N-(2-oxo-1,2-dihydropyridin-4-yl)-4-(trifluoromethyl)benzamide; 2-((1R,5S)-bicyclo[3.1.0]hexan-3-yloxy)-N-(2-oxo-1,2-dihydropyridin-4-yl)-4-(trifluoromethyl)benzamide; 2-((2,2-difluorocyclopropyl)methoxy)-N-(2-oxo-1,2-dihydropyridin-4-yl)-4-(trifluoromethyl)benzamide; 2-(bicyclo[2.2.1]heptan-2-yloxy)-N-(2-oxo-1,2-dihydropyridin-4-yl)-4-(trifluoromethyl)benzamide; 2-(cyclohexyloxy)-N-(2-oxo-1,2-dihydropyridin-4-yl)-4-(trifluoromethyl)benzamide; 4-chloro-N-(2-oxo-1,2-dihydropyridin-4-yl)-2-(4,4,4-trifluorobutoxy)benzamide; 2-(cyclopentylmethoxy)-N-(2-oxo-1,2-dihydropyridin-4-yl)-5-(trifluoromethyl)benzamide; 2-isobutoxy-N-(2-oxo-1,2-dihydropyridin-4-yl)-5-(trifluoromethyl)benzamide; N-(2-oxo-1,2-dihydropyridin-4-yl)-5-(trifluoromethyl)-2-(3,3,3-trifluoropropoxy)benzamide; N-(2-oxo-1,2-dihydropyridin-4-yl)-2-(4,4,4-trifluorobutoxy)-5-(trifluoromethyl)benzamide; 2-((2,2-dimethylcyclopropyl)methoxy)-N-(2-oxo-1,2-dihydropyridin-4-yl)-5-(trifluoromethyl)benzamide; 2-(cyclopentylmethoxy)-N-(2-oxo-1,2-dihydropyridin-4-yl)-5-(trifluoromethoxy)benzamide; 2-(cyclohexyloxy)-N-(2-oxo-1,2-dihydropyridin-4-yl)-5-(trifluoromethoxy)benzamide; N-(2-oxo-1,2-dihydropyridin-4-yl)-5-(trifluoromethoxy)-2-(3,3,3-trifluoropropoxy)benzamide; N-(2-oxo-1,2-dihydropyridin-4-yl)-2-(4,4,4-trifluorobutoxy)-5-(trifluoromethoxy)benzamide; 2-((2,2-dimethylcyclopropyl)methoxy)-N-(2-oxo-1,2-dihydropyridin-4-yl)-5-(trifluoromethoxy)benzamide; 4-(tert-butyl)-N-(2-oxo-1,2-dihydropyridin-4-yl)-2-((6-(trifluoromethyl)pyridin-3-yl)oxy)benzamide; 4-(tert-butyl)-N-(6-oxo-1,6-dihydropyridin-3-yl)-2-((6-(trifluoromethyl)pyridin-3-yl)oxy)benzamide; 4-chloro-N-(2-oxo-1,2-dihydropyridin-4-yl)-2-((6-(trifluoromethyl)pyridin-3-yl)oxy)benzamide; N-(2-oxo-1,2-dihydropyridin-4-yl)-4-(trifluoromethyl)-2-((6-(trifluoromethyl)pyridin-3-yl)oxy)benzamide; N-(6-oxo-1,6-dihydropyridin-3-yl)-4-(trifluoromethyl)-2-((6-(trifluoromethyl)pyridin-3-yl)oxy)benzamide; 2-((6-methylpyridin-3-yl)oxy)-N-(2-oxo-1,2-dihydropyridin-4-yl)-4-(trifluoromethyl)benzamide; 2-((2-methylpyridin-3-yl)oxy)-N-(2-oxo-1,2-dihydropyridin-4-yl)-4-(trifluoromethyl)benzamide; 4-(tert-butyl)-N-(1-methyl-2-oxo-1,2-dihydropyridin-4-yl)-2-((6-(trifluoromethyl)pyridin-3-yl)oxy)benzamide; 4-(tert-butyl)-N-(1-methyl-6-oxo-1,6-dihydropyridin-3-yl)-2-((6-(trifluoromethyl)pyridin-3-yl)oxy)benzamide; 2-((2-methylpyridin-3-yl)oxy)-N-(2-oxo-1,2-dihydropyridin-4-yl)-5-(trifluoromethyl)benzamide; 2-((2-methylpyridin-3-yl)oxy)-N-(2-oxo-1,2-dihydropyridin-4-yl)-5-(trifluoromethoxy)benzamide; 2-(2,4-difluorophenoxy)-N-(2-oxo-1,2-dihydropyridin-4-yl)-4,6-bis(trifluoromethyl)benzamide; 2-(4-fluoro-2-methylphenoxy)-N-(2-oxo-1,2-dihydropyridin-4-yl)-4,6-bis(trifluoromethyl)benzamide; 2-(4-fluoro-2-methoxy-phenoxy)-N-(2-oxo-1,2-dihydropyridin-4-yl)-4,6-bis(trifluoromethyl)benzamide; 2-(4-fluorophenoxy)-N-(2-oxo-1,2-dihydropyridin-4-yl)-4,6-bis(trifluoromethyl)benzamide; N-(2-oxo-1,2-dihydropyridin-4-yl)-2-phenoxy-4,6-bis(trifluoromethyl)benzamide; 2-(4-fluoro-2-(hydroxymethyl)phenoxy)-N-(2-oxo-1,2-dihydropyridin-4-yl)-4-(trifluoromethyl)benzamide; 2-(4-fluoro-2-methoxyphenoxy)-N-(2-oxo-1,2-dihydropyridin-4-yl)-4-(trifluoromethyl)benzamide; 2-((5-fluoro-2-hydroxybenzyl)oxy)-N-(2-oxo-1,2-dihydropyridin-4-yl)-4-(trifluoromethyl)benzamide; 5-fluoro-N-(2-oxo-1,2-dihydropyridin-4-yl)-2-(4-(4,4,4-trifluorobutoxy)phenoxy)benzamide, or combinations thereof.

In another embodiment, the additional appropriate therapeutic agent is an NaV 1.8 inhibitor selected from the following: 3-(4-fluorophenoxy)-N-(3-sulfamoylphenyl)quinoxaline-2-carboxamide; 3-(4-fluoro-2-methoxyphenoxy)-N-(3-sulfamoylphenyl)quinoxaline-2-carboxamide; N-(3-sulfamoylphenyl)-3-(4-(trifluoromethoxy)phenoxy)quinoxaline-2-carboxamide; 3-(2-chloro-4-methoxyphenoxy)-N-(3-sulfamoylphenyl)quinoxaline-2-carboxamide; 3-(2,4- difluorophenoxy)-N-(3-sulfamoylphenyl)quinoxaline-2-carboxamide; 3-(2-chloro-4-fluorophenoxy)-N-(3-sulfamoylphenyl)quinoxaline-2-carboxamide; 3-(3-fluoro-4-methoxyphenoxy)-N-(3-sulfamoylphenyl)quinoxaline-2-carboxamide; 3-(2,4-dimethoxyphenoxy)-N-(3-sulfamoylphenyl)quinoxaline-2-carboxamide; 3-(4-chloro-2-methylphenoxy)-N-(3-sulfamoylphenyl)quinoxaline-2-carboxamide; 3-(2-(difluoromethoxy)phenoxy)-N-(3-sulfamoylphenyl)quinoxaline-2-carboxamide; 3-(4-chloro-2-methoxyphenoxy)-N-(3-sulfamoylphenyl)quinoxaline-2-carboxamide; 3-(2-fluoro-4-methoxyphenoxy)-N-(3-sulfamoylphenyl)quinoxaline-2-carboxamide; 3-phenoxy-N-(3-sulfamoylphenyl)quinoxaline-2-carboxamide; 3-(4-fluoro-2-methylphenoxy)-N-(3-sulfamoylphenyl)quinoxaline-2-carboxamide; N-(3-sulfamoylphenyl)-3-(4-(2,2,2-trifluoroethoxy)phenoxy)quinoxaline-2-carboxamide; 3-(4-fluoro-2-methoxyphenoxy)-N-(3-(N-methylsulfamoyl)phenyl)quinoxaline-2-carboxamide; 4-(3-(4-(trifluoromethoxy)phenoxy)quinoxaline-2-carboxamido)benzoic acid; 5-(3-(4-fluorophenoxy)quinoxaline-2-carboxamido)picolinic acid; 5-(3-(4-fluoro-2-methylphenoxy)quinoxaline-2-carboxamido)picolinic acid; 5-(3-phenoxyquinoxaline-2-carboxamido)picolinic acid; 5-(3-(2-fluoro-4-methoxyphenoxy)quinoxaline-2-carboxamido)picolinic acid; 5-(3-(4-(2,2,2-trifluoroethoxy)phenoxy)quinoxaline-2-carboxamido)picolinic acid; 5-(3-(4-chloro-2-methoxyphenoxy)quinoxaline-2-carboxamido)picolinic acid; 5-(3-(2-(difluoromethoxy)phenoxy)quinoxaline-2-carboxamido)picolinic acid; 5-(3-(4-chloro-2-methylphenoxy)quinoxaline-2-carboxamido)picolinic acid; 5-(3-(2,4-dimethoxyphenoxy)quinoxaline-2-carboxamido)picolinic acid; 5-(3-(3-fluoro-4-methoxyphenoxy)quinoxaline-2-carboxamido)picolinic acid; 5-(3-(2-chloro-4-fluorophenoxy)quinoxaline-2-carboxamido)picolinic acid; 5-(3-(2,4-difluorophenoxy)quinoxaline-2-carboxamido)picolinic acid; 5-(3-(2-chloro-4-methoxyphenoxy)quinoxaline-2-carboxamido)picolinic acid; 5-(3-(4-(trifluoromethoxy)phenoxy)quinoxaline-2-carboxamido)picolinic acid; 5-(3-(4-fluoro-2-methoxyphenoxy)quinoxaline-2-carboxamido)picolinic acid; 44344-(trifluoromethoxy)phenoxy)quinoxaline-2-carboxamido)picolinic acid; 4-(3-(4-fluoro-2-methoxyphenoxy)quinoxaline-2-carboxamido)picolinic acid; 3-(4-fluorophenoxy)-N-(2-oxo-1,2-dihydropyridin-4-yl)quinoxaline-2-carboxamide; 3-(3-(4-fluoro-2-methoxyphenoxy)quinoxaline-2-carboxamido)benzoic acid; 2-(3-(4-fluoro-2-methoxyphenoxy)quinoxaline-2-carboxamido)thiazole-4-carboxylic acid; 3-(4-fluoro-2-methoxyphenoxy)-N-(1H-1,2,4-triazol-3-yl)quinoxaline-2-carboxamide; 2-(3-(4-fluoro-2-methoxyphenoxy)quinoxaline-2-carboxamido)oxazole-4-carboxylic acid; 3-(4-fluoro-2-methoxyphenoxy)-N-(1H-pyrazol-3-yl)quinoxaline-2-carboxamide; 3-(4-fluoro-2-methoxyphenoxy)-N-(1H-tetrazol-5-yl)quinoxaline-2-carboxamide; N-(1H-benzo[d][1,2,3]triazol-5-yl)-3-(4-fluoro-2-methoxyphenoxy)quinoxaline-2-carboxamide; 3-(4-fluoro-2-methoxyphenoxy)-N-(1H-pyrazol-4-yl)quinoxaline-2-carboxamide; 3-(4-fluoro-2-methoxyphenoxy)-N-(2-(hydroxymethyl)-1H-benzo[d]imidazol-5-yl)quinoxaline-2-carboxamide; N-(3-(1H-tetrazol-5-yl)phenyl)-3-(4-fluoro-2-methoxyphenoxy)quinoxaline-2-carboxamide; 3-(4-fluoro-2-methoxyphenoxy)-N-(3-(methylsulfonyl)phenyl)quinoxaline-2-carboxamide; 3-(4-fluoro-2-methoxyphenoxy)-N-(1H-indazol-6-yl)quinoxaline-2-carboxamide; 3-(4-fluoro-2-methoxyphenoxy)-N-(1H-indazol-5-yl)quinoxaline-2-carboxamide; N-(1H-benzo[d]imidazol-6-yl)-3-(4-fluoro-2-methoxyphenoxy)quinoxaline-2-carboxamide; N-(4-cyanopyridin-2-yl)-3-(4-fluoro-2-methoxyphenoxy)quinoxaline-2-carboxamide; N-(6-cyanopyridin-3-yl)-3-(4-fluoro-2-methoxyphenoxy)quinoxaline-2-carboxamide; N-(5-cyanopyridin-2-yl)-3-(4-fluoro-2-methoxyphenoxy)quinoxaline-2-carboxamide; 3-(4-fluoro-2-methoxyphenoxy)-N-(pyridin-4-yl)quinoxaline-2-carboxamide; 3-(4-fluoro-2-methoxyphenoxy)-N-(pyridin-3-yl)quinoxaline-2-carboxamide; N-(4-cyanophenyl)-3-(4-fluoro-2-methoxyphenoxy)quinoxaline-2-carboxamide; N-(3-cyanophenyl)-3-(4-fluoro-2-methoxyphenoxy)quinoxaline-2-carboxamide; 3-(4-fluoro-2-methoxyphenoxy)-N-(2-oxo-2,3-dihydro-1H-benzo[d]imidazol-5-yl)quinoxaline-2-carboxamide; N-(4-carbamoylphenyl)-3-(4-fluoro-2-methoxyphenoxy)quinoxaline-2-carboxamide; N-(3-carbamoylphenyl)-3-(4-fluoro-2-methoxyphenoxy)quinoxaline-2-carboxamide; 2-(4-fluorophenoxy)-N-(3-sulfamoylphenyl)quinoline-3-carboxamide; 2-(4-fluoro-2-methoxyphenoxy)-N-(3-sulfamoylphenyl)quinoline-3-carboxamide; 2-(3-fluoro-4-methoxyphenoxy)-N-(3-sulfamoylphenyl)quinoline-3-carboxamide; 2-(4-fluoro-2-methylphenoxy)-N-(3-sulfamoylphenyl)quinoline-3-carboxamide; 2-phenoxy-N-(3-sulfamoylphenyl)quinoline-3-carboxamide; 2-(2,4-difluorophenoxy)-N-(3-sulfamoylphenyl)quinoline-3-carboxamide; 2-(2-chloro-4-fluorophenoxy)-N-(3-sulfamoylphenyl)quinoline-3-carboxamide; N-(3-sulfamoylphenyl)-2-(4-(2,2,2-trifluoroethoxy)phenoxy)quinoline-3-carboxamide; N-(3-sulfamoylphenyl)-2-(4-(trifluoromethoxy)phenoxy)quinoline-3-carboxamide; 2-(2-chloro-4-methoxyphenoxy)-N-(3-sulfamoylphenyl)quinoline-3-carboxamide; 2-(2-fluoro-4-methoxyphenoxy)-N-(3-sulfamoylphenyl)quinoline-3-carboxamide; 2-(4-chloro-2-methylphenoxy)-N-(3-sulfamoylphenyl)quinoline-3-carboxamide; dimethoxyphenoxy)-N-(3-sulfamoylphenyl)quinoline-3-carboxamide; 2-(4-chloro-2-methoxyphenoxy)-N-(3-sulfamoylphenyl)quinoline-3-carboxamide; 2-(2-(difluoromethoxy)phenoxy)-N-(3-sulfamoylphenyl)quinoline-3-carboxamide; 4-(2-(2,4-difluorophenoxy)quinoline-3-carboxamido)benzoic acid; 4-(2-(4-fluoro-2-methylphenoxy)quinoline-3-carboxamido)benzoic acid; 4-(2-(2-(difluoromethoxy)phenoxy)quinoline-3-carboxamido)benzoic acid; 4-(2-(2,4-dimethoxyphenoxy)quinoline-3-carboxamido)benzoic acid; 5-(2-(2-chloro-4-fluorophenoxy)quinoline-3-carboxamido)picolinic acid; 5-(2-(2,4-difluorophenoxy)quinoline-3-carboxamido)picolinic acid, or combinations thereof.

In another embodiment, the additional appropriate therapeutic agent is an NaV 1.8 inhibitor selected from the following: 4-(2-(2-chloro-4-fluorophenoxy)-4-(perfluoroethyl)benzamido)benzoic acid; 4-(2-(2,4-difluorophenoxy)-4-(perfluoroethyl)benzamido)benzoic acid; 4-(2-(4-fluoro-2-methylphenoxy)-4-(perfluoroethyl)benzamido)benzoic acid; 4-(2-(2-chloro-4-fluorophenoxy)-4-(trifluoromethyl)benzamido)benzoic acid; 4-(2-(4-fluoro-2-methylphenoxy)-4-(trifluoromethyl)benzamido)benzoic acid; 4-(2-(2,4-difluorophenoxy)-4-(trifluoromethyl)benzamido)benzoic acid; 4-(2-(4-(trifluoromethoxy)phenoxy)-4-(trifluoromethyl)benzamido)benzoic acid; 4-(2-(2,4-difluorophenoxy)-4,6-bis(trifluoromethyl)benzamido)benzoic acid; 4-(2-(4-fluoro-2-methylphenoxy)-4,6-bis(trifluoromethyl)benzamido)benzoic acid; 4-(2-(4-fluoro-2-methoxyphenoxy)-4,6-bis(trifluoromethyl)benzamido)benzoic acid; 4-(2-(4-fluorophenoxy)-4,6-bis(trifluoromethyl)benzamido)benzoic acid; 4-(4,5-dichloro-2-(4-fluoro-2-methoxyphenoxy)benzamido)benzoic acid; 4-(4,5-dichloro-2-(4-fluorophenoxy)benzamido)benzoic acid; 4-(4,5-dichloro-2-(4-fluoro-2-methylphenoxy)benzamido)benzoic acid; 4-(4,5-dichloro-2-phenoxybenzamido)benzoic acid; 4-(4,5-dichloro-2-(2- fluoro-4-methoxyphenoxy)benzamido)benzoic acid; 4-(4,5-dichloro-2-(4-(2,2,2-trifluoroethoxy)phenoxy)benzamido) benzoic acid; 4-(4,5-dichloro-2-(4-chloro-2-methoxyphenoxy)benzamido)benzoic acid; 4-(4,5-dichloro-2-(2-(difluoromethoxy)phenoxy)benzamido)benzoic acid; 4-(4,5-dichloro-2-(4-chloro-2-methylphenoxy)benzamido)benzoic acid; 4-(4,5-dichloro-2-(2,4-dimethoxyphenoxy)benzamido)benzoic acid; 4-(4,5-dichloro-2-(3-fluoro-4-methoxyphenoxy)benzamido)benzoic acid; 4-(4,5-dichloro-2-(2-chloro-4-fluorophenoxy)benzamido)benzoic acid; 4-(4,5-dichloro-2-(2,4-difluorophenoxy)benzamido)benzoic acid; 4-(4,5-dichloro-2-(2-chloro-4-methoxyphenoxy)benzamido)benzoic acid; 4-(4,5-dichloro-2-(4-(trifluoromethoxy)phenoxy)benzamido)benzoic acid; 4-(2-(4-fluoro-2-methoxyphenoxy)-4-(perfluoroethyl)benzamido)benzoic acid; 4-(2-(4-fluoro-2-methylphenoxy)-5-(trifluoromethyl)benzamido)benzoic acid; 4-(2-(4-fluoro-2-methylphenoxy)-5-(trifluoromethyl)benzamido)benzoic acid; 5-(4,5-dichloro-2-(4-fluorophenoxy)benzamido)picolinic acid; 5-(4,5-dichloro-2-(4-(isopentyloxy)phenoxy)benzamido)picolinic acid; 5-(4,5-dichloro-2-(4-fluoro-2-methylphenoxy)benzamido)picolinic acid; 5-(4,5-dichloro-2-phenoxybenzamido)picolinic acid; 5-(4,5-dichloro-2-(2-fluoro-4-methoxyphenoxy)benzamido)picolinic acid; 5-(4,5-dichloro-2-(4-(2,2,2-trifluoroethoxy)phenoxy)benzamido)picolinic acid; 5-(4,5-dichloro-2-(4-chloro-2-methoxyphenoxy)benzamido)picolinic acid; 5-(4,5-dichloro-2-(2-(difluoromethoxy)phenoxy)benzamido)picolinic acid; 5-(4,5-dichloro-2-(4-chloro-2-methylphenoxy)benzamido)picolinic acid; 5-(4,5-dichloro-2-(2,4-dimethoxyphenoxy)benzamido)picolinic acid; 5-(4,5-dichloro-2-(3-fluoro-4-methoxyphenoxy)benzamido)picolinic acid; 5-(4,5-dichloro-2-(2-chloro-4-fluorophenoxy)benzamido)picolinic acid; 5-(4,5-dichloro-2-(2,4-difluorophenoxy)benzamido)picolinic acid; 5-(4,5-dichloro-2-(2-chloro-4-methoxyphenoxy)benzamido)picolinic acid; 5-(4,5-dichloro-2-(4-(trifluoromethoxy)phenoxy)benzamido)picolinic acid; 5-(2-(2-methoxyphenoxy)-4,6-bis(trifluoromethyl)benzamido)picolinic acid; 5-(2-(4-methoxyphenoxy)-4,6-bis(trifluoromethyl)benzamido)picolinic acid; 5-(2-(4-fluoro-2-methylphenoxy)-4,6-bis(trifluoromethyl)benzamido)picolinic acid; 5-(2-(4-fluoro-2-methoxyphenoxy)-4,6-bis(trifluoromethyl)benzamido)picolinic acid; 5-(2-(2,4-dimethoxyphenoxy)-4,6-bis(trifluoromethyl)benzamido)picolinic acid; 5-(2-(4-fluorophenoxy)-4,6-bis(trifluoromethyl)benzamido)picolinic acid; 5-(4,5-dichloro-2-(4-fluoro-2-methoxyphenoxy)benzamido)picolinic acid; 5-(4-(tert-butyl)-2-(4-fluoro-2-methoxyphenoxy)benzamido)picolinic acid; 5-(4-(tert-butyl)-2-(4-fluoro-2-methylphenoxy)benzamido)picolinic acid; 5-(4-(tert-butyl)-2-(4-fluorophenoxy)benzamido)picolinic acid; 5-(2-(4-fluorophenoxy)benzamido)picolinic acid; 5-(2-(4-fluorophenoxy)-4-(trifluoromethyl)benzamido)picolinic acid; 5-(2-(4-fluoro-2-methoxyphenoxy)-5-(trifluoromethyl)benzamido) picolinic acid; 5-(2-(2-chloro-4-fluorophenoxy)-5-(trifluoromethyl)benzamido)picolinic acid; 5-(2-(5-fluoro-2-methoxyphenoxy)-5-(trifluoromethyl)benzamido)picolinic acid; 5-(2-(2-(difluoromethoxy)phenoxy)-5-(trifluoromethyl)benzamido)picolinic acid; 5-(2-(4-chloro-2-methylphenoxy)-5-(trifluoromethyl)benzamido)picolinic acid; 5-(2-(2-methoxyphenoxy)-5-(trifluoromethyl)benzamido) picolinic acid; 5-(2-(2-chlorophenoxy)-5-(trifluoromethyl)benzamido)picolinic acid; 5-(2-(2-isopropoxyphenoxy)-5-(trifluoromethyl)benzamido)picolinic acid; 5-(2-(2,4-dimethoxyphenoxy)-5-(trifluoromethyl)benzamido)picolinic acid; 5-(2-(4-chloro-2-methoxyphenoxy)-5-(trifluoromethyl)benzamido)picolinic acid; 5-(2-(4-methoxy-2-methylphenoxy)-5-(trifluoromethyl)benzamido)picolinic acid; 5-(2-(2-chloro-4-methoxyphenoxy)-5-(trifluoromethyl)benzamido)picolinic acid; 5-(2-(3-fluoro-2-methoxyphenoxy)-5-(trifluoromethyl)benzamido)picolinic acid; 5-(2-phenoxy-5-(trifluoromethyl)benzamido)picolinic acid; 5-(2-(4-fluorophenoxy)-5-(trifluoromethyl)benzamido)picolinic acid; 5-(2-(4-fluoro-2-methoxyphenoxy)-4-(perfluoroethyl)benzamido)picolinic acid; 5-(2-(4-fluorophenoxy)-4-(perfluoroethyl)benzamido)picolinic acid; 5-(2-(2-chloro-4-fluorophenoxy)-6-(trifluoromethyl)benzamido)picolinic acid; 5-(2-(4-fluoro-2-methylphenoxy)-5-(trifluoromethyl)benzamido)picolinic acid; 5-(4,5-dichloro-2-(4-fluoro-2-methoxyphenoxy)benzamido)picolinic acid, or combinations thereof.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General Methods $^1$H NMR (400 MHz or 300 MHz) and $^{13}$C NMR (100 MHz) spectra were obtained as solutions in deuterioacetonitrile ($CD_3CN$), chloroform-d ($CDCl_3$), deuteromethanol (MeOD-d4), or dimethyl sulfoxide-$D_6$ (DMSO). Mass spectra (MS) were obtained using an Applied Biosystems API EX LC/MS system equipped with a Phenomenex 50×4.60 mm luna-5µ, C18 column. The LC/MS eluting system was 1-99% or 10-99% acetonitrile in $H_2O$ with 0.035% v/v trifluoroacetic acid, 0.035% v/v formic acid, 5 mM HCl or 5 mM ammonium formate using a 3 or 15 min linear gradient and a flow rate of 12 mL/min. Silica gel chromatography was performed using silica gel-60 with a particle size of 230-400 mesh. Pyridine, DCM ($CH_2Cl_2$), tetrahydrofuran (THF), dimethylformamide (DMF), acetonitrile (ACN), methanol (MeOH), and 1,4-dioxane were from Aldrich Sure-Seal bottles kept under dry nitrogen. All reactions were stirred magnetically unless otherwise noted.

[(3aR,7aR)-7a-phenyl-3a,4,6,7-tetrahydro-[1,3]dioxolo[4,5-c]pyridin-5-yl]-[3-methoxy-4-[2-(trifluoromethoxy)ethoxy]phenyl]methanone

Step 1: tert-butyl 4-phenyl-3,6-dihydro-2H-pyridine-1-carboxylate

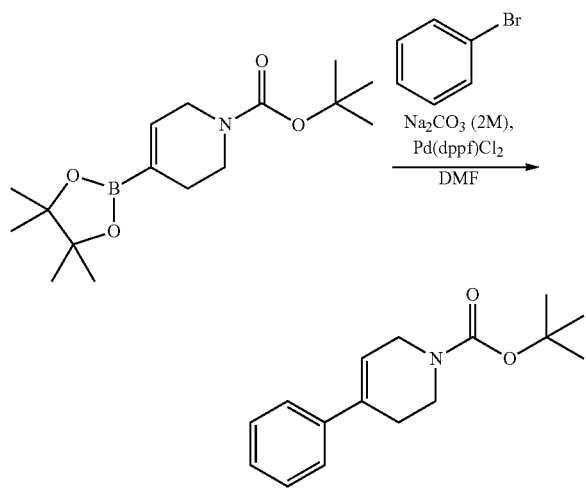

A solution of tert-butyl 4-(4,4,5,5-tetramethyl-1,3,2-dioxaborolan-2-yl)-3,6-dihydro-2H-pyridine-1-carboxylate (10.0 g, 32.3 mmol) and bromobenzene (5.1 g, 3.4 mL, 32.3 mmol) in DMF (30 mL), was treated with sodium carbonate (16.2 mL of 2 M, 32.3 mmol) in water. The reaction mixture was purged with nitrogen and treated with Pd(dppf)Cl$_2$ (1.2 g, 1.6 mmol). The reaction mixture was stirred at 80° C. for 1 h. Volatiles were removed under reduced pressure at 70° C. The remaining residue was partitioned between ethyl acetate (100 mL) and water (100 mL). The mixture was filtered to remove emulsifying solids. The organic layer was further washed with saturated aqueous NaCl, dried over sodium sulfate, filtered and concentrated under reduced pressure. The resulting brown oil was purified by silica gel column chromatography: 120 gram silica gel column, 0-40% ethyl acetate/hexane gradient over 30 min to afford tert-butyl 4-phenyl-3,6-dihydro-2H-pyridine-1-carboxylate (8.13 g, mmol, 97%) as a clear colorless oil. ESI-MS m/z calc. 259.2. found 260.3 (M+1)$^+$; Retention time: 2.05 min (3 min run).

The following compounds were prepared using the procedure reported above:

| Aryl Halide | Product |
|---|---|
| 1-bromo-3,5-difluoro-benzene | tert-butyl 4-(3,5-difluorophenyl)-3,6-dihydro-2H-pyridine-1-carboxylate |
| 1-Bromo-3-fluoro-benzene | tert-butyl 4-(3-fluorophenyl)-3,6-dihydro-2H-pyridine-1-carboxylate |
| 1-bromo-4-fluoro-benzene | tert-butyl 4-(4-fluorophenyl)-3,6-dihydro-2H-pyridine-1-carboxylate |
| 2,6-Dibromopyridine | tert-butyl 4-(6-bromo-2-pyridyl)-3,6-dihydro-2H-pyridine-1-carboxylate |
| 2-bromo-1,4-difluoro-benzene | tert-butyl 4-(2,5-difluorophenyl)-3,6-dihydro-2H-pyridine-1-carboxylate |
| 2-bromo-3-chloro-pyridine | tert-butyl 4-(3-chloro-2-pyridyl)-3,6-dihydro-2H-pyridine-1-carboxylate |
| 2-bromo-3-methoxy-1-oxido-pyridin-1-ium | tert-butyl 4-(3-methoxy-1-oxido-pyridin-1-ium-2-yl)-3,6-dihydro-2H-pyridine-1-carboxylate |
| 2-bromopyrimidine | tert-butyl 4-pyrimidin-2-yl-3,6-dihydro-2H-pyridine-1-carboxylate |
| 2-chloro-3-fluoro-pyridine | tert-butyl 4-(3-fluoro-2-pyridyl)-3,6-dihydro-2H-pyridine-1-carboxylate |
| 3-bromo-1-methyl-pyrazole | tert-butyl 4-(1-methylpyrazol-3-yl)-3,6-dihydro-2H-pyridine-1-carboxylate |
| 3-bromobenzonitrile | tert-butyl 4-(3-cyanophenyl)-3,6-dihydro-2H-pyridine-1-carboxylate |
| 4-bromo-2-methyl-thiazole | tert-butyl 4-(2-methylthiazol-4-yl)-3,6-dihydro-2H-pyridine-1-carboxylate |
| 4-bromothiazole | tert-butyl 4-thiazol-4-yl-3,6-dihydro-2H-pyridine-1-carboxylate |
| bromobenzene | tert-butyl 4-phenyl-3,6-dihydro-2H-pyridine-1-carboxylate |
| 1-bromo-3-chloro-benzene | tert-butyl 4-(3-chlorophenyl)-3,6-dihydro-2H-pyridine-1-carboxylate |
| 1-bromo-2,3-difluoro-benzene | tert-butyl 4-(2,3-difluorophenyl)-5,6-dihydropyridine-1(2H)-carboxylate |
| 2-bromo-1,4-difluoro-benzene | tert-butyl 4-(2,5-difluorophenyl)-3,6-dihydro-2H-pyridine-1-carboxylate |
| 2-bromo-6-(trifluoromethyl)pyridine | tert-butyl 6-(trifluoromethyl)-5',6'-dihydro-[2,4'-bipyridine]-1'(2'H)-carboxylate |
| 2-bromo-4-(trifluoromethyl)pyridine | tert-butyl 4-[4-(trifluoromethyl)-2-pyridyl]-3,6-dihydro-2H-pyridine-1-carboxylate |
| 2,6-dichloro-4-methoxy-pyridine | tert-butyl 4-(6-chloro-4-methoxy-2-pyridyl)-3,6-dihydro-2H-pyridine-1-carboxylate |
| 2,6-dibromopyridine | tert-butyl 6-bromo-5',6'-dihydro-[2,4'-bipyridine]-1'(2'H)-carboxylate |

Step 2: tert-butyl(3R,4R)-3,4-dihydroxy-4-phenyl-piperidine-1-carboxylate

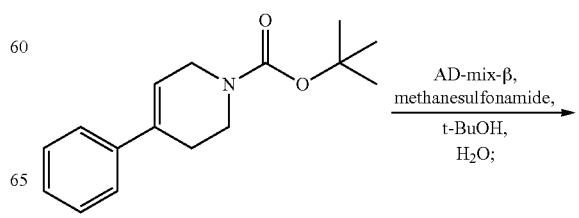

-continued

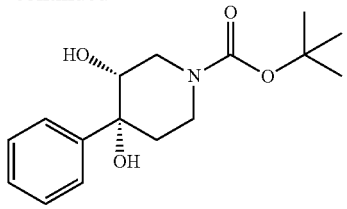

Methanesulfonamide (917 mg, 9.6 mmol) was dissolved in a solution of water (54 mL) and tert-butanol (54 mL). AD-mix-β (7.6 g, 9.6 mmol) was added, and the mixture was allowed to stir at rt for 5 min before cooling to 0° C. To the mixture was added tert-butyl 4-phenyl-3,6-dihydro-2H-pyridine-1-carboxylate (2.5 g, 9.6 mmol) in one portion, and the reaction mixture was allowed to continue stirring at 0° C. for 8 h. Sodium sulfite (6 g) was added, and the mixture was allowed to stir at rt for an additional 30 min and was extracted with ethyl acetate (2×75 mL). The combined organic layers were washed with aqueous 1 N NaOH (1×75 mL), dried over sodium sulfate, filtered and concentrated under reduced pressure to a yellow-orange oil. It was purified by silica gel column chromatography: 40 gram silica gel column, 0-30% ethyl acetate/hexane gradient over 30 min; product eluted at 25% to provide tert-butyl(3R,4R)-3,4-dihydroxy-4-phenyl-piperidine-1-carboxylate (1.6 g, 58%) as a white solid. $^1$H NMR (400 MHz, CDCl$_3$) δ 7.48 (dt, J=3.1, 1.8 Hz, 2H), 7.44-7.35 (m, 2H), 7.33-7.27 (m, 1H), 4.26-4.12 (m, 1H), 4.11-4.01 (m, 1H), 3.95 (d, J=11.7 Hz, 1H), 3.22-3.08 (m, 1H), 3.07-2.93 (m, 1H), 2.71 (s, 1H), 1.96-1.79 (m, 2H), 1.64 (t, J=18.5 Hz, 1H), 1.55-1.44 (m, 9H). ESI-MS m/z calc. 293.2. found 294.5 (M+1)$^+$; Retention time: 1.32 min (3 min run).

The following compounds were prepared using the procedure reported above:

| Product | Precursor |
| --- | --- |
| tert-butyl (3R,4R)-3,4-dihydroxy-4-(3,5-difluorophenyl)-pyridine-1-carboxylate | tert-butyl 4-(3,5-difluorophenyl)-3,6-dihydro-2H-pyridine-1-carboxylate |
| tert-butyl (3R,4R)-3,4-dihydroxy-4-(3-fluorophenyl)-piperidine-1-carboxylate | tert-butyl 4-(3-fluorophenyl)-3,6-dihydro-2H-pyridine-1-carboxylate |
| tert-butyl (3R,4R)-3,4-dihydroxy-4-(4-fluorophenyl)-piperidine-1-carboxylate | tert-butyl 4-(4-fluorophenyl)-3,6-dihydro-2H-pyridine-1-carboxylate |
| tert-butyl (3R,4R)-3,4-dihydroxy-(6-bromo-2-pyridyl)-piperidine-1-carboxylate | tert-butyl 4-(6-bromo-2-pyridyl)-3,6-dihydro-2H-pyridine-1-carboxylate |
| tert-butyl (3R,4R)-3,4-dihydroxy-4-(2,5-difluorophenyl)-piperidine-1-carboxylate | tert-butyl 4-(2,5-difluorophenyl)-3,6-dihydro-2H-pyridine-1-carboxylate |
| tert-butyl (3R,4R)-3,4-dihydroxy-4-(3-chloro-2-pyridyl)-piperidine-1-carboxylate | tert-butyl 4-(3-chloro-2-pyridyl)-3,6-dihydro-2H-pyridine-1-carboxylate |
| tert-butyl (3R,4R)-3,4-dihydroxy-4-(3-methoxy-1-oxido-pyridin-1-ium-2-yl)-piperidine-1-carboxylate | tert-butyl 4-(3-methoxy-1-oxido-pyridin-1-ium-2-yl)-3,6-dihydro-2H-pyridine-1-carboxylate |
| tert-butyl (3R,4R)-3,4-dihydroxy-4-pyrimidin-2-yl-piperidine-1-carboxylate | tert-butyl 4-pyrimidin-2-yl-3,6-dihydro-2H-pyridine-1-carboxylate |
| tert-butyl (3R,4R)-3,4-dihydroxy-4-(3-fluoro-2-pyridyl)-piperidine-1-carboxylate | tert-butyl 4-(3-fluoro-2-pyridyl)-3,6-dihydro-2H-pyridine-1-carboxylate |
| tert-butyl (3R,4R)-3,4-dihydroxy-4-(1-methylpyrazol-3-yl)-piperidine-1-carboxylate | tert-butyl 4-(1-methylpyrazol-3-yl)-3,6-dihydro-2H-pyridine-1-carboxylate |
| tert-butyl (3R,4R)-3,4-dihydroxy-4-(3-cyanophenyl)-piperidine-1-carboxylate | tert-butyl 4-(3-cyanophenyl)-3,6-dihydro-2H-pyridine-1-carboxylate |
| tert-butyl (3R,4R)-3,4-dihydroxy-4-(2-methylthiazol-4-yl)-piperidine-1-carboxylate | tert-butyl 4-(2-methylthiazol-4-yl)-3,6-dihydro-2H-pyridine-1-carboxylate |
| tert-butyl (3R,4R)-3,4-dihydroxy-4-thiazol-4-yl-piperidine-1-carboxylate | tert-butyl 4-thiazol-4-yl-3,6-dihydro-2H-pyridine-1-carboxylate |
| tert-butyl (3R,4R)-3,4-dihydroxy-4-phenyl-piperidine-1-carboxylate | tert-butyl 4-phenyl-3,6-dihydro-2H-pyridine-1-carboxylate |
| tert-butyl (3R,4R)-3,4-dihydroxy-4-(3-chlorophenyl)-piperidine-1-carboxylate | tert-butyl 4-(3-chlorophenyl)-3,6-dihydro-2H-pyridine-1-carboxylate |
| tert-butyl (3R,4R)-3,4-dihydroxy-4-(2,3-difluorophenyl)-piperidine-1-carboxylate | tert-butyl 4-(2,3-difluorophenyl)-5,6-dihydropyridine-1(2H)-carboxylate |
| tert-butyl (3R,4R)-3,4-dihydroxy-4-(2,5-difluorophenyl)-piperidine-1-carboxylate | tert-butyl 4-(2,5-difluorophenyl)-3,6-dihydro-2H-pyridine-1-carboxylate |
| tert-butyl (3R,4R)-3,4-dihydroxy-6-(trifluoromethyl)-piperidine-1-carboxylate | tert-butyl 6-(trifluoromethyl)-5',6'-dihydro-[2,4'-bipyridine]-1'(2'H)-carboxylate |
| tert-butyl (3R,4R)-3,4-dihydroxy-4-[4-(trifluoromethyl)-2-pyridyl]-piperidine-1-carboxylate | tert-butyl 4-[4-(trifluoromethyl)-2-pyridyl]-3,6-dihydro-2H-pyridine-1-carboxylate |
| tert-butyl (3R,4R)-3,4-dihydroxy-4-(6-chloro-4-methoxy-2-pyridyl)-piperidine-1-carboxylate | tert-butyl 4-(6-chloro-4-methoxy-2-pyridyl)-3,6-dihydro-2H-pyridine-1-carboxylate |
| tert-butyl (3R,4R)-4-(6-bromopyridin-2-yl)-3,4-dihydroxypiperidine-1-carboxylate | tert-butyl 6-bromo-5',6'-dihydro-[2,4'-bipyridine]-1'(2'H)-carboxylate |

Step 3: tert-butyl(3aR,7aR)-7a-phenyl-3a,4,6,7-tetrahydro-[1,3]dioxolo[4,5-c]pyridine-5-carboxylate

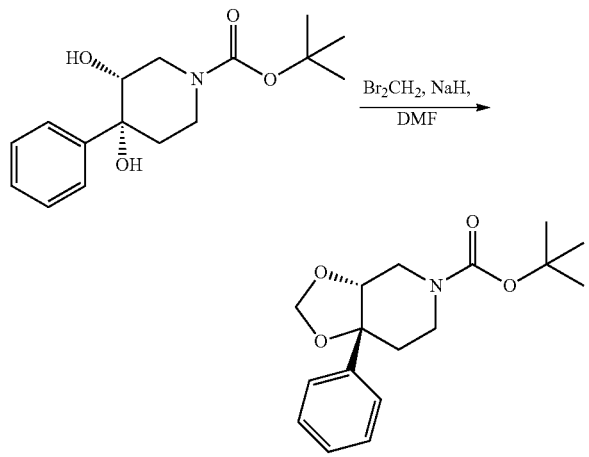

In a 100 mL flask equipped with a nitrogen inlet, tert-butyl(3R,4R)-3,4-dihydroxy-4-phenyl-piperidine-1-carboxylate (1.3 g, 4.5 mmol) was dissolved in DMF (7 mL). The solution was cooled to 0° C. before the addition of sodium hydride (395 mg, 9.86 mmol) (60 wt % dispersion in mineral oil). The reaction mixture was allowed to stir at 0° C. for 20 min before the addition of dibromomethane (344 μL, 4.94 mmol). Following addition, the 0° C. ice bath was removed, and the reaction mixture was allowed to stir at rt for 20 h. Water and saturated aqueous NaCl (total volume of 50 mL) were added and the product was extracted with ethyl acetate (2×30 mL). The organic layers were combined, dried over sodium sulfate, filtered and concentrated under reduced pressure. The obtained oil (1.76 grams) was dissolved in DCM and purified by silica gel column chromatography (80 g column): 0-10% ethyl acetate/hexane gradient over 25 min, then 10-40% over 15 min. The pure fractions were combined and concentrated to provide tert-butyl(3aR,7aR)-7a-phenyl-3a,4,6,7-tetrahydro-[1,3]dioxolo[4,5-c]pyridine-5-carboxylate (1.0 g, 73%) as a colorless viscous oil. $^1$H NMR (400 MHz, CDCl$_3$) δ 7.42-7.34 (m, 4H), 7.33-7.25 (m, 1H), 5.25 (s, 1H), 4.84 (s, 1H), 4.29 (s, 1H), 3.95 (d, J=13.0 Hz, 1H), 3.59-3.50 (m, 2H), 3.43 (td, J=12.3, 3.9 Hz, 1H), 2.15-1.91 (m, 2H), 1.50 (s, 9H). ESI-MS m/z calc. 305.2. found 306.0 (M+1)$^+$; Retention time: 1.74 min (3 min run).

The following compounds were prepared using the procedure reported above:

| Product | Precursor |
| --- | --- |
| tert-butyl (3aR,7aR)-7a-(3,5-difluorophenyl)-3a,4,6,7-tetrahydro-[1,3]dioxolo[4,5-c]pyridine-5-carboxylate | tert-butyl (3R,4R)-3,4-dihydroxy-4-(3,5-difluorophenyl)-pyridine-1-carboxylate |
| tert-butyl (3aR,7aR)-7a-(3-fluorophenyl)-3a,4,6,7-tetrahydro-[1,3]dioxolo[4,5-c]pyridine-5-carboxylate | tert-butyl (3R,4R)-3,4-dihydroxy-4-(3-fluorophenyl)-piperidine-1-carboxylate |
| tert-butyl (3aR,7aR)-7a-(4-fluorophenyl)-3a,4,6,7-tetrahydro-[1,3]dioxolo[4,5-c]pyridine-5-carboxylate | tert-butyl (3R,4R)-3,4-dihydroxy-4-(4-fluorophenyl)-piperidine-1-carboxylate |
| tert-butyl (3aR,7aR)-7a-(6-bromo-2-pyridyl)-3a,4,6,7-tetrahydro-[1,3]dioxolo[4,5-c]pyridine-5-carboxylate | tert-butyl (3R,4R)-3,4-dihydroxy-(6-bromo-2-pyridyl)-piperidine-1-carboxylate |
| tert-butyl (3aR,7aR)-7a-(2,5-difluorophenyl)-3a,4,6,7-tetrahydro-[1,3]dioxolo[4,5-c]pyridine-5-carboxylate | tert-butyl (3R,4R)-3,4-dihydroxy-4-(2,5-difluorophenyl)-piperidine-1-carboxylate |
| tert-butyl (3aR,7aR)-7a-(3-chloro-2-pyridyl)-3a,4,6,7-tetrahydro-[1,3]dioxolo[4,5-c]pyridine-5-carboxylate | tert-butyl (3R,4R)-3,4-dihydroxy-4-(3-chloro-2-pyridyl)-piperidine-1-carboxylate |
| tert-butyl (3aR,7aR)-7a-(3-methoxy-1-oxido-pyridin-1-ium-2-yl)-3a,4,6,7-tetrahydro-[1,3]dioxolo[4,5-c]pyridine-5-carboxylate | tert-butyl (3R,4R)-3,4-dihydroxy-4-(3-methoxy-1-oxido-pyridin-1-ium-2-yl)-piperidine-1-carboxylate |
| tert-butyl (3aR,7aR)-7a-4-pyrimidin-2-yl-piperidine-3a,4,6,7-tetrahydro-[1,3]dioxolo[4,5-c]pyridine-5-carboxylate | tert-butyl (3R,4R)-3,4-dihydroxy-4-pyrimidin-2-yl-piperidine-1-carboxylate |
| tert-butyl (3aR,7aR)-7a-(3-fluoro-2-pyridyl)-piperidine-3a,4,6,7-tetrahydro-[1,3]dioxolo[4,5-c]pyridine-5-carboxylate | tert-butyl (3R,4R)-3,4-dihydroxy-4-(3-fluoro-2-pyridyl)-piperidine-1-carboxylate |
| tert-butyl (3aR,7aR)-7a-(1-methylpyrazol-3-yl)-piperidine-3a,4,6,7-tetrahydro-[1,3]dioxolo[4,5-c]pyridine-5-carboxylate | tert-butyl (3R,4R)-3,4-dihydroxy-4-(1-methylpyrazol-3-yl)-piperidine-1-carboxylate |
| tert-butyl (3aR,7aR)-7a-(3-cyanophenyl)-3a,4,6,7-tetrahydro-[1,3]dioxolo[4,5-c]pyridine-5-carboxylate | tert-butyl (3R,4R)-3,4-dihydroxy-4-(3-cyanophenyl)-piperidine-1-carboxylate |
| tert-butyl (3aR,7aR)-7a-(2-methylthiazol-4-yl)-3a,4,6,7-tetrahydro-[1,3]dioxolo[4,5-c]pyridine-5-carboxylate | tert-butyl (3R,4R)-3,4-dihydroxy-4-(2-methylthiazol-4-yl)-piperidine-1-carboxylate |
| tert-butyl (3aR,7aR)-7a-thiazol-4-yl-3a,4,6,7-tetrahydro-[1,3]dioxolo[4,5-c]pyridine-5-carboxylate | tert-butyl (3R,4R)-3,4-dihydroxy-4-thiazol-4-yl-piperidine-1-carboxylate |
| tert-butyl (3aR,7aR)-7a-phenyl-3a,4,6,7-tetrahydro-[1,3]dioxolo[4,5-c]pyridine-5-carboxylate | tert-butyl (3R,4R)-3,4-dihydroxy-4-phenyl-piperidine-1-carboxylate |
| tert-butyl (3aR,7aR)-7a-(3-chlorophenyl)-3a,4,6,7-tetrahydro-[1,3]dioxolo[4,5-c]pyridine-5-carboxylate | tert-butyl (3R,4R)-3,4-dihydroxy-4-(3-chlorophenyl)-piperidine-1-carboxylate |

| Product | Precursor |
|---|---|
| tert-butyl (3aR,7aR)-7a-(2,3-difluorophenyl)-3a,4,6,7-tetrahydro-[1,3]dioxolo[4,5-c]pyridine-5-carboxylate | tert-butyl (3R,4R)-3,4-dihydroxy-4-(2,3-difluorophenyl)-piperidine-1-carboxylate |
| tert-butyl (3aR,7aR)-7a-(2,5-difluorophenyl)-3a,4,6,7-tetrahydro-[1,3]dioxolo[4,5-c]pyridine-5-carboxylate | tert-butyl (3R,4R)-3,4-dihydroxy-4-(2,5-difluorophenyl)-piperidine-1-carboxylate |
| tert-butyl (3aR,7aR)-7a-(trifluoromethyl)-3a,4,6,7-tetrahydro-[1,3]dioxolo[4,5-c]pyridine-5-carboxylate | tert-butyl (3R,4R)-3,4-dihydroxy-6-(trifluoromethyl)-piperidine-1-carboxylate |
| tert-butyl (3aR,7aR)-7a-[4-(trifluoromethyl)-2-pyridyl]-3a,4,6,7-tetrahydro-[1,3]dioxolo[4,5-c]pyridine-5-carboxylate | tert-butyl (3R,4R)-3,4-dihydroxy-4-[4-(trifluoromethyl)-2-pyridyl]-piperidine-1-carboxylate |
| tert-butyl (3aR,7aR)-7a-(6-chloro-4-methoxy-2-pyridyl)-3a,4,6,7-tetrahydro-[1,3]dioxolo[4,5-c]pyridine-5-carboxylate | tert-butyl (3R,4R)-3,4-dihydroxy-4-(6-chloro-4-methoxy-2-pyridyl)-piperidine-1-carboxylate |
| (3aR,7aR)-tert-butyl 7a-(6-bromopyridin-2-yl)tetrahydro-[1,3]dioxolo[4,5-c]pyridine-5(6H)-carboxylate | tert-butyl (3R,4R)-4-(6-bromopyridin-2-yl)-3,4-dihydroxypiperidine-1-carboxylate |

Step 4: (3aR,7aR)-7a-phenyl-4,5,6,7-tetrahydro-3aH-[1,3]dioxolo[4,5-c]pyridine

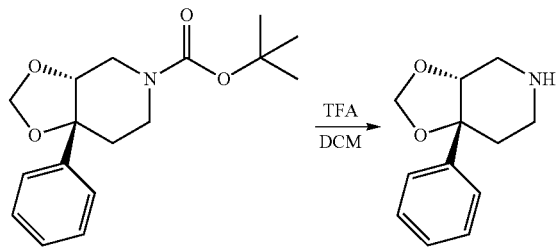 [SMILES: CC(C)(C)OC(=O)N1CC[C@]2(c3ccccc3)OCO[C@@H]2C1 ; c1ccc([C@]23CCNC[C@H]2OCO3)cc1]

A solution of tert-butyl(3aR,7aR)-7a-phenyl-3a,4,6,7-tetrahydro-[1,3]dioxolo[4,5-c]pyridine-5-carboxylate (980 mg, 3.2 mmol) in DCM (8 mL) was treated with 2,2,2-trifluoroacetic acid (2.5 mL). The reaction mixture was stirred at rt for 1.5 h. The reaction mixture was diluted with DCM (40 mL) and quenched by the addition of aqueous 1 N NaOH (50 mL). The organic layer was separated, dried over sodium sulfate, filtered and concentrated under reduced pressure to afford (3aR,7aR)-7a-phenyl-4,5,6,7-tetrahydro-3aH-[1,3]dioxolo[4,5-c]pyridine (608 mg, 93.2%) as a pale brown oil that solidified upon standing. $^1$H NMR (400 MHz, CDCl$_3$) δ 7.45 (dt, J=3.0, 1.8 Hz, 2H), 7.42-7.33 (m, 2H), 7.33-7.27 (m, 1H), 5.28 (d, J=0.9 Hz, 1H), 5.05 (d, J=0.8 Hz, 1H), 4.20 (dd, J=5.7, 4.8 Hz, 1H), 3.16 (dd, J=13.4, 4.6 Hz, 1H), 3.07-2.94 (m, 2H), 2.83 (dt, J=12.6, 5.3 Hz, 1H), 2.15-1.90 (m, 2H), 1.78 (s, 1H). ESI-MS m/z calc. 205.1. found 206.4 (M+1)$^+$; Retention time: 0.45 min (3 min run).

The following compounds were prepared using the procedure reported above:

| Product | Precursor |
|---|---|
| (3aR,7aR)-7a-(3,5-difluorophenyl)-3a,4,6,7-tetrahydro-[1,3]dioxolo[4,5-c]pyridine | tert-butyl (3aR,7aR)-7a-(3,5-difluorophenyl)-3a,4,6,7-tetrahydro-[1,3]dioxolo[4,5-c]pyridine-5-carboxylate |
| (3aR,7aR)-7a-(3-fluorophenyl)-3a,4,6,7-tetrahydro-[1,3]dioxolo[4,5-c]pyridine | tert-butyl (3aR,7aR)-7a-(3-fluorophenyl)-3a,4,6,7-tetrahydro-[1,3]dioxolo[4,5-c]pyridine-5-carboxylate |
| (3aR,7aR)-7a-(4-fluorophenyl)-3a,4,6,7-tetrahydro-[1,3]dioxolo[4,5-c]pyridine | tert-butyl (3aR,7aR)-7a-(4-fluorophenyl)-3a,4,6,7-tetrahydro-[1,3]dioxolo[4,5-c]pyridine-5-carboxylate |
| (3aR,7aR)-7a-(6-bromo-2-pyridyl)-3a,4,6,7-tetrahydro-[1,3]dioxolo[4,5-c]pyridine | tert-butyl (3aR,7aR)-7a-(6-bromo-2-pyridyl)-3a,4,6,7-tetrahydro-[1,3]dioxolo[4,5-c]pyridine-5-carboxylate |
| (3aR,7aR)-7a-(2,5-difluorophenyl)-3a,4,6,7-tetrahydro-[1,3]dioxolo[4,5-c]pyridine | tert-butyl (3aR,7aR)-7a-(2,5-difluorophenyl)-3a,4,6,7-tetrahydro-[1,3]dioxolo[4,5-c]pyridine-5-carboxylate |
| (3aR,7aR)-7a-(3-chloro-2-pyridyl)-3a,4,6,7-tetrahydro-[1,3]dioxolo[4,5-c]pyridine | tert-butyl (3aR,7aR)-7a-(3-chloro-2-pyridyl)-3a,4,6,7-tetrahydro-[1,3]dioxolo[4,5-c]pyridine-5-carboxylate |
| (3aR,7aR)-7a-(3-methoxy-1-oxido-pyridin-1-ium-2-yl)-3a,4,6,7-tetrahydro-[1,3]dioxolo[4,5-c]pyridine | tert-butyl (3aR,7aR)-7a-(3-methoxy-1-oxido-pyridin-1-ium-2-yl)-3a,4,6,7-tetrahydro-[1,3]dioxolo[4,5-c]pyridine-5-carboxylate |
| (3aR,7aR)-7a-4-pyrimidin-2-yl-piperidine-3a,4,6,7-tetrahydro-[1,3]dioxolo[4,5-c]pyridine | tert-butyl (3aR,7aR)-7a-4-pyrimidin-2-yl-piperidine-3a,4,6,7-tetrahydro-[1,3]dioxolo[4,5-c]pyridine-5-carboxylate |
| (3aR,7aR)-7a-(3-fluoro-2-pyridyl)-piperidine-3a,4,6,7-tetrahydro-[1,3]dioxolo[4,5-c]pyridine | tert-butyl (3aR,7aR)-7a-(3-fluoro-2-pyridyl)-piperidine-3a,4,6,7-tetrahydro-[1,3]dioxolo[4,5-c]pyridine-5-carboxylate |
| (3aR,7aR)-7a-(1-methylpyrazol-3-yl)-piperidine-3a,4,6,7-tetrahydro- | tert-butyl (3aR,7aR)-7a-(1-methylpyrazol-3-yl)-piperidine-3a,4,6,7-tetrahydro- |

| Product | Precursor |
| --- | --- |
| [1,3]dioxolo[4,5-c]pyridine (3aR,7aR)-7a-(3-cyanophenyl)-3a,4,6,7-tetrahydro-[1,3]dioxolo[4,5-c]pyridine | [1,3]dioxolo[4,5-c]pyridine-5-carboxylate tert-butyl (3aR,7aR)-7a-(3-cyanophenyl)-3a,4,6,7-tetrahydro-[1,3]dioxolo[4,5-c]pyridine-5-carboxylate |
| (3aR,7aR)-7a-(2-methylthiazol-4-yl)-3a,4,6,7-tetrahydro-[1,3]dioxolo[4,5-c]pyridine | tert-butyl (3aR,7aR)-7a-(2-methylthiazol-4-yl)-3a,4,6,7-tetrahydro-[1,3]dioxolo[4,5-c]pyridine-5-carboxylate |
| (3aR,7aR)-7a-thiazol-4-yl-3a,4,6,7-tetrahydro-[1,3]dioxolo[4,5-c]pyridine | tert-butyl (3aR,7aR)-7a-thiazol-4-yl-3a,4,6,7-tetrahydro-[1,3]dioxolo[4,5-c]pyridine-5-carboxylate |
| (3aR,7aR)-7a-phenyl-4,5,6,7-tetrahydro-3aH-[1,3]dioxolo[4,5-c]pyridine | tert-butyl (3aR,7aR)-7a-phenyl-3a,4,6,7-tetrahydro-[1,3]dioxolo[4,5-c]pyridine-5-carboxylate |
| (3aR,7aR)-7a-(3-chlorophenyl)-3a,4,6,7-tetrahydro-[1,3]dioxolo[4,5-c]pyridine | tert-butyl (3aR,7aR)-7a-(3-chlorophenyl)-3a,4,6,7-tetrahydro-[1,3]dioxolo[4,5-c]pyridine-5-carboxylate |
| (3aR,7aR)-7a-(2,3-difluorophenyl)-3a,4,6,7-tetrahydro-[1,3]dioxolo[4,5-c]pyridine | tert-butyl (3aR,7aR)-7a-(2,3-difluorophenyl)-3a,4,6,7-tetrahydro-[1,3]dioxolo[4,5-c]pyridine-5-carboxylate |
| (3aR,7aR)-7a-(2,5-difluorophenyl)-3a,4,6,7-tetrahydro-[1,3]dioxolo[4,5-c]pyridine | tert-butyl (3aR,7aR)-7a-(2,5-difluorophenyl)-3a,4,6,7-tetrahydro-[1,3]dioxolo[4,5-c]pyridine-5-carboxylate |
| (3aR,7aR)-7a-(trifluoromethyl)-3a,4,6,7-tetrahydro-[1,3]dioxolo[4,5-c]pyridine | tert-butyl (3aR,7aR)-7a-(trifluoromethyl)-3a,4,6,7-tetrahydro-[1,3]dioxolo[4,5-c]pyridine-5-carboxylate |
| (3aR,7aR)-7a--[4-(trifluoromethyl)-2-pyridyl]-3a,4,6,7-tetrahydro-[1,3]dioxolo[4,5-c]pyridine | tert-butyl (3aR,7aR)-7a--[4-(trifluoromethyl)-2-pyridyl]-3a,4,6,7-tetrahydro-[1,3]dioxolo[4,5-c]pyridine-5-carboxylate |
| (3aR,7aR)-7a-(6-chloro-4-methoxy-2-pyridyl)-3a,4,6,7-tetrahydro-[1,3]dioxolo[4,5-c]pyridine | tert-butyl (3aR,7aR)-7a-(6-chloro-4-methoxy-2-pyridyl)-3a,4,6,7-tetrahydro-[1,3]dioxolo[4,5-c]pyridine-5-carboxylate |
| (3aR,7aR)-7a-(pyridin-2-yl)hexahydro-[1,3]dioxolo[4,5-c]pyridine | tert-butyl (3aR,7aR)-7a-(pyridin-2-yl)-3a,4,6,7-tetrahydro-[1,3]dioxolo[4,5-c]pyridine-5-carboxylate |

6-(4-fluorophenyl)-3-azabicyclo[4.1.0]heptane

Step 1: 6-phenyl-3-azabicyclo[4.1.0]heptane

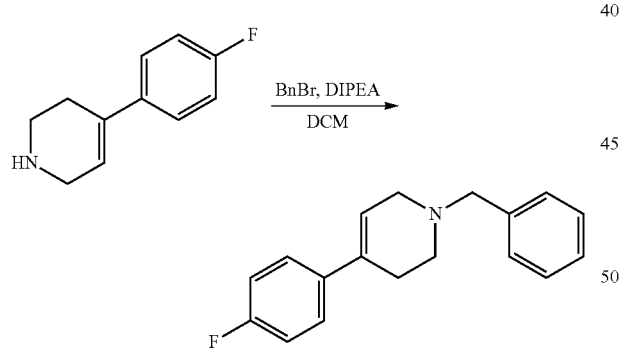

4-(4-fluorophenyl)-1,2,3,6-tetrahydropyridine (2.1 g, 11.6 mmol was dissolved in DMF (15 mL), and DIPEA (1.5 g, 2.0 mL, 11.6 mmol) was added. A solution of benzylbromide (2.0 g, 1.4 mL, 11.6 mmol) in DMF (5 mL) was added dropwise. After 5 min of stirring at rt, the solvent was removed under reduced pressure. The remaining oil was dissolved in ethyl acetate (75 mL) and washed with saturated aqueous NaCl (1×75 mL). The organic layer was dried over sodium sulfate, filtered and concentrated under reduced pressure. The crude product was purified by silica gel column chromatography: 40 gram silica gel column, 0-15% methanol/DCM gradient over 30 min with 1% aqueous ammonium hydroxide to afford 1-benzyl-4-(4-fluorophenyl)-3,6-dihydro-2H-pyridine (3.1 g, 100%) was obtained as a brownish-red oil. $^1$H NMR (400 MHz, CDCl$_3$) δ 7.40-7.31 (m, 6H), 7.27 (ddd, J=7.5, 4.0, 1.7 Hz, 1H), 7.03-6.94 (m, 2H), 6.00 (dt, J=5.0, 1.7 Hz, 1H), 3.64 (s, 2H), 3.16 (dd, J=6.0, 2.9 Hz, 2H), 2.71 (t, J=5.7 Hz, 2H), 2.58-2.48 (m, 2H). ESI-MS m/z calc. 267.1. found 268.4 (M+1)$^+$; Retention time: 1.09 min (3 min run).

The following compounds were prepared using the procedure reported above:

| Product | Precursor |
| --- | --- |
| 1-benzyl-4-phenyl-3,6-dihydro-2H-pyridine | 4-phenyl-1,2,3,6-tetrahydropyridine |
| 1-benzyl-4-(4-fluorophenyl)-3,6-dihydro-2H-pyridine | 4-(4-fluorophenyl)-1,2,3,6-tetrahydropyridine |

Step 2: 3-benzyl-6-phenyl-3-azabicyclo[4.1.0]heptane

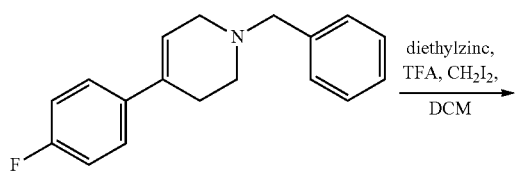

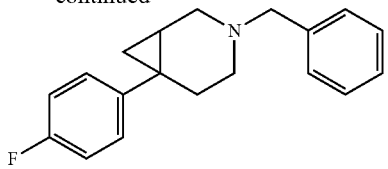

A solution of diethylzinc (39.7 mL of 15% w/v, 48.1 mmol) in toluene was added to anhydrous DCM (25 mL) at 0° C. TFA (3.7 mL, 48.1 mmol) in DCM (12 mL) was added, and the resulting slightly gelatinous mixture was allowed to stir for 20 min at 0° C. Diiodomethane (4.1 mL, 50.5 mmol) in DCM (12 mL) was slowly added dropwise and the reaction mixture was stirred at 0° C. for 20 min forming white slurry. A solution of 1-benzyl-4-(4-fluorophenyl)-3,6-dihydro-2H-pyridine (3.2 g, 12.0 mmol) in DCM (12 mL) was added at 0° C., and the reaction mixture was allowed to stir at rt for 45 min. The reaction mixture was carefully quenched with the addition of saturated aqueous ammonium chloride solution (125 mL). The organic layer was then washed with 1 N HCl (1×100 mL) and saturated aqueous sodium bicarbonate solution (1×100 mL). The organic layer was dried over sodium sulfate, filtered and concentrated under reduced pressure. The remaining oil was purified by silica gel column chromatography: 40 gram silica gel column, 0-30% ethyl acetate/DCM gradient over 25 min; product eluted at 10% while the quaternary side-product eluted at 25%. Pure fractions were combined and concentrated to provide 3-benzyl-6-(4-fluorophenyl)-3-azabicyclo[4.1.0]heptane (1.5 g, 44%) as an orange oil. $^1$H NMR (400 MHz, CDCl$_3$) δ 7.37-7.29 (m, 4H), 7.27-7.19 (m, 3H), 6.98-6.90 (m, 2H), 3.54-3.41 (m, 2H), 2.85-2.71 (m, 2H), 2.34-2.18 (m, 2H), 2.09 (tdd, J=13.5, 9.0, 6.6 Hz, 2H), 1.34 (dtd, J=8.9, 5.6, 2.0 Hz, 1H), 0.92 (dt, J=9.1, 4.1 Hz, 2H). ESI-MS m/z calc. 281.2. found 282.5 (M+1)$^+$; Retention time: 1.13 min (3 min run).

The following compounds were prepared using the procedure reported above:

| Product | Precursor |
| --- | --- |
| 3-benzyl-6-phenyl-3-azabicyclo[4.1.0]heptane | 1-benzyl-4-phenyl-3,6-dihydro-2H-pyridine |
| 3-benzyl-(4-fluorophenyl)-3-azabicyclo[4.1.0]heptane | 1-benzyl-4-(4-fluorophenyl)-3,6-dihydro-2H-pyridine |

Step 3: 6-(4-fluorophenyl)-3-azabicyclo[4.1.0]heptane

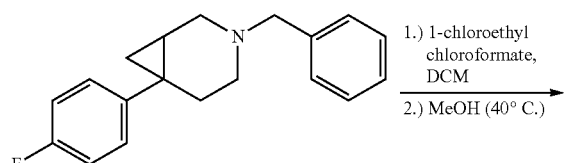

1.) 1-chloroethyl chloroformate, DCM
2.) MeOH (40° C.)

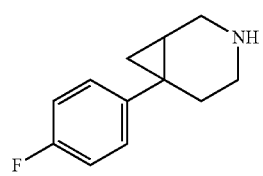

A solution of 1-chloroethyl chloroformate (3.8 g, 2.8 mL, 26.3 mmol) in DCM (3 mL) at 0° C. was treated dropwise with a solution of 3-benzyl-6-(4-fluorophenyl)-3-azabicyclo[4.1.0]heptane (1.5 g, 5.3 mmol) in DCM (6 mL). The reaction mixture was allowed to stir at rt for 30 min. Methanol (25 mL) was added to the solution, and it was stirred at 40° C. for 30 min. The volatiles were removed under reduced pressure, and the remaining solid was suspended in aqueous 1 N HCl (75 mL). The suspension was extracted with ethyl acetate (1×75 mL). The aqueous layer was adjusted to pH 12 with the addition of aqueous 1 N NaOH (100 mL). The resulting cloudy white suspension was extracted with ethyl acetate (2×75 mL). The final organic layers were combined, dried over sodium sulfate, filtered and concentrated under reduced pressure to provide 6-(4-fluorophenyl)-3-azabicyclo[4.1.0]heptane (0.8 g, 79%) as a clear yellow oil that crystallized upon standing. $^1$H NMR (400 MHz, CDCl$_3$) δ 7.26-7.19 (m, 2H), 6.99-6.91 (m, 2H), 3.36 (dd, J=12.8, 5.7 Hz, 1H), 3.08 (d, J=12.7 Hz, 1H), 2.75-2.58 (m, 2H), 2.02 (ddd, J=12.8, 6.3, 4.2 Hz, 1H), 1.96-1.86 (m, 1H), 1.42-1.20 (m, 2H), 0.95 (dd, J=9.3, 4.4 Hz, 1H), 0.81 (dd, J=5.5, 4.8 Hz, 1H). ESI-MS m/z calc. 191.1. found 192.4 (M+1)$^+$; Retention time: 0.58 min (3 min run).

The following compounds were prepared using the procedure reported above:

| Product | Precursor |
| --- | --- |
| 6-(4-fluorophenyl)-3-azabicyclo[4.1.0]heptane | 3-benzyl-6-phenyl-3-azabicyclo[4.1.0]heptane |
| 6-phenyl-3-azabicyclo[4.1.0]heptane | 3-benzyl-(4-fluorophenyl)-3-azabicyclo[4.1.0]heptane |
| 2-[(2S,4S)-2-methyl-4-(trideuteriomethoxy)-4-piperidyl]thiazole | (2S,4S)-tert-butyl 4-methoxy-2-trideutero-methyl-4-(thiazol-2-yl)piperidine-1-carboxylate |

(4-isopropoxy-3-methylphenyl)(6-phenyl-7-oxa-3-azabicyclo[4.2.0]octan-3-yl)-methanone Step 1: tert-butyl 3-[[tert-butyl(dimethyl)silyl]oxymethyl]-4-oxo-piperidine-1-carboxylate

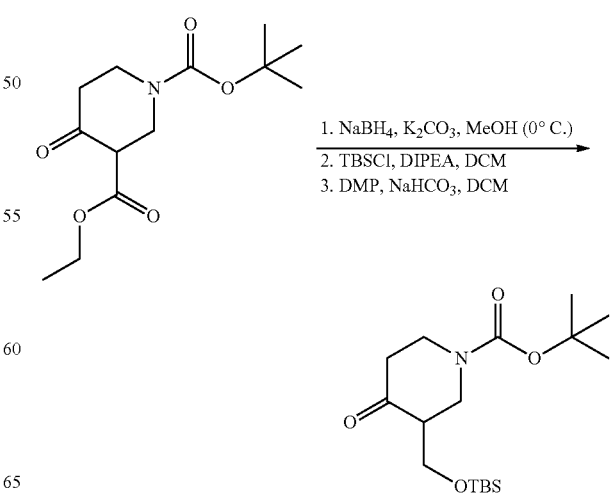

1. NaBH$_4$, K$_2$CO$_3$, MeOH (0° C.)
2. TBSCl, DIPEA, DCM
3. DMP, NaHCO$_3$, DCM

To a solution of O1-tert-butyl O3-ethyl 4-oxopiperidine-1,3-dicarboxylate (5 g, 18.4 mmol) in methanol (50 mL) at 0° C. was added sodium borohydride (1.74 g, 46.1 mmol) portionwise over 15 min. The reaction mixture was stirred at 0° C. for 30 min and was concentrated under reduced pressure. The resulting residue was diluted with water and adjusted to pH 3 with 1N HCl. The mixture was extracted with ethyl acetate (3×) and the combined organic layers were dried over sodium sulfate and concentrated under reduced pressure to afford tert-butyl 4-hydroxy-3-(hydroxymethyl)piperidine-1-carboxylate (4.1 g) as a white solid.

In a 250 mL round bottom flask containing tert-butyl 4-hydroxy-3-(hydroxymethyl)piperidine-1-carboxylate (2.0 g, 8.6 mmol) was added dichloromethane (50.0 mL) followed by triethylamine (2.8 mL, 20 mmol). tert-Butyldimethylsilyl chloride (1.5 g, 10.2 mmol) was added portionwise and the reaction mixture was allowed to stir at rt ovn. The reaction mixture was almost complete by 1 cms. The reaction mixture was quenched with saturated aqueous ammonium chloride and saturated aqueous NaCl and extracted with dichloromethane. The organic layer was separated and dried over sodium sulfate and then concentrated under reduced pressure. The crude product was used in the next step without purification.

To a 250 mL round bottom flask containing crude tert-butyl 3-[[tert-butyl(dimethyl)silyl]oxymethyl]-4-hydroxy-piperidine-1-carboxylate (2.4 g) was added DCM (24 mL) and sodium bicarbonate (2.0 g, 20.4 mmol). The reaction mixture was cooled to 0° C. for 5 min and Dess-Martin periodane (3.6 g, 8.5 mmol) was added. The reaction mixture was stirred for 3 h while warming to rt. The reaction mixture was filtered and concentrated under reduced pressure to dryness. The crude product was purified via silica gel chromatography (0-50%) DCM:ethyl acetate to provide tert-butyl 3-[[tert-butyl(dimethyl)silyl]oxymethyl]-4-oxo-piperidine-1-carboxylate (1.7 g, 71%) as a clear yellow oil. ESI-MS m/z calc. 343.5. found 344.4 (M+1)⁺; Retention time: 2.47 min (3 min run).

Step 2: tert-butyl 4-hydroxy-3-(methylsulfonyloxymethyl)-4-phenyl-piperidine-1-carboxylate

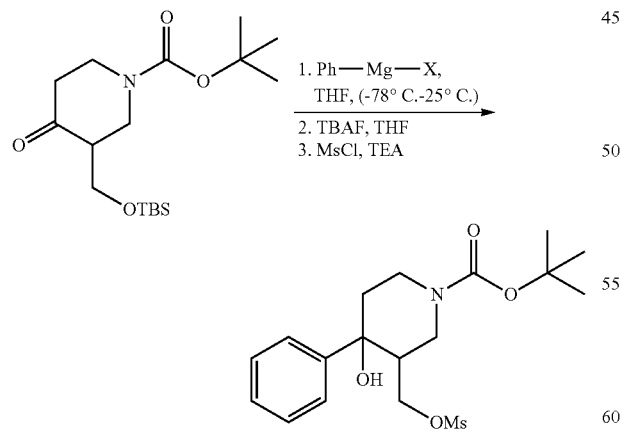

To a 100 mL round bottom flask was added tert-butyl 3-[[tert-butyl(dimethyl)silyl]oxymethyl]-4-oxo-piperidine-1-carboxylate (1.0 g, 2.9 mmol) and THF (9 mL). The mixture was cooled to −78° C. and phenyl magnesium chloride (1.46 ml, 2 M, 2.9 mmol) was added dropwise and the reaction mixture was allowed to warm to rt over 1 h. The reaction mixture was quenched with saturated aqueous ammonium chloride and extracted with ethyl acetate (3×). The organic layers were separated, dried over sodium sulfate, and concentrated under reduced pressure to provide tert-butyl 3-[[tert-butyl(dimethyl)silyl]oxymethyl]-4-hydroxy-4-phenyl-piperidine-1-carboxylate as a clear colorless oil which was diluted with THF (9 mL). The mixture was treated with tetra-n-butylammonium fluoride (4.4 mL of 1 M, 4.4 mmol) and the reaction mixture was allowed to stir at rt for 10 min. The reaction mixture was quenched with water and extracted with ethyl acetate (3×). The organic layers were separated, dried over sodium sulfate, and concentrated under reduced pressure to afford tert-butyl 4-hydroxy-3-(hydroxymethyl)-4-phenyl-piperidine-1-carboxylate which was dissolved in dichloromethane (9 mL) and treated with triethylamine (0.81 mL, 5.8 mmol), and methanesulfonyl chloride (0.23 mL, 2.9 mmol). The reaction mixture was quenched with water and extracted with dichloromethane (3×). The organic layers were dried over sodium sulfate and concentrated under reduced pressure. The crude reaction mixture was purified via silica gel chromatography 0%-25% ethyl acetate in dichloromethane to afford tert-butyl 4-hydroxy-3-(methylsulfonyloxymethyl)-4-phenyl-piperidine-1-carboxylate (0.7 g, 63%) as a pale yellow oil. ESI-MS m/z calc. 385.5. found 386.3 (M+1)⁺; Retention time: 1.80 min (3 min run).

Step 3: (4-hydroxy-4-phenyl-3-piperidyl)methyl methanesulfonate

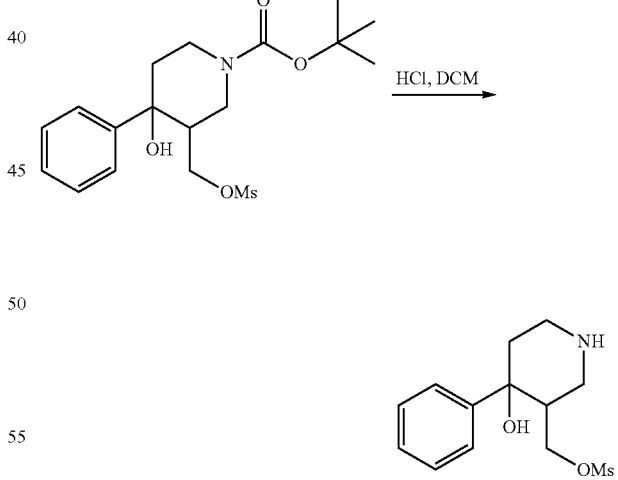

To a 100 mL round bottom flask was added, dichloromethane (10 mL), and HCl (0.45 mL of 4 M, 1.83 mmol) and the reaction mixture was allowed to stir at rt for 4 h. The reaction mixture was concentrated under reduced pressure to afford (4-hydroxy-4-phenyl-3-piperidyl)methyl methanesulfonate hydrochloride (596 mg) which used in the next reaction without purification. ESI-MS m/z calc. 285.1. found 286.3 (M+1)⁺; Retention time: 0.92 min (3 min run).

Step 4: (4-hydroxy-1-(4-isopropoxy-3-methylbenzoyl)-4-phenylpiperidin-3-yl)methyl methanesulfonate

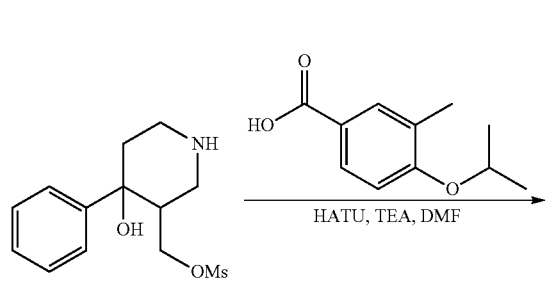

To a vial was added the 4-isopropoxy-3-methyl-benzoic acid (39 mg, 0.2 mmol), HATU (76 mg, 0.2 mmol), DMF (2 mL), and triethylamine (0.7 mL, 5 mmol) and the reaction mixture was allowed to stir for 10 min at rt. A solution of (4-hydroxy-1-(4-isopropoxy-3-methylbenzoyl)-4-phenylpiperidin-3-yl)methyl methanesulfonate (57 mg, 0.2 mmol) dissolved in DMF (1 mL) was added and the reaction mixture was allowed to stir for 15 min. The reaction was quenched with saturated aqueous NaCl and extracted with ethyl acetate. The ethyl acetate layer was further rinsed with saturated aqueous NaCl (3×) to remove any DMF. The organic layers were dried over sodium sulfate, concentrated under reduced pressure, and used in the next reaction without further purification. ESI-MS m/z calc. 461.6. found 462.1 (M+1)$^+$; Retention time: 1.93 min (3 min run).

The following compounds were prepared using the procedure reported above:

Step 5: (4-isopropoxy-3-methylphenyl)(6-phenyl-7-oxa-3-azabicyclo[4.2.0]octan-3-yl)-methanone

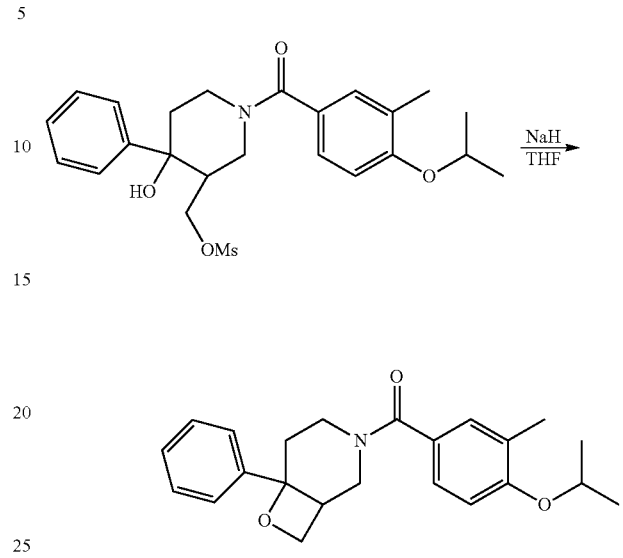

A vial containing the (4-hydroxy-1-(4-isopropoxy-3-methylbenzoyl)-4-phenylpiperidin-3-yl)methyl methanesulfonate (92 mg, 0.2 mmol) in THF (1.5 mL) was treated with NaH in mineral oil (60%, 8 mg, 0.2 mmol). The reaction mixture was stirred at rt for 1 h, filtered and purified by reverse phase HPLC (1-99%) ACN:H$_2$O with no modifier) to afford (4-isopropoxy-3-methylphenyl)(6-phenyl-7-oxa-3-azabicyclo[4.2.0]octan-3-yl)-methanone (13 mg, 18%). $^1$H NMR (400 MHz, MeOD) δ 7.47-7.22 (m, 7H), 6.99 (t, J=9.1 Hz, 1H), 4.72-4.54 (m, 2H), 4.46-4.03 (m, 2H), 3.99-3.74 (m, 2H), 3.66 (dd, J=25.7, 12.9 Hz, 1H), 3.09 (t, J=15.9 Hz, 1H), 2.57-2.25 (m, 1H), 2.21 (d, J=7.8 Hz, 3H), 1.34 (d, J=5.8 Hz, 6H). ESI-MS m/z calc. 365.5. found 366.5 (M+1)$^+$; Retention time: 1.95 min (3 min run).

The following compounds were prepared using the procedure reported above:

| Product | Acid | Amine |
| --- | --- | --- |
| (4-hydroxy-1-(4-isopropoxy-3-methylbenzoyl)-4-phenylpiperidin-3-yl)methyl methanesulfonate | 4-isopropoxy-3-methyl-benzoic acid | (4-hydroxy-4-phenyl-3-piperidyl)methyl methanesulfonate |
| (4-hydroxy-1-(5-isopropoxy-6-methyl-pyridine-2-carboxyl)-4-phenylpiperidin-3-yl)methyl methanesulfonate | 5-isopropoxy-6-methyl-pyridine-2-carboxylic acid | (4-hydroxy-4-phenyl-3-piperidyl)methyl methanesulfonate |
| (4-hydroxy-1-(3-methoxy-4-(2-(trifluoromethoxy)ethoxy)benzoyl)-4-phenylpiperidin-3-yl)methyl methanesulfonate | 3-methoxy-4-(2-(trifluoromethoxy)ethoxy)benzoic acid | (4-hydroxy-4-phenyl-3-piperidyl)methyl methanesulfonate |
| (4-hydroxy-1-(2-fluoro-2-methyl-propoxy)-3-methoxy-benzoyl)-4-phenylpiperidin-3-yl)methyl methanesulfonate | 4-(2-fluoro-2-methyl-propoxy)-3-methoxy-benzoic acid | (4-hydroxy-4-phenyl-3-piperidyl)methyl methanesulfonate |
| (4-hydroxy-1-(quinoline-8-carboxyl)-4-phenylpiperidin-3-yl)methyl methanesulfonate | quinoline-8-carboxylic acid | (4-hydroxy-4-phenyl-3-piperidyl)methyl methanesulfonate |
| (4-hydroxy-1-(3-methoxy-4-[(3R)-tetrahydrofuran-3-yl]oxy-benzoyl)-4-phenylpiperidin-3-yl)methyl methanesulfonate | 3-methoxy-4-[(3R)-tetrahydrofuran-3-yl]oxy-benzoic acid | (4-hydroxy-4-phenyl-3-piperidyl)methyl methanesulfonate |

| Product | Precursor |
|---|---|
| (4-isopropoxy-3-methylphenyl)(6-phenyl-7-oxa-3-azabicyclo[4.2.0]octan-3-yl)-methanone | (4-hydroxy-1-(4-isopropoxy-3-methylbenzoyl)-4-phenylpiperidin-3-yl)methyl methanesulfonate |
| (5-isopropoxy-6-methyl-pyridine-2-carboxyl)-(6-phenyl-7-oxa-3-azabicyclo[4.2.0]octan-3-yl)-methanone | (4-hydroxy-1-(5-isopropoxy-6-methyl-pyridine-2-carboxyl)-4-phenylpiperidin-3-yl)methyl methanesulfonate |
| (3-methoxy-4-(2-(trifluoromethoxy)ethoxy)benzoyl)-(6-phenyl-7-oxa-3-azabicyclo[4.2.0]-octan-3-yl)-methanone | (4-hydroxy-1-(3-methoxy-4-(2-(trifluoromethoxy)ethoxy)benzoyl)-4-phenylpiperidin-3-yl)methyl methanesulfonate |
| (4-(2-fluoro-2-methyl-propoxy)-3-methoxy-benzoyl)-(6-phenyl-7-oxa-3-azabicyclo[4.2.0]octan-3-yl)-methanone | (4-hydroxy-1-(2-fluoro-2-methyl-propoxy)-3-methoxy-benzoyl)-4-phenylpiperidin-3-yl)methyl methanesulfonate |
| quinoline-8-carboxyl)-(6-phenyl-7-oxa-3-azabicyclo[4.2.0]octan-3-yl)-methanone | (4-hydroxy-1-(quinoline-8-carboxyl)-4-phenylpiperidin-3-yl)methylmethanesulfonate |
| 3-methoxy-4-[(3R)-tetrahydrofuran-3-yl]oxy-benzoyl)-(6-phenyl-7-oxa-3-azabicyclo[4.2.0]octan-3-yl)-methanone | (4-hydroxy-1-(3-methoxy-4-[(3R)-tetrahydrofuran-3-yl]oxy-benzoyl)-4-phenylpiperidin-3-yl)methyl methanesulfonate |

(3aR,7aR)-tert-butyl 7a-(pyridin-2-yl)tetrahydro-[1,3]dioxolo[4,5-c]pyridine-5(6H)-carboxylate

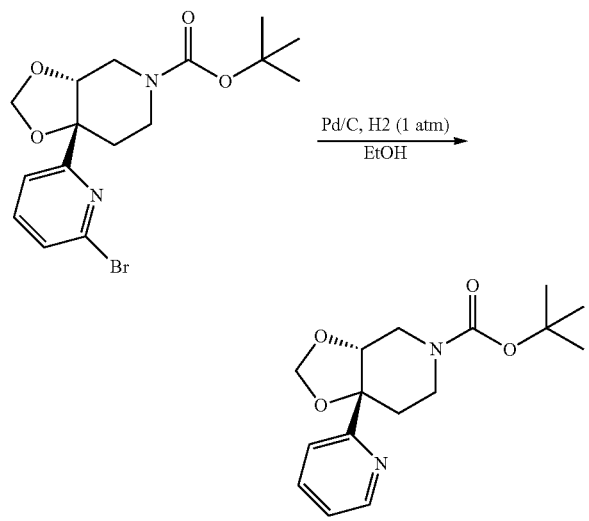

A solution of tert-butyl (3 aR,7aR)-7a-(6-bromo-2-pyridyl)-3a,4,6,7-tetrahydro-[1,3]dioxolo[4,5-c]pyridine-5-carboxylate (342 mg, 0.88 mmol) was dissolved in absolute ethanol (10 mL) and stirred under nitrogen before the addition of 10% palladium on carbon (473 mg, 0.44 mmol). The reaction mixture was evacuated and put under hydrogen gas (1 atm) for 2 h. The reaction mixture was filtered through a pad of celite, rinsed with DCM, and concentrated under reduced pressure to provide tert-butyl(3aR,7aR)-7a-(2-pyridyl)-3a,4,6,7-tetrahydro-[1,3]dioxolo[4,5-c]pyridine-5-carboxylate (266 mg, 99%) as a clear yellow-brown oil. $^1$H NMR (400 MHz, CDCl$_3$) δ 8.99 (s, 1H), 8.44 (s, 1H), 8.09 (s, 1H), 7.91 (s, 1H), 5.35 (s, 1H), 5.13 (s, 1H), 4.72 (s, 1H), 4.23 (s, 1H), 4.07 (d, J=15.1 Hz, 1H), 3.60 (s, 2H), 2.80 (s, 1H), 2.20 (d, J=14.4 Hz, 1H), 1.49 (s, 9H). ESI-MS m/z calc. 306.2. found 307.5 (M+1)$^+$; Retention time: 1.1 min, (3 min run).

[(3aR,7aR)-7a-(3-fluoro-2-pyridyl)-3a,4,6,7-tetrahydro-[1,3]dioxolo[4,5-c]pyridin-5-yl]-(3-chloro-4-fluoro-phenyl)methanone

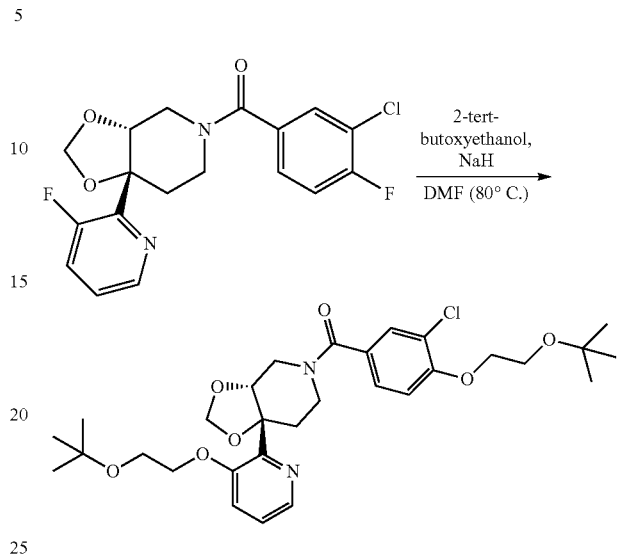

In a vial, 2-tert-butoxyethanol (155 mg, 1.31 mmol) was dissolved in DMF (500 µL). NaH (52 mg, 1.31 mmol) (60% oil dispersion) was added in small portions and the suspension was stirred at rt for 25 min. [(3aR,7aR)-7a-(3-fluoro-2-pyridyl)-3a,4,6,7-tetrahydro-[1,3]dioxolo[4,5-c]pyridin-5-yl]-(3-chloro-4-fluoro-phenyl)methanone (50 mg, 0.13 mmol) as a solution in DMF (100 µL) was added and the reaction mixture was stirred at 80° C. for 1 h. The reaction mixture was quenched by the addition of water and the mixture was extracted with DCM (3×). The combined extracts were dried over sodium sulfate and the volatiles were removed under reduced pressure. The material was dissolved in DMF (1 mL) and purified by preparative HPLC using HCl as a modifier. Evaporation of the volatiles provided [(3aR,7aR)-7a-[3-(2-tert-butoxyethoxy)-2-pyridyl]-3a,4,6,7-tetrahydro-[1,3]dioxolo[4,5-c]pyridin-5-yl]-[4-(2-tert-butoxyethoxy)-3-chloro-phenyl]methanone (38 mg, 46.5%) as a colorless glass. ESI-MS m/z calc. 576.3. found 577.0 (M+1)$^+$; Retention time: 1.48 min (3 min run).

7a-(pyridin-2-yl)octahydrofuro[3,2-c]pyridine

Step 1: benzyl 3-allyl-4-oxo-piperidine-1-carboxylate

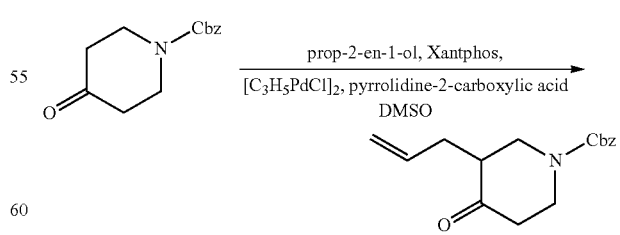

A mixture of benzyl 4-oxopiperidine-1-carboxylate (14.0 g, 60.0 mmol), prop-2-en-1-ol (3.4 mL, 50 mmol), pyrrolidine-2-carboxylic acid (1.7 g, 15.0 mmol) and (5-diphenylphosphinyl-9,9-dimethyl-xanthen-4-yl)-diphenyl-phosphane (1.45 g, 2.5 mmol) in DMSO (100 mL) was purged with nitrogen for 5 min. The mixture was treated with 1,3-diallyl-dichloro-dipalladacyclobutane (457 mg, 1.25 mmol) and heated at 75° C. for 72 h. The reaction mixture was cooled to rt and filtered through celite (ethyl acetate). The filtrate was repartitioned between ethyl acetate and water. The aqueous layer was extracted with ethyl acetate (2×). The combined organic layers were washed with water (3×), dried over MgSO₄, filtered and concentrated to dryness. The crude material was purified by column chromatography (0-10% ethyl acetate-hexanes) to provide benzyl 3-allyl-4-oxo-piperidine-1-carboxylate (11.5 g, 84.1%). ESI-MS m/z calc. 273.3. found 274.5 (M+1)⁺; Retention time: 1.72 min (3 min run).

Step 2: benzyl 6-(2-hydroxyethyl)-1,4-dioxa-8-azaspiro[4.5]decane-8-carboxylate

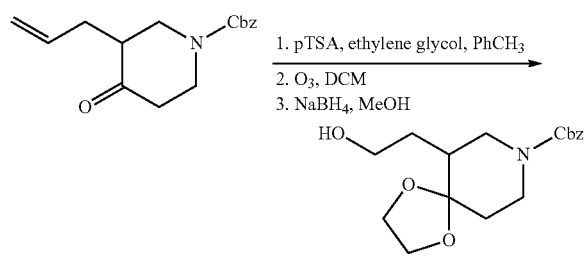

To a solution of benzyl 3-allyl-4-oxo-piperidine-1-carboxylate (6.0 g, 22.0 mmol) in toluene (100 mL) was added ethylene glycol (1.4 g, 1.2 mL, 22.0 mmol) followed by the addition of 4-methylbenzenesulfonic acid-(water) (0.6 mL, 3.3 mmol). The reaction mixture was equipped with a Dean-Stark trap and heated at reflux overnight. The reaction mixture was cooled to rt, washed with saturated sodium bicarbonate (2×), saturated aqueous NaCl, dried over MgSO₄, filtered and concentrated to dryness. The crude material benzyl 6-allyl-1,4-dioxa-8-azaspiro[4.5]decane-8-carboxylate was used directly in next step without further purification.

A solution of benzyl 6-allyl-1,4-dioxa-8-azaspiro[4.5]decane-8-carboxylate (3.2 g, 10.0 mmol) in DCM (30 mL) was cooled to −78° C. Ozone was bubbled through the solution for 10 min until a light blue color persisted. The blue solution was then bubbled with nitrogen gas for 10 min to remove the excess of ozone. MeOH (30 mL) was added followed by the addition of sodium borohydride (380 mg, 10.0 mmol). The reaction mixture was stirred at rt for 5 min, and was repartitioned between ethyl acetate and water. The aqueous layer was extracted with ethyl acetate (3×). The combined organic layers were washed with saturated aqueous NaCl, dried over MgSO₄, filtered, and concentrated to dryness. The crude material was purified by column chromatography (30-40% ethyl acetate-hexanes) to provide benzyl 6-(2-hydroxyethyl)-1,4-dioxa-8-azaspiro[4.5]decane-8-carboxylate (1.7 g, 53%). ESI-MS m/z calc. 321.4. found 322.5 (M+1)⁺; Retention time: 1.44 min (3 min run).

Step 3: Step 4: benzyl 10-(2-chloroethyl)-1,4-dioxa-8-azaspiro[4.5]decane-8-carboxylate

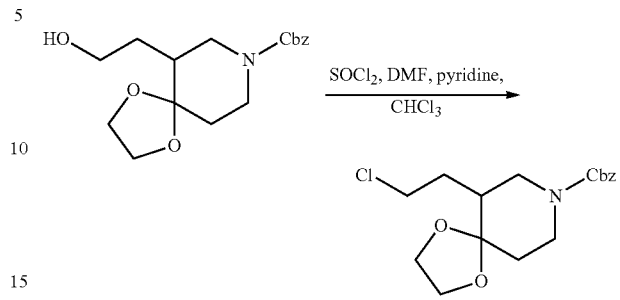

To a solution of benzyl 10-(2-hydroxyethyl)-1,4-dioxa-8-azaspiro[4.5]decane-8-carboxylate (320 mg, 1.0 mmol) in chloroform (10 mL) was added thionyl chloride (290 µL, 4.0 mmol) followed by the addition of a drop of pyridine and a drop of DMF. The reaction mixture was heated at reflux for 1 h, concentrated to dryness and purified by column chromatography (10-20% ethyl acetate-hexanes) to provide benzyl 10-(2-chloroethyl)-1,4-dioxa-8-azaspiro[4.5]decane-8-carboxylate (140 mg, 41%) as a colorless oil. ESI-MS m/z calc. 339.8. found 340.5 (M+1)⁺; Retention time: 1.89 min (3 min run).

Step 4: benzyl 7a-(2-pyridyl)-2,3,3a,4,6,7-hexahydrofuro[3,2-c]pyridine-5-carboxylate

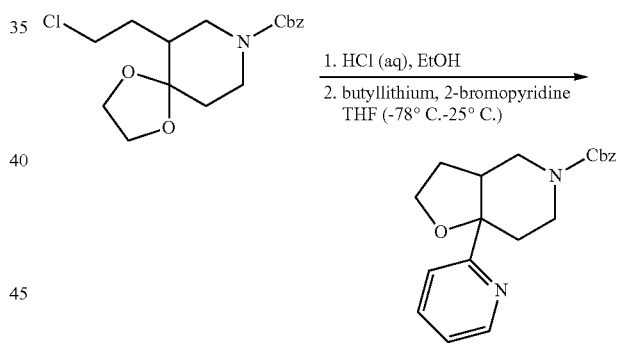

To a solution of benzyl 10-(2-chloroethyl)-1,4-dioxa-8-azaspiro[4.5]decane-8-carboxylate (68 mg, 0.2 mmol) in EtOH (2 mL) was added aqueous HCl (1 mL of 1 M, 1.0 mmol). The reaction mixture was heated in a sealed vial at 70° C. for 3 h. The volume was reduced to ⅓. The residue was repartitioned between ethyl acetate and water. The aqueous layer was extracted with ethyl acetate (2×). The combined organic layers were washed with saturated aqueous NaCl, dried over MgSO₄, filtered and concentrated to dryness to afford crude benzyl 3-(2-chloroethyl)-4-oxo-piperidine-1-carboxylate which was used directly in next step without further purification.

A solution of 2-bromopyridine (49 mg, 0.31 mmol) in THF (5 mL) was cooled to −78° C. and treated with butyllithium (10 mg, 0.16 mmol) (1M in hexanes) dropwise under an argon atmosphere. The reaction mixture was stirred at −78° C. for 30 min and crude benzyl 3-(2-chloroethyl)-4-oxo-piperidine-1-carboxylate (46 mg, 0.16 mmol) in THF (1 mL) was added dropwise. The reaction mixture was allowed to warm to rt and stirred over for 72 h. The reaction mixture was quenched with saturated aqueous ammonium chloride. The aqueous layer was extracted with ethyl acetate (3×). The combined organic layers were washed with saturated aqueous NaCl, dried over MgSO$_4$, filtered and concentrated to dryness. The crude material was purified by column chromatography (20-30% ethyl acetate-hexanes) to provided benzyl 7a-(2-pyridyl)-2,3,3a,4,6,7-hexahydrofuro[3,2-c]pyridine-5-carboxylate. ESI-MS m/z calc. 338.4. found 339.3 (M+1)$^+$; Retention time: 1.28 min (3 min run).

Step 5: 7a-(2-pyridyl)-3,3a,4,5,6,7-hexahydro-2H-furo[3,2-c]pyridine

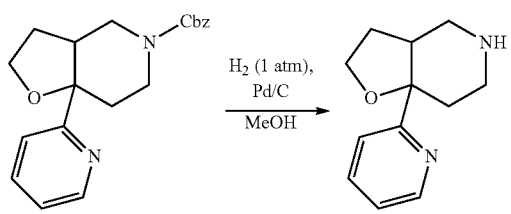 [SMILES: "MeOH" ; O=C(OCc1ccccc1)N1CCC2(c3ccccn3)OCCC2C1 ; c1ccc(C23CCNCC2CCO3)nc1]

A solution of benzyl 7a-(2-pyridyl)-2,3,3a,4,6,7-hexahydrofuro[3,2-c]pyridine-5-carboxylate (22 mg, 0.06 mmol) in MeOH (5 mL) was purged with nitrogen for 5 min. The mixture was treated with 10% palladium on carbon (14 mg, 0.013 mmol). The mixture was the evacuated and put under a hydrogen atmosphere (balloon) at rt. The Pd-catalyst was removed via filtration and washed with MeOH. The solvent was removed under reduced pressure affording crude 7a-(2-pyridyl)-3,3a,4,5,6,7-hexahydro-2H-furo[3,2-c]pyridine which was used directly in next step without further purification. ESI-MS m/z calc. 204.3. found 205.3 (M+1)$^+$; Retention time: 0.184 min (3 min run).

(3aR,7aR)-7a-(6-methyl-2-pyridyl)-4,5,6,7-tetrahydro-3aH-[1,3]dioxolo[4,5-c]pyridine

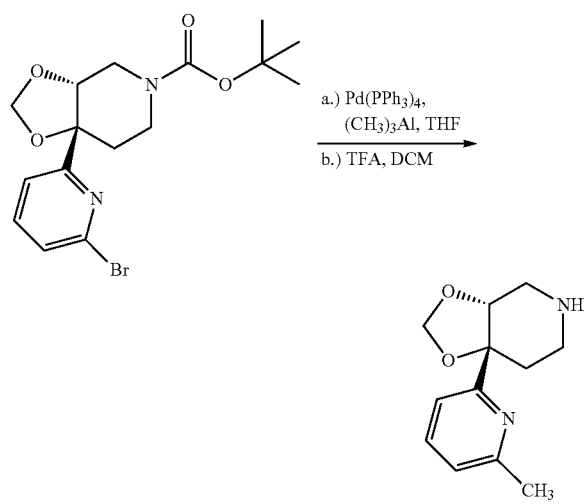

A flask containing tert-butyl(3aR,7aR)-7a-(6-bromo-2-pyridyl)-3a,4,6,7-tetrahydro-[1,3]dioxolo[4,5-c]pyridine-5-carboxylate (84 mg, 0.22 mmol) in THF (1 mL) was treated with Pd(PPh$_3$)$_4$ (126 mg, 0.11 mmol). The mixture was purged with nitrogen and trimethylalumane (31 mg, 42 µL, 0.44 mmol) was added. The solution was heated to 70° C. over 16 h. Water (1 ml) was added and mixture was extracted with EtOAc (3×). The organic layers were combined and washed with 1 ml of saturated aqueous NaCl, dried over sodium sulfate, concentrated, providing the tert-butyl(3aR,7aR)-7a-(2-pyridyl)-3a,4,6,7-tetrahydro-[1,3]dioxolo[4,5-c]pyridine-5-carboxylate as a yellow oil which was treated with a 1:1 mixture of TFA/DCM (1 mL). The reaction mixture was allowed to stir for 1 h and was concentrated under reduced pressure to provide (3aR,7aR)-7a-(6-methyl-2-pyridyl)-4,5,6,7-tetrahydro-3aH-[1,3]dioxolo[4,5-c]pyridine, which was used in the next step without further purification. ESI-MS m/z calc. 220.1. found 221.1 (M+1)+; Retention time: 0.228 min (3 min run).

7a-(6-isobutoxy-2-pyridyl)-4,5,6,7-tetrahydro-3aH-[1,3]dioxolo[4,5-c]pyridine

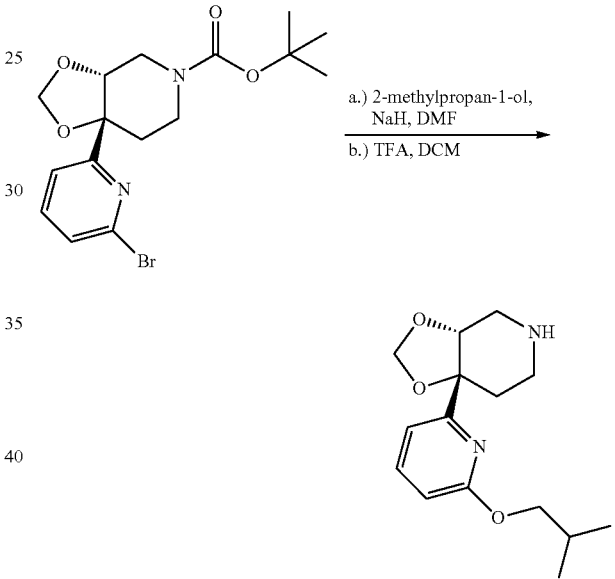

A solution of 2-methylpropan-1-ol (240 µL, 2.60 mmol) in DMF (1 mL) was treated with sodium hydride (104 mg, 2.6 mmol)(60% dispersion in mineral oil) at 0° C. The reaction mixture was allowed to stir for 5 min and tert-butyl (3aR,7aR)-7a-(6-bromo-2-pyridyl)-3a,4,6,7-tetrahydro-[1,3]dioxolo[4,5-c]pyridine-5-carboxylate (100 mg, 0.26 mmol) in DMF (0.5 mL) was added. The reaction mixture was allowed to stir at rt for 16 h. Water (1 ml) was added and mixture was extracted with ethyl acetate (3×). The organic layers were combined and washed with saturated aqueous NaCl, dried over sodium sulfate, and concentrated to afford crude tert-butyl(3aR,7aR)-7a-(2-pyridyl)-3a,4,6,7-tetrahydro-[1,3]dioxolo[4,5-c]pyridine-5-carboxylate as a yellow oil. The crude product was treated with a 1 ml of 1:1 mixture TFA/DCM and the reaction mixture was allowed to stir for 1 h. The reaction mixture was concentrated under reduced pressure to afford 7a-(6-isobutoxy-2-pyridyl)-4,5,6,7-tetrahydro-3aH-[1,3]dioxolo[4,5-c]pyridine as yellow oil (50 mg, 51%). ESI-MS m/z calc. 278.3. found 279.2 (M+1)$^+$; Retention time: 0.23 min (3 min run).

(3-methoxy-4-(2-(trifluoromethoxy)ethoxy)phenyl)
((syn)-7a-(pyridin-2-yl)hexahydrofuro[3,4-c]pyridin-
5(3H)-yl)methanone Step 1: (syn)-tert-butyl 1-oxohexahydrofuro[3,4-c]
pyridine-5(3H)-carboxylate

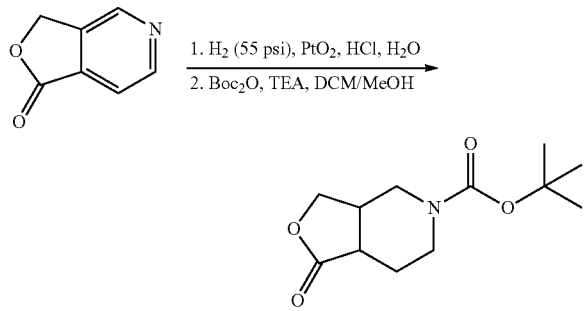

A solution of 3H-furo[3,4-c]pyridin-1-one (3.2 g, 23.7 mmol) in HCl (17 mL of 1 M, 17 mmol) and water (17 mL) in a Parr shaker was treated with PtO$_2$ (700 mg, 3.1 mmol). The mixture was hydrogenated at 55 psi overnight. The catalyst was filtered off and the filtrate was concentrated to afford a yellow oil. The resulting oil was diluted with DCM (237 mL) and MeOH (35 mL) and was treated with TEA (8.3 mL, 59.2 mmol) followed by Boc-anhydride (5.7 g, 26.1 mmol). The reaction mixture was stirred at rt for 16 h. The reaction mixture was diluted with water and extracted with DCM (3×). The combined organics were dried (Na$_2$SO$_4$), filtered, and concentrated under reduced pressure. Purification by flash column chromatography (SiO$_2$-24 g, 30-100% EtOAc-hexanes) afforded (syn)-tert-butyl 1-oxohexahydrofuro[3,4-c]pyridine-5(3H)-carboxylate (3.1 g, 93%). $^1$H NMR (400 MHz, CDCl$_3$) δ 4.27 (dd, J=9.4, 5.6 Hz, 1H), 3.97 (dd, J=9.5, 2.0 Hz, 2H), 3.73 (s, 1H), 2.96-2.76 (m, 3H), 2.72-2.68 (m, 1H), 2.01 (dq, J=13.9, 3.6 Hz, 1H), 1.90-1.82 (m, 1H), 1.44 (s, 9H). ESI-MS m/z calc. 241.1. found 242.5 (M+1)+; Retention time: 1.34 min. (3 min run).

Step 2: tert-butyl 1-oxo-7a-(2-pyridyl)-3a,4,6,7-tetrahydro-3H-furo[3,4-c]pyridine-5-carboxylate

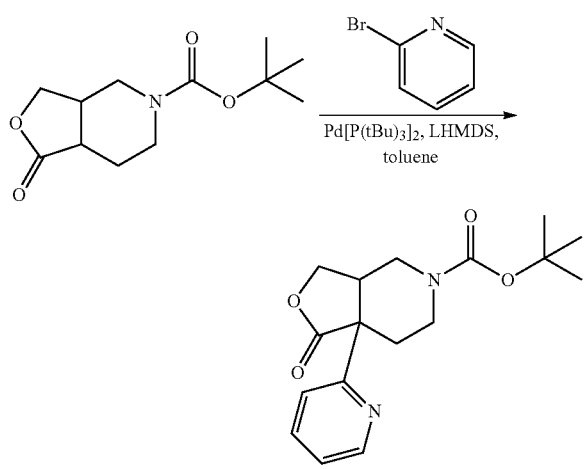

In an oven dried flask was added tert-butyl 1-oxo-3,3a,4,6,7,7a-hexahydrofuro[3,4-c]pyridine-5-carboxylate (60 mg, 0.25 mmol) which was put under an inert atmosphere (nitrogen) and diluted with toluene (300 µL). The mixture was treated with Pd[P(tBu)$_3$]$_2$ (6.3 mg, 0.012 mmol) and LiHMDS (300 µl of 1 M, 0.30 mmol), followed by 2-bromopyridine (36 µl, 0.37 mmol). The reaction mixture was warmed to 50° C. and stirred for 20 h. The reaction mixture was cooled to rt, diluted with saturated aqueous ammonium chloride and extracted with ethyl acetate (3×). The combined organics were washed with saturated aqueous NaCl, dried (Na$_2$SO$_4$), filtered, and concentrated under reduced pressure. Purification by reverse phase HPLC (1-100% ACN/H$_2$O) afforded tert-butyl 1-oxo-7a-(2-pyridyl)-3a,4,6,7-tetrahydro-3H-furo[3,4-c]pyridine-5-carboxylate (30 mg, 38%)$^1$H NMR (400 MHz, CDCl$_3$) δ 8.57 (ddd, J=4.8, 1.7, 0.8 Hz, 1H), 7.73 (td, J=7.8, 1.8 Hz, 1H), 7.55 (d, J=7.9 Hz, 1H), 7.25 (ddt, J=4.9, 2.9, 2.5 Hz, 1H), 4.33 (dd, J=9.2, 6.4 Hz, 1H), 4.03 (dd, J=9.2, 4.2 Hz, 1H), 3.93 (dd, J=13.9, 5.4 Hz, 1H), 3.63-3.49 (m, 2H), 3.29-3.23 (m, 2H), 2.26 (ddd, J=14.0, 5.2, 4.0 Hz, 1H), 2.20-2.06 (m, 1H), 1.47 (s, 9H). ESI-MS m/z calc. 318.2. found 319.1 (M+1)+; Retention time: 1.59 min (3 min run).

Step 3: tert-butyl 3,4-bis(hydroxymethyl)-4-(2-pyridyl)piperidine-1-carboxylate

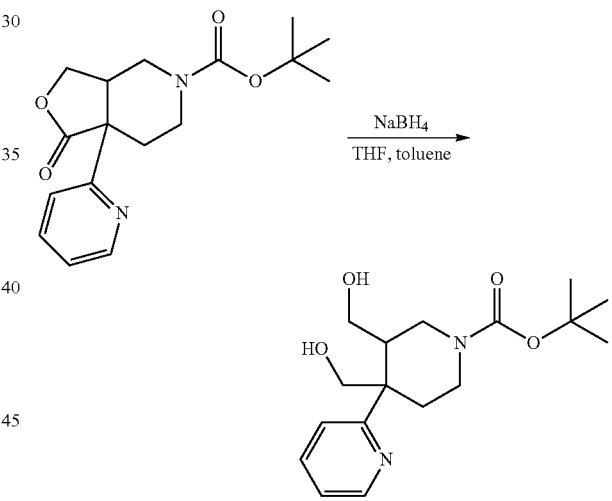

A solution of tert-butyl 1-oxo-7a-(2-pyridyl)-3a,4,6,7-tetrahydro-3H-furo[3,4-c]pyridine-5-carboxylate (0.56 g, 1.76 mmol) in THF (6.5 mL) and toluene (2 mL) was treated with lithium borohydride (153 mg, 7.0 mmol). The reaction mixture was heated to reflux for 2 h. The reaction mixture was cooled to 0° C. and diluted with DCM and ethyl acetate. The reaction mixture was quenched with saturated aqueous ammonium chloride and 1 M HCl and the pH was adjusted to 8 with saturated aqueous sodium bicarbonate. The mixture was extracted with DCM (3×) and the combined organics were dried (Na$_2$SO$_4$), filtered, and concentrated under reduced pressure. Purification by flash column chromatography (SiO$_2$-24 g, 40-100% ethyl acetate-DCM) afforded tert-butyl 3,4-bis(hydroxymethyl)-4-(2-pyridyl)piperidine-1-carboxylate (400 mg, 70.5%). $^1$H NMR (400 MHz, CDCl$_3$) δ 8.52 (dd, J=4.9, 0.9 Hz, 1H), 7.83-7.67 (m, 1H), 7.40 (d, J=8.2 Hz, 1H), 7.22 (ddd, J=7.5, 4.9, 0.9 Hz, 1H), 4.29-2.73 (m, 10H), 2.28 (s, 1H), 2.00-1.88 (m, 1H), 1.73

(ddd, J=14.0, 4.7, 3.5 Hz, 1H), 1.49 (s, 9H). ESI-MS m/z calc. 322.2. found 323.5 (M+1)+; Retention time: 1.02 min (3 min run).

Step 4: tert-butyl 7a-(2-pyridyl)-1,3,3a,4,6,7-hexahydrofuro[3,4-c]pyridine-5-carboxylate

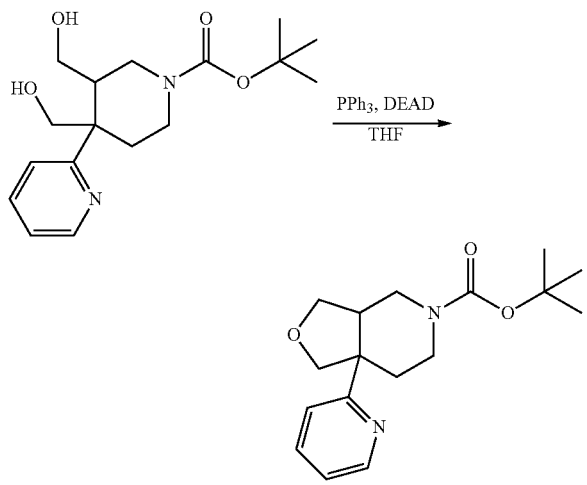

A solution of tert-butyl 3,4-bis(hydroxymethyl)-4-(2-pyridyl)piperidine-1-carboxylate (400 mg, 1.24 mmol) and triphenylphosphine (391 mg, 1.49 mmol) in THF (12.4 mL) was cooled to 0° C. The reaction mixture was stirred for 1 h at 0° C. The reaction mixture was allowed to warm to rt and was concentrated under reduced pressure. Purification by flash column chromatography (SiO$_2$-4 g, 30-100% EtOAc-hexanes) afforded tert-butyl 7a-(2-pyridyl)-1,3,3a,4,6,7-hexahydrofuro[3,4-c]pyridine-5-carboxylate (354 mg, 93.7%). ESI-MS m/z calc. 304.2. found 305.3 (M+1)+; Retention time: 1.2 min (3 min run).

Step 5: (3-methoxy-4-(2-(trifluoromethoxy)ethoxy)phenyl)(7a-(pyridin-2-yl)hexahydrofuro[3,4-c]pyridin-5(3H)-yl)methanone

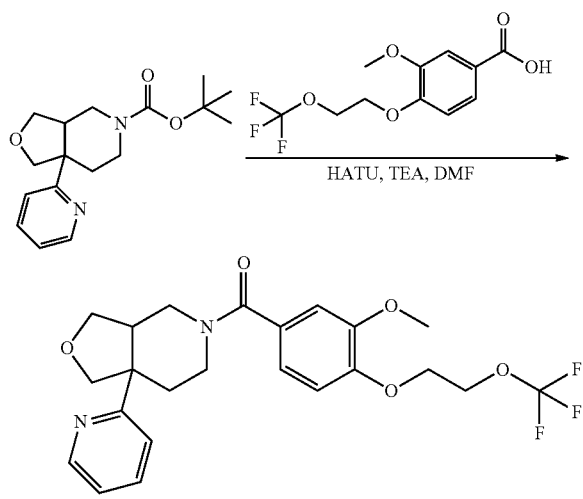

A solution of tert-butyl 7a-(2-pyridyl)-1,3,3a,4,6,7-hexahydrofuro[3,4-c]pyridine-5-carboxylate (52 mg, 0.17 mmol) in DCM (0.5 mL) was treated with hydrogen chloride (500 µL of 4 M, 2.00 mmol) in dioxane. The reaction mixture was stirred for 1 h and was concentrated under reduced pressure. The resulting crude product was diluted with DMF (0.7 mL) and treated with HATU (78 mg, 0.21 mmol) and 3-methoxy-4-[2-(trifluoromethoxy)ethoxy]benzoic acid (48 mg, 0.17 mmol). The mixture was treated with triethylamine (95 µL, 0.68 mmol) and stirred for 1 h. The reaction mixture was filtered and purified by reverse phase HPLC (Water, HCl-modifier, 1-100% ACN/H$_2$O, 30 min) to afford (3-methoxy-4-(2-(trifluoromethoxy)ethoxy)phenyl)(7a-(pyridin-2-yl)hexahydrofuro[3,4-c]pyridin-5(3H)-yl)methanone (HCl salt) (25 mg, 29%) $^1$H NMR (400 MHz, C$_6$D$_6$) δ 8.53 (s, 1H), 7.21-7.04 (m, 3H), 6.78-6.65 (m, J=7.7 Hz, 2H), 6.57 (d, J=8.1 Hz, 1H), 4.15-3.91 (m, 4H), 3.86 (d, J=8.2 Hz, 1H), 3.81-3.70 (m, 4H), 3.68-3.58 (m, 2H), 3.37 (s, 3H), 3.18-2.95 (m, 2H), 2.27-1.98 (m, 2H). ESI-MS m/z calc. 466.17157. found 467.2 (M+1) MS m/z calc. 466.2. found 467.2 (M+1)+; Retention time: 0.964 min (3 min run).

tert-butyl(4aS,8aS)-8a-phenyl-2,3,4a,5,7,8-hexahydro-[1,4]dioxino[2,3-c]pyridine-6-carboxylate

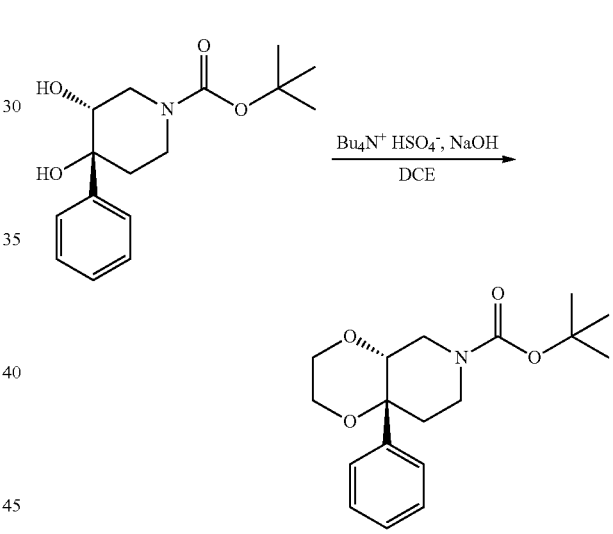

A solution of tert-butyl(3R,4R)-3,4-dihydroxy-4-phenyl-piperidine-1-carboxylate (200 mg, 0.68 mmol) and tetrabutylammonium hydrogensulfate (66 mg, 0.19 mmol) in dichloroethane (5 mL) was treated with NaOH (5 mL of 50% w/w in water). The reaction mixture was stirred at 35° C. overnight and was cooled to rt and diluted with water and EtOAc. The organic layer was separated and the mixture was extracted with ethyl acetate (3×100 mL). The combined organics were washed with saturated aqueous NaCl, dried (Na$_2$SO$_4$), filtered, and concentrated under reduced pressure. Purification by flash column chromatography (SiO$_2$-12 g, 0-100% ethyl acetate-hexanes) afforded tert-butyl(4aS,8aS)-8a-phenyl-2,3,4a,5,7,8-hexahydro-[1,4]dioxino[2,3-c]pyridine-6-carboxylate (86 mg, 40%) $^1$H NMR (400 MHz, CDCl$_3$) δ 7.55-7.27 (m, 5H), 4.34 (s, 1H), 4.01 (ddd, J=11.9, 9.4, 4.2 Hz, 1H), 3.95-3.80 (m, 2H), 3.74-3.61 (m, 2H), 3.46 (dt, J=11.8, 3.3 Hz, 1H), 3.37-3.23 (m, 2H), 2.12 (d, J=14.3 Hz, 1H), 1.77-1.62 (m, 1H), 1.48 (s, 9H). ESI-MS m/z calc. 319.2. found 320.3 (M+1); Retention time: 1.83 min (3 min run).

[(3aR,7aR)-2,2-dimethyl-7a-(2-pyridyl)-3a,4,6,7-tetrahydro[1,3]dioxolo[4,5-c]pyridin-5-yl]-[3-methoxy-4-[2-(trifluoromethoxy)ethoxy]phenyl]methanone Step 1: [(3R,4R)-4-(6-bromo-2-pyridyl)-3,4-dihydroxy-1-piperidyl]-[3-methoxy-4-[2-(trifluoromethoxy)ethoxy]phenyl]methanone

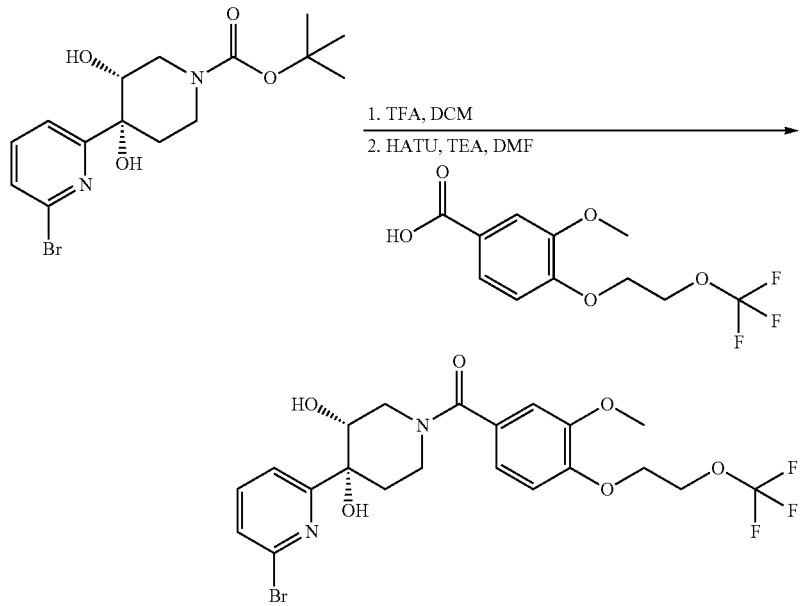

Step 1: To a 100 mL round bottom flask was added tert-butyl(3R,4R)-4-(6-bromo-2-pyridyl)-3,4-dihydroxy-piperidine-1-carboxylate (1.0 g, 2.7 mmol) and DCM (9 mL) followed by TFA (3 mL, 39 mmol). After 1 h, the reaction mixture was concentrated under reduced pressure and used in the next step without purification.

Step 2: To a 100 mL round bottom flask was added 3-methoxy-4-[2-(trifluoromethoxy)ethoxy]benzoic acid (976 mg, 3.48 mmol), HATU (1.0 g, 2.7 mmol), DMF (10 mL), and triethylamine (1.9 mL, 13.4 mmol). The reaction mixture was allowed to stir at rt for 10 min. The amine from Step 1: was dissolved in DMF (3 mL) and added to the reaction mixture dropwise. The reaction mixture was allowed to stir at rt for 15 min. The reaction mixture was quenched with saturated aqueous NaCl, extracted with ethyl acetate (3×), and the combined organic layers were dried over sodium sulfate and concentrated under reduced pressure. The crude reaction mixture was purified via silica gel chromatography 0%-75% ethyl acetate in DCM to provide [(3R,4R)-4-(6-bromo-2-pyridyl)-3,4-dihydroxy-1-piperidyl]-[3-methoxy-4-[2-(trifluoromethoxy)ethoxy]phenyl]methanone (1.4 g, 97%) as a thick yellow oil. ESI-MS m/z calc. 534.1. found 535.3 (M+1)$^+$; Retention time: 1.78 min (3 min run).

Step 2: [(3R,4R)-3,4-dihydroxy-4-(2-pyridyl)-1-piperidyl]-[3-methoxy-4-[2-(trifluoromethoxy)ethoxy]phenyl]methanone

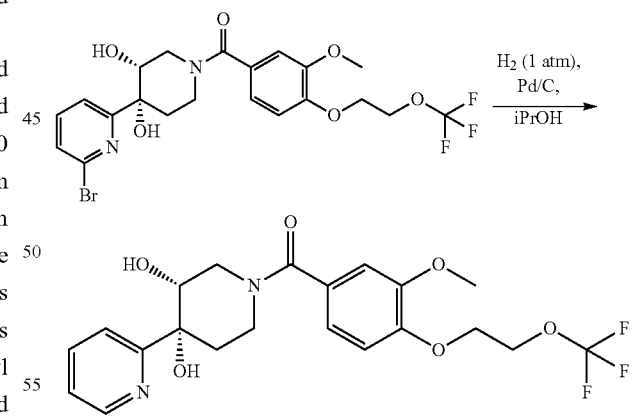

To a 250 mL round bottom flask was added wet Pd/C (1.4 g, 1.3 mmol) and isopropanol (10 mL). The mixture was purged with nitrogen for 10 min and treated with a solution of [(3R,4R)-4-(6-bromo-2-pyridyl)-3,4-dihydroxy-1-piperidyl]-[3-methoxy-4-[2-(trifluoromethoxy)ethoxy]phenyl]methanone (1.4 g, 2.6 mmol) in isopropanol (10 mL). The mixture was evacuated and put under hydrogen (1 atm, balloon). The reaction mixture was allowed to stir at 45° C. overnight. The reaction mixture was filtered and the filter cake was washed with DCM and isopropanol. The solvent was removed and the product was isolated as a white foam. ¹H NMR (400 MHz, MeOD) δ 8.53 (ddd, J=4.9, 1.7, 1.0 Hz, 1H), 7.86-7.80 (m, 1H), 7.78 (dt, J=8.0, 1.2 Hz, 1H), 7.29 (ddd, J=7.3, 4.9, 1.4 Hz, 1H), 7.14 (s, 1H), 7.09-7.03 (m, 2H), 4.55 (d, J=46.0 Hz, 1H), 4.40-4.33 (m, 2H), 4.29 (q, J=4.1 Hz, 2H), 4.18 (s, 1H), 3.89 (s, 3H), 3.74 (d, J=25.1 Hz, 1H), 3.47 (dd, J=22.6, 21.0 Hz, 1H), 3.27-3.03 (m, 1H), 2.23 (s, 1H), 1.64 (t, J=50.8 Hz, 1H). ESI-MS m/z calc. 456.4. found 457.5 (M+1)⁺; Retention time: 1.32 min (3 min run).

Step 3: [(3aR,7aR)-2,2-dimethyl-7a-(2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone

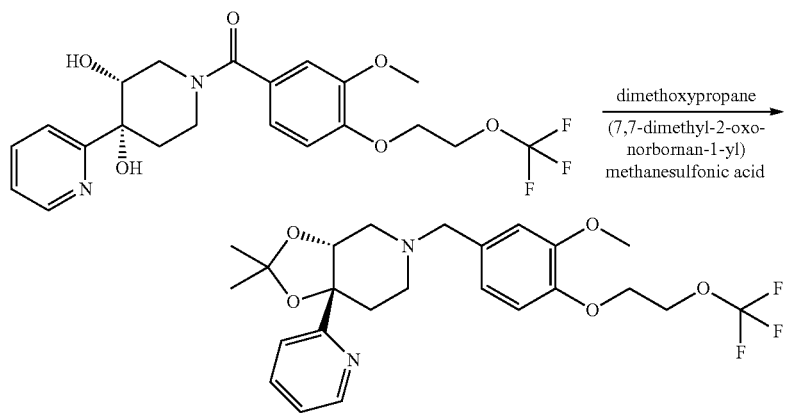

To a vial was added [(3R,4R)-3,4-dihydroxy-4-(2-pyridyl)-1-piperidyl]-[3-methoxy-4-[2-(trifluoromethoxy)ethoxy]phenyl]methanone (45 mg, 0.10 mmol) and dichloromethane (1 mL). [(1R,4S)-7,7-dimethyl-2-oxo-norbornan-1-yl]methanesulfonic acid (2.3 mg, 0.01 mmol) was added followed by 2,2-dimethoxypropane (36 μL, 0.30 mmol). The reaction mixture was heated at 45° C. for 4 h. The reaction mixture was filtered and purified via HPLC (1%-99%) ACN:H2O with no modifier to afford [(3aR,7aR)-2,2-dimethyl-7a-(2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone (4.2 mg, 8.6%) as a white solid. ESI-MS m/z calc. 496.2. found 497.2 (M+1)⁺; Retention time: 1.19 min (3 min run).

(1S,6R)-6-(2-pyridyl)-3-azabicyclo[4.1.0]heptane

Step 1: (1R,2S)-2-(hydroxymethyl)-1-(2-pyridyl)cyclopropanecarbonitrile

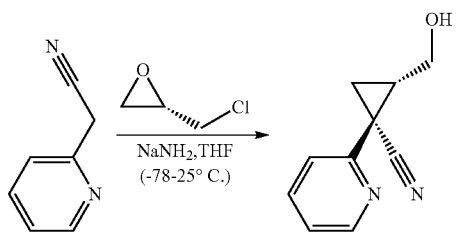

To a suspension of sodium amide (8.6 g, 199.3 mmol) in anhydrous THF (225 mL) under nitrogen at -25° C. (external temp) was added dropwise a solution of 2-(2-pyridyl)acetonitrile (10.7 g, 90.6 mmol) in anhydrous THF (50 mL) over 15 min. The cooling bath was removed and stirring was continued at rt for 2.5 h. A solution of (2S)-2-(chloromethyl)oxirane (21 mL, 272 mmol) in anhydrous THF (20 mL) was added at -25° C. in one portion. The resulting reaction mixture was heated at 35° C. for 16 h and then at 50° C. for 20 h. After cooling to rt the reaction mixture was poured into aqueous saturated aqueous ammonium chloride (100 mL), diluted with saturated aqueous NaCl (200 mL) and extracted with ethyl acetate (4×250 mL). The combined organic phases were washed with saturated aqueous NaCl (250 mL), dried over MgSO₄ and concentrated. Purification using silica gel chromatography (330 g silica, 10-30% ethyl acetate in DCM, 60 min) afforded (1R,2S)-2-(hydroxymethyl)-1-(2-pyridyl)cyclopropanecarbonitrile (5.4 g, 34%) as a yellow-orange solid. ¹H NMR (400 MHz, DMSO) δ 8.51 (ddd, J=4.8, 1.7, 0.9 Hz, 1H), 7.84 (td, J=7.8, 1.8 Hz, 1H), 7.57 (dt, J=7.9, 0.9 Hz, 1H), 7.31 (ddd, J=7.5, 4.8, 1.0 Hz, 1H), 5.03 (t, J=5.2 Hz, 1H), 3.84 (dt, J=11.9, 5.0 Hz, 1H), 3.49 (ddd, J=11.9, 8.4, 5.5 Hz, 1H), 2.13 (dd, J=7.5, 5.1 Hz, 1H), 1.85 (dd, J=8.9, 4.6 Hz, 1H), 1.66 (dd, J=7.5, 4.7 Hz, 1H). ESI-MS m/z calc. 174.1. found 175.1 (M+1)⁺; Retention time: 0.39 min (3 min run).

Step 2: (1R,2S)-2-[[tert-butyl(dimethyl)silyl]oxymethyl]-1-(2-pyridyl)cyclopropanecarbonitrile

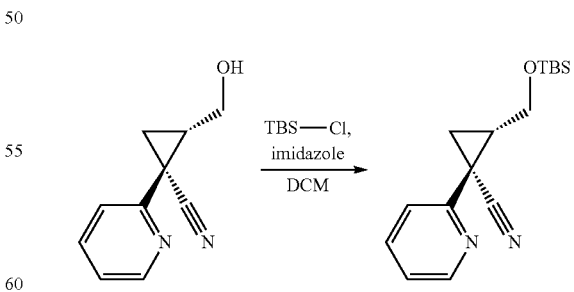

To a solution of (1R,2S)-2-(hydroxymethyl)-1-(2-pyridyl)cyclopropane carbonitrile (5.4 g, 31.3 mmol) and imidazole (4.3 g, 62.5 mmol) in anhydrous DCM (65 mL) at 0° C. was added tert-butyl-chloro-dimethyl-silane (4.9 g, 32 mmol) in portions over 5 min. The cooling bath was removed and stirring was continued at rt for 45 min. The reaction mixture was poured into saturated aqueous ammonium chloride (100 mL), the phases were separated, and the aqueous phase was extracted with DCM (3×100 mL). The combined organic extracts were dried over MgSO$_4$, filtered, and concentrated in vacuo. Purification using silica gel chromatography (330 g silica, 0-10% ethyl acetate in hexane, 35 min) afforded (1R,2S)-2-[[tert-butyl(dimethyl)silyl]oxymethyl]-1-(2-pyridyl)cyclopropanecarbonitrile (8.2 g, 91%) as a colorless oil. $^1$H NMR (400 MHz, DMSO) δ 8.45 (d, J=4.7 Hz, 1H), 7.78 (dd, J=7.7, 1.7 Hz, 1H), 7.52 (d, J=7.9 Hz, 1H), 7.26 (dd, J=6.8, 4.9 Hz, 1H), 4.03 (dd, J=11.6, 4.6 Hz, 1H), 3.62 (dd, J=11.6, 8.5 Hz, 1H), 2.12 (qd, J=8.5, 4.6 Hz, 1H), 1.81 (dd, J=8.9, 4.7 Hz, 1H), 1.68 (dd, J=7.4, 4.7 Hz, 1H), 0.80 (s, 9H), 0.00 (s, 3H), −0.02 (s, 3H). ESI-MS m/z calc. 288.2. found 289.5 (M+1)$^+$; Retention time: 2.0 min (3 min run).

Step 3: (1R,2S)-2-[[tert-butyl(dimethyl)silyl]oxymethyl]-1-(2-pyridyl)cyclopropanecarbaldehyde

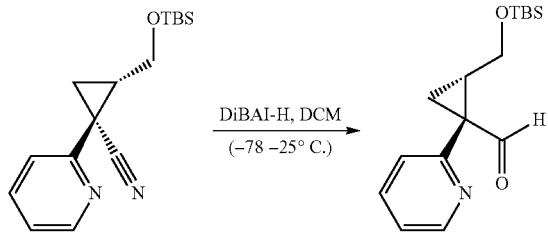 [SMILES: CC(C)(C)[Si](C)(C)OC[C@H]1C[C@]1(C#N)c1ccccn1 ; CC(C)(C)[Si](C)(C)OC[C@H]1C[C@]1(C=O)c1ccccn1]

A solution of (1R,2S)-2-[[tert-butyl(dimethyl)silyl]oxymethyl]-1-(2-pyridyl)cyclopropanecarbonitrile (6.2 g, 21 mmol) in anhydrous DCM (62 mL) at −78° C. under nitrogen was added dropwise to a solution of DIBAL-H (1M in toluene) (32 mL of 1 M, 32 mmol) over 10 min. Stirring was continued at −78° C. for 1 h, followed by 1.5 h at rt. After cooling to −78° C. the reaction mixture was quenched with isopropanol (62 mL) and allowed to warm up to rt. Dichloromethane (300 mL) and 50% aqueous saturated Rochelle's salt solution (100 mL) was added, the phases were separated, and the organic phase was washed with 50% aqueous saturated Rochelles salt solution (2×100 mL). The combined aqueous phases were re-extracted with DCM (150 mL). All combined organic phases were washed with water (100 mL) and saturated aqueous NaCl (100 mL), dried over MgSO$_4$ and concentrated in vacuo. Purification by silica gel chromatography (330 g silica, 0-20% MeOH in DCM, 40 min) afforded (1R,2S)-2-[[tert-butyl(dimethyl)silyl]oxymethyl]-1-(2-pyridyl)cyclopropanecarbaldehyde (2.7 g, 44%) as a yellow oil. $^1$H NMR (400 MHz, DMSO) δ 9.75 (s, 1H), 8.49 (dd, J=4.8, 0.8 Hz, 1H), 7.82-7.70 (m, 1H), 7.56 (d, J=8.0 Hz, 1H), 7.26 (s, 1H), 4.04 (dd, J=11.5, 5.7 Hz, 1H), 3.62 (dd, J=11.5, 9.0 Hz, 1H), 2.28 (qt, J=40.3, 20.1 Hz, 1H), 1.85 (dd, J=7.4, 4.4 Hz, 1H), 1.78 (dd, J=8.6, 4.4 Hz, 1H), 0.87-0.71 (s, 9H), −0.00 (d, J=1.8 Hz, 6H). ESI-MS m/z calc. 291.2. found 292.3 (M+1)+; Retention time: 1.34 min (3 min run).

Step 4: [(1R,2S)-2-[[tert-butyl(dimethyl)silyl]oxymethyl]-1-(2-pyridyl)cyclopropyl]methanol

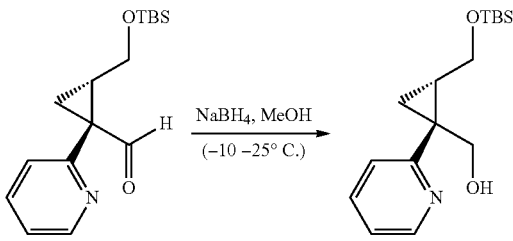 [SMILES: CC(C)(C)[Si](C)(C)OC[C@H]1C[C@]1(C=O)c1ccccn1 ; CC(C)(C)[Si](C)(C)OC[C@H]1C[C@]1(CO)c1ccccn1]

To a solution of (1R,2S)-2-[[tert-butyl(dimethyl)silyl]oxymethyl]-1-(2-pyridyl)cyclopropanecarbaldehyde (3.6 g, 12.4 mmol) in anhydrous MeOH (100 mL) at −10° C. under nitrogen was added NaBH$_4$ (470 mg, 12.4 mmol) in portions over 5 min. Stirring was continued at rt for 45 min, and the reaction mixture was cooled to 0° C. and quenched by addition of water (5 mL). Ethyl acetate (250 mL) and saturated aqueous sodium bicarbonate (100 mL) were added, the phases were separated, and the aqueous phase was extracted with ethyl acetate (150 mL). The combined organic extracts were washed with saturated aqueous NaCl (100 mL), dried over MgSO$_4$ and concentrated to afford [(1R,2S)-2-[[tert-butyl(dimethyl)silyl]oxymethyl]-1-(2-pyridyl)cyclopropyl]methanol (3.6 g, 99%) as a yellow oil. $^1$H NMR (400 MHz, DMSO) δ 8.42-8.32 (m, 1H), 7.68-7.58 (m, 1H), 7.50 (d, J=8.1 Hz, 1H), 7.14-7.03 (m, 1H), 4.42-4.37 (m, 1H), 3.97-3.92 (m, 1H), 3.88-3.68 (m, 3H), 1.75-1.56 (m, 1H), 1.30 (dd, J=8.7, 3.8 Hz, 1H), 0.85 (dd, J=6.2, 3.9 Hz, 1H), 0.80 (s, 9H), 0.00 (s, 3H), −0.02 (s, 3H). ESI-MS m/z calc. 293.2. found 294.5 (M+1)$^+$; Retention time: 1.16 min (3 min run).

Step 5: [(1R,2S)-2-[[tert-butyl(dimethyl)silyl]oxymethyl]-1-(2-pyridyl)cyclopropyl]methyl methanesulfonate

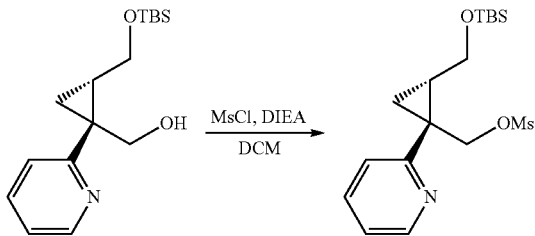 [SMILES: CC(C)(C)[Si](C)(C)OC[C@H]1C[C@]1(CO)c1ccccn1 ; CC(C)(C)[Si](C)(C)OC[C@H]1C[C@]1(COS(C)(=O)=O)c1ccccn1]

[(1R,2S)-2-[[tert-butyl(dimethyl)silyl]oxymethyl]-1-(2-pyridyl)cyclopropyl]methanol (1.5 g, 5.2 mmol) was dissolved in DCM (24 mL), cooled to −10° C., then treated with DIEA (1.1 mL, 6.3 mmol) and dropwise with MsCl (450 µL, 5.7 mmol). The reaction mixture was stirred at 0° C. for 1.5 h then allowed to warm to rt. The reaction mixture was concentrated and purified by silica gel chromatography (80 g silica, 0-50% ethyl acetate/hexane) to provide [(1R,2S)-2-[[tert-butyl(dimethyl)silyl]oxymethyl]-1-(2-pyridyl)cyclopropyl]methyl methanesulfonate (1.6 g, 84%) as a colorless oil. $^1$H NMR (400 MHz, DMSO) δ 8.48 (ddd, J=4.8, 1.7, 0.8 Hz, 1H), 7.74 (td, J=7.8, 1.8 Hz, 1H), 7.40 (d, J=8.1 Hz, 1H), 7.20 (ddd, J=7.5, 4.8, 0.8 Hz, 1H), 4.86 (d, J=10.8

Hz, 1H), 4.71 (d, J=10.8 Hz, 1H), 3.92 (dd, J=11.6, 6.1 Hz, 1H), 3.83 (dd, J=11.5, 7.3 Hz, 1H), 3.19 (s, 3H), 1.84 (dt, J=13.7, 6.7 Hz, 1H), 1.52 (dd, J=8.8, 4.3 Hz, 1H), 1.18 (dd, J=6.6, 4.4 Hz, 1H), 0.86 (s, 9H), 0.06 (s, 3H), 0.03 (s, 3H).

Step 6: 2-[(1R,2S)-2-[[tert-butyl(dimethyl)silyl]oxymethyl]-1-(2-pyridyl)cyclopropyl]acetonitrile

A mixture of [(1R,2S)-2-[[tert-butyl(dimethyl)silyl]oxymethyl]-1-(2-pyridyl)cyclopropyl]methyl methanesulfonate (870 mg, 2.34 mmol) and NaCN (126 mg, 2.58 mmol) in anhydrous DMSO (8.7 mL) under a nitrogen atmosphere was stirred at rt overnight for 16 h. The reaction mixture was diluted with ethyl acetate (200 mL) and washed with 50% saturated sodium bicarbonate solution (100 mL), water (100 mL), and saturated aqueous NaCl (100 mL). The organic layer was dried over MgSO₄ and concentrated. Purification by silica gel chromatography (120 g silica, 10-50% ethyl acetate/hexane) afforded 2-[(1R,2S)-2-[[tert-butyl(dimethyl)silyl]oxymethyl]-1-(2-pyridyl)cyclopropyl]acetonitrile (518 mg, 73.1%) as a colorless oil. $^1$H NMR (400 MHz, DMSO) δ 8.44 (dd, J=4.8, 0.9 Hz, 1H), 7.73-7.67 (m, 1H), 7.26 (d, J=8.1 Hz, 1H), 7.18-7.13 (m, 1H), 3.99-3.86 (m, 1H), 3.72 (dd, J=11.6, 7.8 Hz, 1H), 3.14 (d, J=17.3 Hz, 1H), 3.05 (d, J=17.3 Hz, 1H), 1.66 (dt, J=14.4, 7.2 Hz, 1H), 1.36 (dd, J=9.2, 4.6 Hz, 1H), 0.99 (dd, J=6.6, 4.6 Hz, 1H), 0.55 (s, 9H), −0.00 (s, 3H), −0.02 (s, 3H). ESI-MS m/z calc. 302.2. found 303.3 (M+1)⁺; Retention time: 1.52 min (3 min run).

Step 7: 2-[(1R,2S)-2-[[tert-butyl(dimethyl)silyl]oxymethyl]-1-(2-pyridyl)cyclopropyl]ethanamine

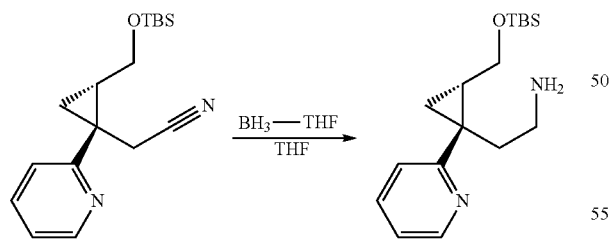

To a solution of 2-[(1R,2S)-2-[[tert-butyl(dimethyl)silyl]oxymethyl]-1-(2-pyridyl)cyclopropyl]acetonitrile (250 mg, 0.83 mmol) in anhydrous THF (7.5 mL) at 0° C. under nitrogen was added a solution of borane-tetrahydrofuran complex (2.5 mL of 1 M, 2.5 mmol) in THF dropwise over 5 min. The resulting mixture was heated at reflux for 2 h. After cooling to 0° C., MeOH (0.75 mL) was added carefully, and the mixture was heated again at reflux for 1 h. After cooling to rt the reaction mixture was concentrated, the residue redissolved in DCM (50 mL), washed with water (30 mL), saturated aqueous NaCl (30 mL), dried over MgSO₄ and concentrated. Purification using silica gel chromatography (40 g silica, 0-20% MeOH in DCM with 2% triethylamine, 30 min) afforded 2-[(1R,2S)-2-[[tert-butyl(dimethyl)silyl]oxymethyl]-1-(2-pyridyl)cyclopropyl]ethanamine (124 mg, 49%) as a colorless oil. $^1$H NMR (400 MHz, DMSO) δ 8.47 (d, J=4.5 Hz, 1H), 7.75-7.68 (m, 1H), 7.32 (d, J=8.0 Hz, 1H), 7.24-7.12 (m, 1H), 4.07-3.85 (m, 1H), 3.63-3.55 (m, 1H), 3.00-2.90 (m, 1H), 2.87-2.75 (m, 3H), 2.40-2.16 (m, 1H), 2.16-1.95 (m, 1H), 1.64-1.55 (m, 1H), 1.32-1.26 (m, 1H), 0.85 (s, 9H), 0.81-0.73 (m, 1H), 0.06 (s, 3H), 0.03 (s, 3H). ESI-MS m/z calc. 306.2. found 307.3 (M+1)⁺; Retention time: 1.04 min (3 min run).

Step 8: [(1S,2R)-2-(2-aminoethyl)-2-(2-pyridyl)cyclopropyl]methanol

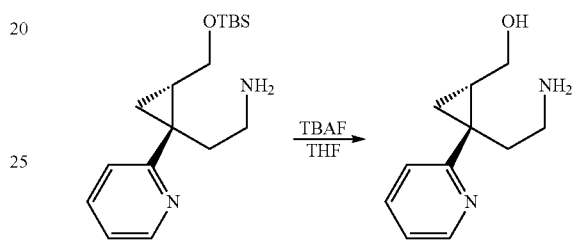

To a solution of 2-[(1R,2S)-2-[[tert-butyl(dimethyl)silyl]oxymethyl]-1-(2-pyridyl)cyclopropyl]ethanamine (124 mg, 0.40 mmol) in anhydrous THF (2.5 mL) under nitrogen at rt was added a solution of tetra-n-butylammonium fluoride (0.4 mL of 1 M, 0.40 mmol) in THF dropwise over 5 min. The reaction mixture was continued to stir at rt for 2.5 h. Additional tetra-n-butylammonium fluoride (50 µL of 1 M, 0.05 mmol) in THF was added, and the reaction mixture was continued to stir at rt for 30 min. The reaction mixture was concentrated and purified using silica gel chromatography (24 g silica, 0-20% MeOH in DCM w/2.5% triethylamine, 20 min). After concentration of product fractions the residue was coconcentrated under reduced pressure with acetonitrile (3×10 mL) to remove traces of triethylamine to afford [(1S,2R)-2-(2-aminoethyl)-2-(2-pyridyl)cyclopropyl]methanol (54 mg, 69%) ESI-MS m/z calc. 192.1. found 193.5 (M+1)⁺; Retention time: 0.26 min (3 min run).

Step 9: (1S,6R)-6-(2-pyridyl)-3-azabicyclo[4.1.0]heptane

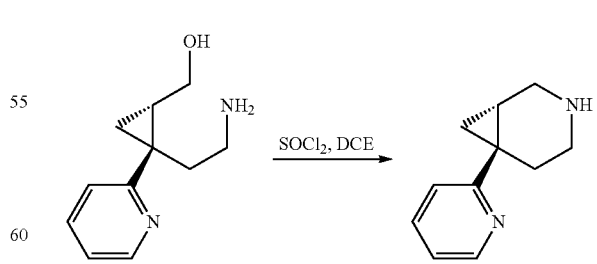

To a suspension of [(1S,2R)-2-(2-aminoethyl)-2-(2-pyridyl)cyclopropyl]methanol (54 mg, 0.28 mmol) in anhydrous DCE (2.5 mL) under nitrogen at 0° C. was added SOCl₂ (25 µL, 0.34 mmol) dropwise. The resulting reaction mixture was stirred at rt for 4 h. After cooling to 0° C.

additional SOCl$_2$ (102 µL, 1.40 mmol). The reaction mixture was concentrated, dissolved in water (20 mL), and adjusted to basic pH with 3.75 M aqueous NaOH The aqueous phase was extracted with DCM (5×40 mL) and the combined organic extracts were dried over MgSO$_4$, filtered, and concentrated to afford crude (1S,6R)-6-(2-pyridyl)-3-azabicyclo [4.1.0]heptane (42 mg, 86%). ESI-MS m/z calc. 174.2. found 175.1 (M+1)$^+$; Retention time: 0.368 min (3 min run).

tert-butyl 7,7-difluoro-6-(2-pyridyl)-3-azabicyclo [4.1.0]heptane-3-carboxylate

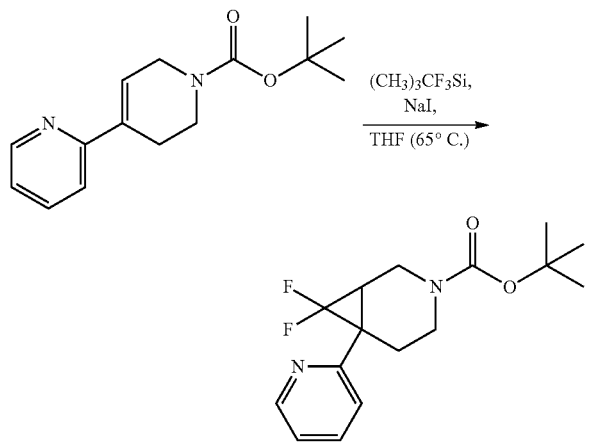

To a 4 ml vial charged with a magnetic stirbar was added tert-butyl 4-(2-pyridyl)-3,6-dihydro-2H-pyridine-1-carboxylate (235 mg, 0.90 mmol), sodium iodide (45 mg, 0.30 mmol) and anhydrous THF (1.5 mL) in under nitrogen atmosphere. To this was added trimethyl-(trifluoromethyl) silane (470 µL, 3.2 mmol). The reaction vessel was sealed and heated to 65° C. for 17 h. The volatiles were removed under reduced pressure and the resulting. residue was purified by flash chromatography on silica gel (24 g column) using a gradient of AcOEt (0 to 60% over 25 min) in hexanes to provide tert-butyl 7,7-difluoro-6-(2-pyridyl)-3-azabicyclo [4.1.0]heptane-3-carboxylate (64 mg, 22.4%) as a brown viscous oil. $^1$H NMR (400 MHz, CDCl$_3$) δ 8.56 (d, J=4.3 Hz, 1H), 7.68 (td, J=7.7, 1.8 Hz, 1H), 7.30 (d, J=8.5 Hz, 1H), 7.20 (ddd, J=7.5, 4.9, 1.0 Hz, 1H), 3.91 (br s, 1H), 3.80 (br s, 1H), 3.70-3.40 (br m, 1H), 3.25-3.00 (br m, 1H), 2.60-2.50 (m, 1H), 2.34 (br s, 1H), 2.21-2.05 (m, 1H), 1.47 (s, 9H). ESI-MS m/z calc. 310.1. found 311.0 (M+1)$^+$; Retention time: 1.02 min (3 min run).

tert-butyl(1R,6R)-6-(2-pyridyl)-8-oxa-3-azabicyclo [4.2.0]octane-3-carboxylate (racemic)

Step 1: tert-butyl 6-(2-pyridyl)-7-oxa-3-azabicyclo [4.1.0]heptane-3-carboxylate

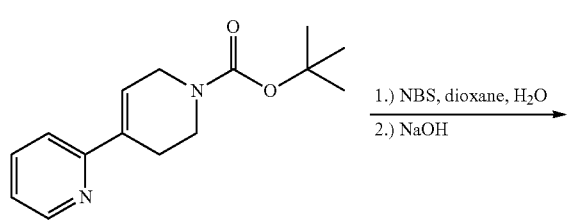

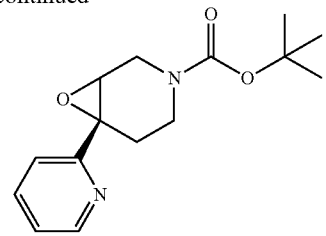

A solution of tert-butyl 4-(2-pyridyl)-3,6-dihydro-2H-pyridine-1-carboxylate (15.1 g, 58.1 mmol) in 1,4-dioxane (100 mL), and water (150 mL) was treated with N-bromosuccinimide (15.5 g, 87.1 mmol). The reaction mixture was allowed to stir at rt for 1 h. An aqueous solution of sodium hydroxide (116 mL of 1 M, 116 mmol) was added, and the reaction mixture was stirred for an additional 15 min. The mixture was extracted with ethyl acetate (3×75 mL). The organic layers were combined, dried over sodium sulfate, filtered and concentrated under reduced pressure. The resulting orange oil was purified by silica gel column chromatography: 220 gram silica gel column, 0-40% ethyl acetate/ hexane gradient; product eluted at 20% to provide tert-butyl 6-(2-pyridyl)-7-oxa-3-azabicyclo[4.1.0]heptane-3-carboxylate (11.5 g, 72%) as a clear yellow oil. $^1$H NMR (400 MHz, CDCl$_3$) δ 8.58 (d, J=4.1 Hz, 1H), 7.70 (td, J=7.8, 1.8 Hz, 1H), 7.37 (d, J=7.8 Hz, 1H), 7.22 (ddd, J=7.5, 4.8, 1.1 Hz, 1H), 3.90 (dt, J=24.8, 14.3 Hz, 2H), 3.66 (s, 1H), 3.30 (d, J=2.4 Hz, 2H), 2.83 (s, 1H), 2.16 (s, 1H), 1.47 (s, 9H). ESI-MS m/z calc. 276.1. found 277.3 (M+1)$^+$; Retention time: 0.96 min (3 min run).

Step 2: provide tert-butyl 4-cyano-3-hydroxy-4-(2-pyridyl)piperidine-1-carboxylate

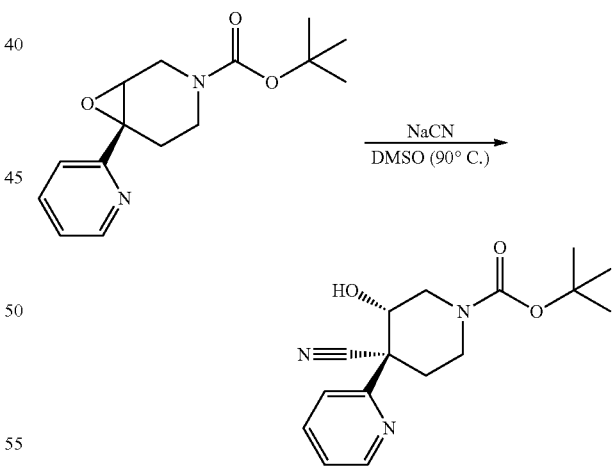

To a solution of tert-butyl 6-(2-pyridyl)-7-oxa-3-azabicyclo[4.1.0]heptane-3-carboxylate (14.4 g, 52.2 mmol) in DMSO (216 mL) was added potassium cyanide (10.2 g, 157 mmol). The reaction mixture was heated at 90° C. for 24 h, cooled to rt, and partitioned between ethyl acetate and water. The aqueous layer was extracted with ethyl acetate (3×). The combined organic layers were washed with water (3×), saturated aqueous NaCl, dried over MgSO$_4$, filtered and concentrated to dryness. Purification by flash column chromatography (SiO$_2$-80 g, 0-100% ethyl acetate-hexanes)

afforded tert-butyl 4-cyano-3-hydroxy-4-(2-pyridyl)piperidine-1-carboxylate (3.5 g, 22%). ESI-MS m/z calc. 303.2. found 304.1 (M+1)⁺; Retention time: 1.48 min (3 min run).

Step 3: tert-butyl(3R,4R)-3-benzyloxy-4-cyano-4-(2-pyridyl)piperidine-1-carboxylate

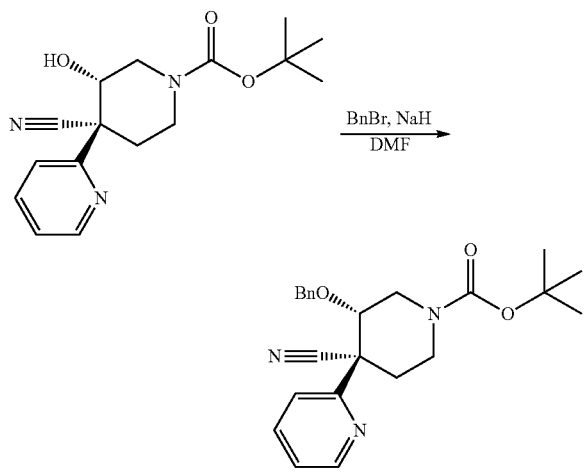

To a solution of tert-butyl 4-cyano-3-hydroxy-4-(2-pyridyl)piperidine-1-carboxylate (2.2 g, 7.1 mmol) in DMF (20 mL) was added sodium hydride (340 mg, 8.5 mmol). The reaction mixture was stirred at rt for 15 min and was treated with benzylbromide (1.0 mL, 8.5 mmol). The reaction mixture was stirred at rt overnight and then partitioned between ethyl acetate and water. The aqueous layer was extracted with ethyl acetate (3×), and the combined organic layers were washed with water (3×), saturated aqueous NaCl, dried over MgSO₄, filtered, and concentrated to dryness. The crude material was purified by column chromatography (0-20% ethyl acetate-hexanes) to provide tert-butyl(3R,4R)-3-benzyloxy-4-cyano-4-(2-pyridyl)piperidine-1-carboxylate (2.6 g, 93%). ESI-MS m/z calc. 393.5. found 394.5 (M+1)⁺; Retention time: 2.14 min (3 min run).

Step 4: O1-tert-butyl O4-methyl(3R,4S)-3-benzyloxy-4-(2-pyridyl)piperidine-1,4-dicarboxylate

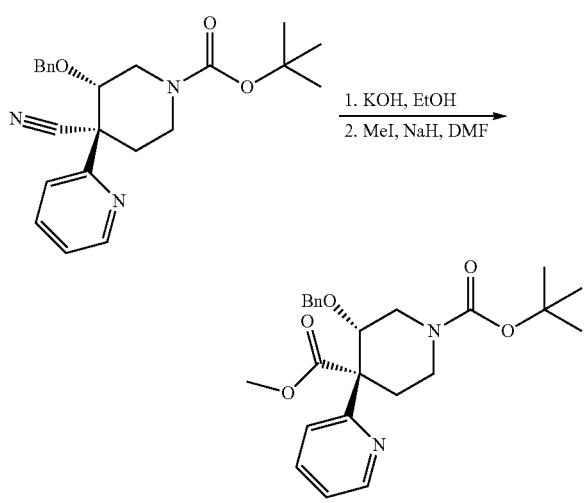

To a solution of tert-butyl 3-benzyloxy-4-cyano-4-(2-pyridyl)piperidine-1-carboxylate (2.4 g, 6.1 mmol) in EtOH (20 mL) was added KOH (20 mL of 50% w/w in water). The reaction mixture was heated at 120° C. for 25 h and the layers were separated. The aqueous layer was extracted with ethyl acetate (3×) and the combined organic layers were washed with saturated aqueous NaCl, dried over MgSO₄, filtered, and concentrated to dryness. The crude product 3-benzyloxy-1-tert-butoxycarbonyl-4-(2-pyridyl)piperidine-4-carboxylic acid (2.4 g, 5.8 mmol) was dissolved in DMF (30 mL) and was treated with sodium hydride (349 mg, 8.7 mmol)(60% dispersion in mineral oil). The reaction mixture was stirred at rt for 15 min and was treated with iodomethane (543 µL, 8.73 mmol). The reaction mixture was stirred at rt for 2 h and was partitioned between EtOAc and water. The aqueous layer was extracted with EtOAc (3×), the combined organic layers were washed with water (3×), saturated aqueous NaCl, dried (MgSO₄), filtered and concentrated to dryness. The crude material was purified by column chromatography (0-20% EtOAc-Hex) to provide O-1-tert-butyl O4-methyl(3R,4S)-3-benzyloxy-4-(2-pyridyl)piperidine-1,4-dicarboxylate (1.1 g, 44%). ESI-MS m/z calc. 426.5. found 427.5 (M+1)⁺; Retention time: 2.13 min (3 min run).

Step 5: tert-butyl(3R,4R)-3-benzyloxy-4-(methylsulfonyloxymethyl)-4-(2-pyridyl)piperidine-1-carboxylate

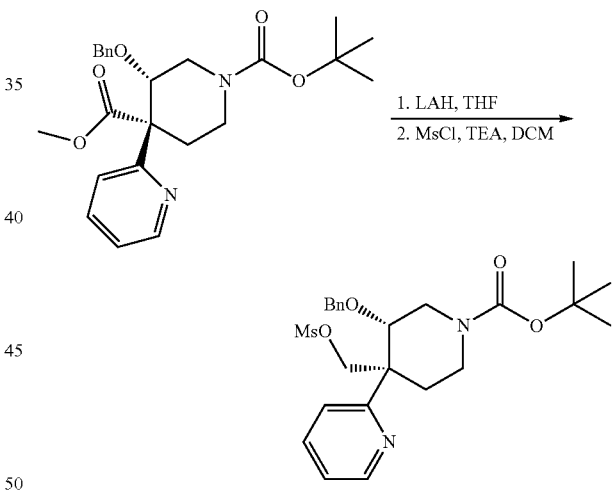

Step 1: To a refluxing solution of O1-tert-butyl O4-methyl (3R,4S)-3-benzyloxy-4-(2-pyridyl)piperidine-1,4-dicarboxylate (1.1 g, 2.6 mmol) in THF (30 mL) was added lithium aluminum hydride (1.5 mL of 2 M in THF, 3.1 mmol). The mixture was heated at reflux for 1 min and was cooled to 0° C. The reaction mixture was quenched sequentially with water (5 drops), 15% aqueous NaOH (5 drops) and water (15 drops). The resulting white precipitate was removed via filtration and washed with EtOAc. The filtrate was dried over MgSO₄, filtered and concentrated to dryness. The crude material was used directly in next step without further purification. To a solution of tert-butyl 3-benzyloxy-4-(hydroxymethyl)-4-(2-pyridyl)piperidine-1-carboxylate (200 mg, 0.50 mmol) in DCM (10 mL) was added triethylamine (210 µL, 1.51 mmol) followed by the addition of methanesulfonyl chloride (58 µl, 0.75 mmol). The reaction mixture was stirred at rt for 5 min, diluted with DCM, washed with water (3×), dried over MgSO$_4$, filtered and concentrated to dryness. The crude material was purified by column chromatography to provide tert-butyl(3R,4R)-3-benzyloxy-4-(methylsulfonyloxymethyl)-4-(2-pyridyl)piperidine-1-carboxylate (210 mg, 88%). ESI-MS m/z calc. 386.5. found 387.5 (M+1)$^+$; Retention time: 1.34 min (3 min run).

Step 6: tert-butyl(3R,4R)-3-hydroxy-4-(methylsulfonyloxymethyl)-4-(2-pyridyl)piperidine-1-carboxylate

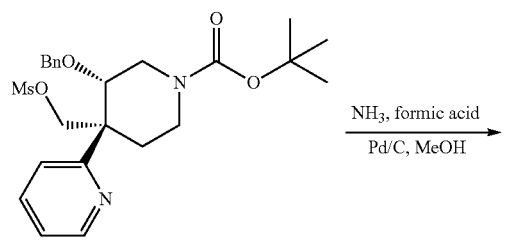

To a solution of tert-butyl 3-benzyloxy-4-(methylsulfonyloxymethyl)-4-(2-pyridyl)piperidine-1-carboxylate (200 mg, 0.42 mmol) in MeOH (20 mL) was added ammonium formate (530 mg, 8.4 mmol) and 10% Pd/C (92 mg, 0.09 mmol). The reaction mixture was heated at reflux for 10 min. The catalyst was removed via filtration through celite and washed with MeOH. The filtrate was concentrated to dryness. The residue was purified by column chromatography to provide tert-butyl(3R,4R)-3-hydroxy-4-(methylsulfonyloxymethyl)-4-(2-pyridyl)piperidine-1-carboxylate (105 mg, 65%) ESI-MS m/z calc. 386.5. found 387.5 (M+1)$^+$; Retention time: 1.34 min (3 min run).

Step 7: tert-butyl(1R,6R)-6-(2-pyridyl)-8-oxa-3-azabicyclo[4.2.0]octane-3-carboxylate

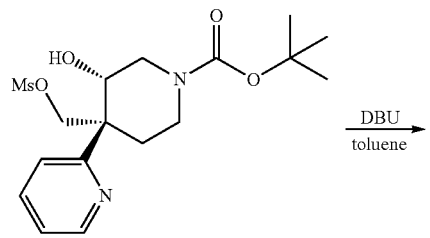

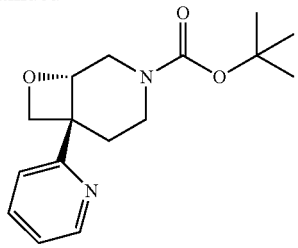

To a solution of tert-butyl(3R,4R)-3-hydroxy-4-(methylsulfonyloxymethyl)-4-(2-pyridyl)piperidine-1-carboxylate (100 mg, 0.26 mmol) in toluene (6 mL) was added DBU (46 µL, 0.31 mmol) The reaction mixture was heated at 120° C. for 16 h, diluted with ethyl acetate, washed with water (3×), dried over MgSO$_4$, filtered, and concentrated to dryness. The crude material was purified by column chromatography to provide tert-butyl(1R,6R)-6-(2-pyridyl)-8-oxa-3-azabicyclo[4.2.0]octane-3-carboxylate (42 mg, 56%). $^1$H NMR (400 MHz, CDCl$_3$) δ 8.59 (ddd, J=4.9, 1.7, 0.9 Hz, 1H), 7.70 (t, J=7.7 Hz, 1H), 7.19 (ddd, J=7.5, 4.9, 0.8 Hz, 1H), 7.09 (t, J=8.7 Hz, 1H), 5.39-5.23 (m, 1H), 4.99 (t, J=6.1 Hz, 1H), 4.72 (d, J=6.0 Hz, 1H), 4.18-3.78 (m, 3H), 3.47 (ddd, J=22.2, 15.4, 1.9 Hz, 1H), 2.20-2.07 (m, 2H), 1.48 (t, J=10.4 Hz, 10H). ESI-MS m/z calc. 290.2. found 291.5 (M+1)$^+$; Retention time: 1.17 min. (3 min run).

tert-butyl(3aR,7aR)-7a-(4-methoxy-2-pyridyl)-3a,4,6,7-tetrahydro-[1,3]dioxolo[4,5-c]pyridine-5-carboxylate

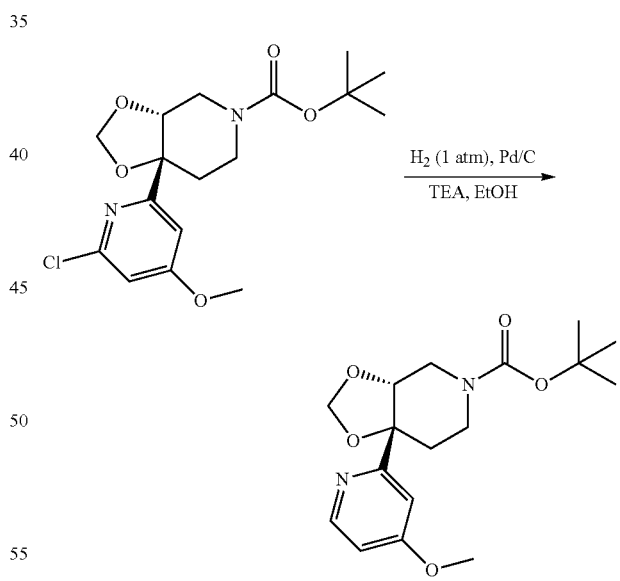

In a 100 mL round bottom flask equipped with a septa, tert-butyl(3aR,7aR)-7a-(6-chloro-4-methoxy-2-pyridyl)-3a,4,6,7-tetrahydro-[1,3]dioxolo[4,5-c]pyridine-5-carboxylate (1.09 g, 2.94 mmol) and triethylamine (410 µL, 2.94 mmol) were dissolved in ethanol (20 mL). Palladium (156 mg, 0.15 mmol) (10% on carbon) was added, and the mixture was degassed by bubbling nitrogen gas. The reaction mixture was vigorously stirred under hydrogen atmosphere (balloon) for 5 h. The suspension was degassed by bubbling nitrogen. The catalyst was removed by filtration through a pad of celite. The solid was thoroughly washed with ethanol. The filtrate was concentrated under reduce pressure to provide a the crude product. Purification by flash chromatography on silica gel (40 g column) using a gradient of AcOEt (0-100% over 20 min). provided tert-butyl(3aR,7aR)-7a-(4-methoxy-2-pyridyl)-3a,4,6,7-tetrahydro-[1,3]dioxolo[4,5-c]pyridine-5-carboxylate (907 mg, 91.7%) as a colorless oil that started to crystallize upon standing. ESI-MS m/z calc. 336.2. found 337.0 (M+1)$^+$; Retention time: 1.64 min (3 min run).

6-ethoxy-5-[2-(trifluoromethoxy)ethoxy]pyridine-2-carboxylic acid

Step 1: 6-chloro-5-hydroxy-pyridine-2-carbonitrile

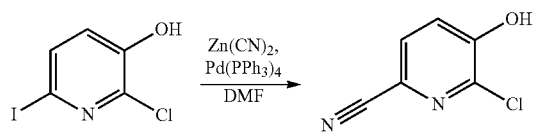

2-chloro-6-iodo-pyridin-3-ol (2.0 g, 7.8 mmol) was dissolved in DMF (15 mL), and dicyanozine (0.7 g, 5.9 mmol) was added. Nitrogen gas was bubbled through the reaction mixture before and after the addition of triphenylphosphine palladium (0) (0.6 g, 0.55 mmol). The reaction vessel was sealed under nitrogen and heated under microwave irradiation at 100° C. for 30 min. Volatiles were removed under reduced pressure. The remaining oil was dissolved in ethyl acetate (100 mL) and washed with water (100 mL) followed by saturated aqueous NaCl (2×100 mL). The organic layer was dried over sodium sulfate, filtered and concentrated under reduced pressure to provide a crystalline solid. Purification by silica gel column chromatography: 40 gram silica gel column, 0-50% ethyl acetate/hexane gradient over 20 min; provided 6-chloro-5-hydroxy-pyridine-2-carbonitrile (0.8 g, 63%) as a crystalline yellow-white solid. $^1$H NMR (400 MHz, CDCl$_3$) δ 7.65-7.59 (m, 1H), 7.42 (d, J=8.2 Hz, 1H). ESI-MS m/z calc. 154.0. found 155.0 (M+1)$^+$; Retention time: 0.72 min (3 min run).

Step 2: methyl 6-chloro-5-hydroxy-pyridine-2-carboxylate

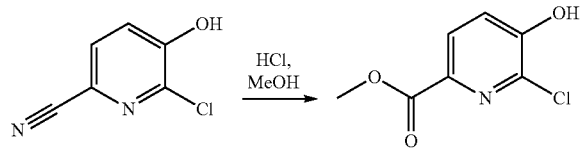

6-chloro-5-hydroxy-pyridine-2-carbonitrile (7.1 g, 45.8 mmol) was dissolved in methanol (25 mL), and a solution of HCl (100 mL of 4 M, 400.0 mmol) in dioxane was added. The reaction mixture was stirred in a pre-heated 80° C. oil bath for 36 h. Additional methanol and HCl/dioxane was sequentially added to help progress the reaction. Volatiles were removed under reduced pressure to obtain a yellow solid which was filtered through a plug of silica gel. The filtrate was concentrated and dissolved in 1,4-dioxane (50 mL) at 65° C. Hot hexane (75 mL) was added to the solution, and the resulting slurry was allowed to slowly cool to rt. The crystalline solids were collected by vacuum filtration, rinsing with hexane. $^1$H NMR (400 MHz, CDCl$_3$) δ 8.07 (d, J=8.3 Hz, 1H), 7.47-7.40 (m, 1H), 6.13 (s, 1H), 3.98 (s, 3H). ESI-MS m/z calc. 187.0. found 188.3 (M+1)$^+$; Retention time: 0.36 min (3 min run).

Step 3: methyl 6-chloro-5-[2-(trifluoromethoxy)ethoxy]pyridine-2-carboxylate

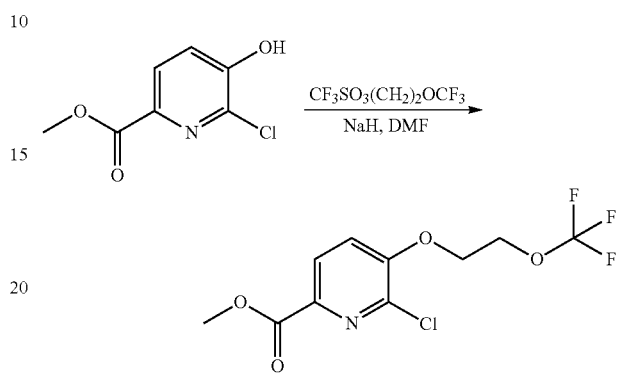

A solution of methyl 6-chloro-5-hydroxy-pyridine-2-carboxylate (2.5 g, 13.3 mmol) in DMF (15 mL) was treated slowly with sodium hydride (0.5 g, 12.6 mmol) (60 wt % dispersion in mineral oil) portionwise. The reaction mixture was allowed to stir at rt for 15 min and cooled to −10° C. prior to the slow dropwise addition of neat 2-(trifluoromethoxy)ethyl trifluoromethanesulfonate (4.5 g, 17.3 mmol) over 5 min. An exotherm was observed during addition. The reaction mixture was then allowed to slowly warm to rt and stirred for 1 h. Water (10 mL) was added, and the mixture was concentrated under reduced pressure. The remaining residue was resuspended in water (75 mL) and extracted with ethyl acetate (3×75 mL). The combined organic layers were dried over sodium sulfate, filtered and concentrated under reduced pressure. The remaining solid was briefly stirred in DCM (50 mL), and the remaining white solids were removed by vacuum filtration. The filtrate was again concentrated under reduced pressure and purified by silica gel column chromatography: 80 gram silica gel column, 0-40% ethyl acetate/hexane gradient over 30 min; product eluted at 30%. Pure fractions were combined and concentrated to afford methyl 6-chloro-5-[2-(trifluoromethoxy)ethoxy]pyridine-2-carboxylate (2.9 g, 74%) as a light brown crystalline solid. $^1$H NMR (400 MHz, CDCl$_3$) δ 8.10 (d, J=8.4 Hz, 1H), 7.28 (d, J=8.4 Hz, 1H), 4.45-4.38 (m, 2H), 4.36 (dd, J=5.8, 3.4 Hz, 2H), 3.98 (s, 3H). ESI-MS m/z calc. 299.0. found 300.4 (M+1)$^+$; Retention time: 1.47 min (3 min run).

Step 4: 6-ethoxy-5-[2-(trifluoromethoxy)ethoxy]pyridine-2-carboxylic acid

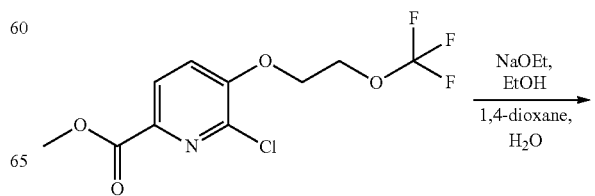

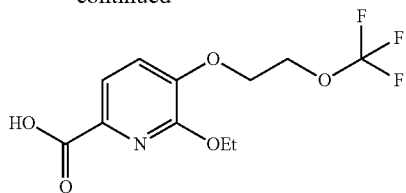

A solution of methyl 6-chloro-5-[2-(trifluoromethoxy)ethoxy]pyridine-2-carboxylate (250 mg, 0.83 mmol) in 1,4-dioxane was treated with sodium ethanolate (2.0 mL of 21% w/v, 6.2 mmol) and water (50 μL, 2.78 mmol). The reaction mixture was heated under microwave irradiation at 100° C. for 1 h. The reaction mixture was partioned between ethyl acetate (75 mL) and water (50 mL). The organic layer was dried over sodium sulfate, filtered, and concentrated under reduced pressure. The crude product was purified by UV-triggered reverse-phase HPLC: 10-99% acetonitrile/water gradient over 15 min to provide 6-ethoxy-5-[2-(trifluoromethoxy)ethoxy]pyridine-2-carboxylic acid (18 mg, 7.3%) as a light brown foaming solid. $^1$H NMR (400 MHz, CDCl$_3$) δ 7.82 (d, J=8.0 Hz, 1H), 7.21 (d, J=8.0 Hz, 1H), 4.47 (q, J=7.1 Hz, 2H), 4.36 (dt, J=15.8, 4.1 Hz, 4H), 1.49 (t, J=7.1 Hz, 3H). ESI-MS m/z calc. 295.1. found 296.4 (M+1)$^+$; Retention time: 1.38 min (3 min run).

The following compounds were prepared using the procedure reported above.

| Product | Precursor |
| --- | --- |
| 6-ethoxy-5-[2-(trifluoromethoxy)ethoxy]pyridine-2-carboxylic acid | methyl 6-chloro-5-hydroxy-pyridine-2-carboxylate |
| 6-methoxy-5-[2-(trifluoromethoxy)ethoxy]pyridine-2-carboxylic acid | methyl 6-chloro-5-hydroxy-pyridine-2-carboxylate |

5-(2-fluoro-2-methyl-propoxy)-6-methoxy-pyridine-2-carboxylic acid

Step 1: methyl 6-chloro-5-(2-hydroxy-2-methyl-propoxy)pyridine-2-carboxylate

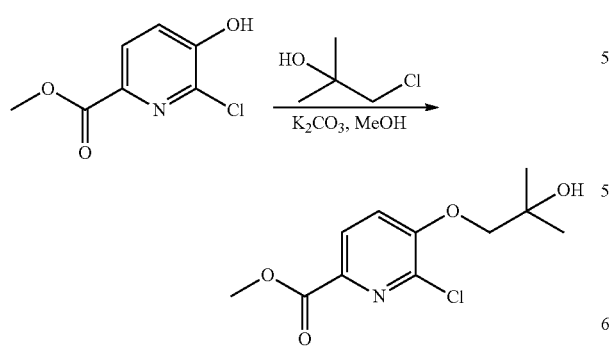

A solution of methyl 6-chloro-5-hydroxy-pyridine-2-carboxylate (1.6 g, 8.3 mmol) in methanol (1.5 mL) was treated with finely ground potassium carbonate (4.6 g, 33.0 mmol). The reaction mixture was heated to 80° C. and 1-chloro-2-methyl-propan-2-ol (1.7 mL, 16.5 mmol) was added. The reaction mixture was heated at 80° C. overnight. The reaction mixture was concentrated under reduced pressure. The remaining residue was suspended in water (75 mL) and extracted with ethyl acetate (2×75 mL). Organic layers were combined, dried over sodium sulfate, filtered and concentrated under reduced pressure. The resulting oil was purified by silica gel column chromatography: 40 gram silica gel column, 0-30% ethyl acetate/hexane gradient over 25 min to afford methyl 6-chloro-5-(2-hydroxy-2-methyl-propoxy)pyridine-2-carboxylate (1.2 g, 54%) was obtained as a colorless solid. $^1$H NMR (400 MHz, CDCl$_3$) δ 8.09 (d, J=8.4 Hz, 1H), 7.27 (d, J=8.4 Hz, 1H), 3.98 (s, 3H), 3.94 (s, 2H), 1.41 (s, 6H). ESI-MS m/z calc. 259.1. found 260.2 (M+1)+; Retention time: 0.99 min (3 min run).

Step 2: methyl 6-chloro-5-(2-fluoro-2-methyl-propoxy)pyridine-2-carboxylate

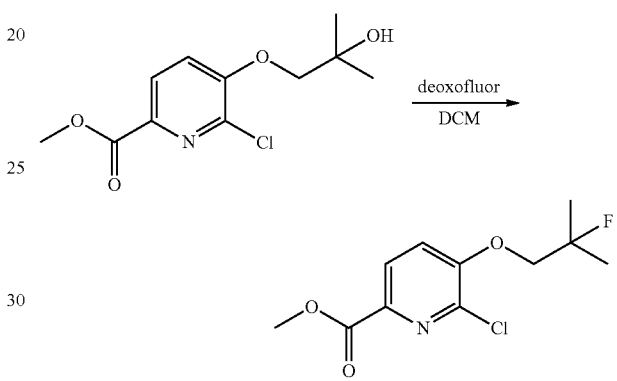

A solution of methyl 6-chloro-5-(2-hydroxy-2-methyl-propoxy)pyridine-2-carboxylate (500 mg, 1.93 mmol) in DCM, and 2-methoxy-N-(2-methoxyethyl)-N-(trifluoro-4-sulfanyl)ethanamine (391 μL, 2.12 mmol) was slowly added at rt. A water bath was used to maintain the reaction mixture near rt. After 2 h, the reaction mixture was diluted with DCM (75 mL) and washed with water (1×75 mL). The aqueous layer was further extracted with DCM (2×75 mL). All organic layers were combined, dried over sodium sulfate, filtered and concentrated under reduced pressure. The crude product was purified by silica gel column chromatography: 12 gram silica gel column, 0-40% ethyl acetate/hexane gradient over 20 min to provide methyl 6-chloro-5-(2-fluoro-2-methyl-propoxy)pyridine-2-carboxylate (170 mg, 34%) was obtained as a clear colorless oil that crystallized upon standing. $^1$H NMR (400 MHz, CDCl$_3$) δ 8.08 (d, J=8.4 Hz, 1H), 7.28 (d, J=8.4 Hz, 1H), 4.09 (d, J=16.5 Hz, 2H), 3.98 (s, 3H), 1.60-1.52 (m, 6H). ESI-MS m/z calc. 261.1. found 262.2 (M+1)$^+$; Retention time: 1.41 min (3 min run).

Step 3: 5-(2-fluoro-2-methyl-propoxy)-6-methoxy-pyridine-2-carboxylic acid

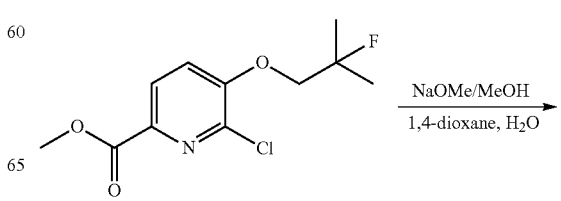

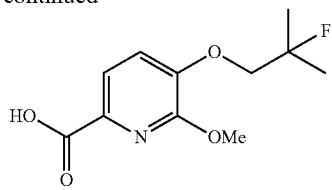

A solution of methyl 6-chloro-5-(2-fluoro-2-methyl-propoxy)pyridine-2-carboxylate (170 mg, 0.65 mmol) in 1,4-dioxane (2 mL) was treated with sodium methoxide (3.00 mL of 0.5 M, 1.500 mmol) in methanol followed by water (50 µL, 2.78 mmol). The reaction mixture was heated by microwave irradiation at 100° C. for 1 h, then at 120° C. for 30 min. Volatiles were removed under reduced pressure, and the remaining solid was dissolved in water (20 mL) and adjusted to pH 2 with the addition of aqueous 1 N HCl solution. The resulting solution was extracted with DCM (3×50 mL). Organic layers were combined, dried over sodium sulfate, filtered and concentrated under reduced pressure to a clear colorless oil. Purification by reverse-phase HPLC (1-99% acetonitrile water gradient over 15 min) provided 5-(2-fluoro-2-methyl-propoxy)-6-methoxy-pyridine-2-carboxylic acid. ESI-MS m/z calc. 243.1. found 244.3 (M+1)$^+$; Retention time: 1.14 min (3 min run).

5-(2-fluoro-2-methyl-propoxy)-6-methoxy-pyridine-2-carboxylic acid

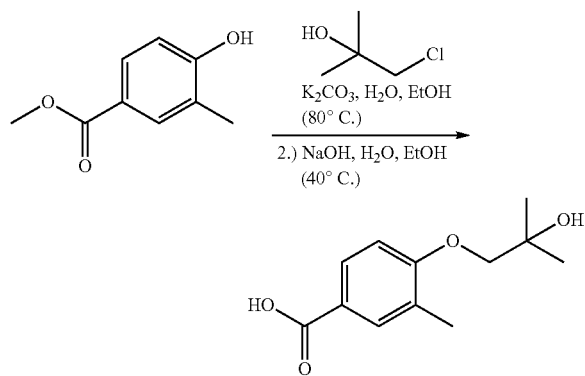

A mixture of 1-chloro-2-methyl-propan-2-ol (10 mL), 4-hydroxy-3-methyl-benzoic acid (2.0 g, 13.2 mmol), K$_2$CO$_3$ (7.3 g, 52.7 mmol), H$_2$O (6.0 mL) and ethanol (60 mL) was heated at 80° C. overnight. The reaction mixture was cooled to rt, partitioned between 1N NaOH and EtOAc and the layers separated. The organic layer was washed with 1N NaOH (2×) and the combined aqueous layers were washed with EtOAc. The combined organics were concentrated under reduced pressure and diluted with EtOH (15 mL). The mixture was treated with H$_2$O (2 mL) and NaOH (1.0 g, 26.3 mmol). The reaction mixture was stirred at 40° C. for 4 h. The reaction mixture was poured into 1N NaOH and extracted with ether (2×). The pH was brought to 2-3 with 6N HCl and the aqueous material was extracted with EtOAc (3×). The organics were combined, washed with saturated aqueous NaCl, dried (Na$_2$SO$_4$), filtered, and evaporated to dryness. The material was triturated with ether to provide 4-(2-hydroxy-2-methyl-propoxy)-3-methyl-benzoic acid (2.2 g, 75%) as a white solid. $^1$H NMR (400 MHz, DMSO) δ 7.75 (dd, J=8.5, 2.0 Hz, 1H), 7.73-7.70 (m, 1H), 6.96 (d, J=8.6 Hz, 1H), 4.67 (s, 1H, OH), 3.76 (s, 2H), 2.20 (s, 3H), 1.22 (s, 6H). ESI-MS m/z calc. 224.1. found 225.5 (M+1)$^+$; Retention time: 1.06 min (3 min run).

The following compounds were prepared using the procedure reported above.

| Product | Precursor |
|---|---|
| 4-(2-hydroxy-2-methylpropoxy)-3-methylbenzoic acid | methyl 4-(2-hydroxy-2-methylpropoxy)-3-methylbenzoate |
| 4-(2-hydroxy-2-methylpropoxy)-3-methoxybenzoic acid | methyl 4-(2-hydroxy-2-methylpropoxy)-3-methoxybenzoate |
| 4-(2-hydroxy-2-methylpropoxy)-3-chlorobenzoic acid | methyl 4-(2-hydroxy-2-methylpropoxy)-3-chlorobenzoate |

6-methyl-5-[2-(trifluoromethoxy)ethoxy]pyridine-2-carboxylic acid

Step 1: methyl 6-methyl-5-[2-(trifluoromethoxy)ethoxy]pyridine-2-carboxylate

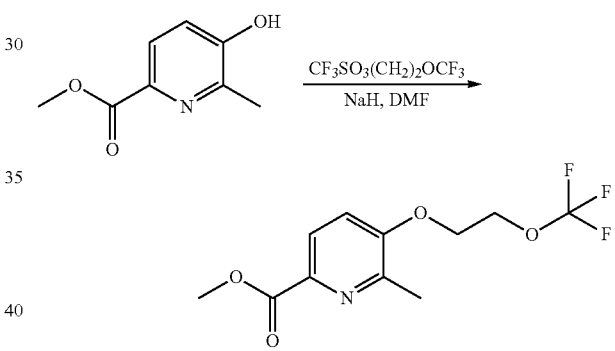

A solution of methyl 5-hydroxy-6-methyl-pyridine-2-carboxylate (2.0 g, 12.1 mmol) in DMF (12 mL) was cooled to 0° C. before the slow addition of sodium hydride (0.5 g, 11.5 mmol) (60 wt % dispersion in mineral oil). The reaction mixture was allowed to stir at rt for 10 min before it was cooled to −10° C. 2-(trifluoromethoxy)ethyl trifluoromethanesulfonate (4.1 g, 15.8 mmol) was slowly added neat to the reaction mixture over 5 min. An exotherm was observed during the addition. The reaction mixture was allowed to stir at rt for 1 h. Water (50 mL) was added to the reaction mixture, and it was concentrated under reduced pressure. The remaining solid was partitioned between ethyl acetate (75 mL) and water (75 mL). The organic layer was dried over sodium sulfate, filtered, and concentrated under reduced pressure. The crude product was purified by silica gel column chromatography: 5-20% ethyl acetate/hexane gradient providing methyl 6-methyl-5-[2-(trifluoromethoxy)ethoxy]pyridine-2-carboxylate (1.6 g, 48%) as a light brown crystalline solid. $^1$H NMR (400 MHz, CDCl$_3$) δ 8.02 (d, J=8.4 Hz, 1H), 7.12 (d, J=8.5 Hz, 1H), 4.38 (dd, J=5.6, 3.5 Hz, 2H), 4.30-4.26 (m, 2H), 3.98 (s, 3H), 2.57 (s, 3H). ESI-MS m/z calc. 279.1. found 280.3 (M+1)$^+$; Retention time: 1.29 min (3 min run).

Step 2: 6-methyl-5-[2-(trifluoromethoxy)ethoxy]pyridine-2-carboxylic acid

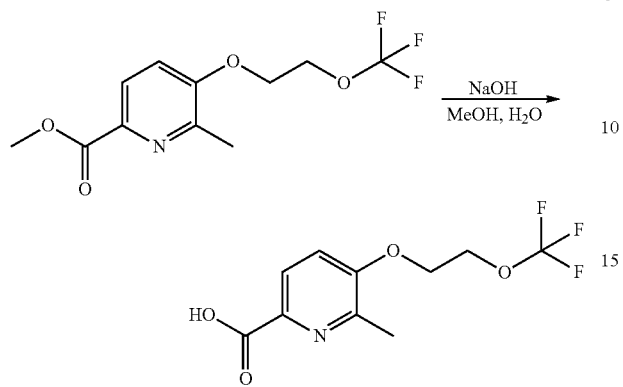

To a solution of methyl 6-methyl-5-[2-(trifluoromethoxy)ethoxy]pyridine-2-carboxylate (1.6 g, 5.9 mmol) in methanol (10 mL) was added a solution of sodium hydroxide (2.3 g, 58.7 mmol) in water (5 mL). The reaction mixture was stirred at 45° C. for 30 min. After cooling to rt, it was acidified to pH 5 with the addition of an aqueous 1 N HCl solution. The mixture was extracted with DCM (3×50 mL). The organic layers were combined, dried over sodium sulfate, filtered and concentrated under reduced pressure to provide 6-methyl-5-[2-(trifluoromethoxy)ethoxy]pyridine-2-carboxylic acid (1.5 g, 94%) as a white powder. $^1$H NMR (400 MHz, CDCl$_3$) δ 8.07 (d, J=8.4 Hz, 1H), 7.24 (t, J=10.5 Hz, 1H), 4.39 (d, J=3.9 Hz, 2H), 4.29 (t, J=13.6 Hz, 2H), 2.53 (s, 3H). ESI-MS m/z calc. 265.1. found 266.3 (M+1)$^+$; Retention time: 0.78 min (3 min run).

5-(2-hydroxy-2-methyl-propoxy)-6-methoxy-pyridine-2-carboxylic acid

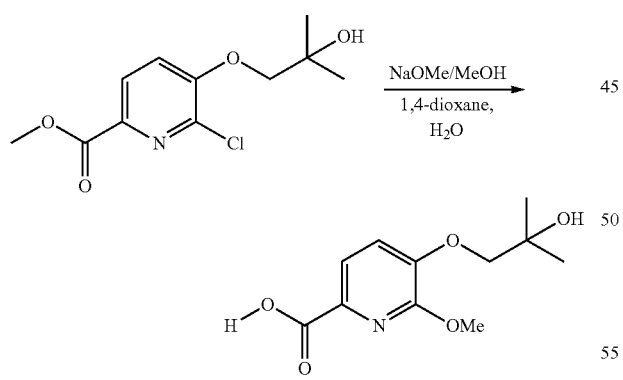

To a solution of methyl 6-chloro-5-(2-hydroxy-2-methyl-propoxy)pyridine-2-carboxylate (200 mg, 0.77 mmol) in 1,4-dioxane (1 mL) was added a solution of sodium methoxide (3 mL of 0.5 M, 1.5 mmol) in methanol, followed by water (50 μL, 2.8 mmol). The reaction mixture was heated under microwave irradiation at 100° C. for 1 h. Volatiles were removed under reduced pressure, and the remaining solid was dissolved in water (20 mL) and adjusted to pH 2 with the addition of aqueous 1 N HCl solution. The resulting solution was extracted with DCM (3×50 mL) and the organic layers were combined, dried over sodium sulfate, filtered and concentrated under reduced pressure to provide a colorless oil. Purification by reverse-phase HPLC (1-99% acetonitrile water gradient over 15 min) provided 5-(2-hydroxy-2-methyl-propoxy)-6-methoxy-pyridine-2-carboxylic acid (49 mg, 24%). $^1$H NMR (400 MHz, CDCl$_3$) δ 7.84 (d, J=8.0 Hz, 1H), 7.20 (d, J=8.0 Hz, 1H), 4.06 (s, 3H), 3.89 (s, 2H), 1.39 (s, 6H). ESI-MS m/z calc. 241.1. found 242.3 (M+1)$^+$; Retention time: 0.77 min (3 min run).

2-(trifluoromethoxymethyl)-2,3-dihydro-1,4-benzodioxine-6-carboxylic acid

Step 1: methyl 2-(methylsulfanylcarbothioyloxymethyl)-2,3-dihydro-1,4-benzodioxine-6-carboxylate

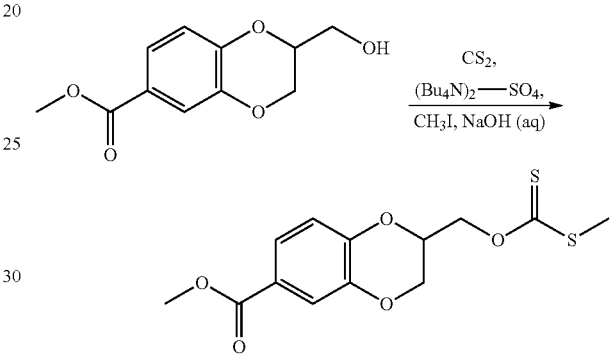

To methyl 2-(hydroxymethyl)-2,3-dihydro-1,4-benzodioxine-6-carboxylate (0.9 g, 4.0 mmol) and tetrabutylammonium sulfate (186 μL, of 50% w/v, 0.16 mmol) under N$_2$ was added NaOH (8 mL of 50% w/v in H$_2$O, 100.0 mmol) portionwise. The viscous mixture was stirred for 10 min and CS$_2$ (7.2 mL, 120.0 mmol) was added dropwise followed by iodomethane (18.8 g, 132.5 mmol). The viscous biphasic mixture was stirred overnight, diluted with water (20 mL), and the organic layer was separated. The aqueous mixture was extracted with dichloromethane (3×20 mL). The combined organics were washed with saturated aqueous NaCl (2×10 mL), dried over MgSO$_4$, evaporated and purified by column chromatography to provide methyl 2-(methylsulfanylcarbothioyloxymethyl)-2,3-dihydro-1,4-benzodioxine-6-carboxylate. $^1$H NMR (400 MHz, CDCl$_3$) δ 7.64-7.54 (m, 2H), 6.99-6.89 (m, 1H), 4.83 (qd, J=11.8, 5.2 Hz, 2H), 4.69-4.60 (m, 1H), 4.37 (dd, J=11.6, 2.4 Hz, 1H), 4.14 (dd, J=11.6, 6.8 Hz, 1H), 3.88 (s, 3H), 2.59 (s, 3H).

Step 2: methyl 2-((trifluoromethoxy)methyl)-2,3-dihydrobenzo[b][1,4]dioxine-6-carboxylate

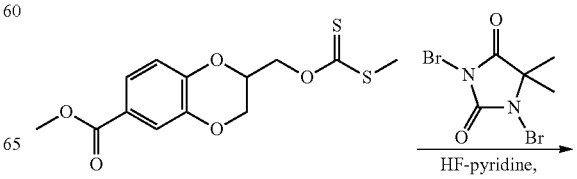

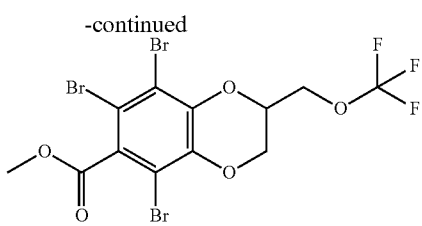

To a suspension of 5,5-dimethyl-1,3-dibromohydantoin (860 mg, 3.0 mmol) in DCM (5 mL) was added pyridine (hydrofluoric acid) (870 μL of 70% w/w, 6.0 mmol) at −78° C. dropwise under Ar. The reaction mixture was stirred at −78° C. for 5 min and treated with methyl 2-(methylsulfanylcarbothioyloxymethyl)-2,3-dihydro-1,4-benzodioxine-6-carboxylate (157 mg, 0.50 mmol) in DCM (2 mL) dropwise. The reaction mixture was stirred at −78° C. for 15 min. The cooling bath was removed and the reaction mixture was allowed to warm to rt and the mixture was stirred at rt overnight. Water was added and the mixture was extracted with DCM (2×). The combined organic layers were dried over MgSO$_4$, filtered and concentrated to dryness. The crude material was purified by column chromatography (0-10%) to provide methyl 5,6,8-tribromo-3-(trifluoromethoxymethyl)-2,3-dihydro-1,4-benzodioxine-7-carboxylate (180 mg, 68%). $^1$H NMR (400 MHz, CDCl$_3$) δ 4.58 (d, J=6.5 Hz, 1H), 4.47 (dd, J=11.8, 2.5 Hz, 1H), 4.24 (tdd, J=10.1, 8.4, 4.1 Hz, 3H), 3.97 (s, 3H).

Step 3: methyl 2-((trifluoromethoxy)methyl)-2,3-dihydrobenzo[b][1,4]dioxine-6-carboxylate

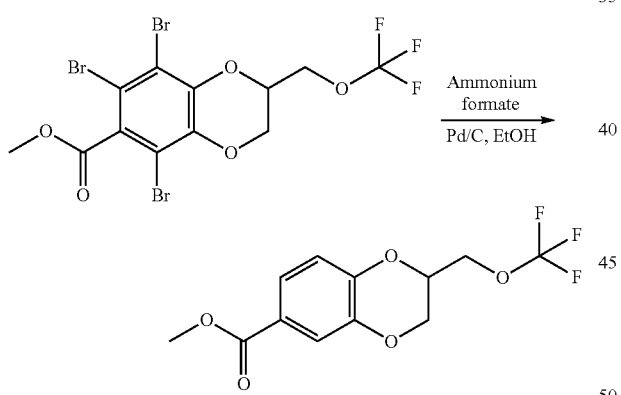

To a solution of methyl 5,6,8-tribromo-3-(trifluoromethoxymethyl)-2,3-dihydro-1,4-benzodioxine-7-carboxylate (3.1 g, 5.8 mmol) in EtOH (100 mL) was added ammonium formate (3.1 g, 49.2 mmol) and 10% palladium/carbon (620 mg, 0.58 mmol). The reaction mixture was heated at reflux for 30 min. The catalyst was removed via filtration and washed with EtOH. The filtrate was concentrated to dryness. The resulting residue was repartitioned between EtOAc and water. The aqueous layer was extracted with EtOAc (3×). The combined organic layers were washed with saturated aqueous NaCl, dried over MgSO$_4$, filtered and concentrated to dryness to provide methyl 2-(trifluoromethoxymethyl)-2,3-dihydro-1,4-benzodioxine-6-carboxylate (1.5 g, 88%). The crude material was used directly in next step without further purification. $^1$H NMR (400 MHz, CDCl$_3$) δ 7.64-7.53 (m, 2H), 7.02-6.88 (m, 1H), 4.50 (dd, J=6.0, 2.0 Hz, 1H), 4.34 (dd, J=11.7, 2.4 Hz, 1H), 4.26-4.08 (m, 3H), 3.88 (s, 3H).

Step 4: 2-(trifluoromethoxymethyl)-2,3-dihydro-1,4-benzodioxine-6-carboxylic acid

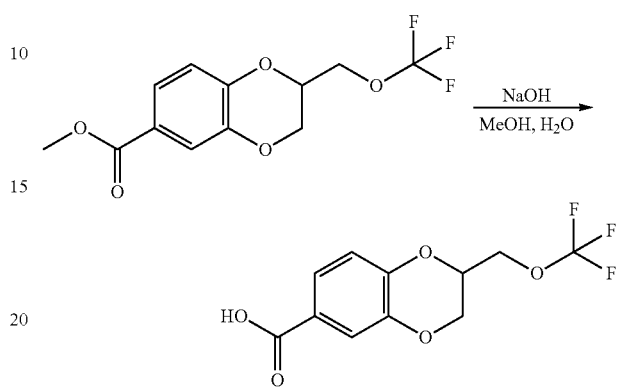

To a solution of methyl 2-(trifluoromethoxymethyl)-2,3-dihydro-1,4-benzodioxine-6-carboxylate (165 mg, 0.56 mmol) in MeOH (3 mL) was added NaOH (113 mg, 2.82 mmol) in water (1 mL). The reaction mixture was stirred at rt for 72 h, diluted with H$_2$O, and acidified using 1 N HCl to pH ~2. The resulting precipitate was collected via vacuum filtration and washed with cold water to provide 2-(trifluoromethoxymethyl)-2,3-dihydro-1,4-benzodioxine-6-carboxylic acid (140 mg, 89.1%). $^1$H NMR (400 MHz, CDCl$_3$) δ 7.67 (td, J=4.5, 2.0 Hz, 2H), 7.04-6.88 (m, 1H), 4.52 (td, J=7.8, 2.4 Hz, 1H), 4.36 (dd, J=11.7, 2.4 Hz, 1H), 4.28-4.07 (m, 3H).

4-(2-fluoro-2-methyl-propoxy)-3-methyl-benzoic acid

Step 1: methyl 4-(2-fluoro-2-methyl-propoxy)-3-methyl-benzoate

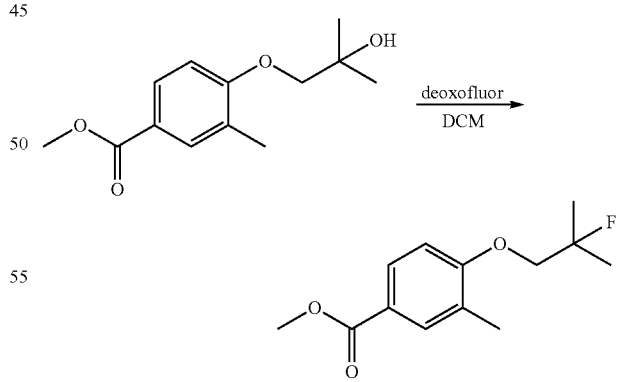

A solution of methyl 4-(2-hydroxy-2-methyl-propoxy)-3-methyl-benzoate (4.0 g, 16.8 mmol) was dissolved in DCM (40 mL) and treated with deoxy-fluor (3.4 mL, 18.5 mmol) slowly while a water bath was used to keep the reaction mixture near rt. The reaction mixture was allowed to stir at rt for 2 h, diluted with DCM (35 mL), and washed with water (75 mL). The organic layer was dried over sodium sulfate, filtered and concentrated under reduced pressure. The crude product was purified by silica gel column chromatography: 80 gram silica gel column, 0-10% ethyl acetate/hexane gradient over 30 min; providing methyl 4-(2-fluoro-2-methyl-propoxy)-3-methyl-benzoate (2.5 g, 62%) as a clear colorless oil. $^1$H NMR (400 MHz, CDCl$_3$) δ 7.90-7.83 (m, 2H), 6.80 (d, J=8.5 Hz, 1H), 3.99 (d, J=16.5 Hz, 2H), 3.88 (s, 3H), 2.28 (s, 3H), 1.52 (d, J=21.4 Hz, 6H). ESI-MS m/z calc. 240.1. found 241.4 (M+1)$^+$; Retention time: 1.86 min (3 min run).

Step 2:
4-(2-fluoro-2-methyl-propoxy)-3-methyl-benzoic acid

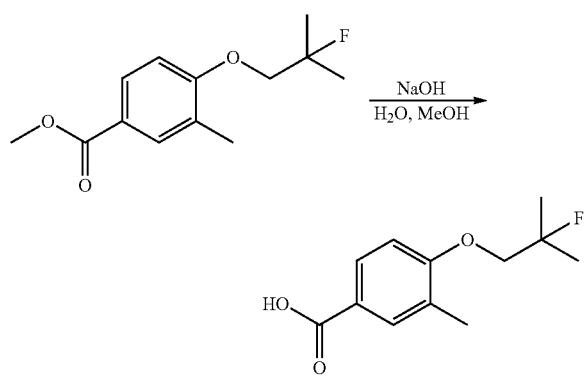

To a solution of methyl 4-(2-fluoro-2-methyl-propoxy)-3-methyl-benzoate (2.5 g, 10.4 mmol) dissolved in methanol (2 mL) was added a solution of sodium hydroxide (1.2 g, 31.1 mmol) in water (6 mL). The reaction mixture was allowed to stir at 55° C. for 30 min. The resulting clear solution was concentrated under reduced pressure. The obtained white solid was redissolved in water (50 mL) and washed with ethyl acetate (1×50 mL). The aqueous layer was adjusted to pH 2 with the addition of aqueous 1 N HCl solution, resulting in a cloudy white suspension. The mixture was extracted with ethyl acetate (2×75 mL) and the combined organics were dried over sodium sulfate, filtered and concentrated under reduced pressure to provide 4-(2-fluoro-2-methyl-propoxy)-3-methyl-benzoic acid (1.9 g, 81%) as a white solid. $^1$H NMR (400 MHz, CDCl$_3$) δ 7.96 (dd, J=8.5, 2.2 Hz, 1H), 7.92 (d, J=1.4 Hz, 1H), 6.84 (d, J=8.6 Hz, 1H), 4.01 (d, J=16.5 Hz, 2H), 2.30 (s, 3H), 1.54 (d, J=21.4 Hz, 6H). ESI-MS m/z calc. 226.1. found 453.3 (M+1)+; Retention time: 1.53 min (3 min run).

3-methoxy-4-(2-(trifluoromethoxy)ethoxy)benzoic acid

Step 1: methyl 3-methoxy-4-[2-(trifluoromethoxy) ethoxy]benzoate

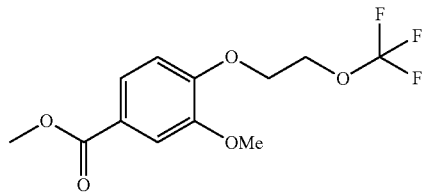

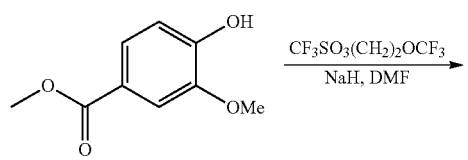

A 100 mL RB flask was fitted with a teflon stirrer bar, a magnetic stirrer, a cooling bath and a nitrogen inlet/outlet. The vessel was charged under a nitrogen atmosphere with 60% sodium hydride (1.1 g, 26.7 mmol) in mineral oil and cooled to 0° C. with an ice bath. The vessel was then charged with N,N-dimethylformamide (35 ml) via syringe and stirring was commenced. The vessel was then charged with methyl 4-hydroxy-3-methoxy-benzoate (4.9 g, 26.7 mmol) as a solid in 4 equal portions over 20 min resulting in slight foaming. The reaction mixture was stirred for 20 min and then treated with 2-(trifluoromethoxy)ethyl trifluoromethanesulfonate (14.0 g, 26.7 mmol) neat via canula over 10 min. The cooling bath was removed and the reaction mixture was continued to stir and allowed to warm to rt. The reaction mixture was heated to 40° C. for 30 min, After cooling to rt the reaction mixture was poured onto crushed ice (150 g). The mixture was diluted with water (150 ml) and then transferred to a separatory funnel and partitioned with ethyl acetate (250 ml). The organic was removed and the aqueous layer was extracted with ethyl acetate (2×100 ml). The combined organics were washed with 0.1 M NaOH aqueous solution (2×150 ml), saturated aqueous sodium chloride (4×150 ml), dried over sodium sulfate (250 g), and filtered through a glass frit Buchner funnel. The filtrate was concentrated under reduced pressure. Purification by flash column chromatography (SiO$_2$-220 g, 0-20% ethyl acetate-hexanes) afforded methyl 3-methoxy-4-[2-(trifluoromethoxy)ethoxy]benzoate (7.5 g, 95%). $^1$H NMR (400 MHz, CDCl$_3$) δ 7.68 (dd, J=8.4, 2.0 Hz, 1H), 7.59 (d, J=2.0 Hz, 1H), 6.92 (d, J=8.4 Hz, 1H), 4.41-4.29 (m, J=8.3, 5.3, 2.7 Hz, 4H), 3.94 (s, 3H), 3.92 (s, 3H).

The following compounds were prepared using the procedure reported above.

| Product | Precursor |
| --- | --- |
| methyl 3-methoxy-4-[2-(trifluoromethoxy)ethoxy]benzoate | Methyl 4-hydroxy-3-methoxy-benzoate |
| methyl 3-methyl-4-[2-(trifluoromethoxy)ethoxy]benzoate | Methyl 4-hydroxy-3-methyl-benzoate |
| methyl 3-chloro-4-(2-(trifluoromethoxy)ethoxy)benzoate | Methyl 4-hydroxy-3-chloro-benzoate |
| methyl 3-fluoro-4-[2-(trifluoromethoxy)ethoxy]benzoate | Methyl 4-hydroxy-3-fluoro-benzoate |
| methyl 3-chloro-5-methoxy-4-(2-(trifluoromethoxy)ethoxy)benzoate | methyl 3-chloro-4-hydroxy-5-methoxybenzoate |

Step 2: 3-methoxy-4-(2-(trifluoromethoxy)ethoxy)benzoic acid

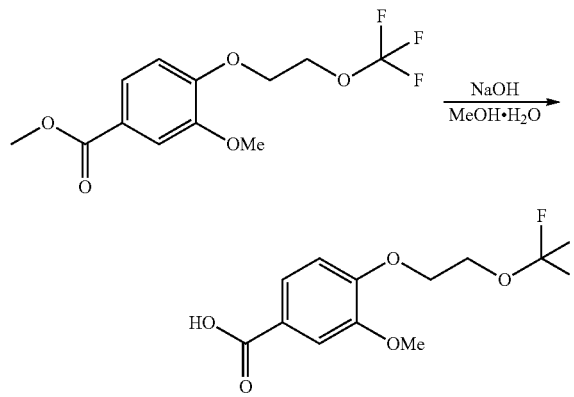

A solution of methyl 3-methoxy-4-[2-(trifluoromethoxy)ethoxy]benzoate (5.1 g, 17.5 mmol) in methyl alcohol (24 mL) was treated with aqueous sodium hydroxide (96.1 mL of 1 M, 96.1 mmol). The reaction mixture was heated to 50° C. for 1 h (reaction mixture became homogeneous during this time). After cooling to rt the methyl alcohol was removed under reduced pressure. The remaining aqueous mixture was treated with cold 37 wt. % HCl until pH-1 which resulted in the formation of a precipitate. The solid was collected by vacuum filtration in a glass frit Buchner funnel and washed with water (2×150 ml). The material was further dried under vacuum to provide 3-methoxy-4-(2-(trifluoromethoxy)ethoxy)benzoic acid (4.3 g, 88%) as a white solid. $^1$H NMR (400 MHz, DMSO) δ 12.73 (s, 1H), 7.55 (dd, J=8.4, 2.0 Hz, 1H), 7.47 (d, J=1.9 Hz, 1H), 7.08 (d, J=8.5 Hz, 1H), 4.43 (dd, J=5.3, 3.0 Hz, 2H), 4.38-4.24 (m, 2H), 3.82 (s, 3H). ESI-MS m/z calc. 280.1. found 281.1 (M+1)$^+$; Retention time: 0.52 min (3 min run).

The following compounds were prepared using the procedure reported above.

| Product | Precursor |
| --- | --- |
| 3-methoxy-4-(2-(trifluoromethoxy)ethoxy)benzoic acid | methyl 3-methoxy-4-[2-(trifluoromethoxy)ethoxy]benzoate |
| 3-methyl-4-(2-(trifluoromethoxy)ethoxy)benzoic acid | methyl 3-methyl-4-[2-(trifluoromethoxy)ethoxy]benzoate |
| 1 3-chloro-4-(2-(trifluoromethoxy)ethoxy)benzoic acid | methyl 3-chloro-4-(2-(trifluoromethoxy)ethoxy)benzoate |
| 3-fluoro-4-[2-(trifluoromethoxy)ethoxy]benzoic acid | methyl 3-fluoro-4-[2-(trifluoromethoxy)ethoxy]benzoate |
| 3-chloro-5-methoxy-4-(2-(trifluoromethoxy)ethoxy)benzoic acid | methyl 3-chloro-5-methoxy-4-(2-(trifluoromethoxy)ethoxy)benzoate |

3-methyl-4-(2,2,2-trifluoroethoxy)benzoic acid

Step 1: methyl 3-methyl-4-(2,2,2-trifluoroethoxy)benzoate

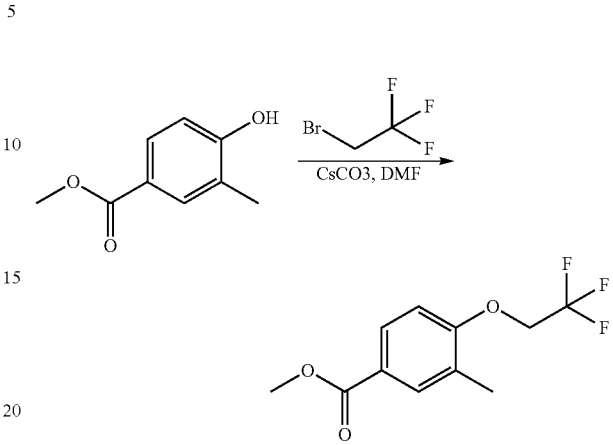

To a solution of methyl 4-hydroxy-3-methyl-benzoate (1.6 g, 10 mmol) in DMF (20 mL) was added cesium carbonate (2.7 g, 20.0 mmol) and 2-bromo-1,1,1-trifluoro-ethane (1.8 mL, 20.0 mmol). The reaction mixture was heated at 80° C. overnight and was recharged with 2-bromo-1,1,1-trifluoro-ethane (1 mL, 11 mmol) and heated at 80° C. overnight. The reaction mixture was recharged again with 2-bromo-1,1,1-trifluoro-ethane (2 mL, 22 mmol) and heated at 80° C. for 6 h. The reaction mixture was quenched and partitioned between ethyl acetate and water. The aqueous layer was extracted with ethyl acetate (3×). The combined organic layers were washed with water (3×), 1N aqueous NaOH, saturated aqueous NaCl, dried over MgSO$_4$, filtered and concentrated to dryness. The crude material was used directly in next step without further purification. ESI-MS m/z calc. 248.2. found 249.3 (M+1)$^+$; Retention time: 2.02 min (3 min run).

Step 2: 3-methyl-4-(2,2,2-trifluoroethoxy)benzoic acid

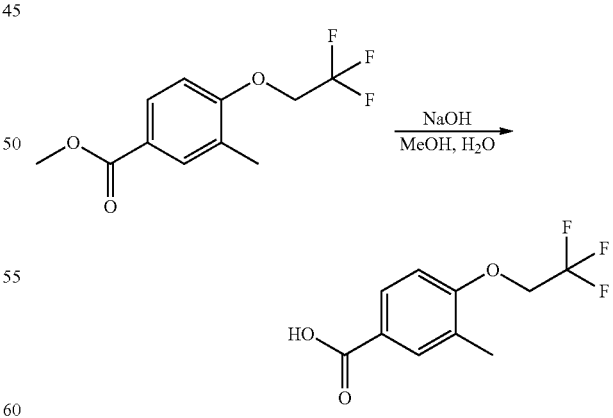

To a suspension of methyl 3-methyl-4-(2,2,2-trifluoroethoxy)benzoate (1.7 g, 6.8 mmol) in MeOH (20 mL) and water (10 mL) was added NaOH (1.4 g, 34.2 mmol). The reaction mixture was stirred at rt overnight, turned clear, and concentrated (removing MeOH) under reduced pressure. The residual solution was diluted with water and acidified with

385

1 N HCl. The resulting precipitate was collected via filtration, washed with water and dried to provide 3-methyl-4-(2,2,2-trifluoroethoxy)benzoic acid (1.6 g, 100%) as an off-white solid. ESI-MS m/z calc. 234.2. found 235.2 (M+1)+; Retention time: 1.73 min (3 min run).

[(3aR,7aR)-7a-[3-(2-tert-butoxyethoxy)-2-pyridyl]-3a,4,6,7-tetrahydro-[1,3]dioxolo[4,5-c]pyridin-5-yl]-[4-(2-tert-butoxyethoxy)-3-chloro-phenyl]methanone Step 1: [(3aR,7aR)-7a-(3-fluoro-2-pyridyl)-3a,4,6,7-tetrahydro-[1,3]dioxolo[4,5-c]pyridin-5-yl]-(3-chloro-4-fluoro-phenyl)methanone

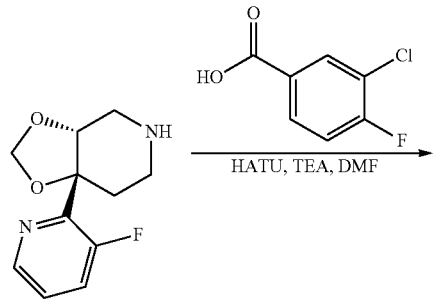

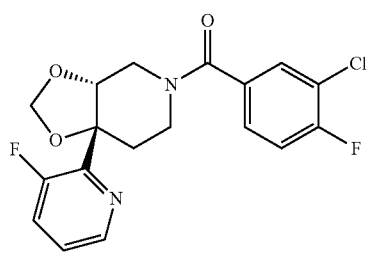

A 20 mL vial was charged with (3aR,7aR)-7a-(3-fluoro-2-pyridyl)-4,5,6,7-tetrahydro-3aH-[1,3]dioxolo[4,5-c]pyridine (258 mg, 1.15 mmol), 3-chloro-4-fluoro-benzoic acid (201 mg, 1.15 mmol), HATU (481 mg, 1.27 mmol) and DMF (5 mL). To the resulting solution was added triethylamine (640 µL, 4.6 mmol) and the reaction mixture was stirred at rt for 2 h. Water (50 mL) was added, and the resulting mixture was extracted with DCM (3×25 mL). The combined extracts were washed with water (25 mL), dried over sodium sulfate and concentrated under reduced pressure. The crude residue was purified by flash chromatography on silica gel (12 g column) using a gradient of AcOEt (0 to 100%) in hexanes over 12 min affording [(3aR,7aR)-7a-(3-fluoro-2-pyridyl)-3a,4,6,7-tetrahydro-[1,3]dioxolo[4,5-c]pyridin-5-yl]-(3-chloro-4-fluoro-phenyl)methanone (365 mg, 78%) as a viscous colorless oil. ESI-MS m/z calc. 380.1. found 381.0 (M+1)+; Retention time: 1.09 min (3 min run).

386

Step 2: [(3aR,7aR)-7a-[3-(2-tert-butoxyethoxy)-2-pyridyl]-3a,4,6,7-tetrahydro-[1,3]dioxolo[4,5-c]pyridin-5-yl]-[4-(2-tert-butoxyethoxy)-3-chloro-phenyl]methanone

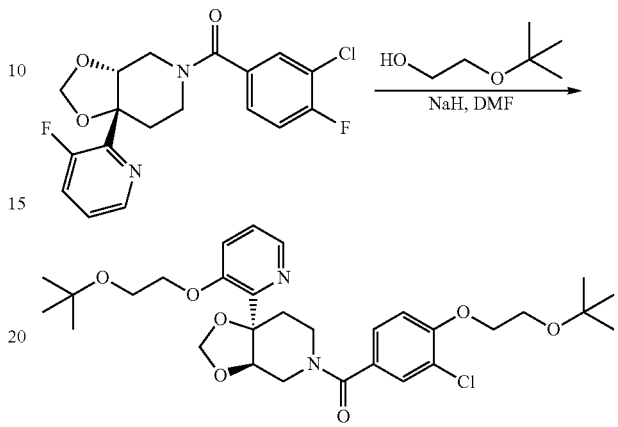

In a vial, 2-tert-butoxyethanol (155 mg, 1.31 mmol) was dissolved in DMF (500 NaH (53 mg, 1.3 mmol) (60% oil dispersion) was added in small portions and the suspension was stirred at rt for 25 min. [(3aR,7aR)-7a-(3-fluoro-2-pyridyl)-3a,4,6,7-tetrahydro-[1,3]dioxolo[4,5-c]pyridin-5-yl]-(3-chloro-4-fluoro-phenyl)methanone (50 mg, 0.13 mmol) as a solution in DMF (100 µL) was added and the reaction mixture was stirred at 80° C. for 1 h. The reaction mixture was quenched by the addition of water. The resultant mixture was extracted with DCM (3×). The combined extracts were dried over sodium sulfate and the volatiles were removed under reduced pressure. The crude product was purified by reverse phase HPLC (HCl as a modifier) providing [(3aR,7aR)-7a-[3-(2-tert-butoxyethoxy)-2-pyridyl]-3a,4,6,7-tetrahydro-[1,3]dioxolo[4,5-c]pyridin-5-yl]-[4-(2-tert-butoxyethoxy)-3-chloro-phenyl]methanone (38 mg, 47%) as a colorless solid. ESI-MS m/z calc. 576.3. found 577.0 (M+1)+; Retention time: 1.48 min (3 min run).

3-(trifluoromethyl)-4-(3,3,3-trifluoropropoxy)benzoic acid

Step 1: Methyl 4-hydroxy-3-(trifluoromethyl)benzoate

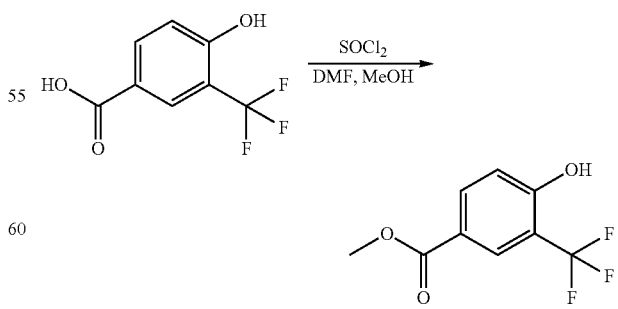

4-hydroxy-3-(trifluoromethyl)benzoic acid (4.9 g, 23.7 mmol) was dissolved in methanol (15 mL) and DMF (18 µL, 0.24 mmol), thionyl chloride (5.2 mL, 71.0 mmol) was added dropwise (over a period of 10 min) to the reaction mixture, and it was allowed to stir for 18 h at rt. Volatiles were then removed under reduced pressure. The remaining solid was partitioned between ethyl acetate (50 mL) and saturated aqueous sodium bicarbonate (50 mL). The aqueous layer was further extracted with ethyl acetate (2×50 mL). All organic layers were combined, dried over sodium sulfate, filtered and concentrated under reduced pressure to provide methyl 4-hydroxy-3-(trifluoromethyl)benzoate (4.9 g, 93%) as an off-white solid. $^1$H NMR (400 MHz, DMSO) δ 11.68 (s, 1H), 8.00-8.10 (m, 2H), 7.20-7.07 (m, 1H), 3.83 (s, 3H). ESI-MS m/z calc. 220.0. found 221.0 (M+1)$^+$; Retention time: 1.41 min (3 min run).

Step 2: methyl 3-(trifluoromethyl)-4-(3,3,3-trifluoropropoxy)benzoate

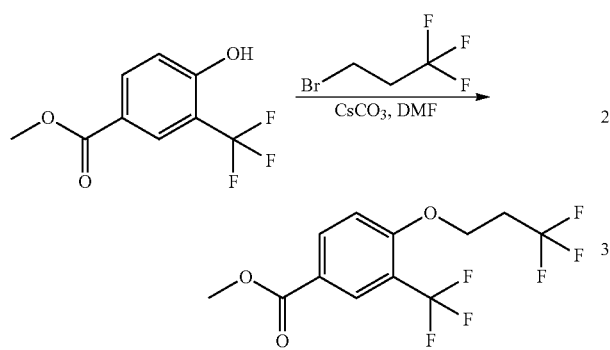

In a vial, methyl 4-hydroxy-3-(trifluoromethyl)benzoate (1.04 g, 4.73 mmol) was dissolved in DMF (2 mL). Cesium carbonate (4.6 g, 14.2 mmol) was added followed by 3-bromo-1,1,1-trifluoro-propane (760 µl, 7.1 mmol). The vial was tightly capped and the heterogenous mixture was stirred at 80° C. for 1 h. The resulting thick slurry was diluted with DMF (5 mL) and treated with additional 3-bromo-1,1,1-trifluoro-propane (760 µL, 7.1 mmol). The reaction mixture was stirred at 80° C. for 15 h and treated with additional 3-bromo-1,1,1-trifluoro-propane (1.5 mL, 14.2 mmol). The reaction mixture was stirred at 80° C. under nitrogen atmosphere for 4 days and treated with additional 3-bromo-1,1,1-trifluoro-propane (1.5 mL, 14.2 mmol). The reaction mixture was heated at 80° C. for 24 h and was cooled and filtered. The solids were washed with methanol. The filtrate was concentrated under reduced pressure. Water (50 mL) and ethyl acetate (50 mL) were added and separated. The aqueous phase was further extracted with ethyl acetate (50 mL). The combined extracts were washed with saturated aqueous NaCl, dried over sodium sulfate, filtered, and the volatiles were removed under reduced pressure. Purification by flash chromatography on silica gel (24 g column) using a gradient of AcOEt (0 to 50% over 20 min) in hexanes provided methyl 3-(trifluoromethyl)-4-(3,3,3-trifluoropropoxy)benzoate (387 mg, 26%) as a white solid. $^1$H NMR (400 MHz, CDCl$_3$) δ 8.29 (d, J=2.0 Hz, 1H), 8.21 (dd, J=8.7, 2.1 Hz, 1H), 7.02 (d, J=8.7 Hz, 1H), 4.34 (t, J=6.5 Hz, 2H), 3.92 (s, 3H), 2.72 (qt, J=10.4, 6.5 Hz, 2H). ESI-MS m/z calc. 316.1. found 317.0 (M+1)$^+$.

Retention time: 1.88 min (3 min run).

Step 3: 3-(trifluoromethyl)-4-(3,3,3-trifluoropropoxy)benzoic acid

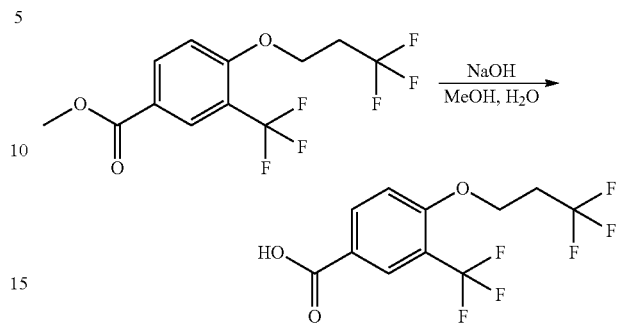

A solution of methyl 3-(trifluoromethyl)-4-(3,3,3-trifluoropropoxy)benzoate (380 mg, 1.20 mmol) in methanol (2 mL) was treated with aqueous sodium hydroxide (600 µl of 6 M, 3.6 mmol). The thick suspension was stirred at 60° C. and became a clear solution after 5 min. After stirring at 60° C. for 1.5 h the reaction mixture was diluted with water (25 mL) and was acidified with 6N HCl to pH=1. The resulting white precipitate was extracted with ethyl acetate (2×25 mL). The combined extracts were dried over sodium sulfate, filtered, and the volatiles were removed under reduced pressure to afford 3-(trifluoromethyl)-4-(3,3,3-trifluoropropoxy)benzoic acid (342 mg, 94%) as a white solid. $^1$H NMR (400 MHz, DMSO) δ 13.18 (s, 1H), 8.19 (dd, J=8.7, 2.1 Hz, 1H), 8.11 (d, J=2.0 Hz, 1H), 7.43 (d, J=8.8 Hz, 1H), 4.44 (t, J=5.6 Hz, 2H), 2.84 (ddq, J=16.8, 11.2, 5.7 Hz, 2H). ESI-MS m/z calc. 302.0. found 303.0 (M+1)$^+$; Retention time: 1.62 min (3 min run).

3-chloro-4-(2-fluoro-2-methyl-propoxy)benzoic acid

Step 1: methyl 3-chloro-4-(2-hydroxy-2-methylpropoxy)benzoate

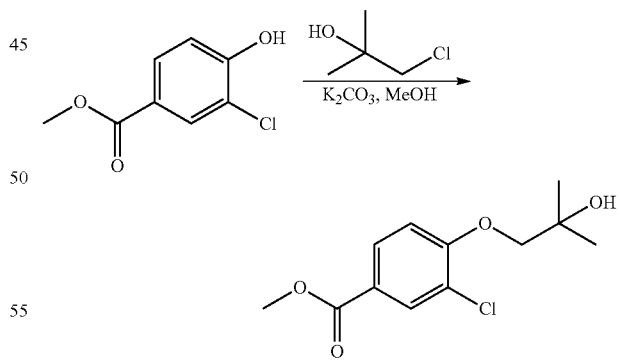

A 500 ml 3 neck RB flask was fitted with a mechanical stirrer, a J-Kem temperature probe/controller, an addition funnel, a water cooled reflux condenser and a nitrogen inlet/outlet. The vessel was charged under a nitrogen atmosphere with methyl 3-chloro-4-hydroxy-benzoate (10 g, 53.6 mmol) and methyl alcohol (40 ml) which provided a clear pale yellow solution. Stirring was commenced and the pot temperature was recorded at 19° C. The vessel was then charged with potassium carbonate (30 g, 0.21 mol) added as a solid in one portion which resulted in an exotherm to 23° C. Note: The potassium carbonate was ground to a fine powder prior to use. The resulting suspension was continued to stir at rt for 15 min and then treated with 1-chloro-2-methyl-propan-2-ol (11.6 g, 0.11 mol) added neat dropwise via addition funnel over 10 min. The resulting reaction mixture/suspension was then heated to 70° C. and stirred for 20 h. The reaction mixture was cooled to rt and diluted with ethyl acetate (250 ml). The mixture was filtered through a glass frit Buchner funnel with a 10 mm layer of Celite. The filter cake was washed with ethyl acetate (2×100 ml). The filtrate was transferred to a separatory funnel and partitioned with 1 M aqueous NaOH (250 ml). The organic was removed and washed with 1 M aqueous NaOH (2×150 ml), saturated aqueous sodium chloride (150 ml), dried over sodium sulfate (250 g) and filtered through a glass frit Buchner funnel. The filtrate was concentrated under reduced pressure to provide methyl 3-chloro-4-(2-hydroxy-2-methylpropoxy)benzoate (9.0 g, 65%) as a clear pale yellow oil. The material was used without further purification in the next synthetic step. ESI-MS m/z calc. 258.7. found 259.2 (M+1)$^+$; Retention time: 1.46 min (3 min run).

Step 2: methyl 3-chloro-4-(2-fluoro-2-methyl-propoxy)benzoate

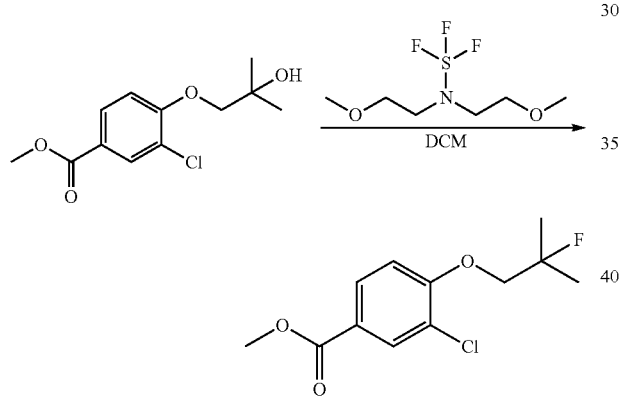

A solution of methyl 3-chloro-4-(2-hydroxy-2-methyl-propoxy)benzoate (6.2 g, 24.0 mmol) in DCM (60 mL) was treated slowly with 2-methoxy-N-(2-methoxyethyl)-N-(trifluoro-4-sulfanyl)ethanamine (4.9 mL, 26.4 mmol) while a water bath was used to keep the reaction temperature near rt. The reaction mixture was allowed to stir at rt for 2 h. The reaction mixture was quenched with the addition of ice-cold water (75 mL) and diluted with DCM (50 mL). The phases were separated and the organic phase was washed with saturated aqueous NaCl (2×75 mL), dried over sodium sulfate, filtered and concentrated under reduced pressure. Purification by silica gel column chromatography: 40 gram silica gel column, 0-10% ethyl acetate/hexane gradient over 30 min provided methyl 3-chloro-4-(2-fluoro-2-methyl-propoxy)benzoate (2.4 g, 39%) as a yellow oil. $^1$H NMR (400 MHz, CDCl$_3$) δ 8.07 (d, J=2.1 Hz, 1H), 7.92 (dd, J=8.6, 2.1 Hz, 1H), 6.93 (d, J=8.6 Hz, 1H), 4.06 (t, J=9.8 Hz, 2H), 3.90 (s, 3H), 1.55 (d, J=21.5 Hz, 6H). ESI-MS m/z calc. 260.1. found 261.2 (M+1)$^+$; Retention time: 1.83 min (3 min run).

Step 3: 3-chloro-4-(2-fluoro-2-methyl-propoxy)benzoic acid

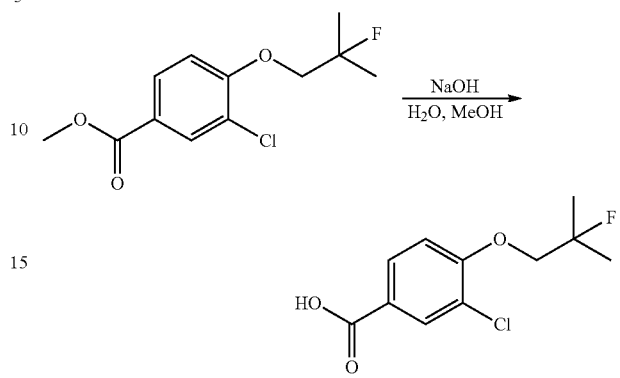

A solution of methyl 3-chloro-4-(2-fluoro-2-methyl-propoxy)benzoate (2.4 g, 9.3 mmol) in methanol (5 mL) was treated with a solution of sodium hydroxide (1.1 g, 28.0 mmol) in water (10 mL). The reaction mixture was allowed to stir at 60° C. for 1.5 h. The resulting clear solution was diluted with ethyl acetate (75 mL) and mixed with aqueous 1 N HCl (75 mL). The organic layer was dried over sodium sulfate, filtered and concentrated under reduced pressure to provide 3-chloro-4-(2-fluoro-2-methyl-propoxy)benzoic acid (2.1 g, 93%) as a white solid. $^1$H NMR (400 MHz, CDCl$_3$) δ 8.14 (d, J=2.1 Hz, 1H), 8.00 (dd, J=8.6, 2.1 Hz, 1H), 6.97 (d, J=8.7 Hz, 1H), 4.07 (d, J=16.1 Hz, 2H), 1.56 (d, J=21.5 Hz, 6H). ESI-MS m/z calc. 246.0. found 247.2 (M+1)$^+$; Retention time: 1.5 min (3 min run).

Methyl 3-methoxy-4-(3,3,3-trifluoropropoxy)benzoic acid

Step 1: methyl 3-methoxy-4-(3,3,3-trifluoropropoxy)benzoate

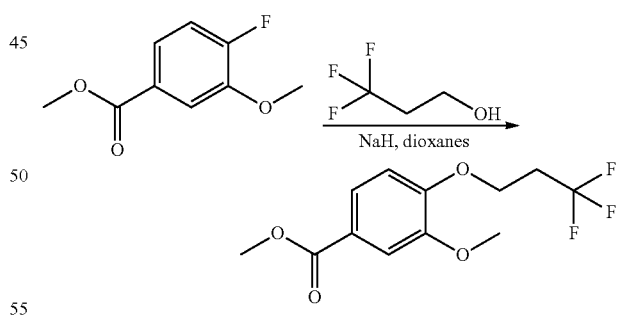

A solution of 3,3,3-trifluoropropan-1-ol (1.2 g, 10.9 mmol) in 1,4-dioxane (4.5 mL) was cooled to 0° C. To the mixture was added a 60% dispersion of sodium hydride in mineral oil (0.4 g, 10.9 mmol) portion wise. A great deal of foaming was observed. After completion of addition (20 min), the reaction mixture was allowed to stir at rt for 1 h. The reaction mixture was treated a solution of methyl 4-fluoro-3-methoxy-benzoate (1.0 g, 5.4 mmol) in 1,4-dioxane (2 mL) and was stirred at rt for 12 h. The reaction mixture was diluted with EtOAc (75 mL) and washed with a pH 14 solution of NaOH. The aqueous layer was acidified to pH 10 with the addition of 1 N HCl, and was extracted with EtOAc (1×75 mL). The organic layer was dried over sodium sulfate, filtered and concentrated under reduced pressure to afford a yellow oil. Purification by flash column chromatography (SiO$_2$-24 g, 0-30% EtOAc-hexanes) afforded methyl 3-methoxy-4-(3,3,3-trifluoropropoxy)benzoate (0.6 g, 39.7%). ESI-MS m/z calc. 278.2 found 279.2 (M+1)$^+$; Retention time: 0.62 min (3 min run).

The following compounds were prepared using the procedure reported above.

| Product | Precursor |
| --- | --- |
| methyl 3-methoxy-4-(3,3,3-trifluoropropoxy)benzoate | methyl 4-fluoro-3-methoxy-benzoate |
| methyl 3-methoxy-4-((4,4,4-trifluorobutan-2-yl)oxy)benzoate | methyl 4-fluoro-3-methoxy-benzoate |
| methyl 3-methoxy-4-((1,1,1-trifluoropropan-2-yl)oxy)benzoate | methyl 4-fluoro-3-methoxy-benzoate |

Step 2: methyl 3-methoxy-4-(3,3,3-trifluoropropoxy)benzoic acid

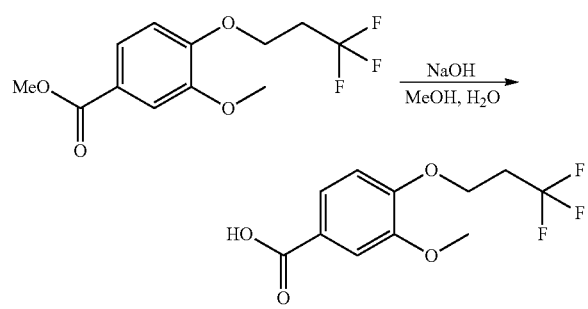

Intermediate methyl 3-methoxy-4-(3,3,3-trifluoropropoxy)benzoate (480 mg, 1.73 mmol) was dissolved in methanol (1.3 mL), and a solution of sodium hydroxide (414 mg, 10.4 mmol) in water (2.6 mL) was added. The reaction mixture was stirred at 60° C. for 1 h and was diluted with water (50 mL) and acidified to pH 1 with the addition of 1 N HCl. The resulting opaque white suspension was extracted with EtOAc (2×75 mL). The organic layers were combined, dried over sodium sulfate, filtered and concentrated to provide 3-methoxy-4-(3,3,3-trifluoropropoxy)benzoic acid (357 mg, 78.4%) as a white solid. $^1$H NMR (400 MHz, DMSO) δ 12.73 (s, 1H), 7.55 (dd, J=8.4, 2.0 Hz, 1H), 7.46 (d, J=1.9 Hz, 1H), 7.11 (d, J=8.5 Hz, 1H), 4.27 (t, J=6.0 Hz, 2H), 3.81 (s, 3H), 2.95-2.72 (m, 2H). ESI-MS m/z calc. 264.2. found 265.2 (M+1)$^+$; Retention time: 0.5 min (3 min run).

The following compounds were prepared using the procedure reported above.

| Product | Precursor |
| --- | --- |
| 3-methoxy-4-(3,3,3-trifluoropropoxy)benzoic acid | methyl 3-methoxy-4-(3,3,3-trifluoropropoxy)benzoate |
| 3-methoxy-4-((4,4,4-trifluorobutan-2-yl)oxy)benzoic acid | methyl 3-methoxy-4-((4,4,4-trifluorobutan-2-yl)oxy)benzoate |
| 3-methoxy-4-((1,1,1-trifluoropropan-2-yl)oxy)benzoic acid | methyl 3-methoxy-4-((1,1,1-trifluoropropan-2-yl)oxy)benzoate |

3-fluoro-5-methoxy-4-(3,3,3-trifluoropropoxy)benzoic acid

Step 1: 3-fluoro-5-methoxy-4-(3,3,3-trifluoropropoxy)benzaldehyde

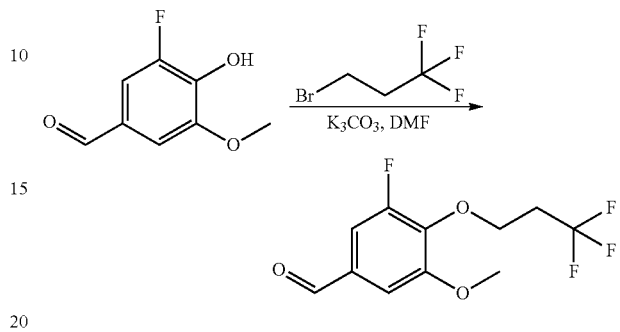

In a flask, 3-fluoro-4-hydroxy-5-methoxy-benzaldehyde (1.1 g, 6.2 mmol) was dissolved in DMF (7 mL). The mixture was treated with potassium carbonate (2.2 g, 15.9 mmol) and 3-bromo-1,1,1-trifluoro-propane (1.3 mL, 12.5 mmol) and the reaction mixture was stirred under nitrogen atmosphere at 80° C. for 17 h. Additional 3-bromo-1,1,1-trifluoro-propane (2.6 mL, 24.9 mmol) was added and the reaction mixture was stirred at 65° C. for 5 h (50% conversion). Another load of 3-bromo-1,1,1-trifluoro-propane (1.3 mL, 12.5 mmol) was added and the reaction mixture was stirred at 65° C. for 2.5 d. The solids were filtered and washed with methanol. The filtrate was concentrated under reduced pressure and diluted with water (50 mL) and ethyl acetate (50 mL). The phases were separated after being mixed and the aqueous phase was extracted with ethyl acetate (50 mL). The combined extracts were washed with saturated aqueous NaCl (50 mL), dried over sodium sulfate, filtered, and the volatiles were removed in vacuo. The crude solid was purified by flash chromatography on silica gel (80 g column) using a gradient of AcOEt (0 to 50% over 40 min) in hexanes. The product eluted at 15-25% ethyl acetate (13-20 min) to provide 3-fluoro-5-methoxy-4-(3,3,3-trifluoropropoxy)benzaldehyde (0.80 g, 48%) as a colorless liquid. $^1$H NMR (400 MHz, CDCl$_3$) δ 9.86 (d, J=1.2 Hz, 1H), 7.29-7.25 (m, 2H), 4.38 (td, J=6.8, 0.5 Hz, 2H), 3.95 (s, 3H), 2.66 (qt, J=10.6, 6.8 Hz, 2H). ESI-MS m/z calc. 266.1. found 267.0 (M+1)$^+$; Retention time: 1.63 min (3 min run).

Step 2: 3-fluoro-5-methoxy-4-(3,3,3-trifluoropropoxy)benzoic acid

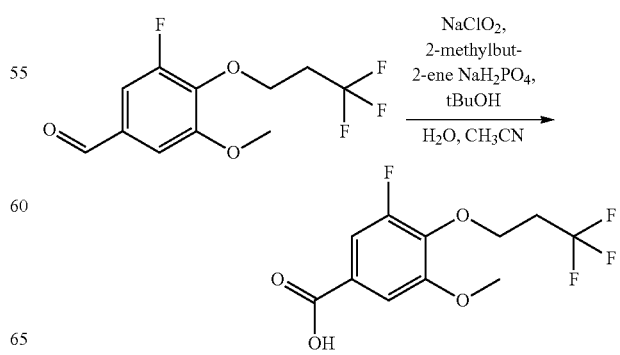

To a solution of 3-fluoro-5-methoxy-4-(3,3,3-trifluoropropoxy)benzaldehyde (780 mg, 2.9 mmol) in tBuOH (8 mL), water (5 mL) and acetonitrile (5 mL) was added sodium dihydrogen phosphate (352 mg, 2.9 mmol), 2-methylbut-2-ene (1.0 g, 14.7 mmol) and sodium chlorite (265 mg, 2.9 mmol). The reaction mixture was stirred at 25° C. for 21 h and additional sodium dihydrogen phosphate (563 mg, 4.7 mmol), 2-methyl-2-butene (1.5 mL, 14.6 mmol) and NaClO$_2$ (795 mg, 8.79 mmol) were added. The reaction mixture was stirred at rt for 7 h, acidified with 1N HCl, and diluted with ethyl acetate. The layers were separated and the aqueous layer was extracted with ethyl acetate (2×). The organics were combined, dried with sodium sulfate, filtered and concentrated under reduced pressure to give a waxy solid. The compound was triturated in hexanes, filtered, and dried in a vacuum oven at 40° C. overnight to provide 3-fluoro-5-methoxy-4-(3,3,3-trifluoropropoxy)benzoic acid (620 mg, 75%) as an off-white solid. $^1$H NMR (400 MHz, DMSO) δ 12.97 (s, 1H), 7.43-7.40 (m, 1H), 7.38 (dd, J=10.5, 1.9 Hz, 1H), 4.27 (t, J=5.9 Hz, 2H), 3.89 (s, 3H), 2.75 (qt, J=11.4, 5.9 Hz, 2H). ESI-MS m/z calc. 282.1. found 283.0 (M+1)$^+$; Retention time: 1.49 min (3 min run).

5-chloro-6-[2-(trifluoromethoxy)ethoxy]pyridine-3-carboxylic acid

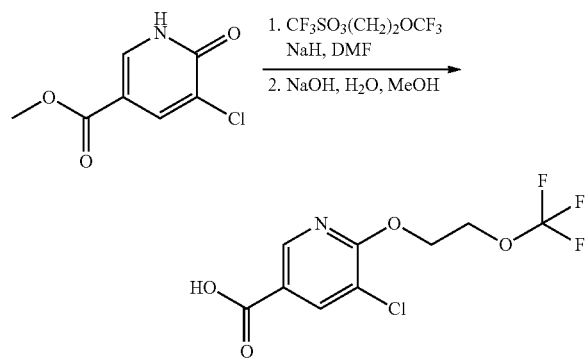

Step 1: A solution of methyl 5-chloro-6-oxo-1H-pyridine-3-carboxylate (1.0 g, 5.3 mmol) in DMF and cooled to 0° C. and treated slowly with 60% sodium hydride in mineral oil (213 mg, 5.3 mmol). After stirring at rt for 10 min, 2-(trifluoromethoxy)ethyl trifluoromethanesulfonate (3.0 g, 5.9 mmol) was added. The reaction mixture was allowed to stir overnight at rt. It was then diluted with ethyl acetate (75 mL) and washed with saturated aqueous NaCl (2×75 mL). The organic layer was dried over sodium sulfate, filtered and concentrated under reduced pressure to provide methyl 5-chloro-6-[2-(trifluoromethoxy)ethoxy]pyridine-3-carboxylate (330 mg) as a brown solid which was dissolved in methanol (680 µL). The mixture was treated with a solution of sodium hydroxide (1.3 mL of 2.5 M, 3.3 mmol). The reaction mixture was allowed to stir at 60° C. for 1.5 h. The resulting clear solution was diluted with ethyl acetate (75 mL) and mixed with aqueous 1 N HCl. The organic layer was separated, dried over sodium sulfate, filtered and concentrated under reduced pressure to provide 5-chloro-6-[2-(trifluoromethoxy)ethoxy]pyridine-3-carboxylic acid (300 mg, 95.4%) as a white solid. $^1$H NMR (400 MHz, DMSO) δ 13.32 (s, 1H), 8.65 (d, J=2.0 Hz, 1H), 8.27 (d, J=2.0 Hz, 1H), 4.78-4.58 (m, 2H), 4.48 (dd, J=5.1, 3.4 Hz, 2H). ESI-MS m/z calc. 285.0. found 286.03 (M+1)$^+$; Retention time: 1.55 min (3 min run).

5-[(3,3-difluorocyclobutyl)methoxy]-6-methoxy-pyridine-2-carboxylic acid

Step 1: methyl 6-chloro-5-[(3,3-difluorocyclobutyl)methoxy]pyridine-2-carboxylate

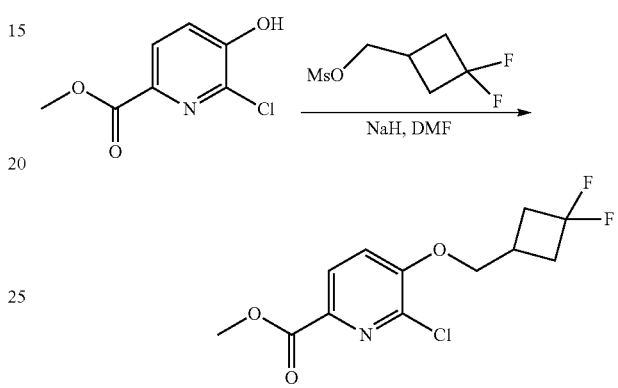

To methyl 6-chloro-5-hydroxy-pyridine-2-carboxylate (500 mg, 2.7 mmol) in dry DMF (4 mL) was added NaH (117 mg, 2.9 mmol) (60% dispersion in oil). The mixture was stirred at rt for 15 min before being treated with (3,3-difluorocyclobutyl)methyl methanesulfonate (865 mg, 4.32 mmol). The resulting reaction mixture was stirred at 90° C. for 5 h. The reaction mixture was cooled down to rt overnight. Water was added and the resulting beige precipitate was filtered and washed with water. The wet solid was dissolved in DCM, dried over sodium sulfate, and filtered. The filtrate was concentrated under reduced pressure and subjected to flash chromatography on silica gel (24 g column) using a gradient of AcOEt (0 to 60%) in hexanes over 25 min affording methyl 6-chloro-5-[(3,3-difluorocyclobutyl)methoxy]pyridine-2-carboxylate (384 mg, 49.4%) as a white solid. $^1$H NMR (400 MHz, CDCl$_3$) δ 8.09 (d, J=8.4 Hz, 1H), 7.25 (d, J=8.5 Hz, 1H), 4.15 (d, J=5.3 Hz, 2H), 3.98 (s, 3H), 2.86-2.68 (m, 3H), 2.68-2.52 (m, 2H). ESI-MS m/z calc. 291.0. found 292.0 (M+1)$^+$; Retention time: 1.51 min (3 min run).

The following compounds were prepared using the procedure reported above.

| Product | Precursor |
| --- | --- |
| methyl 6-chloro-5-[(3,3-difluorocyclobutyl)methoxy]pyridine-2-carboxylate | methyl 6-chloro-5-hydroxy-pyridine-2-carboxylate |
| methyl 6-chloro-5-[[1-(trifluoromethyl)cyclopropyl]methoxy]-pyridine-2-carboxylate | methyl 6-chloro-5-hydroxy-pyridine-2-carboxylate |
| methyl 6-chloro-5-(cyclobutylmethoxy)pyridine-2-carboxylate | methyl 6-chloro-5-hydroxy-pyridine-2-carboxylate |

Step 2: 5-[(3,3-difluorocyclobutyl)methoxy]-6-methoxy-pyridine-2-carboxylic acid

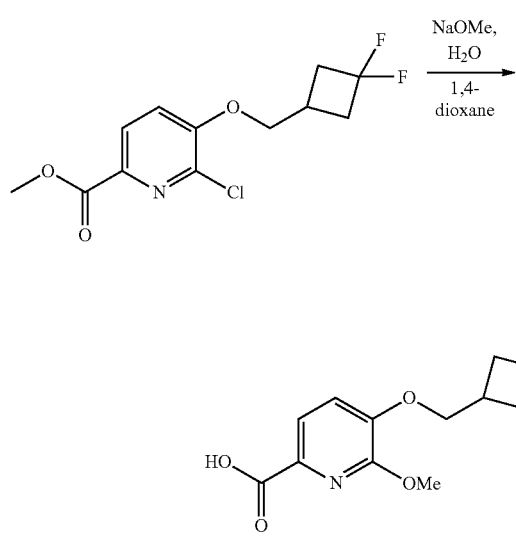

A microwave vessel was charged with methyl 6-chloro-5-[(3,3-difluorocyclobutyl)methoxy]pyridine-2-carboxylate (300 mg, 1.03 mmol), dioxane (4 mL), sodium methoxide (1.4 mL of 25% w/w, 6.2 mmol) and water (61 µL, 3.40 mmol). The reaction mixture was stirred under microwave irradiation at 110° C. for 30 min. The resulting reaction mixture was concentrated under reduced pressure. The remaining white solid was redissolved in water (50 mL) and was washed with ethyl acetate (1×50 mL). The aqueous layer was acidified to pH 1 with the addition of 6 N HCl solution and extracted with ethyl acetate (2×75 mL). The organic layers were combined, dried over sodium sulfate, filtered and concentrated under reduced pressure affording 5-[(3,3-difluorocyclobutyl)methoxy]-6-methoxy-pyridine-2-carboxylic acid (263 mg, 84.6%) as a colorless viscous oil that solidified upon standing. $^1$H NMR (400 MHz, CDCl$_3$) δ 7.84 (d, J=8.0 Hz, 1H), 7.18 (d, J=8.0 Hz, 1H), 4.12 (d, J=5.8 Hz, 2H), 4.06 (s, 3H), 2.91-2.61 (m, 3H), 2.59-2.42 (m, 2H). ESI-MS m/z calc. 273.1. found 274.0 (M+1)$^+$; Retention time: 1.29 min (3 min run.

The following compounds were prepared using the procedure reported above.

| Product | Precursor |
|---|---|
| 5-[(3,3-difluorocyclobutyl)methoxy]-6-methoxy-pyridine-2-carboxylic acid | methyl 6-chloro-5-[(3,3-difluorocyclobutyl)methoxy]-pyridine-2-carboxylate |
| 5-[[1-(trifluoromethyl)cyclopropyl]methoxy]-6-methoxy-pyridine-2-carboxylic acid | methyl 6-chloro-5-[[1-(trifluoromethyl)cyclopropyl]-methoxy]pyridine-2-carboxylate |
| 5-(cyclobutylmethoxy)-6-methoxy-pyridine-2-carboxylic acid | methyl 6-chloro-5-(cyclobutylmethoxy)pyridine-2-carboxylate |

6-methoxy-5-(2,2,2-trifluoro-1-methyl-ethoxy)pyridine-2-carboxylic acid

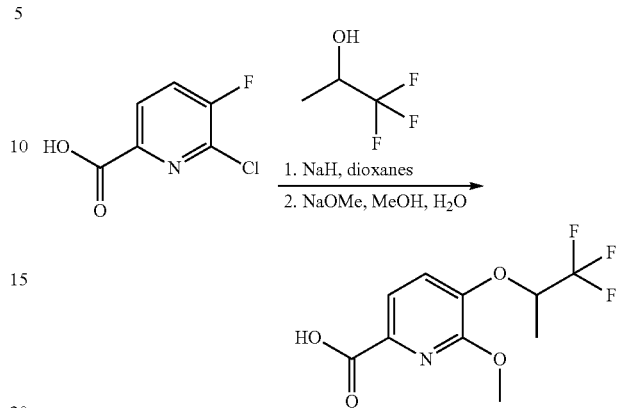

1,1,1-trifluoropropan-2-ol (43 µL, 0.47 mmol) was dissolved in 1,4-dioxane (700 µL), and sodium hydride (38 mg, 0.94 mmol) (60 wt % in mineral oil) was added. The mixture was stirred at rt for 10 min before 6-chloro-5-fluoro-pyridine-2-carboxylic acid (75 mg, 0.43 mmol) was added, and the reaction mixture was stirred at 70° C. overnight. The reaction mixture was treated with sodium methoxide (555 µl of 25% w/v, 2.56 mmol) (in methanol) and was stirred at 65° C. for 2 h. The reaction mixture was diluted with water (50 mL) and washed with ethyl acetate (1×75 mL). The aqueous layer was acidified to pH 3 with the addition of 1 N HCl and extracted with DCM (3×75 mL). The final organic layers were combined, dried over sodium sulfate, filtered, and concentrated under reduced pressure to provide 6-methoxy-5-(2,2,2-trifluoro-1-methyl-ethoxy)pyridine-2-carboxylic acid as a slightly yellow oil that crystallized upon standing. ESI-MS m/z calc. 265.1. found 266.3 (M+1)$^+$; Retention time: 1.24 min (3 min run).

The following compounds were prepared using the procedure reported above.

| Product | Precursor |
|---|---|
| 6-methoxy-5-(2,2,2-trifluoro-1-methyl-ethoxy)pyridine-2-carboxylic acid | 6-chloro-5-fluoro-pyridine-2-carboxylic acid |
| 6-methoxy-5-(2,2,3,3-tetrafluoropropoxy)picolinic acid | 6-chloro-5-fluoro-pyridine-2-carboxylic acid |

(5-(((6,6-difluorospiro[3.3]heptan-2-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone

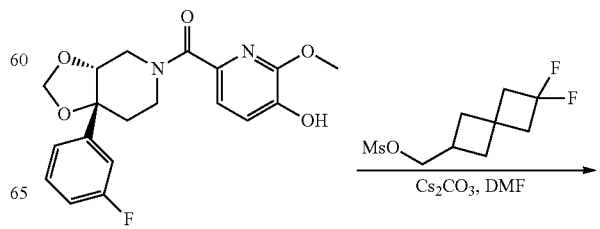

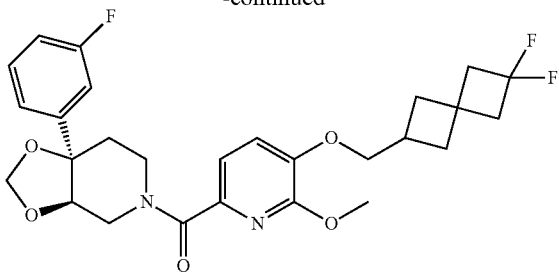

A solution of [(3aR,7aR)-7a-(3-fluorophenyl)-3a,4,6,7-tetrahydro-[1,3]dioxolo[4,5-c]pyridin-5-yl]-(5-hydroxy-6-methoxy-2-pyridyl)methanone (85 mg, 0.23 mmol), (2,2-difluorospiro[3.3]heptan-6-yl)methyl methanesulfonate (109 mg, 0.45 mmol), and powdered potassium carbonate (110 mg, 0.79 mmol) in N,N-dimethylformamide (1.1 mL) was heated at 80° C. for 4 h. The reaction mixture was cooled to rt, filtered and purified by reverse phase HPLC (HCl modifier-1-100% ACN/H$_2$O) to afford (5-((6,6-difluorospiro[3.3]heptan-2-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone (10 mg, 7.8%). $^1$H NMR (400 MHz, CDCl$_3$) δ 7.44 (d, J=7.9 Hz, 1H), 7.36 (td, J=8.0, 5.9 Hz, 1H), 7.20-7.12 (m, J=8.0 Hz, 2H), 7.09 (t, J=7.0 Hz, 1H), 7.04-6.96 (m, 1H), 5.30 (d, J=31.5 Hz, 1H), 4.89 (d, J=29.1 Hz, 1H), 4.52-4.22 (m, 1H), 4.13-4.04 (m, 2H), 4.03 (s, 3H), 4.02-3.91 (m, 4H), 3.84-3.49 (m, 1H), 2.87-2.70 (m, 1H), 2.68-2.47 (m, 3H), 2.41-2.01 (m, 6H). ESI-MS m/z calc. 518.2. found 519.2 (M+1)$^+$; Retention time: 1.621 min (3 min run).

The following compounds were prepared using the procedure reported above.

| Product | Mesylate |
| --- | --- |
| [(3aR,7aR)-7a-(3-fluorophenyl)-3a,4,6,7-tetrahydro-[1,3]dioxolo[4,5-c]pyridin-5-yl]-[5-[(2,2-difluorospiro[3.3]heptan-6-yl)methoxy]-6-methoxy-2-pyridyl]methanone | (2,2-difluorospiro[3.3]-heptan-6-yl)methyl methanesulfonate |
| [(3aR,7aR)-7a-(3-fluorophenyl)-3a,4,6,7-tetrahydro-[1,3]dioxolo[4,5-c]pyridin-5-yl]-[6-methoxy-5-[(2,2,3,3-tetrafluorocyclobutyl)methoxy]-2-pyridyl]methanone | (2,2,3,3-tetrafluorocyclobutyl)-methyl methanesulfonate |
| [(3aR,7aR)-7a-(3-fluorophenyl)-3a,4,6,7-tetrahydro-[1,3]dioxolo[4,5-c]pyridin-5-yl]-[5-[(3,3-difluorocyclopentyl)methoxy]-6-methoxy-2-pyridyl]methanone | (3,3-difluorocyclopentyl)-methyl methanesulfonate |
| [(3aR,7aR)-7a-(3-fluorophenyl)-3a,4,6,7-tetrahydro-[1,3]dioxolo[4,5-c]pyridin-5-yl]-[6-methoxy-5-(2,2,3,3-tetrafluoro-1-methyl-propoxy)-2-pyridyl]methanone | (2,2,3,3-tetrafluoro-1-methyl-propyl) methanesulfonate |
| [(3aR,7aR)-7a-(3-fluorophenyl)-3a,4,6,7-tetrahydro-[1,3]dioxolo[4,5-c]pyridin-5-yl]-[5-(3,3-difluorocyclobutoxy)-6-methoxy-2-pyridyl]methanone | (3,3-difluorocyclobutyl) methanesulfonate |
| [(3aR,7aR)-7a-(3-fluorophenyl)-3a,4,6,7-tetrahydro-[1,3]dioxolo[4,5-c]pyridin-5-yl]-[5-(cyclopent-3-en-1-ylmethoxy)-6-methoxy-2-pyridyl]methanone | cyclopent-3-en-1-ylmethyl methanesulfonate |
| [(3aR,7aR)-7a-(3-fluorophenyl)-3a,4,6,7-tetrahydro-[1,3]dioxolo[4,5-c]pyridin-5-yl]-(5-cyclopent-3-en-1-yloxy-6-methoxy-2-pyridyl)methanone | cyclopent-3-en-1-yl methanesulfonate |
| [(3aR,7aR)-7a-(3-fluorophenyl)-3a,4,6,7-tetrahydro-[1,3]dioxolo[4,5-c]pyridin-5-yl]-[5-[1-(3,3-difluorocyclobutyl)ethoxy]-6-methoxy-2-pyridyl]methanone | 1-(3,3-difluorocyclobutyl)-ethyl methanesulfonate |
| [(3aR,7aR)-7a-(3-fluorophenyl)-3a,4,6,7-tetrahydro-[1,3]dioxolo[4,5-c]pyridin-5-yl]-[5-[2-(3,3-difluorocyclobutyl)ethoxy]-6-methoxy-2-pyridyl]methanone | 2-(3,3-difluorocyclobutyl)-ethyl methanesulfonate |
| [(3aR,7aR)-7a-(3-fluorophenyl)-3a,4,6,7-tetrahydro-[1,3]dioxolo[4,5-c]pyridin-5-yl]-[5-[(3,3-difluoro-6-bicyclo[3.1.0]hexanyl)methoxy]-6-methoxy-2-pyridyl]methanone | (3,3-difluoro-6-bicyclo[3.1.0]hexanyl)-methyl methanesulfonate |

4-[2-(2,2-difluorocyclopropyl)ethoxy]-3-methoxy-benzoic acid

Step 1: methyl 4-but-3-enoxy-3-methoxy-benzoate

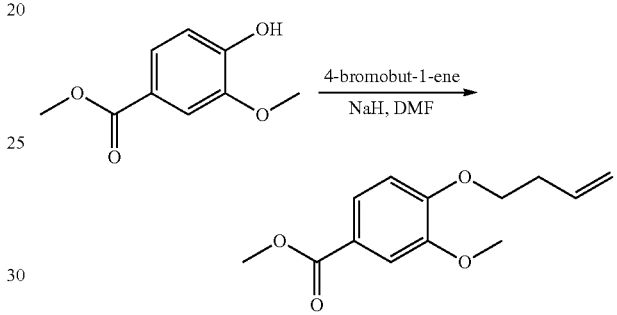

In a vial, methyl 4-hydroxy-3-methoxy-benzoate (675 mg, 3.70 mmol) was dissolved in DMF (4 mL) under a nitrogen atmosphere. The mixture was treated with NaH (98 mg, 4.07 mmol) (60% dispersion in mineral oil) in small portions and the reaction mixture was stirred at rt for 20 min before being treated dropwise with 4-bromobut-1-ene (1.0 g, 7.4 mmol). The vial was capped, covered with aluminium foil, and was stirred at 80° C. for 21 hours. The reaction mixture was cooled to rt and quenched by the addition of water. The resulting mixture was extracted with ethyl acetate (2×). The combined extracts were washed with water, dried over sodium sulfate, and concentrated under reduced pressure. Purification by flash chromatography on silica gel (40 g column) using a gradient of AcOEt (0 to 40% over 25 min) in hexanes provided methyl 4-but-3-enoxy-3-methoxy-benzoate (191 mg, 21.6%) as a colorless oil. $^1$H NMR (400 MHz, CDCl$_3$) δ 7.66 (dd, J=8.4, 2.0 Hz, 1H), 7.55 (d, J=2.0 Hz, 1H), 6.89 (d, J=8.5 Hz, 1H), 5.91 (ddt, J=17.1, 10.2, 6.8 Hz, 1H), 5.19 (dq, J=17.2, 1.6 Hz, 1H), 5.13 (ddd, J=10.2, 2.9, 1.2 Hz, 1H), 4.12 (t, J=7.1 Hz, 2H), 3.92 (s, 3H), 3.89 (s, 3H), 2.63 (qt, J=7.0, 1.3 Hz, 2H). ESI-MS m/z calc. 236.1. found 237.0 (M+1)$^+$; Retention time: 1.59 min (3 min run).

Step 2: methyl 4-[2-(2,2-difluorocyclopropyl)ethoxy]-3-methoxy-benzoate

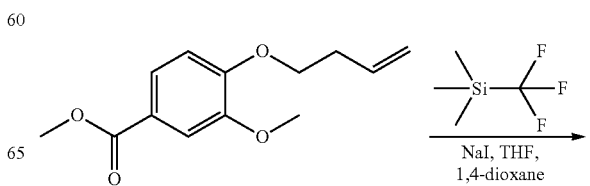

-continued

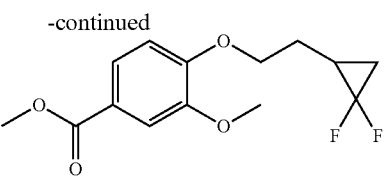

To a 15 mL pressure bottle charged with a magnetic stirbar was added methyl 4-but-3-enoxy-3-methoxy-benzoate (191 mg, 0.80 mmol), sodium iodide (30 mg, 0.20 mmol) and anhydrous THF (1.2 mL) under a nitrogen atmosphere. To the mixture was added trimethyl-(trifluoromethyl)silane (414 μL, 2.80 mmol). The reaction vessel was sealed and heated to 65° C. for 21 h. The reaction mixture was cooled to rt and the volatiles were removed by blowing nitrogen over the vessel. The residue was redissolved in dioxane (1.2 mL) before adding sodium iodide (30 mg, 0.20 mmol) and trimethyl-(trifluoromethyl)silane (473 μL, 3.20 mmol) under nitrogen. The pressure vessel was sealed and stirred at 100° C. for 24 h. The vessel was cooled to rt and the volatiles were removed by blowing nitrogen over the reaction mixture. The vessel was charged again with THF (1.2 mL), sodium iodide (30 mg, 0.20 mmol), trimethyl-(trifluoromethyl)silane (414 μL, 2.80 mmol) and stirred at 65° C. for 24 h. The reaction mixture was cooled and the solvents were removed under reduced pressure. The residue was dissolved in DCM and the organic phase was washed with water, 10% sodium sulfite, saturated sodium bicarbonate and saturated aqueous NaCl. After drying over sodium sulfate, the solvent was removed by evaporation. The crude material was purified by flash chromatography on silica gel (24 g column) using a gradient of AcOEt (0 to 40%) in hexanes over 25 min affording methyl 4-[2-(2,2-difluorocyclopropyl)ethoxy]-3-methoxy-benzoate (147 mg, 63.3%) as an off-white solid. $^1$H NMR (400 MHz, CDCl$_3$) δ 7.66 (dd, J=8.4, 2.0 Hz, 1H), 7.55 (d, J=2.0 Hz, 1H), 6.89 (d, J=8.5 Hz, 1H), 4.21-4.10 (m, 2H), 3.92 (s, 3H), 3.90 (s, 3H), 2.15-1.91 (m, 2H), 1.76 (ddq, J=14.9, 11.3, 7.5 Hz, 1H), 1.53-1.40 (m, 1H), 1.10-0.98 (m, 1H). ESI-MS m/z calc. 286.1. found 287.0 (M+1)$^+$; Retention time: 1.39 min (3 min run).

Step 3: 4-[2-(2,2-difluorocyclopropyl)ethoxy]-3-methoxy-benzoic acid

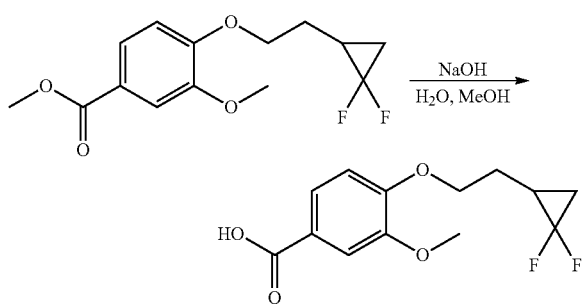

A solution of methyl 4-[2-(2,2-difluorocyclopropyl)ethoxy]-3-methoxy-benzoate (144 mg, 0.50 mmol) in methanol (1 mL) was treated with sodium hydroxide (250 μL, 1.50 mmol) (6N aqueous solution) and the resulting reaction mixture was stirred at 60° C. The reaction mixture was diluted with water (50 mL) and was acidified with 6N HCl to pH=1 inducing formation of a white precipitate. The precipitate was filtered, washed with water and dried overnight under vacuum oven at 40° C. affording 4-[2-(2,2-difluorocyclopropyl)ethoxy]-3-methoxy-benzoic acid (125 mg, 87.8%) as a white solid. $^1$H NMR (400 MHz, CDCl$_3$) δ 7.75 (dd, J=8.4, 2.0 Hz, 1H), 7.60 (d, J=2.0 Hz, 1H), 6.92 (d, J=8.5 Hz, 1H), 4.18 (t, J=6.1 Hz, 2H), 3.93 (s, 3H), 2.04 (tdd, J=14.3, 13.0, 7.0 Hz, 2H), 1.77 (ddq, J=14.8, 11.2, 7.4 Hz, 1H), 1.54-1.40 (m, 1H), 1.11-0.94 (m, 1H). ESI-MS m/z calc. 272.1. found 273.0 (M+1)$^+$; Retention time: 1.08 min.

(5-(((1R,3r,5S)-6,6-difluorobicyclo[3.1.0]hexan-3-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone and (5-(((1R,3s,5S)-6,6-difluorobicyclo[3.1.0]hexan-3-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone

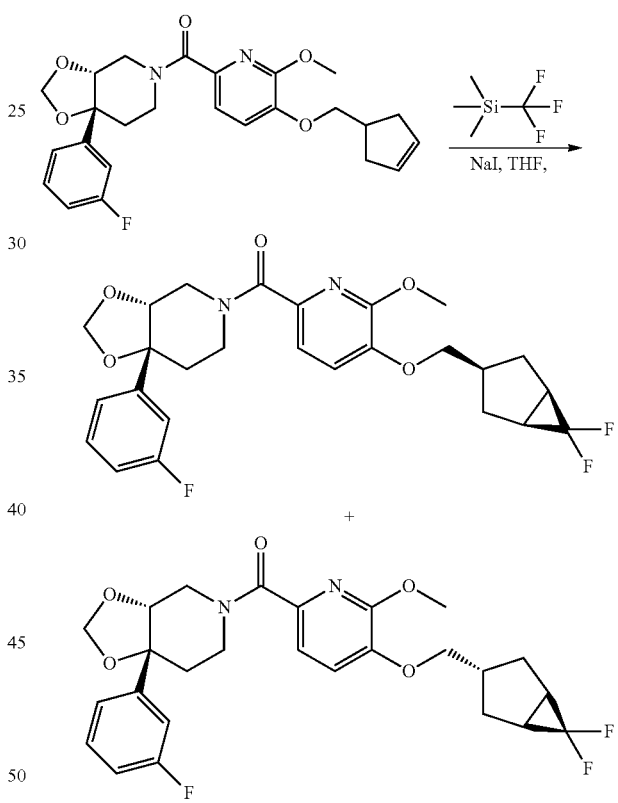

To a solution of [(3aR,7aR)-7a-(3-fluorophenyl)-3a,4,6,7-tetrahydro-[1,3]dioxolo[4,5-c]pyridin-5-yl]-[5-(cyclopent-3-en-1-ylmethoxy)-6-methoxy-2-pyridyl]methanone (90 mg, 0.20 mmol) in THF (2 mL) was added sodium iodide (59 mg, 0.40 mmol). The mixture was purged with nitrogen for 2 min and trimethyl-(trifluoromethyl)silane (70 mg, 0.49 mmol) was added. The reaction mixture was sealed and heated at 80° C. for 20 h. The reaction mixture was cooled to rt and partitioned between ethyl acetate and water. The aqueous layer was extracted with ethyl acetate (3×). The combined organic layers were washed with saturated aqueous NaCl, dried over MgSO$_4$, filtered and concentrated to dryness. The crude material was purified by column chromatography to provide (5-(((1R,3r,5S)-6,6-difluorobicyclo[3.1.0]hexan-3-yl)methoxy)-6-methoxypyridin-2-yl)((3aR, 7aR)-7a-(3-fluorophenyl)tetrahydro-[1,3]dioxolo[4,5-c]pyridin-5(6H)-yl)methanone (3.2 mg, 3.0%). ESI-MS m/z calc. 504.5. found 505.3 (M+1)⁺; Retention time: 1.08 min. and (5-(((1R,3s,5S)-6,6-difluorobicyclo[3.1.0]hexan-3-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone (2.9 mg, 2.8%). ESI-MS m/z calc. 504.5. found 505.3 (M+1)⁺; Retention time: 2.01 min (3 min run).

[(3aR,7aR)-7a-(3-fluorophenyl)-3a,4,6,7-tetrahydro-[1,3]dioxolo[4,5-c]pyridin-5-yl]-[5-(2-cyclopropyl-2,2-difluoro-ethoxy)-6-methoxy-2-pyridyl]methanone Step 1: 2-[[6-[(3aR,7aR)-7a-(3-fluorophenyl)-3a,4,6,7-tetrahydro-[1,3]dioxolo[4,5-c]pyridine-5-carbonyl]-2-methoxy-3-pyridyl]oxy]-N-methoxy-N-methyl-acetamide

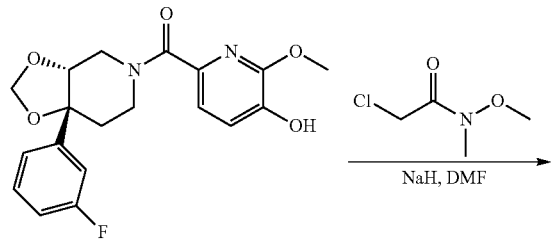

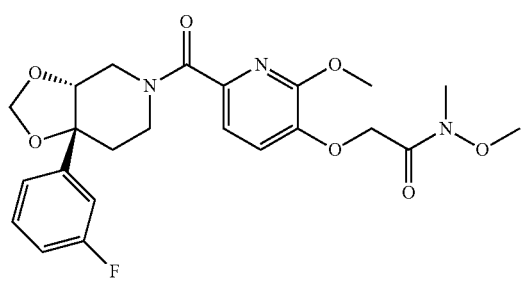

To a 25 mL round bottom flask was added [(3aR,7aR)-7a-(3-fluorophenyl)-3a,4,6,7-tetrahydro-[1,3]dioxolo[4,5-c]pyridin-5-yl]-(5-hydroxy-6-methoxy-2-pyridyl)methanone (75 mg, 0.20 mmol) and DMF (2 mL). The reaction mixture was cooled to 0° C. and sodium hydride (8 mg, 0.20 mmol) was added. After 5 min, 2-chloro-N-methoxy-N-methyl-acetamide (28 mg, 0.20 mmol) was added and the reaction mixture was heated at 45° C. overnight. The reaction mixture was filtered and purified via HPLC (1%-99%) ACN:H₂O with a 0.1% HCl modifier affording 2-[[6-[(3aR,7aR)-7a-(3-fluorophenyl)-3a,4,6,7-tetrahydro-[1,3]dioxolo[4,5-c]pyridine-5-carbonyl]-2-methoxy-3-pyridyl]oxy]-N-methoxy-N-methyl-acetamide (28 mg, 28%) as a white solid. ESI-MS m/z calc. 475.2. found 476.3 (M+1)+; Retention time: 1.73 min (3 min run).

Step 2: 1-cyclopropyl-2-((6-(7a-(3-fluorophenyl)hexahydro-[1,3]dioxolo[4,5-c]pyridine-5-carbonyl)-2-methoxypyridin-3-yl)oxy)ethanone

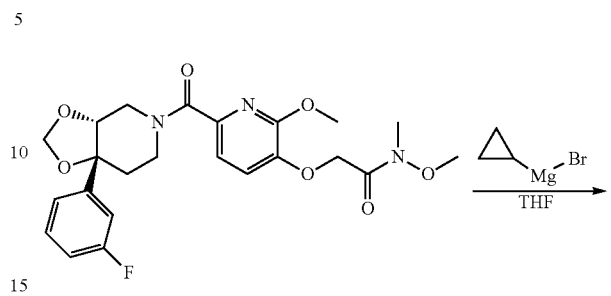

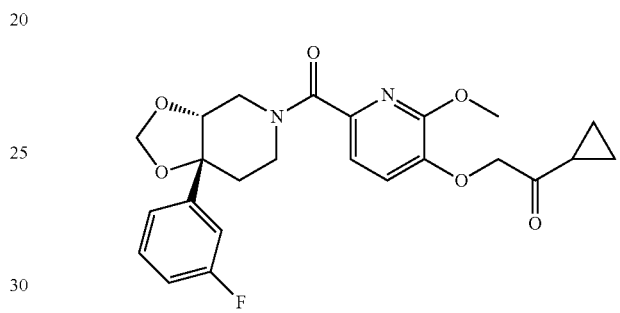

To a 10 mL round bottom flask containing 2-[[6-[(3aR,7aR)-7a-(3-fluorophenyl)-3a,4,6,7-tetrahydro-[1,3]dioxolo[4,5-c]pyridine-5-carbonyl]-2-methoxy-3-pyridyl]oxy]-N-methoxy-N-methyl-acetamide (23 mg, 0.05 mmol) was added THF (1 mL). The mixture was cooled to 0° C. and treated dropwise with cyclopropyl magnesium bromide (106 µL of 0.5 M in THF, 0.05 mmol). The reaction mixture was allowed to stir while warming to rt. The reaction mixture was quenched with saturated aqueous ammonium chloride and extracted with ethyl acetate. The organic layers were dried over sodium sulfate and concentrated under reduced pressure. The crude reaction mixture was purified via reverse phase HPLC (1%-99%) ACN:H₂O. ESI-MS m/z calc. 475.2. found 476.3 (M+1)⁺; Retention time: 1.73 min (3 min run).

Step 3: [(3aR,7aR)-7a-(3-fluorophenyl)-3a,4,6,7-tetrahydro-[1,3]dioxolo[4,5-c]pyridin-5-yl]-[5-(2-cyclopropyl-2,2-difluoro-ethoxy)-6-methoxy-2-pyridyl]methanone

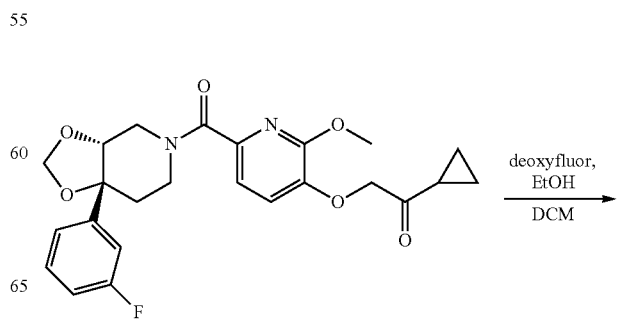

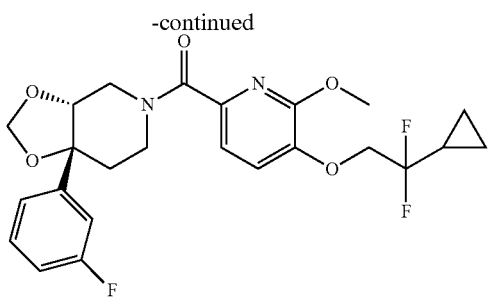

To a 10 mL round bottom flask containing 2-[[6-[(3aR,7aR)-7a-(3-fluorophenyl)-3a,4,6,7-tetrahydro-[1,3]dioxolo[4,5-c]pyridine-5-carbonyl]-2-methoxy-3-pyridyl]oxy]-1-cyclopropyl-ethanone (16 mg, 0.03 mmol) was added dichloromethane (1 mL). The reaction mixture was cooled to 0° C. and treated with ethanol (0.4 µL, 0.007 mmol) followed by the dropwise addition of deoxy-fluor (16 L, 0.085 mmol). The reaction mixture was allowed to stir overnight while warming to rt. Deoxy-fluor (16 µL, 0.085 mmol) was added again and after 3 h the reaction mixture was diluted with dichloroethane (2 mL) and heated at 50° C. oil bath overnight. The reaction mixture was quenched with saturated aqueous ammonium chloride and extracted with dichloromethane. The dichloromethane was dried over sodium sulfate and concentrated under reduced pressure. The crude product was purified via reverse phase HPLC (1%-99%) ACN:H$_2$O with a 0.1% HCl modifier to afford [(3aR,7aR)-7a-(3-fluorophenyl)-3a,4,6,7-tetrahydro-[1,3]dioxolo[4,5-c]pyridin-5-yl]-[5-(2-cyclopropyl-2,2-difluoro-ethoxy)-6-methoxy-2-pyridyl]methanone (8.2 mg, 45.4%). ESI-MS m/z calc. 478.2. found 479.3 (M+1)$^+$; Retention time: 1.82 min (3 min run).

4-[(3,3-difluorocyclobutyl)methylamino]-3-methoxy-benzoic acid

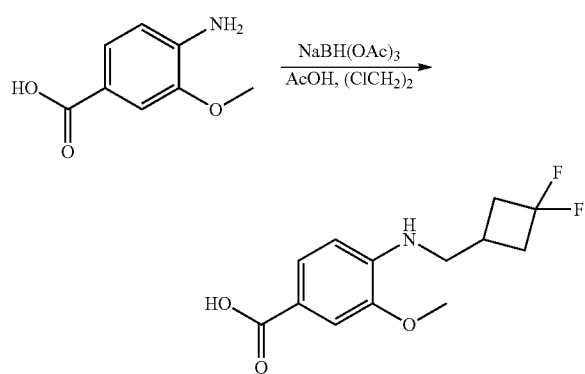

A solution of 4-amino-3-methoxy-benzoic acid (200 mg, 1.20 mmol) and 3,3-difluorocyclobutanecarbaldehyde (144 mg, 1.20 mmol) in 1,2-dichloroethane (4 mL) were treated with sodium triacetoxy borohydride (317 mg, 1.68 mmol) and acetic acid (68 µL, 1.20 mmol). A drop of TFA was added and the heterogenous reaction mixture was vigorously stirred at rt for 16 h. To the mixture was added 1N NaOH (50 mL) and DCM (50 mL) and the two phases were separated. The aqueous phase was acidified to pH=6 using 6N HCl and was extracted with DCM:methanol (10:1) (40 mL). The aqueous phase was further acidified to pH=1 and then was extracted with DCM:methanol (10:1) (2×30 mL). The combined organic extracts were dried over sodium sulfate, filtered, and concentrated under reduced pressure. The crude product purified by reverse phase preparative HPLC using HCl as a modifier. Evaporation of the volatiles under reduced pressure provided 4-[(3,3-difluorocyclobutyl)methylamino]-3-methoxy-benzoic acid (17 mg, 5.1%) as a white solid. ESI-MS m/z calc. 271.1. found 272.0 (M+1)$^+$; Retention time: 1.3 min (3 min run).

4-[(3,3-difluorocyclobutyl)methoxy]-3-methoxy-benzoic acid

Step 1: methyl 3-chloro-4-((3,3-difluorocyclobutyl)methoxy)benzoate

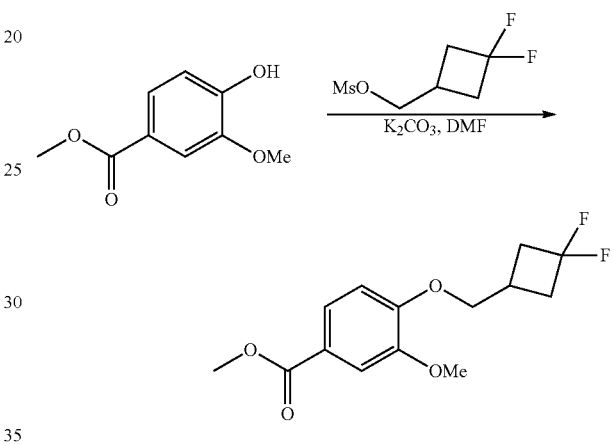

A 1 L flask equipped with a nitrogen inlet, a condenser and a magnetic stirbar was charged with (3,3-difluorocyclobutyl)methyl methanesulfonate (19.7 g, 88.6 mmol) and anhydrous DMF (400 mL). The mixture was treated with methyl 4-hydroxy-3-methoxy-benzoate (16.1 g, 88.5 mmol) and powdered K$_2$CO$_3$ (24.5 g, 177.1 mmol). The reaction mixture was heated at 80° C. for 30 min. Once the bath reached this temperature, the reaction mixture turned into a very thick gel that rendered magnetic stirring almost inoperative. The reaction mixture required intermittent manual stirring of the gel with a spatula for 3 h. Progressively, efficient stirring was restored and the reaction was stirred for an additionally 4 h. The reaction mixture was cooled down to rt overnight and poured into ice-cold water under stirring (divided into 2×1.4 L). The resulting suspensions were stirred at rt for 4 h and were filtered on the same buchner filter. The combined white solid was washed with water (2×200 mL) and partially dried by suction. The wet solid was dissolved in DCM (200 mL) and the residual water was separated by decantation. The organic layer was dried over sodium sulfate, filtered, and the solvents concentrated under reduced pressure to afford a crude pink solid. Purification by flash chromatography on silica gel (330 g column) using a gradient of AcOEt (0 to 70% over 30 min) in hexanes provided methyl 3-chloro-4-((3,3-difluorocyclobutyl)methoxy)benzoate (22 g, 88% yield) as a white solid. ESI-MS m/z calc. 286.0. found 287.0 (M+1); Retention time: 1.57 min (3 min run).

The following compounds were prepared using the procedure reported above.

| Product | Benzoate | Mesylate |
|---|---|---|
| methyl 3-chloro-4-((3,3-difluorocyclobutyl)methoxy)benzoate | methyl 3-chloro-4-hydroxybenzoate | (3,3-difluorocyclobutyl)methyl methanesulfonate |
| methyl 3-chloro-4-[[1-(trifluoromethyl)cyclopropyl]-methoxy]benzoate | methyl 3-chloro-4-hydroxybenzoate | (1-(trifluoromethyl)cyclopropyl)methyl methanesulfonate |
| methyl4-[(3,3-difluorocyclopentyl)methoxy]-3-methoxy-benzoate | methyl 3-methoxy-4-hydroxybenzoate | (3,3-difluorocyclopentyl methanesulfonate |
| methyl 4-[(3,3-difluorocyclobutyl)methoxyl]-3-methoxy-benzoate | methyl 3-methoxy-4-hydroxybenzoate | (3,3-difluorocyclobutyl)methyl methanesulfonate |
| methyl 3-methoxy-4-[[1-(trifluoromethyl)cyclopropyl]-methoxy]benzoate | methyl 3-methoxy-4-hydroxybenzoate | (1-(trifluoromethyl)cyclopropyl)methyl methanesulfonate |
| methyl 3-methoxy-4-(2,2,3,3-tetrafluoropropoxy)bbenzoate | methyl 3-methoxy-4-hydroxybenzoate | 2,2,3,3-tetrafluoropropoxy methanesulfonate |

Step 2: 4-[(3,3-difluorocyclobutyl)methoxy]-3-methoxy-benzoic acid

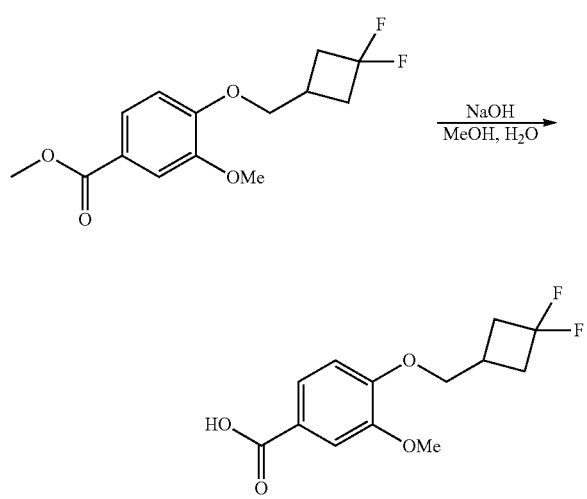

| Product | Precursor |
|---|---|
| 3-chloro-4-[(3,3-difluorocyclobutyl)methoxy]benzoic acid | methyl 3-chloro-4-((3,3-difluorocyclobutyl)methoxy)-benzoate |
| 3-chloro-4-[[1-(trifluoromethyl)cyclopropyl]methoxy]-benzoic acid | methyl 3-chloro-4-[[1-(trifluoromethyl)cyclopropyl]-methoxy]benzoate |
| 4-[(3,3-difluorocyclopentyl)methoxy]-3-methoxy-benzoic acid | methyl4-[(3,3-difluorocyclopentyl)methoxy]-3-methoxy-benzoate |
| 4-[(3,3-difluorocyclobutyl)methoxy]-3-methoxy-benzoic acid | methyl 4-[(3,3-difluorocyclobutyl)methoxy]-3-methoxy-benzoate |
| 3-methoxy-4-[[1-(trifluoromethyl)cyclopropyl]-methoxy]benzoic acid | methyl 3-methoxy-4-[[1-(trifluoromethyl)cyclopropyl]-methoxy]-benzoate |
| 3-methoxy-4-(2,2,3,3-tetrafluoropropoxy)benzoic acid | methyl 3-methoxy-4-(2,2,3,3-tetrafluoropropoxy)bbenzoate |

[(3aR,7aR)-7a-(3-fluorophenyl)-3a,4,6,7-tetrahydro-[1,3]dioxolo[4,5-c]pyridin-5-yl]-[4-[(3,3-difluorocyclobutyl)methyl-methyl-amino]-3-methoxy-phenyl] methanone In a 500 mL round bottom flask equipped with a magnetic stirbar, methyl 3-chloro-4-((3,3-difluorocyclobutyl)methoxy)benzoate (22 g, 77 mmol) was suspended in MeOH (100 mL) and was stirred at 60° C. until all solids dissolved. NaOH (30 mL of 6 M, 180.0 mmol) (6N aqueous) was added and the mixture was stirred at 60° C. for 1 h. The reaction mixture was cooled to rt, transferred into a 1 L erlenmeyer flask and diluted with water (500 mL). The solution was neutralized by dropwise addition of aqueous 6N HCl (30 mL) over 20 min, until the solution reached pH=2. More water was added (200 mL). The resulting white precipitate was filtered, washed with water (3×100 mL) and dried under vacuum (40° C.) for 3 d affording 4-[(3,3-difluorocyclobutyl)methoxy]-3-methoxy-benzoic acid (20.8 g, 86%) as a white solid. $^1$H NMR (400 MHz, CDCl$_3$) δ 7.75 (dd, J=8.4, 2.0 Hz, 1H), 7.61 (d, J=2.0 Hz, 1H), 6.91 (d, J=8.5 Hz, 1H), 4.13 (d, J=6.2 Hz, 2H), 3.92 (s, 3H), 2.90-2.63 (m, 3H), 2.63-2.34 (m, 2H). ESI-MS m/z calc. 272.1. found 273.0 (M+1)+; Retention time: 1.26 min (3 min run).

The following compounds were prepared using the procedure reported above.

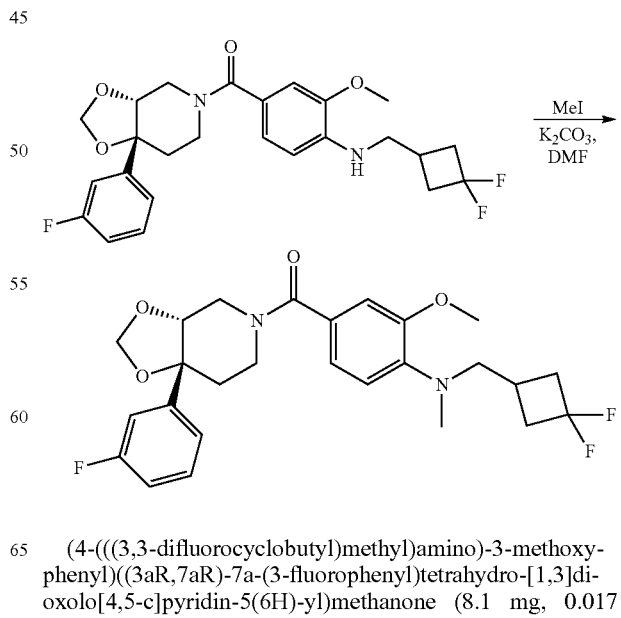

(4-(((3,3-difluorocyclobutyl)methyl)amino)-3-methoxy-phenyl)((3aR,7aR)-7a-(3-fluorophenyl)tetrahydro-[1,3]dioxolo[4,5-c]pyridin-5(6H)-yl)methanone (8.1 mg, 0.017 mmol) was dissolved in DMF (100 µL). K₂CO₃ (7.0 mg, 0.051 mmol) and MeI (5 µL, 0.08 mmol) were added and the reaction mixture was stirred at rt for 3 days. The reaction mixture was diluted with water (50 uL) and DMF (850 uL), filtered and purified by preparative HPLC using HCl as a modifier. The pure fraction were collected and the solvents removed by evaporation under reduced pressure to afford [(3aR,7aR)-7a-(3-fluorophenyl)-3a,4,6,7-tetrahydro-[1,3]dioxolo[4,5-c]pyridin-5-yl]-[4-[(3,3-difluorocyclobutyl)methyl-methyl-amino]-3-methoxy-phenyl]methanone (2.5 mg, 30.0%) as a colorless film. ESI-MS m/z calc. 490.5. found 491.4 (M+1)⁺; Retention time: 1.29 min (3 min run).

(5-((3,3-difluorobicyclo[3.1.0]hexan-6-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone Step 1: (5-((3-((tert-butyldimethylsilyl)oxy)bicyclo[3.1.0]hexan-6-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone

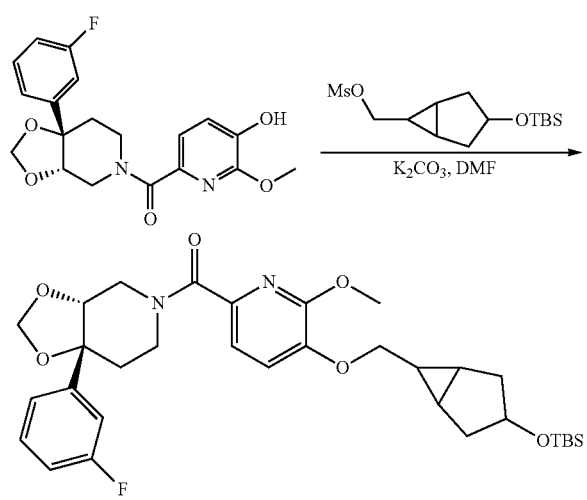

To a solution of [(3 aR,7aR)-7a-(3-fluorophenyl)-3a,4,6,7-tetrahydro-[1,3]dioxolo[4,5-c]pyridin-5-yl]-(5-hydroxy-6-methoxy-2-pyridyl)methanone (400 mg, 1.07 mmol) in DMF (5 mL) was added potassium carbonate (221 mg, 1.60 mmol) followed by the addition of (3-((tert-butyldimethylsilyl)oxy)bicyclo[3.1.0]hexan-6-yl)methyl methanesulfonate (377 mg, 1.18 mmol). The mixture was heated at 80° C. overnight. The reaction mixture was recharged with (3-((tert-butyldimethylsilyl)oxy)bicyclo[3.1.0]hexan-6-yl)methyl methanesulfonate (377 mg, 1.18 mmol) and heated at 140° C. overnight. After cooling to rt, the mixture was repartitioned between EtOAc and water. The aqueous layer was extracted with EtOAc (3×). The combined organic layers were washed with saturated aqueous NaCl (4×), dried over MgSO₄, filtered and concentrated to dryness. The crude material was purified by column chromatography (20-30% EtOAc-Hex) to provide (5-((3-((tert-butyldimethylsilyl)oxy)bicyclo[3.1.0]hexan-6-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone (220 mg, 34.4%). ESI-MS m/z calc. 598.3. found 599.5 (M+1)⁺; Retention time: 2.65 min (3 min run).

Step 2: ((3aR,7aR)-7a-(3-fluorophenyl)tetrahydro-[1,3]dioxolo[4,5-c]pyridin-5(6H)-yl)(5-((3-hydroxybicyclo[3.1.0]hexan-6-yl)methoxy)-6-methoxypyridin-2-yl)methanone

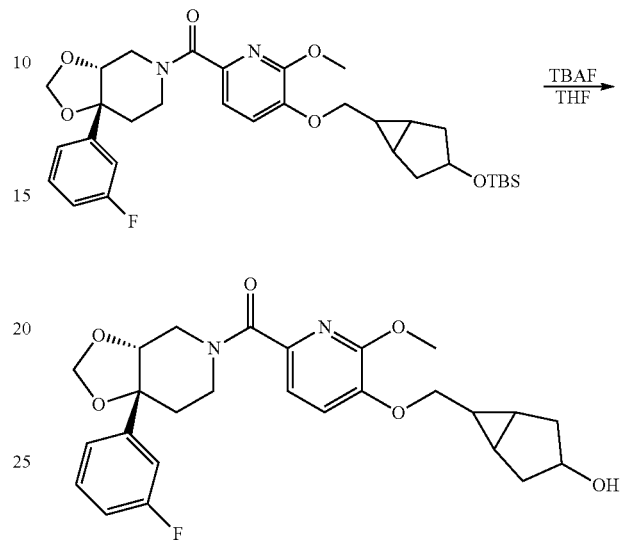

To a solution of (5-((3-((tert-butyldimethylsilyl)oxy)bicyclo[3.1.0]hexan-6-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone (220 mg, 0.37 mmol) in THF (5 mL) was added tetrabutylammonium fluoride (108 µL, 0.37 mmol). The mixture was heated at 70° C. for 1 h. The reaction mixture was stirred at 50° C. for 24 h and repartitioned between EtOAc and water. The aqueous layer was extracted with EtOAc (3×). The combined organic layers were washed with saturated aqueous NaCl, dried over MgSO₄, filtered, and concentrated to dryness. The crude material was purified by column chromatography (80-100% EtOAc-Hex) to provide ((3aR,7aR)-7a-(3-fluorophenyl)tetrahydro-[1,3]dioxolo[4,5-c]pyridin-5(6H)-yl)(5-((3-hydroxybicyclo[3.1.0]hexan-6-yl)methoxy)-6-methoxypyridin-2-yl)methanone (105 mg, 56%). ESI-MS m/z calc. 484.2. found 485.5 (M+1)+; Retention time: 1.71 min (3 min run).

Step 3: 6-[[6-[(3aR,7aR)-7a-(3-fluorophenyl)-3a,4,6,7-tetrahydro-[1,3]dioxolo[4,5-c]pyridine-5-carbonyl]-2-methoxy-3-pyridyl]oxymethyl]bicyclo[3.1.0]hexan-3-one

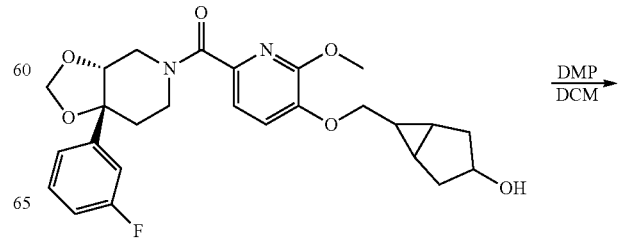

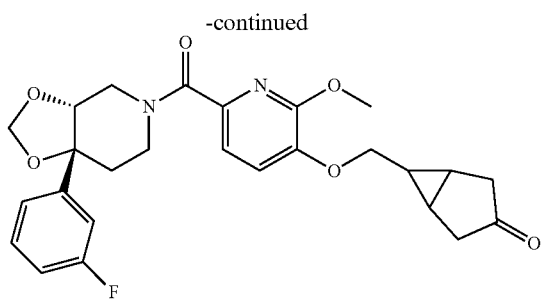

To a solution of ((3aR,7aR)-7a-(3-fluorophenyl)tetrahydro-[1,3]dioxolo[4,5-c]pyridin-5(6H)-yl)(5-((3-hydroxybicyclo[3.1.0]hexan-6-yl)methoxy)-6-methoxypyridin-2-yl)methanone (90 mg, 0.19 mmol) in dichloromethane (10 mL) was added Dess Martin periodinane (87 mg, 0.20 mmol). The reaction mixture was stirred at rt for 30 min, diluted with DCM, washed with saturated aqueous Na$_2$S$_2$O$_3$ (2×), saturated aqueous NaHCO$_3$, saturated aqueous NaCl, dried over MgSO$_4$, filtered and concentrated to dryness. The crude material was purified by column chromatography to provide 6-[[6-[(3aR,7aR)-7a-(3-fluorophenyl)-3a,4,6,7-tetrahydro-[1,3]dioxolo[4,5-c]pyridine-5-carbonyl]-2-methoxy-3-pyridyl]oxymethyl]bicyclo[3.1.0]hexan-3-one (72 mg, 80%) as a mixture of diastereomers. $^1$H NMR (400 MHz, CDCl$_3$) δ 7.44 (d, J=8.0 Hz, 1H), 7.36 (td, J=8.0, 5.9 Hz, 1H), 7.20-7.06 (m, 3H), 7.07-6.95 (m, 1H), 5.37-5.21 (m, 1H), 4.89 (d, J=28.4 Hz, 1H), 4.40 (dt, J=28.2, 4.3 Hz, 1H), 4.12-3.90 (m, 8H), 3.82-3.52 (m, 1H), 2.65 (dd, J=20.8, 2.7 Hz, 2H), 2.37-2.08 (m, 4H), 1.67 (s, 2H), 1.10-0.90 (m, 1H). ESI-MS m/z calc. 482.2. found 483.7 (M+1)$^+$; Retention time: 1.77 min (3 min run).

Step 4: (5-((3,3-difluorobicyclo[3.1.0]hexan-6-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone

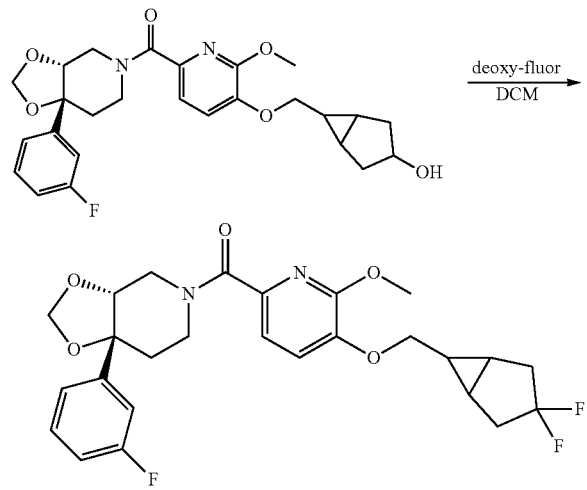

A solution of 6-[[6-[(3aR,7aR)-7a-(3-fluorophenyl)-3a,4,6,7-tetrahydro-[1,3]dioxolo[4,5-c]pyridine-5-carbonyl]-2-methoxy-3-pyridyl]oxymethyl]bicyclo[3.1.0]hexan-3-one (23 mg, 0.05 mmol) in DCM (2 mL) and EtOH (0.6 µL, 0.010 mmol) was purged with nitrogen for 5 min. Deoxyfluor (26 mg, 0.12 mmol) was added and the reaction mixture was heated at 50° C. for 30 min. The reaction mixture was recharged with deoxy-fluor (26 mg, 0.12 mmol) and heated at 50° C. for 18 h. The reaction was recharged with deoxy-fluor (26 mg, 0.12 mmol) and heated at 50° C. for 60 h. The reaction mixture was quenched with saturated aqueous ammonium chloride and extracted with DCM. The combined organics were dried over sodium sulfate, filtered, and concentrated under reduced pressure. Purification by column chromatography (40-60% EtOAc-Hex) afforded (5-((3,3-difluorobicyclo[3.1.0]hexan-6-yl)methoxy)-6-methoxypyridin-2-yl)((3aR,7aR)-7a-(3-fluorophenyl)tetrahydro-[1,3]dioxolo[4,5-c]pyridin-5(6H)-yl)methanone (5.5 mg, 20.6%). $^1$H NMR (400 MHz, CDCl$_3$) δ 7.43 (d, J=8.0 Hz, 1H), 7.36 (td, J=8.0, 6.0 Hz, 1H), 7.15 (d, J=7.2 Hz, 2H), 7.13-7.06 (m, 1H), 7.00 (dd, J=9.7, 7.4 Hz, 1H), 5.30 (t, J=15.3 Hz, 1H), 4.89 (d, J=28.6 Hz, 1H), 4.38 (dd, J=18.1, 14.0 Hz, 1H), 4.09-3.85 (m, 8H), 3.79-3.55 (m, 1H), 2.51-2.08 (m, 6H), 1.47 (s, 2H), 1.24 (dt, J=11.4, 6.4 Hz, 1H). ESI-MS m/z calc. 504.2. found 505.5 (M+1)$^+$; Retention time: 1.84 min (3 min run).

[(3aR,7aR)-7a-(3,5-difluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone

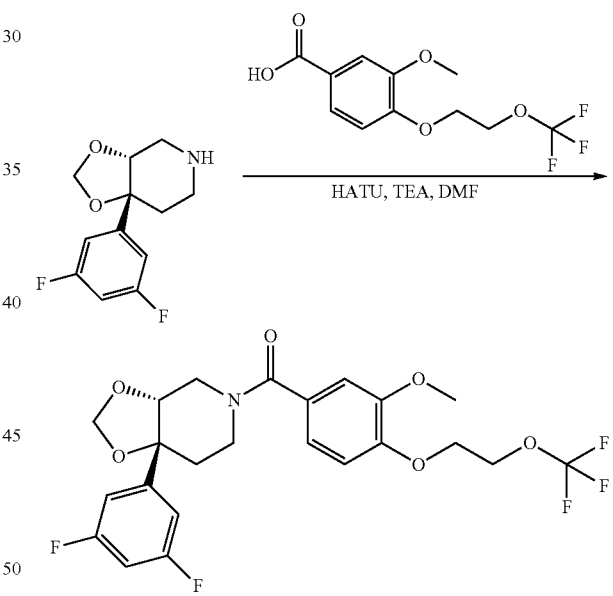

A 20 mL vial was charged with (3aR,7aR)-7a-(3,5-difluorophenyl)-4,5,6,7-tetrahydro-3aH-[1,3]dioxolo[4,5-c]pyridine (215 mg, 0.89 mmol), 3-methoxy-4-[2-(trifluoromethoxy)ethoxy]benzoic acid (250 mg, 0.89 mmol) and HATU (372.8 mg, 0.98 mmol). Anhydrous DMF (3.5 mL) was added and the mixture was stirred until all solids dissolved. Triethyl amine (497 µL, 3.56 mmol) was added and the mixture was stirred at rt for 2.5 h at which time LCMS indicated completion of the reaction. Water and saturated aqueous NaCl were added. The gummy material that formed was separated from the aqueous phase and was dissolved in DCM (50 mL). The organic phase was dried over sodium sulfate and the solvent concentrated under reduced pressure. The product was purified by flash chromatography on silica gel (24 g column) using a gradient of AcOEt (0 to 100% over 15 min) in hexanes. The product eluted at 65-85% ethyl acetate (10-13 min run). The pure fractions were collected and the solvents removed under reduced pressure. [(3aR,7aR)-7a-(3,5-difluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone (268 mg, 59.4%) was isolated as a solid off-white foam. $^1$H NMR (400 MHz, CDCl$_3$) δ 7.11 (broad s, 1H), 7.06 (dd, J=8.2, 1.9 Hz, 1H), 6.96-6.87 (m, 3H), 6.76 (tt, J=8.7, 2.3 Hz, 1H), 5.31 (s, 1H), 4.85 (s, 1H), 4.42-4.25 (m, 4H), 4.2-4.0 (broad d, 2H), 3.90 (s, 3H), 3.72 (broad s, 3H), 2.32-1.90 (broad m, 2H).

ESI-MS m/z calc. 503.1. found 504.0 (M+1)+; Retention time: 1.91 min (3 min run).

The following compounds were prepared using the procedure reported above.

| Product | Acid | Amine |
| --- | --- | --- |
| (4-isopropoxy-3-methyl-phenyl)-(6-phenyl-3-azabicyclo[4.1.0]heptan-3-yl)methanone | 4-isopropoxy-3-methyl-benzoic acid | 6-phenyl-3-azabicyclo[4.1.0]heptane |
| [3-methoxy-4-[2-(trifluoromethoxy)ethoxy]phenyl]-(6-phenyl-3-azabicyclo[4.1.0]heptane-3-yl)methanone | 3-methoxy-4-[2-(trifluoromethoxy)ethoxy]benzoic acid | 6-phenyl-3-azabicyclo[4.1.0]heptan |
| (4-isopentyloxy-3-methoxy-phenyl)-(6-phenyl-3-azabicyclo[4.1.0]heptan-3-yl)methanone | 4-isopentyloxy-3-methoxy-benzoic acid | 6-phenyl-3-azabicyclo[4.1.0]heptane |
| [4-(1-hydroxy-1-methyl-ethyl)-3-methoxy-phenyl]-(6-phenyl-3-azabicyclo[4.1.0]heptan-3-yl)methanone | 4-(1-hydroxy-1-methyl-ethyl)-3-methoxy-benzoic acid | 6-phenyl-3-azabicyclo[4.1.0]heptane |
| [3-methoxy-4-(tetrahydrofuran-2-ylmethoxy)phenyl]-(6-phenyl-3-azabicyclo[4.1.0]heptan-3-yl)methanone | 3-methoxy-4-(tetrahydrofuran-2-ylmethoxy)benzoic acid | 6-phenyl-3-azabicyclo[4.1.0]heptane |
| [6-methoxy-5-[2-(trifluoromethoxy)ethoxy]-2-pyridyl]-(6-phenyl-3-azabicyclo[4.1.0]heptan-3-yl)methanone | 6-methoxy-5-[2-(trifluoromethoxy)ethoxy]pyridine-2-carboxylic acid | 6-phenyl-3-azabicyclo[4.1.0]heptane |
| (5-isopropoxy-6-methyl-2-pyridyl)-(6-phenyl-3-azabicyclo[4.1.0]heptan-3-yl)methanone | 5-isopropoxy-6-methyl-pyridine-2-carboxylic acid | 6-phenyl-3-azabicyclo[4.1.0]heptane |
| [5-(2-fluoro-2-methyl-propoxy)-6-methoxy-2-pyridyl]-(6-phenyl-3-azabicyclo[4.1.0]heptan-3-yl)methanone | 5-(2-fluoro-2-methyl-propoxy)-6-methoxy-pyridine-2-carboxylic acid | 6-phenyl-3-azabicyclo[4.1.0]heptane |
| [4-(2-fluoro-2-methyl-propoxy)-3-methoxy-phenyl]-(6-phenyl-3-azabicyclo[4.1.0]heptan-3-yl)methanone | 4-(2-fluoro-2-methyl-propoxy)-3-methoxy-benzoic acid | 6-phenyl-3-azabicyclo[4.1.0]heptane |
| [4-(2-hydroxy-2-methyl-propoxy)-3-methyl-phenyl]-(6-phenyl-3-azabicyclo[4.1.0]heptan-3-yl)methanone | 4-(2-hydroxy-2-methyl-propoxy)-3-methyl-benzoic acid | 6-phenyl-3-azabicyclo[4.1.0]heptane |
| [4-(1-hydroxy-1-methyl-ethyl)phenyl]-(6-phenyl-3-azabicyclo[4.1.0]heptan-3-yl)methanone | 4-(1-hydroxy-1-methyl-ethyl)benzoic acid | 6-phenyl-3-azabicyclo[4.1.0]heptane |
| [3-fluoro-4-(1-hydroxy-1-methyl-ethyl)phenyl]-(6-phenyl-3-azabicyclo[4.1.0]heptan-3-yl)methanone | 3-fluoro-4-(1-hydroxy-1-methyl-ethyl)benzoic acid | 6-phenyl-3-azabicyclo[4.1.0]heptane |
| [3-methoxy-4-(3,3,3-trifluoropropoxymethyl)phenyl]-(6-phenyl-3-azabicyclo[4.1.0]heptan-3-yl)methanone | 3-methoxy-4-(3,3,3-trifluoropropoxymethyl)benzoic acid | 6-phenyl-3-azabicyclo[4.1.0]heptane |
| [4-(1-hydroxy-1-methyl-ethyl)-3-methyl-phenyl]-(6-phenyl-3-azabicyclo[4.1.0]heptan-3-yl)methanone | 4-(1-hydroxy-1-methyl-ethyl)-3-methyl-benzoic acid | 6-phenyl-3-azabicyclo[4.1.0]heptane |

| Product | Acid | Amine |
|---|---|---|
| (6-isopropoxy-3-pyridyl)-(6-phenyl-3-azabicyclo[4.1.0]heptan-3-yl)methanone | 6-isopropoxypyridine-3-carboxylic acid | 6-phenyl-3-azabicyclo[4.1.0]heptane |
| [6-methyl-5-[2-(trifluoromethoxy)ethoxy]-2-pyridyl]-(6-phenyl-3-azabicyclo[4.1.0]heptan-3-yl)methanone | 6-methyl-5-[2-(trifluoromethoxy)ethoxy]pyridine-2-carboxylic acid | 6-phenyl-3-azabicyclo[4.1.0]heptane |
| (3-fluoro-2-methoxy-phenyl)-(6-phenyl-3-azabicyclo[4.1.0]heptan-3-yl)methanone | 3-fluoro-2-methoxy-benzoic acid | 6-phenyl-3-azabicyclo[4.1.0]heptane |
| 2,3-dihydrobenzofuran-7-yl-(6-phenyl-3-azabicyclo[4.1.0]heptan-3-yl)methanone | 2,3-dihydrobenzofuran-7-carboxylic acid | 6-phenyl-3-azabicyclo[4.1.0]heptane |
| (6-phenyl-3-azabicyclo[4.1.0]heptan-3-yl)-(8-quinolyl)methanone | quinoline-8-carboxylic acid | 6-phenyl-3-azabicyclo[4.1.0]heptane |
| [4-(2-hydroxy-2-methyl-propoxy)-3-methoxy-phenyl]-(6-phenyl-3-azabicyclo[4.1.0]heptan-3-yl)methanone | 4-(2-hydroxy-2-methyl-propoxy)-3-methoxy-benzoic acid | 6-phenyl-3-azabicyclo[4.1.0]heptane |
| 2-isopropoxy-5-(6-phenyl-3-azabicyclo[4.1.0]heptane-3-carbonyl)benzonitrile | 3-cyano-4-isopropoxy-benzoic acid | 6-phenyl-3-azabicyclo[4.1.0]heptane |
| (3-fluoro-4-isopropoxy-phenyl)-(6-phenyl-3-azabicyclo[4.1.0]heptan-3-yl)methanone | 3-fluoro-4-isopropoxy-benzoic acid | 6-phenyl-3-azabicyclo[4.1.0]heptane |
| (6-isopropoxy-5-methyl-3-pyridyl)-(6-phenyl-3-azabicyclo[4.1.0]heptan-3-yl)methanone | 6-isopropoxy-5-methyl-pyridine-3-carboxylic acid | 6-phenyl-3-azabicyclo[4.1.0]heptane |
| [4-(1-hydroxycyclobutyl)phenyl]-(6-phenyl-3-azabicyclo[4.1.0]heptan-3-yl)methanone | 4-(1-hydroxycyclobutyl)benzoic acid | 6-phenyl-3-azabicyclo[4.1.0]heptane |
| [3-fluoro-4-(2-hydroxy-2-methyl-propyl)phenyl]-(6-phenyl-3-azabicyclo[4.1.0]heptan-3-yl)methanone | 3-fluoro-4-(2-hydroxy-2-methyl-propyl)benzoic acid | 6-phenyl-3-azabicyclo[4.1.0]heptane |
| (4-isopropoxy-2-methoxy-phenyl)-(6-phenyl-3-azabicyclo[4.1.0]heptan-3-yl)methanone | 4-isopropoxy-2-methoxy-benzoic acid | 6-phenyl-3-azabicyclo[4.1.0]heptane |
| N-cyclopropyl-4-(6-phenyl-3-azabicyclo[4.1.0]heptane-3-carbonyl)benzenesulfonamide | 4-(cyclopropylsulfamoyl)benzoic acid | 6-phenyl-3-azabicyclo[4.1.0]heptane |
| (4-ethylsulfonyl-3-methyl-phenyl)-(6-phenyl-3-azabicyclo[4.1.0]heptan-3-yl)methanone | 4-ethylsulfonyl-3-methyl-benzoic acid | 6-phenyl-3-azabicyclo[4.1.0]heptane |
| (2-fluoro-4-isopropoxy-phenyl)-(6-phenyl-3-azabicyclo[4.1.0]heptan-3-yl)methanone | 2-fluoro-4-isopropoxy-benzoic acid | 6-phenyl-3-azabicyclo[4.1.0]heptane |
| [3-methoxy-4-(2,2,2-trifluoroethoxymethyl)phenyl]-(6-phenyl-3-azabicyclo[4.1.0]heptan-3-yl)methanone | 3-methoxy-4-(2,2,2-trifluoroethoxymethyl)benzoic acid | 6-phenyl-3-azabicyclo[4.1.0]heptane |
| (5-methoxy-6-methyl-2-pyridyl)-(6-phenyl-3-azabicyclo[4.1.0]heptan-3-yl)methanone | 5-methoxy-6-methyl-pyridine-2-carboxylic acid | 6-phenyl-3-azabicyclo[4.1.0]heptane |
| (5-isobutoxy-2-pyridyl)-(6-phenyl-3-azabicyclo[4.1.0]heptan-3-yl)methanone | 5-isobutoxypyridine-2-carboxylic acid | 6-phenyl-3-azabicyclo[4.1.0]heptane |

| Product | Acid | Amine |
|---|---|---|
| [5-(2-hydroxy-2-methyl-propoxy)-6-methoxy-2-pyridyl]-(6-phenyl-3-azabicyclo[4.1.0]heptan-3-yl)methanone | 5-(2-hydroxy-2-methyl-propoxy)-6-methoxy-pyridine-2-carboxylic acid | 6-phenyl-3-azabicyclo[4.1.0]heptane |
| (4-isopropoxy-3-methyl-phenyl)-(6-phenyl-7-oxa-3-azabicyclo[4.2.0]octan-3-yl)methanone | 4-isopropoxy-3-methyl-benzoic acid | 6-phenyl-7-oxa-3-azabicyclo[4.2.0]octane |
| (5-isopropoxy-6-methyl-2-pyridyl)-(6-phenyl-7-oxa-3-azabicyclo[4.2.0]octan-3-yl)methanone | 5-isopropoxy-6-methyl-pyridine-2-carboxylic acid | 6-phenyl-7-oxa-3-azabicyclo[4.2.0]octane |
| [3-methoxy-4-[2-(trifluoromethoxy)ethoxy]phenyl]-(6-phenyl-7-oxa-3-azabicyclo[4.2.0]octan-3-yl)methanone | 3-methoxy-4-[2-(trifluoromethoxy)ethoxy]benzoic acid | 6-phenyl-7-oxa-3-azabicyclo[4.2.0]octane |
| (6-phenyl-7-oxa-3-azabicyclo[4.2.0]octan-3-yl)-(8-quinolyl)methanone | quinoline-8-carboxylic acid | 6-phenyl-7-oxa-3-azabicyclo[4.2.0]octane |
| [(3aS,7aS)-7a-phenyl-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aS,7aS)-7a-phenyl-4,5,6,7-tetrahydro-3aH-[1,3]dioxolo[4,5-c]pyridine |
| [(3aS,7aS)-7a-phenyl-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aS,7aS)-7a-phenyl-4,5,6,7-tetrahydro-3aH-[1,3]dioxolo[4,5-c]pyridine |
| [(3aS,7aS)-7a-phenyl-3a,4,6,7-tetrahydro-[1,3]dioxolo[4,5-c]pyridin-5-yl]-[4-(2-hydroxy-2-methyl-propoxy)-3-methyl-phenyl]methanone | 4-(2-hydroxy-2-methyl-propoxy)-3-methyl-benzoic acid | (3aS,7aS)-7a-phenyl-4,5,6,7-tetrahydro-3aH-[1,3]dioxolo[4,5-c]pyridine |
| [(3aS,7aS)-7a-phenyl-3a,4,6,7-tetrahydro-[1,3]dioxolo[4,5-c]pyridin-5-yl]-(4-isopropoxy-3-methyl-phenyl)methanone | 4-isopropoxy-3-methyl-benzoic acid | (3aS,7aS)-7a-phenyl-4,5,6,7-tetrahydro-3aH-[1,3]dioxolo[4,5-c]pyridine |
| [(3aS,7aS)-7a-phenyl-3a,4,6,7-tetrahydro-[1,3]dioxolo[4,5-c]pyridin-5-yl]-[4-(2-hydroxy-2-methyl-propoxy)-3-methoxy-phenyl]methanone | 4-(2-hydroxy-2-methyl-propoxy)-3-methoxy-benzoic acid | (3aS,7aS)-7a-phenyl-4,5,6,7-tetrahydro-3aH-[1,3]dioxolo[4,5-c]pyridine |
| [(3aS,7aS)-7a-phenyl-3a,4,6,7-tetrahydro-[1,3]dioxolo[4,5-c]pyridin-5-yl]-[4-(1-hydroxy-1-methyl-ethyl)-3-methyl-phenyl]methanone | 4-(1-hydroxy-1-methyl-ethyl)-3-methyl-benzoic acid | (3aS,7aS)-7a-phenyl-4,5,6,7-tetrahydro-3aH-[1,3]dioxolo[4,5-c]pyridine |
| [(3aS,7aS)-7a-phenyl-3a,4,6,7-tetrahydro-[1,3]dioxolo[4,5-c]pyridin-5-yl]-(8-quinolyl)methanone | quinoline-8-carboxylic acid | (3aS,7aS)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aR,7aR)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[4-(2-hydroxy-2-methyl-propoxy)-3-methyl-phenyl]methanone | 4-(2-hydroxy-2-methyl-propoxy)-3-methyl-benzoic acid | (3aR,7aR)-7a-phenyl-4,5,6,7-tetrahydro-3aH-[1,3]dioxolo[4,5-c]pyridine |

-continued

| Product | Acid | Amine |
|---|---|---|
| [(3aR,7aR)-7a-phenyl-3a,4,6,7-tetrahydro-[1,3]dioxolo[4,5-c]pyridin-5-yl]-(4-isopropoxy-3-methyl-phenyl)methanone | 4-isopropoxy-3-methyl-benzoic acid | (3aR,7aR)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[4-(2-hydroxy-2-methyl-propoxy)-3-methoxy-phenyl]methanone | 4-(2-hydroxy-2-methyl-propoxy)-3-methoxy-benzoic acid | (3aR,7aR)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[4-(1-hydroxy-1-methyl-ethyl)-3-methyl-phenyl]methanone | 4-(1-hydroxy-1-methyl-ethyl)-3-methyl-benzoic acid | (3aR,7aR)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-(8-quinolyl)methanone | quinoline-8-carboxylic acid | (3aR,7aR)-7a-phenyl-4,5,6,7-tetrahydro-3aH-[1,3]dioxolo[4,5-c]pyridine |
| [5-cyclopropyl-7-(trifluoromethyl)-4,5,6,7-tetrahydropyrazolo[1,5-a]pyrimidin-2-yl]-(6-phenyl-3-azabicyclo[4.1.0]heptan-3-yl)methanone | 5-cyclopropyl-7-(trifluoromethyl)-4,5,6,7-tetrahydropyrazolo[1,5-a]pyrimidine-2-carboxylic acid | 6-phenyl-3-azabicyclo[4.1.0]heptane |
| [6-(4-fluorophenyl)-3-azabicyclo[4.1.0]heptan-3-yl]-[4-(2-hydroxy-2-methyl-propoxy)-3-methyl-phenyl]methanone | 4-(2-hydroxy-2-methyl-propoxy)-3-methyl-benzoic acid | 6-(4-fluorophenyl)-3-azabicyclo[4.1.0]heptane |
| [4-(2-hydroxy-2-methyl-propoxy)-3-methyl-phenyl]-[(1R,6S)-6-phenyl-3-azabicyclo[4.1.0]heptan-3-yl]methanone | 4-(2-hydroxy-2-methyl-propoxy)-3-methyl-benzoic acid | (1R,6S)-6-phenyl-3-azabicyclo[4.1.0]heptane |
| [4-(2-hydroxy-2-methyl-propoxy)-3-methyl-phenyl]-[(1S,6R)-6-phenyl-3-azabicyclo[4.1.0]heptan-3-yl]methanone | 4-(2-hydroxy-2-methyl-propoxy)-3-methyl-benzoic acid | (1S,6R)-6-phenyl-3-azabicyclo[4.1.0]heptane |
| [(3aS,7aS)-7a-phenyl-3a,4,6,7-tetrahydro-[1,3]dioxolo[4,5-c]pyridin-5-yl]-[2-(trifluoromethoxymethyl)-2,3-dihydro-1,4-benzodioxin-6-yl]methanone | 2-(trifluoromethoxymethyl)-2,3-dihydro-1,4-benzodioxine-6-carboxylic acid | (3aS,7aS)-7a-phenyl-4,5,6,7-tetrahydro-3aH-[1,3]dioxolo[4,5-c]pyridine |
| [(3aS,7aS)-7a-phenyl-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aS,7aS)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[2-(trifluoromethoxymethyl)-2,3-dihydro-1,4-benzodioxin-6-yl]methanone | 2-(trifluoromethoxymethyl)-2,3-dihydro-1,4-benzodioxine-6-carboxylic acid | (3aR,7aR)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-phenyl-4,5,6,7-tetrahydro-3aH-[1,3]dioxolo[4,5-c]pyridine |
| [(3aS,7aS)-7a-(4-fluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aS,7aS)-7a-(4-fluorophenyl)-4,5,6,7-tetrahydro-3aH-[1,3]dioxolo[4,5-c]pyridine |

| Product | Acid | Amine |
| --- | --- | --- |
| [(3aR,7aR)-7a-(4-fluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(4-fluorophenyl)-4,5,6,7-tetrahydro-3aH-[1,3]dioxolo[4,5-c]pyridine |
| [(3aR,7aR)-7a-pyrimidin-2-yl-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-pyrimidin-2-yl-4,5,6,7-tetrahydro-3aH-[1,3]dioxolo[4,5-c]pyridine |
| [(3aS,7aS)-7a-(1-methylpyrazol-3-yl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aS,7aS)-7a-(1-methylpyrazol-3-yl)-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[4-(2-hydroxy-2-methyl-propoxy)-3-methyl-phenyl]methanone | 4-(2-hydroxy-2-methyl-propoxy)-3-methyl-benzoic acid | (3aS,7aR)-7a-thiazol-2-yl-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aS,7aR)-7a-thiazol-2-yl-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aS,7aR)-7a-thiazol-2-yl-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aS,7aR)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[4-(2-hydroxy-2-methyl-propoxy)-3-methyl-phenyl]methanone | 4-(2-hydroxy-2-methyl-propoxy)-3-methyl-benzoic acid | (3aR,7aS)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aS)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aR,7aS)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aS)-7a-thiazol-2-yl-4,5,6,7-tetrahydro-3aH-[1,3]dioxolo[4,5-c]pyridine |
| [(3aS,7aS)-7a-(4-fluorophenyl)-3a,4,6,7-tetrahydro-[1,3]dioxolo[4,5-c]pyridin-5-yl]-[4-(2-hydroxy-2-methyl-propoxy)-3-methyl-phenyl]methanone | 4-(2-hydroxy-2-methyl-propoxy)-3-methyl-benzoic acid | (3aS,7aS)-7a-(4-fluorophenyl)-4,5,6,7-tetrahydro-3aH-[1,3]dioxolo[4,5-c]pyridine |
| [(3aS,7aS)-7a-(4-fluorophenyl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aS,7aS)-7a-(4-fluorophenyl)-4,5,6,7-tetrahydro-3aH-[1,3]dioxolo[4,5-c]pyridine |

-continued

| Product | Acid | Amine |
|---|---|---|
| [(3aS,7aS)-7a-(4-fluorophenyl)-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aS,7aS)-7a-(4-fluorophenyl)-4,5,6,7-tetrahydro-3aH-[1,3]dioxolo[4,5-c]pyridine |
| [(3aS,7aS)-7a-(4-fluorophenyl)-3a,4,6,7-tetrahydro-[1,3]dioxolo[4,5-c]pyridin-5-yl]-[3-methoxy-4-(3,3,3-trifluoropropoxymethyl)phenyl]methanone | 3-methoxy-4-(3,3,3-trifluoropropoxymethyl)benzoic acid | (3aS,7aS)-7a-(4-fluorophenyl)-4,5,6,7-tetrahydro-3aH-[1,3]dioxolo[4,5-c]pyridine |
| [(3aR,7aR)-7a-(4-fluorophenyl)-3a,4,6,7-tetrahydro-[1,3]dioxolo[4,5-c]pyridin-5-yl]-[4-(2-hydroxy-2-methyl-propoxy)-3-methyl-phenyl]methanone | 4-(2-hydroxy-2-methyl-propoxy)-3-methyl-benzoic acid | (3aR,7aR)-7a-(4-fluorophenyl)-4,5,6,7-tetrahydro-3aH-[1,3]dioxolo[4,5-c]pyridine |
| [(3aR,7aR)-7a-(4-fluorophenyl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-(4-fluorophenyl)-4,5,6,7-tetrahydro-3aH-[1,3]dioxolo[4,5-c]pyridine |
| [(3aR,7aR)-7a-(4-fluorophenyl)-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aR,7aR)-7a-(4-fluorophenyl)-4,5,6,7-tetrahydro-3aH-[1,3]dioxolo[4,5-c]pyridine |
| [(3aR,7aR)-7a-(4-fluorophenyl)-3a,4,6,7-tetrahydro-[1,3]dioxolo[4,5-c]pyridin-5-yl]-[3-methoxy-4-(3,3,3-trifluoropropoxymethyl)phenyl]methanone | 3-methoxy-4-(3,3,3-trifluoropropoxymethyl)benzoic acid | (3aR,7aR)-7a-(4-fluorophenyl)-4,5,6,7-tetrahydro-3aH-[1,3]dioxolo[4,5-c]pyridine |
| [(3aR,7aR)-7a-pyrimidin-2-yl-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-pyrimidin-2-yl-4,5,6,7-tetrahydro-3aH-[1,3]dioxolo[4,5-c]pyridine |
| [(3aR,7aR)-7a-pyrimidin-2-yl-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aR,7aR)-7a-pyrimidin-2-yl-4,5,6,7-tetrahydro-3aH-[1,3]dioxolo[4,5-c]pyridine |
| [(3aR,7aR)-7a-pyrimidin-2-yl-3a,4,6,7-tetrahydro-[1,3]dioxolo[4,5-c]pyridin-5-yl]-(4-isopropoxy-3-methyl-phenyl)methanone | 4-isopropoxy-3-methyl-benzoic acid | (3aR,7aR)-7a-pyrimidin-2-yl-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aS,7aR)-7a-thiazol-2-yl-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aS,7aR)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aS)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aS)-7a-thiazol-2-yl-4,5,6,7-tetrahydro-3aH-[1,3]dioxolo[4,5-c]pyridine |

-continued

| Product | Acid | Amine |
| --- | --- | --- |
| [(3aR,7aR)-7a-thiazol-4-yl-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-thiazol-4-yl-4,5,6,7-tetrahydro-3aH-[1,3]dioxolo[4,5-c]pyridine |
| [(3aR,7aR)-7a-thiazol-4-yl-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-thiazol-4-yl-4,5,6,7-tetrahydro-3aH-[1,3]dioxolo[4,5-c]pyridine |
| [(3aR,7aR)-7a-thiazol-4-yl-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-thiazol-4-yl-4,5,6,7-tetrahydro-3aH-[1,3]dioxolo[4,5-c]pyridine |
| [7a-(2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | 7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-(2-fluoro-2-methyl-propoxy)-3-methoxy-phenyl]methanone | 4-(2-fluoro-2-methyl-propoxy)-3-methoxy-benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-(2-pyridyl)-4,5,6,7-tetrahydro-3aH-[1,3]dioxolo[4,5-c]pyridine |
| [(3aR,7aR)-7a-(6-bromo-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(6-bromo-2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-(2-hydroxy-2-methyl-propoxy)-3-methyl-phenyl]methanone | 4-(2-hydroxy-2-methyl-propoxy)-3-methyl-benzoic acid | (3aR,7aR)-7a-(2-pyridyl)-4,5,6,7-tetrahydro-3aH-[1,3]dioxolo[4,5-c]pyridine |
| [(3aR,7aR)-7a-(3-chloro-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(3-chloro-2-pyridyl)-4,5,6,7-tetrahydro-3aH-[1,3]dioxolo[4,5-c]pyridine |
| [(3aR,7aR)-7a-(3-chloro-2-pyridyl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(3-chloro-2-pyridyl)-4,5,6,7-tetrahydro-3aH-[1,3]dioxolo[4,5-c]pyridine |
| [(3aR,7aR)-7a-(3-chloro-2-pyridyl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-(3-chloro-2-pyridyl)-4,5,6,7-tetrahydro-3aH-[1,3]dioxolo[4,5-c]pyridine |
| [(3aR,7aR)-7a-(3-chloro-2-pyridyl)-3a,4,6,7-tetrahydro-[1,3]dioxolo[4,5-c]pyridin-5-yl]-(5-isopropoxy-6-methyl-2-pyridyl)methanone | 5-isopropoxy-6-methyl-pyridine-2-carboxylic acid | (3aR,7aR)-7a-(3-chloro-2-pyridyl)-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[3-methyl-4-(2,2,2-trifluoroethoxy)phenyl]methanone | 3-methyl-4-(2,2,2-trifluoroethoxy)benzoic acid | (3aS,7aR)-7a-thiazol-2-yl-4,5,6,7-tetrahydro-3aH-[1,3]dioxolo[4,5-c]pyridine |

-continued

| Product | Acid | Amine |
|---|---|---|
| [(3aS,7aR)-7a-thiazol-2-yl-3a,4,6,7-tetrahydro-[1,3]dioxolo[4,5-c]pyridin-5-yl]-[3-chloro-4-(2-hydroxy-2-methyl-propoxy)phenyl]methanone | 3-chloro-4-(2-hydroxy-2-methyl-propoxy)benzoic acid | (3aS,7aR)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[3-methyl-4-(2,2,2-trifluoroethoxy)phenyl]methanone | 3-methyl-4-(2,2,2-trifluoroethoxy)benzoic acid | (3aR,7aS)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[3-chloro-4-(2-hydroxy-2-methyl-propoxy)phenyl]methanone | 3-chloro-4-(2-hydroxy-2-methyl-propoxy)benzoic acid | (3aR,7aS)-7a-thiazol-2-yl-4,5,6,7-tetrahydro-3aH-[1,3]dioxolo[4,5-c]pyridine |
| [(3aR,7aR)-7a-(3-methoxy-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(3-methoxy-2-pyridyl)-4,5,6,7-tetrahydro-3aH-[1,3]dioxolo[4,5-c]pyridine |
| [(3aR,7aR)-7a-(3-methoxy-2-pyridyl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(3-methoxy-2-pyridyl)-4,5,6,7-tetrahydro-3aH-[1,3]dioxolo[4,5-c]pyridine |
| [(3aR,7aR)-7a-(3-methoxy-2-pyridyl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-7a-(3-methoxy-2-pyridyl)-4,5,6,7-tetrahydro-3aH-[1,3]dioxolo[4,5-c]pyridine |
| [(3aR,7aR)-7a-(3-methoxy-2-pyridyl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-(3-methoxy-2-pyridyl)-4,5,6,7-tetrahydro-3aH-[1,3]dioxolo[4,5-c]pyridine |
| [(3aR,7aR)-7a-(3-fluoro-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(3-fluoro-2-pyridyl)-4,5,6,7-tetrahydro-3aH-[1,3]dioxolo[4,5-c]pyridine |
| [(3aR,7aR)-7a-(3-fluoro-2-pyridyl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(3-fluoro-2-pyridyl)-4,5,6,7-tetrahydro-3aH-[1,3]dioxolo[4,5-c]pyridine |
| [(3aR,7aR)-7a-(3-fluoro-2-pyridyl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-(3-fluoro-2-pyridyl)-4,5,6,7-tetrahydro-3aH-[1,3]dioxolo[4,5-c]pyridine |
| [(3aR,7aR)-7a-(3-fluoro-2-pyridyl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-7a-(3-fluoro-2-pyridyl)-4,5,6,7-tetrahydro-3aH-[1,3]dioxolo[4,5-c]pyridine |
| [(3aR,7aR)-7a-(3-fluoro-2-pyridyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-(3-fluoro-2-pyridyl)-4,5,6,7-tetrahydro-3aH-[1,3]dioxolo[4,5-c]pyridine |
| [(3aR,7aR)-7a-(2-methylthiazol-4-yl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(2-methylthiazol-4-yl)-4,5,6,7-tetrahydro-3aH-[1,3]dioxolo[4,5-c]pyridine |
| [(3aR,7aR)-7a-(2-methylthiazol-4-yl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(2-methylthiazol-4-yl)-4,5,6,7-tetrahydro-3aH-[1,3]dioxolo[4,5-c]pyridine |

-continued

| Product | Acid | Amine |
|---|---|---|
| [(3aR,7aR)-7a-(2-methylthiazol-4-yl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-(2-methylthiazol-4-yl)-4,5,6,7-tetrahydro-3aH-[1,3]dioxolo[4,5-c]pyridine |
| [(3aR,7aR)-7a-(2-methylthiazol-4-yl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-7a-(2-methylthiazol-4-yl)-4,5,6,7-tetrahydro-3aH-[1,3]dioxolo[4,5-c]pyridine |
| [(3aR,7aR)-7a-(2-methylthiazol-4-yl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-(2-methylthiazol-4-yl)-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aS,7aR)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aS)-7a-thiazol-2-yl-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-7a-(2-pyridyl)-4,5,6,7-tetrahydro-3aH-[1,3]dioxolo[4,5-c]pyridine |
| [4-(2-hydroxy-1,1-dimethyl-ethyl)-3-methoxy-phenyl]-(6-phenyl-3-azabicyclo[4.1.0]heptan-3-yl)methanone | 4-(2-hydroxy-1,1-dimethyl-ethyl)-3-methoxy-benzoic acid | 6-phenyl-3-azabicyclo[4.1.0]heptane |
| [(3aS,7aR)-7a-thiazol-2-yl-3a,4,6,7-tetrahydro-[1,3]dioxolo[4,5-c]pyridin-5-yl]-[6-ethoxy-5-[2-(trifluoromethoxy)ethoxy]-2-pyridyl]methanone | 6-ethoxy-5-[2-(trifluoromethoxy)ethoxy]pyridine-2-carboxylic acid | (3aS,7aR)-7a-thiazol-2-yl-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[6-ethoxy-5-[2-(trifluoromethoxy)ethoxy]-2-pyridyl]methanone | 6-ethoxy-5-[2-(trifluoromethoxy)ethoxy]pyridine-2-carboxylic acid | (3aR,7aS)-7a-thiazol-2-yl-4,5,6,7-tetrahydro-3aH-[1,3]dioxolo[4,5-c]pyridine |
| [(3aR,7aR)-7a-(2-methylthiazol-4-yl)-3a,4,6,7-tetrahydro-[1,3]dioxolo[4,5-c]pyridin-5-yl]-[6-ethoxy-5-[2-(trifluoromethoxy)ethoxy]-2-pyridyl]methanone | 6-ethoxy-5-[2-(trifluoromethoxy)ethoxy]pyridine-2-carboxylic acid | (3aR,7aR)-7a-(2-methylthiazol-4-yl)-4,5,6,7-tetrahydro-3aH-[1,3]dioxolo[4,5-c]pyridine |
| [(3aR,7aS)-7a-thiazol-2-yl-3a,4,6,7-tetrahydro-[1,3]dioxolo[4,5-c]pyridin-5-yl]-[3-fluoro-4-[2-(trifluoromethoxy)ethoxy]phenyl]methanone | 3-fluoro-4-[2-(trifluoromethoxy)ethoxy]benzoic acid | (3aR,7aS)-7a-thiazol-2-yl-4,5,6,7-tetrahydro-3aH-[1,3]dioxolo[4,5-c]pyridine |
| [(3aS,7aR)-7a-thiazol-2-yl-3a,4,6,7-tetrahydro-[1,3]dioxolo[4,5-c]pyridin-5-yl]-[3-fluoro-4-[2-(trifluoromethoxy)ethoxy]phenyl]methanone | 3-fluoro-4-[2-(trifluoromethoxy)ethoxy]benzoic acid | (3aS,7aR)-7a-thiazol-2-yl-4,5,6,7-tetrahydro-3aH-[1,3]dioxolo[4,5-c]pyridine |

| Product | Acid | Amine |
|---|---|---|
| [(3aR,7aR)-7a-(2-pyridyl)-3a,4,6,7-tetrahydro-[1,3]dioxolo[4,5-c]pyridin-5-yl]-[3-chloro-4-(2,2-dimethylpropoxy)phenyl]methanone | 3-chloro-4-(2,2-dimethylpropoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-[2-(2,2,2-trifluoroethoxy)ethoxy]phenyl]methanone | 3-chloro-4-[2-(2,2,2-trifluoroethoxy)ethoxy]benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-(4,4,4-trifluoro-2-methyl-butoxy)phenyl]methanone | 3-chloro-4-(4,4,4-trifluoro-2-methyl-butoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-[(3,3-difluorocyclobutyl)methoxy]phenyl]methanone | 3-chloro-4-[(3,3-difluorocyclobutyl)methoxy]benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-(2,2,3,3-tetrafluoropropoxy)phenyl]methanone | 3-chloro-4-(2,2,3,3-tetrafluoropropoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[6-methyl-5-[2-(trifluoromethoxy)ethoxy]-2-pyridyl]methanone | 6-methyl-5-[2-(trifluoromethoxy)ethoxy]pyridine-2-carboxylic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-(trifluoromethyl)-4-(3,3,3-trifluoropropoxy)phenyl]methanone | 3-(trifluoromethyl)-4-(3,3,3-trifluoropropoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-(2-fluoro-2-methyl-propoxy)-3-(trifluoromethyl)phenyl]methanone | 4-(2-fluoro-2-methyl-propoxy)-3-(trifluoromethyl)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-(2-fluoro-2-methyl-propoxy)phenyl]methanone | 3-chloro-4-(2-fluoro-2-methyl-propoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-(3-chloro-4-hydroxy-phenyl)methanone | 3-chloro-4-hydroxy-benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-(2,2-difluoropropoxy)phenyl]methanone | 3-chloro-4-(2,2-difluoropropoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-(2,2,2-trifluoro-1-methyl-ethoxy)phenyl]methanone | 3-chloro-4-(2,2,2-trifluoro-1-methyl-ethoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-4-[(2,2-difluorocyclopropyl)methoxy]phenyl]methanone | 3-chloro-4-[(2,2-difluorocyclopropyl)methoxy]benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-(2-tert-butoxyethoxy)-3-chloro-phenyl]methanone | 4-(2-tert-butoxyethoxy)-3-chloro-benzoic acid | (3aR,7aR)-7a-(2-pyridyl)-4,5,6,7-tetrahydro-3aH-[1,3]dioxolo[4,5-c]pyridine |

| Product | Acid | Amine |
|---|---|---|
| [7a-(2-pyridyl)-2,3,3a,4,6,7-hexahydrofuro[3,2-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | 7a-(2-pyridyl)-3,3a,4,5,6,7-hexahydro-2H-furo[3,2-c]pyridine |
| [(3aR,7aR)-7a-(6-methyl-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(6-methyl-2-pyridyl)-4,5,6,7-tetrahydro-3aH-[1,3]dioxolo[4,5-c]pyridine |
| [(3aR,7aR)-7a-(6-methyl-2-pyridyl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(6-methyl-2-pyridyl)-4,5,6,7-tetrahydro-3aH-[1,3]dioxolo[4,5-c]pyridine |
| [(3aR,7aR)-7a-(6-methoxy-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(6-methoxy-2-pyridyl)-4,5,6,7-tetrahydro-3aH-[1,3]dioxolo[4,5-c]pyridine |
| [(3aR,7aR)-7a-(6-methoxy-2-pyridyl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(6-methoxy-2-pyridyl)-4,5,6,7-tetrahydro-3aH-[1,3]dioxolo[4,5-c]pyridine |
| [(3aR,7aR)-7a-(6-isobutoxy-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(6-isobutoxy-2-pyridyl)-4,5,6,7-tetrahydro-3aH-[1,3]dioxolo[4,5-c]pyridine |
| [(3aR,7aR)-7a-(6-isobutoxy-2-pyridyl)-3a,4,6,7-tetrahydro-[1,3]dioxolo[4,5-c]pyridin-5-yl]-[3-methyl-4-[2-(trifluoromethoxy)ethoxy]phenyl]methanone | 3-methyl-4-[2-(trifluoromethoxy)ethoxy]benzoic acid | (3aR,7aR)-7a-(6-isobutoxy-2-pyridyl)-4,5,6,7-tetrahydro-3aH-[1,3]dioxolo[4,5-c]pyridine |
| [(3aR,7aR)-7a-(2-pyridyl)-1,3,3a,4,6,7-hexahydrofuro[3,4-c]pyridin-5-yl]-[3-methoxy-4-[2-(trifluoromethoxy)ethoxy]phenyl]methanone; [(3aS,7aS)-7a-(2-pyridyl)-1,3,3a,4,6,7-hexahydrofuro[3,4-c]pyridin-5-yl]-[3-methoxy-4-[2-(trifluoromethoxy)ethoxy]phenyl]methanone | [(3aS,7aS)-7a-(2-pyridyl)-1,3,3a,4,6,7-hexahydrofuro[3,4-c]pyridin-5-yl]-[3-methoxy-4-[2-(trifluoromethoxy)ethoxy]phenyl]methanone; 3-methoxy-4-[2-(trifluoromethoxy)ethoxy]benzoic acid | (3aR,7aR)-7a-(2-pyridyl)-3,3a,4,5,6,7-hexahydro-1H-furo[3,4-c]pyridine |
| [(3aR,7aR)-7a-phenyl-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-7a-phenyl-4,5,6,7-tetrahydro-3aH-[1,3]dioxolo[4,5-c]pyridine |
| [(3aR,7aR)-7a-phenyl-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-phenyl-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-fluoro-5-methoxy-4-(3,3,3-trifluoropropoxy)phenyl]methanone | 3-fluoro-5-methoxy-4-(3,3,3-trifluoropropoxy)benzoic acid | (3aR,7aR)-7a-(2-pyridyl)-4,5,6,7-tetrahydro-3aH-[1,3]dioxolo[4,5-c]pyridine |

-continued

| Product | Acid | Amine |
|---|---|---|
| [(3aR,7aR)-7a-(2-pyridyl)-3a,4,6,7-tetrahydro-[1,3]dioxolo[4,5-c]pyridin-5-yl]-[4-[(2,2-difluorocyclopropyl)methoxy]-3-(trifluoromethyl)phenyl]methanone | 4-[(2,2-difluorocyclopropyl)methoxy]-3-(trifluoromethyl)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-(2,2,3,3-tetrafluoropropoxy)-3-(trifluoromethyl)phenyl]methanone | 4-(2,2,3,3-tetrafluoropropoxy)-3-(trifluoromethyl)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-chloro-5-methoxy-4-[2-(trifluoromethoxy)ethoxy]phenyl]methanone | 3-chloro-5-methoxy-4-[2-(trifluoromethoxy)ethoxy]benzoic acid | (3aR,7aR)-7a-(2-pyridyl)-4,5,6,7-tetrahydro-3aH-[1,3]dioxolo[4,5-c]pyridine |
| [(4aR,8aR)-8a-phenyl-2,3,4a,5,7,8-hexahydro-[1,4]dioxino[2,3-c]pyridin-6-yl]-[3-methoxy-4-[2-(trifluoromethoxy)ethoxy]phenyl]methanone | 3-methoxy-4-[2-(trifluoromethoxy)ethoxy]benzoic acid | (4aR,8aR)-8a-phenyl-3,4a,5,6,7,8-hexahydro-2H-[1,4]dioxino[2,3-c]pyridine |
| [(3aR,7aR)-7a-phenyl-3a,4,6,7-tetrahydro-[1,3]dioxolo[4,5-c]pyridin-5-yl]-[3-methoxy-4-(3,3,3-trifluoropropoxy)phenyl]methanone | 3-methoxy-4-(3,3,3-trifluoropropoxy)benzoic acid | (3aR,7aR)-7a-phenyl-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-methoxy-4-(3,3,3-trifluoropropoxy)phenyl]methanone | 3-methoxy-4-(3,3,3-trifluoropropoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-methoxy-4-(3,3,3-trifluoro-1-methyl-propoxy)phenyl]methanone | 3-methoxy-4-(3,3,3-trifluoro-1-methyl-propoxy)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-(2,2-difluoropropoxy)-3-(trifluoromethyl)phenyl]methanone | 4-(2,2-difluoropropoxy)-3-(trifluoromethyl)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[4-[(3,3-difluorocyclobutyl)methoxy]-3-(trifluoromethyl)phenyl]methanone | 4-[(3,3-difluorocyclobutyl)methoxy]-3-(trifluoromethyl)benzoic acid | (3aR,7aR)-7a-(2-pyridyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[3-(trifluoromethyl)-4-(2,2,2-trifluoro-1-methyl-ethoxy)phenyl]methanone | 3-(trifluoromethyl)-4-(2,2,2-trifluoro-1-methyl-ethoxy)benzoic acid | (3aR,7aR)-7a-(2-pyridyl)-4,5,6,7-tetrahydro-3aH-[1,3]dioxolo[4,5-c]pyridine |
| [(3aR,7aR)-2,2-dideuterio-7a-(3,5-difluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-2,2-dideuterio-7a-(3,5-difluorophenyl)-4,5,6,7-tetrahydro-3aH-[1,3]dioxolo[4,5-c]pyridine |
| [(3aR,7aR)-2,2-dideuterio-7a-(3,5-difluorophenyl)-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-2,2-dideuterio-7a-(3,5-difluorophenyl)-4,5,6,7-tetrahydro-3aH-[1,3]dioxolo[4,5-c]pyridine |
| [(3aR,7aR)-2,2-dideuterio-7a-(3,5-difluorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-2,2-dideuterio-7a-(3,5-difluorophenyl)-4,5,6,7-tetrahydro-3aH-[1,3]dioxolo[4,5-c]pyridine |

-continued

| Product | Acid | Amine |
|---|---|---|
| [(3aR,7aR)-2,2-dideuterio-7a-(3,5-difluorophenyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-2,2-dideuterio-7a-(3,5-difluorophenyl)-4,5,6,7-tetrahydro-3aH-[1,3]dioxolo[4,5-c]pyridine |
| [(3aR,7aR)-2,2-dideuterio-7a-(3,5-difluorophenyl)-3a,4,6,7-tetrahydro-[1,3]dioxolo[4,5-c]pyridin-5-yl]-[6-methyl-5-[2-(trifluoromethoxy)ethoxy]-2-pyridyl]methanone | 6-methyl-5-[2-(trifluoromethoxy)ethoxy]pyridine-2-carboxylic acid | (3aR,7aR)-2,2-dideuterio-7a-(3,5-difluorophenyl)-4,5,6,7-tetrahydro-3aH-[1,3]dioxolo[4,5-c]pyridine |
| [(3aR,7aR)-2,2-dideuterio-7a-(3-fluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-2,2-dideuterio-7a-(3-fluorophenyl)-4,5,6,7-tetrahydro-3aH-[1,3]dioxolo[4,5-c]pyridine |
| [(3aR,7aR)-2,2-dideuterio-7a-(3-fluorophenyl)-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-2,2-dideuterio-7a-(3-fluorophenyl)-4,5,6,7-tetrahydro-3aH-[1,3]dioxolo[4,5-c]pyridine |
| [(3aR,7aR)-2,2-dideuterio-7a-(3-fluorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-2,2-dideuterio-7a-(3-fluorophenyl)-4,5,6,7-tetrahydro-3aH-[1,3]dioxolo[4,5-c]pyridine |
| [(3aR,7aR)-2,2-dideuterio-7a-(3-fluorophenyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-2,2-dideuterio-7a-(3-fluorophenyl)-4,5,6,7-tetrahydro-3aH-[1,3]dioxolo[4,5-c]pyridine |
| [(3aR,7aR)-2,2-dideuterio-7a-(3-fluorophenyl)-3a,4,6,7-tetrahydro-[1,3]dioxolo[4,5-c]pyridin-5-yl]-[6-methyl-5-[2-(trifluoromethoxy)ethoxy]-2-pyridyl]methanone | 6-methyl-5-[2-(trifluoromethoxy)ethoxy]pyridine-2-carboxylic acid | (3aR,7aR)-2,2-dideuterio-7a-(3-fluorophenyl)-4,5,6,7-tetrahydro-3aH-[1,3]dioxolo[4,5-c]pyridine |
| [(3aR,7aR)-2,2-dideuterio-7a-(2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-2,2-dideuterio-7a-(2-pyridyl)-4,5,6,7-tetrahydro-3aH-[1,3]dioxolo[4,5-c]pyridine |
| [(3aR,7aR)-2,2-dideuterio-7a-(2-pyridyl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-2,2-dideuterio-7a-(2-pyridyl)-4,5,6,7-tetrahydro-3aH-[1,3]dioxolo[4,5-c]pyridine |
| [(3aR,7aR)-2,2-dideuterio-7a-(2-pyridyl)-3a,4,6,7-tetrahydro-[1,3]dioxolo[4,5-c]pyridin-5-yl]-[6-methyl-5-[2-(trifluoromethoxy)ethoxy]-2-pyridyl]methanone | 6-methyl-5-[2-(trifluoromethoxy)ethoxy]pyridine-2-carboxylic acid | (3aR,7aR)-2,2-dideuterio-7a-(2-pyridyl)-4,5,6,7-tetrahydro-3aH-[1,3]dioxolo[4,5-c]pyridine |
| [(3aR,7aR)-2,2-dideuterio-7a-phenyl-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-2,2-dideuterio-7a-phenyl-4,5,6,7-tetrahydro-3aH-[1,3]dioxolo[4,5-c]pyridine |
| [3-chloro-4-[2-(trifluoromethoxy)ethoxy]phenyl]-[6-(4-fluorophenyl)-3-azabicyclo[4.1.0]heptan-3-yl]methanone | 3-chloro-4-[2-(trifluoromethoxy)ethoxy]benzoic acid | 6-(4-fluorophenyl)-3-azabicyclo[4.1.0]heptane |
| [6-(4-fluorophenyl)-3-azabicyclo[4.1.0]heptan-3-yl]-[3-methoxy-4-[2-(trifluoromethoxy)ethoxy]phenyl]methanone | 3-methoxy-4-[2-(trifluoromethoxy)ethoxy]benzoic acid | 6-(4-fluorophenyl)-3-azabicyclo[4.1.0]heptane |

| Product | Acid | Amine |
|---|---|---|
| [6-(4-fluorophenyl)-3-azabicyclo[4.1.0]heptan-3-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | 6-(4-fluorophenyl)-3-azabicyclo[4.1.0]heptane |
| [4-[(3,3-difluorocyclobutyl)methoxy]-3-methoxy-phenyl]-[6-(4-fluorophenyl)-3-azabicyclo[4.1.0]heptan-3-yl]methanone | 4-[(3,3-difluorocyclobutyl)methoxy]-3-methoxy-benzoic acid | 6-(4-fluorophenyl)-3-azabicyclo[4.1.0]heptane |
| [6-(4-fluorophenyl)-3-azabicyclo[4.1.0]heptan-3-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | 6-(4-fluorophenyl)-3-azabicyclo[4.1.0]heptane |
| [5-chloro-6-[2-(trifluoromethoxy)ethoxy]-3-pyridyl]-[6-(4-fluorophenyl)-3-azabicyclo[4.1.0]heptan-3-yl]methanone | 5-chloro-6-[2-(trifluoromethoxy)ethoxy]pyridine-3-carboxylic acid | 6-(4-fluorophenyl)-3-azabicyclo[4.1.0]heptane |
| [(3aR,7aR)-7a-phenyl-3a,4,6,7-tetrahydro-[1,3]dioxolo[4,5-c]pyridin-5-yl]-[5-chloro-6-[2-(trifluoromethoxy)ethoxy]-3-pyridyl]methanone | 5-chloro-6-[2-(trifluoromethoxy)ethoxy]pyridine-3-carboxylic acid | (3aR,7aR)-7a-phenyl-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[5-chloro-6-[2-(trifluoromethoxy)ethoxy]-3-pyridyl]methanone | 5-chloro-6-[2-(trifluoromethoxy)ethoxy]pyridine-3-carboxylic acid | (3aR,7aR)-7a-(2-pyridyl)-4,5,6,7-tetrahydro-3aH-[1,3]dioxolo[4,5-c]pyridine |
| [(3aR,7aR)-2,2-dideuterio-7a-phenyl-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-2,2-dideuterio-7a-phenyl-4,5,6,7-tetrahydro-3aH-[1,3]dioxolo[4,5-c]pyridine |
| 3-[(3aR,7aR)-5-[3-methoxy-4-[2-(trifluoromethoxy)ethoxy]benzoyl]-3a,4,6,7-tetrahydro-[1,3]dioxolo[4,5-c]pyridin-7a-yl]benzonitrile | 3-methoxy-4-[2-(trifluoromethoxy)ethoxy]benzoic acid | 3-[(3aR,7aR)-4,5,6,7-tetrahydro-3aH-[1,3]dioxolo[4,5-c]pyridin-7a-yl]benzonitrile |
| 3-[(3aR,7aR)-5-[6-methoxy-5-[2-(trifluoromethoxy)ethoxy]pyridine-2-carbonyl]-3a,4,6,7-tetrahydro-[1,3]dioxolo[4,5-c]pyridin-7a-yl]benzonitrile | 6-methoxy-5-[2-(trifluoromethoxy)ethoxy]pyridine-2-carboxylic acid | 3-[(3aR,7aR)-4,5,6,7-tetrahydro-3aH-[1,3]dioxolo[4,5-c]pyridin-7a-yl]benzonitrile |
| 3-[(3aR,7aR)-5-[4-[(3,3-difluorocyclobutyl)methoxy]-3-methoxy-benzoyl]-3a,4,6,7-tetrahydro-[1,3]dioxolo[4,5-c]pyridin-7a-yl]benzonitrile | 4-[(3,3-difluorocyclobutyl)methoxy]-3-methoxy-benzoic acid | 3-[(3aR,7aR)-4,5,6,7-tetrahydro-3aH-[1,3]dioxolo[4,5-c]pyridin-7a-yl]benzonitrile |
| 3-[(3aR,7aR)-5-[3-methoxy-4-(2,2,2-trifluoro-1-methyl-ethoxy)benzoyl]-3a,4,6,7-tetrahydro-[1,3]dioxolo[4,5-c]pyridin-7a-yl]benzonitrile | 3-methoxy-4-(2,2,2-trifluoro-1-methyl-ethoxy)benzoic acid | 3-[(3aR,7aR)-4,5,6,7-tetrahydro-3aH-[1,3]dioxolo[4,5-c]pyridin-7a-yl]benzonitrile |
| [(3aR,7aR)-7a-(2,5-difluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(2,5-difluorophenyl)-4,5,6,7-tetrahydro-3aH-[1,3]dioxolo[4,5-c]pyridine |
| [(3aR,7aR)-7a-(2,5-difluorophenyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-(2,5-difluorophenyl)-4,5,6,7-tetrahydro-3aH-[1,3]dioxolo[4,5-c]pyridine |

| Product | Acid | Amine |
| --- | --- | --- |
| [(3aR,7aR)-7a-(2,5-difluorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(2,5-difluorophenyl)-4,5,6,7-tetrahydro-3aH-[1,3]dioxolo[4,5-c]pyridine |
| [(3aR,7aR)-7a-(2,5-difluorophenyl)-3a,4,6,7-tetrahydro-[1,3]dioxolo[4,5-c]pyridin-5-yl]-[3-methoxy-4-(3,3,3-trifluoropropoxy)phenyl]methanone | 3-methoxy-4-(3,3,3-trifluoropropoxy)benzoic acid | (3aR,7aR)-7a-(2,5-difluorophenyl)-4,5,6,7-tetrahydro-3aH-[1,3]dioxolo[4,5-c]pyridine |
| [(3aR,7aR)-7a-(2,5-difluorophenyl)-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-7a-(2,5-difluorophenyl)-4,5,6,7-tetrahydro-3aH-[1,3]dioxolo[4,5-c]pyridine |
| [3-methoxy-4-[2-(trifluoromethoxy)ethoxy]phenyl]-[6-(2-pyridyl)-3-azabicyclo[4.1.0]heptan-3-yl]methanone | 3-methoxy-4-[2-(trifluoromethoxy)ethoxy]benzoic acid | 6-(2-pyridyl)-3-azabicyclo[4.1.0]heptane |
| [(3aR,7aR)-2,2-dideuterio-7a-(3-fluorophenyl)-3a,4,6,7-tetrahydro-[1,3]dioxolo[4,5-c]pyridin-5-yl]-[5-(cyclobutylmethoxy)-6-methoxy-2-pyridyl]methanone | 5-(cyclobutylmethoxy)-6-methoxy-pyridine-2-carboxylic acid | (3aR,7aR)-2,2-dideuterio-7a-(3-fluorophenyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(3-chlorophenyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(3-chlorophenyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[3-methoxy-4-(3,3,3-trifluoropropoxy)phenyl]methanone | 3-methoxy-4-(3,3,3-trifluoropropoxy)benzoic acid | (3aR,7aR)-7a-(3-chlorophenyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-7a-(3-chlorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(2,3-difluorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(2,3-difluorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[3-methoxy-4-(3,3,3-trifluoropropoxy)phenyl]methanone | 3-methoxy-4-(3,3,3-trifluoropropoxy)benzoic acid | (3aR,7aR)-7a-(2,3-difluorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-7a-(2,3-difluorophenyl)-4,5,6,7-tetrahydro-3aH-[1,3]dioxolo[4,5-c]pyridine |

-continued

| Product | Acid | Amine |
|---|---|---|
| [(3aR,7aR)-7a-(3-chlorophenyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-(3-chlorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-(2,3-difluorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-7a-(2,3-difluorophenyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-7a-(3-chlorophenyl)-4,5,6,7-tetrahydro-3aH-[1,3]dioxolo[4,5-c]pyridine |
| [(3aR,7aR)-2,2-dideuterio-7a-(3,5-difluorophenyl)-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-2,2-dideuterio-7a-(3,5-difluorophenyl)-4,5,6,7-tetrahydro-3aH-[1,3]dioxolo[4,5-c]pyridine |
| [(3aR,7aR)-2,2-dideuterio-7a-(3-fluorophenyl)-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-2,2-dideuterio-7a-(3-fluorophenyl)-4,5,6,7-tetrahydro-3aH-[1,3]dioxolo[4,5-c]pyridine |
| [(3aR,7aR)-7a-(2-pyridyl)-1,3,3a,4,6,7-hexahydrofuro[3,4-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(2-pyridyl)-3,3a,4,5,6,7-hexahydro-1H-furo[3,4-c]pyridine |
| (3aS,7aS)-5-[3-methoxy-4-[2-(trifluoromethoxy)ethoxy]benzoyl]-7a-(2-pyridyl)-3a,4,6,7-tetrahydro-3H-furo[3,4-c]pyridin-1-one | 3-methoxy-4-[2-(trifluoromethoxy)ethoxy]benzoic acid | (3aS,7aS)-7a-(2-pyridyl)-3,3a,4,5,6,7-hexahydrofuro[3,4-c]pyridin-1-one |
| [(3aR,7aR)-7a-(3-fluorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(3-fluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-(3-fluorophenyl)-4,5,6,7-tetrahydro-3aH-[1,3]dioxolo[4,5-c]pyridine |
| [(3aS,7aS)-7a-(2-pyridyl)-1,3,3a,4,6,7-hexahydrofuro[3,4-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aS,7aS)-7a-(2-pyridyl)-3,3a,4,5,6,7-hexahydro-1H-furo[3,4-c]pyridine |
| [(3aR,7aR)-7a-[6-(trifluoromethyl)-2-pyridyl]-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-[6-(trifluoromethyl)-2-pyridyl]-4,5,6,7-tetrahydro-3aH-[1,3]dioxolo[4,5-c]pyridine |

| Product | Acid | Amine |
|---|---|---|
| [(3aR,7aR)-7a-[6-(trifluoromethyl)-2-pyridyl]-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-[6-(trifluoromethyl)-2-pyridyl]-4,5,6,7-tetrahydro-3aH-[1,3]dioxolo[4,5-c]pyridine |
| [(3aR,7aR)-7a-[6-(trifluoromethyl)-2-pyridyl]-3a,4,6,7-tetrahydro-[1,3]dioxolo[4,5-c]pyridin-5-yl]-[3-methoxy-4-(3,3,3-trifluoropropoxy)phenyl]methanone | 3-methoxy-4-(3,3,3-trifluoropropoxy)benzoic acid | (3aR,7aR)-7a-[6-(trifluoromethyl)-2-pyridyl]-4,5,6,7-tetrahydro-3aH-[1,3]dioxolo[4,5-c]pyridine |
| [(3aR,7aR)-7a-[6-(trifluoromethyl)-2-pyridyl]-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aR,7aR)-7a-[6-(trifluoromethyl)-2-pyridyl]-4,5,6,7-tetrahydro-3aH-[1,3]dioxolo[4,5-c]pyridine |
| [(3aR,7aR)-7a-[6-(trifluoromethyl)-2-pyridyl]-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-[6-(trifluoromethyl)-2-pyridyl]-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[6-methoxy-5-[[1-(trifluoromethyl)cyclopropyl]methoxy]-2-pyridyl]methanone | 6-methoxy-5-[[1-(trifluoromethyl)cyclopropyl]methoxy]pyridine-2-carboxylic acid | (3aR,7aR)-7a-(2,3-difluorophenyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[6-methoxy-5-[[1-(trifluoromethyl)cyclopropyl]methoxy]-2-pyridyl]methanone | 6-methoxy-5-[[1-(trifluoromethyl)cyclopropyl]methoxy]pyridine-2-carboxylic acid | (3aR,7aR)-7a-(3-chlorophenyl)-4,5,6,7-tetrahydro-3aH-[1,3]dioxolo[4,5-c]pyridine |
| [(3aR,7aR)-2,2-dideuterio-7a-(3,5-difluorophenyl)-3a,4,6,7-tetrahydro-[1,3]dioxolo[4,5-c]pyridin-5-yl]-[6-methoxy-5-[[1-(trifluoromethyl)cyclopropyl]methoxy]-2-pyridyl]methanone | 6-methoxy-5-[[1-(trifluoromethyl)cyclopropyl]methoxy]pyridine-2-carboxylic acid | (3aR,7aR)-2,2-dideuterio-7a-(3,5-difluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[6-methoxy-5-[[1-(trifluoromethyl)cyclopropyl]methoxy]-2-pyridyl]methanone | 6-methoxy-5-[[1-(trifluoromethyl)cyclopropyl]methoxy]pyridine-2-carboxylic acid | (3aR,7aR)-7a-(3-fluorophenyl)-4,5,6,7-tetrahydro-3aH-[1,3]dioxolo[4,5-c]pyridine |
| [(3aR,7aR)-7a-[6-(trifluoromethyl)-2-pyridyl]-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-7a-[6-(trifluoromethyl)-2-pyridyl]-4,5,6,7-tetrahydro-3aH-[1,3]dioxolo[4,5-c]pyridine |
| [3-methoxy-4-[2-(trifluoromethoxy)ethoxy]phenyl]-[(1S,6R)-6-(2-pyridyl)-3-azabicyclo[4.1.0]heptan-3-yl]methanone | 3-methoxy-4-[2-(trifluoromethoxy)ethoxy]benzoic acid | (1S,6R)-6-(2-pyridyl)-3-azabicyclo[4.1.0]heptane |
| [3-methoxy-4-[2-(trifluoromethoxy)ethoxy]phenyl]-[(1R,6S)-6-(2-pyridyl)-3-azabicyclo[4.1.0]heptan-3-yl]methanone | 3-methoxy-4-[2-(trifluoromethoxy)ethoxy]benzoic acid | (1R,6S)-6-(2-pyridyl)-3-azabicyclo[4.1.0]heptane |

-continued

| Product | Acid | Amine |
|---|---|---|
| [(3aR,7aR)-7a-phenyl-3a,4,6,7-tetrahydro-[1,3]dioxolo[4,5-c]pyridin-5-yl]-[6-methoxy-5-[[1-(trifluoromethyl)cyclopropyl]methoxy]-2-pyridyl]methanone | 6-methoxy-5-[[1-(trifluoromethyl)cyclopropyl]methoxy]pyridine-2-carboxylic acid | (3aR,7aR)-7a-phenyl-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[6-methoxy-5-(2,2,2-trifluoro-1-methyl-ethoxy)-2-pyridyl]methanone | 6-methoxy-5-(2,2,2-trifluoro-1-methyl-ethoxy)pyridine-2-carboxylic acid | (3aR,7aR)-7a-(3-fluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[6-methoxy-5-(2,2,3,3-tetrafluoropropoxy)-2-pyridyl]methanone | 6-methoxy-5-(2,2,3,3-tetrafluoropropoxy)pyridine-2-carboxylic acid | (3aR,7aR)-7a-(3-fluorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[6-methoxy-5-(2,2,2-trifluoro-1-methyl-ethoxy)-2-pyridyl]methanone | 6-methoxy-5-(2,2,2-trifluoro-1-methyl-ethoxy)pyridine-2-carboxylic acid | (3aR,7aR)-7a-(2,3-difluorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[6-methoxy-5-(2,2,3,3-tetrafluoropropoxy)-2-pyridyl]methanone | 6-methoxy-5-(2,2,3,3-tetrafluoropropoxy)pyridine-2-carboxylic acid | (3aR,7aR)-7a-(2,3-difluorophenyl)-4,5,6,7-tetrahydro-3aH-[1,3]dioxolo[4,5-c]pyridine |
| [(3aR,7aR)-7a-(2-pyridyl)-3a,4,6,7-tetrahydro-[1,3]dioxolo[4,5-c]pyridin-5-yl]-[6-methoxy-5-[[1-(trifluoromethyl)cyclopropyl]methoxy]-2-pyridyl]methanone | 6-methoxy-5-[[1-(trifluoromethyl)cyclopropyl]methoxy]pyridine-2-carboxylic acid | (3aR,7aR)-7a-(2-pyridyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[4-(difluoromethylsulfonyl)phenyl]methanone | 4-(difluoromethylsulfonyl)benzoic acid | (3aR,7aR)-7a-(3-fluorophenyl)-4,5,6,7-tetrahydro-3aH-[1,3]dioxolo[4,5-c]pyridine |
| [7,7-difluoro-6-(2-pyridyl)-3-azabicyclo[4.1.0]heptan-3-yl]-[3-methoxy-4-[2-(trifluoromethoxy)ethoxy]phenyl]methanone | 3-methoxy-4-[2-(trifluoromethoxy)ethoxy]benzoic acid | 7,7-difluoro-6-(2-pyridyl)-3-azabicyclo[4.1.0]heptane |
| [4-[(3,3-difluorocyclobutyl)methoxy]-3-methoxy-phenyl]-[7,7-difluoro-6-(2-pyridyl)-3-azabicyclo[4.1.0]heptan-3-yl]methanone | 4-[(3,3-difluorocyclobutyl)methoxy]-3-methoxy-benzoic acid | 7,7-difluoro-6-(2-pyridyl)-3-azabicyclo[4.1.0]heptane |
| [(3aR,7aR)-7a-(2,3-difluorophenyl)-3a,4,6,7-tetrahydro-[1,3]dioxolo[4,5-c]pyridin-5-yl]-[3-methoxy-4-[(1S)-2,2,2-trifluoro-1-methyl-ethoxy]phenyl]methanone | 3-methoxy-4-[(1S)-2,2,2-trifluoro-1-methyl-ethoxy]benzoic acid | (3aR,7aR)-7a-(2,3-difluorophenyl)-4,5,6,7-tetrahydro-3aH-[1,3]dioxolo[4,5-c]pyridine |
| [(3aR,7aR)-7a-(2,3-difluorophenyl)-3a,4,6,7-tetrahydro-[1,3]dioxolo[4,5-c]pyridin-5-yl]-[3-methoxy-4-[(1R)-2,2,2-trifluoro-1-methyl-ethoxy]phenyl]methanone | 3-methoxy-4-[(1R)-2,2,2-trifluoro-1-methyl-ethoxy]benzoic acid | (3aR,7aR)-7a-(2,3-difluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-(3-fluorophenyl)-4,5,6,7-tetrahydro-3aH-[1,3]dioxolo[4,5-c]pyridine |

| Product | Acid | Amine |
| --- | --- | --- |
| [(3aR,7aR)-7a-(3-fluorophenyl)-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-7a-(3-fluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-7a-(3-fluorophenyl)-4,5,6,7-tetrahydro-3aH-[1,3]dioxolo[4,5-c]pyridine |
| [3-chloro-4-[2-(trifluoromethoxy)ethoxy]phenyl]-[(1S,6R)-6-(2-pyridyl)-8-oxa-3-azabicyclo[4.2.0]octan-3-yl]methanone | 3-chloro-4-[2-(trifluoromethoxy)ethoxy]benzoic acid | (1S,6R)-6-(2-pyridyl)-8-oxa-3-azabicyclo[4.2.0]octane |
| [3-chloro-4-[2-(trifluoromethoxy)ethoxy]phenyl]-[(1R,6R)-6-(2-pyridyl)-8-oxa-3-azabicyclo[4.2.0]octan-3-yl]methanone | 3-chloro-4-[2-(trifluoromethoxy)ethoxy]benzoic acid | (1R,6R)-6-(2-pyridyl)-8-oxa-3-azabicyclo[4.2.0]octane |
| [(3aR,7aR)-7a-(3-fluorophenyl)-3a,4,6,7-tetrahydro-[1,3]dioxolo[4,5-c]pyridin-5-yl]-[4-[2-(2,2-difluorocyclopropyl)ethoxy]-3-methoxy-phenyl]methanone | 4-[2-(2,2-difluorocyclopropyl)ethoxy]-3-methoxy-benzoic acid | (3aR,7aR)-7a-(3-fluorophenyl)-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[6-methoxy-5-[2-(trifluoromethoxy)ethoxy]-2-pyridyl]methanone | 6-methoxy-5-[2-(trifluoromethoxy)ethoxy]pyridine-2-carboxylic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[3-methoxy-4-(3,3,3-trifluoropropoxy)phenyl]methanone | 3-methoxy-4-(3,3,3-trifluoropropoxy)benzoic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[6-ethoxy-5-[2-(trifluoromethoxy)ethoxy]-2-pyridyl]methanone | 6-ethoxy-5-[2-(trifluoromethoxy)ethoxy]pyridine-2-carboxylic acid | (3aR,7aR)-7a-(3-fluorophenyl)-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-[4-(trifluoromethyl)-2-pyridyl]-4,5,6,7-tetrahydro-3aH-[1,3]dioxolo[4,5-c]pyridine |
| [3-chloro-4-[2-(trifluoromethoxy)ethoxy]phenyl]-[7,7-difluoro-6-(2-pyridyl)-3-azabicyclo[4.1.0]heptan-3-yl]methanone | 3-chloro-4-[2-(trifluoromethoxy)ethoxy]benzoic acid | 7,7-difluoro-6-(2-pyridyl)-3-azabicyclo[4.1.0]heptane |

| Product | Acid | Amine |
| --- | --- | --- |
| [(3aR,7aR)-7a-(4-methoxy-2-pyridyl)-3a,4,6,7-tetrahydro-[1,3]dioxolo[4,5-c]pyridin-5-yl]-[5-[(3,3-difluorocyclobutyl)methoxy]-6-methoxy-2-pyridyl]methanone | 5-[(3,3-difluorocyclobutyl)methoxy]-6-methoxy-pyridine-2-carboxylic acid | (3aR,7aR)-7a-(4-methoxy-2-pyridyl)-4,5,6,7-tetrahydro-3aH-[1,3]dioxolo[4,5-c]pyridine |
| [(3aR,7aR)-7a-(4-methoxy-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(4-methoxy-2-pyridyl)-4,5,6,7-tetrahydro-3aH-[1,3]dioxolo[4,5-c]pyridine |
| [(3aR,7aR)-7a-(4-methoxy-2-pyridyl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aR,7aR)-7a-(4-methoxy-2-pyridyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[3-methoxy-4-[(1S)-2,2,2-trifluoro-1-methyl-ethoxy]phenyl]methanone | 3-methoxy-4-[(1S)-2,2,2-trifluoro-1-methyl-ethoxy]benzoic acid | (3aR,7aR)-7a-(3-chlorophenyl)-4,5,6,7-tetrahydro-3aH-[1,3]dioxolo[4,5-c]pyridine |
| [(3aR,7aR)-7a-(3-chlorophenyl)-3a,4,6,7-tetrahydro-[1,3]dioxolo[4,5-c]pyridin-5-yl]-[3-methoxy-4-[(1R)-2,2,2-trifluoro-1-methyl-ethoxy]phenyl]methanone | 3-methoxy-4-[(1R)-2,2,2-trifluoro-1-methyl-ethoxy]benzoic acid | (3aR,7aR)-7a-(3-chlorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-(4-fluoro-3-methoxy-phenyl)methanone | 4-fluoro-3-methoxy-benzoic acid | (3aR,7aR)-7a-(3-fluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[4-(cyclobutylmethoxy)-3-methoxy-phenyl]methanone | 4-(cyclobutylmethoxy)-3-methoxy-benzoic acid | (3aR,7aR)-7a-(3-fluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[4-[(3-fluorocyclobutyl)methoxy]-3-methoxy-phenyl]methanone | 4-[(3-fluorocyclobutyl)methoxy]-3-methoxy-benzoic acid | (3aR,7aR)-7a-(3-fluorophenyl)-4,5,6,7-tetrahydro-3aH-[1,3]dioxolo[4,5-c]pyridine |
| [(3aR,7aR)-7a-(3-fluorophenyl)-3a,4,6,7-tetrahydro-[1,3]dioxolo[4,5-c]pyridin-5-yl]-[3-methoxy-4-(2,2,3,3-tetrafluoro-1-methyl-propoxy)phenyl]methanone | 3-methoxy-4-(2,2,3,3-tetrafluoro-1-methyl-propoxy)benzoic acid | (3aR,7aR)-7a-(3-fluorophenyl)-4,5,6,7-tetrahydro-3aH-[1,3]dioxolo[4,5-c]pyridine |
| [3-chloro-4-[2-(trifluoromethoxy)ethoxy]phenyl]-[(1S,6R)-6-(2-pyridyl)-3-azabicyclo[4.1.0]heptan-3-yl]methanone | 3-chloro-4-[2-(trifluoromethoxy)ethoxy]benzoic acid | (1S,6R)-6-(2-pyridyl)-3-azabicyclo[4.1.0]heptane |
| [(3aR,7aR)-7a-(3-fluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(3-fluorophenyl)-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-[4-(trifluoromethyl)-2-pyridyl]-4,5,6,7-tetrahydro-3aH-[1,3]dioxolo[4,5-c]pyridine |

| Product | Acid | Amine |
|---|---|---|
| [(3aR,7aR)-7a-(3,5-difluorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(3,5-difluorophenyl)-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[4-[2-(2,2-difluorocyclopropyl)ethoxy]-3-methoxy-phenyl]methanone | 4-[2-(2,2-difluorocyclopropyl)ethoxy]-3-methoxy-benzoic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-(6-chloro-4-methoxy-2-pyridyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(6-chloro-4-methoxy-2-pyridyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[3-fluoro-4-[2-(trifluoromethoxy)ethoxy]phenyl]methanone | 3-fluoro-4-[2-(trifluoromethoxy)ethoxy]benzoic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[4-(2-fluoro-2-methyl-propoxy)-3-(trifluoromethyl)phenyl]methanone | 4-(2-fluoro-2-methyl-propoxy)-3-(trifluoromethyl)benzoic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[3-(trifluoromethyl)-4-(3,3,3-trifluoropropoxy)phenyl]methanone | 3-(trifluoromethyl)-4-(3,3,3-trifluoropropoxy)benzoic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[3-chloro-4-(2-fluoro-2-methyl-propoxy)phenyl]methanone | 3-chloro-4-(2-fluoro-2-methyl-propoxy)benzoic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[3-chloro-4-[2-(trifluoromethoxy)ethoxy]phenyl]methanone | 3-chloro-4-[2-(trifluoromethoxy)ethoxy]benzoic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[6-methoxy-5-[[1-(trifluoromethyl)cyclopropyl]methoxy]-2-pyridyl]methanone | 6-methoxy-5-[[1-(trifluoromethyl)cyclopropyl]methoxy]pyridine-2-carboxylic acid | (3aS,7aS)-7a-(3-fluorophenyl)-4,5,6,7-tetrahydro-3aH-[1,3]dioxolo[4,5-c]pyridine |
| [(3aS,7aS)-7a-(3-fluorophenyl)-3a,4,6,7-tetrahydro-[1,3]dioxolo[4,5-c]pyridin-5-yl]-[3-methoxy-4-(2,2,2-trifluoro-1-methyl-ethoxy)phenyl]methanone | 3-methoxy-4-(2,2,2-trifluoro-1-methyl-ethoxy)benzoic acid | (3aS,7aS)-7a-(3-fluorophenyl)-4,5,6,7-tetrahydro-3aH-[1,3]dioxolo[4,5-c]pyridine |

-continued

| Product | Acid | Amine |
|---|---|---|
| [(3aR,7aR)-7a-(3-fluorophenyl)-3a,4,6,7-tetrahydro-[1,3]dioxolo[4,5-c]pyridin-5-yl]-[4-[(3,3-difluorocyclobutyl)methylamino]-3-methoxy-phenyl]methanone | 4-[(3,3-difluorocyclobutyl)methylamino]-3-methoxy-benzoic acid | (3aR,7aR)-7a-(3-fluorophenyl)-4,5,6,7-tetrahydro-3aH-[1,3]dioxolo[4,5-c]pyridine |
| [4-[(3,3-difluorocyclobutyl)methoxy]-3-methoxy-phenyl]-[(1R,6R)-6-(2-pyridyl)-8-oxa-3-azabicyclo[4.2.0]octan-3-yl]methanone | 4-[(3,3-difluorocyclobutyl)methoxy]-3-methoxy-benzoic acid | (1R,6R)-6-(2-pyridyl)-8-oxa-3-azabicyclo[4.2.0]octane |
| [6-methoxy-5-(2,2,3,3-tetrafluoropropoxy)-2-pyridyl]-[(1R,6R)-6-(2-pyridyl)-8-oxa-3-azabicyclo[4.2.0]octan-3-yl]methanone | 6-methoxy-5-(2,2,3,3-tetrafluoropropoxy)pyridine-2-carboxylic acid | (1R,6R)-6-(2-pyridyl)-8-oxa-3-azabicyclo[4.2.0]octane |
| [3-chloro-4-[(3,3-difluorocyclobutyl)methoxy]phenyl]-[(1R,6R)-6-(2-pyridyl)-8-oxa-3-azabicyclo[4.2.0]octan-3-yl]methanone | 3-chloro-4-[(3,3-difluorocyclobutyl)methoxy]benzoic acid | (1R,6R)-6-(2-pyridyl)-8-oxa-3-azabicyclo[4.2.0]octane |
| [3-chloro-4-[[1-(trifluoromethyl)cyclopropyl]methoxy]phenyl]-[(1R,6R)-6-(2-pyridyl)-8-oxa-3-azabicyclo[4.2.0]octan-3-yl]methanone | 3-chloro-4-[[1-(trifluoromethyl)cyclopropyl]methoxy]benzoic acid | (1R,6R)-6-(2-pyridyl)-8-oxa-3-azabicyclo[4.2.0]octane |
| [3-methyl-4-[2-(trifluoromethoxy)ethoxy]phenyl]-[(1R,6R)-6-(2-pyridyl)-8-oxa-3-azabicyclo[4.2.0]octan-3-yl]methanone | 3-methyl-4-[2-(trifluoromethoxy)ethoxy]benzoic acid | (1R,6R)-6-(2-pyridyl)-8-oxa-3-azabicyclo[4.2.0]octane |
| [4-(2-fluoro-2-methyl-propoxy)-3-(trifluoromethyl)phenyl]-[(1R,6R)-6-(2-pyridyl)-8-oxa-3-azabicyclo[4.2.0]octan-3-yl]methanone | 4-(2-fluoro-2-methyl-propoxy)-3-(trifluoromethyl)benzoic acid | (1R,6R)-6-(2-pyridyl)-8-oxa-3-azabicyclo[4.2.0]octane |
| [(3aR,7aR)-7a-[4-(trifluoromethyl)-2-pyridyl]-3a,4,6,7-tetrahydro-[1,3]dioxolo[4,5-c]pyridin-5-yl]-[4-[(3,3-difluorocyclopentyl)methoxy]-3-methoxy-phenyl]methanone | 4-[(3,3-difluorocyclopentyl)methoxy]-3-methoxy-benzoic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-(4-methoxy-2-pyridyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(4-methoxy-2-pyridyl)-4,5,6,7-tetrahydro-3aH-[1,3]dioxolo[4,5-c]pyridine |
| [3-chloro-4-[2-(trifluoromethoxy)ethoxy]phenyl]-[(1R,6R)-6-(2-pyridyl)-8-oxa-3-azabicyclo[4.2.0]octan-3-yl]methanone | 3-chloro-4-[2-(trifluoromethoxy)ethoxy]benzoic acid | (1R,6R)-6-(2-pyridyl)-8-oxa-3-azabicyclo[4.2.0]octane |
| [3-chloro-4-[2-(trifluoromethoxy)ethoxy]phenyl]-[(1S,6S)-6-(2-pyridyl)-8-oxa-3-azabicyclo[4.2.0]octan-3-yl]methanone | 3-chloro-4-[2-(trifluoromethoxy)ethoxy]benzoic acid | (1S,6S)-6-(2-pyridyl)-8-oxa-3-azabicyclo[4.2.0]octane |
| [(3aR,7aR)-7a-[4-(trifluoromethyl)-2-pyridyl]-3a,4,6,7-tetrahydro-[1,3]dioxolo[4,5-c]pyridin-5-yl]-[3-methoxy-4-[[1-(trifluoromethyl)cyclopropyl]methoxy]phenyl]methanone | 3-methoxy-4-[[1-(trifluoromethyl)cyclopropyl]methoxy]benzoic acid | (3aR,7aR)-7a-[4-(trifluoromethyl)-2-pyridyl]-4,5,6,7-tetrahydro-3aH-[1,3]dioxolo[4,5-c]pyridine |

-continued

| Product | Acid | Amine |
|---|---|---|
| [(3aR,7aR)-7a-[4-(trifluoromethyl)-2-pyridyl]-3a,4,6,7-tetrahydro-[1,3]dioxolo[4,5-c]pyridin-5-yl]-[3-methoxy-4-(2,2,3,3-tetrafluoropropoxy)phenyl]methanone | 3-methoxy-4-(2,2,3,3-tetrafluoropropoxy)benzoic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-(3,5-difluorophenyl)-3a,4,6,7-tetrahydro-[1,3]dioxolo[4,5-c]pyridin-5-yl]-[3-methoxy-4-[2-(trifluoromethoxy)ethoxy]phenyl]methanone | 3-methoxy-4-[2-(trifluoromethoxy)ethoxy]benzoic acid | (3aR,7aR)-7a-(3,5-difluorophenyl)-4,5,6,7-tetrahydro-3aH-[1,3]dioxolo[4,5-c]pyridine |
| [(3aR,7aR)-7a-(4-methoxy-2-pyridyl)-3a,4,6,7-tetrahydro-[1,3]dioxolo[4,5-c]pyridin-5-yl]-[3-methoxy-4-(2,2,3,3-tetrafluoropropoxy)phenyl]methanone | 3-methoxy-4-(2,2,3,3-tetrafluoropropoxy)benzoic acid | (3aR,7aR)-7a-(4-methoxy-2-pyridyl)-4,5,6,7-tetrahydro-3aH-[1,3]dioxolo[4,5-c]pyridine |
| [(3aR,7aR)-7a-[4-(trifluoromethyl)-2-pyridyl]-3a,4,6,7-tetrahydro-[1,3]dioxolo[4,5-c]pyridin-5-yl]-[4-(2-fluoro-2-methyl-propoxy)-3-methyl-phenyl]methanone | 4-(2-fluoro-2-methyl-propoxy)-3-methyl-benzoic acid | (3aR,7aR)-7a-[4-(trifluoromethyl)-2-pyridyl]-4,5,6,7-tetrahydro-3aH-[1,3]dioxolo[4,5-c]pyridine |
| [(3aR,7aR)-7a-(3-fluoro-2-pyridyl)-3a,4,6,7-tetrahydro-[1,3]dioxolo[4,5-c]pyridin-5-yl]-[4-[(3,3-difluorocyclobutyl)methoxy]-3-methoxy-phenyl]methanone | 4-[(3,3-difluorocyclobutyl)methoxy]-3-methoxy-benzoic acid | (3aR,7aR)-7a-(3-fluoro-2-pyridyl)-4,5,6,7-tetrahydro-3aH-[1,3]dioxolo[4,5-c]pyridine |

(3-chloro-4-((3,3-difluorocyclobutyl)methoxy)phenyl)((3aR,7aR)-7a-(pyridin-2-yl)tetrahydro-[1,3]dioxolo[4,5-c]pyridin-5(6H)-yl)methanone Step 1: [(3aR,7aR)-7a-(2-pyridyl)-3a,4,6,7-tetrahydro-[1,3]dioxolo[4,5-c]pyridin-5-yl]-(3-chloro-4-fluoro-phenyl)methanone

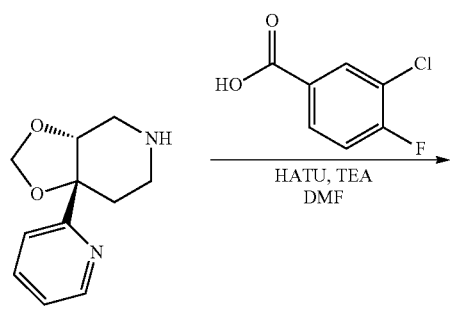

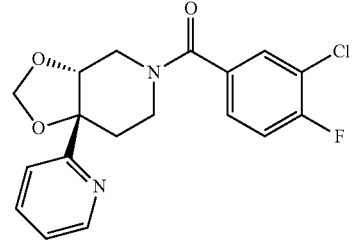

A solution of 3-chloro-4-fluoro-benzoic acid (440 mg, 2.52 mmol) in DMF (7.2 mL) was treated with HATU (960 mg, 2.5 mmol) and the reaction mixture was allowed to stir for 5 min. A solution of (3aR,7aR)-7a-(pyridin-2-yl)hexahydro-[1,3]dioxolo[4,5-c]pyridine (500 mg, 2.4 mmol) and triethylamine (2.5 mL, 14.5 mmol) in DMF (7.1 mL) was added to the mixture and the reaction mixture was stirred at rt for 2 h. The product was diluted with water and extracted with EtOAc (3×). The combined organics were washed with water, saturated aqueous NaCl, dried ($Na_2SO_4$), filtered and concentrated. Purification by flash chromatography (ethyl acetate-hexanes 10-50%) afforded [(3aR,7aR)-7a-(2-pyridyl)-3a,4,6,7-tetrahydro-[1,3]dioxolo[4,5-c]pyridin-5-yl]-(3-chloro-4-fluoro-phenyl)methanone (643 mg, 73%) which was used directly in the following reaction. ESI-MS m/z calc. 362.8. found 363.13 (M+1)+; Retention time: 1.27 min (3 min run).

The following compounds were prepared using the procedure reported above.

| Product | Amine | Benzoic Acid |
| --- | --- | --- |
| (3-chloro-4-fluorophenyl)((3aR,7aR)-7a-(pyridin-2-yl)tetrahydro-[1,3]dioxolo[4,5-c]pyridin-5(6H)-yl)methanone | [dimethylamino-(triazolo[5,4-b]pyridin-3-yloxy)methylene]-dimethyl-ammonium | 3-chloro-4-fluoro-benzoic acid |
| (4-fluoro-3-(trifluoromethyl)phenyl)((3aR,7aR)-7a-(pyridin-2-yl)tetrahydro-[1,3]dioxolo[4,5-c]pyridin-5(6H)-yl)methanone | [dimethylamino-(triazolo[5,4-b]pyridin-3-yloxy)methylene]-dimethyl-ammonium | 4-fluoro-3-(trifluoromethyl)benzoic acid |
| (3-chloro-4-fluorophenyl)((3aR,7aR)-7a-(3-fluorophenyl)tetrahydro-[1,3]dioxolo[4,5-c]pyridin-5(6H)-yl)methanone | (3aR,7aR)-7a-(3-fluorophenyl)hexahydro-[1,3]dioxolo[4,5-c]pyridine | 3-chloro-4-fluoro-benzoic acid |

Step 2: (3-chloro-4-((3,3-difluorocyclobutyl)methoxy)phenyl)((3aR,7aR)-7a-(pyridin-2-yl)tetrahydro-[1,3]dioxolo[4,5-c]pyridin-5(6H)-yl)methanone

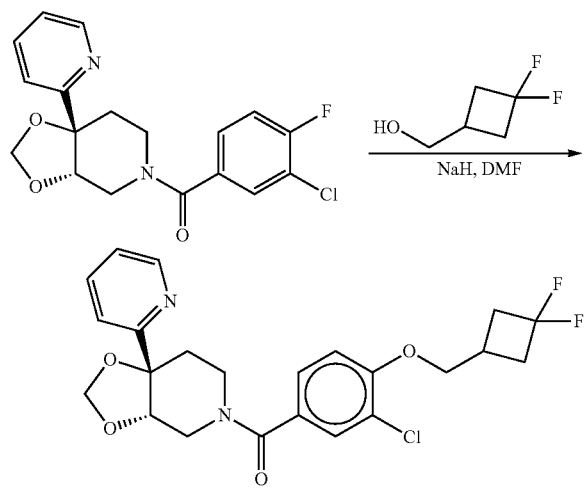

A solution of (3,3-difluorocyclobutyl)methanol (118 mg, 0.96 mmol) in DMF (1 mL) was treated with sodium hydride (42 mg, 1.06 mmol) and the reaction mixture was allowed to stir for 5 min. [(3aR,7aR)-7a-(2-pyridyl)-3a,4,6,7-tetrahydro-[1,3]dioxolo[4,5-c]pyridin-5-yl]-(3-chloro-4-fluorophenyl)methanone (175 mg, 0.48 mmol) was added as a solution in DMF (1 mL). The reaction mixture was allowed to stir at rt for 1 h, diluted with ethyl acetate (75 mL) and washed with saturated aqueous NaCl (1×75 mL). The organic layer was dried over sodium sulfate, filtered and concentrated under reduced pressure. The crude product was purified by silica gel column chromatography: 4 gram silica gel column, 25-75% ethyl acetate/hexane gradient over 15 min to provide [(3aR,7aR)-7a-(2-pyridyl)-3a,4,6,7-tetrahydro-[1,3]dioxolo[4,5-c]pyridin-5-yl]-[3-chloro-4-[(3,3-difluorocyclobutyl)methoxy]phenyl]methanone (130 mg, 58%) as a thick oil. $^1$H NMR (400 MHz, CDCl$_3$) δ 8.58 (s, 1H), 7.75 (s, 1H), 7.62 (d, J=25.5 Hz, 2H), 7.44 (s, 1H), 7.26 (s, 1H), 6.93 (d, J=8.2 Hz, 1H), 5.32 (s, 1H), 4.85 (s, 1H), 4.40 (s, 1H), 4.09 (d, J=5.2 Hz, 2H), 3.87 (t, J=53.2 Hz, 4H), 2.69 (dd, J=45.1, 10.2 Hz, 5H), 2.35 (s, 1H), 2.09 (d, J=63.9 Hz, 1H). ESI-MS m/z calc. 464.1. found 465.3 (M+1)$^+$; Retention time: 1.57 min (3 min run).

The following compounds were prepared using the procedure reported above.

| Product | Precursor |
| --- | --- |
| (3-chloro-4-(neopentyloxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |
| (3-chloro-4-(4,4,4-trifluoro-2-methylbutoxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |
| (3-chloro-4-((3,3-difluorocyclobutyl)methoxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |
| (3-chloro-4-((2,2-difluorocyclopropyl)methoxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |

-continued

| Product | Precursor |
|---|---|
| (4-(2-(tert-butoxy)ethoxy)-3-chlorophenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |
| (4-((2,2-difluorocyclopropyl)methoxy)-3-(trifluoromethyl)phenyl)((3aR,7aR)-7a-(pyridin-2-yl)tetrahydro-[1,3]dioxolo[4,5-c]pyridin-5(6H)-yl)methanone | (4-fluoro-3-(trifluoromethyl)phenyl)((3aR,7aR)-7a-(pyridin-2-yl)tetrahydro-[1,3]dioxolo[4,5-c]pyridin-5(6H)-yl)methanone |
| (4-(2,2-difluoropropoxy)-3-(trifluoromethyl)phenyl)((3aR,7aR)-7a-(pyridin-2-yl)tetrahydro-[1,3]dioxolo[4,5-c]pyridin-5(6H)-yl)methanone | (4-fluoro-3-(trifluoromethyl)phenyl)((3aR,7aR)-7a-(pyridin-2-yl)tetrahydro-[1,3]dioxolo[4,5-c]pyridin-5(6H)-yl)methanone |
| (4-((3,3-difluorocyclobutyl)methoxy)-3-(trifluoromethyl)phenyl)((3aR,7aR)-7a-(pyridin-2-yl)tetrahydro-[1,3]dioxolo[4,5-c]pyridin-5(6H)-yl)methanone | (4-fluoro-3-(trifluoromethyl)phenyl)((3aR,7aR)-7a-(pyridin-2-yl)tetrahydro-[1,3]dioxolo[4,5-c]pyridin-5(6H)-yl)methanone |
| ((3aR,7aR)-7a-(pyridin-2-yl)tetrahydro-[1,3]dioxolo[4,5-c]pyridin-5(6H)-yl)(3-(trifluoromethyl)-4-((1,1,1-trifluoropropan-2-yl)oxy)phenyl)methanone | (4-fluoro-3-(trifluoromethyl)phenyl)((3aR,7aR)-7a-(pyridin-2-yl)tetrahydro-[1,3]dioxolo[4,5-c]pyridin-5(6H)-yl)methanone |
| (4-(cyclobutylmethoxy)-3-methoxyphenyl)((3aR,7aR)-7a-(3-fluorophenyl)tetrahydro-[1,3]dioxolo[4,5-c]pyridin-5(6H)-yl)methanone | (3-chloro-4-fluorophenyl)((3aR,7aR)-7a-(3-fluorophenyl)tetrahydro-[1,3]dioxolo[4,5-c]pyridin-5(6H)-yl)methanone |
| (4-(((1r,3R)-3-fluorocyclobutyl)methoxy)-3-methoxyphenyl)((3aR,7aR)-7a-(3-fluorophenyl)tetrahydro-[1,3]dioxolo[4,5-c]pyridin-5(6H)-yl)methanone | (3-chloro-4-fluorophenyl)((3aR,7aR)-7a-(3-fluorophenyl)tetrahydro-[1,3]dioxolo[4,5-c]pyridin-5(6H)-yl)methanone |
| (3-chloro-4-(2-(2,2,2-trifluoroethoxy)ethoxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |
| (3-chloro-4-(2,2,3,3-tetrafluoropropoxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |
| (3-chloro-4-(2,2-difluoropropoxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |
| (3-chloro-4-((1,1,1-trifluoropropan-2-yl)oxy)phenyl)((3aR,7aR)-7a-(pyridin-2-yl)tetrahydro-[1,3]dioxolo[4,5-c]pyridin-5(6H)-yl)methanone | (3-chloro-4-fluorophenyl)((3aR,7aR)-7a-(pyridin-2-yl)tetrahydro-[1,3]dioxolo[4,5-c]pyridin-5(6H)-yl)methanone |

Table 3 below recites the analytical data for the compounds of Table 1.

TABLE 3

| Cmpd. No. | LC/MS M + 1 | LC/RT min | NMR |
|---|---|---|---|
| 1 | 479.00 | 1.52 | $^1$H NMR (400 MHz, CDCl$_3$) δ 8.41 (d, J = 4.3 Hz, 1H), 7.57-7.44 (m, 1H), 7.35 (dt, J = 8.4, 4.2 Hz, 1H), 7.19-6.98 (m, 2H), 6.89 (d, J = 8.2 Hz, 1H), 5.34 (broad s, 1H), 4.93 (broad s, 1H), 4.68 (broad s, 1H), 4.38 (broad m, 1H), 4.08 (d, J = 6.4 Hz, 2H), 4.02 (broad s, 1H), 3.88 (s, 3H), 3.77 (broad s, 1H), 3.49 (broad m, 1H), 2.91-2.62 (m, 3H), 2.60-2.42 (m, 2H), 2.33 (broad m, 2H). |
| 2 | 483.20 | 1.94 | |
| 3 | 501.10 | 1.15 | |

TABLE 3-continued

| Cmpd. No. | LC/MS M + 1 | LC/RT min | NMR |
|---|---|---|---|
| 4 | 504.50 | 1.97 | $^1$H NMR (400 MHz, CDCl$_3$) δ 7.11 (broad s, 1H), 7.06 (dd, J = 8.2, 1.9 Hz, 1H), 6.96-6.87 (m, 3H), 6.76 (tt, J = 8.7, 2.3 Hz, 1H), 5.31 (s, 1H), 4.85 (s, 1H), 4.42-4.25 (m, 4H), 4.2-4.0 (broad d, 2H), 3.90 (s, 3H), 3.72 (broad s, 3H), 2.32-1.90 (broad m, 2H). |
| 5 | 384.40 | 1.68 | |
| 6 | 437.25 | 1.52 | |
| 7 | 432.50 | 1.54 | |
| 8 | 428.32 | 1.46 | |
| 9 | 361.40 | 0.90 | |
| 10 | 337.40 | 1.89 | |
| 11 | 326.11 | 1.82 | |
| 12 | 470.40 | 1.60 | $^1$H NMR (400 MHz, MeOD) δ 9.11-8.93 (m, 2H), 7.80-7.60 (m, 1H), 7.19-7.00 (m, 3H), 5.38 (s, 1H), 4.96 (s, 1H), 4.54 (s, 1H), 4.40-4.35 (m, 2H), 4.30 (d, J = 4.0 Hz, 2H), 4.09 (d, J = 14.4 Hz, 1H), 3.88 (s, 3H), 3.87-3.76 (m, 2H), 3.70 (s, 1H), 2.67-2.16 (m, 2H). |
| 13 | 366.50 | 1.95 | $^1$H NMR (400 MHz, MeOD) δ 7.47-7.22 (m, 7H), 6.99 (t, J = 9.1 Hz, 1H), 4.72-4.54 (m, 2H), 4.46-4.03 (m, 2H), 3.99-3.74 (m, 2H), 3.66 (dd, J = 25.7, 12.9 Hz, 1H), 3.09 (t, J = 15.9 Hz, 1H), 2.57-2.25 (m, 1H), 2.21 (d, J = 7.8 Hz, 3H), 1.34 (d, J = 5.8 Hz, 6H). |
| 14 | 323.13 | 1.54 | |
| 15 | 384.13 | 1.69 | |
| 16 | 354.16 | 2.00 | |
| 17 | 439.30 | 1.39 | |
| 18 | 351.18 | 2.07 | |
| 19 | 354.16 | 2.04 | |
| 20 | 320.12 | 1.77 | |
| 21 | 351.18 | 1.98 | |
| 22 | 439.30 | 1.39 | |
| 23 | 431.23 | 1.30 | |
| 24 | 437.25 | 1.52 | |
| 25 | 413.10 | 1.15 | |
| 26 | 397.12 | 1.68 | |
| 27 | 416.40 | 1.68 | |
| 28 | 348.17 | 1.68 | |
| 29 | 336.40 | 1.59 | |
| 30 | 419.26 | 1.33 | |
| 31 | 419.26 | 1.33 | |
| 32 | 484.30 | 1.88 | |
| 33 | 345.50 | 1.42 | |
| 34 | 445.50 | 1.18 | |
| 35 | 361.16 | 1.91 | |
| 36 | 430.28 | 1.75 | |
| 37 | 368.16 | 1.71 | |
| 38 | 448.28 | 1.76 | |
| 39 | 475.20 | 1.71 | |
| 40 | 471.00 | 1.18 | |
| 41 | 499.50 | 1.09 | |
| 42 | 428.28 | 1.45 | |
| 43 | 361.25 | 1.33 | |
| 44 | 398.40 | 1.79 | $^1$H NMR (400 MHz, CDCl$_3$) δ 7.28-7.19 (m, 4H), 7.02-6.94 (m, 2H), 6.81 (d, J = 8.0 Hz, 1H), 3.89 (s, 2H), 3.82 (s, 2H), 3.45 (s, 1H), 2.28 (s, 3H), 2.14 (s, 2H), 1.74 (s, 2H), 1.38 (s, 6H), 1.04 (s, 1H), 0.88 (t, J = 5.3 Hz, 1H). |
| 45 | 382.29 | 1.51 | |
| 46 | 472.30 | 1.45 | |
| 47 | 448.31 | 1.76 | |
| 48 | 484.26 | 1.88 | |
| 49 | 382.29 | 1.50 | |
| 50 | 453.30 | 1.32 | |
| 51 | 466.30 | 1.87 | |
| 52 | 421.20 | 1.80 | |
| 53 | 430.29 | 1.61 | |
| 54 | 466.40 | 1.87 | |
| 55 | 451.90 | 1.42 | |
| 56 | 367.50 | 1.58 | |
| 57 | 354.50 | 1.69 | |
| 58 | 430.29 | 1.61 | |
| 59 | 463.00 | 1.24 | |
| 60 | 397.19 | 1.65 | |
| 61 | 467.40 | 1.41 | |

TABLE 3-continued

| Cmpd. No. | LC/MS M + 1 | LC/RT min | NMR |
|---|---|---|---|
| 62 | 463.00 | 1.24 | ¹H NMR (400 MHz, MeOD) δ 7.82 (d, J = 3.3 Hz, 1H), 7.58 (d, J = 3.3 Hz, 1H), 7.29-7.34 (m, 2H), 7.20 (t, J = 8.4 Hz, 1H), 5.34 (s, 1H), 4.99 (s, 1H), 4.54-4.25 (m, 5H), 4.07-3.53 (m, 4H), 2.55-2.02 (m, 2H). |
| 63 | 429.40 | 1.69 | |
| 64 | 467.20 | 0.96 | ¹H NMR (400 MHz, C$_6$D$_6$) δ 8.53 (s, 1H), 7.21-7.04 (m, 3H), 6.78-6.65 (m, J = 7.7 Hz, 2H), 6.57 (d, J = 8.1 Hz, 1H), 4.15-3.91 (m, 4H), 3.86 (d, J = 8.2 Hz, 1H), 3.81-3.70 (m, 4H), 3.68-3.58 (m, 2H), 3.37 (s, 3H), 3.18-2.95 (m, J = 29.0, 16.9 Hz, 2H), 2.27-1.98 (m, J = 53.8, 18.8 Hz, 2H). |
| 65 | 408.30 | 1.85 | |
| 66 | 467.30 | 1.35 | |
| 67 | 418.30 | 1.63 | |
| 68 | 469.10 | 1.40 | ¹H NMR (400 MHz, DMSO) δ 8.59 (d, J = 4.2 Hz, 1H), 7.85 (td, J = 7.8, 1.7 Hz, 1H), 7.61 (d, J = 7.9 Hz, 1H), 7.40-7.26 (m, 1H), 7.06 (d, J = 23.8 Hz, 3H), 5.31 (s, 1H), 4.73 (s, 1H), 4.41 (dd, J = 5.3, 3.0 Hz, 2H), 4.33 (s, 1H), 4.29-4.25 (m, 2H), 3.96-3.83 (m, 1H), 3.80 (s, 3H), 3.73 (d, J = 13.9 Hz, 1H), 3.62 (dd, J = 6.8, 4.7 Hz, 1H), 3.55-3.45 (m, 1H), 2.30 (d, J = 14.7 Hz, 1H), 2.04 (d, J = 14.7 Hz, 1H). |
| 69 | 461.30 | 1.50 | |
| 70 | 429.40 | 1.68 | |
| 71 | 430.28 | 1.74 | ¹H NMR (400 MHz, CDCl$_3$) δ 7.44-7.36 (m, 4H), 7.36-7.28 (m, 1H), 7.11 (s, 1H), 7.07 (dd, J = 8.2, 1.9 Hz, 1H), 6.92 (d, J = 8.2 Hz, 1H), 5.30 (s, 1H), 4.87 (s, 1H), 4.27 (s, 1H), 4.03 (t, J = 14.4 Hz, 2H), 3.90 (d, J = 8.6 Hz, 3H), 3.70 (s, 3H), 2.13 (s, 2H), 1.62 (s, 1H), 1.52 (d, J = 21.4 Hz, 6H). |
| 72 | 453.30 | 1.40 | |
| 73 | 412.32 | 1.57 | |
| 74 | 435.50 | 171.10 | |
| 75 | 412.29 | 1.57 | |
| 76 | 361.40 | 1.34 | |
| 77 | 382.40 | 1.96 | |
| 78 | 489.20 | 1.60 | ¹H NMR (400 MHz, CDCl$_3$) δ 7.27 (d, J = 9.7 Hz, 1H), 7.13 (s, 1H), 7.09 (d, J = 8.2 Hz, 1H), 6.91 (d, J = 8.2 Hz, 1H), 5.32 (s, 1H), 4.98 (s, 1H), 4.40 (s, 1H), 4.36-4.24 (m, 4H), 4.01 (s, 2H), 3.90 (s, 4H), 3.71 (s, 2H), 2.88 (s, 3H), 2.58 (s, 2H), 2.18 (s, 1H). |
| 79 | 350.30 | 2.27 | |
| 80 | 525.20 | 2.22 | |
| 81 | 382.30 | 1.96 | |
| 82 | 421.29 | 1.67 | |
| 83 | 420.15 | 2.03 | |
| 84 | 485.00 | 1.24 | |
| 85 | 475.27 | 1.56 | |
| 86 | 475.23 | 1.56 | |
| 87 | 577.00 | 1.48 | |
| 88 | 490.20 | 1.60 | |
| 89 | 483.70 | 1.26 | |
| 90 | 461.40 | 1.36 | |
| 91 | 412.50 | 1.73 | |
| 92 | 469.10 | 1.37 | ¹H NMR (400 MHz, DMSO) δ 8.64-8.55 (m, 1H), 7.86 (td, J = 7.8, 1.7 Hz, 1H), 7.61 (d, J = 7.9 Hz, 1H), 7.35 (ddd, J = 7.5, 4.8, 1.0 Hz, 1H), 7.10 (s, 1H), 7.04 (s, 2H), 5.32 (s, 1H), 4.87-4.69 (m, 1H), 4.42 (dd, J = 5.3, 3.1 Hz, 2H), 4.34 (bs, 1H), 4.31-4.23 (m, 2H), 4.17-3.85 (m, 1H), 3.81 (s, 3H), 3.74 (d, J = 13.5 Hz, 1H), 3.68-3.57 (m, 1H), 3.57-3.45 (m, 1H), 2.37-2.21 (m, 1H), 2.13-1.98 (m, 1H). |
| 93 | 487.30 | 1.53 | ¹H NMR (400 MHz, CDCl$_3$) δ 8.60 (s, 1H), 7.69 (s, 1H), 7.53 (s, 1H), 7.12 (s, 1H), 7.08 (d, J = 8.2 Hz, 1H), 6.92 (d, J = 8.2 Hz, 1H), 5.39 (s, 1H), 5.05 (s, 1H), 4.67 (s, 2H), 4.32 (tt, J = 8.8, 2.7 Hz, 4H), 4.08 (s, 1H), 3.96-3.69 (m, 5H), 3.62 (s, 1H), 2.25 (d, J = 60.2 Hz, 2H). |
| 94 | 503.50 | 1.26 | |
| 95 | 415.20 | 1.45 | ¹H NMR (400 MHz, DMSO) δ 8.60 (d, J = 4.0 Hz, 1H), 7.86 (td, J = 7.7, 1.7 Hz, 1H), 7.61 (d, J = 7.9 Hz, 1H), 7.35 (ddd, J = 7.5, 4.8, 1.0 Hz, 1H), 7.30 (s, 2H), 7.05-6.94 (m, 1H), 5.30 (s, 1H), 4.73 (bs, 1H), 4.31 (bs, 1H), 4.05 (d, J = 19.6 Hz, 2H), 3.95-3.81 (m, 1H), 3.74 (d, J = 13.1 Hz, 1H), 3.67-3.42 (m, 2H), 2.38-2.23 (m, 1H), 2.22 (s, 3H), 2.14-1.89 (m, J = 17.1, 13.4 Hz, 1H), 1.46 (d, J = 21.4 Hz, 6H). |

TABLE 3-continued

| Cmpd. No. | LC/MS M + 1 | LC/RT min | NMR |
|---|---|---|---|
| 96 | 488.30 | 1.54 | |
| 97 | 421.25 | 1.67 | |
| 98 | 366.17 | 1.97 | |
| 99 | 486.30 | 1.84 | $^1$H NMR (400 MHz, CDCl$_3$) δ 7.36 (dd, J = 8.5, 5.3 Hz, 2H), 7.09 (dd, J = 16.0, 7.5 Hz, 4H), 6.92 (d, J = 7.9 Hz, 1H), 5.30 (s, 1H), 4.85 (s, 1H), 4.32 (dd, J = 7.7, 4.9 Hz, 4H), 4.07 (s, 1H), 3.90 (s, 3H), 3.71 (s, 3H), 2.09 (s, 1H), 1.62 (s, 2H). |
| 100 | 433.40 | 1.64 | $^1$H NMR (400 MHz, CDCl$_3$) δ 8.39 (d, J = 4.6 Hz, 1H), 7.47 (ddd, J = 10.9, 8.3, 1.2 Hz, 1H), 7.39-7.27 (m, 3H), 6.80 (d, J = 8.9 Hz, 1H), 5.31 (broad s, 1H), 4.91 (broad s, 1H), 4.66 (broad s, 1H), 4.43-4.02 (m, 1H), 3.96 (d, J = 16.4 Hz, 3H, overlapped with broad s, 1H), 3.79 (broad m, 1H), 3.50 (broad s, 1H), 2.28 (s, 3H, overlapped with broad m, 2H), 1.55 (s, 3H), 1.50 (s, 3H). |
| 101 | 437.20 | 0.84 | $^1$H NMR (400 MHz, DMSO-d6) δ 8.45 (d, J = 4.4 Hz, 1H), 7.71 (td, J = 7.7, 1.9 Hz, 1H), 7.34 (d, J = 8.1 Hz, 1H), 7.16 (ddd, J = 7.5, 4.8, 1.0 Hz, 1H), 7.05-7.00 (m, 2H), 6.95 (dd, J = 8.1, 1.9 Hz, 1H), 4.45-4.38 (m, 2H), 4.31-4.24 (m, 2H), 3.90 (br s, 1H), 3.79 (s, 3H), 3.74 (br s, 1H), 3.46 (br s, 1H), 3.28 (br s, 1H), 2.59 (br s, 1H), 2.10 (s, 1H), 1.70 (s, 1H), 1.28 (dd, J = 9.1, 4.4 Hz, 1H), 1.05 (br s, 1H). |
| 102 | 452.10 | 1.81 | $^1$H NMR (400 MHz, CDCl$_3$) δ 7.44-7.36 (m, 4H), 7.36-7.28 (m, 1H), 7.13 (s, 1H), 7.09 (dd, J = 8.2, 1.8 Hz, 1H), 6.90 (d, J = 8.2 Hz, 1H), 5.31 (s, 1H), 4.87 (s, 1H), 4.28 (t, J = 6.9 Hz, 3H), 4.07 (s, 1H), 3.90 (s, 3H), 3.77 (d, J = 49.0 Hz, 3H), 2.70 (qt, J = 10.6, 7.0 Hz, 2H), 2.21 (d, J = 29.3 Hz, 2H). |
| 103 | 504.30 | 1.69 | |
| 104 | 396.21 | 1.63 | |
| 105 | 503.00 | 1.26 | |
| 106 | 439.20 | 1.43 | |
| 107 | 470.19 | 1.36 | |
| 108 | 487.10 | 1.49 | |
| 109 | 432.28 | 1.90 | |
| 110 | 435.20 | 1.47 | |
| 111 | 476.20 | 1.59 | |
| 112 | 499.30 | 1.12 | $^1$H NMR (400 MHz, CDCl$_3$) δ 8.64 (d, J = 6.4 Hz, 1H), 7.47 (s, 1H), 7.21 (d, J = 5.9 Hz, 1H), 7.15 (s, 1H), 7.13-7.07 (m, 1H), 6.91 (d, J = 8.1 Hz, 1H), 5.39 (s, 1H), 4.99 (s, 1H), 4.71 (s, 1H), 4.62 (d, J = 15.1 Hz, 1H), 4.38-4.21 (m, 4H), 4.14 (s, 3H), 3.97 (dd, J = 15.1, 2.1 Hz, 1H), 3.90 (s, 3H), 3.84-3.79 (m, 1H), 3.08-2.86 (m, 1H), 2.21 (d, J = 14.6 Hz, 1H), 1.69-1.61 (m, 1H). |
| 113 | 350.30 | 1.69 | |
| 114 | 380.20 | 1.78 | |
| 115 | 380.50 | 1.89 | |
| 116 | 457.50 | 1.54 | |
| 117 | 452.20 | 1.84 | |
| 118 | 490.20 | 1.69 | |
| 119 | 431.50 | 1.96 | |
| 120 | 414.50 | 1.91 | $^1$H NMR (400 MHz, CDCl$_3$) δ 7.44-7.36 (m, 4H), 7.36-7.28 (m, 3H), 6.84-6.78 (m, 1H), 5.30 (s, 1H), 4.87 (s, 1H), 4.25 (s, 1H), 3.98 (t, J = 15.7 Hz, 3H), 3.75 (s, 3H), 2.28 (s, 3H), 2.16 (d, J = 36.8 Hz, 2H), 1.52 (d, J = 21.4 Hz, 6H). |
| 121 | 431.20 | 1.75 | |
| 122 | 486.50 | 1.85 | $^1$H NMR (400 MHz, CDCl$_3$) δ 7.36 (dd, J = 8.5, 5.2 Hz, 2H), 7.09 (dd, J = 16.0, 7.5 Hz, 4H), 6.92 (d, J = 7.7 Hz, 1H), 5.30 (s, 1H), 4.85 (s, 1H), 4.38-4.27 (m, 5H), 4.07 (s, 1H), 3.90 (s, 3H), 3.71 (s, 3H), 2.09 (s, 1H), 1.61 (s, 2H). |
| 123 | 509.00 | 1.25 | |
| 124 | 432.32 | 1.89 | |
| 125 | 399.50 | 1.95 | |
| 126 | 476.20 | 1.61 | |
| 127 | 469.40 | 1.56 | |
| 128 | 491.30 | 1.58 | |
| 129 | 471.40 | 1.69 | |
| 130 | 480.00 | 1.47 | $^1$H NMR (400 MHz, CDCl$_3$) 2 conformers observed (ca. 30:70) δ 8.60 (br s, 1H), 7.87-7.72 (m, 1H), 7.66 (dd, J = 22.8, 7.5 Hz, 1H), 7.40 (d, J = 8.0 Hz, 1H), 7.26 (br m, 1H), 7.13 (d, J = 8.0 Hz, 1H), 5.36 (s, 30% of 1H), 5.29 (s, 70% of 1H), 4.95 (s, 30% of 1H), 4.84 (s, 70% of 1H), 4.60 (br m, 30% of 1H), 4.51 (br m, |

TABLE 3-continued

| Cmpd. No. | LC/MS M + 1 | LC/RT min | NMR |
|---|---|---|---|
| | | | 70% of 1H), 4.33-4.28 (m, 1H), 4.23-4.05 (m, 3H), 4.02 (s, 70% of 3H), 3.97 (s, 30% of 3H), 3.94-3.69 (m, 2H), 2.44 (br m, 1H), 2.24-1.96 (m, 1H), 1.21-1.08 (m, 2H), 0.97 (s, 2H). |
| 131 | 486.23 | 1.89 | $^1$H NMR (400 MHz, CDCl$_3$) δ 7.40 (s, 1H), 7.37-7.27 (m, 2H), 7.24 (dd, J = 5.2, 3.6 Hz, 1H), 7.12 (s, 1H), 7.08 (dd, J = 8.2, 1.7 Hz, 1H), 6.90 (d, J = 8.2 Hz, 1H), 5.31 (s, 1H), 4.85 (s, 1H), 4.28 (t, J = 6.9 Hz, 2H), 4.25-3.93 (m, 2H), 3.90 (s, 3H), 3.85-3.54 (m, 3H), 2.70 (qt, J = 10.6, 7.0 Hz, 2H), 2.32-1.92 (m, 2H). |
| 132 | 482.20 | 1.33 | $^1$H NMR (400 MHz, CDCl$_3$) δ 7.52 (d, J = 7.4 Hz, 2H), 7.41 (t, J = 7.6 Hz, 2H), 7.32 (t, J = 7.3 Hz, 1H), 7.11-6.83 (m, 3H), 4.59-3.90 (m, 8H), 3.88 (s, 3H), 3.81-3.40 (m, 6H), 2.80-1.40 (m, 2H). |
| 133 | 380.40 | 1.78 | $^1$H NMR (400 MHz, CDCl$_3$) δ 7.35-7.22 (m, 6H), 7.22-7.17 (m, 1H), 6.81 (d, J = 8.1 Hz, 1H), 3.92 (s, 1H), 3.82 (s, 2H), 3.49 (s, 2H), 2.28 (s, 3H), 2.14 (d, J = 41.4 Hz, 2H), 1.57 (d, J = 27.3 Hz, 2H), 1.38 (s, 6H), 1.08 (s, 1H), 0.89 (t, J = 5.2 Hz, 1H). |
| 134 | 351.40 | 1.77 | |
| 135 | 451.40 | 1.45 | |
| 136 | 434.40 | 2.06 | |
| 137 | 490.20 | 1.67 | |
| 138 | 479.30 | 1.76 | |
| 139 | 460.40 | 1.81 | $^1$H NMR (400 MHz, CDCl$_3$) δ 7.41-7.37 (m, 4H), 7.36-7.28 (m, 1H), 7.11 (broad s, 1H), 7.08 (dd, J = 8.2, 1.8 Hz, 1H), 6.89 (d, J = 8.2 Hz, 1H), 5.30 (broad s, 1H), 4.87 (s, 1H), 4.27 (broad m, 1H), 4.08 (d, J = 6.3 Hz, 2H, overlapped with broad s, 1H), 3.88 (s, 3H), 3.70 (broad s, 3H), 2.89-2.61 (m, 3H), 2.61-2.35 (m, 2H), 2.07 (d, broad m, 2H). |
| 140 | 479.30 | 1.75 | |
| 141 | 547.10 | 1.80 | $^1$H NMR (400 MHz, DMSO) δ 7.83 (t, J = 7.8 Hz, 1H), 7.64 (dd, J = 10.5, 7.7 Hz, 2H), 7.09 (s, 1H), 7.04 (s, 2H), 5.31 (s, 1H), 4.75 (s, 1H), 4.42 (dd, J = 5.3, 3.1 Hz, 2H), 4.37-4.22 (m, 3H), 4.04-3.85 (m, 1H), 3.81 (s, 3H), 3.75-3.57 (m, 2H), 3.55-3.43 (m, 1H), 2.37-2.17 (m, 1H), 2.15-1.97 (m, 1H). |
| 142 | 459.40 | 1.88 | |
| 143 | 329.12 | 1.50 | |
| 144 | 473.30 | 1.78 | |
| 145 | 491.20 | 1.69 | |
| 146 | 465.20 | 1.56 | $^1$H NMR (400 MHz, CDCl$_3$) δ 8.58 (s, 1H), 7.75 (s, 1H), 7.62 (d, J = 25.5 Hz, 2H), 7.44 (s, 1H), 7.26 (s, 1H), 6.93 (d, J = 8.2 Hz, 1H), 5.32 (s, 1H), 4.85 (s, 1H), 4.40 (s, 1H), 4.09 (d, J = 5.2 Hz, 2H), 3.87 (t, J = 53.2 Hz, 4H), 2.69 (dd, J = 45.1, 10.2 Hz, 5H), 2.35 (s, 1H), 2.09 (d, J = 63.9 Hz, 1H), 1.58 (s, 3H). |
| 147 | 366.30 | 1.79 | |
| 148 | 468.29 | 1.78 | |
| 149 | 493.20 | 1.76 | |
| 150 | 468.26 | 1.78 | $^1$H NMR (400 MHz, CDCl$_3$) δ 7.40 (dd, J = 7.6, 5.7 Hz, 4H), 7.36-7.28 (m, 1H), 7.13 (s, 1H), 7.08 (dd, J = 8.2, 1.6 Hz, 1H), 6.92 (d, J = 8.1 Hz, 1H), 5.30 (s, 1H), 4.87 (s, 1H), 4.37-4.26 (m, 4H), 4.08 (s, 1H), 3.90 (s, 3H), 3.71 (s, 2H), 2.20 (d, J = 35.6 Hz, 2H), 1.60 (s, 2H). |
| 151 | 394.10 | 2.30 | |
| 152 | 449.30 | 1.95 | |
| 153 | 538.40 | 1.89 | |
| 154 | 483.20 | 1.29 | |
| 155 | 503.20 | 1.95 | |
| 156 | 457.40 | 1.54 | |
| 157 | 473.10 | 1.54 | $^1$H NMR (400 MHz, DMSO) δ 8.61 (d, J = 4.1 Hz, 1H), 7.89 (td, J = 7.8, 1.7 Hz, 1H), 7.63 (d, J = 7.9 Hz, 1H), 7.57 (s, 1H), 7.45 (d, J = 7.9 Hz, 1H), 7.38 (dd, J = 7.0, 5.3 Hz, 1H), 7.25 (d, J = 8.5 Hz, 1H), 5.31 (s, 1H), 4.73 (s, 1H), 4.46 (dd, J = 5.5, 2.6 Hz, 2H), 4.40 (d, J = 4.6 Hz, 2H), 4.37-4.29 (m, 1H), 3.89-3.71 (m, 2H), 3.55-3.46 (m, 2H), 2.36-2.21 (m, 1H), 2.08-1.88 (m, 1H). |
| 158 | 398.30 | 1.93 | |
| 159 | 471.40 | 1.81 | $^1$H NMR (400 MHz, CDCl$_3$) δ 7.46-7.36 (m, 5H), 7.31 (ddd, J = 6.7, 5.5, 2.4 Hz, 1H), 7.20-7.13 (m, 1H), 4.50-4.32 (m, 3H), 4.30 (dd, J = 5.3, 3.1 Hz, 2H), |

TABLE 3-continued

| Cmpd. No. | LC/MS M + 1 | LC/RT min | NMR |
|---|---|---|---|
| | | | 4.05 (d, J = 4.4 Hz, 4H), 3.98 (s, 1H), 3.96-3.88 (m, 1H), 3.84-3.61 (m, 1H), 2.26 (ddd, J = 20.3, 12.1, 4.5 Hz, 1H), 2.20-2.10 (m, 1H). |
| 160 | 454.40 | 1.28 | |
| 161 | 414.40 | 1.91 | $^1$H NMR (400 MHz, CDCl$_3$) δ 7.39 (t, J = 4.5 Hz, 4H), 7.37-7.28 (m, 3H), 6.83-6.78 (m, 1H), 5.30 (s, 1H), 4.87 (s, 1H), 4.29 (s, 1H), 3.96 (d, J = 16.4 Hz, 3H), 3.74 (s, 3H), 2.28 (s, 3H), 2.12 (s, 2H), 1.52 (d, J = 21.4 Hz, 7H). |
| 162 | 505.20 | 1.80 | $^1$H NMR (400 MHz, CDCl$_3$) δ 7.42 (d, J = 7.5 Hz, 2H), 7.20 (t, J = 21.1 Hz, 3H), 5.30 (d, J = 28.2 Hz, 1H), 4.81 (d, J = 35.5 Hz, 1H), 4.39 (t, J = 39.8 Hz, 5H), 4.17-3.60 (m, 7H), 2.18 (dd, J = 82.8, 67.7 Hz, 2H), 1.63 (s, 1H). |
| 163 | 504.30 | 1.87 | $^1$H NMR (400 MHz, CDCl$_3$) δ 7.37-7.30 m, 1H), 7.11 (s, 1H), 7.10-6.95 (m, 3H), 6.92 (d, J = 8.2 Hz, 1H), 5.30 (br s, 1H), 4.79 (br s, 1H), 4.35-4.20 (m, 5H), 4.05-3.92 (m, 1H), 3.89 (s, 3H), 3.82-3.55 (m, 3H), 2.42-2.28 (m, 1H), 2.18-2.06 (m, 1H). |
| 164 | 485.10 | 1.70 | |
| 165 | 453.10 | 1.53 | |
| 166 | 475.10 | 1.51 | |
| 167 | 459.30 | 1.76 | $^1$H NMR (400 MHz, CDCl$_3$) δ 7.81 (d, J = 3.2 Hz, 1H), 7.41-7.28 (m, 3H), 6.85-6.75 (m, 1H), 5.35 (s, 1H), 5.06 (s, 1H), 4.33 (dd, J = 5.8, 3.3 Hz, 3H), 4.26-4.19 (m, 2H), 3.98-3.60 (m, 3H), 2.52-2.21 (m, 6H). |
| 168 | 459.30 | 1.76 | |
| 169 | 537.23 | 1.87 | |
| 170 | 486.23 | 1.99 | |
| 171 | 380.40 | 1.77 | |
| 172 | 498.30 | 1.93 | |
| 173 | 490.20 | 1.98 | |
| 174 | 506.30 | 1.91 | $^1$H NMR (400 MHz, CDCl$_3$) δ 7.11 (s, 1H), 7.06 (dd, J = 8.2, 1.9 Hz, 1H), 6.92 (d, J = 8.2 Hz, 3H), 6.80-6.72 (m, 1H), 5.29 (s, 0H), 4.83 (s, 0H), 4.38-4.26 (m, 4H), 4.26-4.13 (m, 1H), 4.05 (s, 1H), 3.90 (s, 3H), 3.72 (s, 3H), 2.10 (s, 2H). |
| 175 | 495.00 | 1.50 | |
| 176 | 494.23 | 1.93 | |
| 177 | 480.40 | 1.87 | |
| 178 | 437.40 | 1.99 | |
| 179 | 537.40 | 1.81 | $^1$H NMR (400 MHz, CDCl$_3$) δ 8.76 (d, J = 5.0 Hz, 1H), 7.87 (s, 1H), 7.55-7.41 (m, 1H), 7.22-7.03 (m, 2H), 6.92 (d, J = 8.1 Hz, 1H), 5.36 (s, 1H), 4.88 (s, 1H), 4.54-4.24 (m, 5H), 4.19-3.96 (m, 1H), 3.90 (s, 3H), 3.90-3.51 (m, 3H), 2.40-1.93 (m, 2H). |
| 180 | 479.00 | 1.60 | $^1$H NMR (400 MHz, CDCl$_3$) δ 7.44 (d, J = 8.0 Hz, 1H), 7.40-7.30-(m, 1H), 7.20-7.10 (m, 3H), 7.04-6.95 (m, 1H), 5.34 and 5.26 (2 s, 30%:70%, total 1H), 4.93 and 4.85 (2 s, 30%:70%, total 1H), 4.44 and 4.36 (2 t, J = 4.1 Hz, 30%:70%, total 1H), 4.17-3.51 (m, 9H), 2.87-2.59 (m, 3H), 2.58-2.39 (m, 2H), 2.34-2.06 (m, 2H). |
| 181 | 488.40 | 1.85 | $^1$H NMR (400 MHz, CDCl$_3$) δ 7.37 (td, J = 8.1, 5.9 Hz, 1H), 7.20-7.10 (m, 3H), 7.07 (dd, J = 8.2, 1.9 Hz, 1H), 7.01 (td, J = 8.0, 2.2 Hz, 1H), 6.92 (d, J = 8.2 Hz, 1H), 4.49-4.17 (m, 5H), 4.08 (s, 1H), 3.90 (s, 3H), 3.71 (s, 3H), 2.05 (d, J = 35.4 Hz, 2H). |
| 182 | 487.20 | 2.00 | |
| 183 | 503.20 | 1.94 | |
| 184 | 496.31 | 1.87 | $^1$H NMR (400 MHz, CDCl$_3$) δ 7.38 (t, J = 7.0 Hz, 1H), 7.21-7.09 (m, 3H), 7.07 (dd, J = 8.2, 1.9 Hz, 1H), 6.89 (d, J = 8.2 Hz, 1H), 5.30 (broad s, 1H), 4.78 (broad s, 1H), 4.28 (broad s, 1H), 4.07 (d, J = 6.3 Hz, 2H), 3.99 (broad s, 1H), 3.88 (s, 3H), 3.77 (broad s, 3H), 2.88-2.58 (m, 3H), 2.58-2.42 (m, 2H), 2.36 (broad s, 1H), 2.11 (broad s, 1H). |
| 185 | 489.40 | 1.84 | $^1$H NMR (400 MHz, CDCl$_3$) δ 7.47-7.32 (m, 2H), 7.29-7.10 (m, 3H), 7.01 (dd, J = 9.4, 7.7 Hz, 1H), 6.30-5.92 (m, 1H), 5.30 (d, J = 29.8 Hz, 1H), 4.88 (d, J = 27.8 Hz, 1H), 4.51-4.30 (m, 3H), 4.14-3.88 (m, 6H), 3.82-3.57 (m, 1H), 2.18 (ddd, J = 23.1, 15.1, 9.9 Hz, 2H). |
| 186 | 504.24 | 1.83 | |
| 187 | 488.25 | 1.93 | |
| 188 | 487.30 | 1.86 | $^1$H NMR (400 MHz, CDCl$_3$) δ 7.44 (d, J = 7.9 Hz, 1H), 7.36 (td, J = 8.0, 5.9 Hz, 1H), 7.16 (dd, J = 10.5, 7.3 Hz, 3H), 7.05-6.97 (m, 1H), 5.30 (d, J = 30.4 Hz, 1H), |

TABLE 3-continued

| Cmpd. No. | LC/MS M + 1 | LC/RT min | NMR |
|---|---|---|---|
| | | | 4.89 (d, J = 28.6 Hz, 1H), 4.47-4.25 (m, 5H), 4.04 (s, 4H), 3.96 (d, J = 14.8 Hz, 2H), 3.82-3.57 (m, 1H), 3.49 (s, 0H), 2.33-2.08 (m, 2H), 1.59 (s, 1H). |
| 189 | 489.40 | 1.88 | |
| 190 | 483.20 | 1.92 | $^1$H NMR (400 MHz, DMSO) δ 7.80-7.71 (m, 1H), 7.30 (d, J = 7.2 Hz, 2H), 7.16 (d, J = 7.2 Hz, 1H), 7.01 (d, J = 8.4 Hz, 1H), 6.75 (d, J = 8.2 Hz, 1H), 5.29 (s, 1H), 4.76 (s, 1H), 4.49-4.42 (m, 2H), 4.33-4.26 (m, 2H), 4.23 (dt, J = 9.7, 4.1 Hz, 1H), 3.86 (s, 3H), 3.82-3.70 (m, 1H), 3.70-3.59 (m, 1H), 3.59-3.45 (m, 1H), 3.40-3.34 (m, 1H), 2.40-2.24 (m, 1H), 2.19 (s, 3H), 2.07-1.78 (m, 1H). |
| 191 | 421.20 | 1.91 | |
| 192 | 499.20 | 1.78 | |
| 193 | 478.30 | 1.86 | $^1$H NMR (400 MHz, CDCl$_3$) δ 7.37 (td, J = 8.1, 5.9 Hz, 1H), 7.13 (dd, J = 12.9, 5.5 Hz, 3H), 7.07 (dd, J = 8.2, 1.8 Hz, 1H), 7.01 (td, J = 8.3, 2.4 Hz, 1H), 6.89 (d, J = 8.2 Hz, 1H), 5.31 (s, 1H), 4.86 (s, 1H), 4.24 (s, 1H), 4.08 (d, J = 6.3 Hz, 3H), 3.88 (s, 3H), 3.72 (d, J = 14.5 Hz, 2H), 3.49 (s, 0H), 2.85-2.62 (m, 3H), 2.58-2.40 (m, 2H), 2.09 (s, 2H), 1.53 (d, J = 28.0 Hz, 1H). |
| 194 | 467.20 | 1.50 | $^1$H NMR (400 MHz, DMSO) δ 7.74 (t, J = 7.7 Hz, 1H), 7.40 (d, J = 7.7 Hz, 1H), 7.30 (s, 2H), 7.21 (d, J = 7.7 Hz, 1H), 7.01 (d, J = 9.0 Hz, 1H), 5.28 (s, 1H), 4.72 (s, 1H), 4.50-4.39 (m, 2H), 4.39-4.20 (m, 3H), 4.20-3.79 (m, 1H), 3.78-3.67 (m, 1H), 3.68-3.56 (m, 1H), 3.56-3.46 (m, 1H), 2.48 (s, 3H), 2.36-2.22 (m, 1H), 2.19 (s, 3H), 2.14-1.86 (m, 1H). |
| 195 | 436.30 | 2.11 | |
| 196 | 505.50 | 1.84 | |
| 197 | 539.40 | 1.85 | |
| 198 | 547.40 | 1.95 | |
| 199 | 491.00 | 1.29 | |
| 200 | 493.30 | 2.04 | $^1$H NMR (400 MHz, CDCl$_3$) δ 7.45 (d, J = 8.0 Hz, 1H), 7.43-7.32 (m, 1H), 7.15 (d, J = 7.1 Hz, 2H), 7.09 (t, J = 7.0 Hz, 1H), 7.05-6.95 (m, 1H), 5.30 (d, J = 31.1 Hz, 1H), 4.89 (d, J = 28.8 Hz, 1H), 4.40 (dt, J = 28.2, 4.1 Hz, 1H), 4.08 (t, J = 7.0 Hz, 2H), 4.03 (s, 3H), 4.00-3.90 (m, 3H), 3.86-3.48 (m, J = 16.2, 13.5, 5.4 Hz, 1H), 2.86-2.65 (m, 2H), 2.48-2.10 (m, 5H), 2.06 (q, J = 6.4 Hz, 2H). |
| 201 | 457.50 | 1.35 | |
| 202 | 457.50 | 1.35 | |
| 203 | 491.40 | 1.12 | |
| 204 | 543.40 | 1.91 | |
| 205 | 453.50 | 1.54 | |
| 206 | 437.10 | 1.49 | |
| 207 | 467.50 | 1.58 | |
| 208 | 449.30 | 1.11 | |
| 209 | 456.40 | 0.91 | |
| 210 | 445.50 | 0.92 | |
| 211 | 477.00 | 1.79 | |
| 212 | 470.50 | 2.04 | |
| 213 | 497.50 | 2.08 | |
| 214 | 486.50 | 2.01 | |
| 215 | 478.50 | 2.02 | |
| 216 | 490.30 | 2.09 | |
| 217 | 452.30 | 2.08 | |
| 218 | 508.30 | 2.14 | |
| 219 | 486.50 | 2.14 | |
| 220 | 474.30 | 2.06 | |
| 221 | 533.40 | 1.70 | |
| 222 | 529.00 | 1.85 | |
| 223 | 519.20 | 1.62 | $^1$H NMR (400 MHz, CDCl$_3$) δ 7.44 (d, J = 7.9 Hz, 1H), 7.36 (td, J = 8.0, 5.9 Hz, 1H), 7.20-7.12 (m, J = 8.0 Hz, 2H), 7.09 (t, J = 7.0 Hz, 1H), 7.04-6.96 (m, 1H), 5.30 (d, J = 31.5 Hz, 1H), 4.89 (d, J = 29.1 Hz, 1H), 4.52-4.22 (m, 1H), 4.13-4.04 (m, 2H), 4.03 (s, 3H), 4.02-3.91 (m, 4H), 3.84-3.49 (m, 1H), 2.87-2.70 (m, 1H), 2.68-2.47 (m, 3H), 2.41-2.01 (m, 6H). |
| 224 | 493.20 | 1.53 | $^1$H NMR (400 MHz, CDCl$_3$) δ 7.42 (d, J = 7.7 Hz, 1H), 7.36 (dd, J = 14.0, 8.0 Hz, 1H), 7.23-7.11 (m, 3H), 7.08-6.95 (m, 1H), 5.30 (d, J = 29.9 Hz, 1H), 4.89 (d, J = 28.3 Hz, 1H), 4.40 (d, J = 27.3 Hz, 2H), 4.07 (s, 1H), 4.02 (s, 3H), 3.96 (s, 2H), 3.86-3.53 (m, 1H), 2.81-2.35 (m, 5H), 2.35-2.07 (m, 2H), 1.28 (d, J = 5.3 Hz, 3H). |

TABLE 3-continued

| Cmpd. No. | LC/MS M + 1 | LC/RT min | NMR |
|---|---|---|---|
| 225 | 496.40 | 1.72 | $^1$H NMR (400 MHz, CDCl$_3$) δ 7.13-7.00 (m, 2H), 6.96-6.84 (m, 3H), 6.76 (tt, J = 8.7, 2.3 Hz, 1H), 5.31 (s, 1H), 4.85 (s, 1H), 4.37-4.13 (m, 1H), 4.12-3.95 (m, 3H), 3.89 (s, 3H), 3.84-3.54 (m, 3H), 2.86-2.59 (m, 3H), 2.59-2.38 (m, 2H), 2.35-1.81 (m, 2H). |
| 226 | 529.40 | 1.73 | $^1$H NMR (400 MHz, CDCl$_3$) δ 8.76 (d, J = 5.0 Hz, 1H), 7.87 (s, 1H), 7.57-7.40 (m, 1H), 7.18-7.01 (m, 2H), 6.89 (d, J = 8.1 Hz, 1H), 5.36 (s, 1H), 4.89 (s, 1H), 4.55-4.18 (m, 1H), 4.16-4.09 (m, 1H), 4.08 (d, J = 6.3 Hz, 2H), 3.95-3.89 (m, 1H), 3.89 (s, 3H), 3.88-3.60 (m, 2H), 2.87-2.60 (m, 3H), 2.60-2.40 (m, 2H), 2.40-2.07 (m, 2H). |
| 227 | 479.30 | 1.82 | |
| 228 | 486.50 | 1.77 | $^1$H NMR (400 MHz, CDCl$_3$) δ 7.37 (td, J = 8.1, 6.0 Hz, 1H), 7.13 (d, J = 3.4 Hz, 3H), 7.08 (d, J = 8.2 Hz, 1H), 7.05-6.97 (m, 1H), 6.92 (d, J = 8.2 Hz, 1H), 5.31 (s, 1H), 4.86 (s, 1H), 4.29 (tt, J = 90.1, 45.2 Hz, 6H), 3.90 (s, 3H), 3.74 (s, 3H), 2.11 (s, 2H). |
| 229 | 491.50 | 1.88 | |
| 230 | 491.50 | 1.92 | |
| 231 | 441.50 | 1.99 | |
| 232 | 455.70 | 2.15 | |
| 233 | 465.20 | 1.41 | $^1$H NMR (400 MHz, CDCl$_3$) δ 7.43 (d, J = 7.8 Hz, 1H), 7.36 (dd, J = 14.0, 7.9 Hz, 1H), 7.15 (d, J = 7.4 Hz, 2H), 6.99 (dt, J = 14.4, 7.5 Hz, 2H), 5.30 (d, J = 29.9 Hz, 1H), 4.89 (d, J = 28.3 Hz, 1H), 4.69 (s, 1H), 4.39 (dt, J = 6.8, 3.7 Hz, 1H), 4.05 (s, 3H), 4.11-3.89 (m, 3H), 3.83-3.54 (m, 1H), 3.21-3.05 (m, 2H), 2.95-2.76 (m, 2H), 2.34-2.08 (m, 2H). |
| 234 | 503.20 | 1.52 | $^1$H NMR (400 MHz, CDCl$_3$) δ 7.50-7.30 (m, 2H), 7.30-7.21 (m, 1H), 7.15 (d, J = 7.5 Hz, 2H), 7.01 (dd, J = 9.6, 7.7 Hz, 1H), 6.38-5.94 (m, 1H), 5.30 (d, J = 28.7 Hz, 1H), 4.88 (d, J = 27.5 Hz, 1H), 4.81-4.65 (m, 1H), 4.39 (dt, J = 33.8, 4.0 Hz, 1H), 4.10-4.04 (m, 1H), 4.04 (s, 3H), 4.00-3.87 (m, 2H), 3.82-3.51 (m, 1H), 2.19 (ddd, J = 23.4, 15.0, 10.0 Hz, 2H), 1.48 (d, J = 5.8 Hz, 3H). |
| 235 | 493.10 | 1.64 | $^1$H NMR (400 MHz, CDCl$_3$) δ 7.44 (d, J = 8.0 Hz, 1H), 7.36 (td, J = 8.0, 5.8 Hz, 1H), 7.23-7.08 (m, 3H), 7.00 (td, J = 7.8, 7.3, 2.1 Hz, 1H), 5.30 (d, J = 31.2 Hz, 1H), 4.89 (d, J = 28.9 Hz, 1H), 4.53-4.26 (m, 1H), 4.13-3.88 (m, 7H), 3.83-3.51 (m, 1H), 2.82-2.64 (m, 1H), 2.37 (dd, J = 22.7, 11.8 Hz, 1H), 2.32-1.89 (m, 5H), 1.78-1.57 (m, 3H). |
| 236 | 505.30 | 2.01 | |
| 237 | 505.30 | 1.98 | |
| 238 | 441.30 | 1.43 | |
| 239 | 502.00 | 7.17 | |
| 240 | 460.00 | 6.71 | |
| 241 | 442.00 | 7.13 | |
| 242 | 376.00 | 1.57 | |
| 243 | | | $^1$H NMR (400 MHz, CDCl$_3$) δ 7.40 (s, 1H), 7.37-7.21 (m, 3H), 7.13 (s, 1H), 7.03 (s, 2H), 5.30 (s, 1H), 4.85 (s, 1H), 4.61 (dt, J = 12.7, 6.3 Hz, 1H), 4.48-3.98 (m, 2H), 3.90 (s, 3H), 3.87-3.39 (m, 3H), 2.35-1.88 (m, 2H), 1.52 (d, J = 6.5 Hz, 3H). |
| 244 | | | $^1$H NMR (400 MHz, CDCl$_3$) δ 7.40 (s, 1H), 7.36-7.27 (m, 2H), 7.27-7.21 (m, 1H), 7.13 (s, 1H), 7.03 (s, 2H), 5.30 (s, 1H), 4.84 (s, 1H), 4.60 (hept, J = 6.4 Hz, 1H), 4.42-3.96 (m, 2H), 3.90 (s, 3H), 3.84-3.48 (m, 3H), 2.35-1.89 (m, 2H), 1.52 (d, J = 6.5 Hz, 3H). |
| 245 | 503.20 | 1.26 | |
| 246 | 492.40 | 1.13 | |
| 247 | 477.00 | 5.84 | |
| 248 | 541.40 | 1.94 | |
| 249 | 501.50 | 2.08 | |
| 250 | 530.40 | 1.92 | |
| 251 | 521.40 | 1.85 | $^1$H NMR (400 MHz, CDCl$_3$) δ 8.77 (d, J = 5.0 Hz, 1H), 7.87 (s, 1H), 7.46 (dd, J = 5.0, 1.0 Hz, 1H), 7.31-6.98 (m, 2H), 6.91 (d, J = 8.2 Hz, 1H), 5.36 (s, 1H), 4.89 (s, 1H), 4.56-4.33 (m, 1H), 4.28 (t, J = 6.9 Hz, 2H), 4.17-4.01 (m, 1H), 3.90 (s, 3H), 4.02-3.50 (m, 3H), 2.70 (qt, J = 10.6, 6.9 Hz, 2H), 2.25 (d, J = 43.9 Hz, 2H). |
| 252 | 478.00 | 1.80 | |
| 253 | 457.50 | 1.44 | |
| 254 | 515.40 | 1.78 | |
| 255 | 490.30 | 1.99 | |

TABLE 3-continued

| Cmpd. No. | LC/MS M + 1 | LC/RT min | NMR |
|---|---|---|---|
| 256 | 432.50 | 1.88 | $^1$H NMR (400 MHz, CDCl$_3$) δ 7.45-7.26 (m, 3H), 7.22-7.06 (m, 2H), 7.08-6.93 (m, 1H), 6.87-6.72 (m, 1H), 5.31 (broad s, 1H), 4.86 (broad s, 1H), 4.22 (broad s, 1H), 3.96 (d, J = 16.4 Hz, 2H, overlapped with broad s, 1H), 3.72 (broad s, 3H), 2.28 (s, 3H), 2.25-1.87 (m, 2H), 1.55 (s, 3H), 1.50 (s, 3H). |
| 257 | 488.10 | 1.63 | $^1$H NMR (400 MHz, CDCl$_3$) δ 7.38 (t, J = 6.9 Hz, 1H), 7.21-7.09 (m, 3H), 7.02 (d, J = 8.4 Hz, 2H), 5.30 (s, 1H), 4.77 (bs, 1H), 4.61 (dt, J = 12.7, 6.3 Hz, 1H), 4.28 (bs, 1H), 4.04-3.92 (m, 1H), 3.89 (s, 3H), 3.87-3.67 (m, 3H), 2.45-2.26 (m, 1H), 2.24-2.08 (m, 1H), 1.51 (d, J = 6.5 Hz, 3H). |
| 258 | 488.10 | 1.85 | $^1$H NMR (400 MHz, CDCl$_3$) δ 7.38 (t, J = 7.0 Hz, 1H), 7.20-7.08 (m, 3H), 7.07-6.95 (m, 2H), 5.30 (s, 1H), 4.77 (s, 1H), 4.60 (dt, J = 12.8, 6.4 Hz, 1H), 4.28 (bs, 1H), 4.03-3.92 (m, 1H), 3.89 (s, 3H), 3.86-3.63 (m, 3H), 2.44-2.28 (m, 1H), 2.27-2.08 (m, 1H), 1.52 (d, J = 6.5 Hz, 3H). |
| 259 | 465.00 | 1.38 | |
| 260 | 473.00 | 1.37 | |
| 261 | 442.50 | 1.80 | |
| 262 | 507.40 | 1.86 | |
| 263 | 489.20 | 1.91 | |
| 264 | 471.40 | 1.88 | |
| 265 | 479.00 | 1.83 | |
| 266 | 437.20 | 0.83 | $^1$H NMR (400 MHz, DMSO-d6) δ 8.45 (d, J = 3.5 Hz, 1H), 7.71 (td, J = 7.8, 1.9 Hz, 1H), 7.34 (d, J = 8.1 Hz, 1H), 7.16 (ddd, J = 7.5, 4.8, 1.0 Hz, 1H), 7.05-7.00 (m, 2H), 6.95 (dd, J = 8.2, 1.9 Hz, 1H), 4.46-4.37 (m, 2H), 4.31-4.23 (m, 2H), 3.89 (br s, 1H), 3.79 (s, 3H), 3.61 (br s, 1H), 3.53 (br s, 1H), 3.28 (br s, 1H), 2.59 (br s, 1H), 2.10 (br s, 1H), 1.70 (br s, 1H), 1.28 (dd, J = 8.9, 4.4 Hz, 1H), 1.05 (br s, 1H), 1.95-1.55 (m, 1H). |
| 267 | 530.00 | 1.48 | |
| 268 | 497.00 | 1.48 | |
| 269 | 517.00 | 1.52 | |
| 270 | 513.00 | 1.56 | |
| 271 | 515.00 | 1.51 | |
| 272 | 538.24 | 1.85 | |
| 273 | 521.24 | 1.90 | |
| 274 | 521.24 | 1.85 | |
| 275 | 529.30 | 1.91 | |
| 276 | 467.20 | 0.98 | |
| 277 | 481.20 | 1.15 | |
| 278 | 467.20 | 0.98 | |
| 279 | 481.00 | 1.42 | |
| 280 | 499.00 | 1.46 | |
| 281 | 497.00 | 1.45 | |
| 282 | 488.25 | 1.83 | |
| 283 | 502.22 | 1.91 | |
| 284 | 445.00 | 1.50 | $^1$H NMR (400 MHz, MeOD) δ 7.45-7.37 (m, 1H), 7.33-7.21 (m, 4H), 7.07-6.98 (m, 1H), 4.45-4.30 (m, 1H), 4.25-4.15 (m, 1H), 4.07-3.92 (m, 6H), 3.92-3.79 (m, 1H), 3.71 (dd, J = 8.3, 3.0 Hz, 1H), 2.91-2.67 (m, 1H), 2.34-1.85 (m, 8H). |
| 285 | 437.20 | 0.85 | |
| 286 | 488.10 | 1.93 | |
| 287 | 488.40 | 1.83 | |
| 288 | 496.40 | 1.89 | |
| 289 | 505.30 | 1.89 | |
| 290 | 477.30 | 1.80 | |
| 291 | 485.40 | 1.76 | |
| 292 | 494.40 | 1.76 | |
| 293 | 493.40 | 1.74 | |
| 294 | 474.10 | 1.53 | |
| 295 | 473.10 | 1.90 | |
| 296 | 459.16 | 2.06 | |
| 297 | 438.10 | 2.01 | |
| 298 | 446.20 | 1.96 | |
| 299 | 455.20 | 1.96 | |
| 300 | 454.10 | 1.94 | |
| 301 | 458.10 | 2.08 | |
| 302 | 470.40 | 1.81 | $^1$H NMR (400 MHz, CDCl$_3$) δ 7.40 (dd, J = 7.7, 5.8 Hz, 4H), 7.36-7.28 (m, 1H), 7.13 (s, 1H), 7.08 (dd, J = 8.2, 1.8 Hz, 1H), 6.92 (d, J = 8.2 Hz, 1H), 4.55-3.96 (m, 6H), 3.90 (s, 3H), 3.71 (s, 3H), 2.09 (d, J = 38.5 Hz, 2H), 1.60 (s, 2H), 0.05--0.05 (m, 3H). |

TABLE 3-continued

| Cmpd. No. | LC/MS M + 1 | LC/RT min | NMR |
|---|---|---|---|
| 303 | 456.40 | 1.32 | |
| 304 | 475.10 | 1.56 | |
| 305 | 471.40 | 1.37 | $^1$H NMR (400 MHz, CDCl$_3$) δ 8.60 (d, J = 3.9 Hz, 1H), 7.81 (s, 1H), 7.69 (s, 1H), 7.29 (s, 1H), 7.14 (s, 1H), 7.10 (d, J = 8.0 Hz, 1H), 6.92 (d, J = 8.2 Hz, 1H), 4.45 (s, 1H), 4.38-4.21 (m, 4H), 4.08 (s, 1H), 3.90 (s, 4H), 3.76 (s, 2H), 2.28 (d, J = 91.8 Hz, 2H). |
| 306 | 473.30 | 1.82 | |
| 307 | 472.30 | 1.93 | |
| 308 | 491.30 | 1.89 | |
| 309 | 507.40 | 1.94 | |
| 310 | 497.20 | 1.19 | |
| 311 | 491.00 | 1.27 | |
| 312 | 499.00 | 1.29 | |
| 313 | 473.00 | 1.22 | |
| 314 | 541.30 | 2.06 | $^1$H NMR (400 MHz, DMSO) δ 7.73 (dd, J = 8.0, 7.6 Hz, 1H), 7.20-6.93 (m, 4H), 6.77-6.65 (m, 1H), 5.30 (s, 1H), 4.76 (s, 1H), 4.42 (dd, J = 5.3, 3.0 Hz, 2H), 4.33-4.15 (m, 3H), 4.10-3.97 (m, 2H), 3.90 (dd, J = 7.2, 5.3 Hz, 1H), 3.80 (s, 3H), 3.76-3.67 (m, 1H), 3.66-3.48 (m, 2H), 2.40-2.11 (m, 1H), 2.11-1.82 (m, 2H), 0.96 (d, J = 6.7 Hz, 6H). |

ASSAYS FOR DETECTING AND MEASURING NAV INHIBITION PROPERTIES OF COMPOUND

E-VIPR Optical Membrane Potential Assay Method with Electrical Stimulation

Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

24 hours before the assay on E-VIPR, HEK cells expressing human NaV subtype, like NaV 1.7, are seeded in 384-well poly-lysine coated plates at 15,000-20,000 cells per well. Other subtypes are performed in an analogous mode in a cell line expressing the NaV of interest. HEK cells are grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; Gibco-BRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

Reagents and Solutions 100 mg/mL Pluronic F-127 (Sigma #P2443), in dry DMSO

Compound Plates: 384-well round bottom plate, e.g. Corning 384-well Polypropylene Round Bottom #3656

Cell Plates: 384-well tissue culture treated plate, e.g. Greiner #781091-1B 10 mM DiSBAC$_6$(3) (Aurora #00-100-010) in dry DMSO 10 mM CC2-DMPE (Aurora #00-100-008) in dry DMSO 200 mM ABSC1 in H$_2$O Bath1 buffer. Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).

Hexyl Dye Solution: Bath1 Buffer+0.5% β-cyclodextrin (make this prior to use, Sigma #C4767), 8 µM CC2-DMPE+ 2.5 µM DiSBAC$_6$(3). To make the solution Add volume of 10% Pluronic F127 stock equal to volumes of CC2-DMPE+ DiSBAC$_6$(3). The order of preparation is first mix Pluronic and CC2-DMPE, then add DiSBAC$_6$(3) while vortexing, then add Bath1+β-Cyclodextrin.

Assay Protocol

1) Pre-spot compounds (in neat DMSO) into compound plates. Vehicle control (neat DMSO), the positive control (20 mM DMSO stock tetracaine, 125 µM final in assay) and test compounds are added to each well at 160× desired final concentration in neat DMSO. Final compound plate volume will be 80 µL (80-fold intermediate dilution from 1 µL DMSO spot; 160-fold final dilution after transfer to cell plate). Final DMSO concentration for all wells in assay is 0.625%.

2) Prepare Hexyl Dye Solution.

3) Prepare cell plates. On the day of the assay, medium is aspirated and cells are washed three times with 100 µL of Bath1 Solution, maintaining 25 µL residual volume in each well.

4) Dispense 25 µL per well of Hexyl Dye Solution into cell plates. Incubate for 20-35 minutes at room temp or ambient conditions.

5) Dispense 80 µL per well of Bath1 into compound plates. Acid Yellow-17 (1 mM) is added and Potassium Chloride can be altered from 4.5 to 20 mM depending on the NaV subtype and assay sensitivity.

6) Wash cell plates three times with 100 μL per well of Bath1, leaving 25 μL of residual volume. Then transfer 25 uL per well from Compound Plates to Cell Plates. Incubate for 20-35 minutes at room temp/ambient condition 7) Read Plate on E-VIPR. Use the current-controlled amplifier to deliver stimulation wave pulses for typically 9 seconds and a scan rate of 400 Hz. A pre-stimulus recording is performed for 0.5 seconds to obtain the un-stimulated intensities baseline. The stimulatory waveform is applied for 9 seconds followed by 0.5 seconds of post-stimulation recording to examine the relaxation to the resting state. The stimulatory waveform of the electrical stimulation is specific for each cell type and can vary the magnitude, duration and frequency of the applied current to provide an optimal assay signal.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\,nm} - \text{background}_{460\,nm})}{(\text{intensity}_{580\,nm} - \text{background}_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R\square\square = R_f/R_i$ is then calculated and reported as a function of time.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

IonWorks assays.

Sodium currents were recorded using the automated patch clamp system, IonWorks (Molecular Devices Corporation, Inc.). Cells expressing Nav subtypes are harvested from tissue culture and placed in suspension at 0.5-4 million cells per mL Bath1. The IonWorks instrument measures changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents are measured at the test potential.

1-Benzazepin-2-One Binding Assay

The sodium channel inhibiting properties of the compounds of the invention can also be determined by assay methods described in Williams, B. S. et al., "Characterization of a New Class of Potent Inhibitors of the Voltage-Gated Sodium Channel NaV 1.7," *Biochemistry*, 2007, 46, 14693-14703, the entire contents of which are incorporated herein by reference.

The exemplified compounds of Table 1 herein are active against one or more sodium channels as measured using the assays described herein above as presented in Table 4.

TABLE 4

| [A1] |
|---|
| IC50: +++ <= 2.0 μM < ++ <= 5.0 μM < + |

| Cmpd. No. | Binned Activity Data |
|---|---|
| 1 | +++ |
| 2 | +++ |
| 3 | +++ |
| 4 | +++ |
| 5 | + |
| 6 | + |
| 7 | + |
| 8 | + |
| 9 | + |
| 10 | + |
| 11 | + |
| 12 | + |
| 13 | + |
| 14 | ++ |
| 15 | ++ |
| 16 | ++ |
| 17 | ++ |
| 18 | ++ |
| 19 | ++ |
| 20 | ++ |
| 21 | ++ |
| 22 | ++ |
| 23 | ++ |
| 24 | ++ |
| 25 | ++ |
| 26 | ++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |

TABLE 4-continued

[A1]
IC50: +++ <= 2.0 µM < ++ <= 5.0 µM < +

| Cmpd. No. | Binned Activity Data |
|---|---|
| 38 | +++ |
| 39 | + |
| 40 | +++ |
| 41 | +++ |
| 42 | +++ |
| 43 | ++ |
| 44 | +++ |
| 45 | +++ |
| 46 | +++ |
| 47 | +++ |
| 48 | +++ |
| 49 | + |
| 50 | +++ |
| 51 | ++ |
| 52 | ++ |
| 53 | +++ |
| 54 | +++ |
| 55 | +++ |
| 56 | +++ |
| 57 | + |
| 58 | +++ |
| 59 | +++ |
| 60 | +++ |
| 61 | +++ |
| 62 | ++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |
| 72 | +++ |
| 73 | +++ |
| 74 | +++ |
| 75 | +++ |
| 76 | +++ |
| 77 | +++ |
| 78 | +++ |
| 79 | +++ |
| 80 | +++ |
| 81 | ++ |
| 82 | +++ |
| 83 | +++ |
| 84 | +++ |
| 85 | +++ |
| 86 | +++ |
| 87 | +++ |
| 88 | +++ |
| 89 | +++ |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | +++ |
| 112 | +++ |

TABLE 4-continued

[A1]
IC50: +++ <= 2.0 µM < ++ <= 5.0 µM < +

| Cmpd. No. | Binned Activity Data |
|---|---|
| 113 | +++ |
| 114 | +++ |
| 115 | +++ |
| 116 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | +++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |
| 156 | +++ |
| 157 | +++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |
| 173 | +++ |
| 174 | +++ |
| 175 | +++ |
| 176 | +++ |
| 177 | +++ |
| 178 | +++ |
| 179 | +++ |
| 180 | +++ |
| 181 | +++ |
| 182 | +++ |
| 183 | +++ |
| 184 | +++ |
| 185 | +++ |
| 186 | +++ |
| 187 | +++ |

TABLE 4-continued

[A1]
IC50: +++ <= 2.0 μM < ++ <= 5.0 μM < +

| Cmpd. No. | Binned Activity Data |
| --- | --- |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |
| 197 | +++ |
| 198 | +++ |
| 199 | +++ |
| 200 | +++ |
| 201 | +++ |
| 202 | +++ |
| 203 | +++ |
| 204 | +++ |
| 205 | + |
| 206 | +++ |
| 207 | +++ |
| 208 | +++ |
| 209 | +++ |
| 210 | ++ |
| 211 | +++ |
| 212 | ++ |
| 213 | +++ |
| 214 | +++ |
| 215 | +++ |
| 216 | +++ |
| 217 | ++ |
| 218 | +++ |
| 219 | + |
| 220 | ++ |
| 221 | +++ |
| 222 | +++ |
| 223 | +++ |
| 224 | +++ |
| 225 | +++ |
| 226 | +++ |
| 227 | +++ |
| 228 | +++ |
| 229 | +++ |
| 230 | +++ |
| 231 | +++ |
| 232 | +++ |
| 233 | +++ |
| 234 | +++ |
| 235 | +++ |
| 236 | +++ |
| 237 | +++ |
| 238 | +++ |
| 239 | +++ |
| 240 | +++ |
| 241 | ++ |
| 242 |  |
| 243 | +++ |
| 244 | +++ |
| 245 | +++ |
| 246 | +++ |
| 247 | +++ |
| 248 | +++ |
| 249 | +++ |
| 250 | +++ |
| 251 | +++ |
| 252 | +++ |
| 253 | +++ |
| 254 | +++ |
| 255 | +++ |
| 256 | +++ |
| 257 | +++ |
| 258 | +++ |
| 259 | +++ |
| 260 | +++ |
| 261 | + |
| 262 | +++ |
| 263 | +++ |
| 264 | +++ |
| 265 | +++ |
| 266 | +++ |
| 267 | +++ |
| 268 | +++ |
| 269 | +++ |
| 270 | +++ |
| 271 | +++ |
| 272 | +++ |
| 273 | +++ |
| 274 | +++ |
| 275 | +++ |
| 276 | + |
| 277 | +++ |
| 278 | +++ |
| 279 | +++ |
| 280 | +++ |
| 281 | +++ |
| 282 | +++ |
| 283 | +++ |
| 284 | +++ |
| 285 | +++ |
| 286 | +++ |
| 287 | +++ |
| 288 | +++ |
| 289 | +++ |
| 290 | + |
| 291 | +++ |
| 292 | +++ |
| 293 | +++ |
| 294 | +++ |
| 295 | +++ |
| 296 | ++ |
| 297 | + |
| 298 | +++ |
| 299 | +++ |
| 300 | +++ |
| 301 | +++ |
| 302 | +++ |
| 303 | +++ |
| 304 | +++ |
| 305 | +++ |
| 306 | +++ |
| 307 | +++ |
| 308 | +++ |
| 309 | +++ |
| 310 | +++ |
| 311 | +++ |
| 312 | +++ |
| 313 | ++ |
| 314 | +++ |

Many modifications and variations of the embodiments described herein may be made without departing from the scope, as is apparent to those skilled in the art. The specific embodiments described herein are offered by way of example only.

We claim:
1. A compound of formula I:

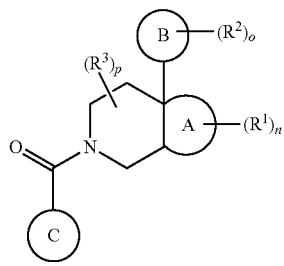

or a pharmaceutically acceptable salt thereof,
wherein, independently for each occurrence,
ring A is

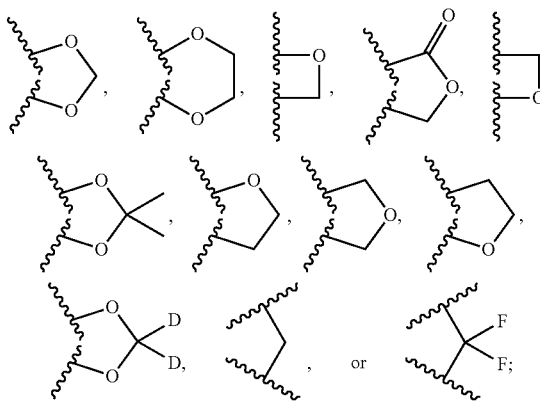

ring B is a phenyl, pyridyl, thiazole, pyrimidine, pyrazole, furan, thiophene, pyrrole, oxazole, imidazole, isoxazole, isothiazole, pyridazine, or pyrazine ring, each of which is substituted by $(R^2)_o$;
ring C is

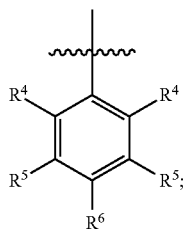

$R^1$ is C1-C6 alkyl, C1-C6 alkoxy, halo, fluoro-C1-C6 alkyl, fluoro-C1-C6 alkoxy, or oxo;
$R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$;
$R^3$ is C1-C6 alkyl, C1-C6 alkoxy, halo, CN, fluoro-C1-C6 alkyl, or fluoro-C1-C6 alkoxy;
n, o, and p are integers from 0 to 4 inclusive;
$R^4$ is H, C1-C6 alkyl, C1-C6 alkoxy, halo, CN, or OH;

$R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-C6 alkyl, or fluoro-C1-C6 alkoxy;
$R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$;
$R^7$ is H, C1-C6 alkyl, $CHF_2$, $CF_3$, or C3-C8 cycloalkyl; and
$R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$.

2. The compound of claim 1, wherein $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$.

3. The compound of claim 2, wherein $R^2$ is $CH_3$, $OCH_3$, $CF_3$, F, Cl, Br, CN, $OCH_2CH_2OtBu$, $OCH_2CH(CH_3)_2$.

4. The compound of claim 1, wherein ring A is

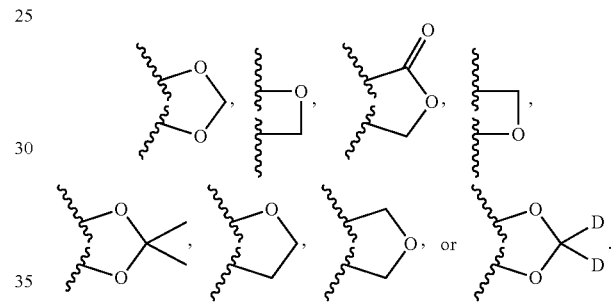

5. The compound of claim 1, wherein ring B is a phenyl ring, which is optionally substituted by halo, cyano, oxoalkoxy, hydroxy, amino, nitro, aryl, haloalkyl, or alkyl.

6. The compound of claim 1, wherein ring B is

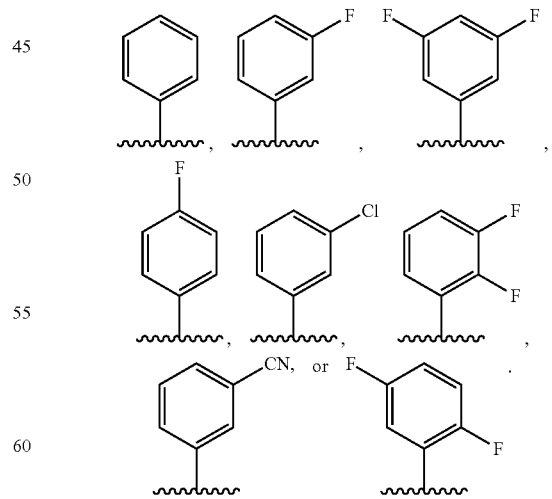

7. The compound of claim 1, wherein ring B is a pyridyl, thiazole, pyrimidine, pyrazole, furan, thiophene, pyrrole, oxazole, imidazole, isoxazole, isothiazole, pyridazine, or pyrazine ring.

8. The compound of claim 1, wherein ring C is an unsubstituted phenyl ring.

9. The compound of claim 1, wherein $R^4$ is H, C1-C6 alkoxy, or halo.

10. The compound of claim 9, wherein $R^4$ is H, $OCH_3$, or F.

11. The compound of claim 1, wherein $R^5$ is H, $CH_3$, $OCH_3$, F, Cl, CN, OH, or $CF_3$.

12. The compound of claim 11, wherein $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$.

13. The compound of claim 12, wherein $R^6$ is H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$,

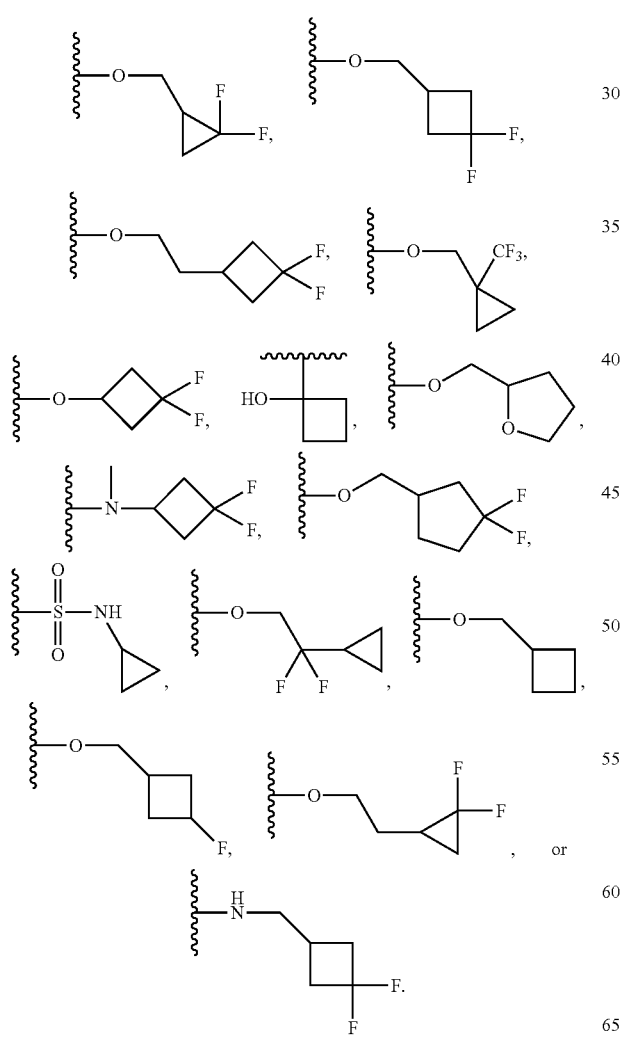

14. A compound of formula I:

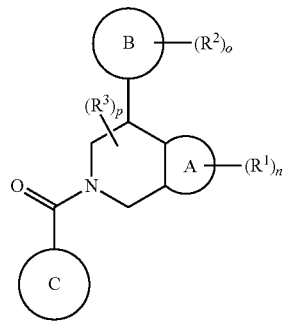

or a pharmaceutically acceptable salt thereof, wherein, independently for each occurrence, ring A is

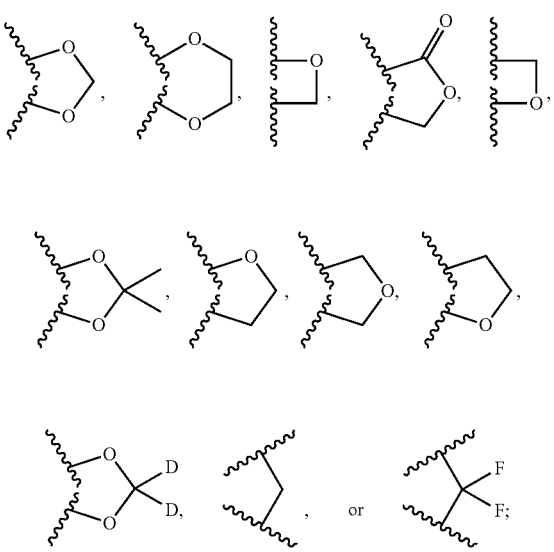

ring B is a phenyl, pyridyl, thiazole, pyrimidine, pyrazole, furan, thiophene, pyrrole, oxazole, imidazole, isoxazole, isothiazole, pyridazine, or pyrazine ring, each of which is substituted by $(R^2)_o$; and ring C is selected from the group consisting of:

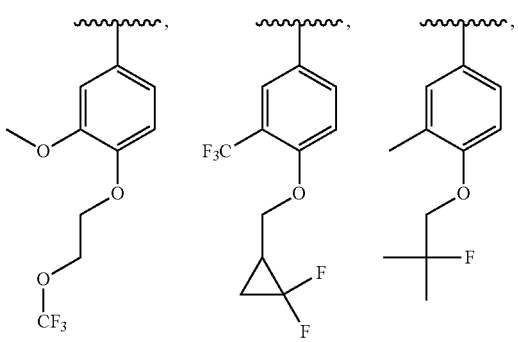

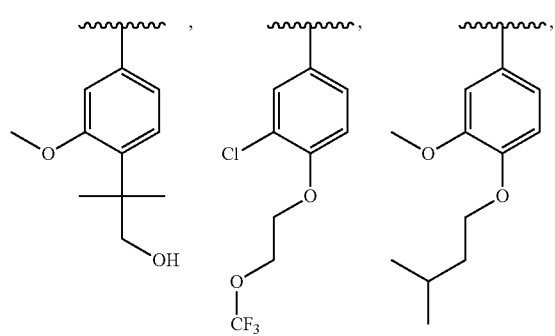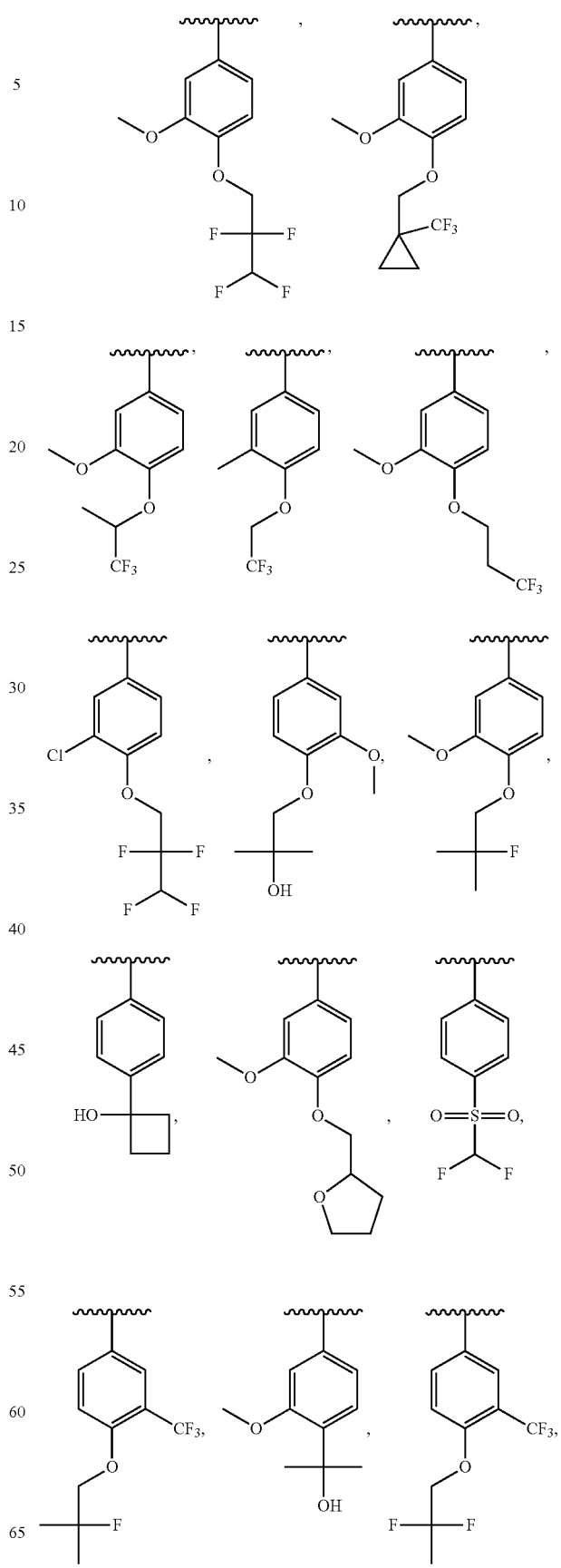

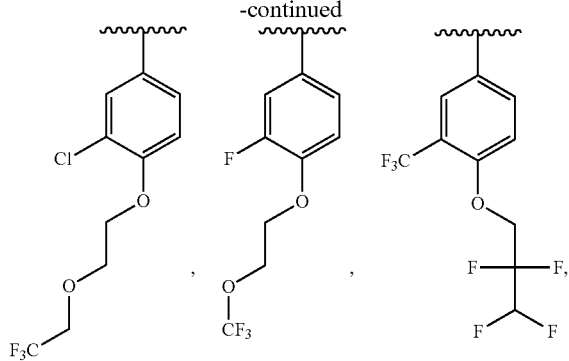
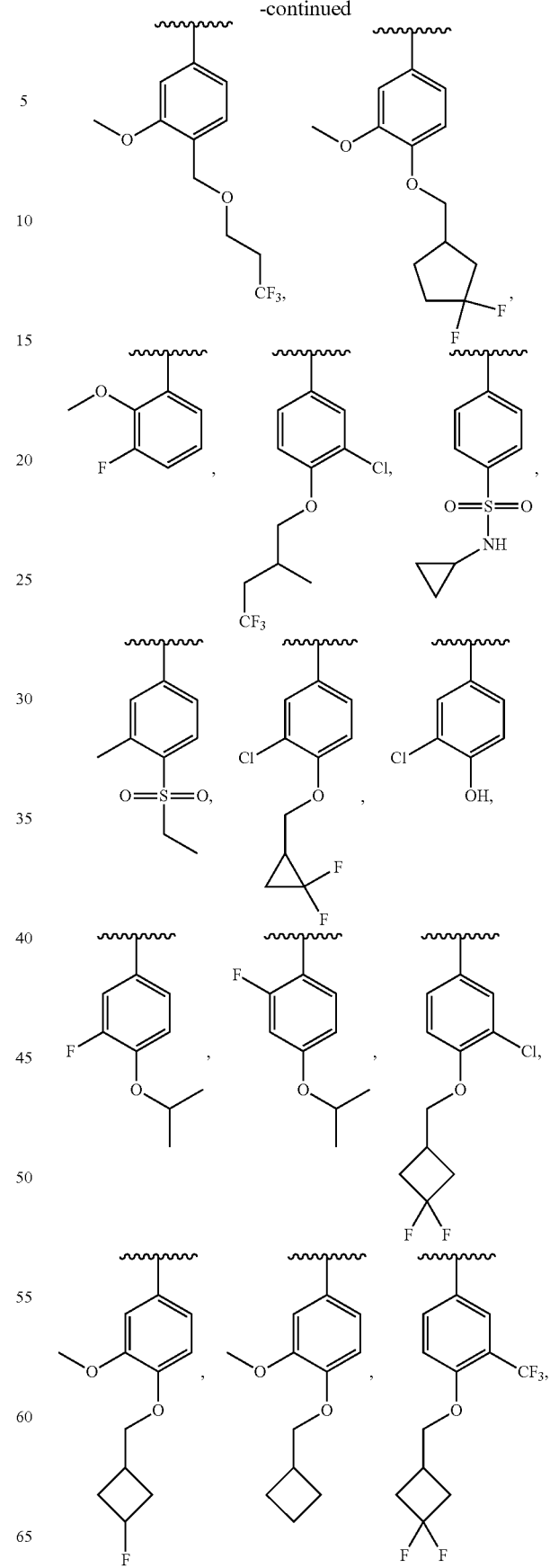

-continued

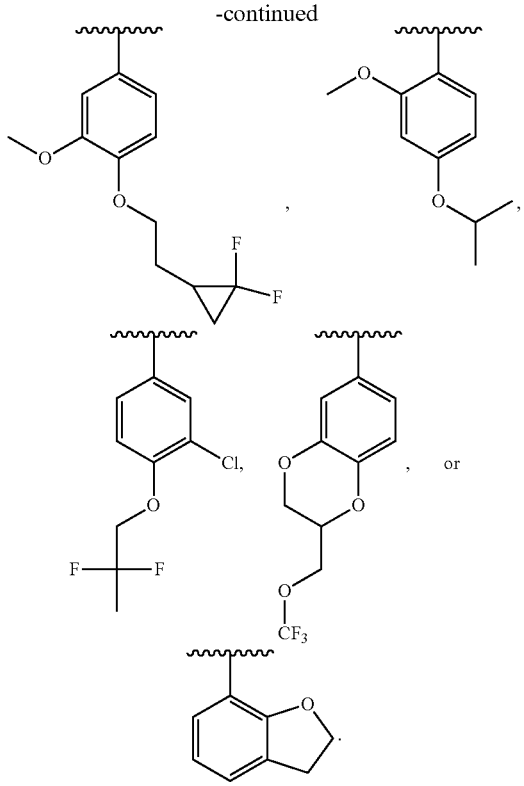

15. The compound of claim 1, wherein the compound has formula IA:

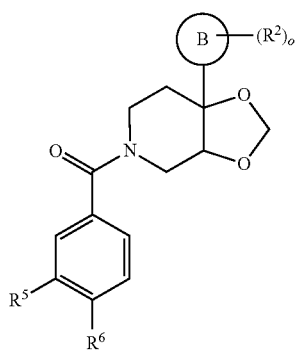

or a pharmaceutically acceptable salt thereof,
wherein, independently for each occurrence,
  ring B is a phenyl, pyridyl, thiazole, pyrimidine, pyrazole, furan, thiophene, pyrrole, oxazole, imidazole, isoxazole, isothiazole, pyridazine, or pyrazine ring, each of which is optionally substituted by halo, cyano, oxoalkoxy, hydroxy, amino, nitro, aryl, haloalkyl, or alkyl;
  $R^2$ is C1-C6 alkyl, C1-C6 alkoxy, halo, CN, fluoro-C1-C6 alkyl, fluoro-C1-C6 alkoxy, $N(R^7)_2$, $NR^7SO_2R^7$, $SO_2R^7$, $CO_2R^7$, $SO_2N(R^7)_2$, or (C1-C8)-$R^8$ wherein up to two $CH_2$ units may be replaced with O, CO, $CF_2$, or $NR^7$;
  o is an integer from 0 to 4 inclusive;
  $R^5$ is H, C1-C6 alkyl, C1-C6 alkoxy, halo, CN, OH, $OR^7$, $N(R^7)_2$, $NR^7SO_2R^7$, $SO_2R^7$, $CO_2R^7$, $SO_2N(R^7)_2$, fluoro-C1-C6 alkyl, or fluoro-C1-C6 alkoxy;
  $R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$;
  $R^7$ is H, C1-C6 alkyl, $CHF_2$, $CF_3$, or C3-C8 cycloalkyl; and
  $R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$.

16. The compound of claim 15, wherein $R^2$ is C1-C6 alkyl, C1-C6 alkoxy, fluoro-C1-C6 alkyl, halo, CN, or (C1-C8)-$R^8$ wherein up to two $CH_2$ units may be replaced with O, CO, $CF_2$, or $NR^7$.

17. The compound of claim 15, wherein $R^2$ is $CH_3$, $OCH_3$, $CF_3$, F, Cl, Br, CN, $OCH_2CH_2OtBu$, $OCH_2CH(CH_3)_2$.

18. The compound of claim 15, wherein ring B is a pyridyl, thiazole, pyrimidine, pyrazole, furan, thiophene, pyrrole, oxazole, imidazole, isoxazole, isothiazole, pyridazine, or pyrazine ring.

19. The compound of claim 15, wherein $R^5$ is H, C1-C6 alkyl, C1-C6 alkoxy, halo, CN, OH, or fluoro-C1-C6 alkyl.

20. The compound of claim 15, wherein $R^5$ is H, $CH_3$, $OCH_3$, F, Cl, CN, OH, or $CF_3$.

21. The compound of claim 15, wherein $R^6$ is H, C1-C6 alkoxy, fluoro-C1-C6 alkoxy, $SO_2R^7$, $SO_2N(R^7)_2$, or a straight chain, branched, or cyclic (C1-C8)-$R^8$ or fluoro-(C1-C8)-$R^8$ wherein up to three $CH_2$ units may be replaced with O, CO, S, SO, $SO_2$, or $NR^7$.

22. The compound of claim 15, wherein $R^6$ is H, $OCH_2CH_2CF_3$, $OCH_2CF(CH_3)_2$, $C(CH_3)_2CH_2OH$, $OCH_2CH_2CH(CH_3)_2$, $OCH(CH_3)CF_3$, $CH_2OCH_2CH_2CF_3$, $C(CH_3)_2OH$, $OCH_2CH_2OtBu$, $CH_2C(CH_3)_2OH$, $OCH(CH_3)_2$, $OCH_2C(CH_3)_2OH$, $OCH_2CF_2CHF_2$, $OCH_2CF_3$, $OCH_2CH_2OCF_3$, $OCH(CH_3)CF_2CHF_2$, $SO_2CHF_2$, $OCH_2CF_2CH_3$, $OCH_2CH_2OCH_2CF_3$, $OCH_2CF_3$, $OCH_2C(CH_3)_3$, $OCH_2CH(CH_3)CH_2CF_3$, $SO_2CH_2CH_3$, $OCH(CH_3)CH_2CF_3$, $OCH_2CF_2CHF_2$,

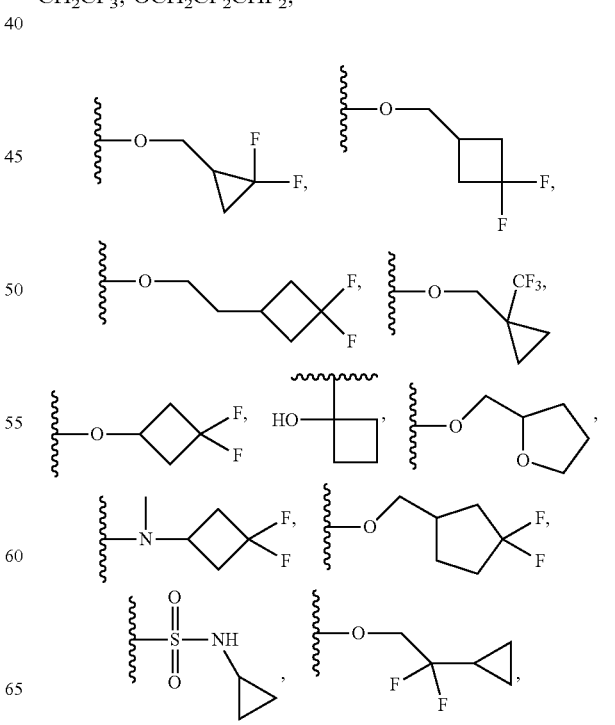

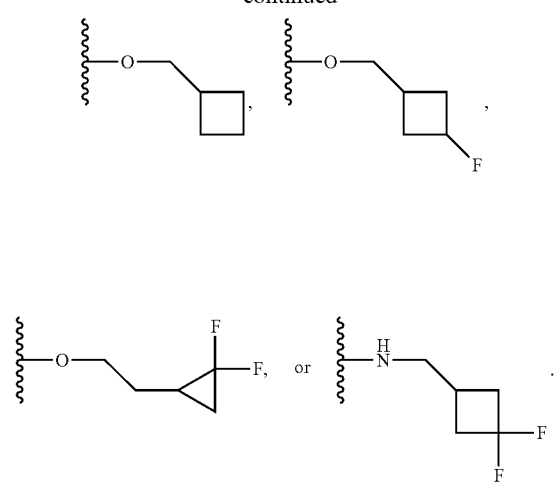
23. The compound of claim 15, wherein
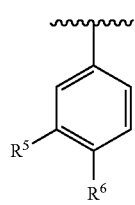
is selected from:
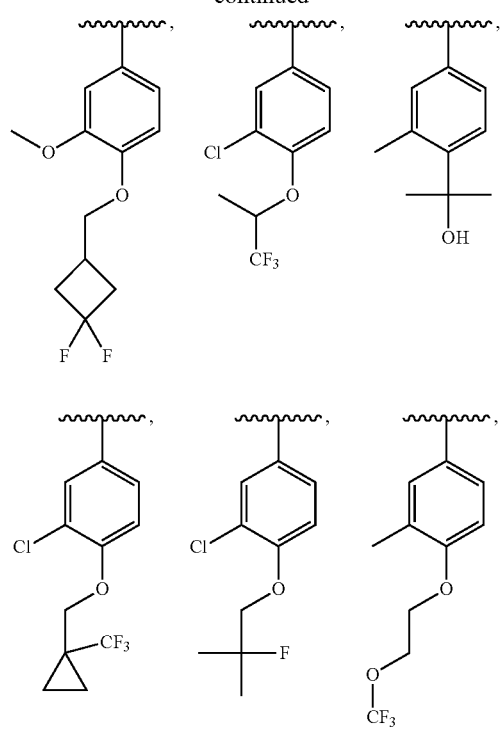
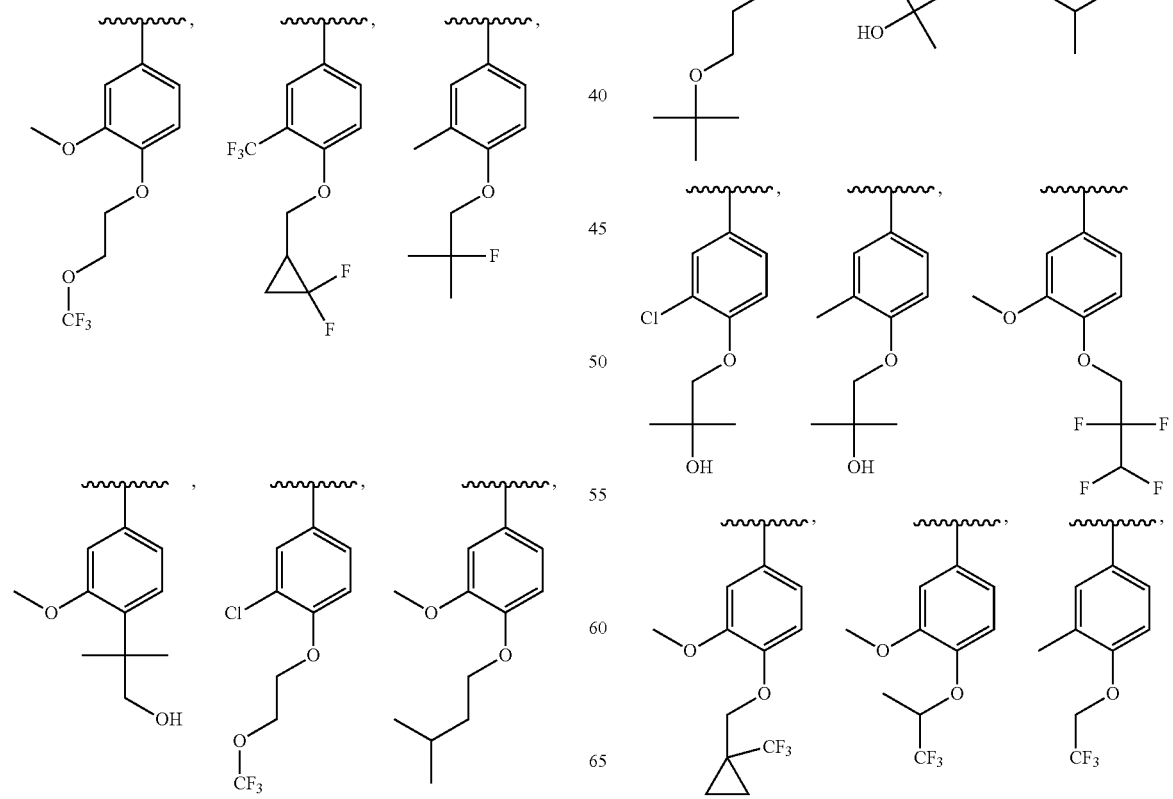
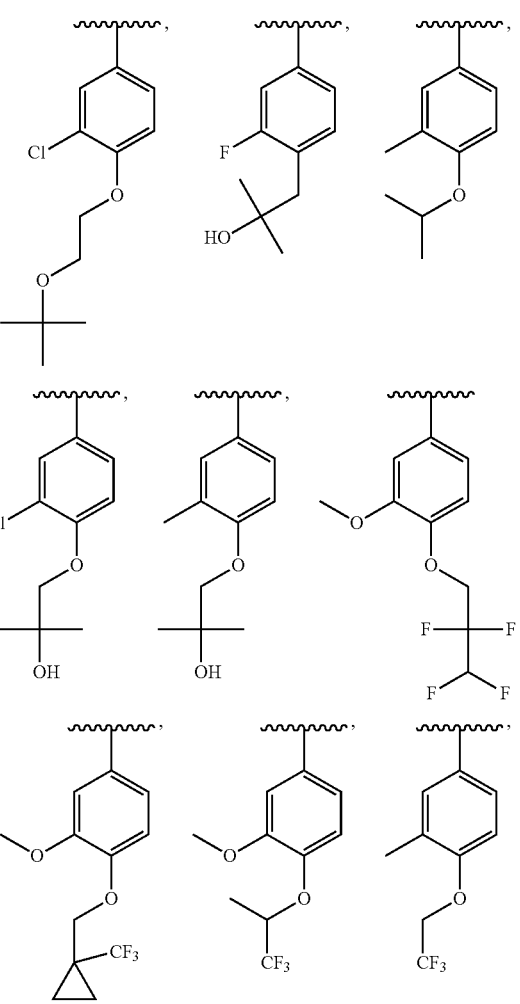

497
-continued
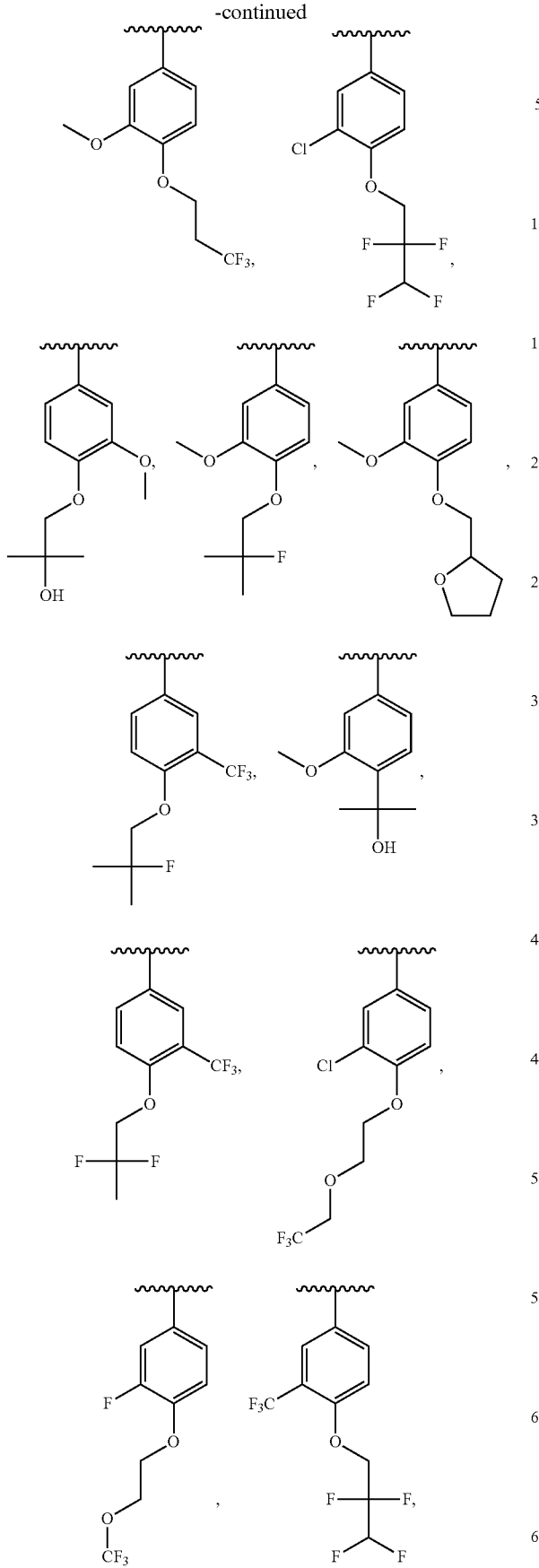
498
-continued
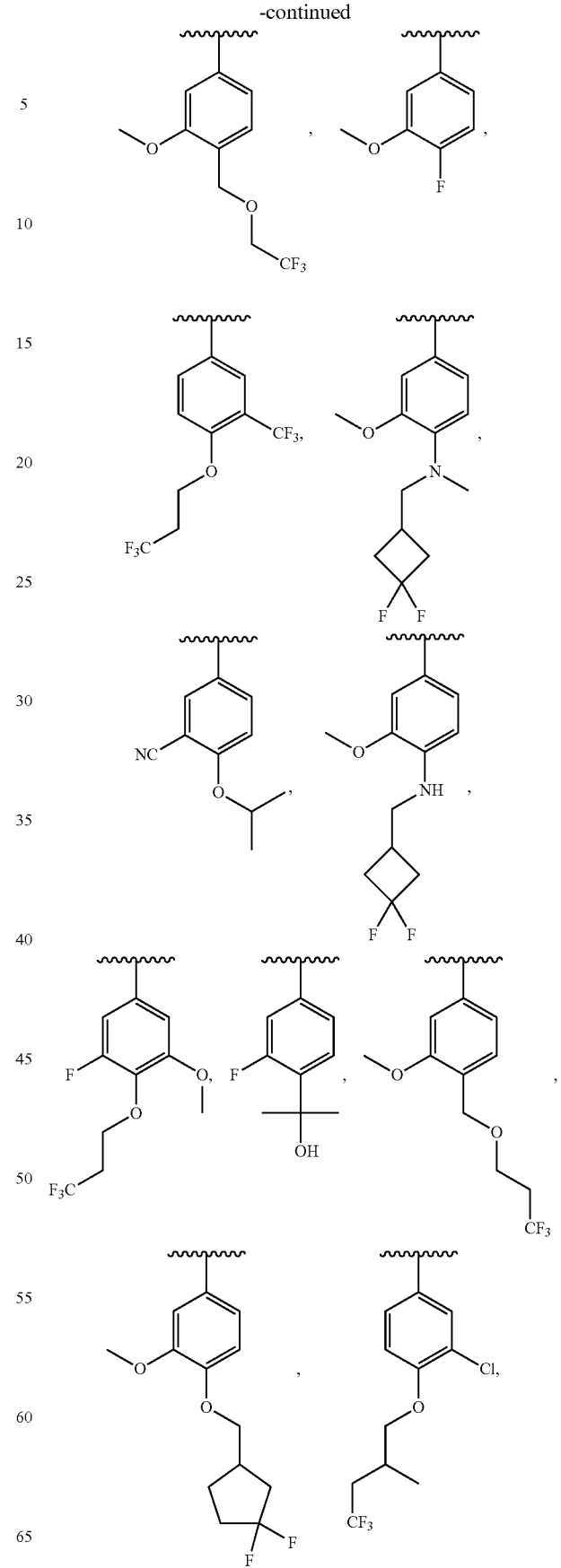

499
-continued
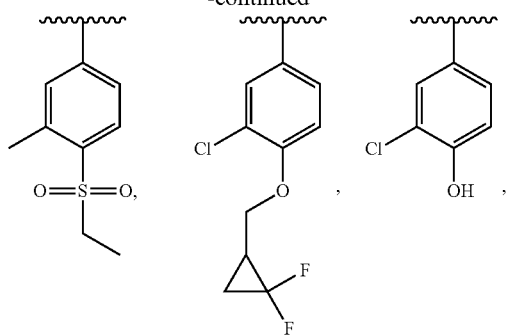
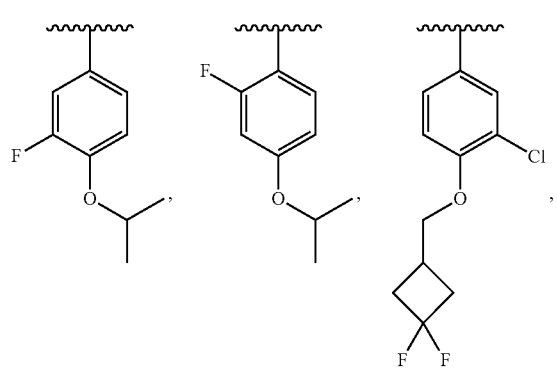
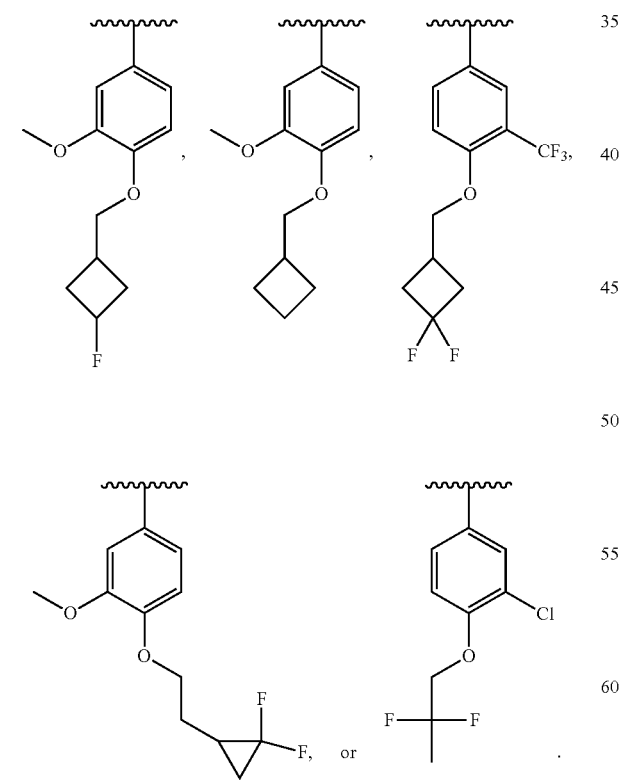
24. The compound of claim 1 or 14, selected from the table:
500
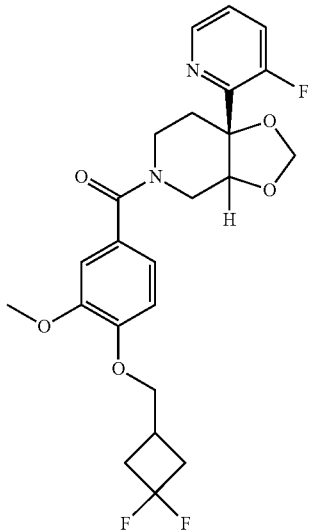 [SMILES: COc1cc(C(=O)N2CC[C@]3(c4ncccc4F)OCOC3C2)ccc1OCC1CC(F)(F)C1]
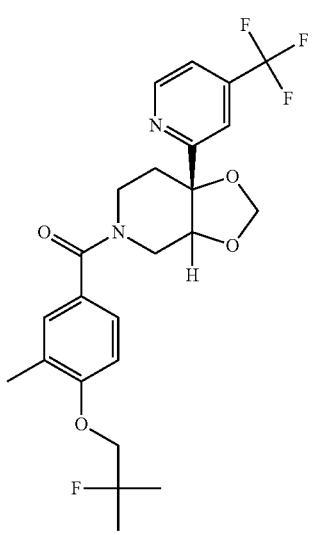 [SMILES: Cc1cc(C(=O)N2CC[C@]3(c4cc(C(F)(F)F)ccn4)OCOC3C2)ccc1OCC(C)(C)F]
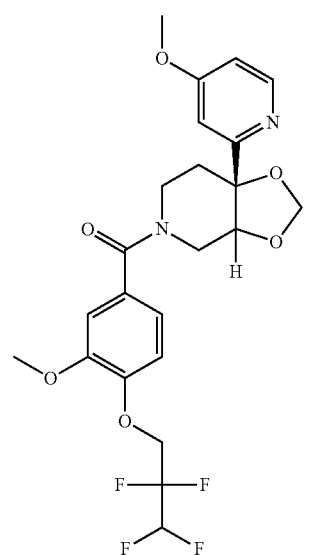 [SMILES: COc1ccnc([C@]23CCN(C(=O)c4ccc(OCC(F)(F)C(F)F)c(OC)c4)CC2OCO3)c1]

-continued
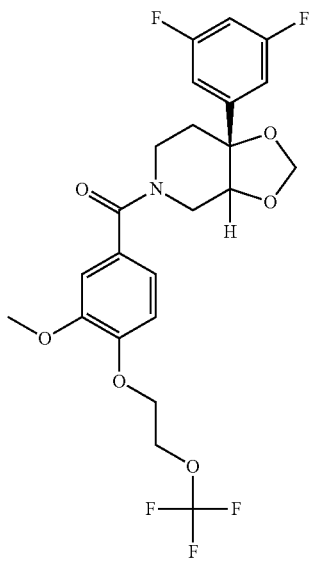 [SMILES: COc1cc(C(=O)N2CC[C@]3(c4cc(F)cc(F)c4)OCOC3C2)ccc1OCCOC(F)(F)F]
4
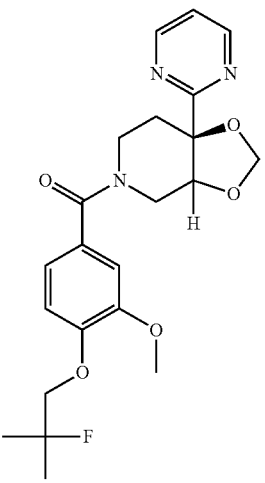
7
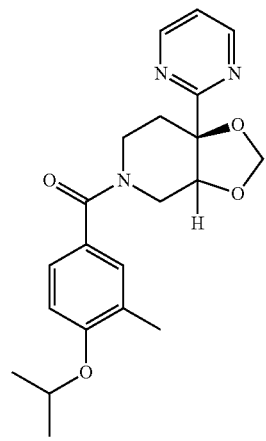
5
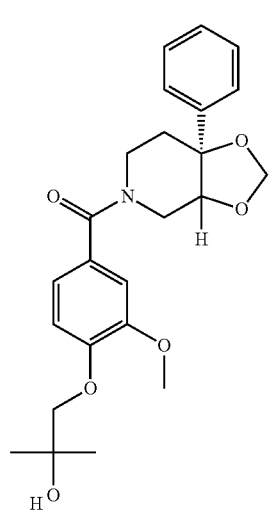
8
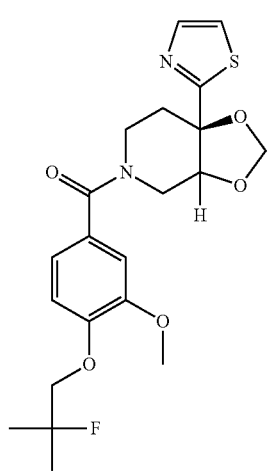
6
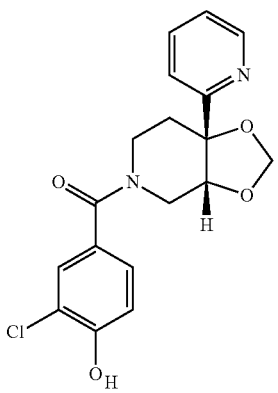
9

503
-continued
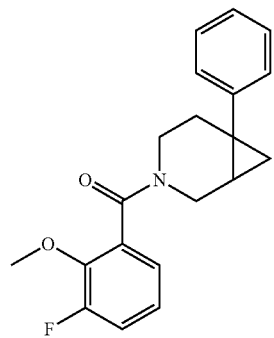 [SMILES: COc1c(F)cccc1C(=O)N1CCC2(c3ccccc3)CC2C1]
11
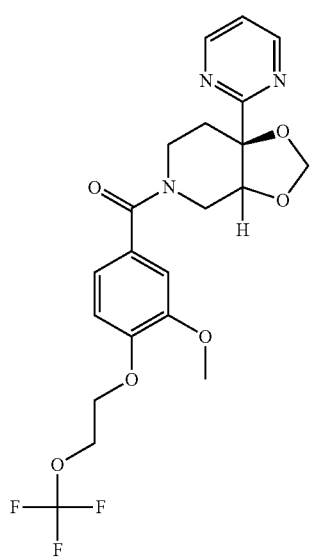
12
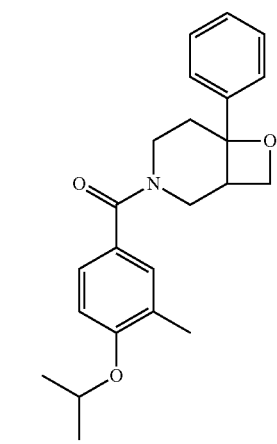 [SMILES: Cc1cc(C(=O)N2CCC3(c4ccccc4)OCC3C2)ccc1OC(C)C]
13
504
-continued
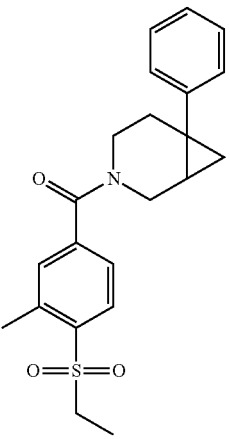 [SMILES: CCS(=O)(=O)c1ccc(C(=O)N2CCC3(c4ccccc4)CC3C2)cc1C]
15
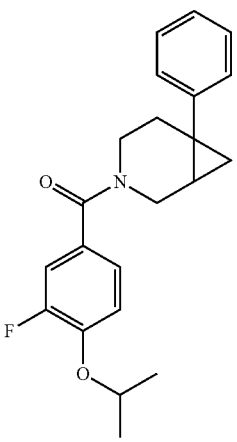 [SMILES: CC(C)Oc1ccc(C(=O)N2CCC3(c4ccccc4)CC3C2)cc1F]
16
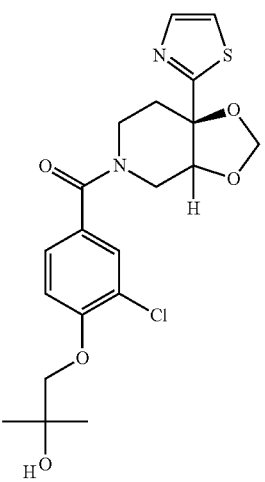
17

| 505 -continued | 506 -continued |
|---|---|
| 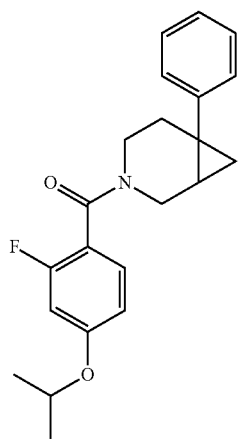 [SMILES: CC(C)Oc1ccc(C(=O)N2CCC3(c4ccccc4)CC3C2)c(F)c1] 19 | 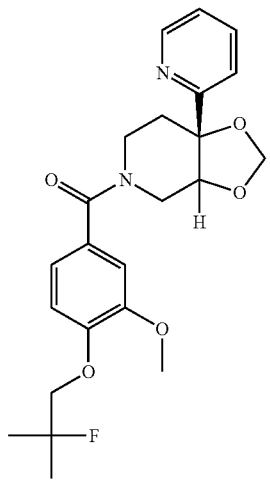 23 |
| 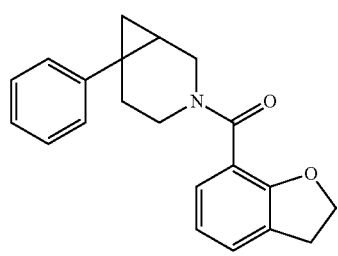 [SMILES: O=C(c1cccc2c1OCC2)N1CCC2(c3ccccc3)CC2C1] 20 | 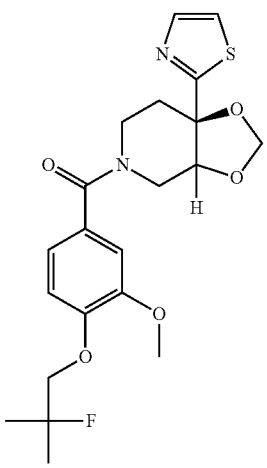 24 |
| 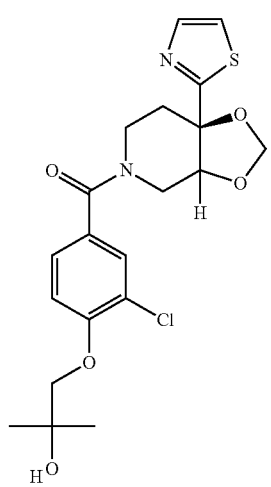 22 | 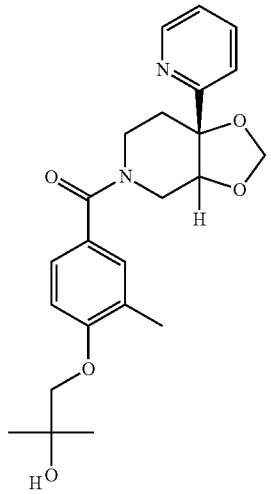 25 |

| 507 -continued | 508 -continued |
|---|---|
| 26 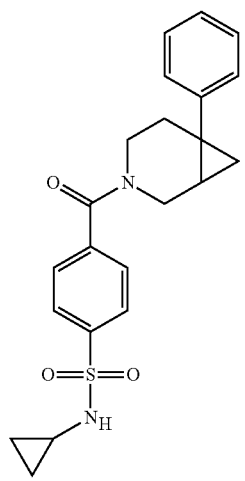 | 29 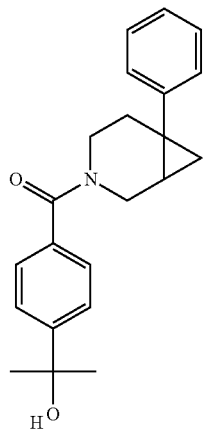 |
| 27 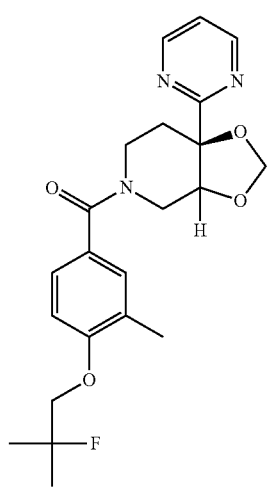 | 30 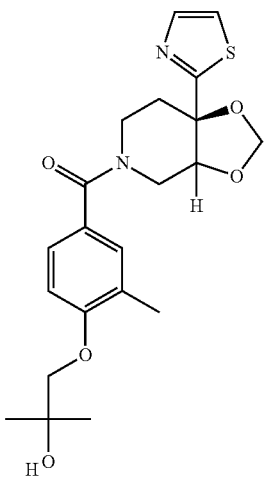 |
| 28 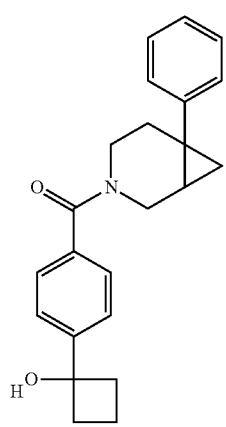 | 31 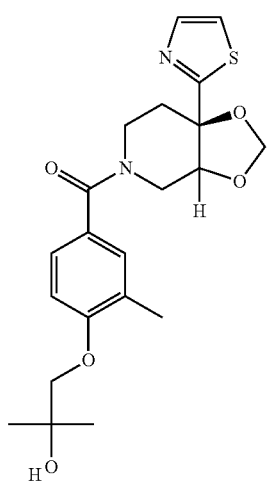 |

| 509 -continued | 510 -continued |
|---|---|
| 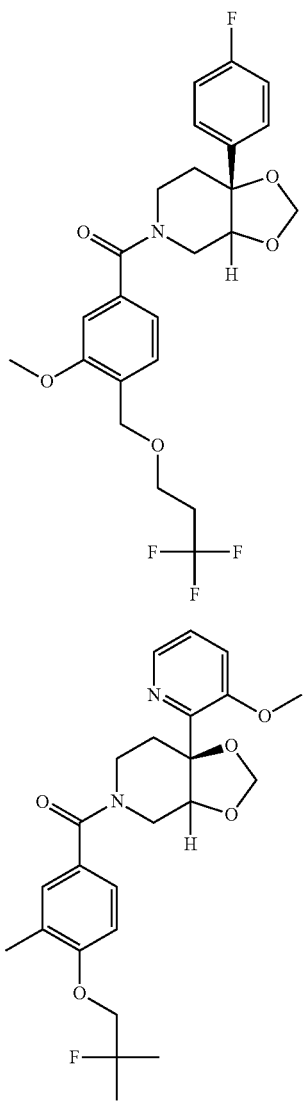 32<br><br>34 | 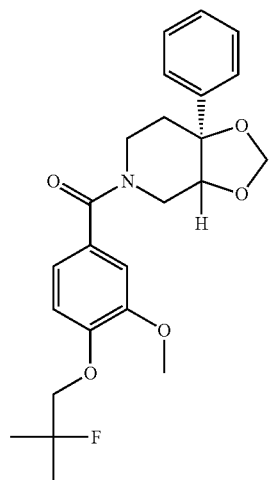 [SMILES: COc1cc(C(=O)N2CC[C@@]3(c4ccccc4)OCOC3C2)ccc1OCC(C)(C)F] 36<br><br>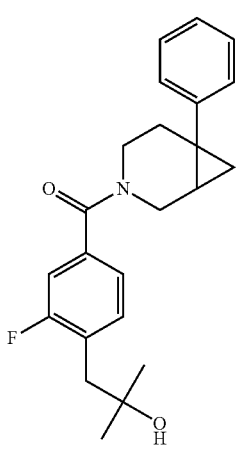 [SMILES: CC(C)(O)Cc1ccc(C(=O)N2CCC3(c4ccccc4)CC3C2)cc1F] 37 |
| 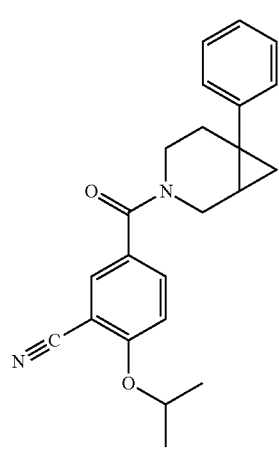 35 | 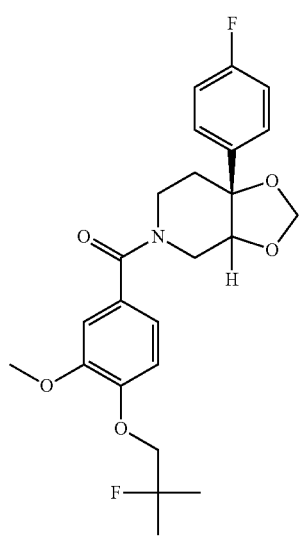 [SMILES: COc1cc(C(=O)N2CC[C@]3(c4ccc(F)cc4)OCOC3C2)ccc1OCC(C)(C)F] 38 |

| 511 -continued | 512 -continued |
|---|---|
| 39 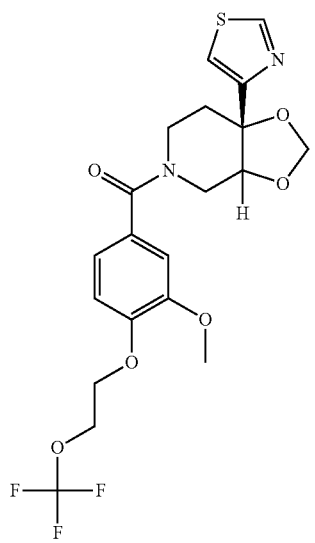 [SMILES: COc1cc(C(=O)N2CC[C@]3(c4cscn4)OCOC3C2)ccc1OCCOC(F)(F)F] | 42 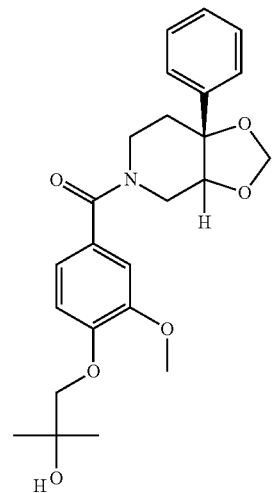 |
| 40 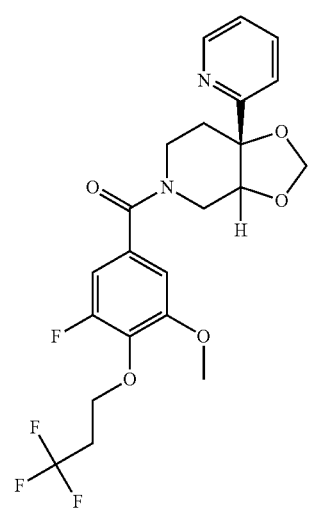 [SMILES: COc1cc(C(=O)N2CC[C@]3(c4ccccn4)OCOC3C2)cc(F)c1OCCC(F)(F)F] | 44 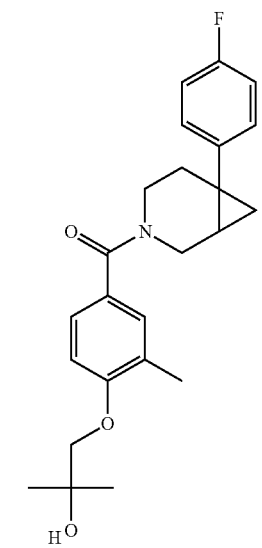 |
| 41 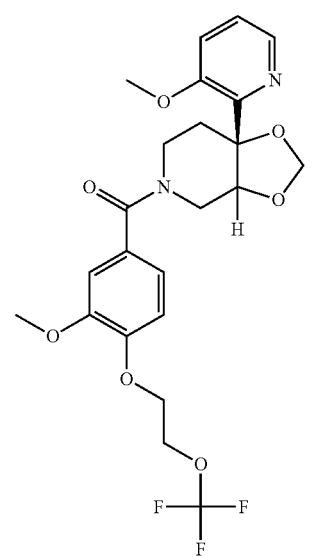 [SMILES: COc1cc(C(=O)N2CC[C@]3(c4ncccc4OC)OCOC3C2)ccc1OCCOC(F)(F)F] | 45 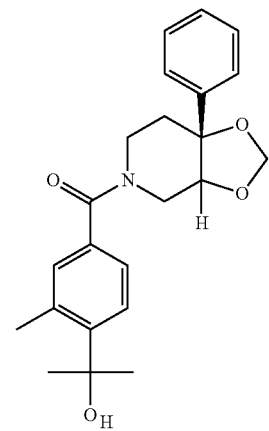 |

| 513 -continued | 514 -continued |
|---|---|
| 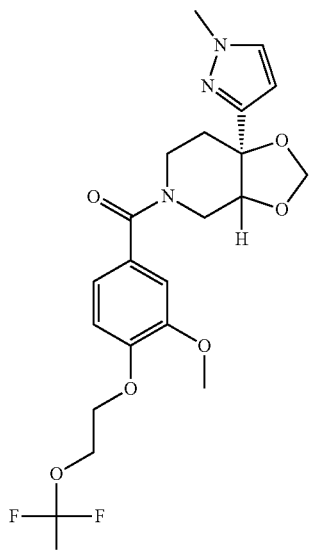 46 | 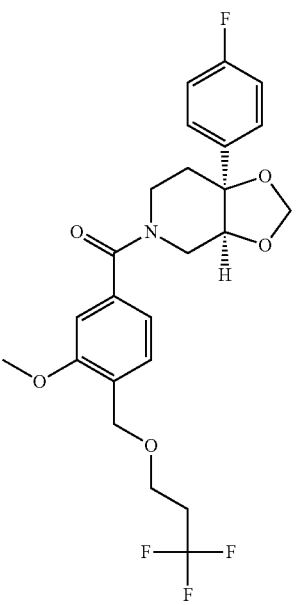 [SMILES: COc1cc(C(=O)N2CC[C@@]3(c4ccc(F)cc4)OCO[C@H]3C2)ccc1COCCC(F)(F)F] 48 |
| | 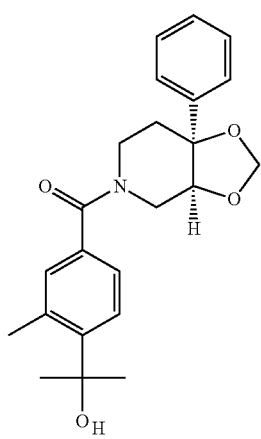 49 |
| 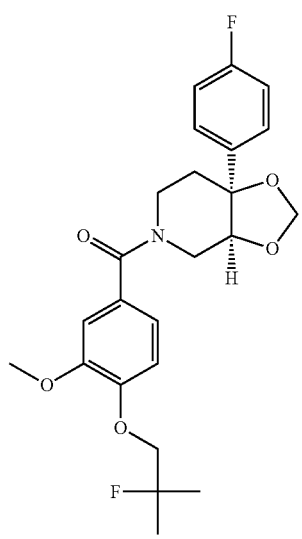 47 | 50 |

515
-continued
| | |
|---|---|
| 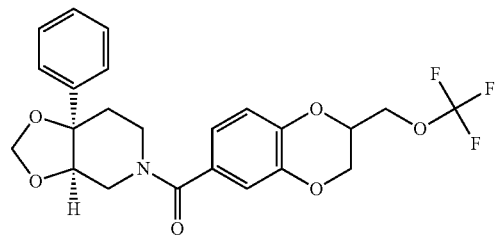 [SMILES: O=C(c1ccc2c(c1)OCC(COC(F)(F)F)O2)N1CC[C@]2(c3ccccc3)OCO[C@@H]2C1] | 51 |
| 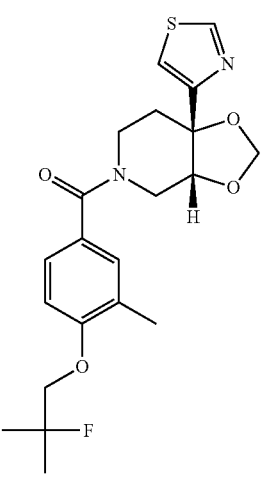 [SMILES: Cc1cc(C(=O)N2CC[C@]3(c4cscn4)OCO[C@@H]3C2)ccc1OCC(C)(C)F] | 52 |
| 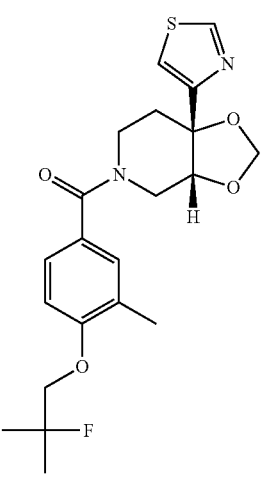 [SMILES: Cc1cc(C(=O)N2CC[C@]3(c4cscn4)OCO[C@@H]3C2)ccc1OCC(C)(C)F] | 53 |
| 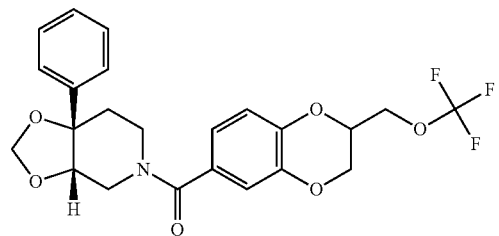 [SMILES: O=C(c1ccc2c(c1)OCC(COC(F)(F)F)O2)N1CC[C@@]2(c3ccccc3)OCO[C@H]2C1] | 54 |
516
-continued
| | |
|---|---|
| 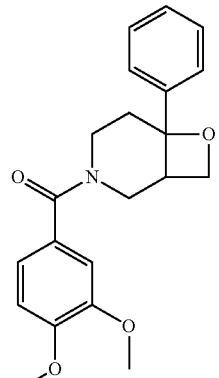 | 55 |
| 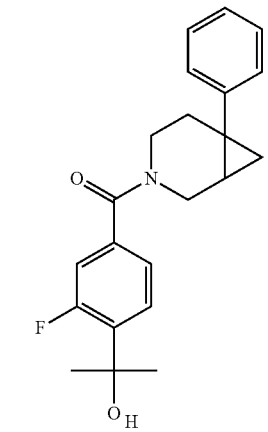 | 57 |
| 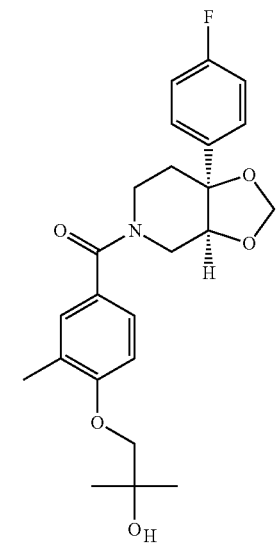 | 58 |

| 517 -continued | 518 -continued |
|---|---|
| 59 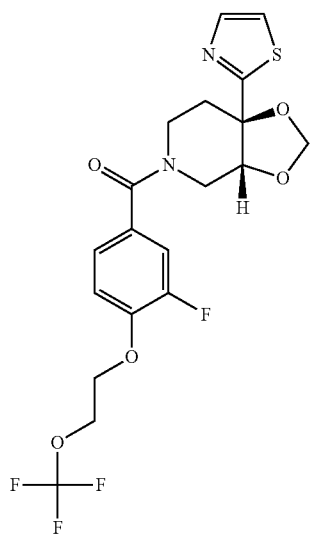 [SMILES: O=C(c1ccc(OCCOC(F)(F)F)c(F)c1)N1CC[C@@]2(c3nccs3)OCO[C@@H]2C1] | 63 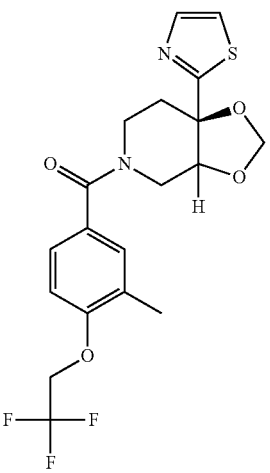 |
| 61 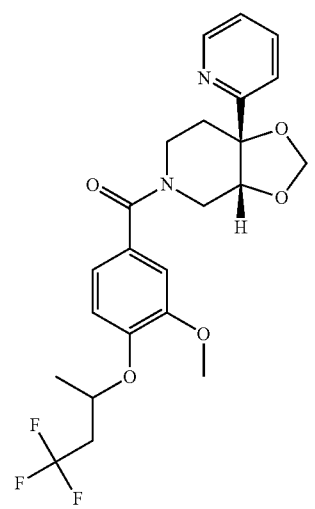 [SMILES: COc1cc(C(=O)N2CC[C@]3(c4ccccn4)OCO[C@@H]3C2)ccc1OC(C)CC(F)(F)F] | 64 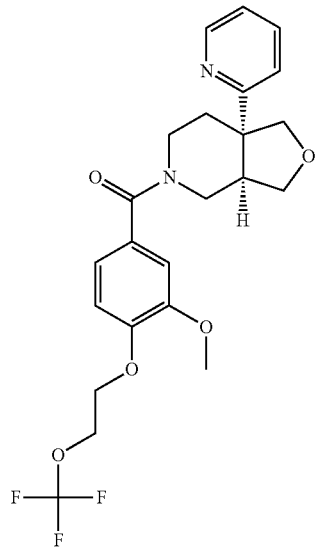 |
| 62 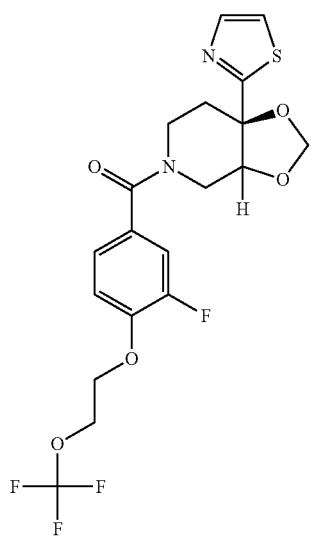 | 65 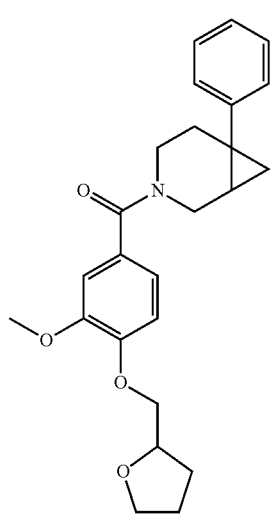 [SMILES: COc1cc(C(=O)N2CCC3(c4ccccc4)CC3C2)ccc1OCC1CCCO1] |

| 66 | 69 |
|---|---|
| 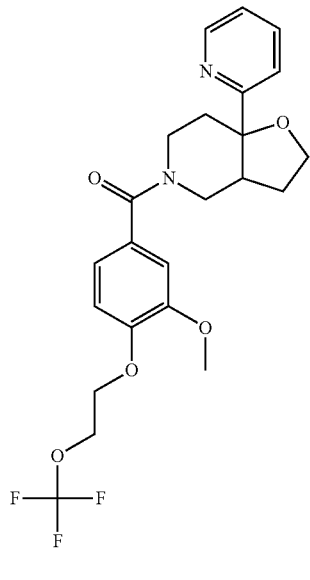 | 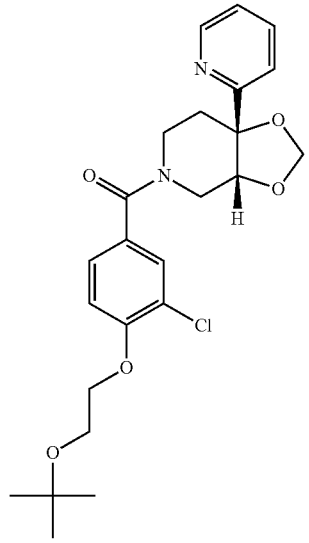 |
| | 70 |
|---|---|
| | 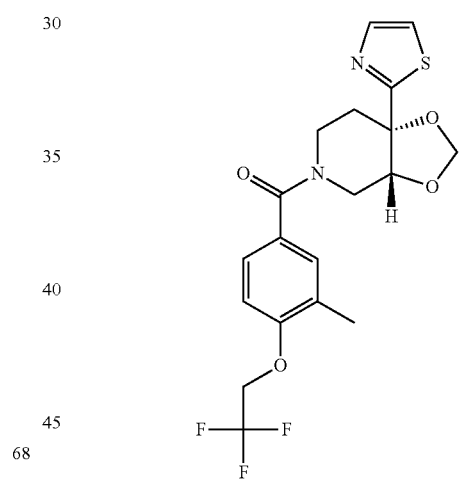 |
| 68 | 71 |
|---|---|
| 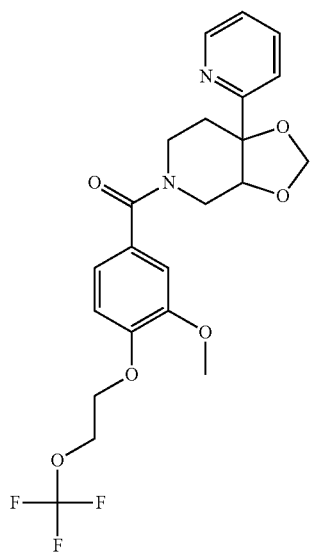 [SMILES: COc1cc(C(=O)N2CCC3(c4ccccn4)OCOC3C2)ccc1OCCOC(F)(F)F] | 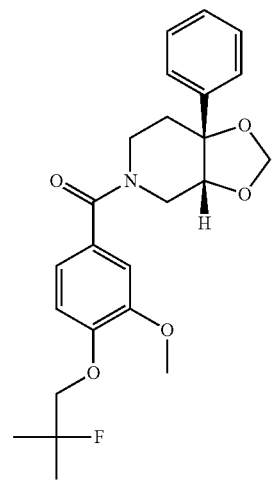 [SMILES: COc1cc(C(=O)N2CC[C@]3(c4ccccc4)OCO[C@@H]3C2)ccc1OCC(C)(C)F] |

| 521 -continued | 522 -continued |
|---|---|
| 72 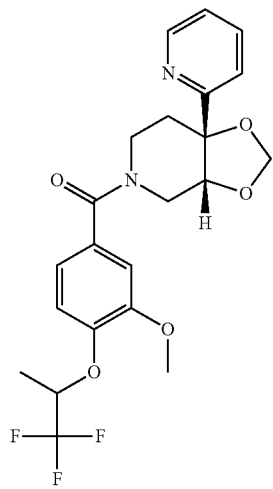 [SMILES: COc1cc(C(=O)N2CC[C@]3(c4ccccn4)OCO[C@@H]3C2)ccc1OC(C)C(F)(F)F] | 75 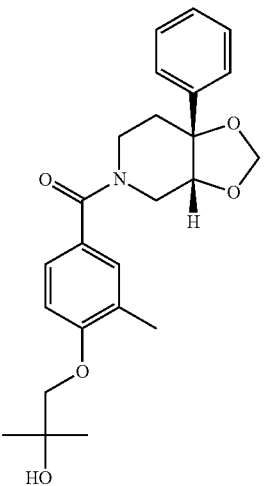 |
| 73 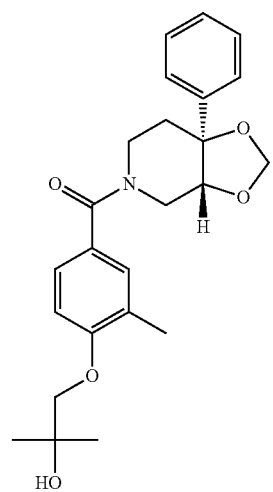 [SMILES: Cc1cc(C(=O)N2CC[C@@]3(c4ccccc4)OCO[C@@H]3C2)ccc1OCC(C)(C)O] | 77 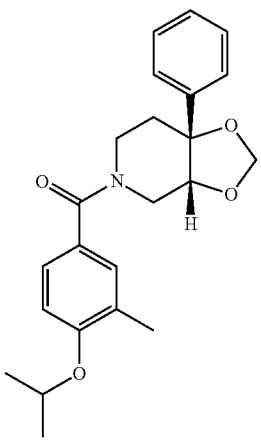 |
| 74 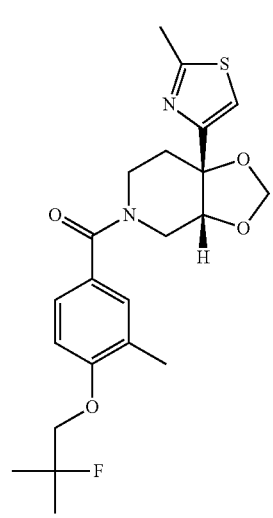 [SMILES: Cc1nc([C@]23CCN(C(=O)c4ccc(OCC(C)(C)F)c(C)c4)C[C@H]2OCO3)cs1] | 78 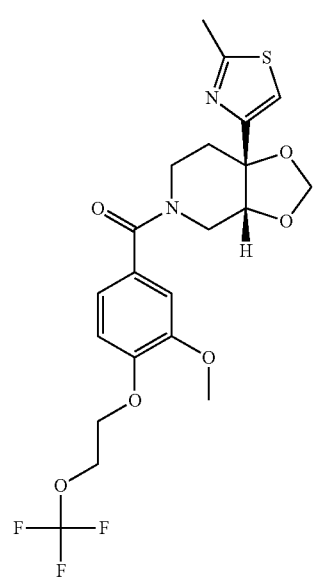 [SMILES: COc1cc(C(=O)N2CC[C@]3(c4csc(C)n4)OCO[C@@H]3C2)ccc1OCCOC(F)(F)F] |

523
-continued
524
-continued
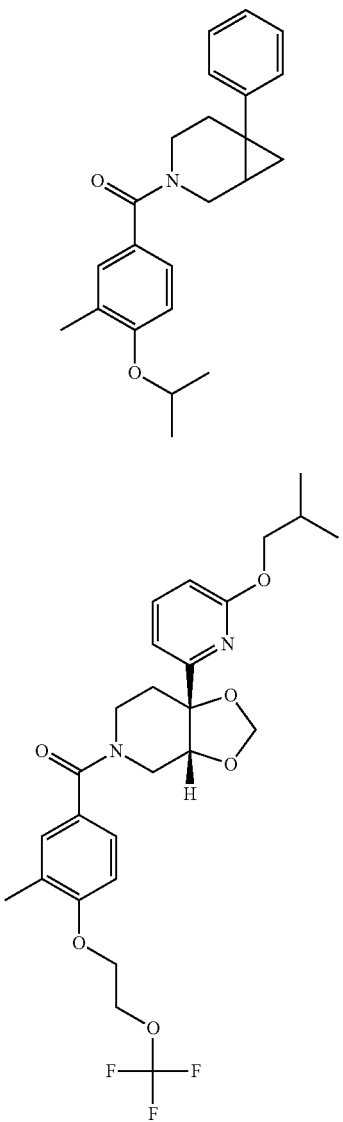
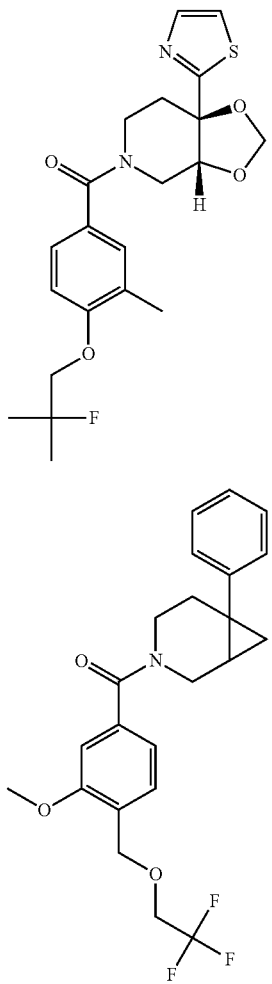

| 525 -continued | 526 -continued |
|---|---|
| 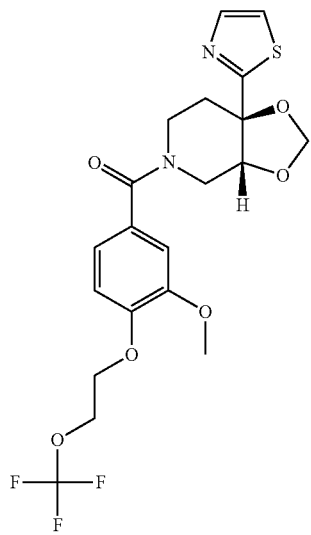 [SMILES: COc1cc(C(=O)N2CC[C@@]3(c4nccs4)OCO[C@@H]3C2)ccc1OCCOC(F)(F)F] 85 | 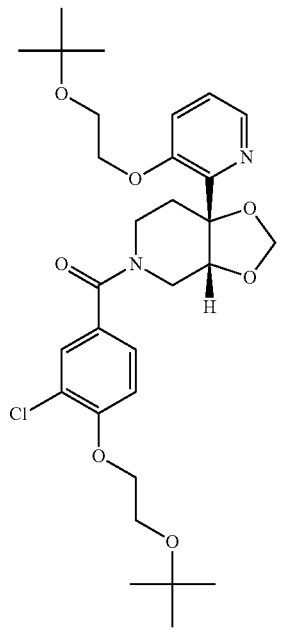 87 |
| 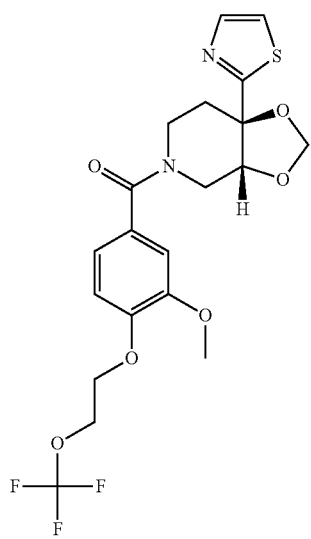 [SMILES: COc1cc(C(=O)N2CC[C@@]3(c4nccs4)OCO[C@@H]3C2)ccc1OCCOC(F)(F)F] 86 | 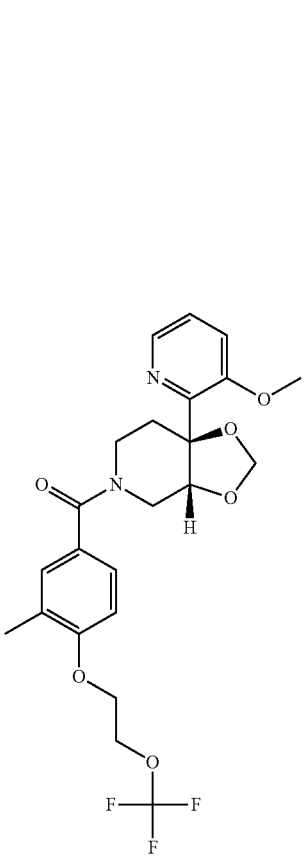 89 |

| 527 -continued | 528 -continued |
|---|---|
| 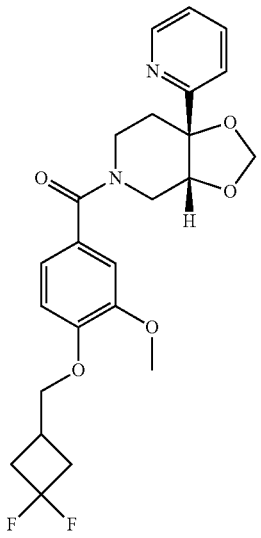 [SMILES: COc1cc(C(=O)N2CC[C@]3(c4ccccn4)OCO[C@@H]3C2)ccc1OCC1CC(F)(F)C1] 90 | 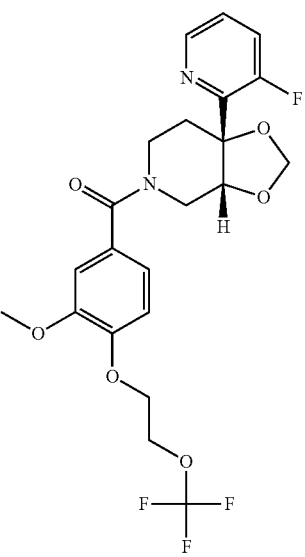 93 |
| 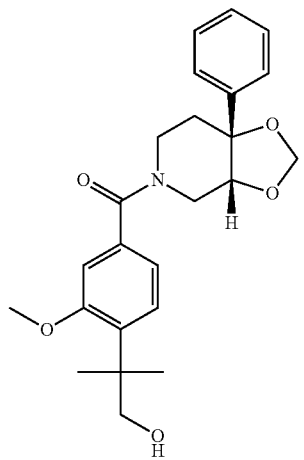 [SMILES: COc1cc(C(=O)N2CC[C@]3(c4ccccc4)OCO[C@@H]3C2)ccc1C(C)(C)CO] 91 | 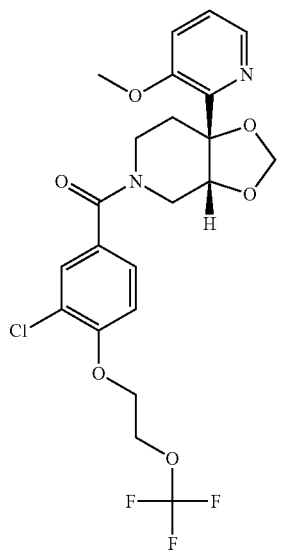 94 |
| 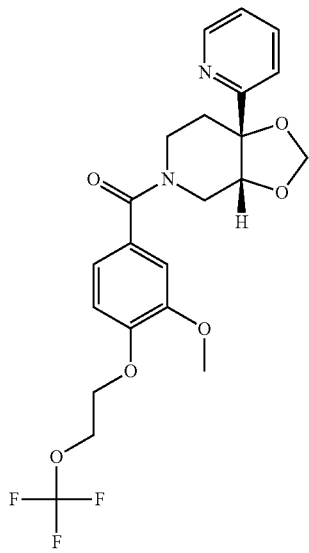 [SMILES: COc1cc(C(=O)N2CC[C@]3(c4ccccn4)OCO[C@@H]3C2)ccc1OCCOC(F)(F)F] 92 | 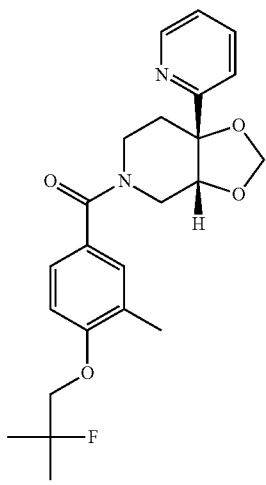 [SMILES: Cc1cc(C(=O)N2CC[C@]3(c4ccccn4)OCO[C@@H]3C2)ccc1OCC(C)(C)F] 95 |

| 97 | 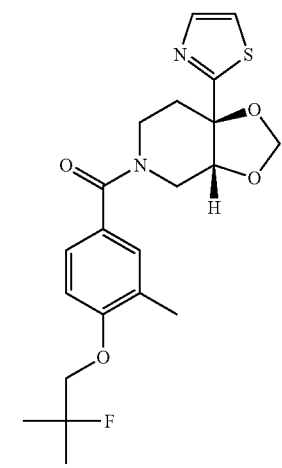 [SMILES: Cc1cc(C(=O)N2CC[C@@]3(c4nccs4)OCO[C@@H]3C2)ccc1OCC(C)(C)F] | 100 | 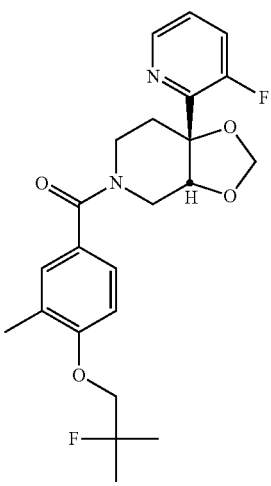 |
| --- | --- | --- | --- |
| 98 | 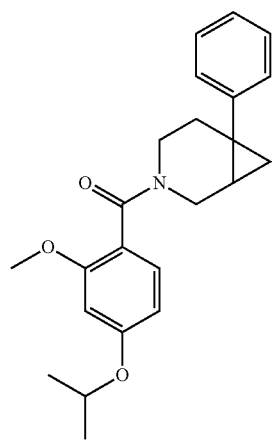 [SMILES: COc1cc(OC(C)C)ccc1C(=O)N1CCC2(c3ccccc3)CC2C1] | 101 | 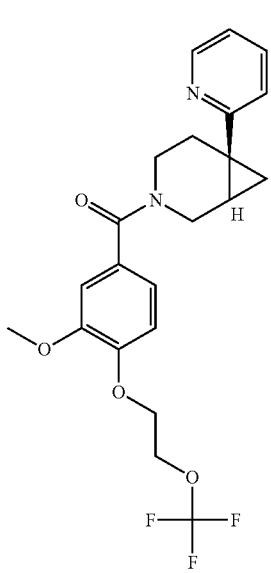 |
| 99 | 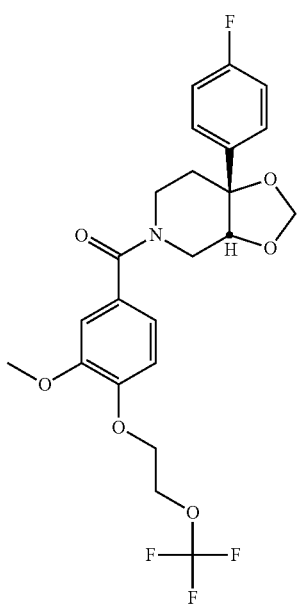 | 102 | 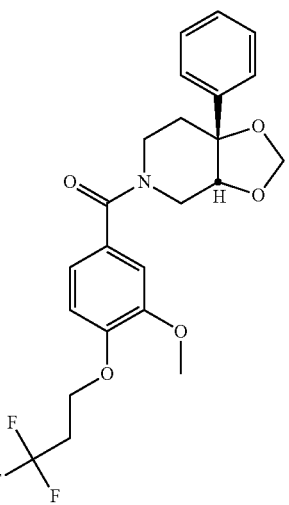 |

| 531 -continued | 532 -continued |
|---|---|
| 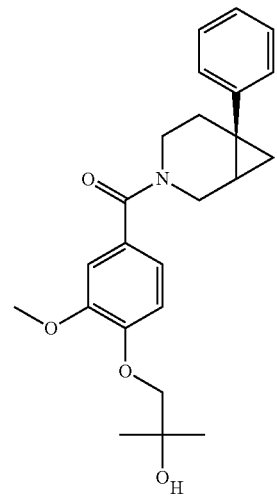 104 | 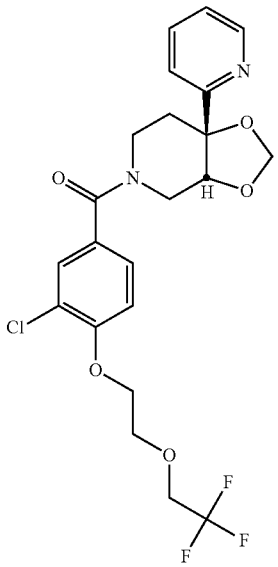 108 |
| 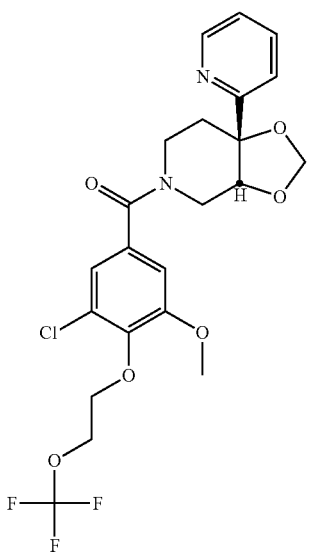 105 | 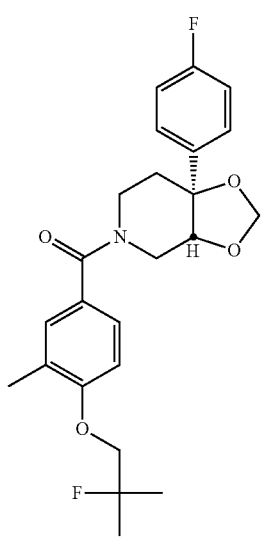 109 |
| 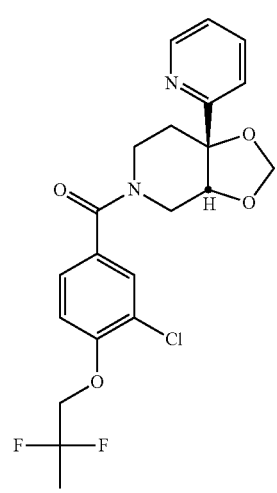 106 | 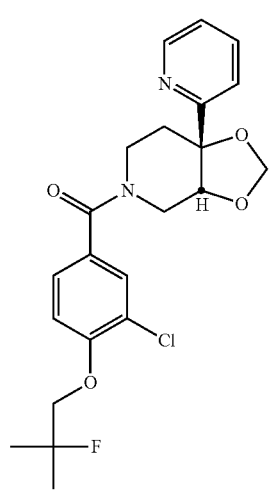 110 |

| 533 -continued | 534 -continued |
|---|---|
| 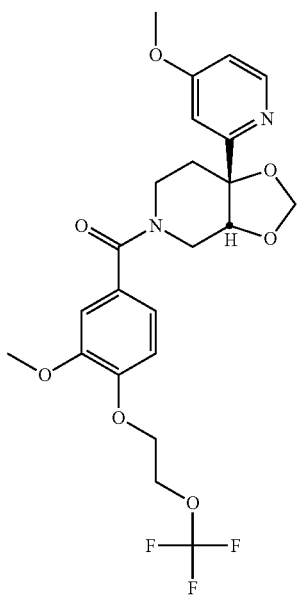 112 | 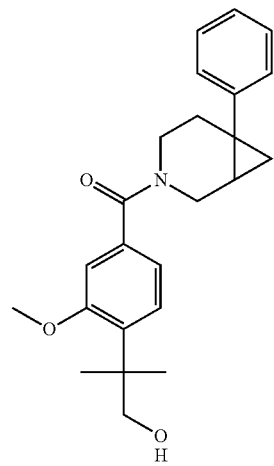 115 |
| 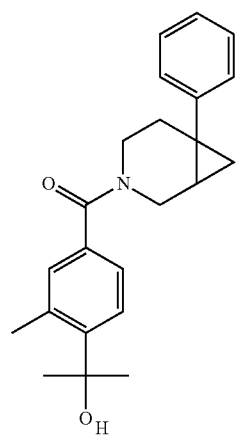 113 | 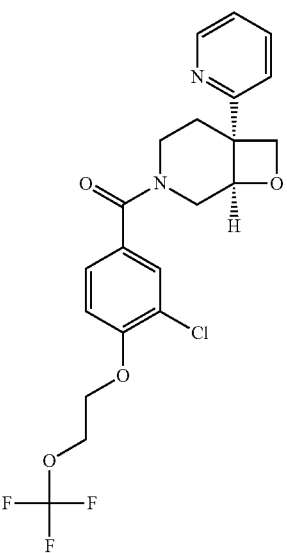 116 |
| 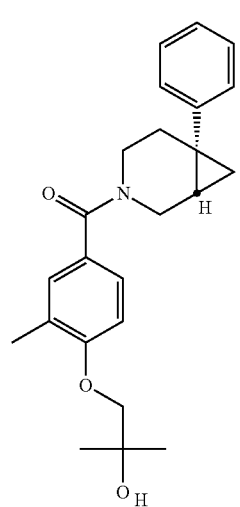 114 | 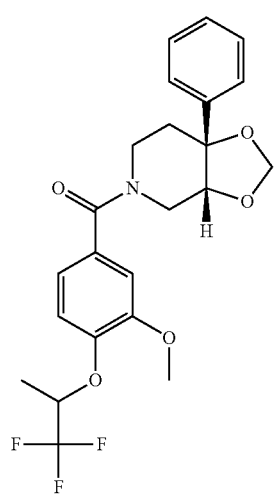 [SMILES: COc1cc(C(=O)N2CC[C@]3(c4ccccc4)OCO[C@@H]3C2)ccc1OC(C)C(F)(F)F] 117 |

| 535 -continued | | 536 -continued | |
|---|---|---|---|
| 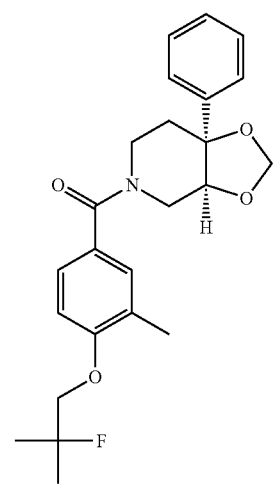 [SMILES: Cc1cc(C(=O)N2CC[C@@]3(c4ccccc4)OCO[C@H]3C2)ccc1OCC(C)(C)F] | 120 | 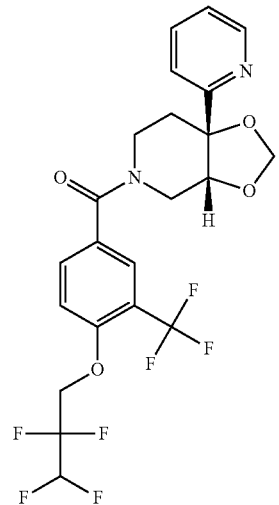 [SMILES: O=C(c1ccc(OCC(F)(F)C(F)F)c(C(F)(F)F)c1)N1CC[C@]2(c3ccccn3)OCO[C@@H]2C1] | 123 |
| 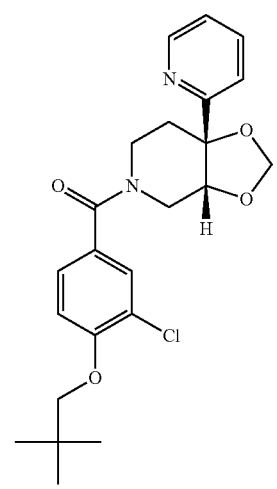 | 121 | 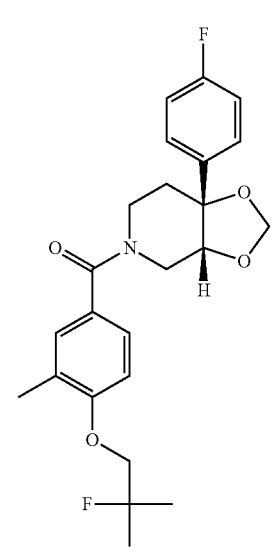 [SMILES: Cc1cc(C(=O)N2CC[C@]3(c4ccc(F)cc4)OCO[C@@H]3C2)ccc1OCC(C)(C)F] | 124 |
| 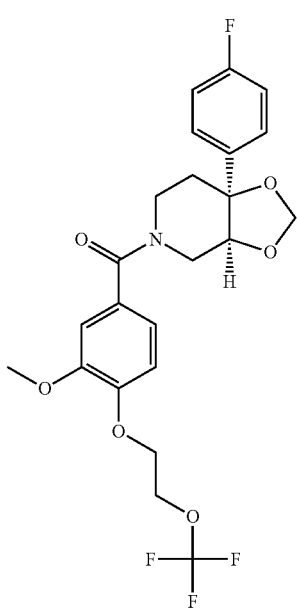 | 122 | 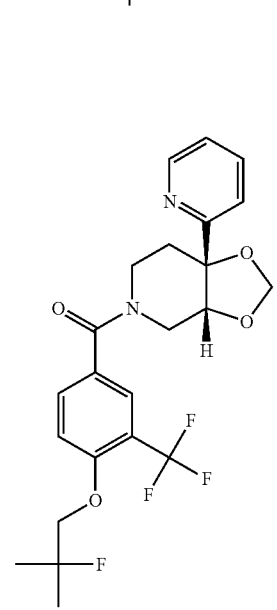 | 127 |

537
-continued
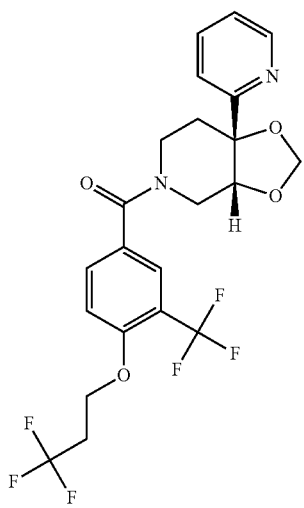 [SMILES: O=C(c1ccc(OCCC(F)(F)F)c(C(F)(F)F)c1)N1CC[C@]2(c3ccccn3)OCO[C@@H]2C1]
128
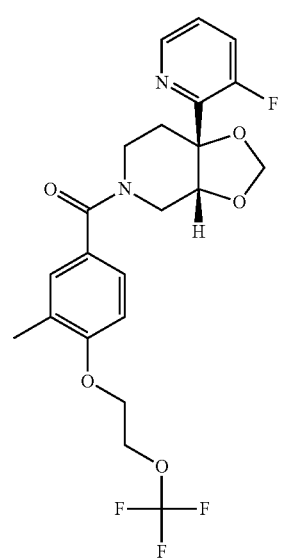 [SMILES: Cc1cc(C(=O)N2CC[C@]3(c4ncccc4F)OCO[C@@H]3C2)ccc1OCCOC(F)(F)F]
129
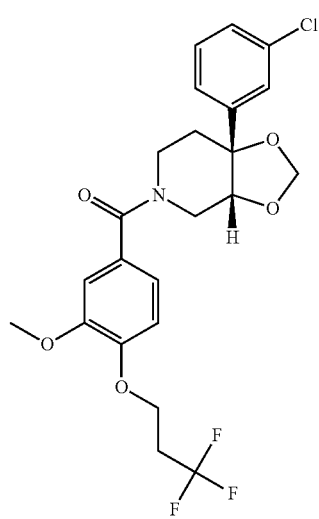 [SMILES: COc1cc(C(=O)N2CC[C@]3(c4cccc(Cl)c4)OCO[C@@H]3C2)ccc1OCCC(F)(F)F]
131
538
-continued
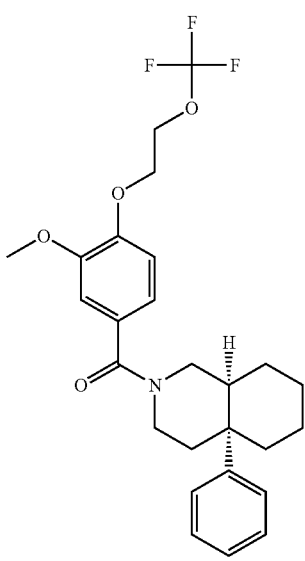 [SMILES: COc1cc(C(=O)N2CC[C@]3(c4ccccc4)CCCC[C@@H]3C2)ccc1OCCOC(F)(F)F]
132
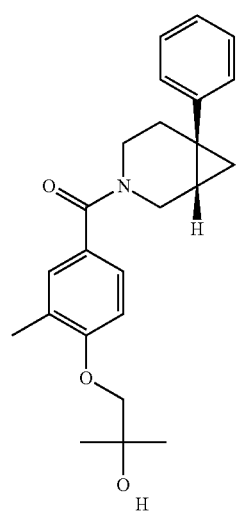
133
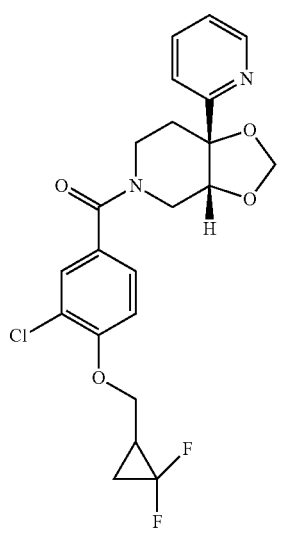 [SMILES: O=C(c1ccc(OCC2CC2(F)F)c(Cl)c1)N1CC[C@]2(c3ccccn3)OCO[C@@H]2C1]
135

| 539 -continued | 540 -continued |
|---|---|
| 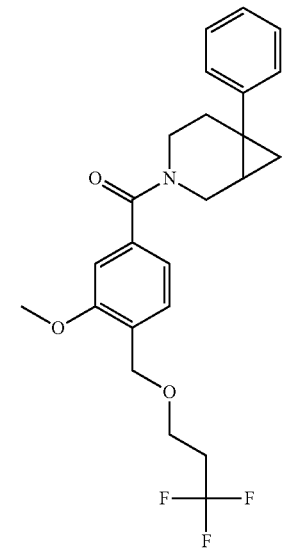 136 | 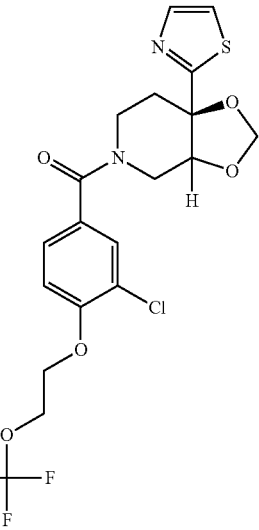 140 |
| 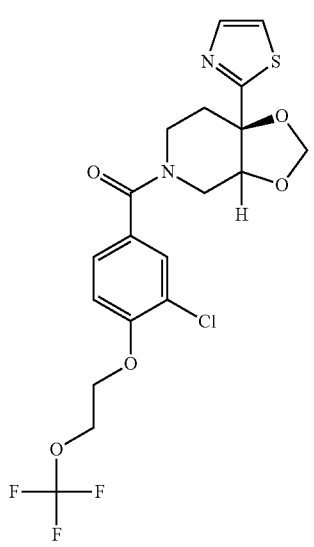 138 | 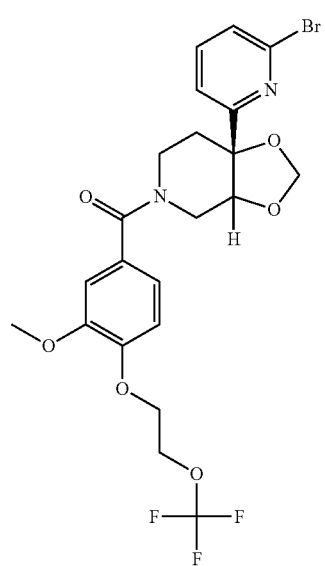 141 |
| 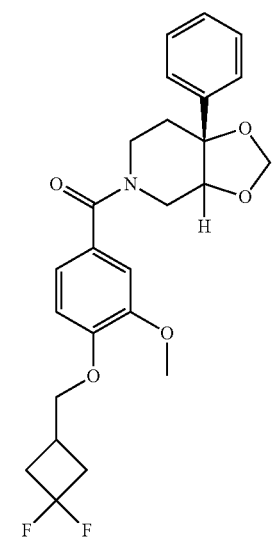 [SMILES: COc1cc(C(=O)N2CC[C@]3(c4ccccc4)OCOC3C2)ccc1OCC1CC(F)(F)C1] 139 | 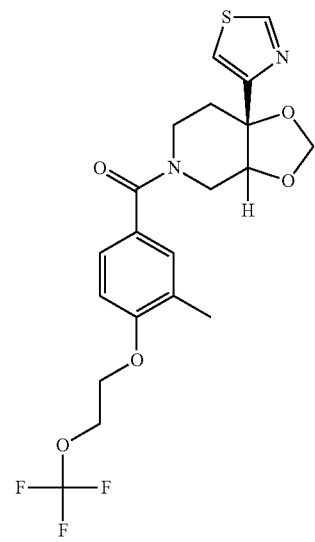 [SMILES: Cc1cc(C(=O)N2CC[C@]3(c4cscn4)OCOC3C2)ccc1OCCOC(F)(F)F] 142 |

541
-continued
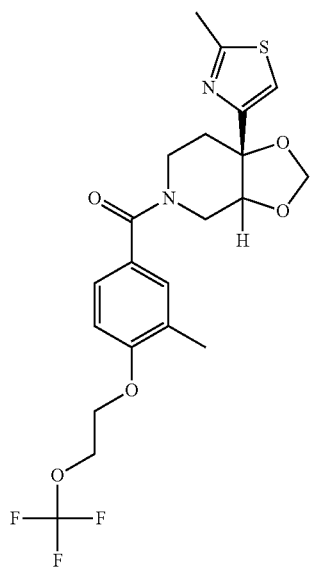 [SMILES: Cc1nc([C@]23CCN(C(=O)c4ccc(OCCOC(F)(F)F)c(C)c4)CC2OCO3)cs1]
144
145
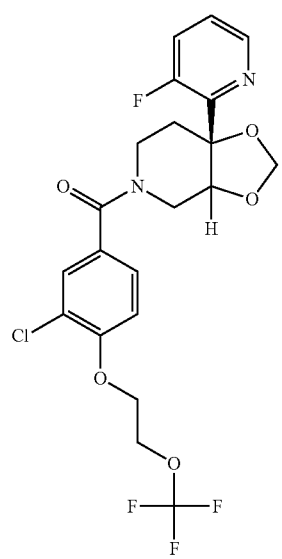 [SMILES: O=C(c1ccc(OCCOC(F)(F)F)c(Cl)c1)N1CC[C@]2(c3ncccc3F)OCOC2C1]
542
-continued
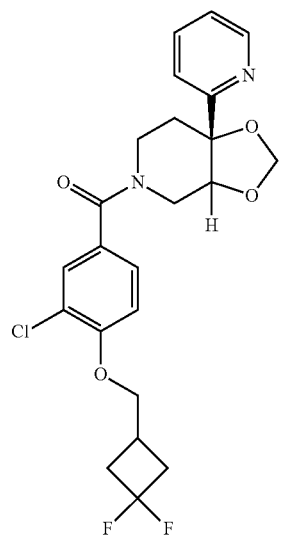 [SMILES: O=C(c1ccc(OCC2CC(F)(F)C2)c(Cl)c1)N1CC[C@]2(c3ccccn3)OCOC2C1]
146
147
148
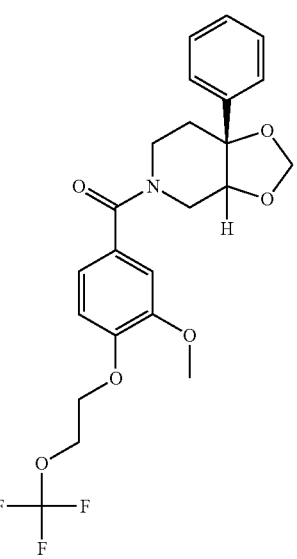

| 543 -continued | 544 -continued |
|---|---|
| 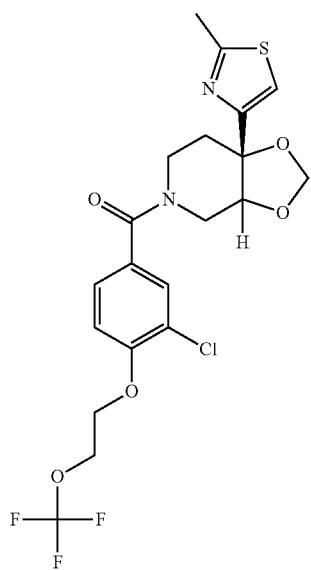 [SMILES: Cc1nc([C@]23CCN(C(=O)c4ccc(OCCOC(F)(F)F)c(Cl)c4)CC2OCO3)cs1] 149 | 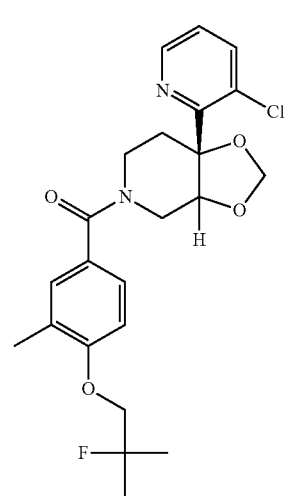 152 |
| 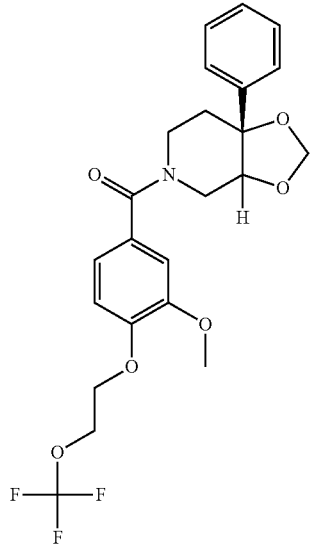 [SMILES: COc1cc(C(=O)N2CC[C@]3(c4ccccc4)OCOC3C2)ccc1OCCOC(F)(F)F] 150 | 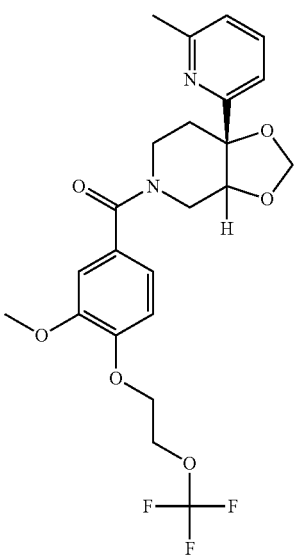 154 |
| 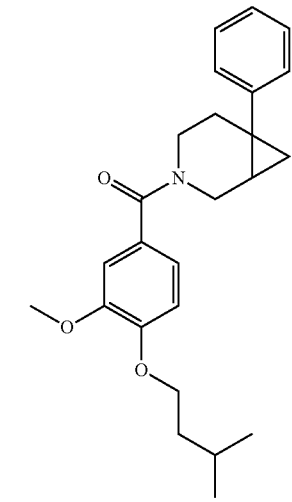 [SMILES: COc1cc(C(=O)N2CCC3(c4ccccc4)CC3C2)ccc1OCCC(C)C] 151 | 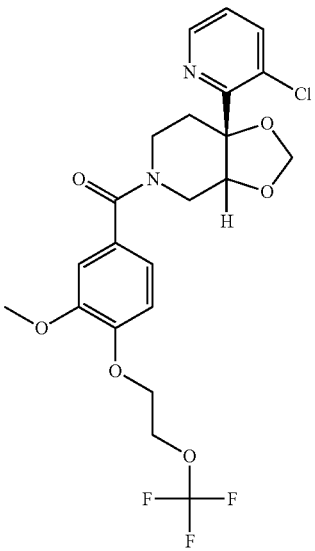 [SMILES: COc1cc(C(=O)N2CC[C@]3(c4ncccc4Cl)OCOC3C2)ccc1OCCOC(F)(F)F] 155 |

| 545 -continued | 546 -continued |
|---|---|
| 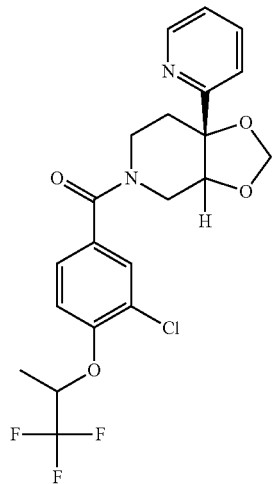 [SMILES: CC(Oc1ccc(C(=O)N2CC[C@]3(c4ccccn4)OCOC3C2)cc1Cl)C(F)(F)F] 156 | 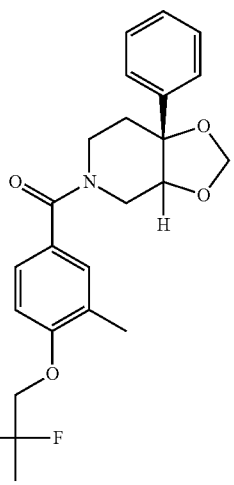 161 |
| 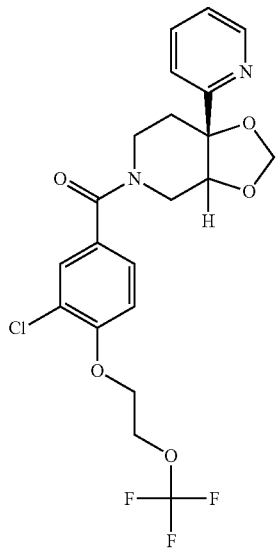 [SMILES: O=C(c1ccc(OCCOC(F)(F)F)c(Cl)c1)N1CC[C@]2(c3ccccn3)OCOC2C1] 157 | 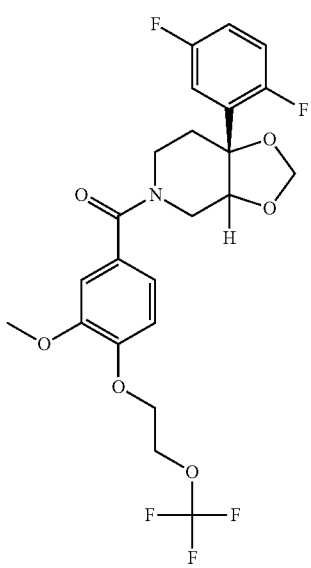 163 |
| 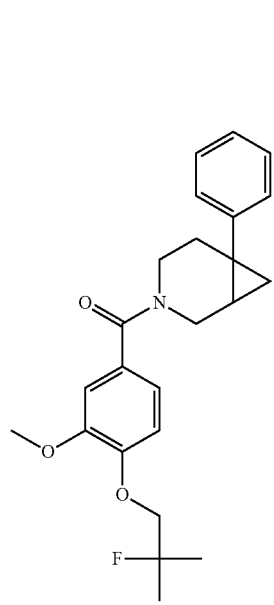 [SMILES: COc1cc(C(=O)N2CCC3(c4ccccc4)CC3C2)ccc1OCC(C)(C)F] 158 | 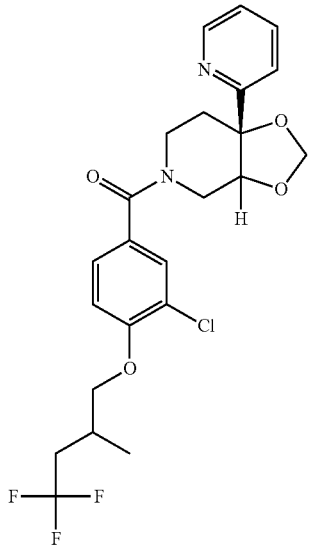 [SMILES: CC(COc1ccc(C(=O)N2CC[C@]3(c4ccccn4)OCOC3C2)cc1Cl)CC(F)(F)F] 164 |

| 547 -continued | 548 -continued |
|---|---|
| 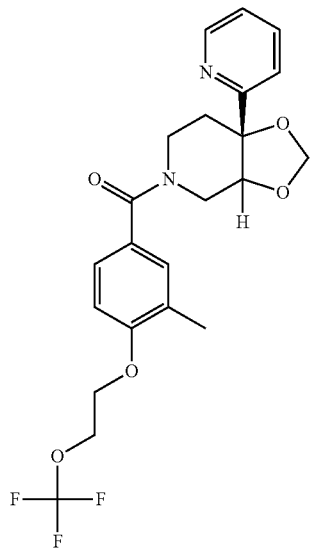 [SMILES: Cc1cc(C(=O)N2CC[C@]3(c4ccccn4)OCOC3C2)ccc1OCCOC(F)(F)F] 165 | 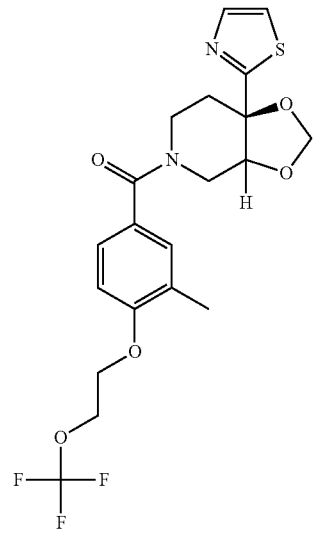 168 |
| 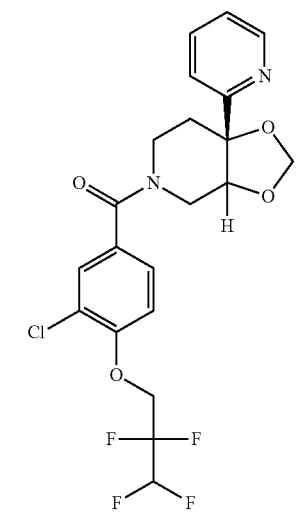 [SMILES: O=C(c1ccc(OCC(F)(F)C(F)F)c(Cl)c1)N1CC[C@]2(c3ccccn3)OCOC2C1] 166 | 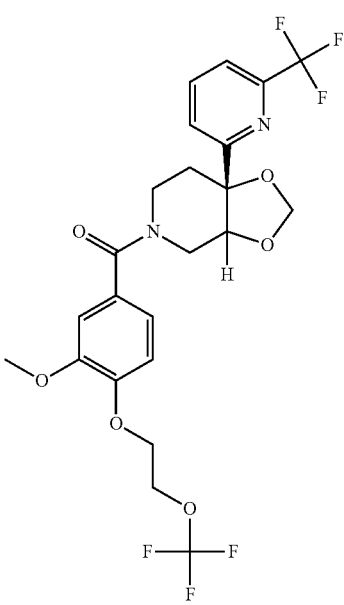 169 |
| 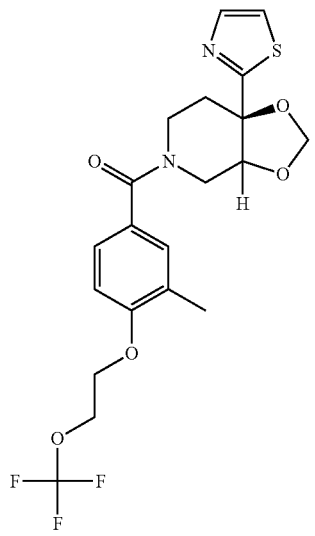 167 | 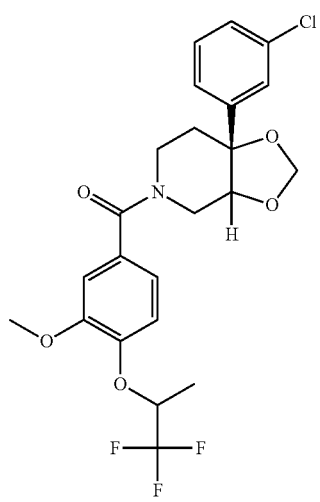 [SMILES: COc1cc(C(=O)N2CC[C@]3(c4cccc(Cl)c4)OCOC3C2)ccc1OC(C)C(F)(F)F] 170 |

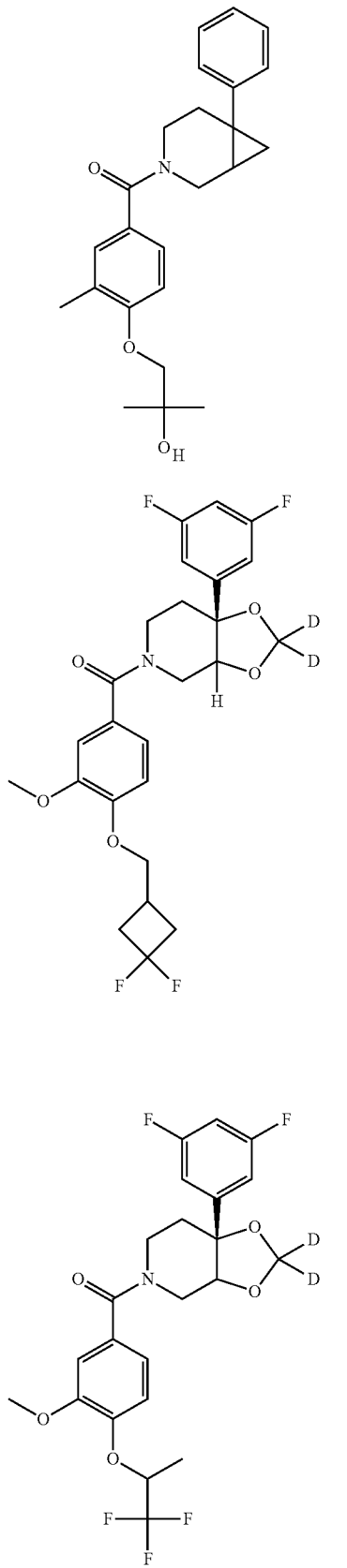

551
-continued
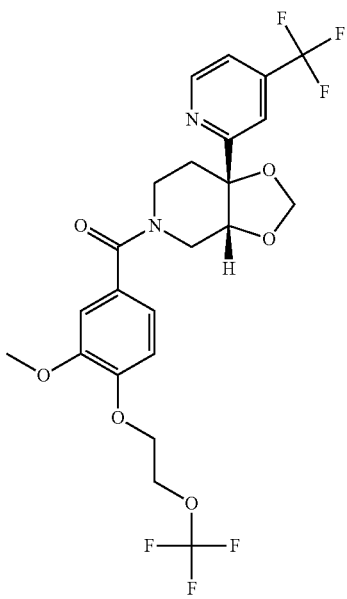 [SMILES: COc1cc(C(=O)N2CC[C@]3(c4cc(C(F)(F)F)ccn4)OCO[C@@H]3C2)ccc1OCCOC(F)(F)F]
179
181
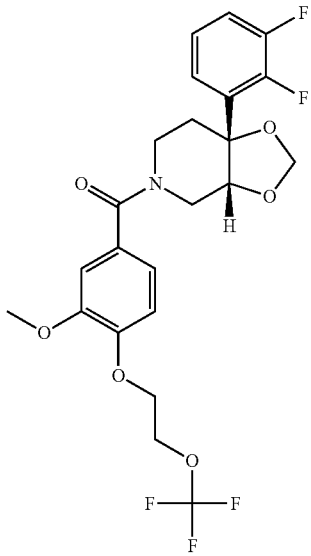
552
-continued
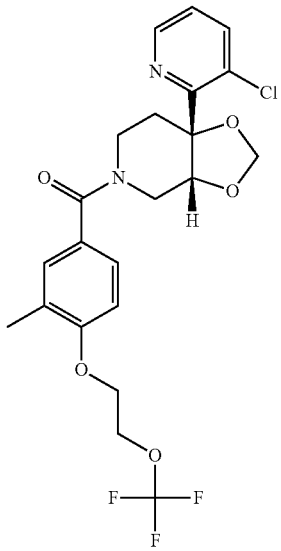 [SMILES: Cc1cc(C(=O)N2CC[C@]3(c4ncccc4Cl)OCO[C@@H]3C2)ccc1OCCOC(F)(F)F]
182
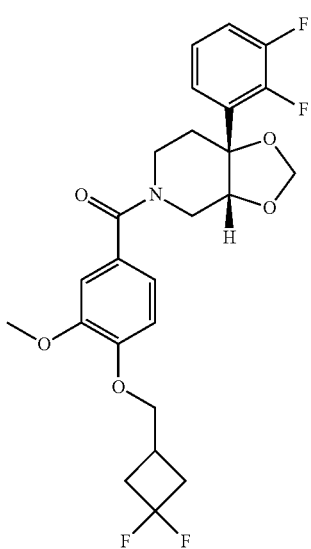 [SMILES: COc1cc(C(=O)N2CC[C@]3(c4cccc(F)c4F)OCO[C@@H]3C2)ccc1OCC1CC(F)(F)C1]
184
186

553
-continued
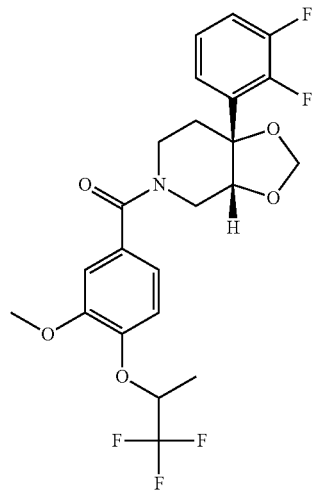 [SMILES: COc1cc(C(=O)N2CC[C@]3(c4cccc(F)c4F)OCO[C@@H]3C2)ccc1OC(C)C(F)(F)F]
187
190
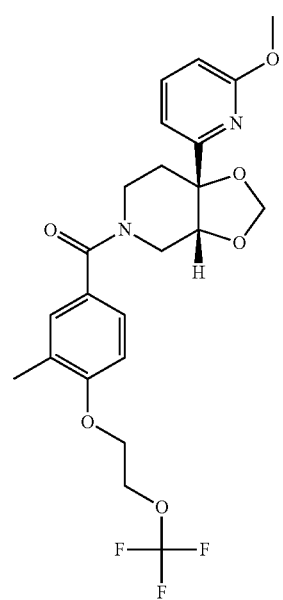
554
-continued
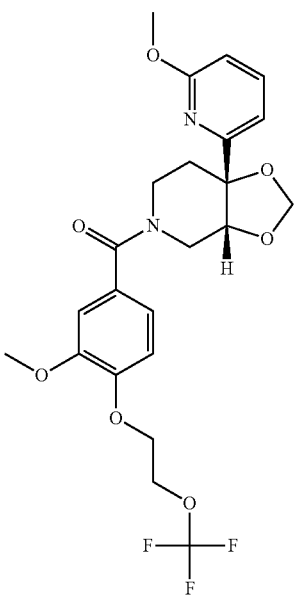 [SMILES: COc1cccc([C@]23CCN(C(=O)c4ccc(OCCOC(F)(F)F)c(OC)c4)C[C@H]2OCO3)n1]
192
193
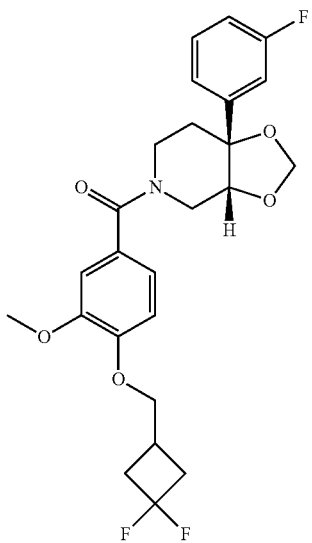 [SMILES: COc1cc(C(=O)N2CC[C@]3(c4cccc(F)c4)OCO[C@@H]3C2)ccc1OCC1CC(F)(F)C1]

| 555 -continued | | 556 -continued | |
|---|---|---|---|
| 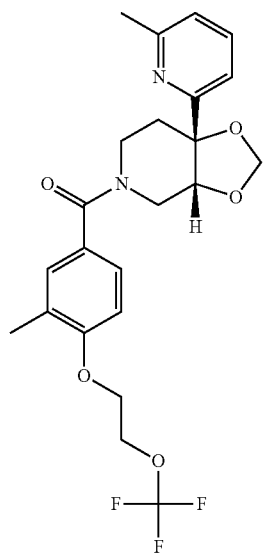 [SMILES: Cc1cccc([C@]23CCN(C(=O)c4ccc(OCCOC(F)(F)F)c(C)c4)C[C@H]2OCO3)n1] | 194 | 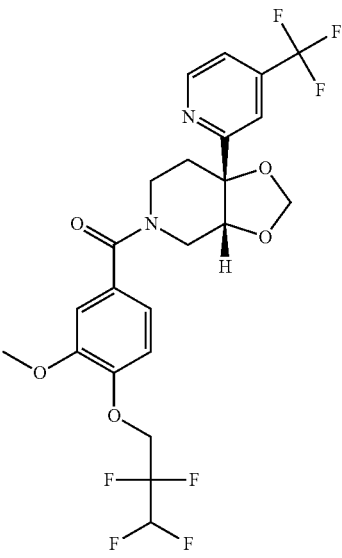 [SMILES: COc1cc(C(=O)N2CC[C@]3(c4cc(C(F)(F)F)ccn4)OCO[C@@H]3C2)ccc1OCC(F)(F)C(F)F] | 197 |
| | | 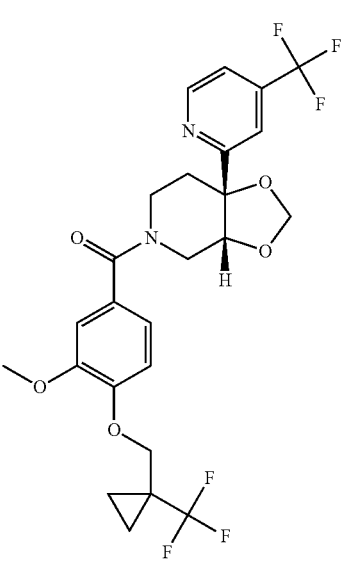 [SMILES: COc1cc(C(=O)N2CC[C@]3(c4cc(C(F)(F)F)ccn4)OCO[C@@H]3C2)ccc1OCC1(C(F)(F)F)CC1] | 198 |
| 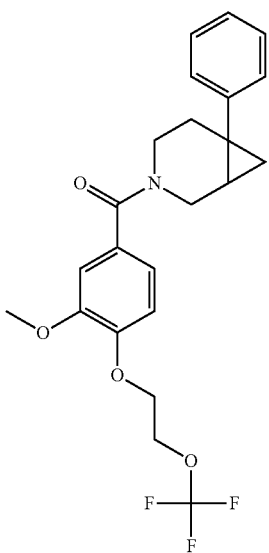 | 195 | 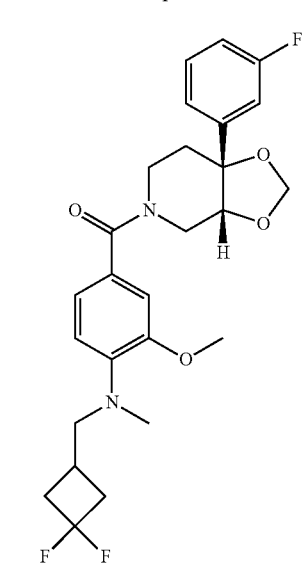 | 199 |

| 557 -continued | 558 -continued |
|---|---|
| 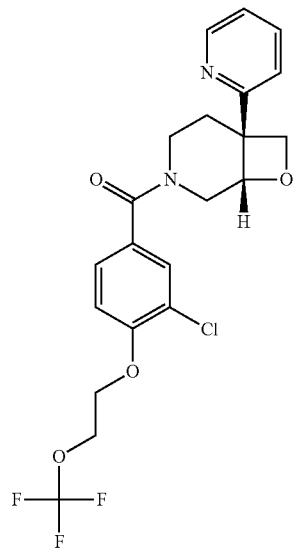 [SMILES: O=C(c1ccc(OCCOC(F)(F)F)c(Cl)c1)N1CC[C@]2(c3ccccn3)CO[C@@H]2C1] 201 | 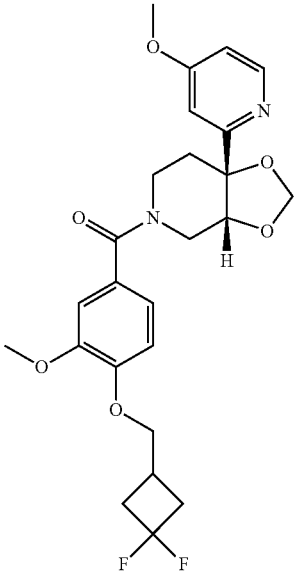 [SMILES: COc1ccnc([C@]23CCN(C(=O)c4ccc(OCC5CC(F)(F)C5)c(OC)c4)C[C@H]2OCO3)c1] 203 |
| 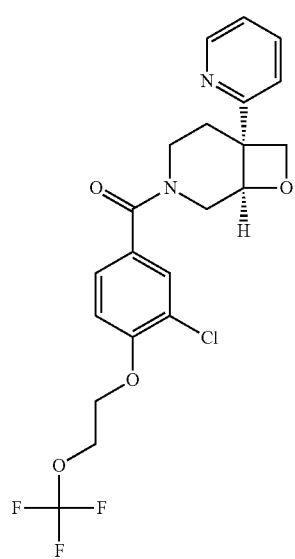 202 | 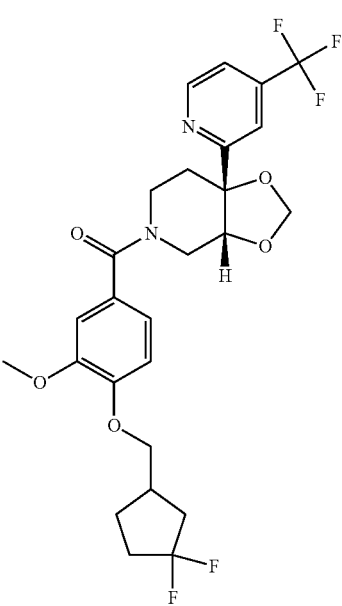 [SMILES: COc1cc(C(=O)N2CC[C@]3(c4cc(C(F)(F)F)ccn4)OCO[C@@H]3C2)ccc1OCC1CCC(F)(F)C1] 204 |

| 559 -continued | 560 -continued |
|---|---|
| 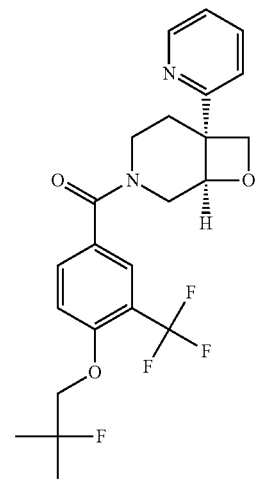 [SMILES: CC(C)(F)COc1ccc(C(=O)N2CC[C@@]3(c4ccccn4)CO[C@H]3C2)cc1C(F)(F)F] 205 | 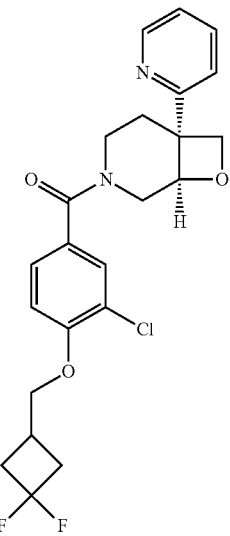 208 |
| 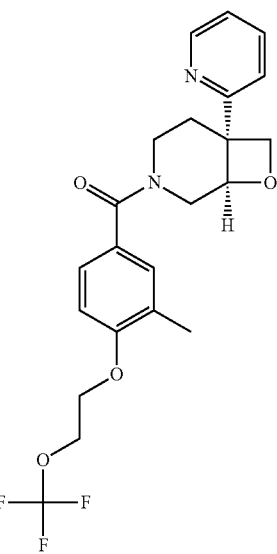 206 | 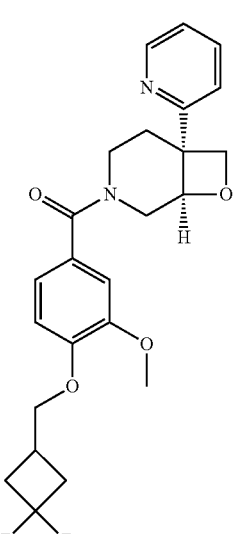 210 |
| 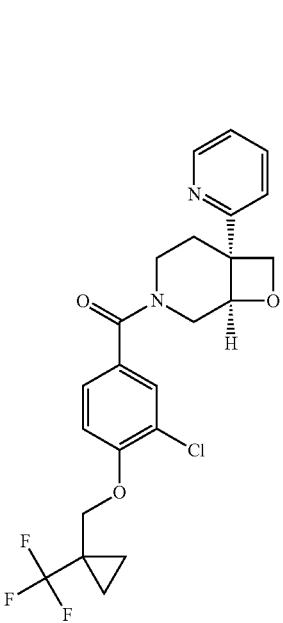 [SMILES: O=C(c1ccc(OCC2(C(F)(F)F)CC2)c(Cl)c1)N1CC[C@@]2(c3ccccn3)CO[C@H]2C1] 207 | 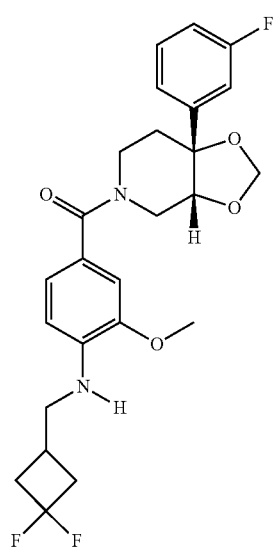 [SMILES: COc1cc(C(=O)N2CC[C@]3(c4cccc(F)c4)OCO[C@@H]3C2)ccc1NCC1CC(F)(F)C1] 211 |

| 561 -continued | 562 -continued |
|---|---|
| 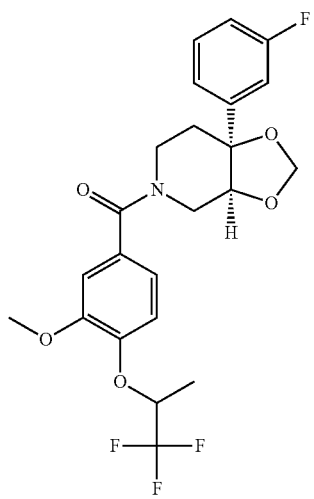 [SMILES: COc1cc(C(=O)N2CC[C@@]3(c4cccc(F)c4)OCO[C@H]3C2)ccc1OC(C)C(F)(F)F] 212 | 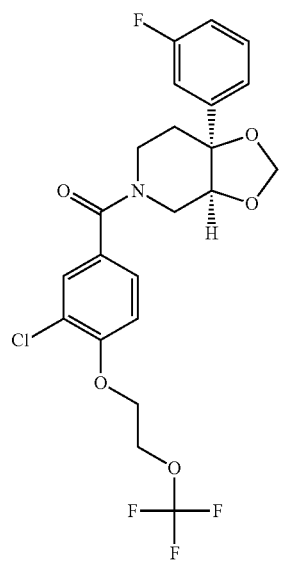 216 |
| 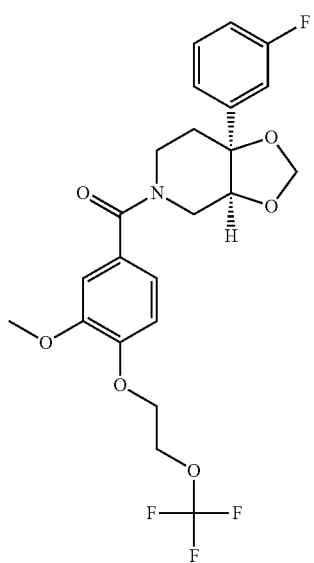 214 | 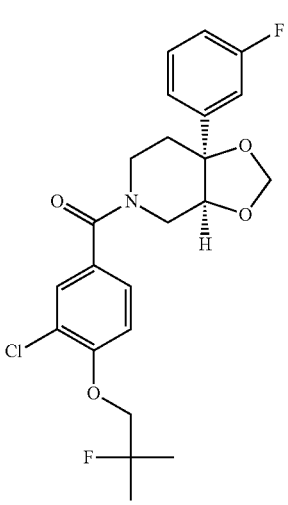 217 |
| 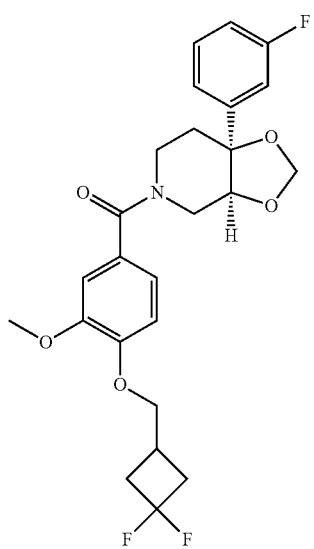 [SMILES: COc1cc(C(=O)N2CC[C@@]3(c4cccc(F)c4)OCO[C@H]3C2)ccc1OCC1CC(F)(F)C1] 215 | 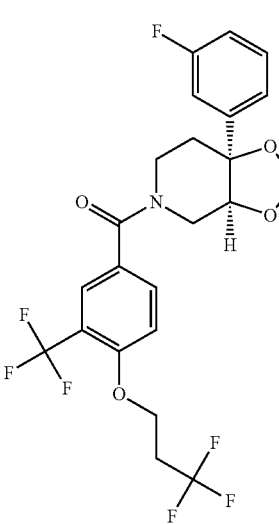 218 |

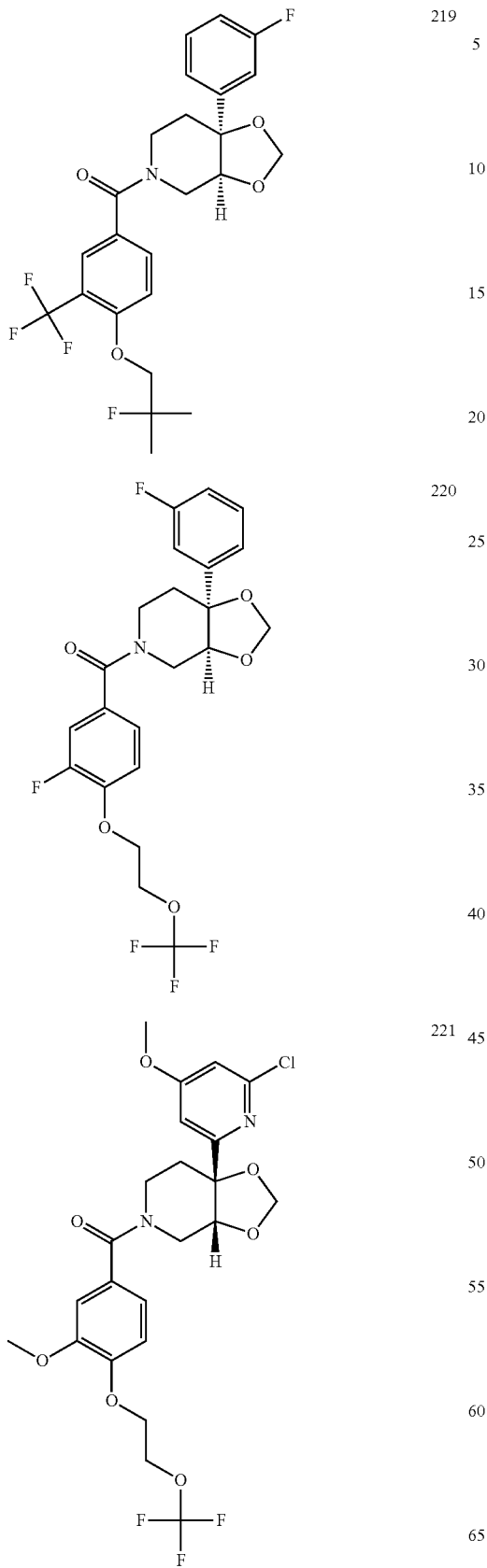

| 226 | 238 |
|---|---|
| 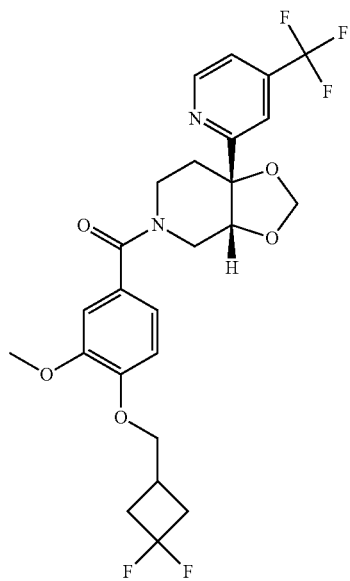 [SMILES: COc1cc(C(=O)N2CC[C@]3(c4cc(C(F)(F)F)ccn4)OCO[C@@H]3C2)ccc1OCC1CC(F)(F)C1] | 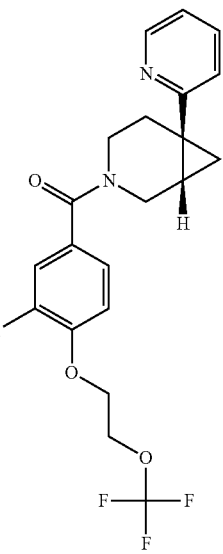 |
| 228 | 239 |
| 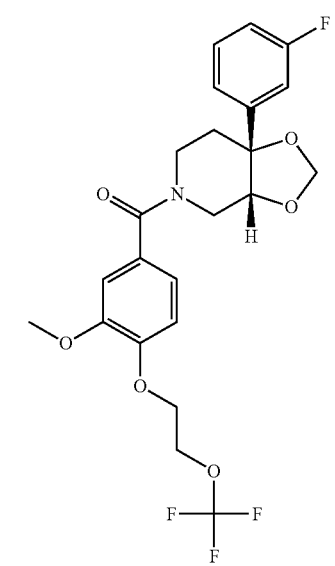 [SMILES: COc1cc(C(=O)N2CC[C@]3(c4cccc(F)c4)OCO[C@@H]3C2)ccc1OCCOC(F)(F)F] | 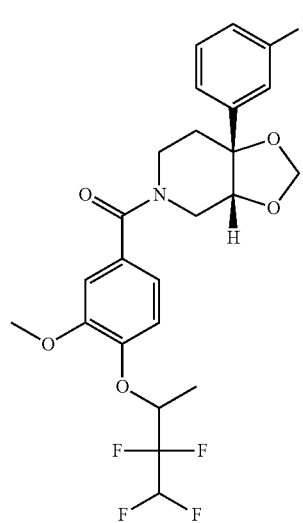 |
| | 240 |
| | 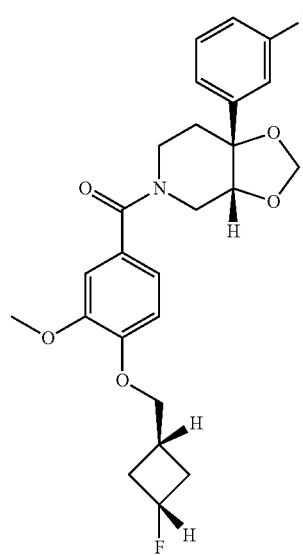 |

567
-continued
568
-continued
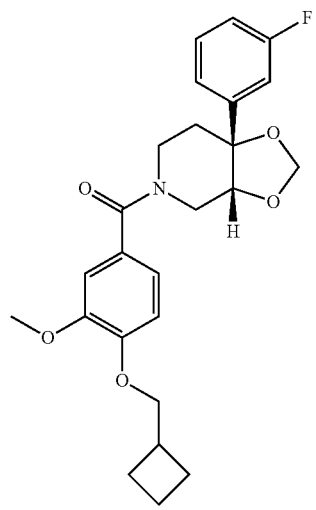 [SMILES: COc1cc(C(=O)N2CC[C@]3(c4cccc(F)c4)OCO[C@@H]3C2)ccc1OCC1CCC1]
241
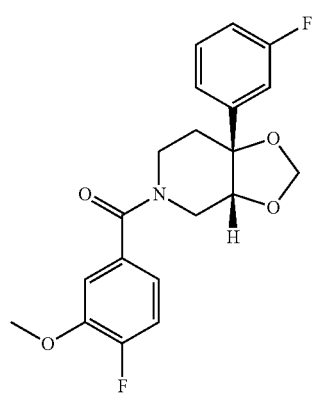 [SMILES: COc1cc(C(=O)N2CC[C@]3(c4cccc(F)c4)OCO[C@@H]3C2)ccc1F]
242
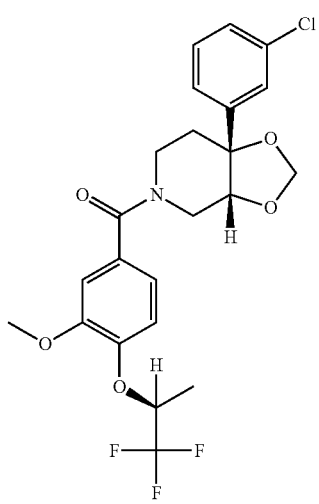 [SMILES: COc1cc(C(=O)N2CC[C@]3(c4cccc(Cl)c4)OCO[C@@H]3C2)ccc1O[C@@H](C)C(F)(F)F]
243
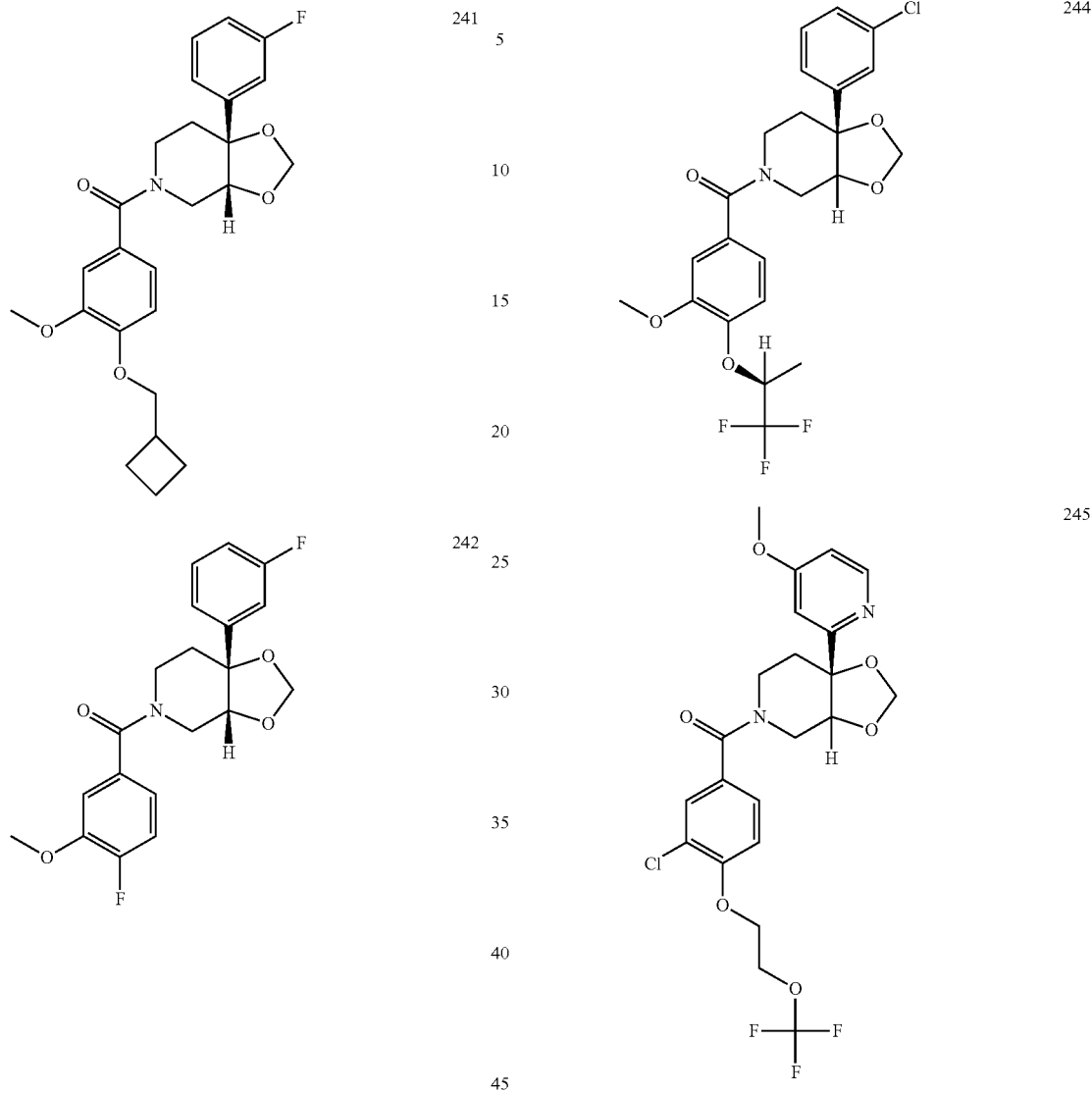
244
245
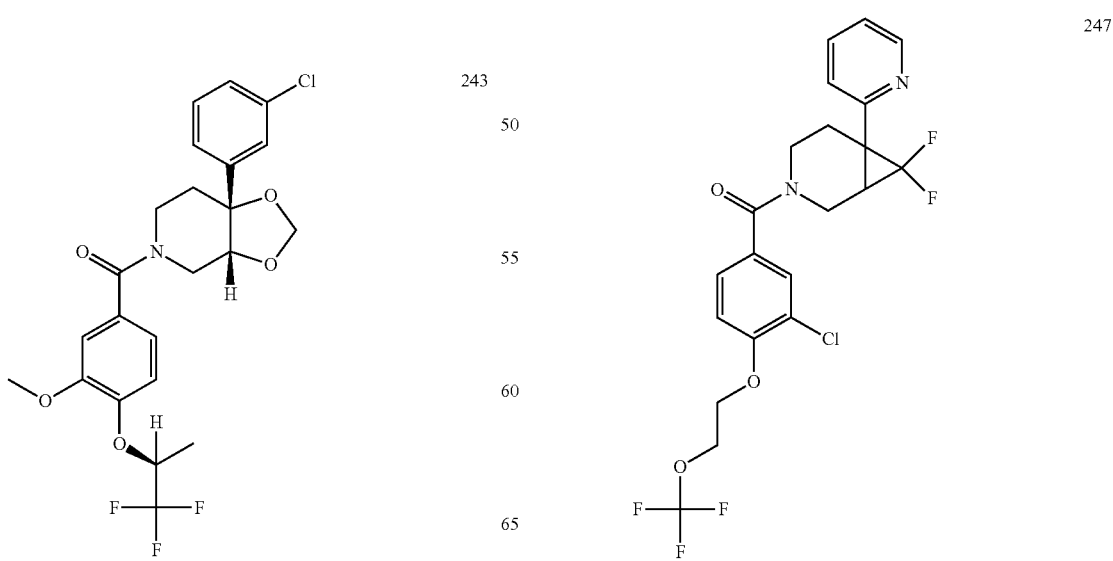
247

| 569 -continued | | 570 -continued | |
|---|---|---|---|
| 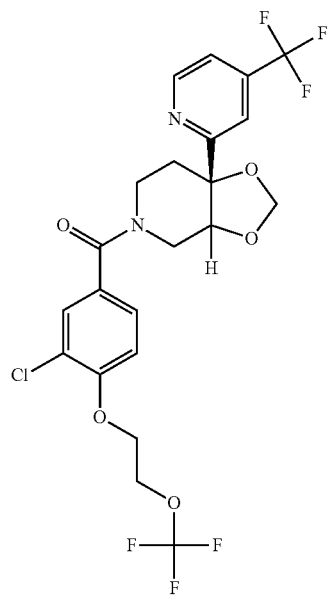 [SMILES: O=C(c1ccc(OCCOC(F)(F)F)c(Cl)c1)N1CC[C@]2(c3cc(C(F)(F)F)ccn3)OCOC2C1] | 248 | 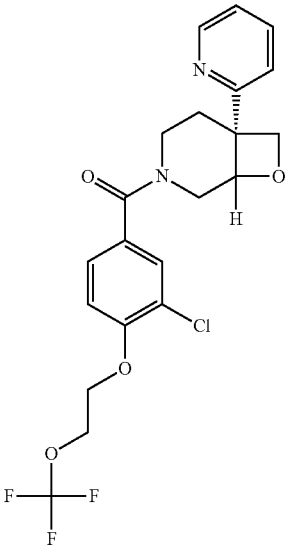 | 253 |
| 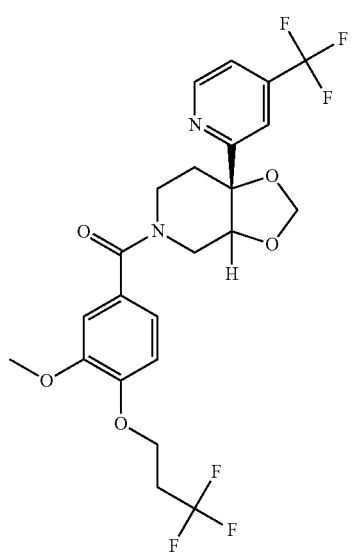 [SMILES: COc1cc(C(=O)N2CC[C@]3(c4cc(C(F)(F)F)ccn4)OCOC3C2)ccc1OCCC(F)(F)F] | 251 | 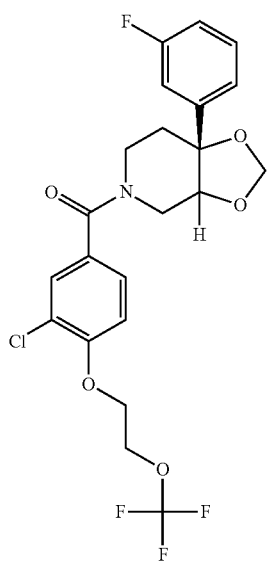 | 255 |
| 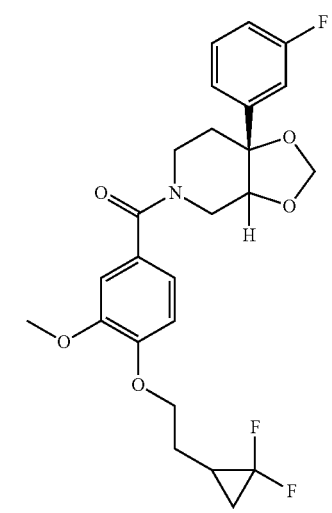 [SMILES: COc1cc(C(=O)N2CC[C@]3(c4cccc(F)c4)OCOC3C2)ccc1OCCC1CC1(F)F]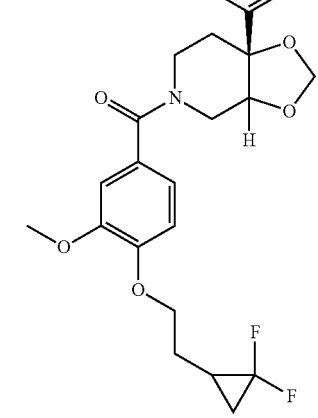 | 252 | 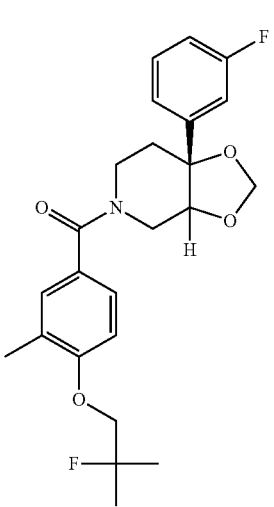 [SMILES: Cc1cc(C(=O)N2CC[C@]3(c4cccc(F)c4)OCOC3C2)ccc1OCC(C)(C)F] | 256 |

| 571 -continued | 572 -continued |
|---|---|
| 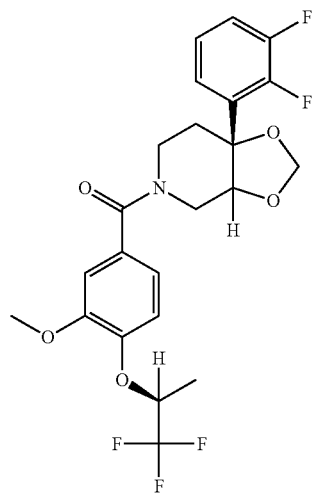 [SMILES: COc1cc(C(=O)N2CC[C@]3(c4cccc(F)c4F)OCOC3C2)ccc1O[C@@H](C)C(F)(F)F] 257 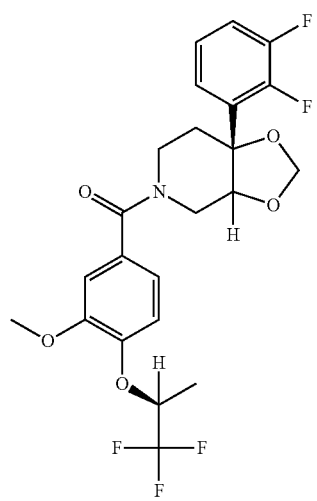 [SMILES: COc1cc(C(=O)N2CC[C@]3(c4cccc(F)c4F)OCOC3C2)ccc1O[C@@H](C)C(F)(F)F] 258 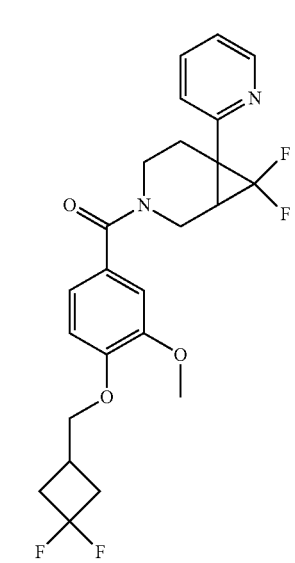 259 | 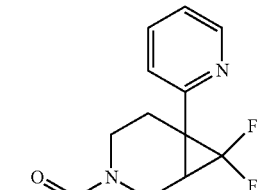 260 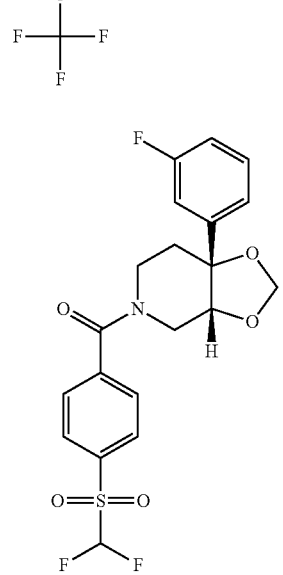 261 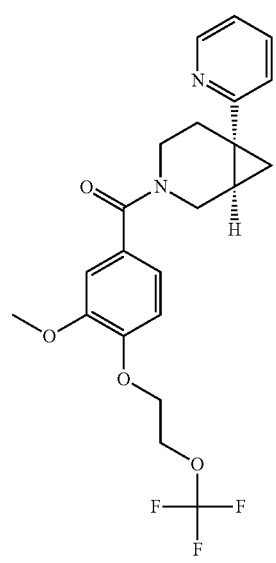 [SMILES: COc1cc(C(=O)N2CC[C@@]3(c4ccccn4)C[C@H]3C2)ccc1OCCOC(F)(F)F] 266 |

| 573 -continued | 574 -continued |
|---|---|
| 273 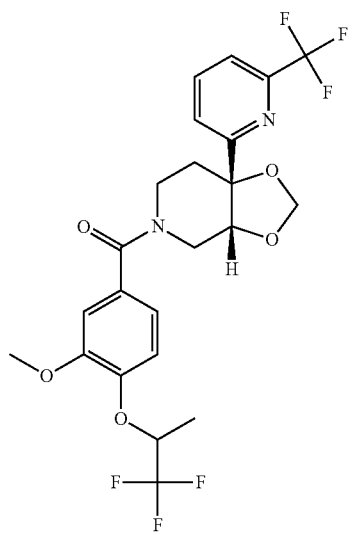 [SMILES: COc1cc(C(=O)N2CC[C@]3(c4cccc(C(F)(F)F)n4)OCO[C@@H]3C2)ccc1OC(C)C(F)(F)F] | 275 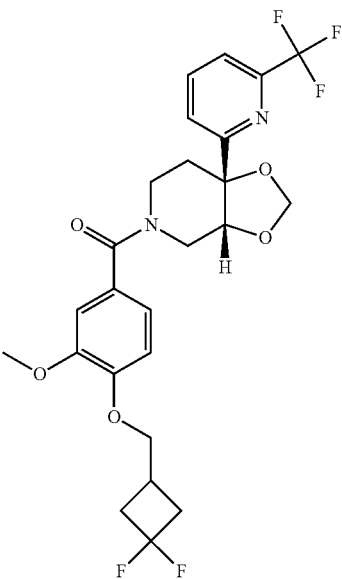 |
| 274 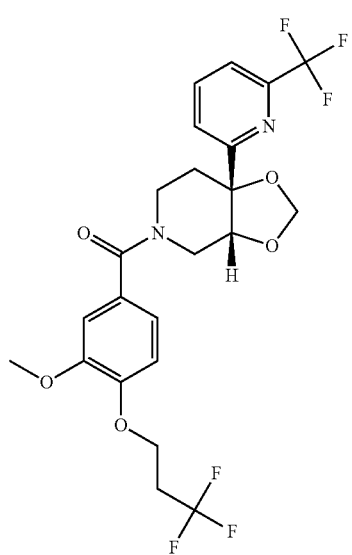 [SMILES: COc1cc(C(=O)N2CC[C@]3(c4cccc(C(F)(F)F)n4)OCO[C@@H]3C2)ccc1OCCC(F)(F)F] | 276 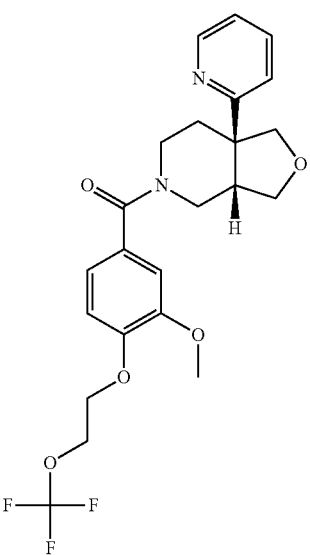 [SMILES: COc1cc(C(=O)N2CC[C@]3(c4ccccn4)COC[C@@H]3C2)ccc1OCCOC(F)(F)F] |

| 277 | 283 |
|---|---|
| 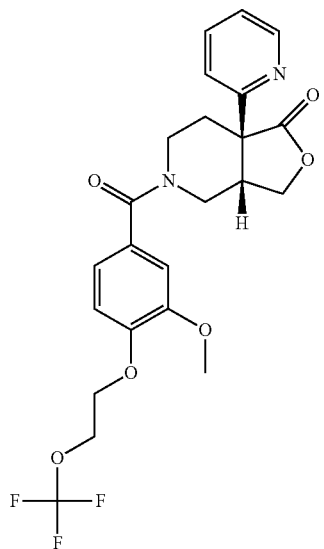 [SMILES: COc1cc(C(=O)N2CC[C@]3(c4ccccn4)C(=O)OC[C@@H]3C2)ccc1OCCOC(F)(F)F] | 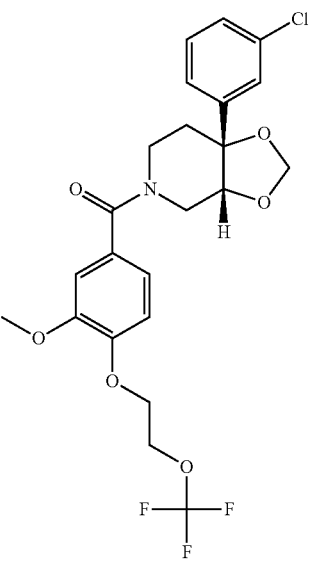 [SMILES: COc1cc(C(=O)N2CC[C@]3(c4cccc(Cl)c4)OCO[C@@H]3C2)ccc1OCCOC(F)(F)F] |
| 278 | 285 |
|---|---|
| 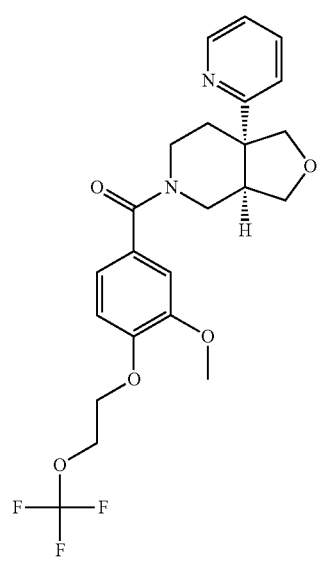 | 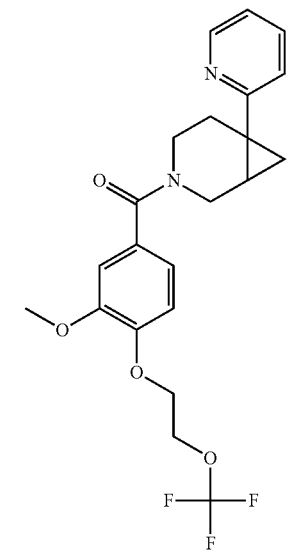 |
| 282 | 286 |
|---|---|
| 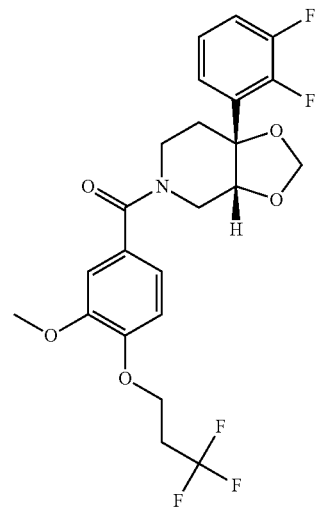 | 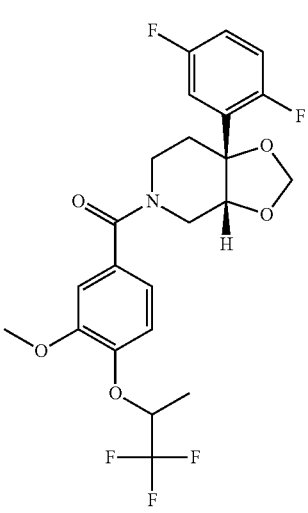 [SMILES: COc1cc(C(=O)N2CC[C@]3(c4cc(F)ccc4F)OCO[C@@H]3C2)ccc1OC(C)C(F)(F)F] |

577
-continued
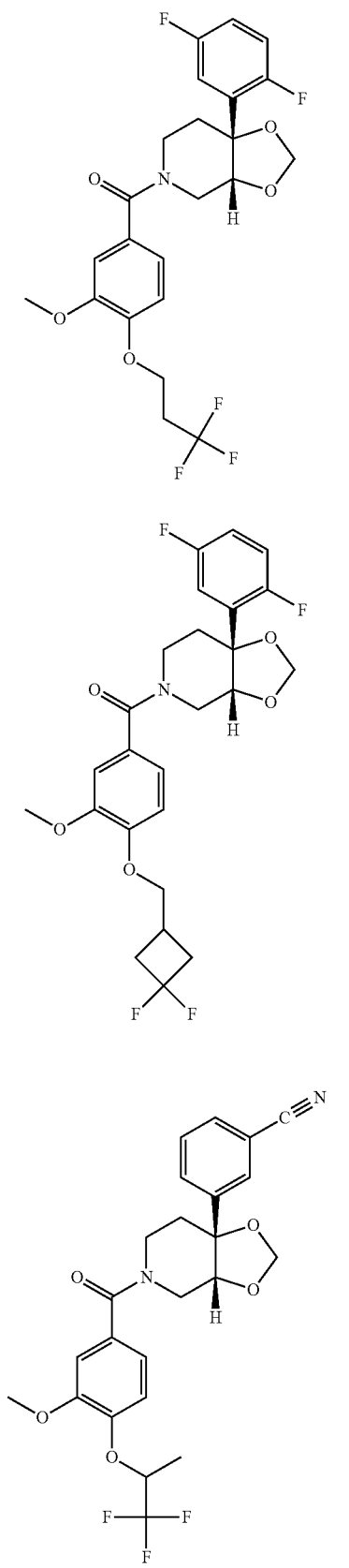
578
-continued
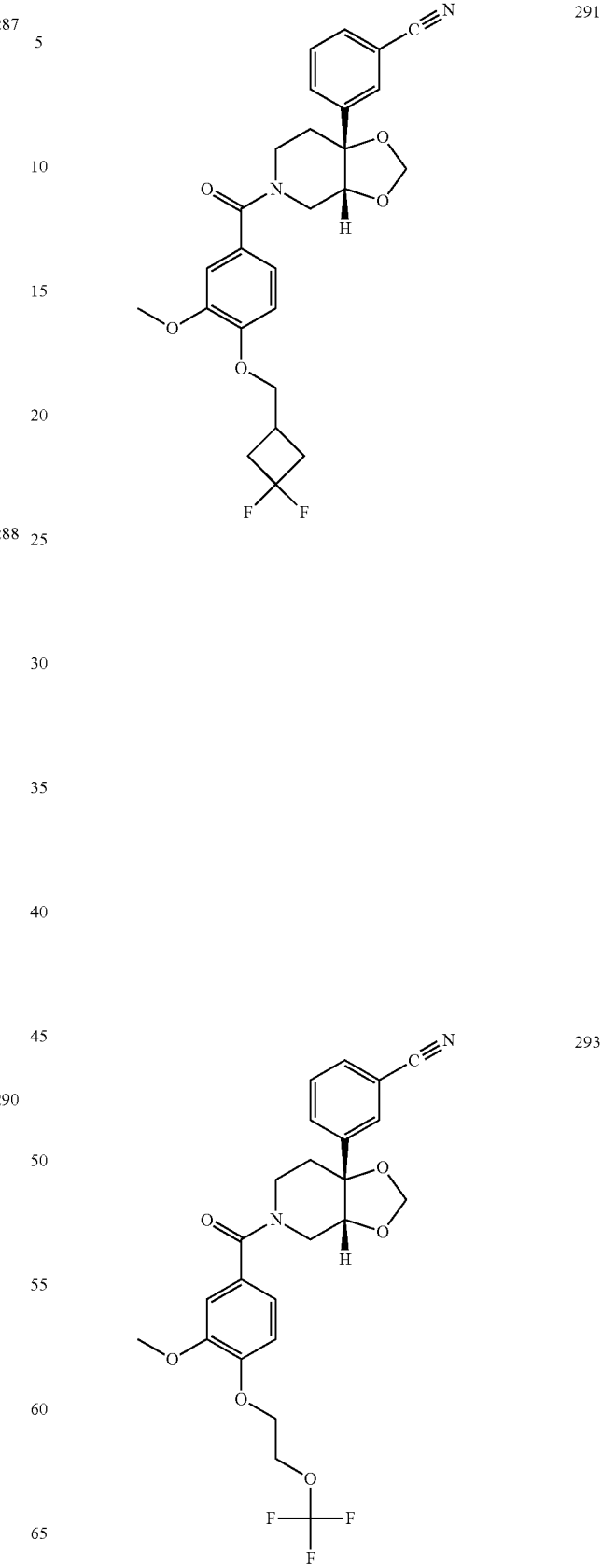

| 579 | 580 |
|---|---|
| 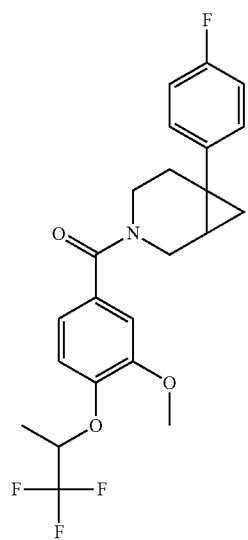 [SMILES: COc1cc(C(=O)N2CCC3(c4ccc(F)cc4)CC3C2)ccc1OC(C)C(F)(F)F] 297 | 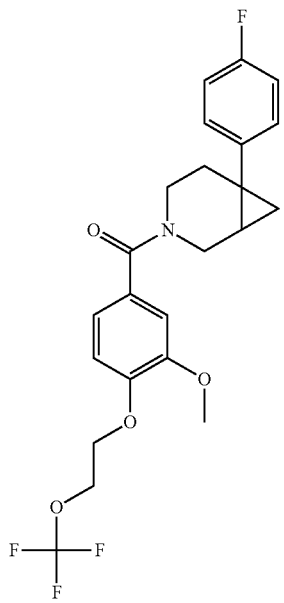 300 |
| 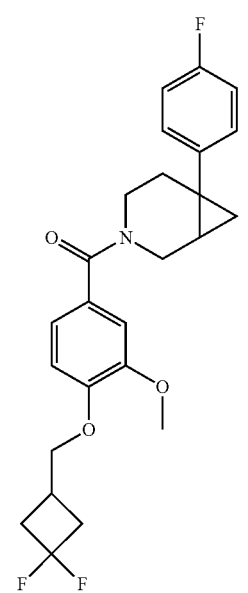 [SMILES: COc1cc(C(=O)N2CCC3(c4ccc(F)cc4)CC3C2)ccc1OCC1CC(F)(F)C1] 298 | 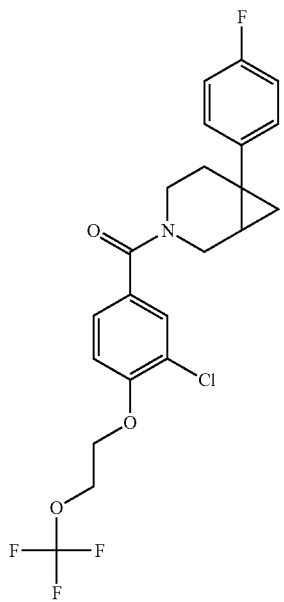 301 |

| 581 -continued | 582 -continued |
|---|---|
| 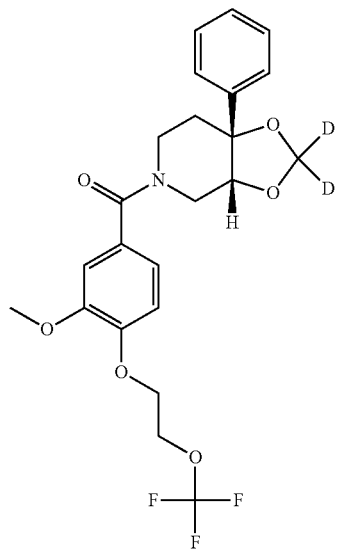 302 | 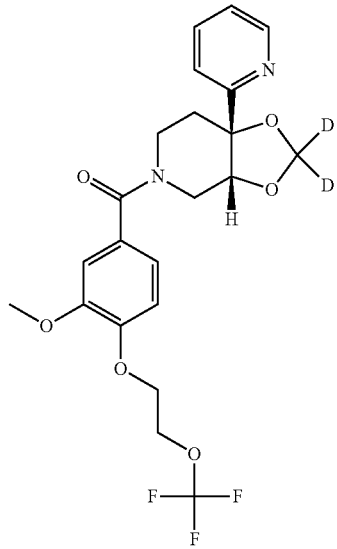 305 |
| 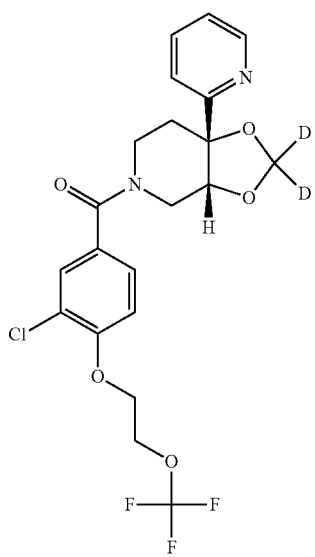 [SMILES: [2H]C1([2H])O[C@@H]2CN(C(=O)c3ccc(OCCOC(F)(F)F)c(Cl)c3)CC[C@]2(c2ccccn2)O1] 304 | 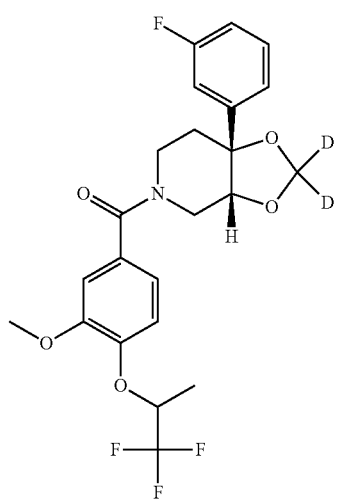 [SMILES: [2H]C1([2H])O[C@@H]2CN(C(=O)c3ccc(OC(C)C(F)(F)F)c(OC)c3)CC[C@]2(c2cccc(F)c2)O1] 307 |

583
-continued
| | |
|---|---|
| 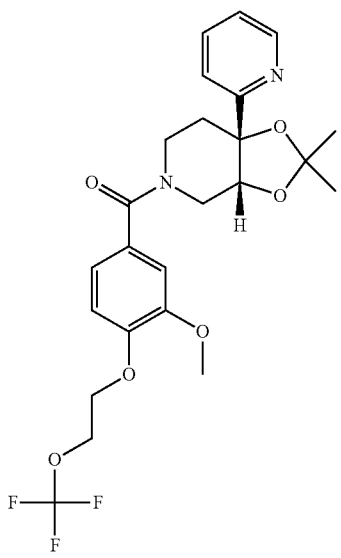 [SMILES: COc1cc(C(=O)N2CC[C@]3(c4ccccn4)OC(C)(C)O[C@@H]3C2)ccc1OCCOC(F)(F)F] 310 | |
| 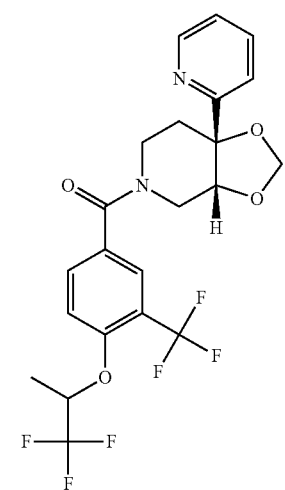 [SMILES: CC(Oc1ccc(C(=O)N2CC[C@]3(c4ccccn4)OCO[C@@H]3C2)cc1C(F)(F)F)C(F)(F)F] 311 | |
| 312 | |
584
-continued
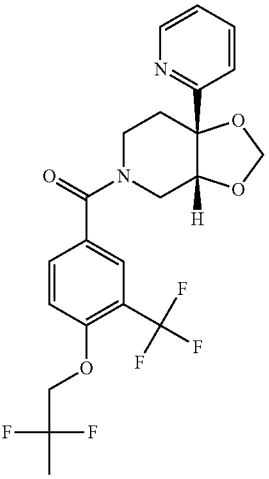 [SMILES: CC(F)(F)COc1ccc(C(=O)N2CC[C@]3(c4ccccn4)OCO[C@@H]3C2)cc1C(F)(F)F] 313
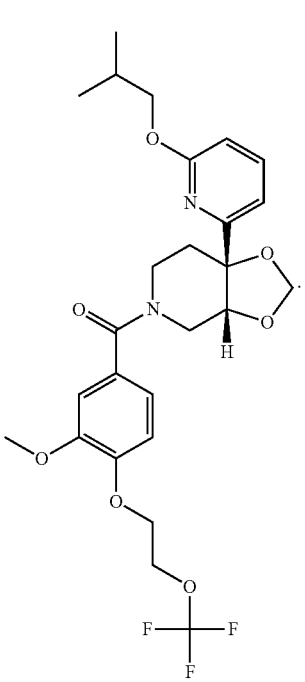 [SMILES: COc1cc(C(=O)N2CC[C@]3(c4cccc(OCC(C)C)n4)OCO[C@@H]3C2)ccc1OCCOC(F)(F)F] 314

25. The compound of claim 1 or 14, selected from the table:
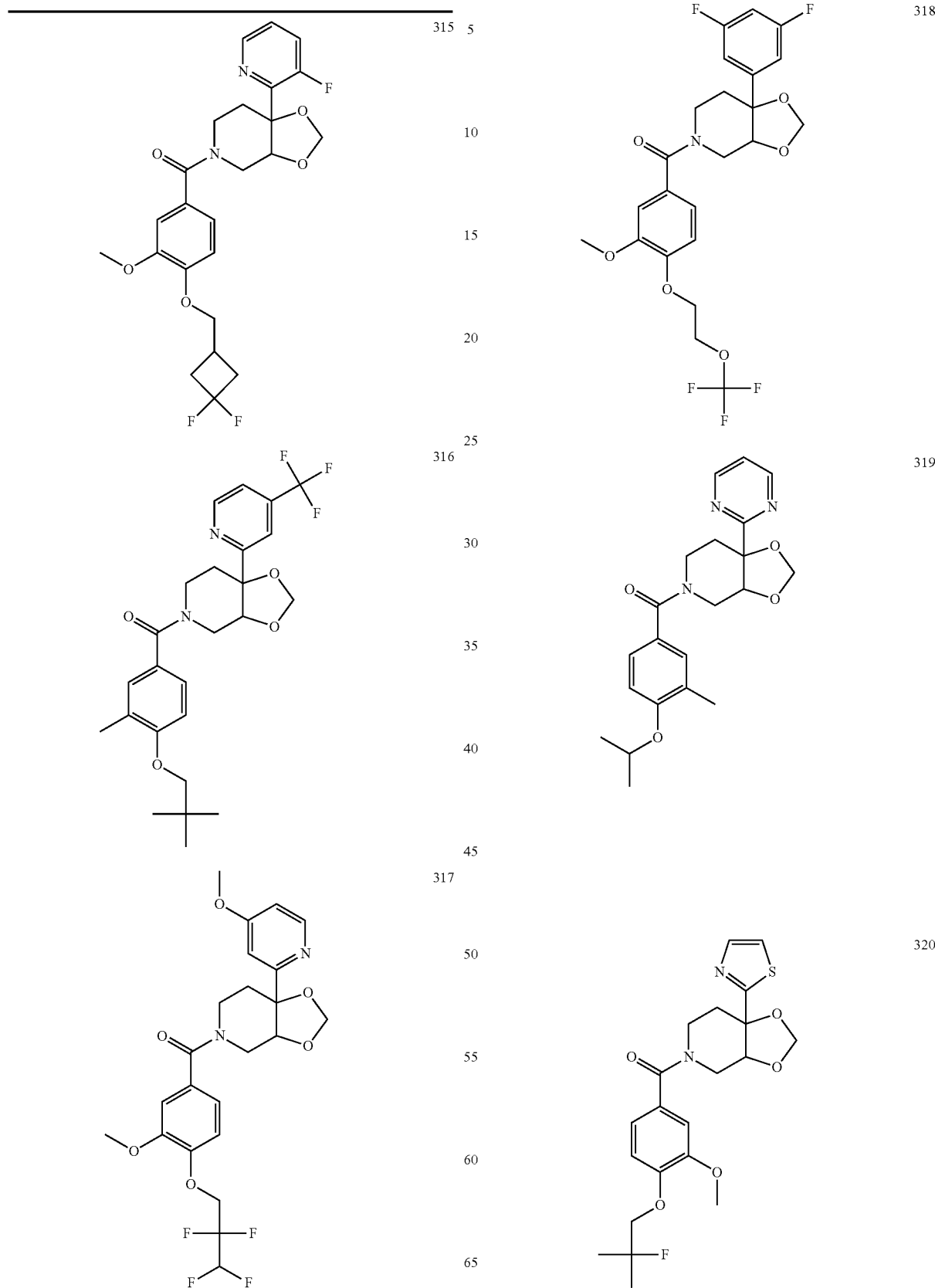

| 587 -continued | 588 -continued |
|---|---|
| 321 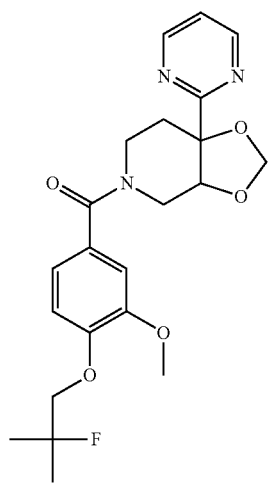 | 325 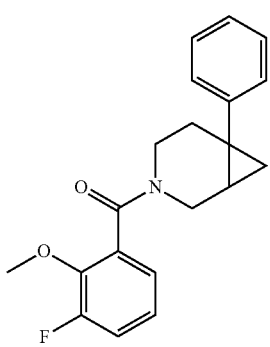 |
| 322 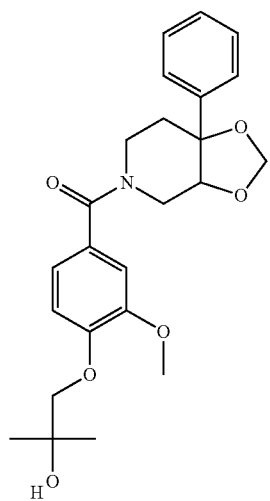 | 326 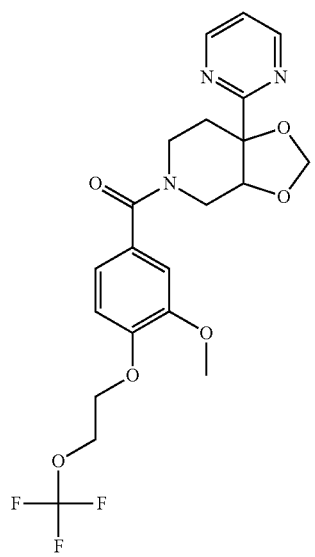 |
| 323 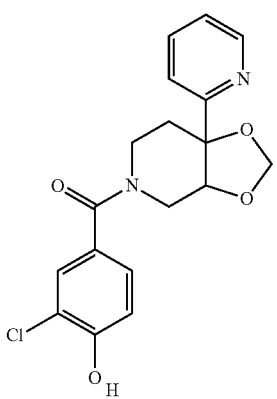 | 327 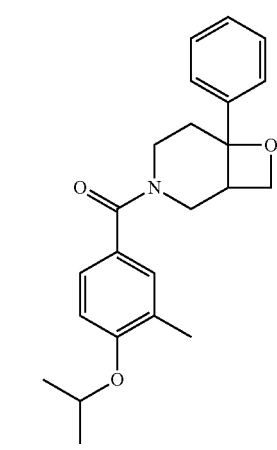 [SMILES: Cc1cc(C(=O)N2CCC3(c4ccccc4)OCC3C2)ccc1OC(C)C] |

| 589 -continued | 590 -continued |
|---|---|
| 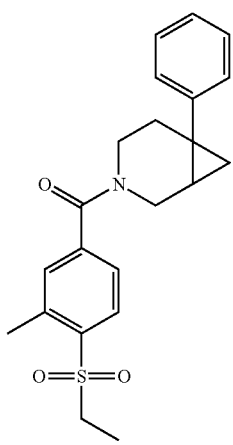 [SMILES: CCS(=O)(=O)c1ccc(C(=O)N2CCC3(c4ccccc4)CC3C2)cc1C] 329 | 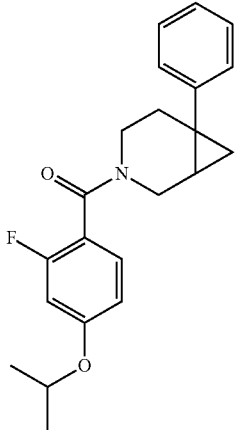 [SMILES: CC(C)Oc1ccc(C(=O)N2CCC3(c4ccccc4)CC3C2)c(F)c1] 333 |
| 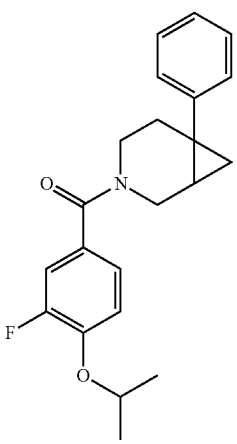 330 | 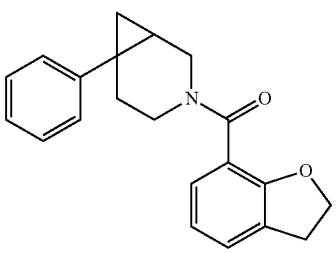 [SMILES: O=C(c1cccc2c1OCC2)N1CCC2(c3ccccc3)CC2C1] 334 |
| 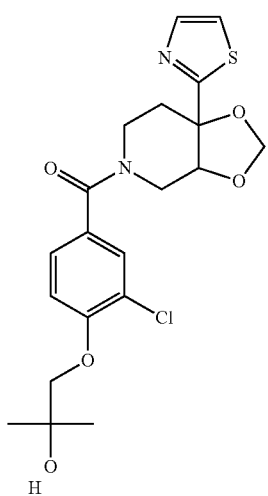 331 | 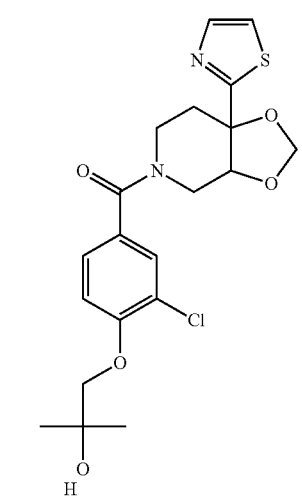 336 |

| 591 -continued | 592 -continued |
|---|---|
| 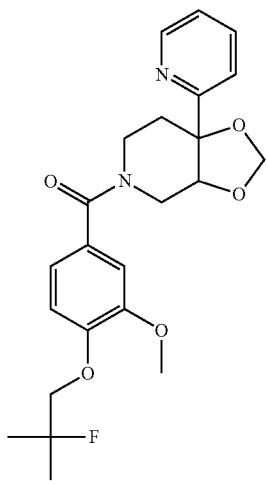 337 | 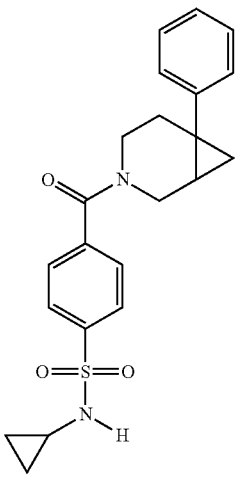 340 |
| 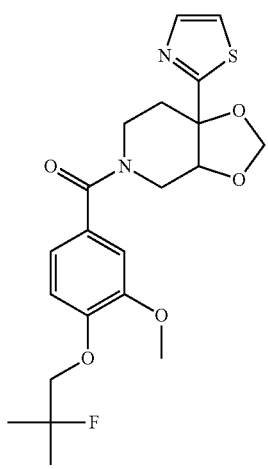 [SMILES: COc1cc(C(=O)N2CCC3(c4nccs4)OCOC3C2)ccc1OCC(C)(C)F] 338 | 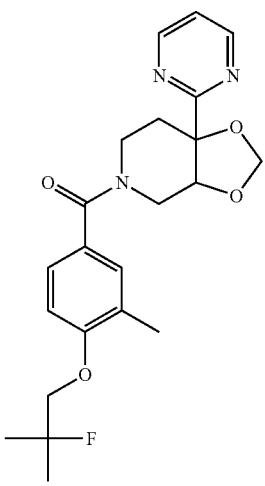 341 |
| 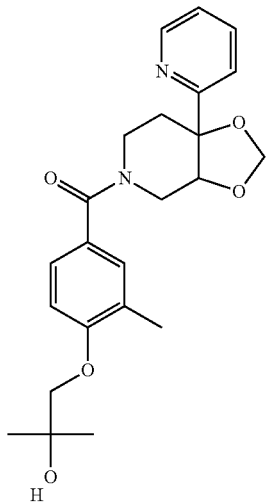 339 | 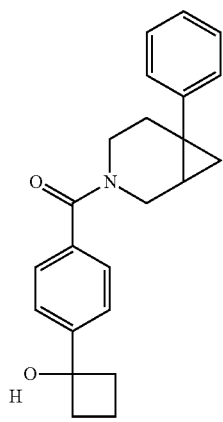 342 |

| 343 | 346 |
|---|---|
| 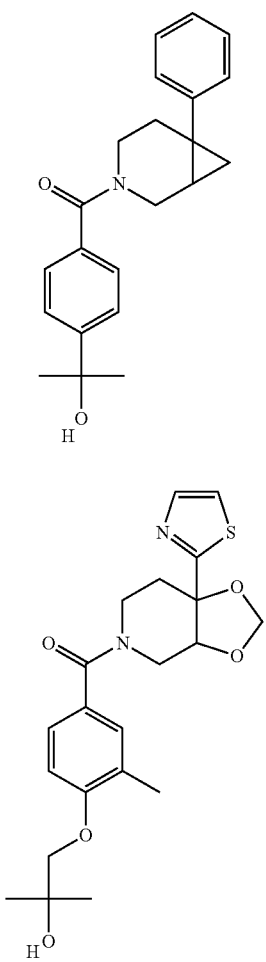 | 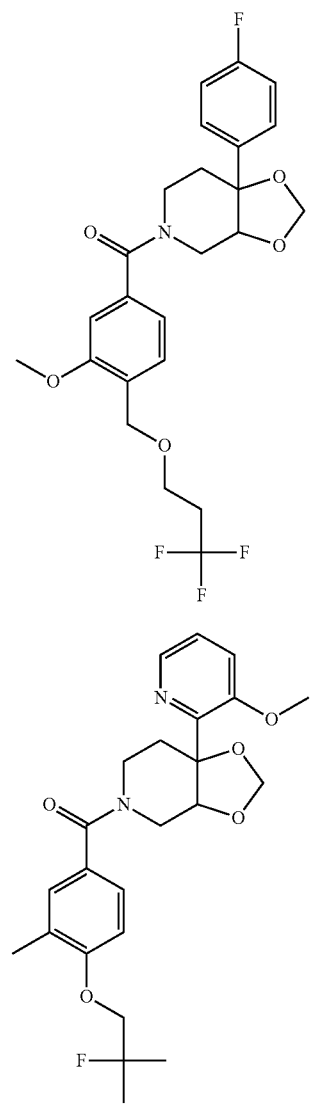 |
| 344 | 348 |
| 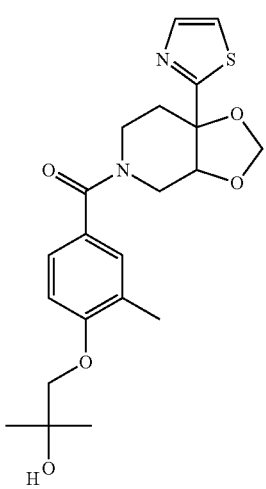 | 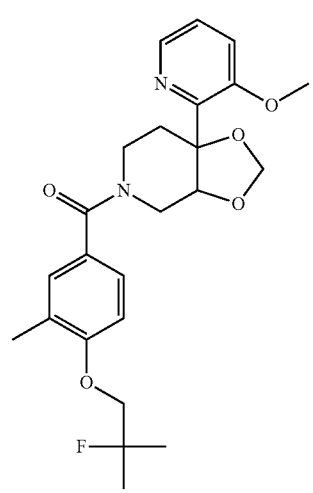 |
| 345 | 349 |
| 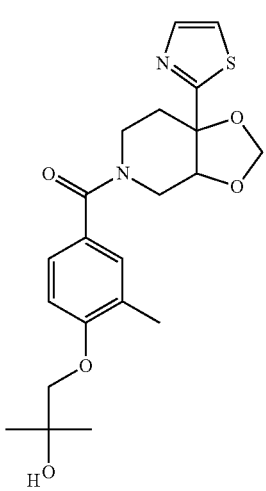 | 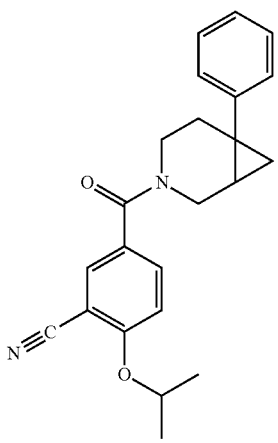 [SMILES: CC(C)Oc1ccc(C(=O)N2CCC3(c4ccccc4)CC3C2)cc1C#N] |

| 595 -continued | 596 -continued |
|---|---|
| 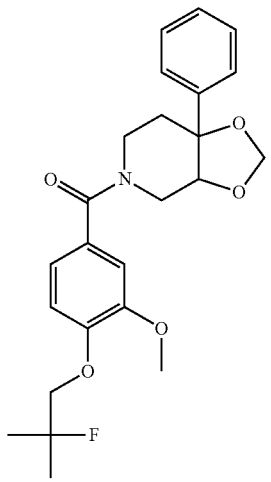 [SMILES: COc1cc(C(=O)N2CCC3(c4ccccc4)OCOC3C2)ccc1OCC(C)(C)F] 350 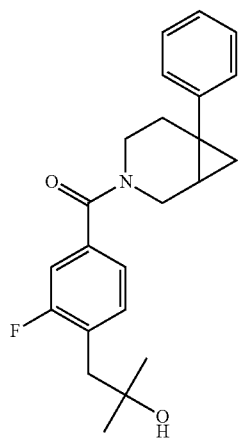 351 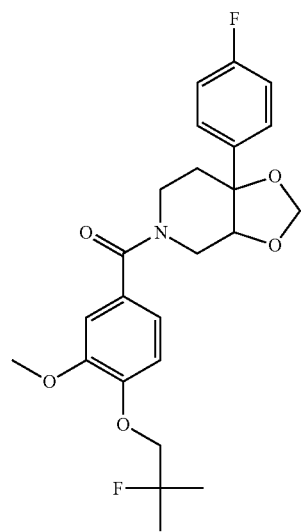 [SMILES: COc1cc(C(=O)N2CCC3(c4ccc(F)cc4)OCOC3C2)ccc1OCC(C)(C)F] 352 | 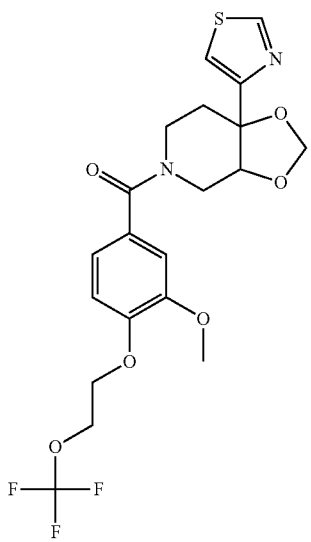 [SMILES: COc1cc(C(=O)N2CCC3(c4cscn4)OCOC3C2)ccc1OCCOC(F)(F)F] 353 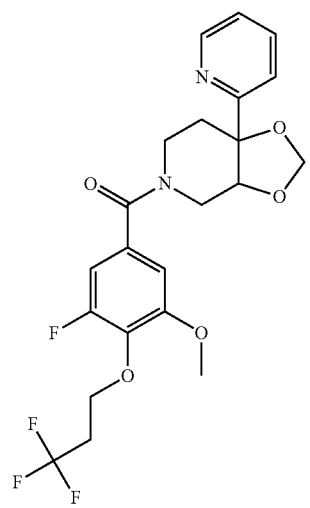 354 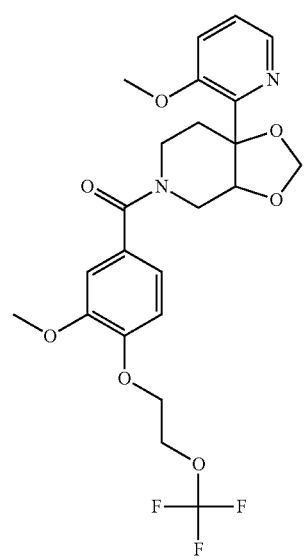 [SMILES: COc1cc(C(=O)N2CCC3(c4ncccc4OC)OCOC3C2)ccc1OCCOC(F)(F)F] 355 |

356
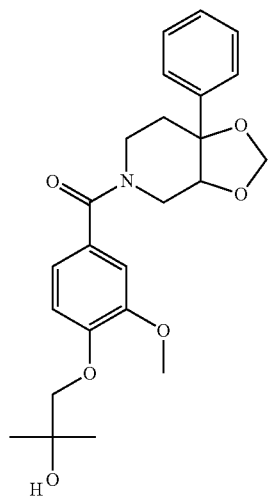
358
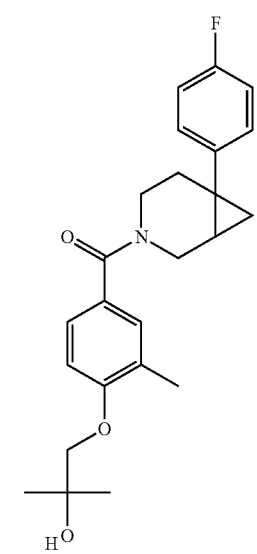
359
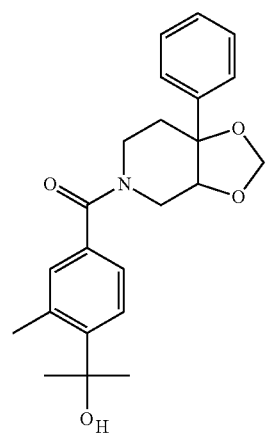
360
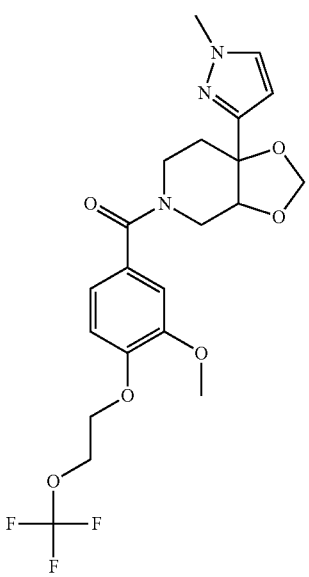 [SMILES: COc1cc(C(=O)N2CCC3(c4ccn(C)n4)OCOC3C2)ccc1OCCOC(F)(F)F]
361
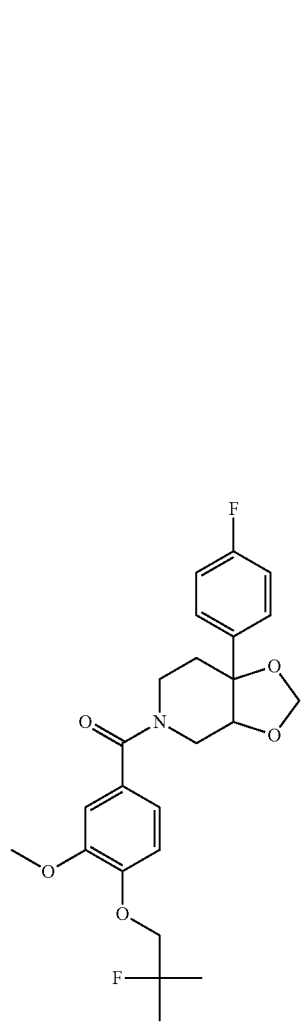 [SMILES: COc1cc(C(=O)N2CCC3(c4ccc(F)cc4)OCOC3C2)ccc1OCC(C)(C)F]

| 599 -continued | 600 -continued |
|---|---|
| 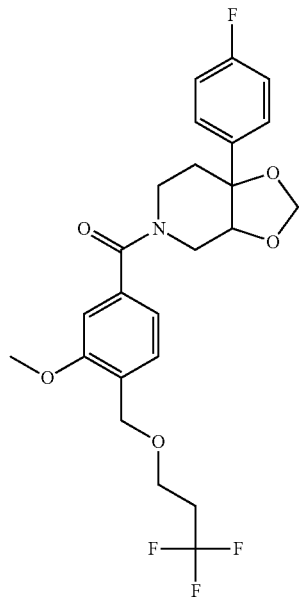 [SMILES: COc1cc(C(=O)N2CCC3(c4ccc(F)cc4)OCOC3C2)ccc1COCCC(F)(F)F] 362<br><br>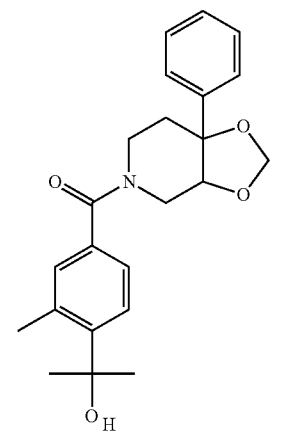 363<br><br>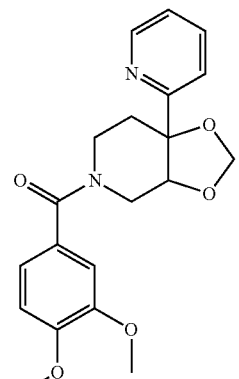 364<br>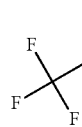 | 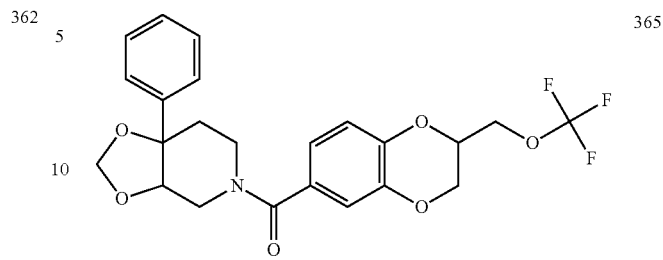 365<br><br>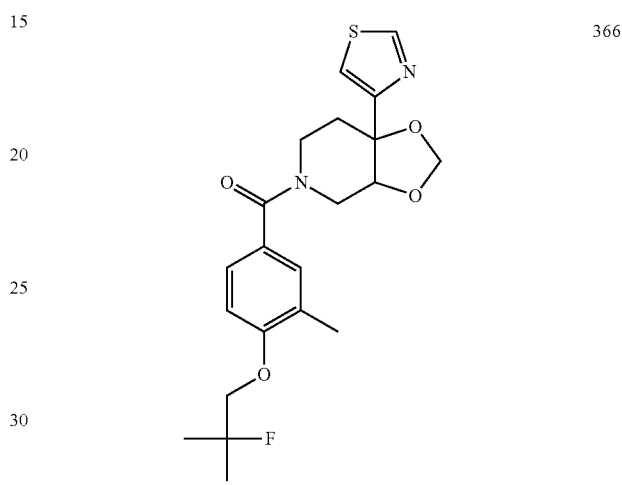 366<br><br>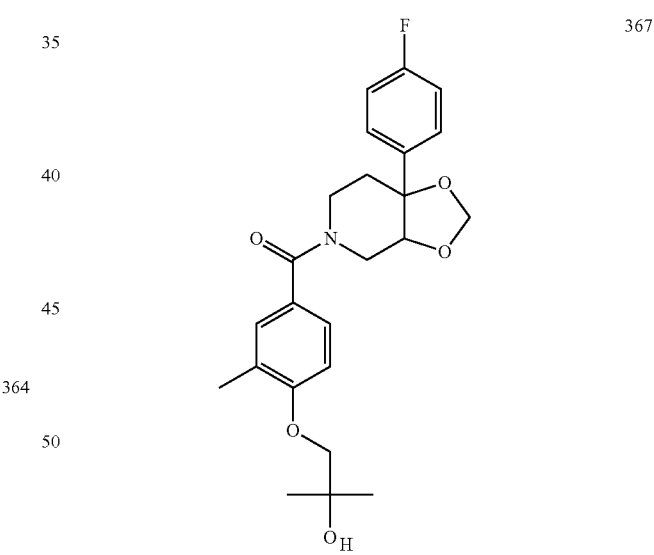 367<br><br>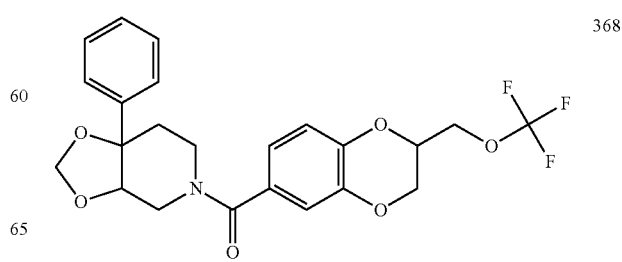 368 |

601
-continued
369
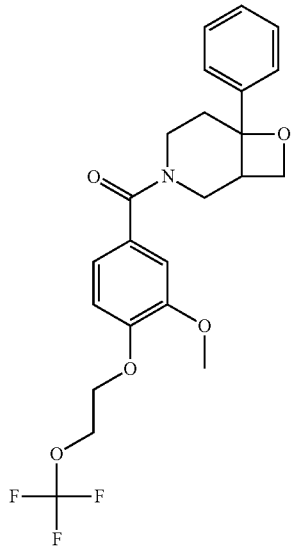
371
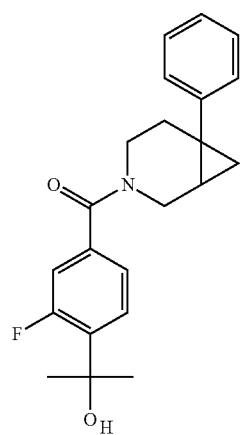
372
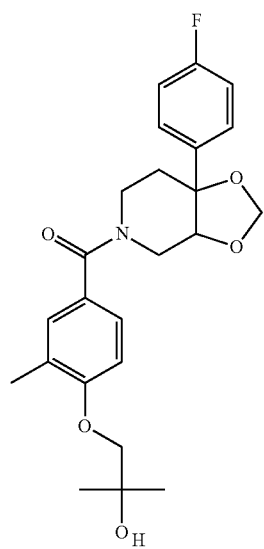
602
-continued
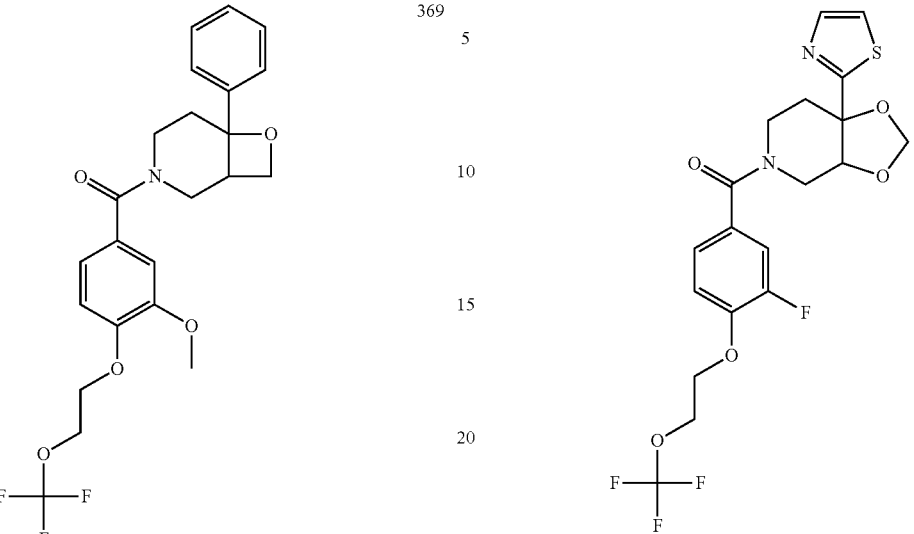
376
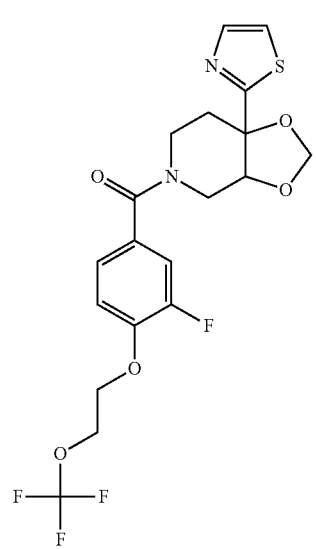

| 603 -continued | 604 -continued |
|---|---|
| 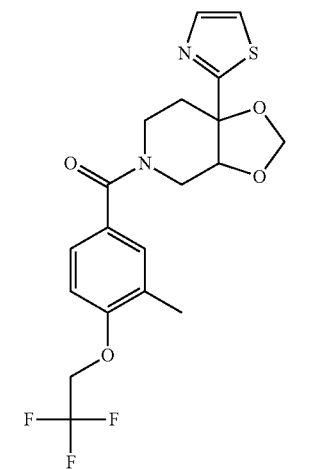 [SMILES: Cc1cc(C(=O)N2CCC3(c4nccs4)OCOC3C2)ccc1OCC(F)(F)F] 377 | 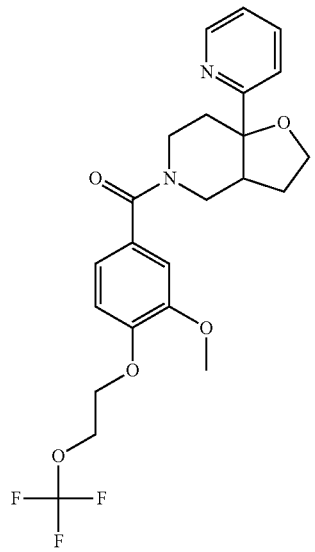 380 |
| 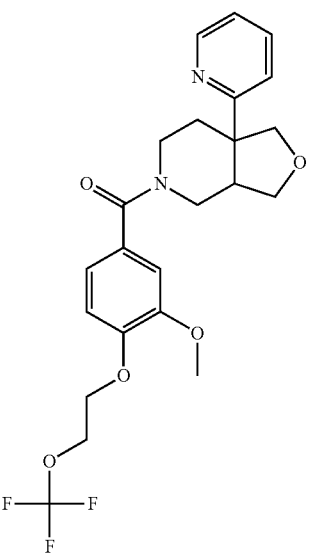 378 | 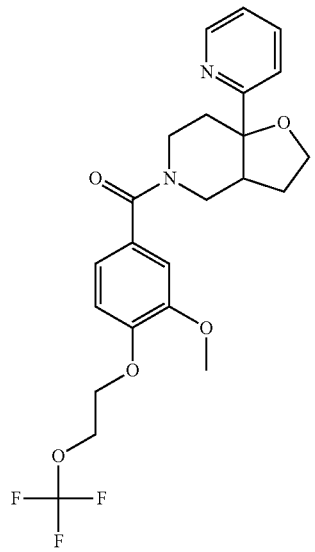 382 |
| 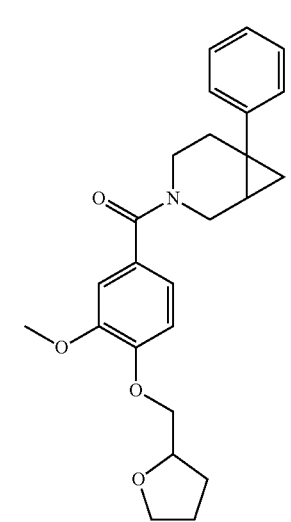 [SMILES: COc1cc(C(=O)N2CCC3(c4ccccc4)CC3C2)ccc1OCC1CCCO1] 379 | 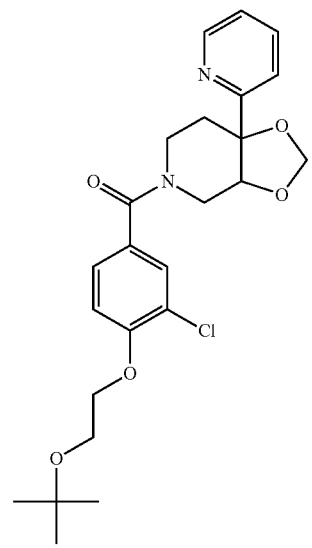 [SMILES: CC(C)(C)OCCOc1ccc(C(=O)N2CCC3(c4ccccn4)OCOC3C2)cc1Cl] 383 |

| 605 -continued | 606 -continued |
|---|---|
| 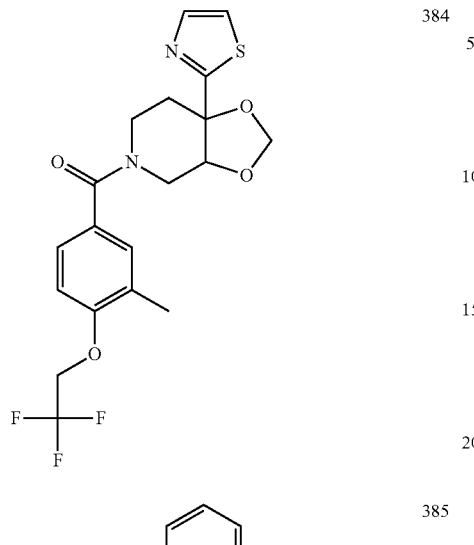 384 | 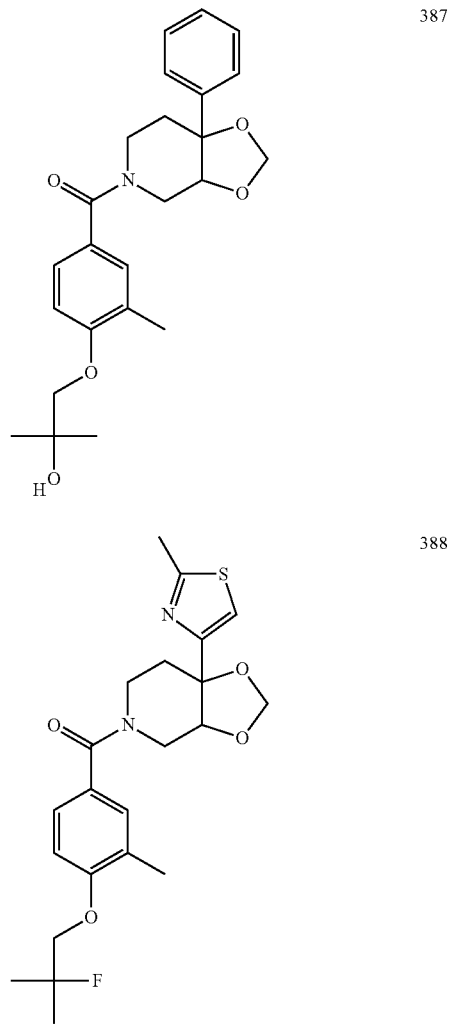 387 388 389 |
| 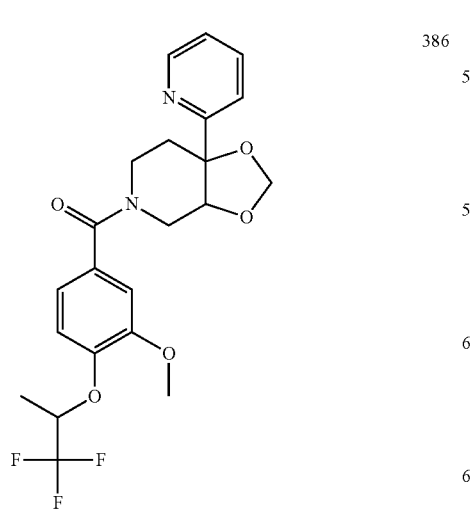 385 386 | |

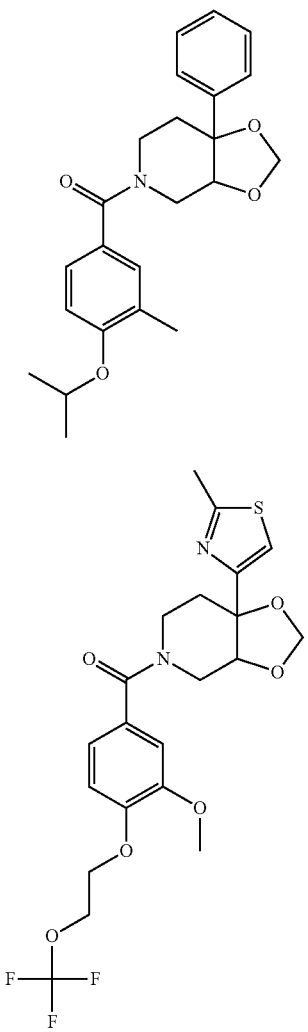
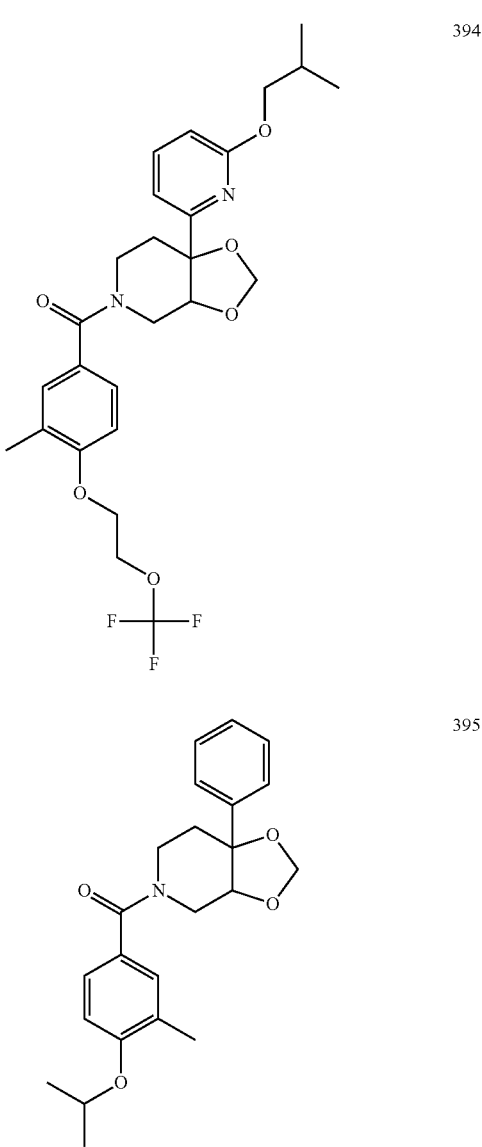
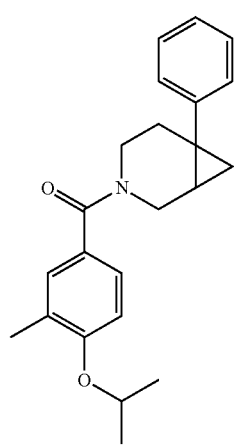 [SMILES: Cc1cc(C(=O)N2CCC3(c4ccccc4)CC3C2)ccc1OC(C)C]
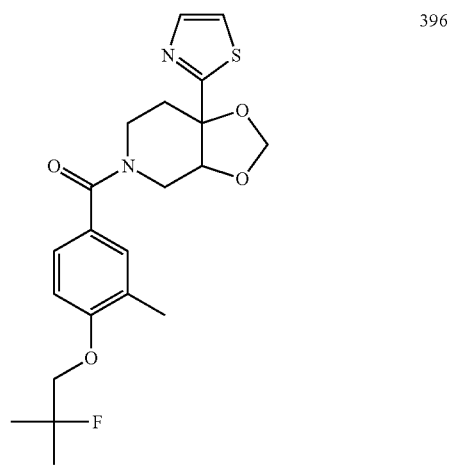

| 609 -continued | 610 -continued |
|---|---|
| 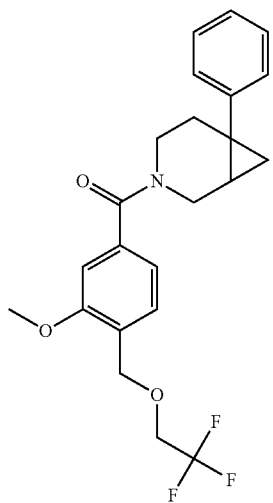 [SMILES: COc1cc(C(=O)N2CCC3(c4ccccc4)CC3C2)ccc1COCC(F)(F)F] 397 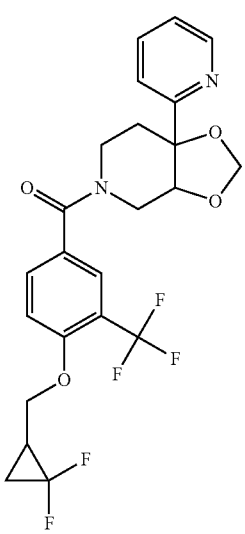 [SMILES: O=C(c1ccc(OCC2CC2(F)F)c(C(F)(F)F)c1)N1CCC2(c3ccccn3)OCOC2C1] 398 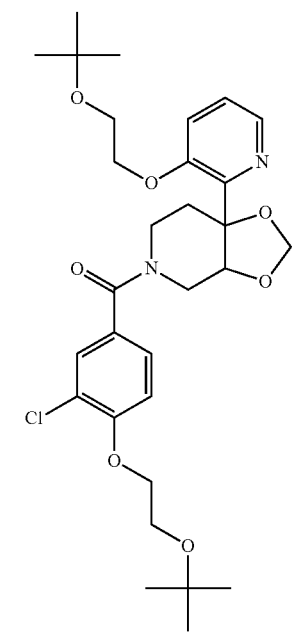 [SMILES: CC(C)(C)OCCOc1ccc(C(=O)N2CCC3(c4ncccc4OCCOC(C)(C)C)OCOC3C2)cc1Cl] 399 | 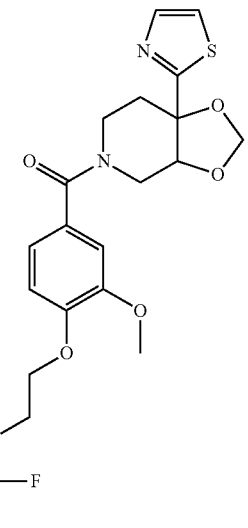 400 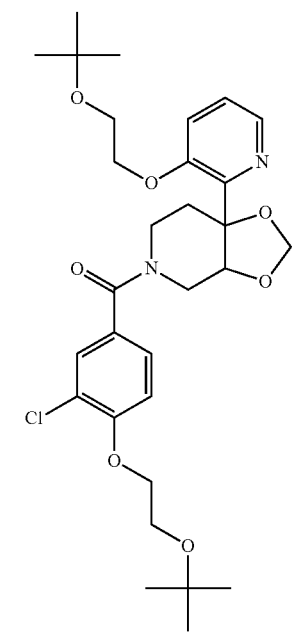 [SMILES: CC(C)(C)OCCOc1ccc(C(=O)N2CCC3(c4ncccc4OCCOC(C)(C)C)OCOC3C2)cc1Cl] 401 |

| 611 -continued | 612 -continued |
|---|---|
| 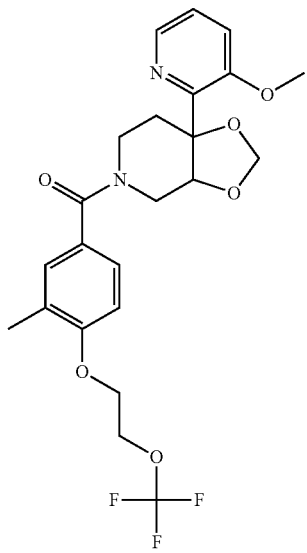 403<br>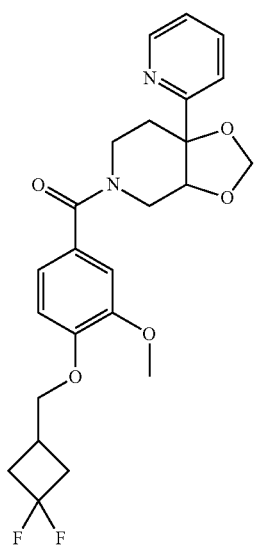 [SMILES: COc1cc(C(=O)N2CCC3(c4ccccn4)OCOC3C2)ccc1OCC1CC(F)(F)C1] 404<br>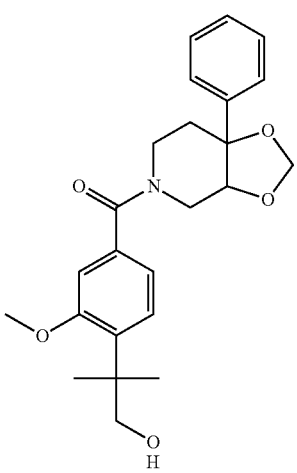 405 | 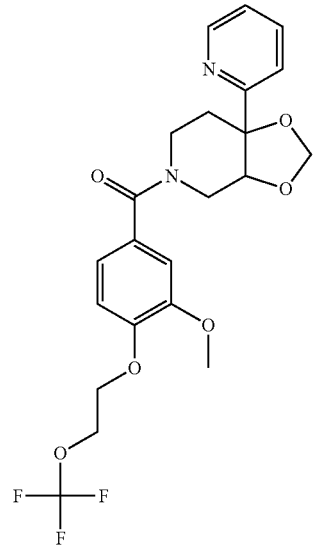 406<br>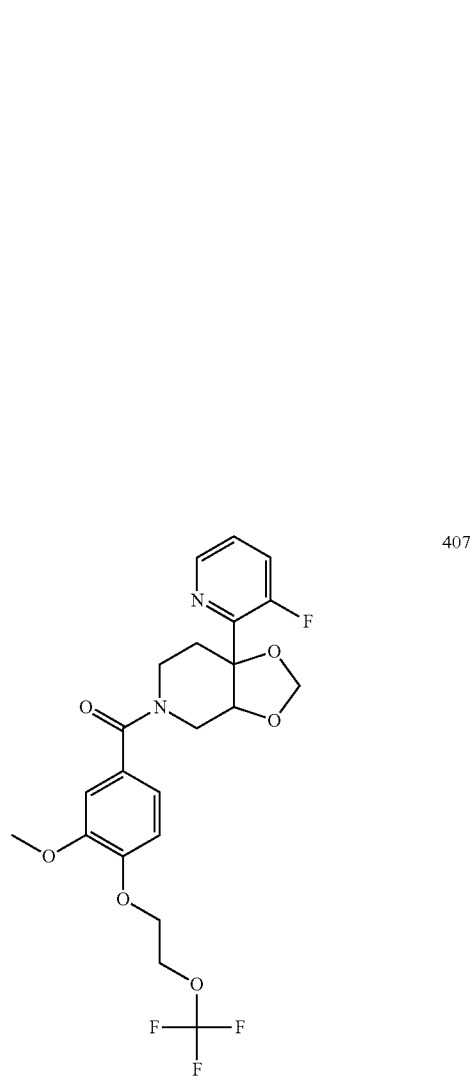 407 |

613
-continued
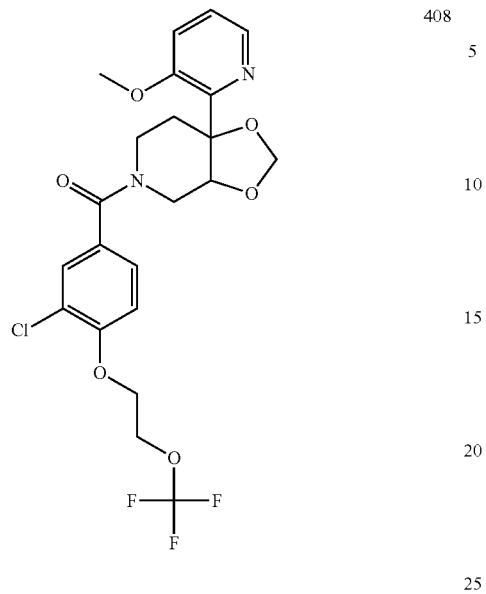
408
409
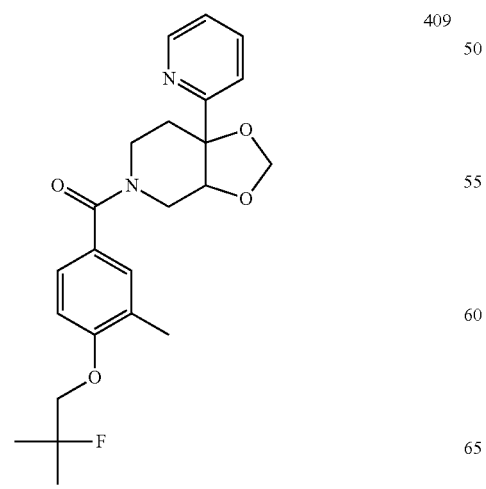
614
-continued
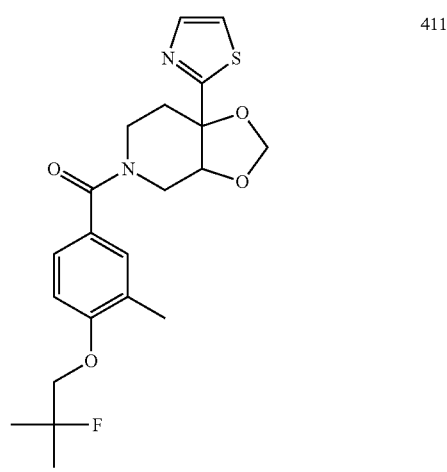
411
412
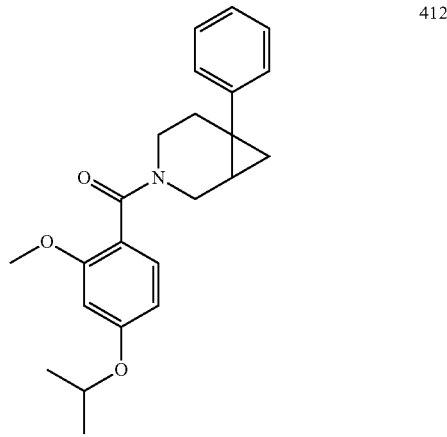

| 615 -continued | | 616 -continued | |
|---|---|---|---|
| 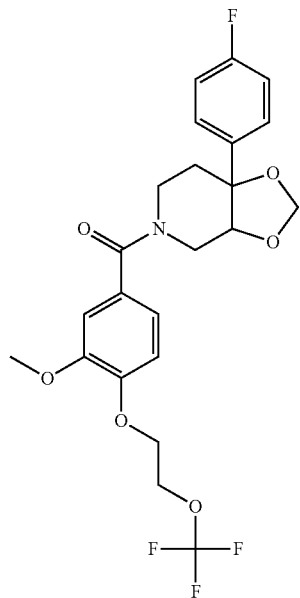 [SMILES: COc1cc(C(=O)N2CCC3(c4ccc(F)cc4)OCOC3C2)ccc1OCCOC(F)(F)F] | 413 | 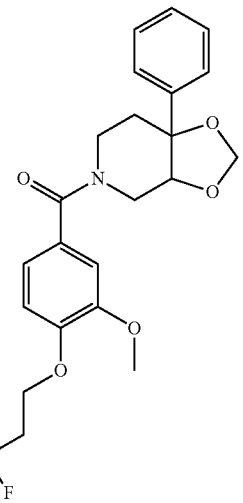 | 416 |
| 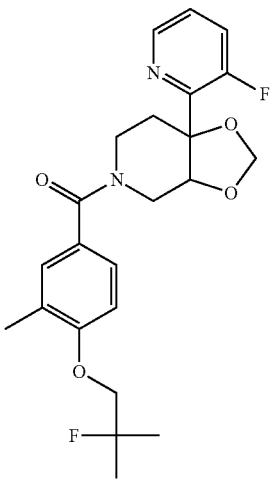 [SMILES: Cc1cc(C(=O)N2CCC3(c4ncccc4F)OCOC3C2)ccc1OCC(C)(C)F] | 414 | 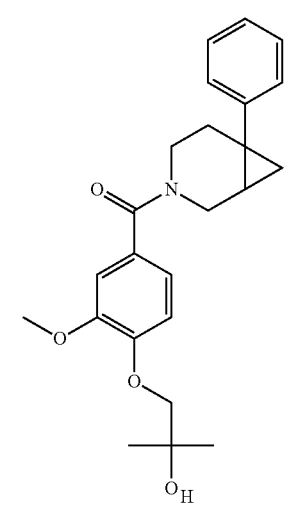 | 418 |
| 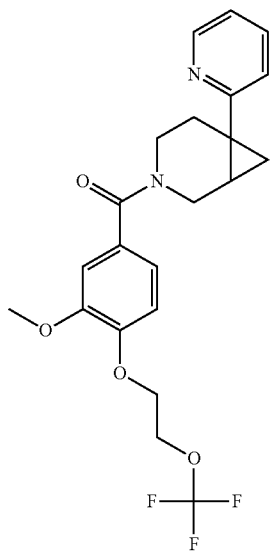 | 415 | 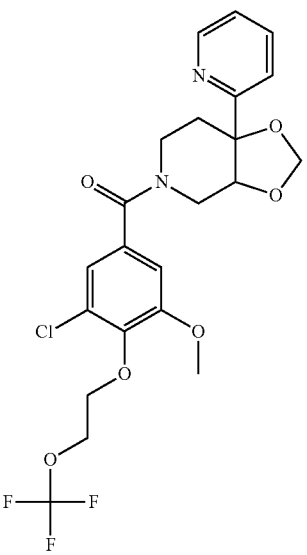 [SMILES: COc1cc(C(=O)N2CCC3(c4ccccn4)OCOC3C2)cc(Cl)c1OCCOC(F)(F)F] | 419 |

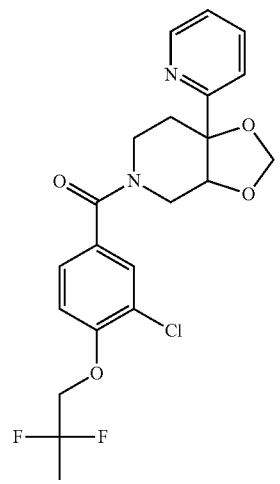 [SMILES: CC(F)(F)COc1ccc(C(=O)N2CCC3(c4ccccn4)OCOC3C2)cc1Cl]
420
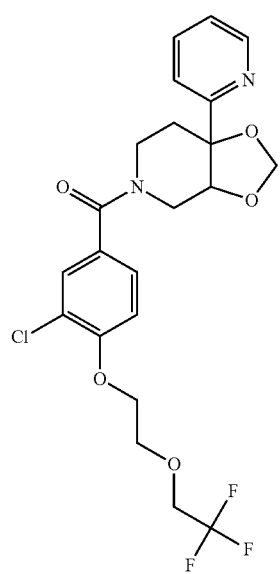 [SMILES: O=C(c1ccc(OCCOCC(F)(F)F)c(Cl)c1)N1CCC2(c3ccccn3)OCOC2C1]
422
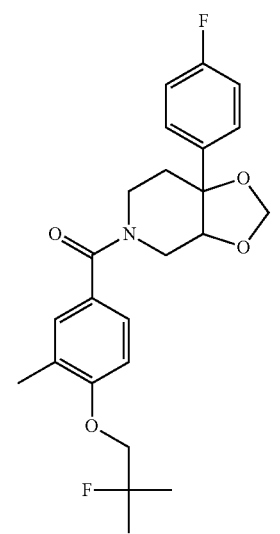 [SMILES: Cc1cc(C(=O)N2CCC3(c4ccc(F)cc4)OCOC3C2)ccc1OCC(C)(C)F]
423
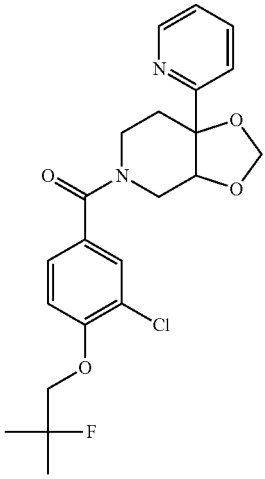
424
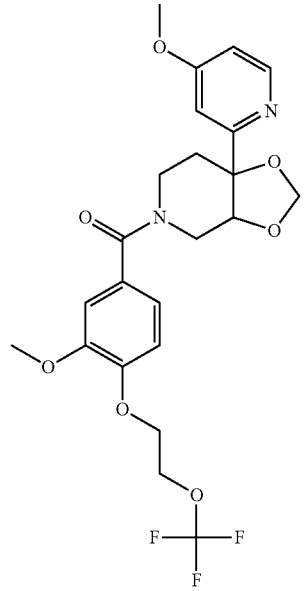 [SMILES: COc1ccnc(C23CCN(C(=O)c4ccc(OCCOC(F)(F)F)c(OC)c4)CC2OCO3)c1]
426
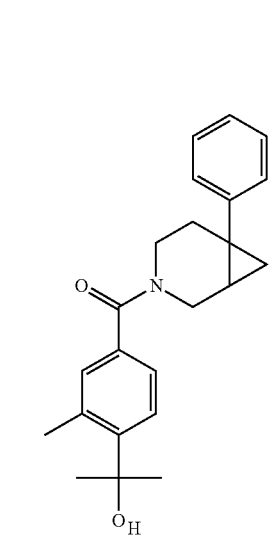
427

| 428 | 431 |
|---|---|
| 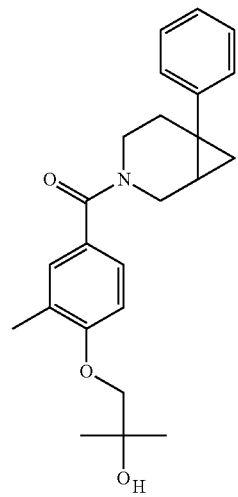 | 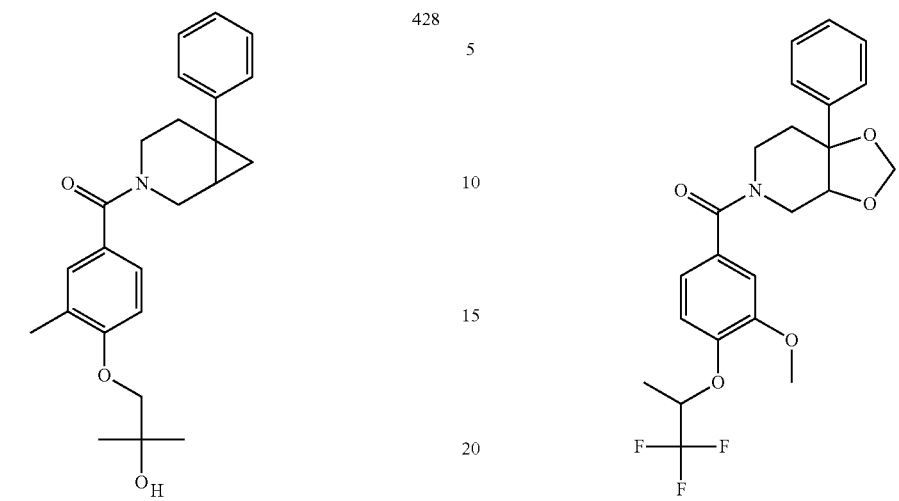 |
| 429 | 434 |
| 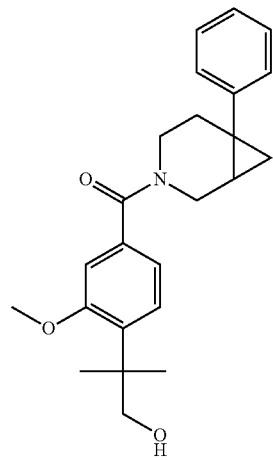 [SMILES: COc1cc(C(=O)N2CCC3(c4ccccc4)CC3C2)ccc1C(C)(C)CO] | 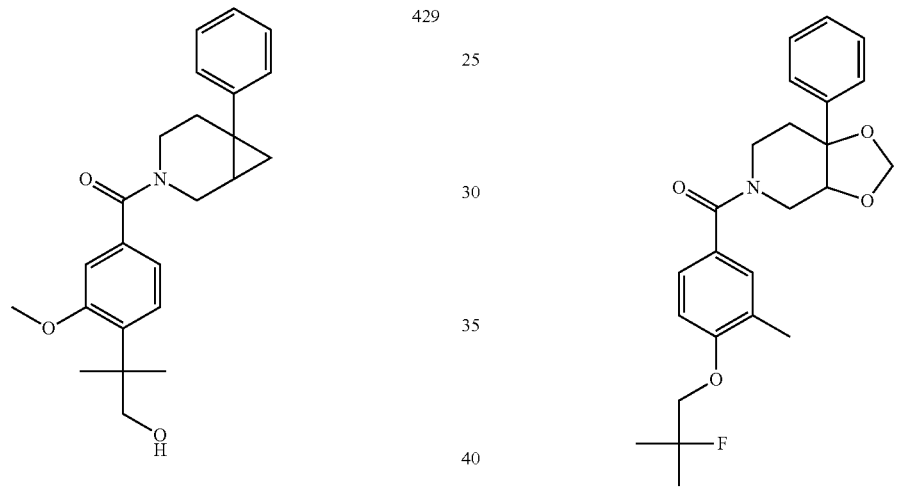 |
| 430 | 435 |
| 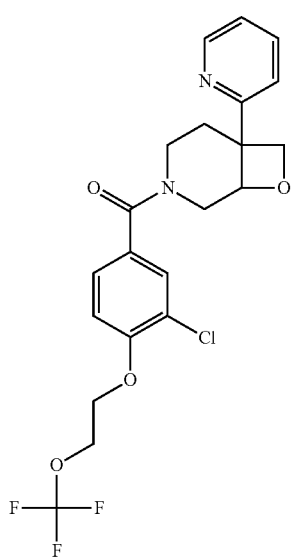 | 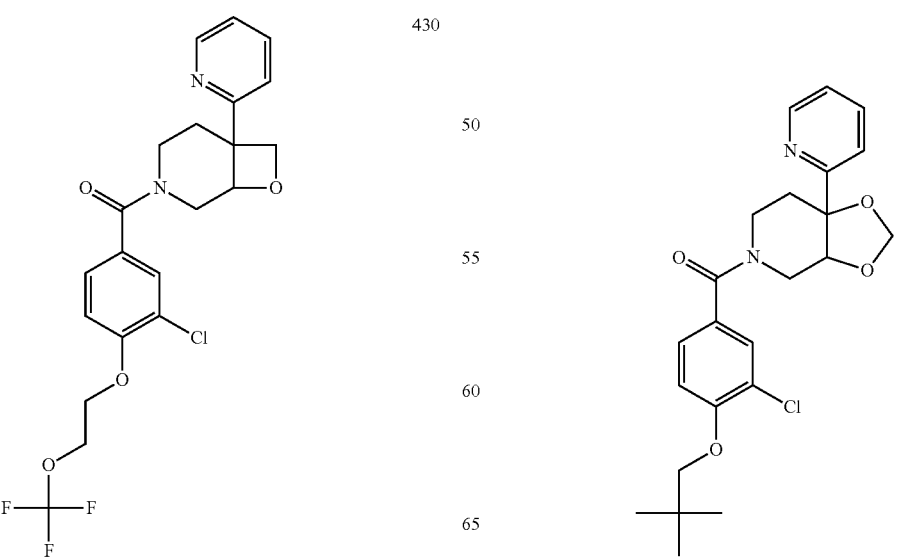 |

-continued
436
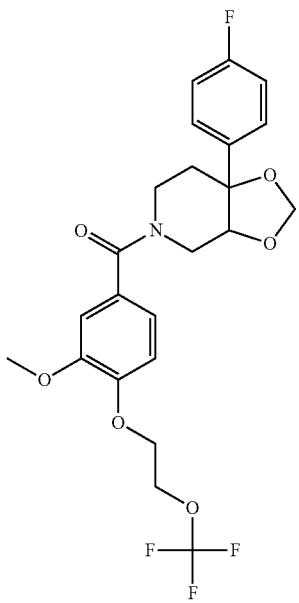 [SMILES: COc1cc(C(=O)N2CCC3(c4ccc(F)cc4)OCOC3C2)ccc1OCCOC(F)(F)F]
437
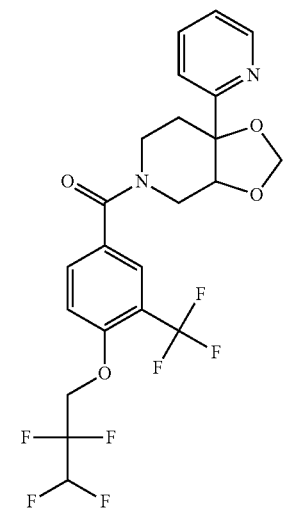
438
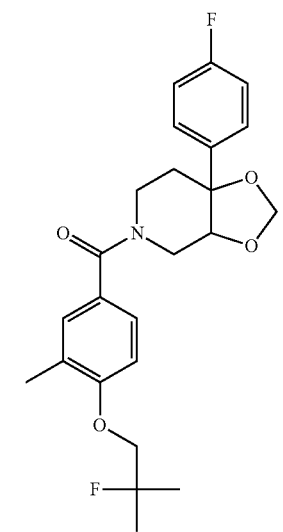 [SMILES: Cc1cc(C(=O)N2CCC3(c4ccc(F)cc4)OCOC3C2)ccc1OCC(C)(C)F]
-continued
441
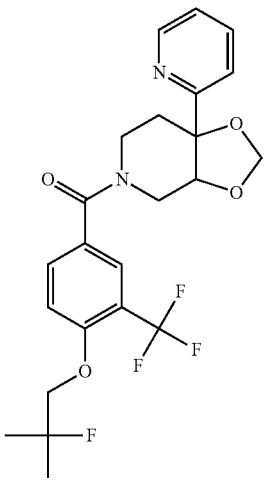 [SMILES: CC(C)(F)COc1ccc(C(=O)N2CCC3(c4ccccn4)OCOC3C2)cc1C(F)(F)F]
442
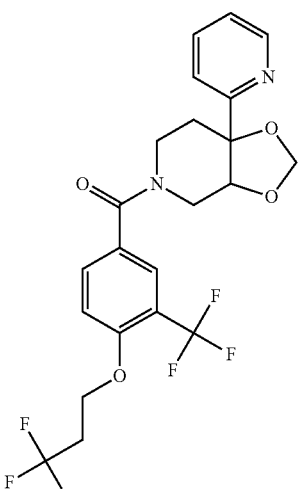
443
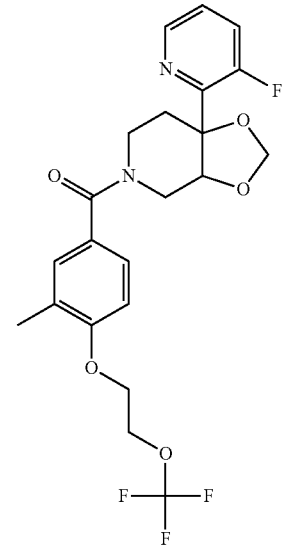 [SMILES: Cc1cc(C(=O)N2CCC3(c4ncccc4F)OCOC3C2)ccc1OCCOC(F)(F)F]

| 623 -continued | | 624 -continued | |
|---|---|---|---|
| 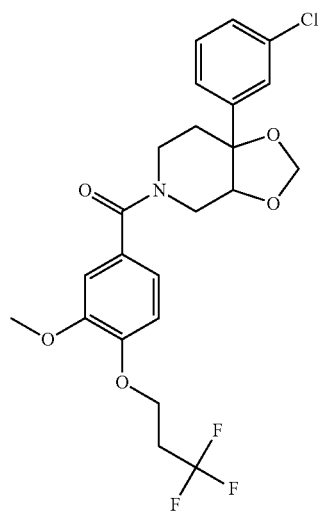 [SMILES: COc1cc(C(=O)N2CCC3(c4cccc(Cl)c4)OCOC3C2)ccc1OCCC(F)(F)F] | 445 | 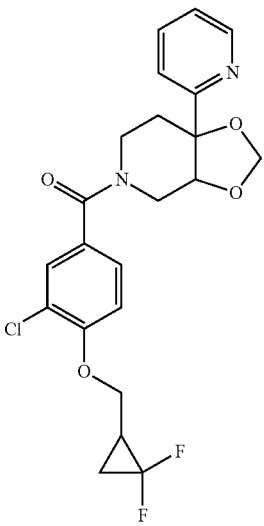 | 449 |
| 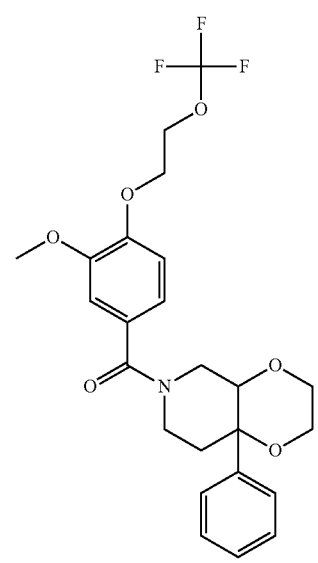 [SMILES: COc1cc(C(=O)N2CCC3(c4ccccc4)OCCOC3C2)ccc1OCCOC(F)(F)F] | 446 | 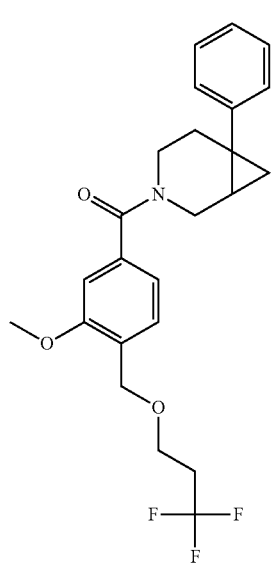 | 450 |
| 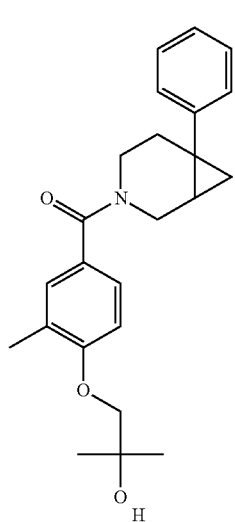 | 447 | 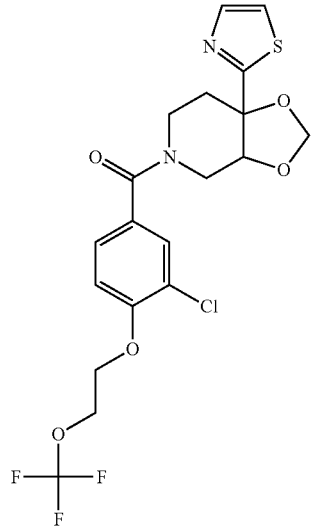 | 452 |

-continued
453
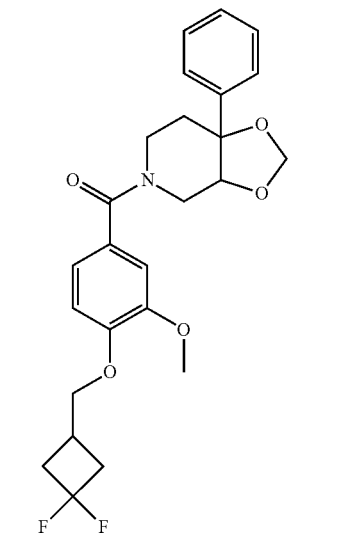 [SMILES: COc1cc(C(=O)N2CCC3(c4ccccc4)OCOC3C2)ccc1OCC1CC(F)(F)C1]
454
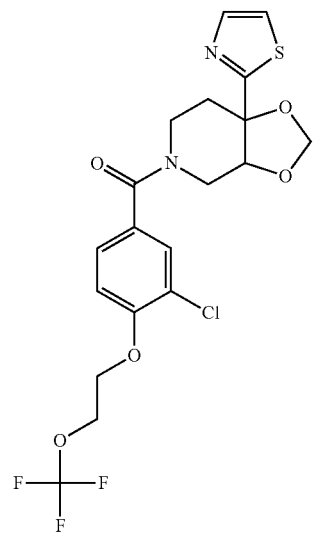
455
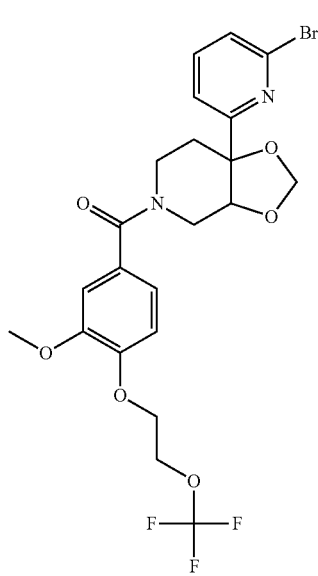 [SMILES: COc1cc(C(=O)N2CCC3(c4cccc(Br)n4)OCOC3C2)ccc1OCCOC(F)(F)F]
-continued
456
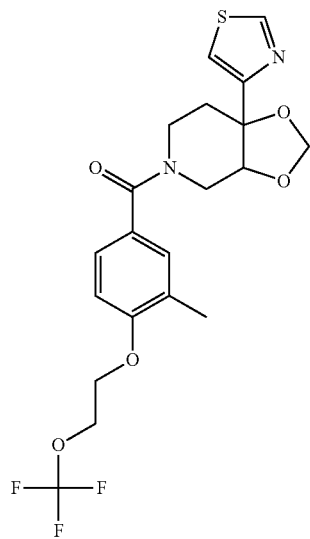 [SMILES: Cc1cc(C(=O)N2CCC3(c4cscn4)OCOC3C2)ccc1OCCOC(F)(F)F]
458
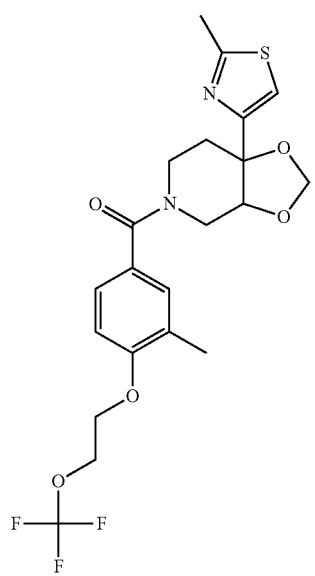 [SMILES: Cc1nc(C23CCN(C(=O)c4ccc(OCCOC(F)(F)F)c(C)c4)CC2OCO3)cs1]

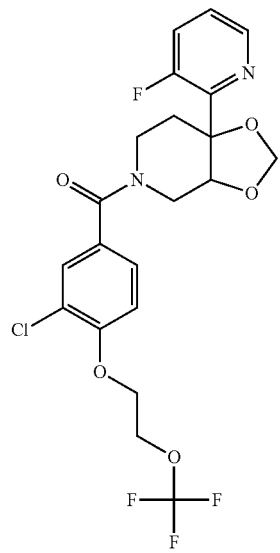 [SMILES: O=C(c1ccc(OCCOC(F)(F)F)c(Cl)c1)N1CCC2(c3ncccc3F)OCOC2C1]
459
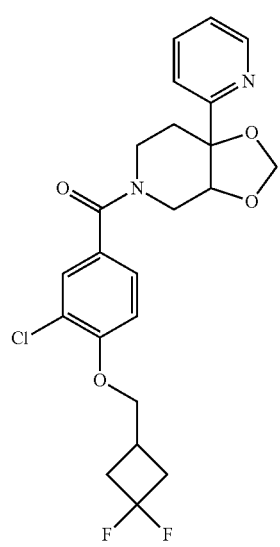 [SMILES: O=C(c1ccc(OCC2CC(F)(F)C2)c(Cl)c1)N1CCC2(c3ccccn3)OCOC2C1]
460
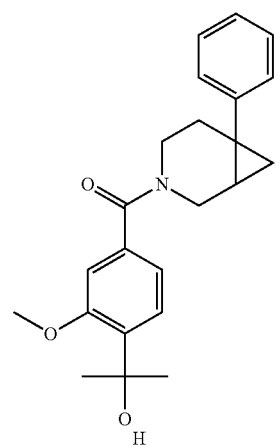
461
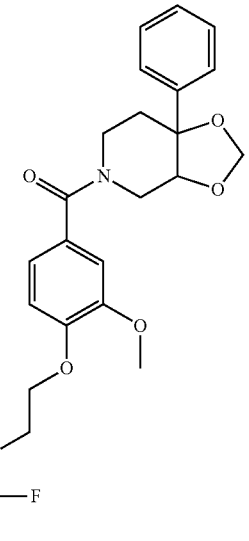
462
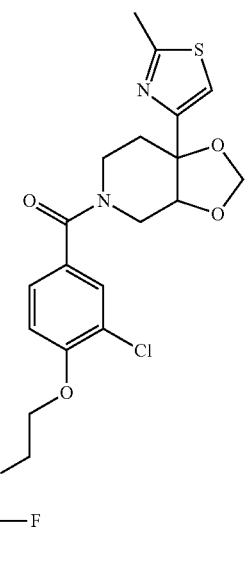
463

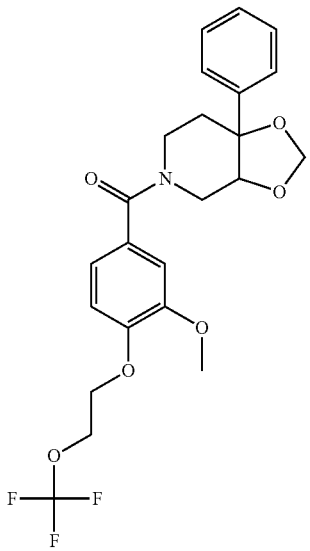
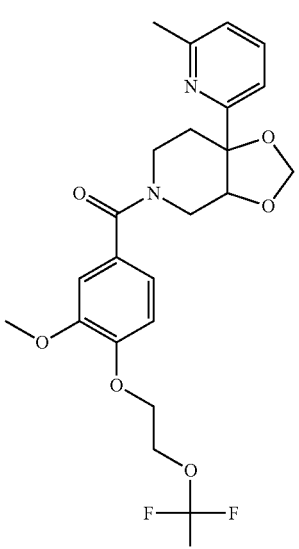
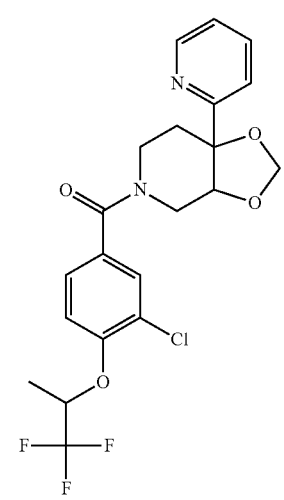

| 631 -continued | 632 -continued |
|---|---|
| 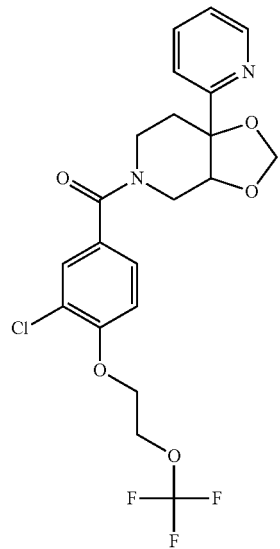 471 | 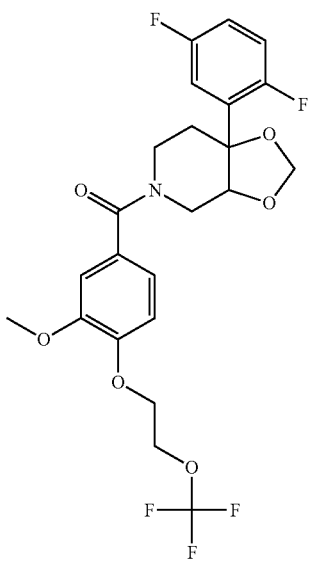 477 |
| 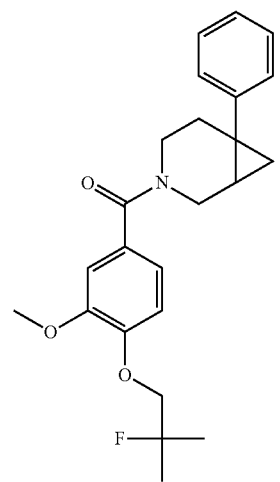 472 | |
| 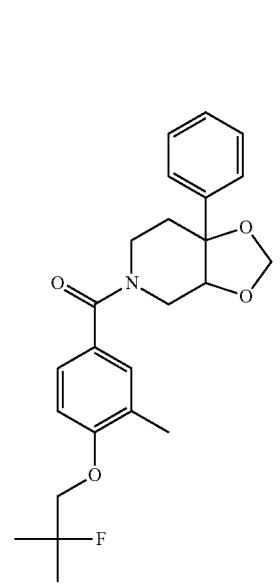 475 | 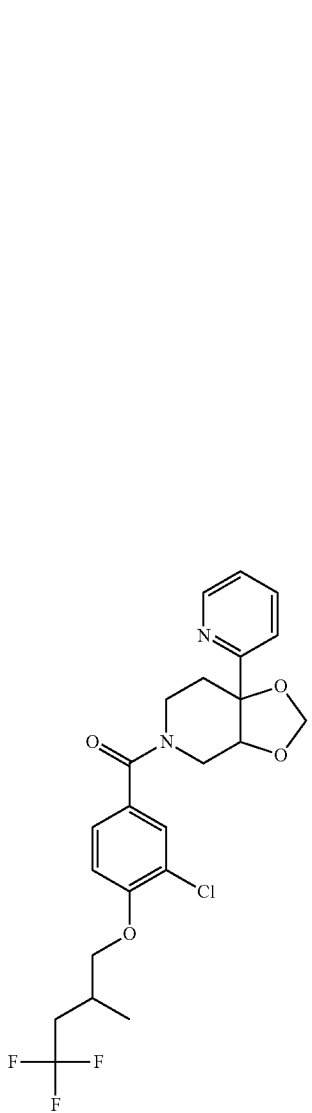 [SMILES: CC(COc1ccc(C(=O)N2CCC3(c4ccccn4)OCOC3C2)cc1Cl)CC(F)(F)F] 478 |

633
-continued
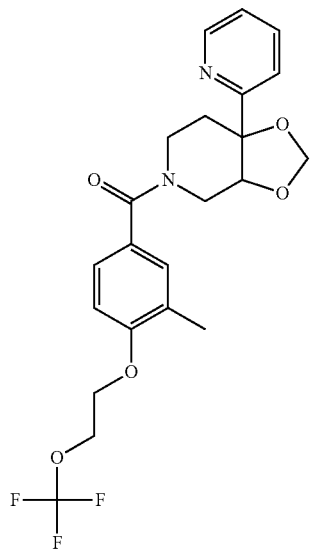
479
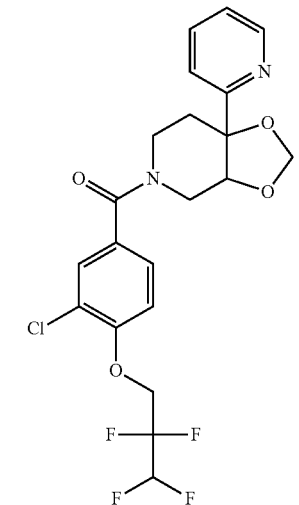 [SMILES: O=C(c1ccc(OCC(F)(F)C(F)F)c(Cl)c1)N1CCC2(c3ccccn3)OCOC2C1]
480
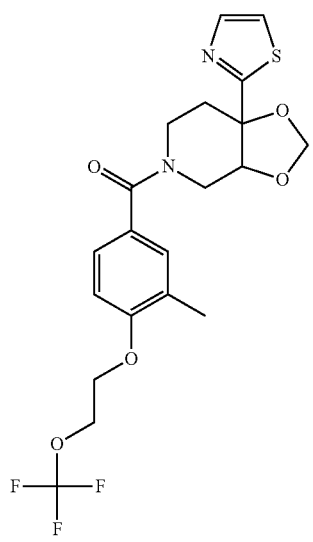 [SMILES: Cc1cc(C(=O)N2CCC3(c4nccs4)OCOC3C2)ccc1OCCOC(F)(F)F]
481
634
-continued
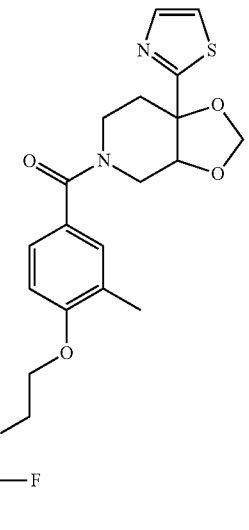
482
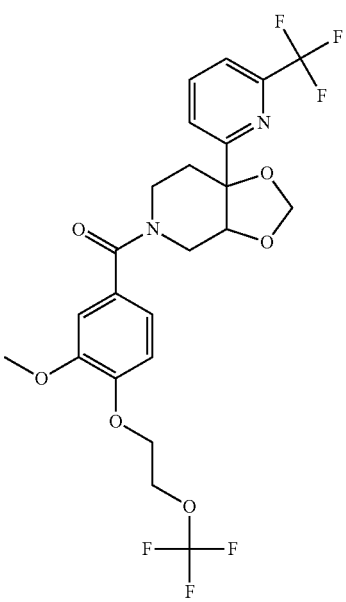 [SMILES: COc1cc(C(=O)N2CCC3(c4cccc(C(F)(F)F)n4)OCOC3C2)ccc1OCCOC(F)(F)F]
483
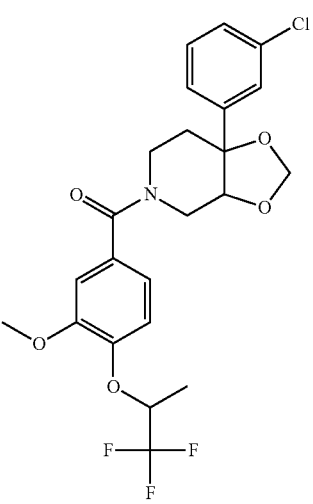 [SMILES: COc1cc(C(=O)N2CCC3(c4cccc(Cl)c4)OCOC3C2)ccc1OC(C)C(F)(F)F]
484

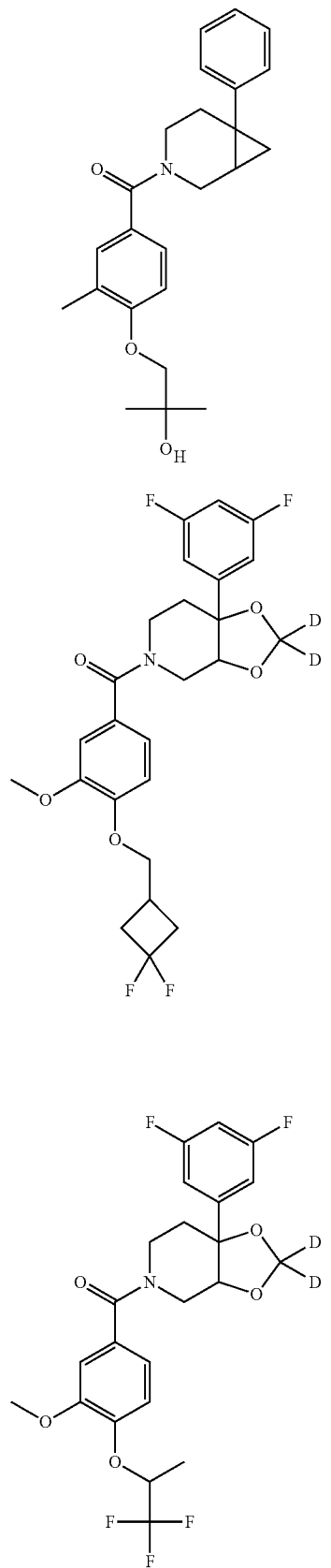
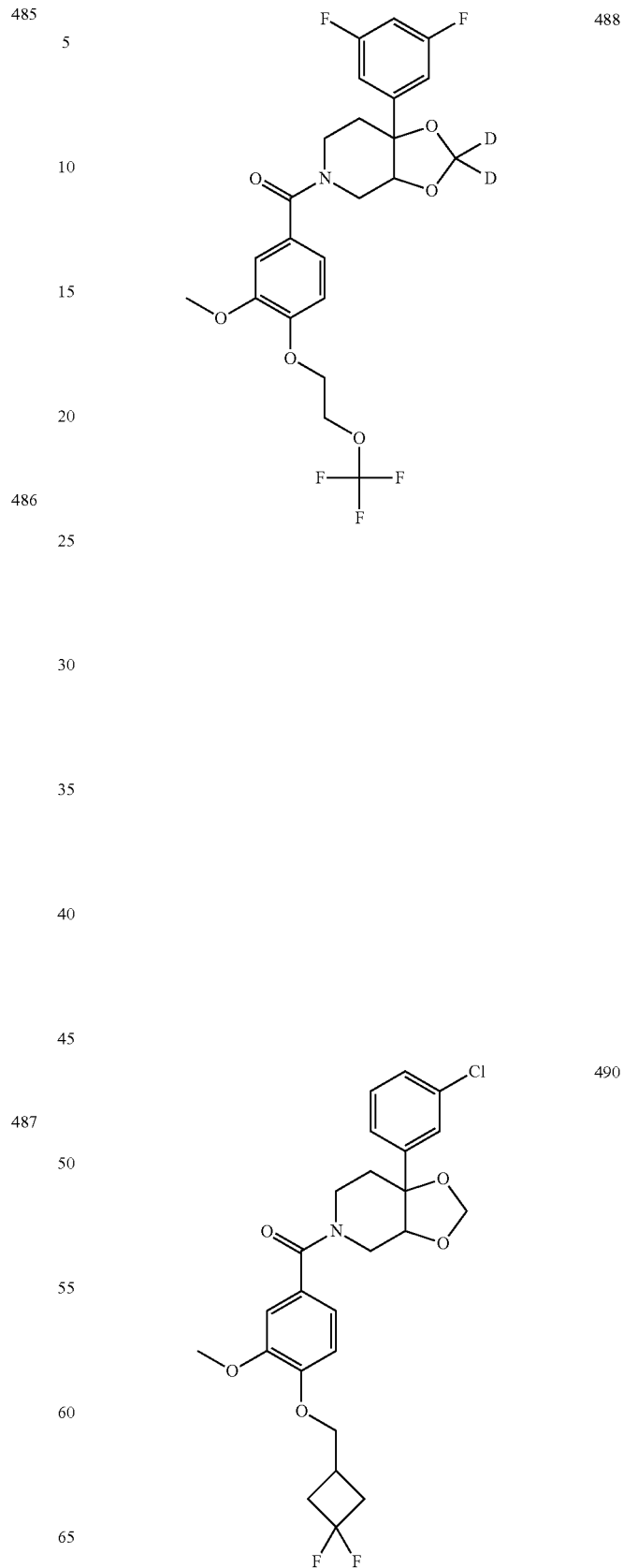

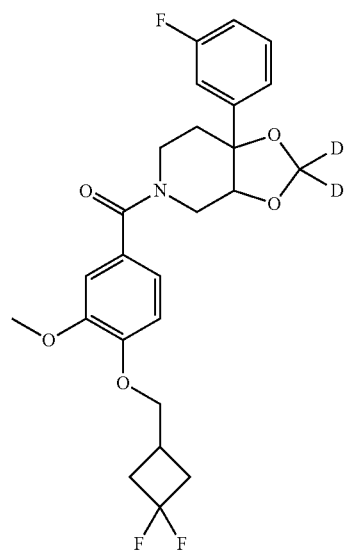 [SMILES: [2H]C1([2H])OC2CN(C(=O)c3ccc(OCC4CC(F)(F)C4)c(OC)c3)CCC2(c2cccc(F)c2)O1]
491
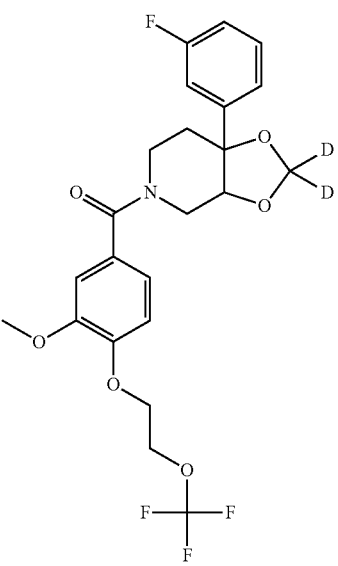
495
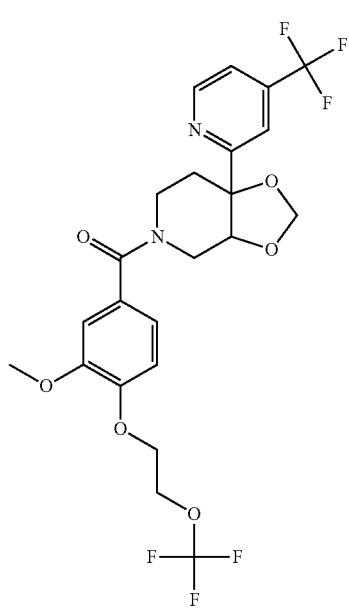 [SMILES: COc1cc(C(=O)N2CCC3(c4cc(C(F)(F)F)ccn4)OCOC3C2)ccc1OCCOC(F)(F)F]
493
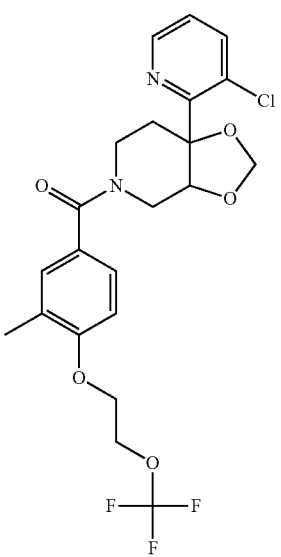 [SMILES: Cc1cc(C(=O)N2CCC3(c4ncccc4Cl)OCOC3C2)ccc1OCCOC(F)(F)F]
496

498
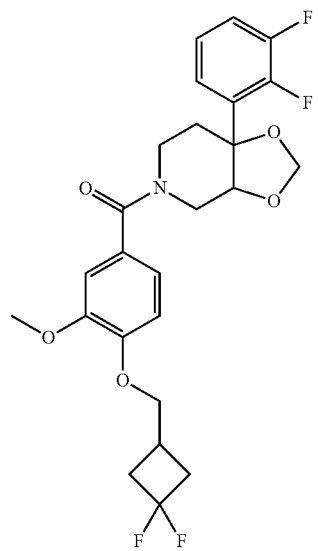 [SMILES: COc1cc(C(=O)N2CCC3(c4cccc(F)c4F)OCOC3C2)ccc1OCC1CC(F)(F)C1]
500
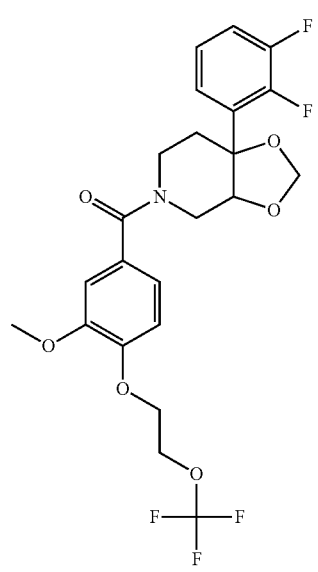
501
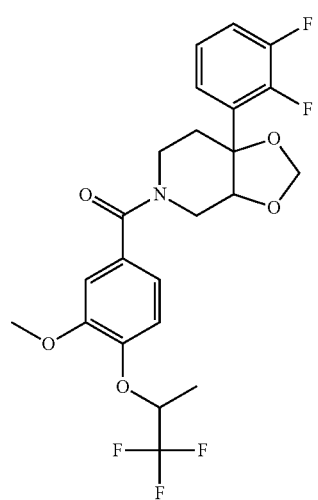 [SMILES: COc1cc(C(=O)N2CCC3(c4cccc(F)c4F)OCOC3C2)ccc1OC(C)C(F)(F)F]
504
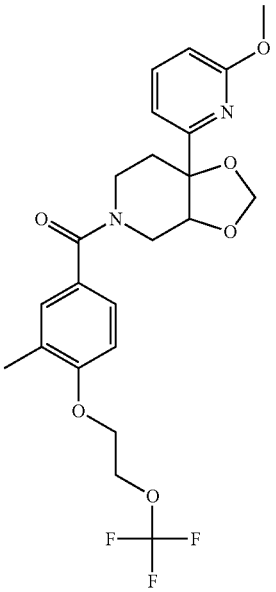
506
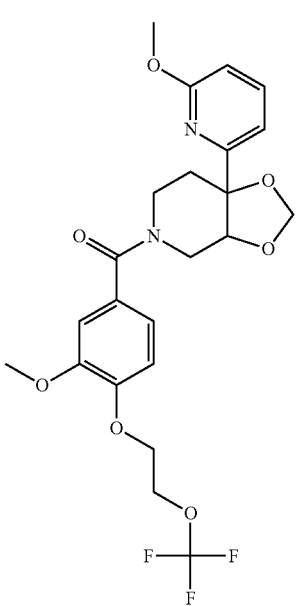 [SMILES: COc1cccc(C23CCN(C(=O)c4ccc(OCCOC(F)(F)F)c(OC)c4)CC2OCO3)n1]

-continued
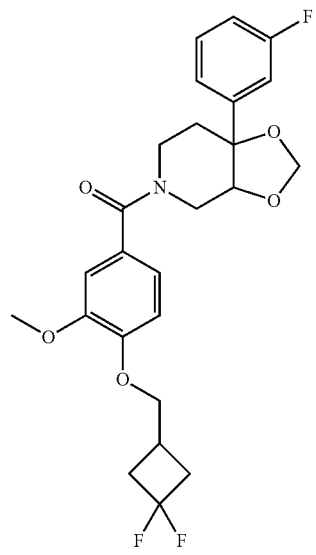 [SMILES: COc1cc(C(=O)N2CCC3(c4cccc(F)c4)OCOC3C2)ccc1OCC1CC(F)(F)C1]
507
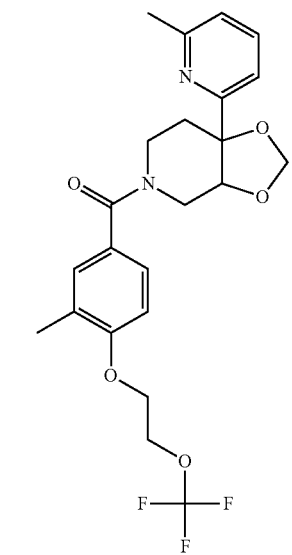 [SMILES: Cc1cccc(C23CCN(C(=O)c4ccc(OCCOC(F)(F)F)c(C)c4)CC2OCO3)n1]
508
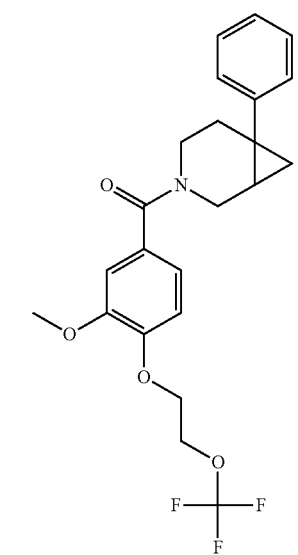
509
-continued
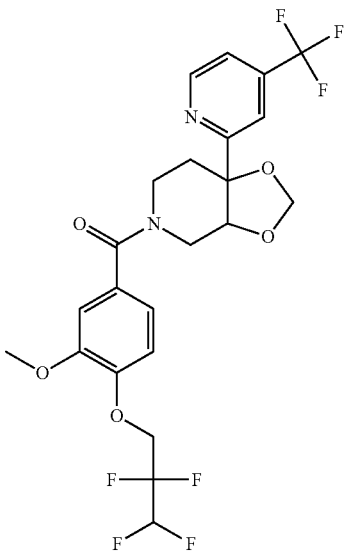 [SMILES: COc1cc(C(=O)N2CCC3(c4cc(C(F)(F)F)ccn4)OCOC3C2)ccc1OCC(F)(F)C(F)F]
511
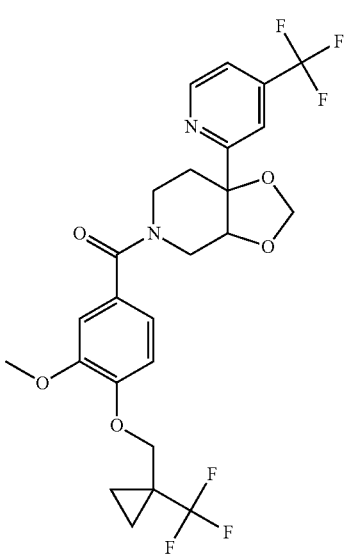 [SMILES: COc1cc(C(=O)N2CCC3(c4cc(C(F)(F)F)ccn4)OCOC3C2)ccc1OCC1(C(F)(F)F)CC1]
512
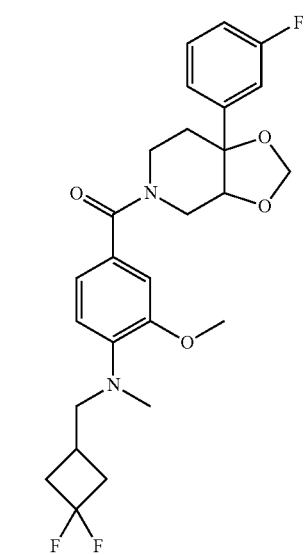 [SMILES: COc1cc(C(=O)N2CCC3(c4cccc(F)c4)OCOC3C2)ccc1N(C)CC1CC(F)(F)C1]
513

| 643 -continued | 644 -continued |
|---|---|
| 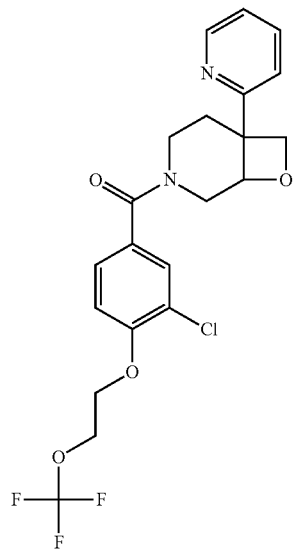 515 | 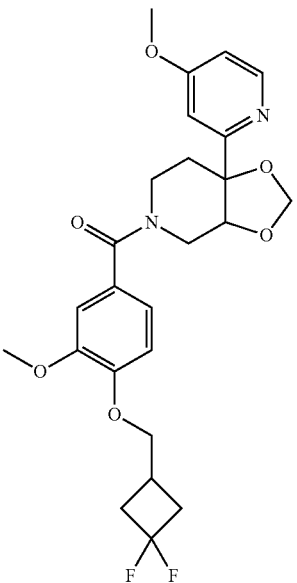 517 |
| 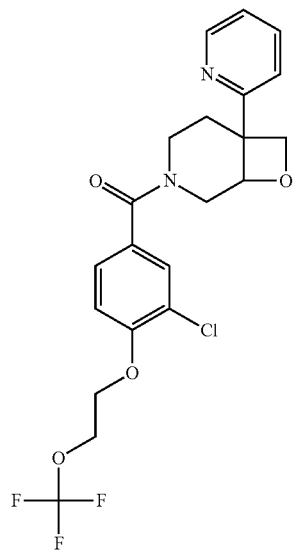 516 | 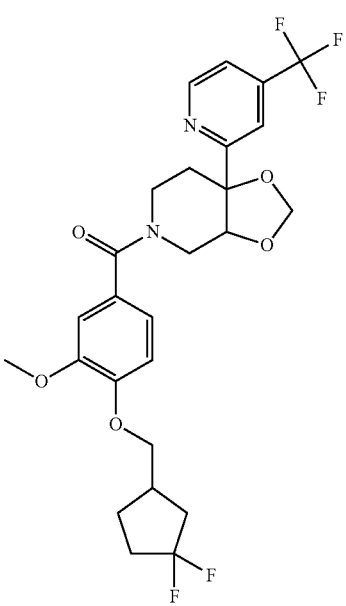 [SMILES: COc1cc(C(=O)N2CCC3(c4cc(C(F)(F)F)ccn4)OCOC3C2)ccc1OCC1CCC(F)(F)C1] 518 |

| 645 -continued | | 646 -continued | |
|---|---|---|---|
| 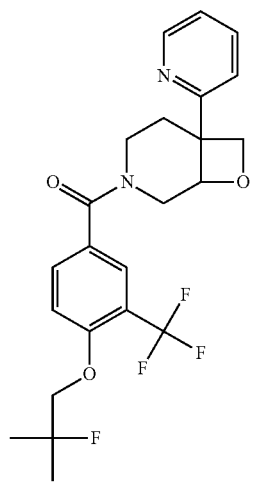 [SMILES: CC(C)(F)COc1ccc(C(=O)N2CCC3(c4ccccn4)COC3C2)cc1C(F)(F)F] | 519 | 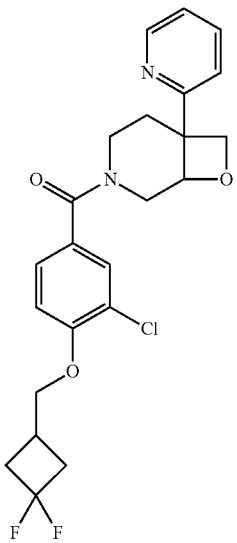 | 522 |
| 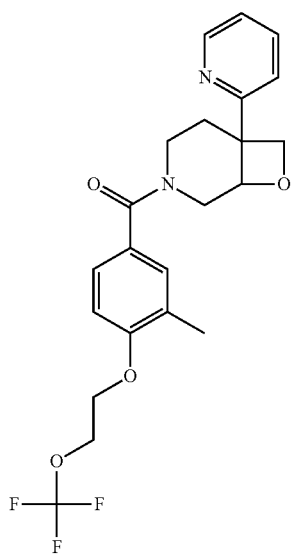 [SMILES: Cc1cc(C(=O)N2CCC3(c4ccccn4)COC3C2)ccc1OCCOC(F)(F)F] | 520 | 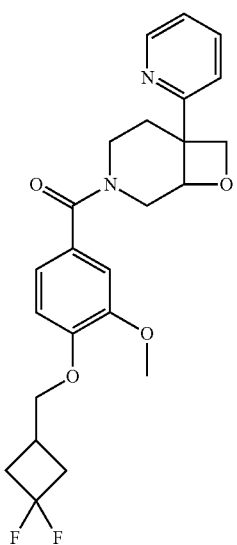 | 524 |
| 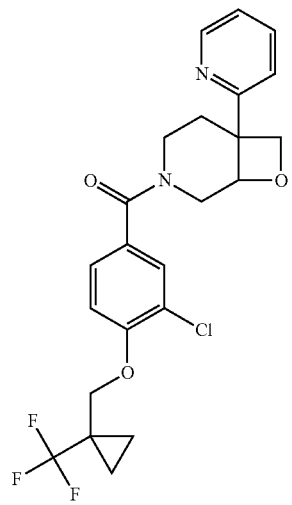 [SMILES: O=C(c1ccc(OCC2(C(F)(F)F)CC2)c(Cl)c1)N1CCC2(c3ccccn3)COC2C1] | 521 | 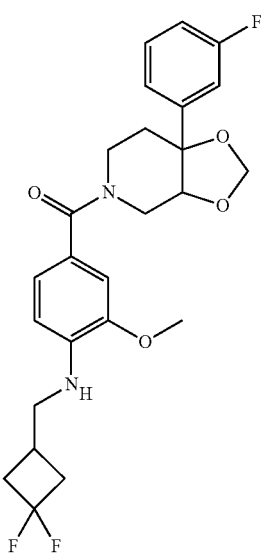 | 525 |

| 647 -continued | | 648 -continued | |
|---|---|---|---|
| 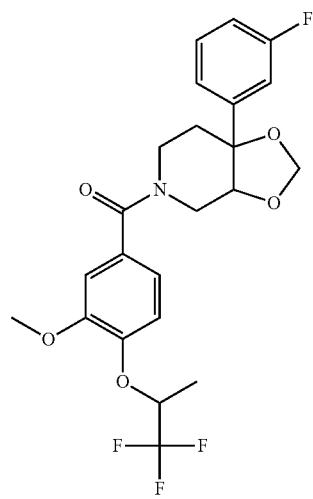 | 526 | 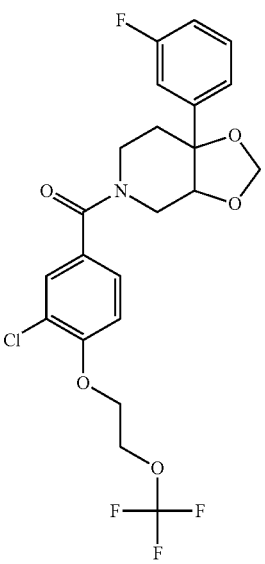 | 530 |
| 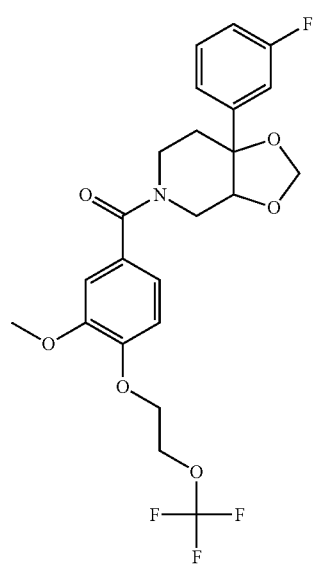 [SMILES: COc1cc(C(=O)N2CCC3(c4cccc(F)c4)OCOC3C2)ccc1OCCOC(F)(F)F] | 528 | 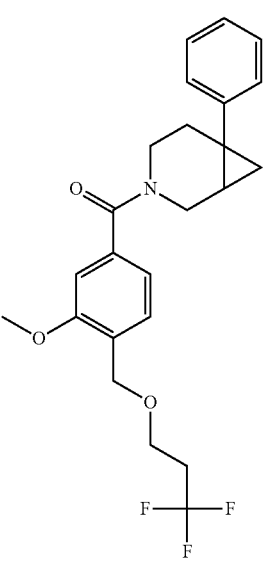 | 531 |
| 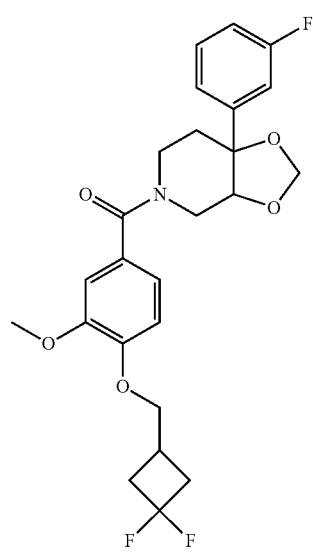 [SMILES: COc1cc(C(=O)N2CCC3(c4cccc(F)c4)OCOC3C2)ccc1OCC1CC(F)(F)C1] | 529 | 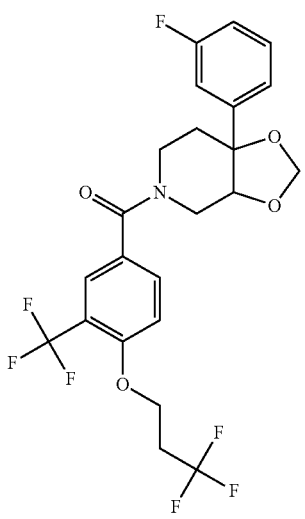 [SMILES: O=C(c1ccc(OCCC(F)(F)F)c(C(F)(F)F)c1)N1CCC2(c3cccc(F)c3)OCOC2C1] | 532 |

649
-continued
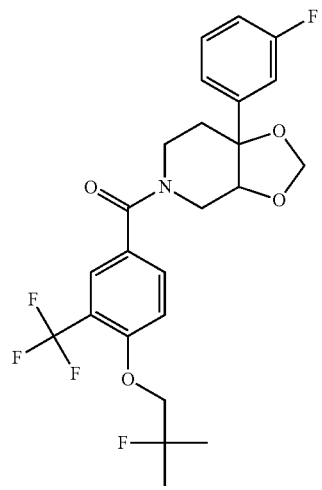 [SMILES: CC(C)(F)COc1ccc(C(=O)N2CCC3(c4cccc(F)c4)OCOC3C2)cc1C(F)(F)F]
533
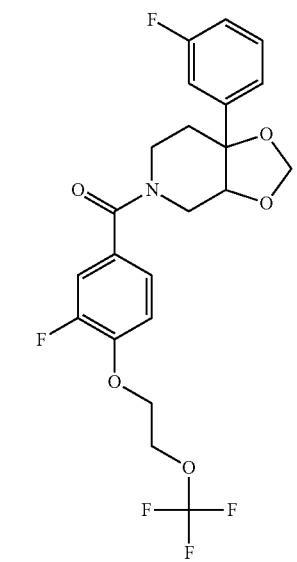 [SMILES: O=C(c1ccc(OCCOC(F)(F)F)c(F)c1)N1CCC2(c3cccc(F)c3)OCOC2C1]
534
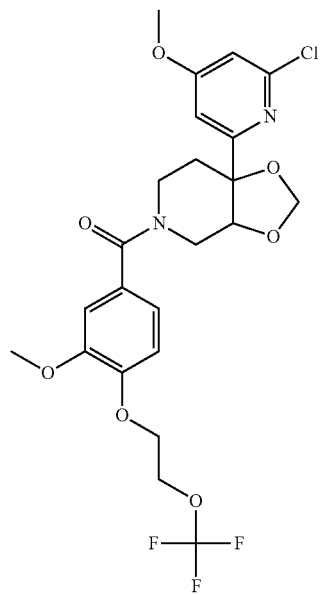 [SMILES: COc1cc(Cl)nc(C23CCN(C(=O)c4ccc(OCCOC(F)(F)F)c(OC)c4)CC2OCO3)c1]
535
650
-continued
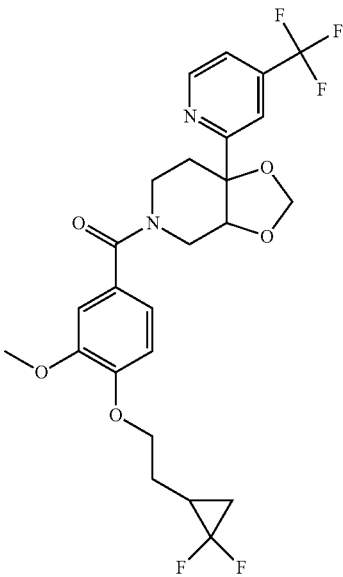 [SMILES: COc1cc(C(=O)N2CCC3(c4cc(C(F)(F)F)ccn4)OCOC3C2)ccc1OCCC1CC1(F)F]
536
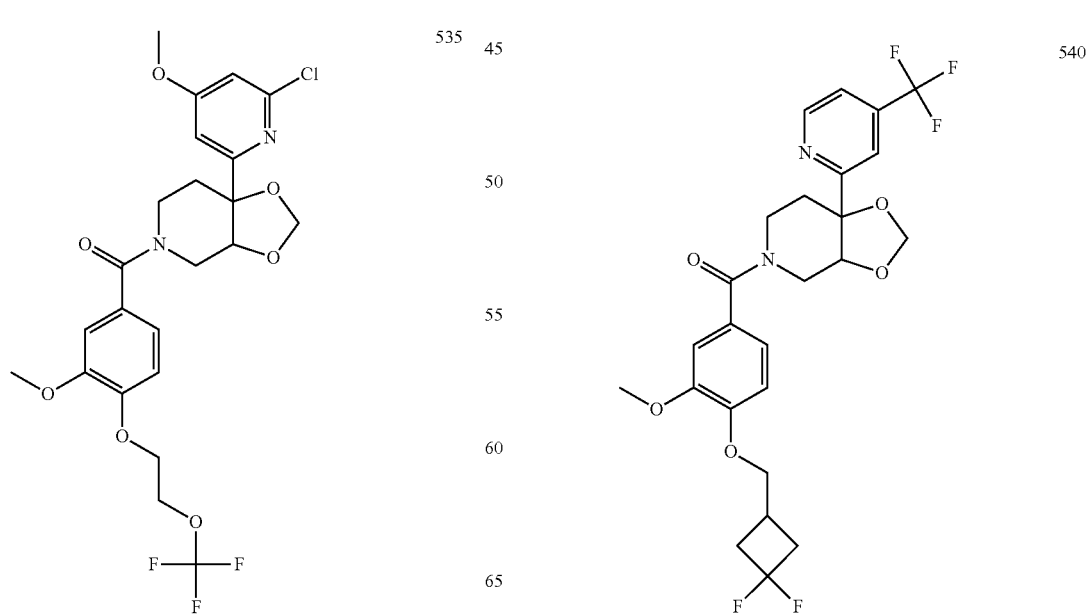
540

651
-continued
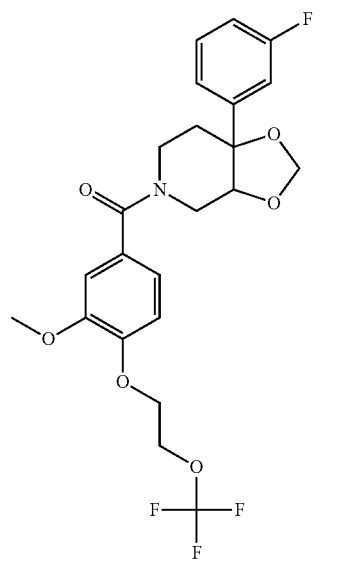 [SMILES: COc1cc(C(=O)N2CCC3(c4cccc(F)c4)OCOC3C2)ccc1OCCOC(F)(F)F]
542
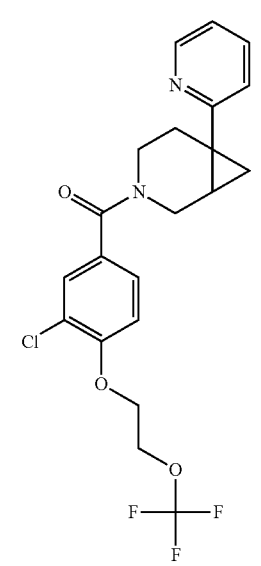 [SMILES: O=C(c1ccc(OCCOC(F)(F)F)c(Cl)c1)N1CCC2(c3ccccn3)CC2C1]
552
553
652
-continued
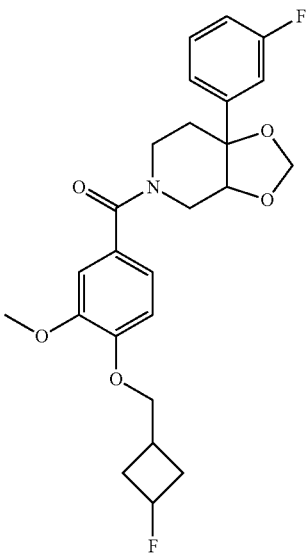 [SMILES: COc1cc(C(=O)N2CCC3(c4cccc(F)c4)OCOC3C2)ccc1OCC1CC(F)C1]
554
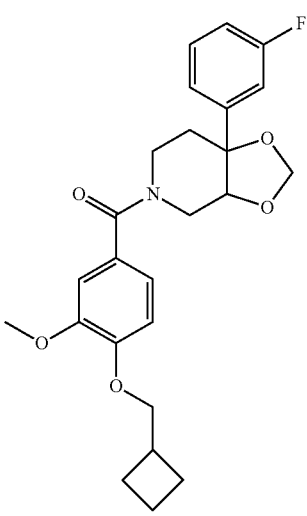 [SMILES: COc1cc(C(=O)N2CCC3(c4cccc(F)c4)OCOC3C2)ccc1OCC1CCC1]
555
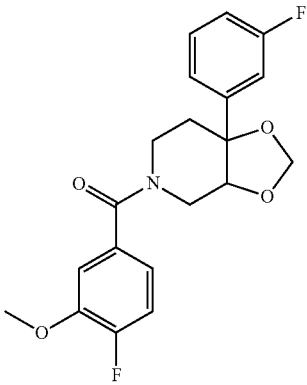 [SMILES: COc1cc(C(=O)N2CCC3(c4cccc(F)c4)OCOC3C2)ccc1F]
556

653
-continued
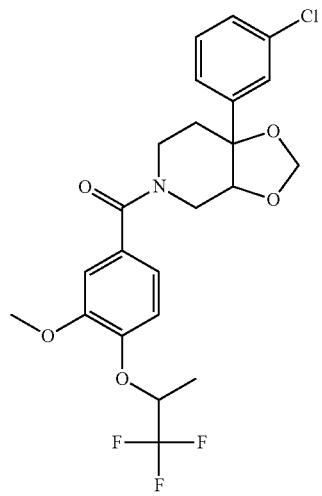 [SMILES: COc1cc(C(=O)N2CCC3(c4cccc(Cl)c4)OCOC3C2)ccc1OC(C)C(F)(F)F]
557
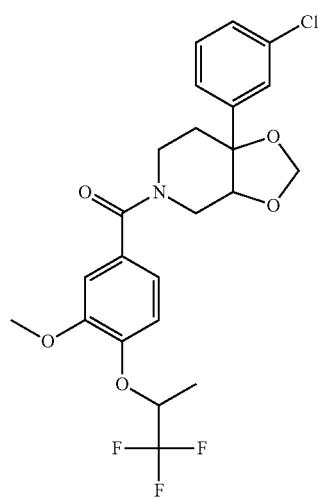 [SMILES: COc1cc(C(=O)N2CCC3(c4cccc(Cl)c4)OCOC3C2)ccc1OC(C)C(F)(F)F]
558
562
654
-continued
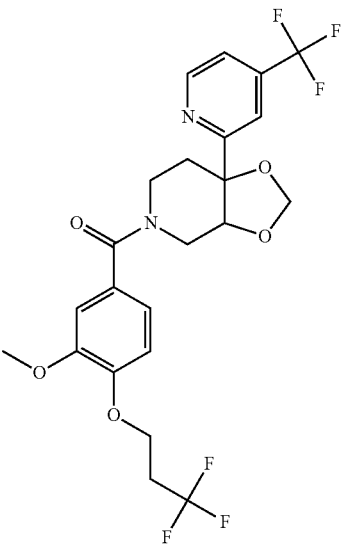 [SMILES: COc1cc(C(=O)N2CCC3(c4cc(C(F)(F)F)ccn4)OCOC3C2)ccc1OCCC(F)(F)F]
565
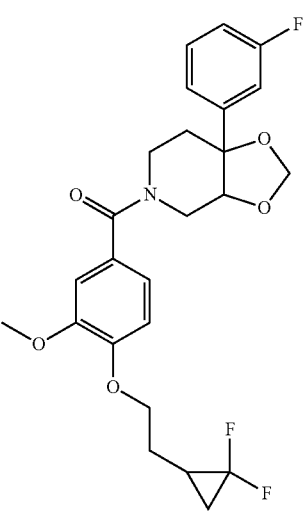 [SMILES: COc1cc(C(=O)N2CCC3(c4cccc(F)c4)OCOC3C2)ccc1OCCC1CC1(F)F]
566
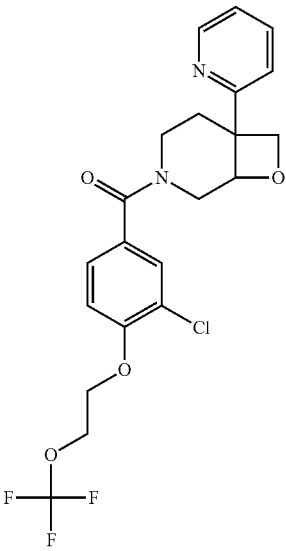
567

| 655 -continued | 656 -continued |
|---|---|
| 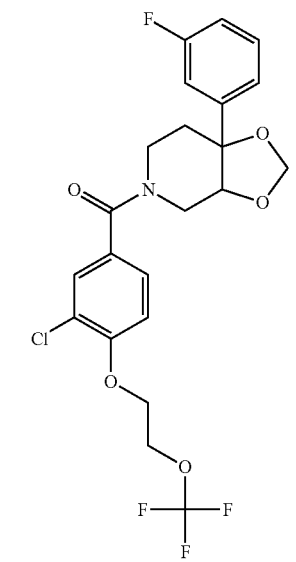 569 | 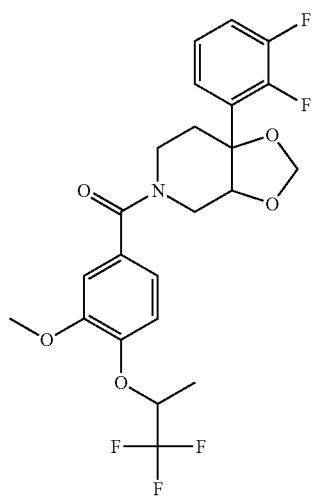 572 |
| 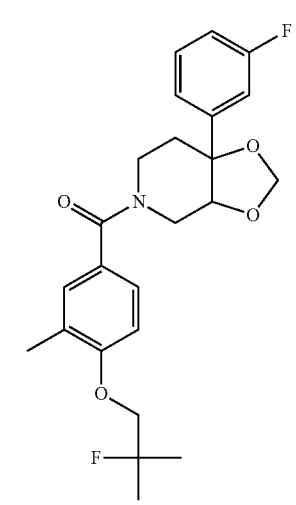 [SMILES: Cc1cc(C(=O)N2CCC3(c4cccc(F)c4)OCOC3C2)ccc1OCC(C)(C)F] 570 | 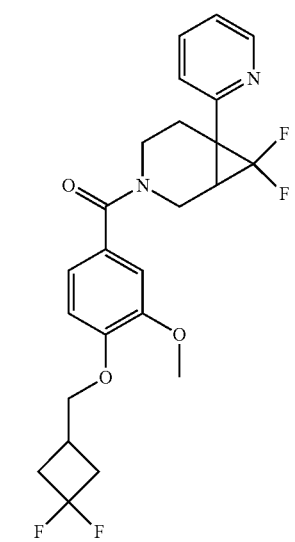 573 |
| 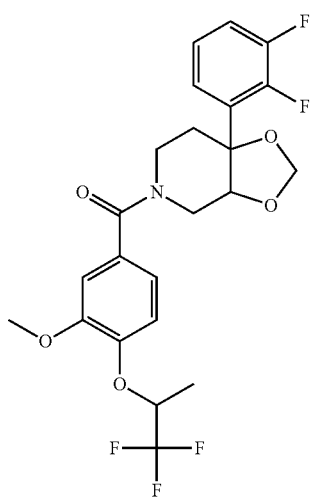 [SMILES: COc1cc(C(=O)N2CCC3(c4cccc(F)c4F)OCOC3C2)ccc1OC(C)C(F)(F)F] 571 | 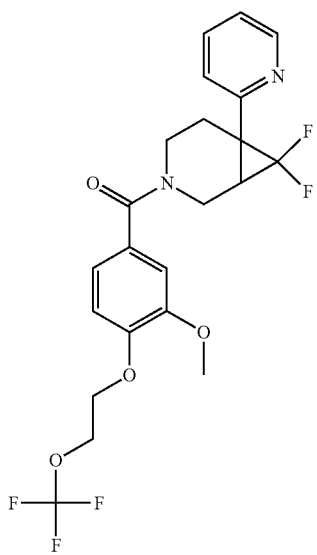 [SMILES: COc1cc(C(=O)N2CCC3(c4ccccn4)C(C2)C3(F)F)ccc1OCCOC(F)(F)F] 574 |

| 575 | 588 |
|---|---|
| 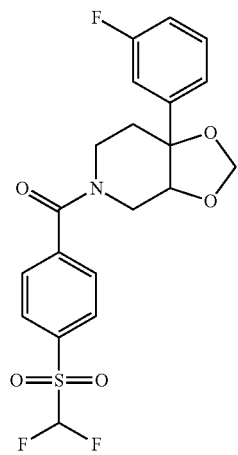 [SMILES: O=C(c1ccc(S(=O)(=O)C(F)F)cc1)N1CCC2(c3cccc(F)c3)OCOC2C1] | 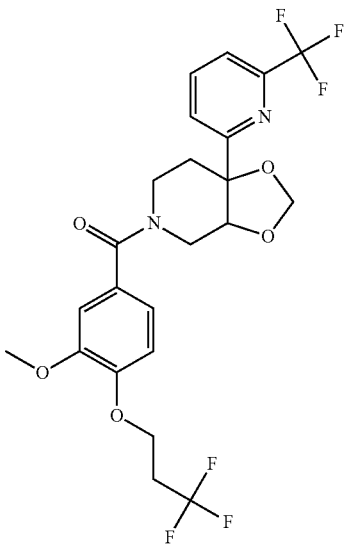 |
| 580 | |
|---|---|
| 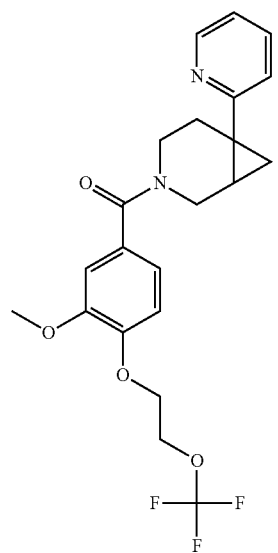 [SMILES: COc1cc(C(=O)N2CCC3(c4ccccn4)CC3C2)ccc1OCCOC(F)(F)F] | |
| 581 | 589 |
|---|---|
| 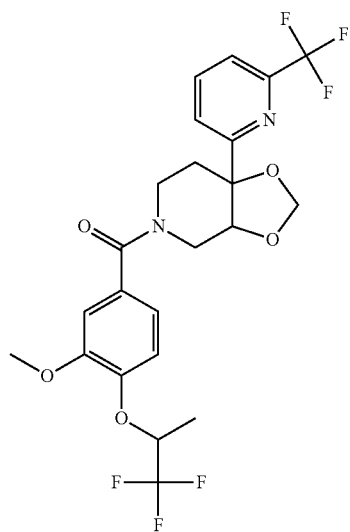 [SMILES: COc1cc(C(=O)N2CCC3(c4cccc(C(F)(F)F)n4)OCOC3C2)ccc1OC(C)C(F)(F)F] | 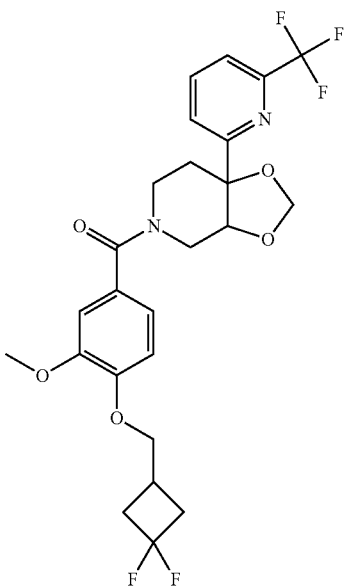 [SMILES: COc1cc(C(=O)N2CCC3(c4cccc(C(F)(F)F)n4)OCOC3C2)ccc1OCC1CC(F)(F)C1] |

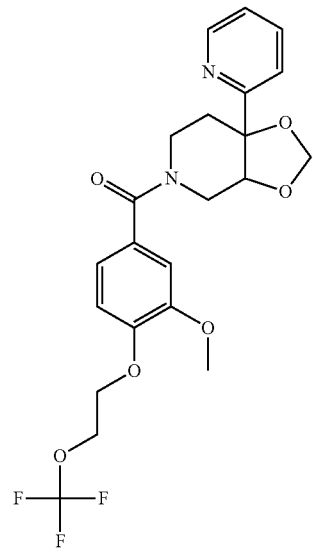
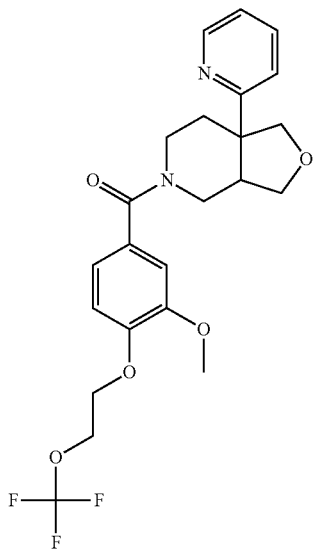 [SMILES: COc1cc(C(=O)N2CCC3(c4ccccn4)COCC3C2)ccc1OCCOC(F)(F)F]

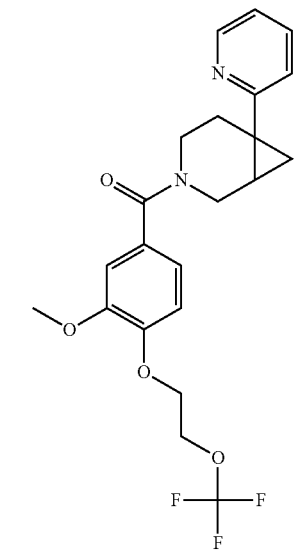 [SMILES: COc1cc(C(=O)N2CCC3(c4ccccn4)CC3C2)ccc1OCCOC(F)(F)F]
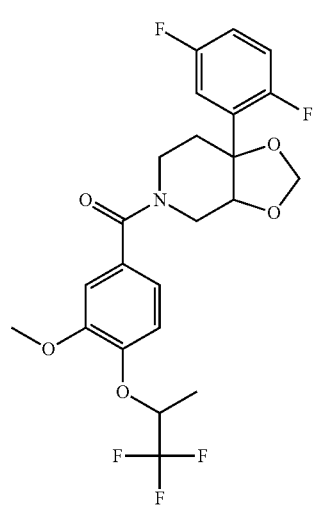 [SMILES: COc1cc(C(=O)N2CCC3(c4cc(F)ccc4F)OCOC3C2)ccc1OC(C)C(F)(F)F]
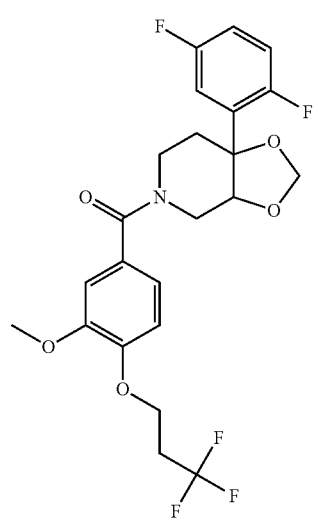 [SMILES: COc1cc(C(=O)N2CCC3(c4cc(F)ccc4F)OCOC3C2)ccc1OCCC(F)(F)F]
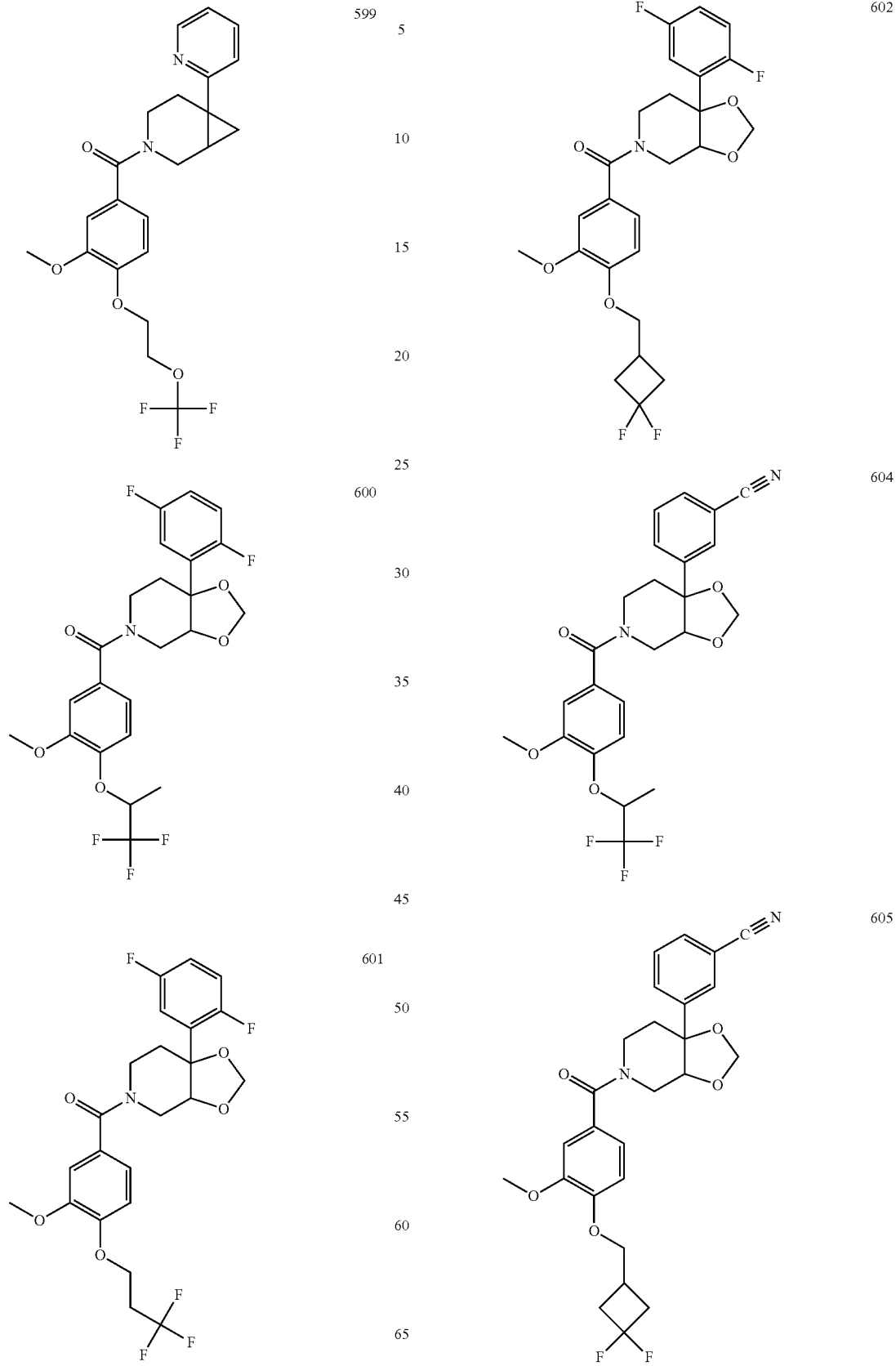

663
-continued
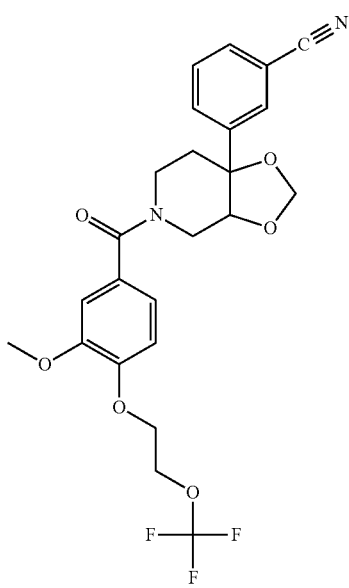 [SMILES: COc1cc(C(=O)N2CCC3(c4cccc(C#N)c4)OCOC3C2)ccc1OCCOC(F)(F)F]
607
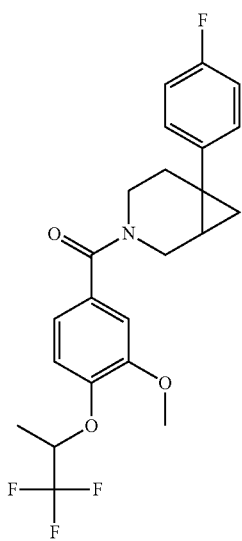
611
664
-continued
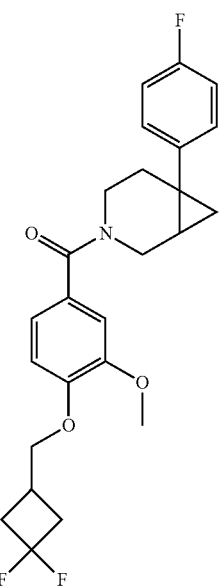
612
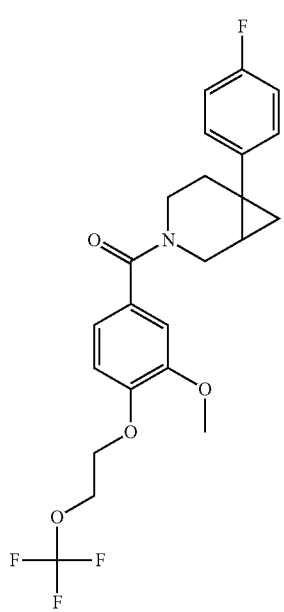 [SMILES: COc1cc(C(=O)N2CCC3(c4ccc(F)cc4)CC3C2)ccc1OCCOC(F)(F)F]
614

| 665 -continued | 666 -continued |
|---|---|
| 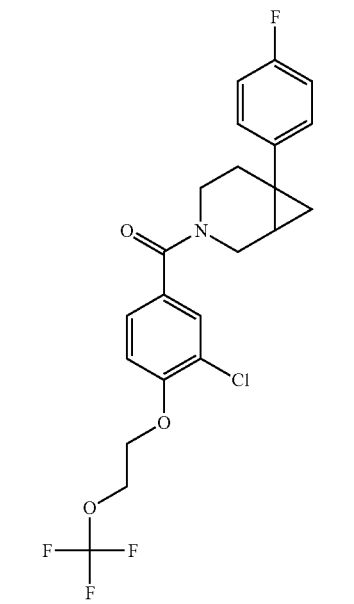 [SMILES: O=C(c1ccc(OCCOC(F)(F)F)c(Cl)c1)N1CCC2(c3ccc(F)cc3)CC2C1] 615 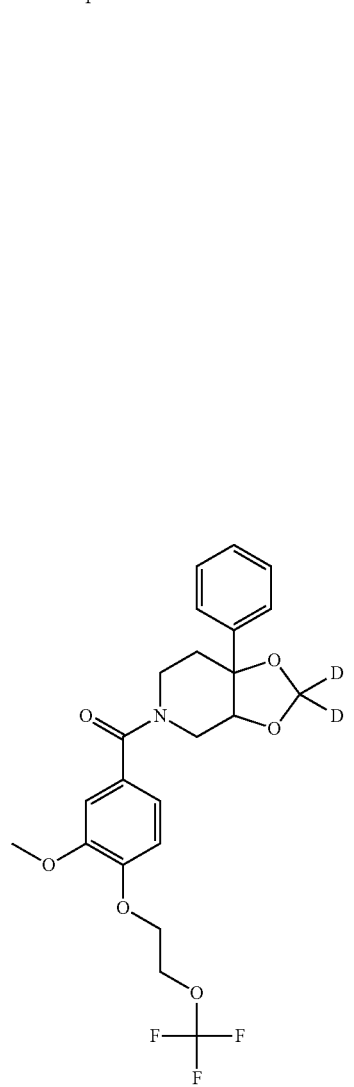 616 | 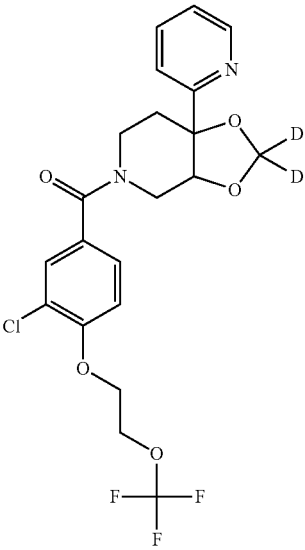 [SMILES: [2H]C1([2H])OC2CN(C(=O)c3ccc(OCCOC(F)(F)F)c(Cl)c3)CCC2(c2ccccn2)O1] 618 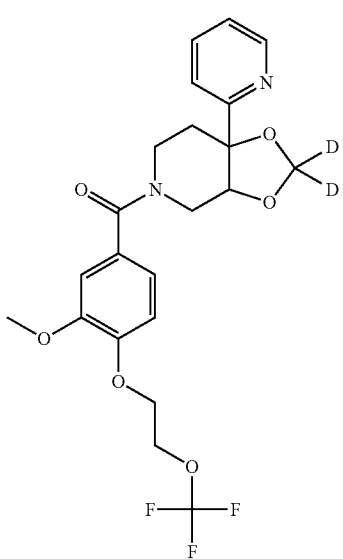 619 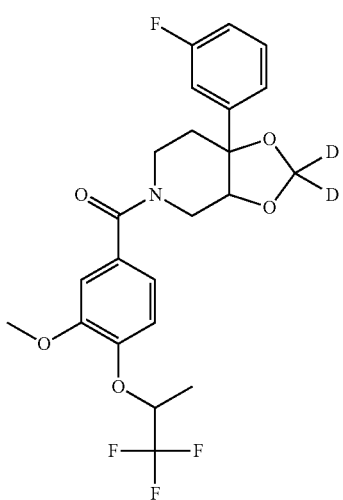 [SMILES: [2H]C1([2H])OC2CN(C(=O)c3ccc(OC(C)C(F)(F)F)c(OC)c3)CCC2(c2cccc(F)c2)O1] 621 |

-continued

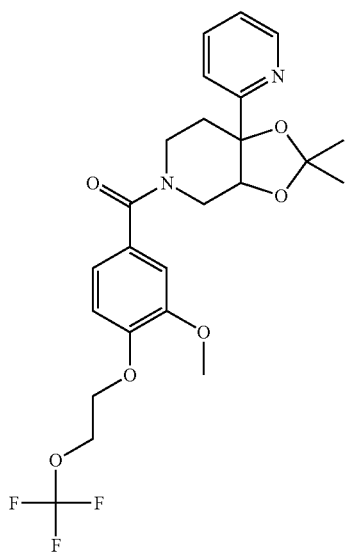 [SMILES: COc1cc(C(=O)N2CCC3(c4ccccn4)OC(C)(C)OC3C2)ccc1OCCOC(F)(F)F]

624

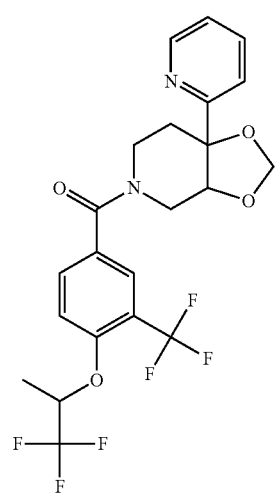 [SMILES: CC(Oc1ccc(C(=O)N2CCC3(c4ccccn4)OCOC3C2)cc1C(F)(F)F)C(F)(F)F]

625

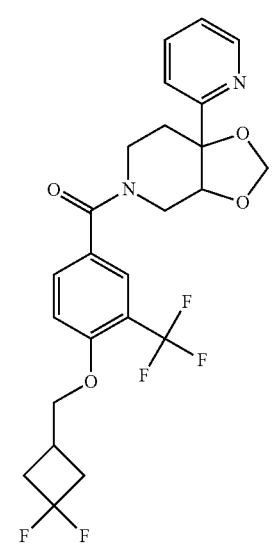 [SMILES: O=C(c1ccc(OCC2CC(F)(F)C2)c(C(F)(F)F)c1)N1CCC2(c3ccccn3)OCOC2C1]

626

-continued

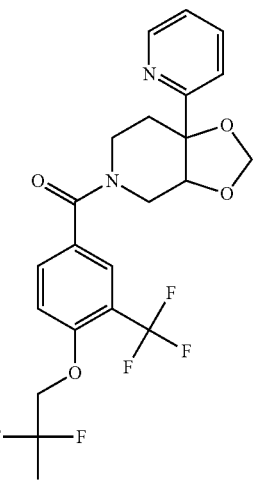

627

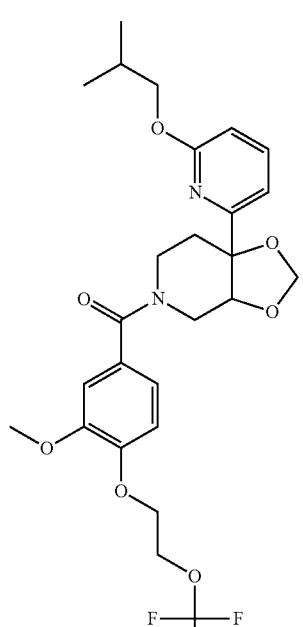

628

26. A pharmaceutical composition comprising the compound of claim 1 and a pharmaceutically acceptable carrier.

27. A method of inhibiting a voltage-gated sodium ion channel in:
   a patient; or
   a biological sample;
   comprising administering to the patient, or contacting the biological sample, with the compound of claim 1.

28. The method of claim 27, wherein the voltage-gated sodium ion channel is NaV 1.7.

29. A method of treating or lessening the severity of acute pain, chronic pain, neuropathic pain, inflammatory pain, visceral pain, osteoarthritis pain, radicular pain, sciatica, back pain, head pain, neck pain, severe pain, intractable pain, nociceptive pain, breakthrough pain, postsurgical pain, or pain associated with cancer in a subject, comprising administering to said subject an effective amount of a compound claim 1.

30. The compound of claim 15, wherein ring B is a phenyl ring optionally substituted by halo, cyano, oxoalkoxy, hydroxy, amino, nitro, aryl, haloalkyl, or alkyl.
31. The compound of claim 30, wherein ring B is
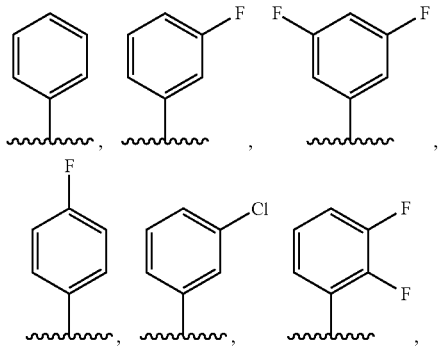
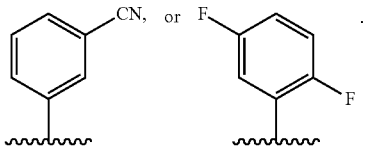
32. The compound of claim 1, wherein ring A is
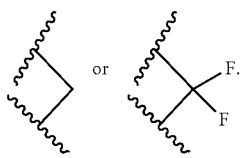

UNITED STATES PATENT AND TRADEMARK OFFICE
CERTIFICATE OF CORRECTION

PATENT NO. : 10,233,191 B2
APPLICATION NO. : 14/903475
DATED : March 19, 2019
INVENTOR(S) : Michael Paul Deninno et al.

Page 1 of 1

It is certified that error appears in the above-identified patent and that said Letters Patent is hereby corrected as shown below:

In the Claims

Column 498, Lines 40-50, delete " 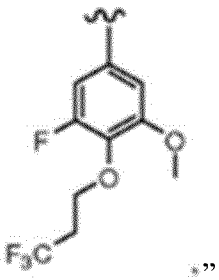 "

Column 499, Lines 20-30, delete " 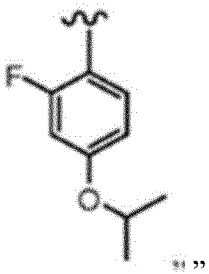 "

Signed and Sealed this
Twenty-fourth Day of November, 2020

Andrei Iancu
*Director of the United States Patent and Trademark Office*